United States Patent
Roobrouck et al.

(10) Patent No.: US 10,927,186 B2
(45) Date of Patent: Feb. 23, 2021

(54) T CELL RECRUITING POLYPEPTIDES BASED ON TCR ALPHA/BETA REACTIVITY

(71) Applicant: Ablynx N.V., Ghent-Zwijnaarde (BE)

(72) Inventors: Annelies Roobrouck, Oudenaarde (BE); Diane Van Hoorick, Laarne (BE); João Vieira, Didcot (GB)

(73) Assignee: Ablynx N.V., Ghent-Zwijnaarde (BE)

( * ) Notice: Subject to any disclaimer, the term of this patent is extended or adjusted under 35 U.S.C. 154(b) by 454 days.

(21) Appl. No.: 15/573,288

(22) PCT Filed: May 13, 2016

(86) PCT No.: PCT/EP2016/060859
§ 371 (c)(1),
(2) Date: Nov. 10, 2017

(87) PCT Pub. No.: WO2016/180969
PCT Pub. Date: Nov. 17, 2016

(65) Prior Publication Data
US 2019/0112392 A1    Apr. 18, 2019

Related U.S. Application Data

(60) Provisional application No. 62/319,486, filed on Apr. 7, 2016, provisional application No. 62/160,757, filed on May 13, 2015.

(51) Int. Cl.

| | |
|---|---|
| *C07K 16/28* | (2006.01) |
| *C07K 16/46* | (2006.01) |
| *C07K 16/30* | (2006.01) |
| *C07K 16/32* | (2006.01) |
| *A61K 47/60* | (2017.01) |
| *C07K 16/18* | (2006.01) |
| *A61K 39/00* | (2006.01) |

(52) U.S. Cl.
CPC ............ *C07K 16/468* (2013.01); *A61K 47/60* (2017.08); *C07K 16/18* (2013.01); *C07K 16/2809* (2013.01); *C07K 16/2863* (2013.01); *C07K 16/2887* (2013.01); *C07K 16/3007* (2013.01); *C07K 16/32* (2013.01); *A61K 2039/505* (2013.01); *C07K 2317/22* (2013.01); *C07K 2317/24* (2013.01); *C07K 2317/31* (2013.01); *C07K 2317/32* (2013.01); *C07K 2317/33* (2013.01); *C07K 2317/565* (2013.01); *C07K 2317/567* (2013.01); *C07K 2317/569* (2013.01); *C07K 2317/75* (2013.01); *C07K 2317/92* (2013.01); *C07K 2317/94* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 7,728,114 B2 * | 6/2010 | Mach ..................... | A61P 17/00 530/388.15 |
| 2014/0154253 A1 | 6/2014 | Ng et al. | |
| 2015/0056206 A1 * | 2/2015 | Zhou .................... | C07K 14/705 424/136.1 |

FOREIGN PATENT DOCUMENTS

WO    WO 2015/006749 A2    1/2015

OTHER PUBLICATIONS

Saerens et al. (J Mol Biol. Sep. 23, 2005;352(3):597-607). (Year: 2005).*

(Continued)

*Primary Examiner* — Zachary S Skelding
(74) *Attorney, Agent, or Firm* — Wolf, Greenfield & Sacks, P.C.

(57) ABSTRACT

T cell recruiting polypeptides are provided that bind the constant domain of TCR on a T cell. The polypeptides can be used in methods for treatment of cancers.

20 Claims, 56 Drawing Sheets

Specification includes a Sequence Listing.

(56) References Cited

OTHER PUBLICATIONS

Muyldermans et al., Reviews in Molecular Biotechnology 74 (2001), 277-302). (Year: 2001).*
Zabetakis et al. (PLoS ONE 8(10): e77678 (2013). (Year: 2013).*
Harlow et al. (Antibodies, a Laboratory Manual, Cold Spring Harbor laboratory, 1988, pp. 37-47). (Year: 1988).*
Edwards et al. (J. Mol. Biol. (2003) 334, 103-118). (Year: 2003).*
Lloyd et al., Protein Engineering, Design & Selection vol. 22 No. 3 pp. 159-168, 2009. (Year: 2009).*
Vajdos et al. (J Mol Biol. Jul. 5, 2002;320(2):415-28). (Year: 2002).*
Colman (Research in Immunology, 145:33-36, 1994). (Year: 1994).*
Rudikoff et al. (Proc. Natl. Acad. Sci. USA, 79: 1979-1983, Mar. 1982). (Year: 1982).*
Muyldermans et al., Annu. Rev. Biochem. 2013. 82:775-97, (2013). (Year: 2013).*
Alignment of ISV SEQ ID Nos. 1-118, Sep. 18, 2020, pp. 1-3. (Year: 2020).*
Majidzadeh et al., Production of anti-cancer Bi-functional nanobody in bacterial host. Annual Meeting—Cancer Immunotherapy. May 11, 2015; 263-263. XP055284551. URL:http://www.meeting.cimt.eu/cms/diskfiles/download/6/44f802fe32fbdc40dl7db6cbf0fcOc9d/CIMT_ Abstracts 2015.pdf [retrieved on Jun. 29, 2016].
Moore et al., Application of dual affinity retargeting molecules to achieve optimal redirected T-cell killing of B-cell lymphoma. Blood. Apr. 28, 2011;117(17):4542-51. doi: 10.1182/blood-2010-09-306449. Epub Feb. 7, 2011. PubMed PMID: 21300981.
Spiess et al., Alternative molecular formats and therapeutic applications for bispecific antibodies. Mol Immunol. Oct. 2015;67(2 Pt A):95-106. doi: 10.1016/j.molimm.2015.01.003. Epub Jan. 2015.
PCT/EP2016/060859, Sep. 15, 2016, International Search Report and Written Opinion.
PCT/EP2016/060859, Nov. 23, 2017, International Preliminary Report on Patentability.

* cited by examiner

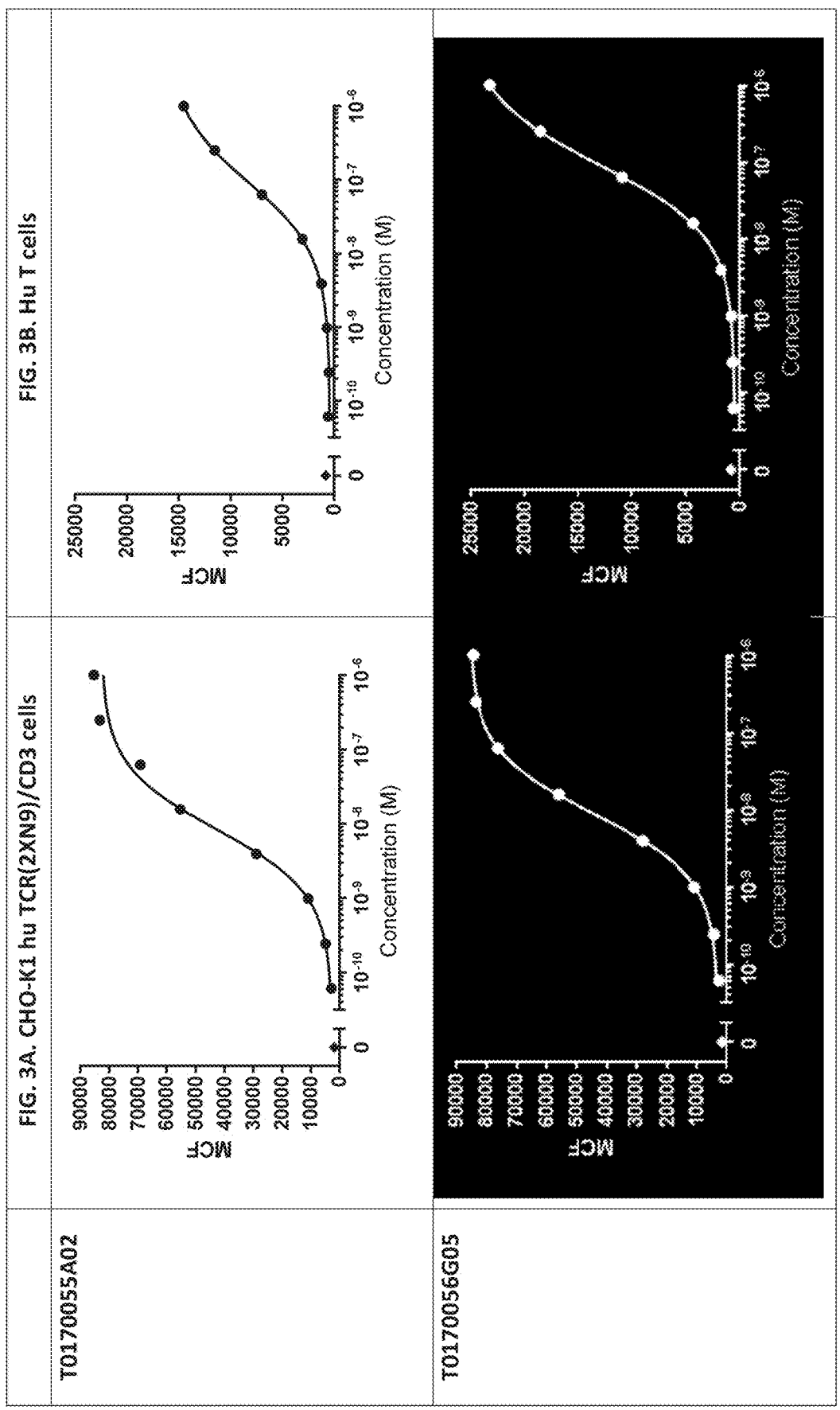

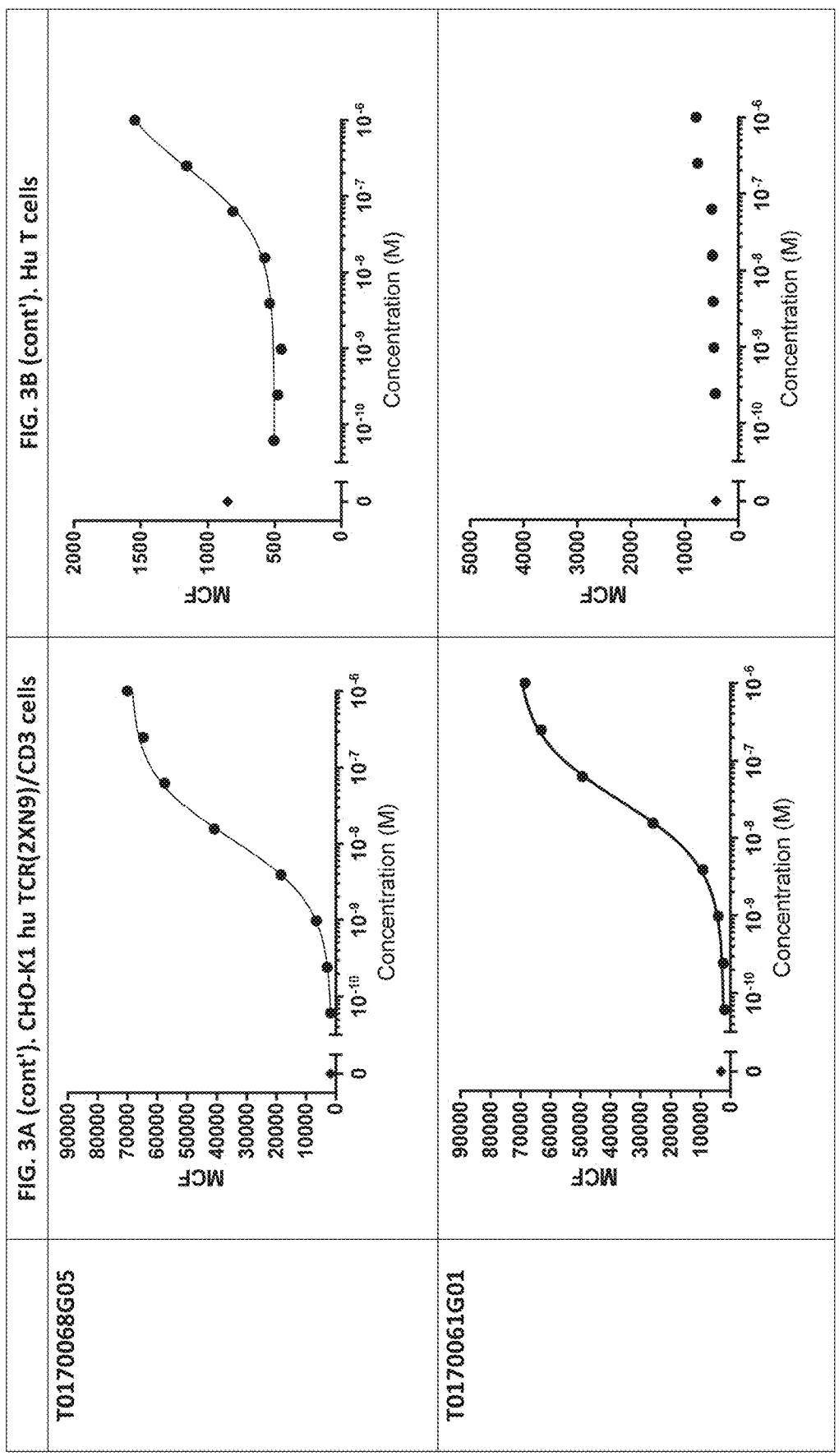

Figure 4:
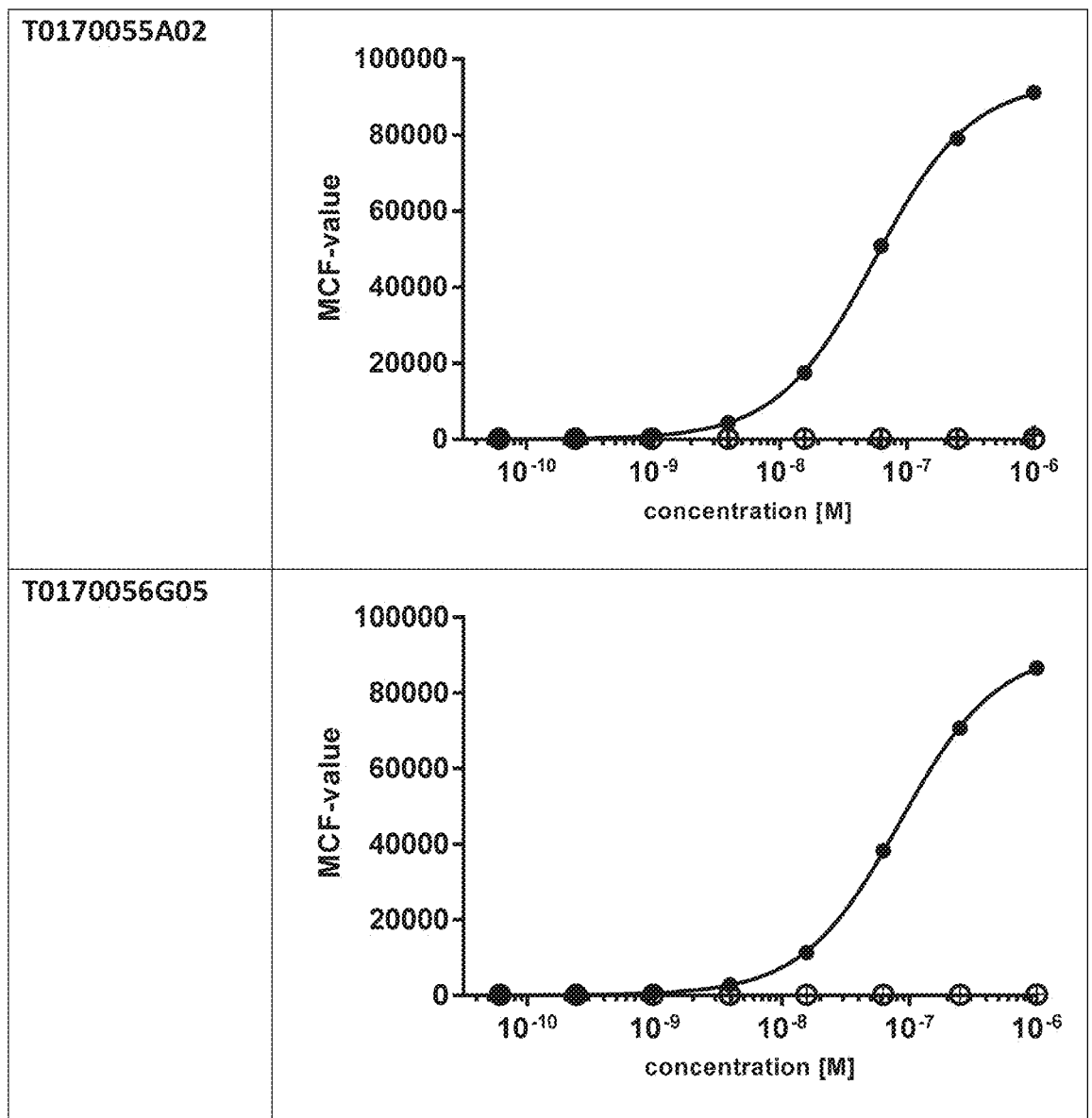

FIG. 4 cont'
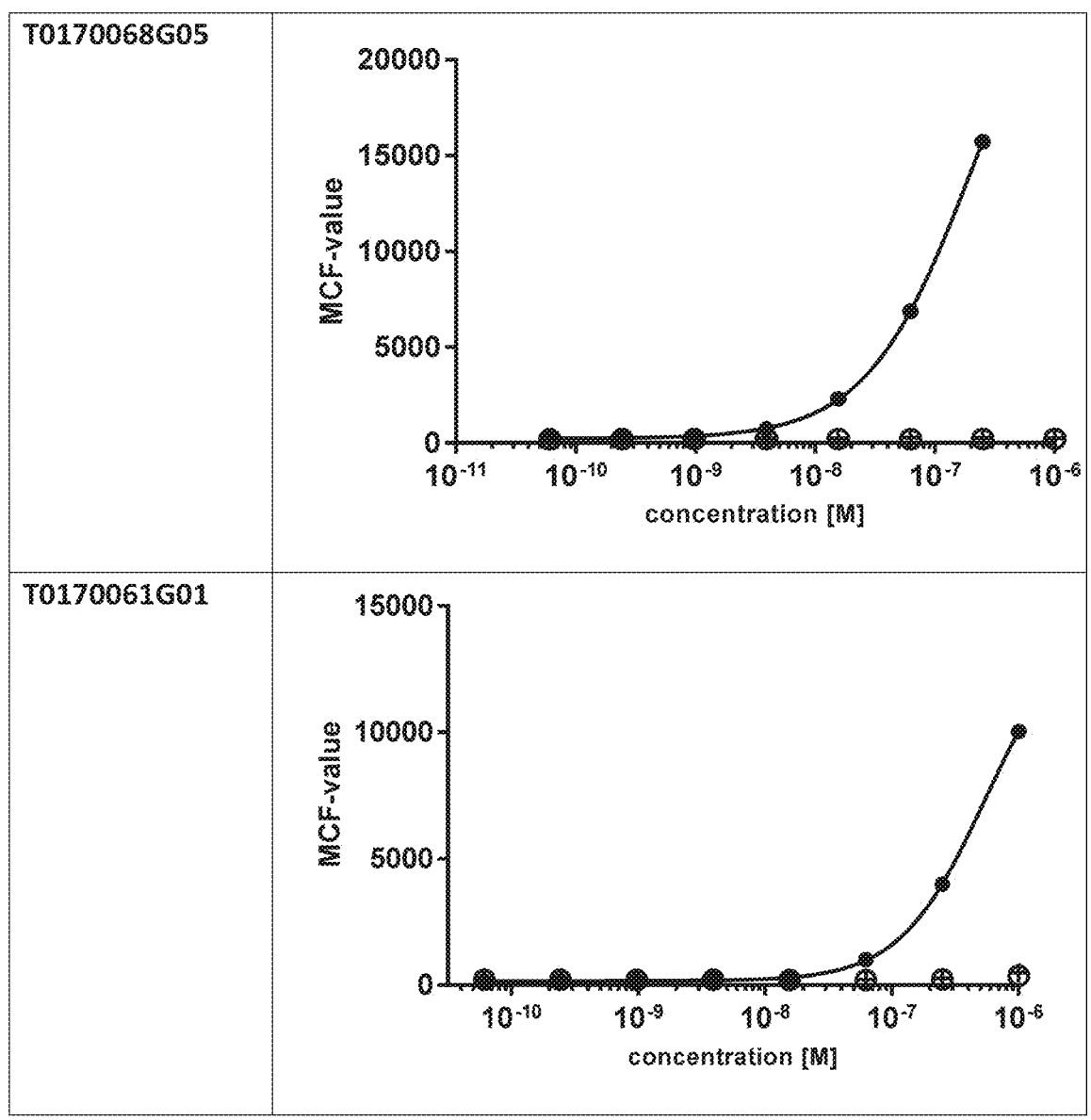

Figure 5:
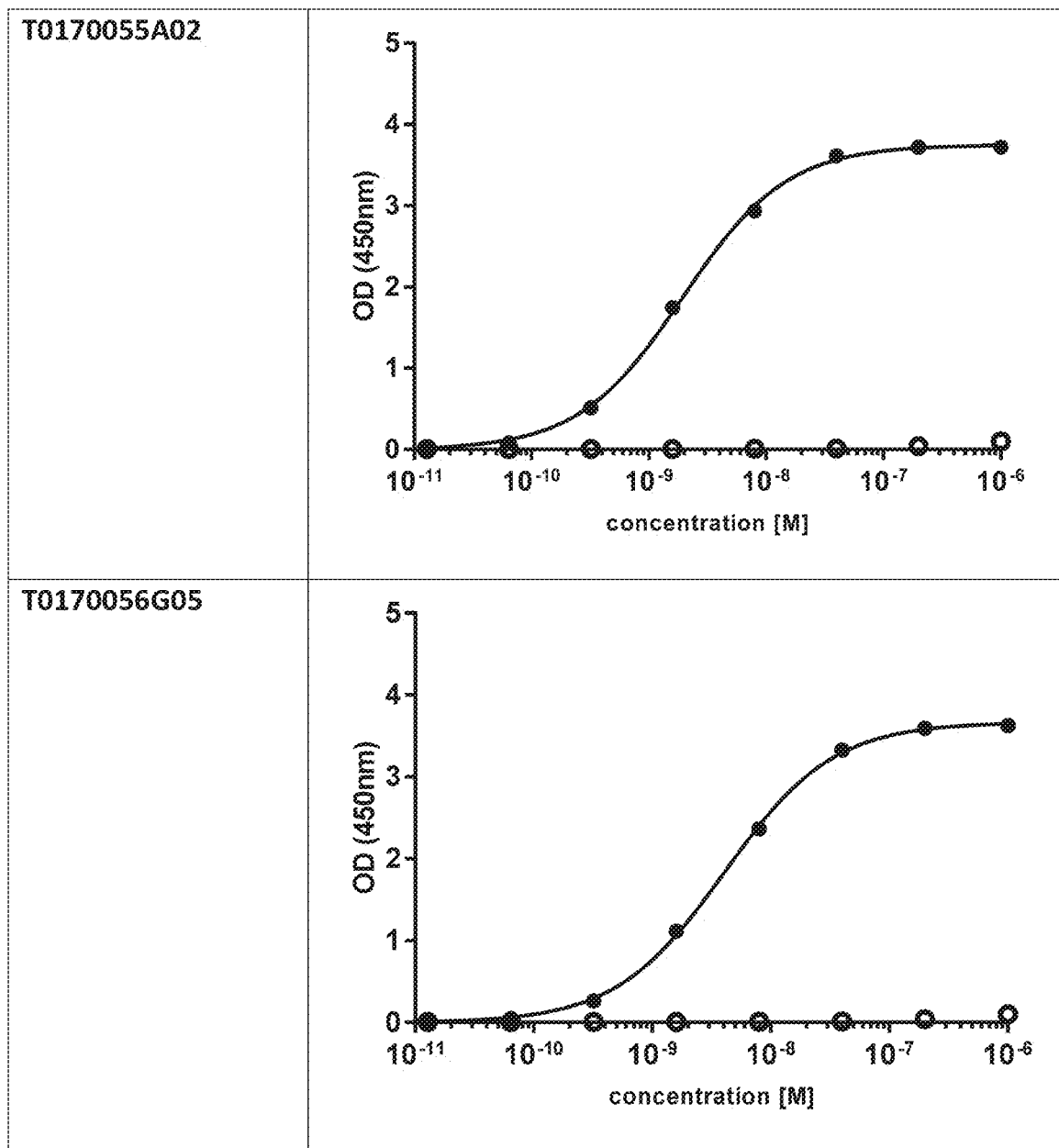

*FIG. 5 cont'*
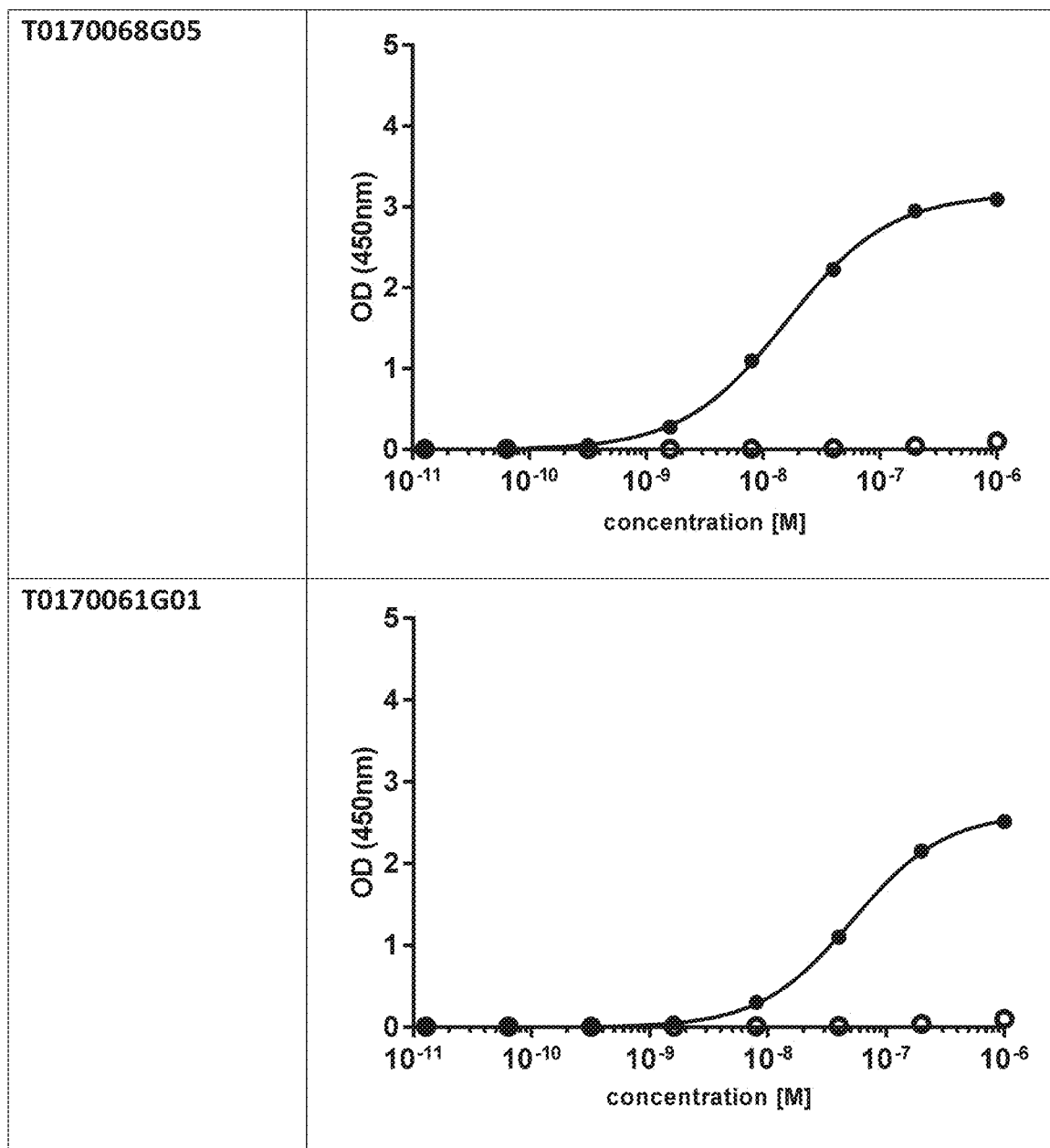

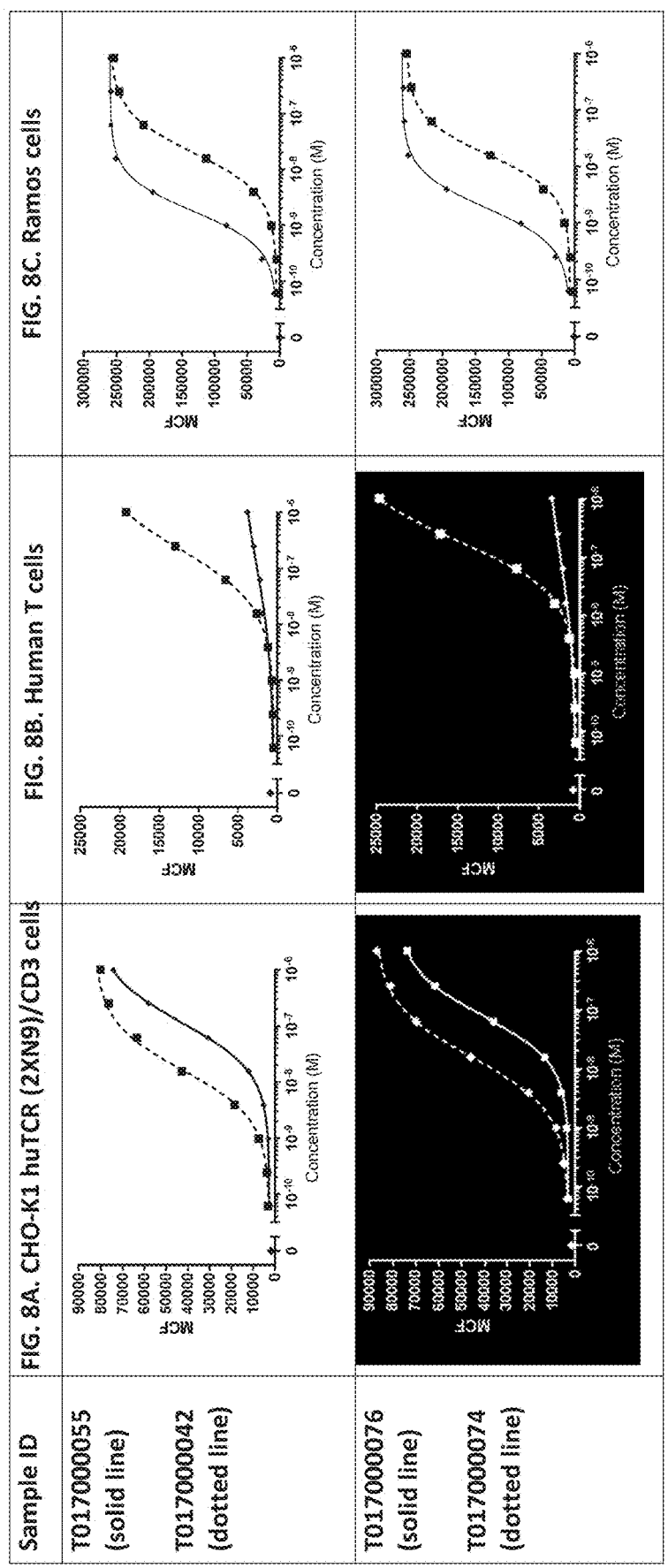

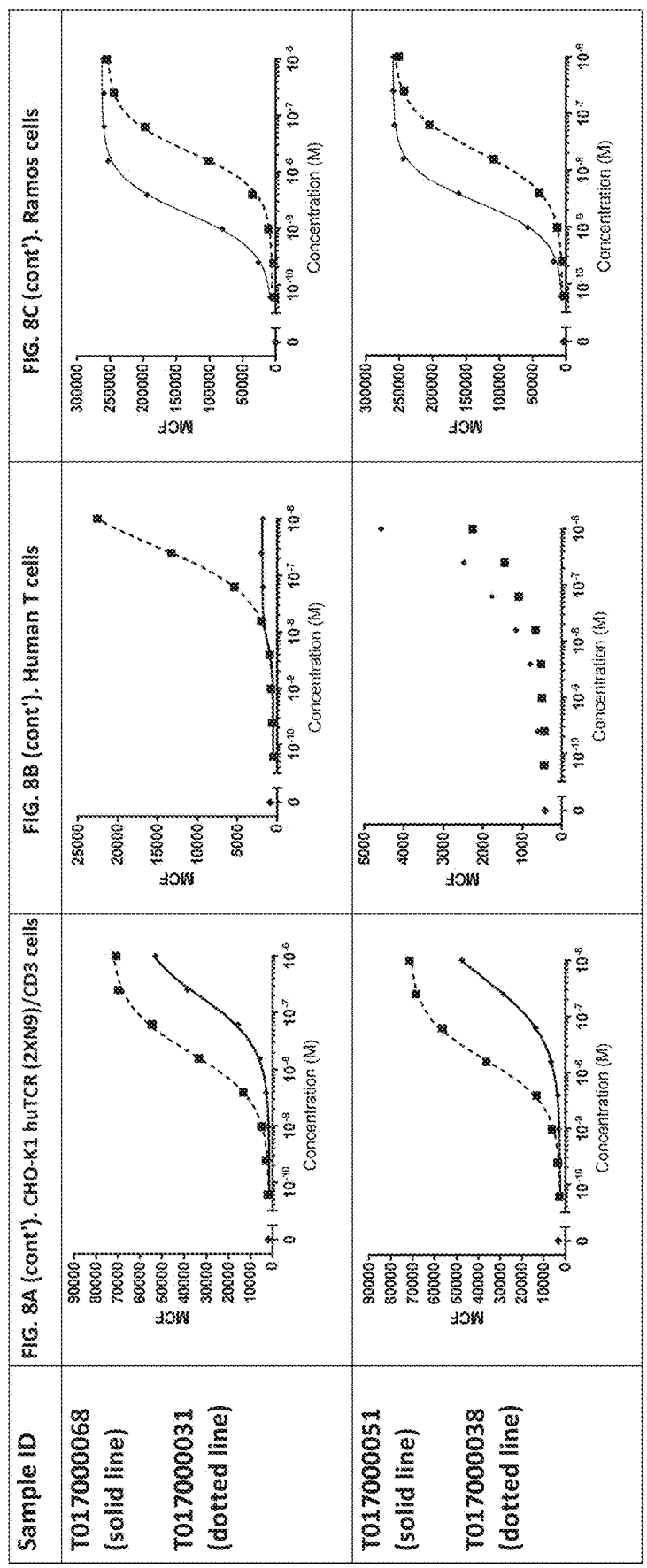

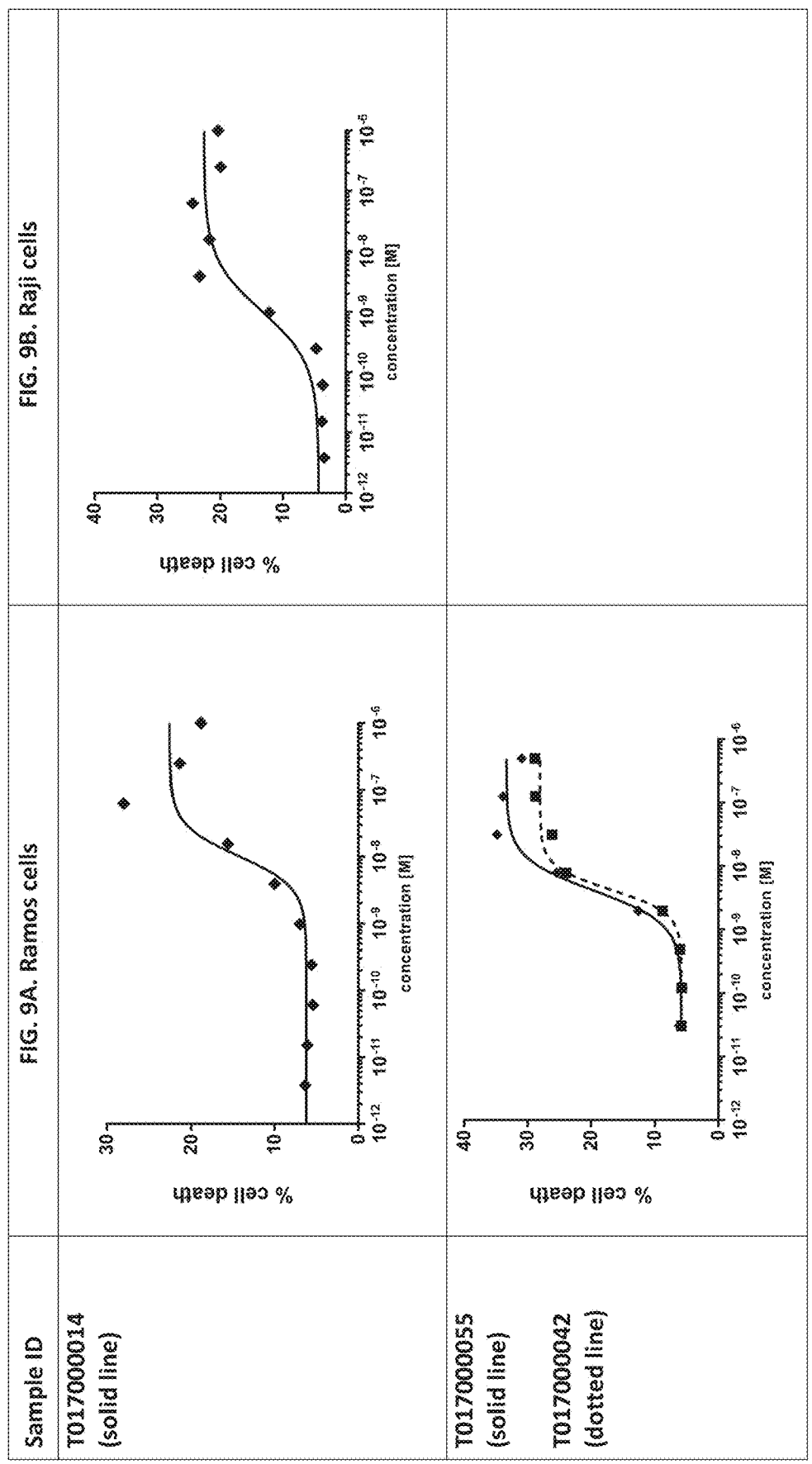

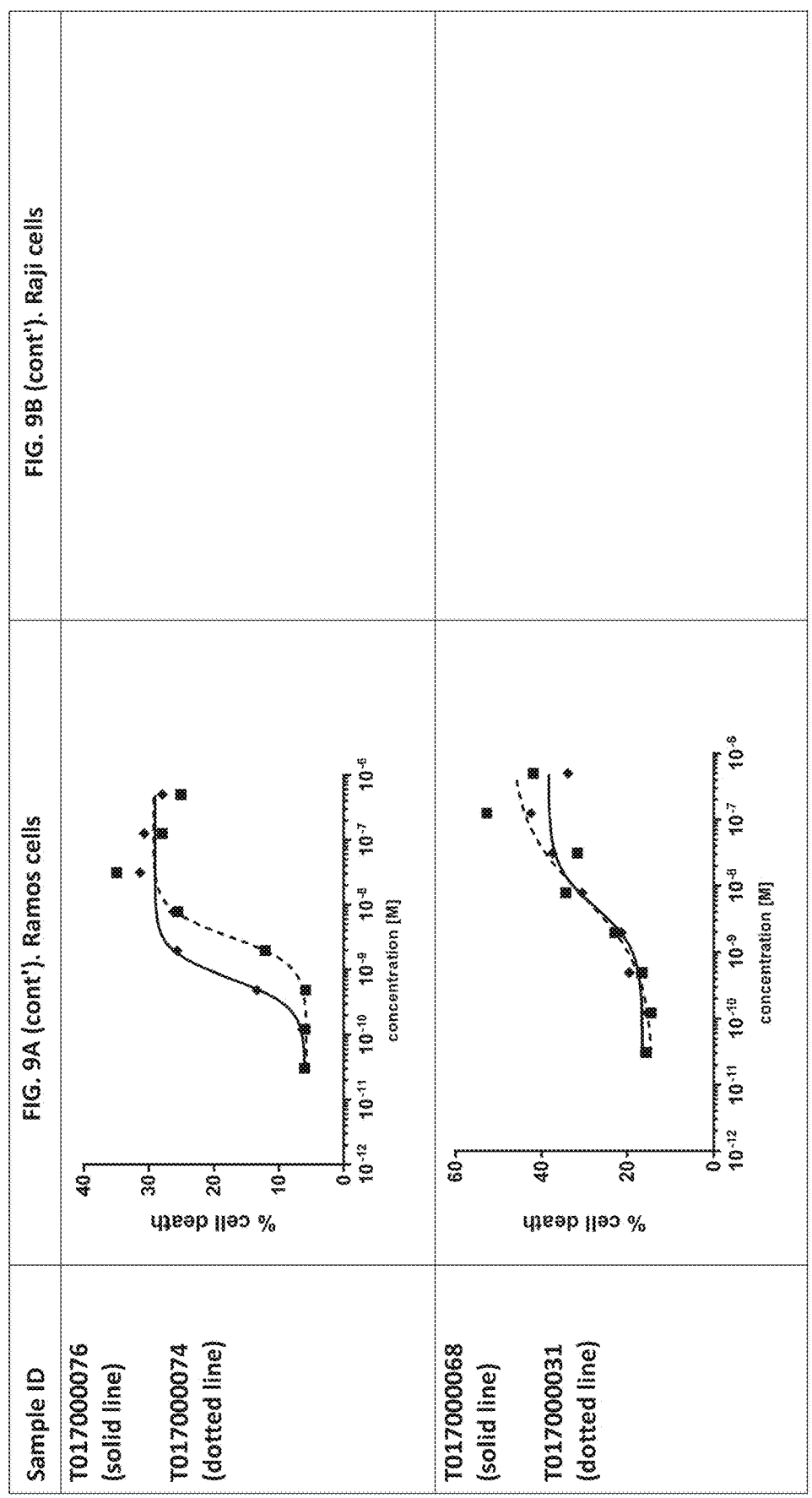

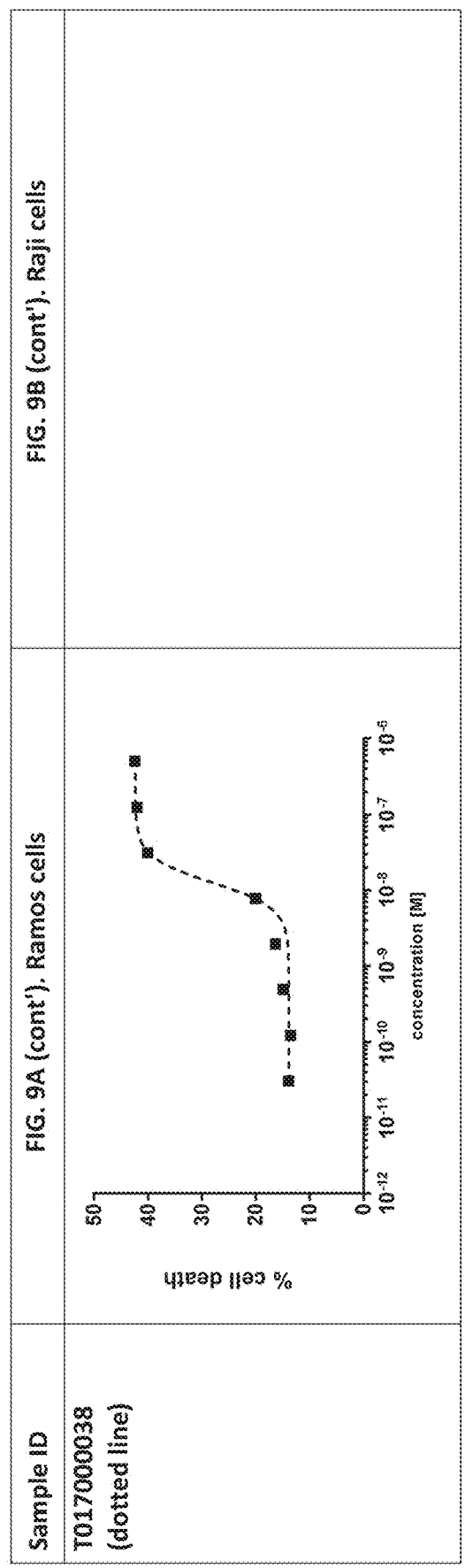

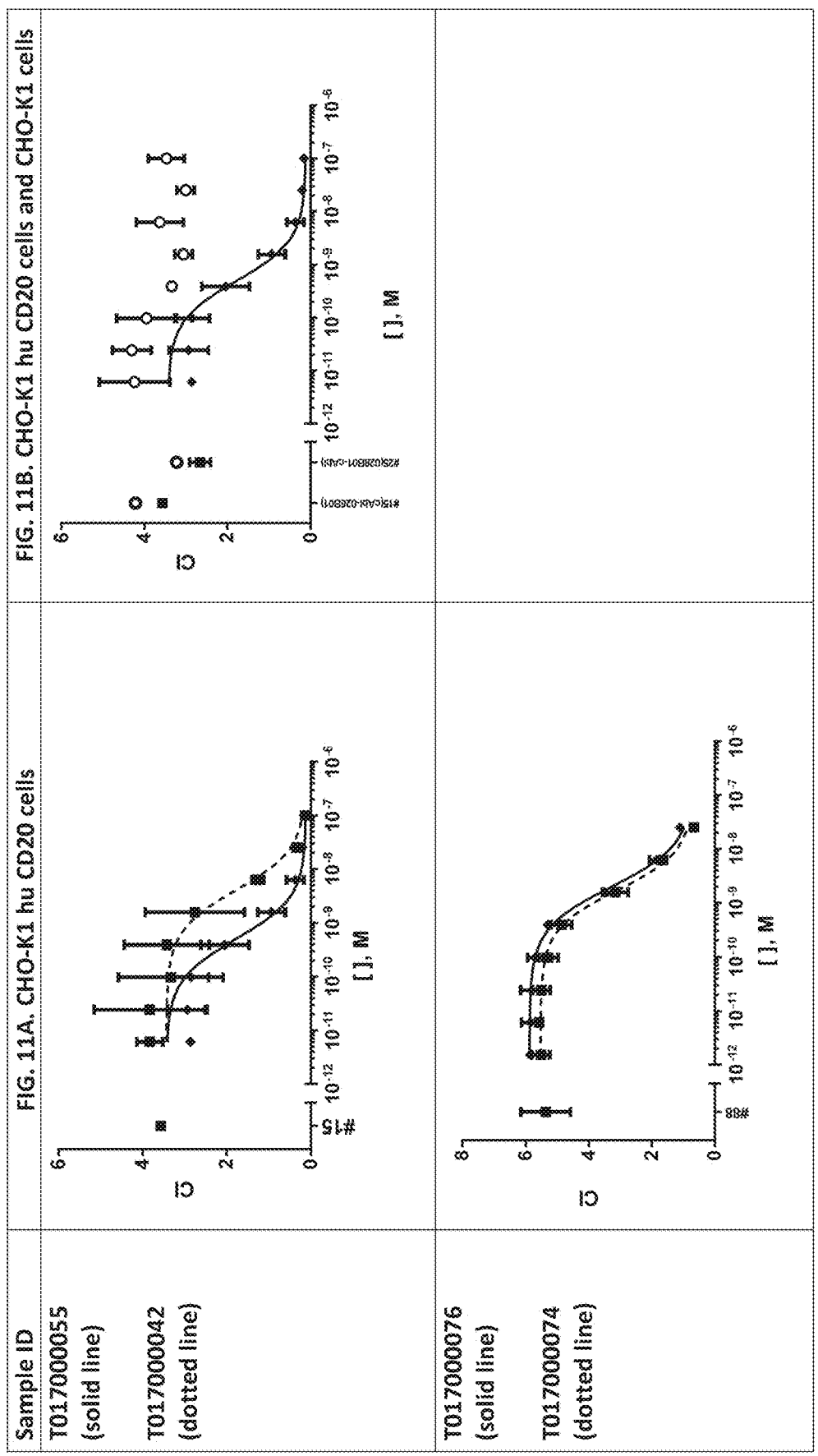

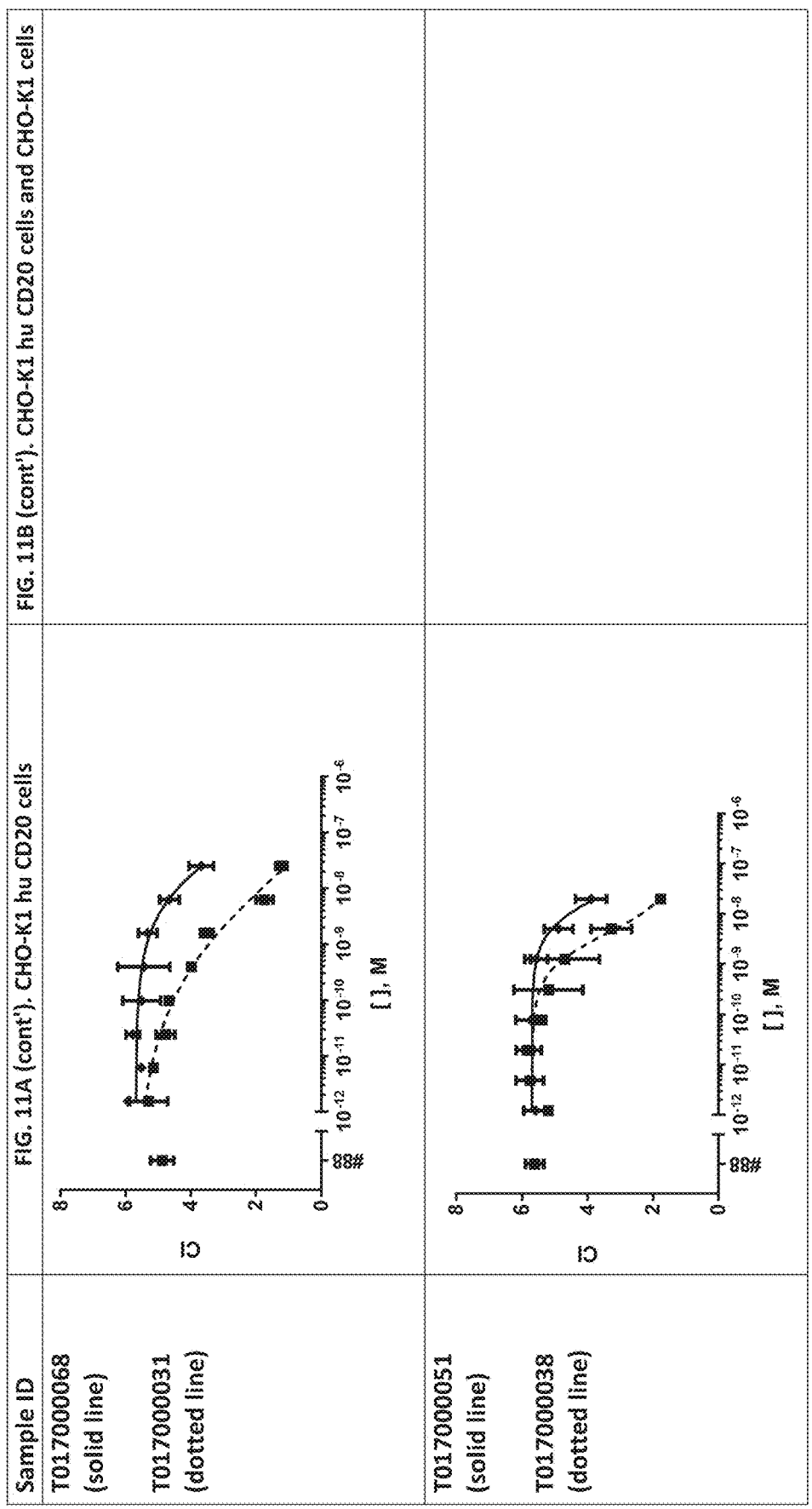

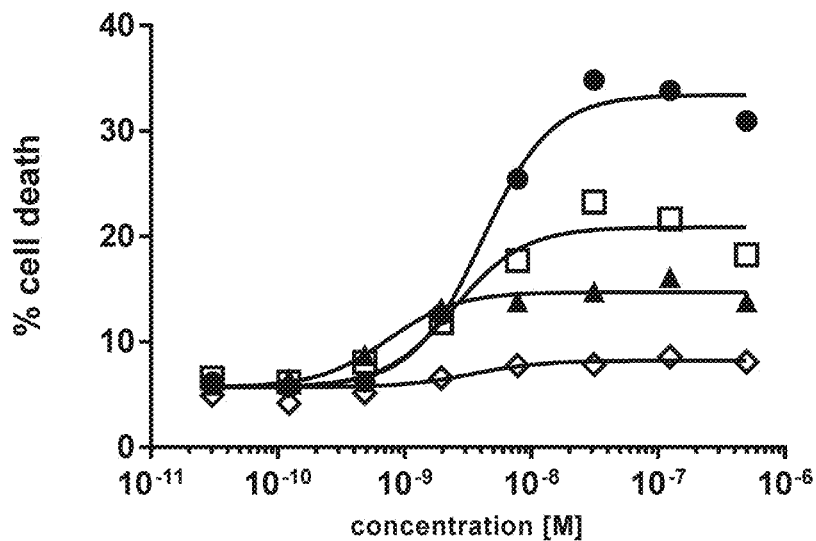
FIG. 13A. T017000055
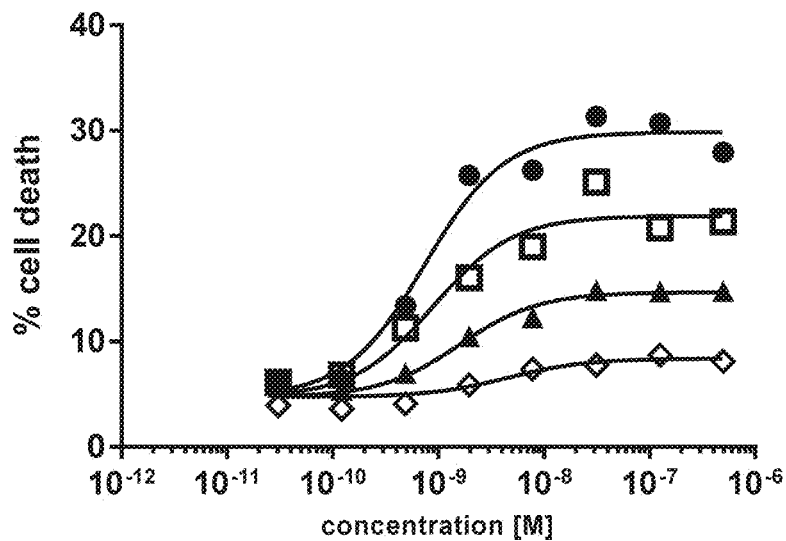
FIG. 13B. T017000076

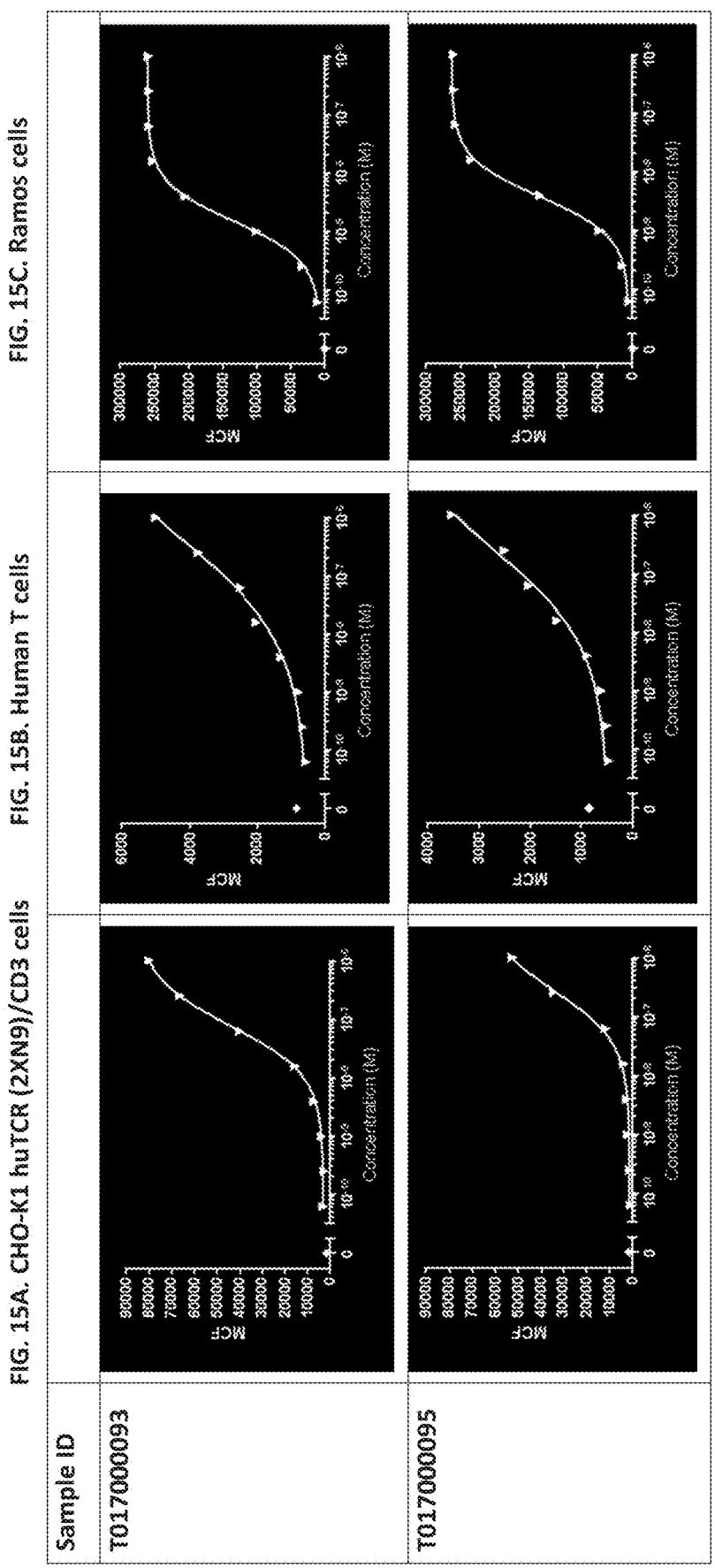

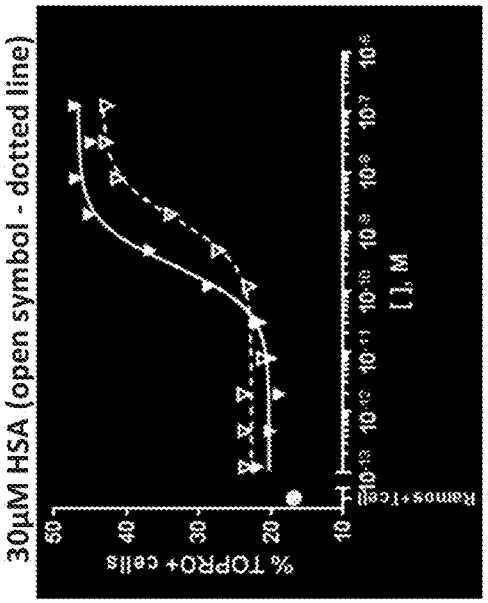
FIG. 16A. T017000076 (square) vs T017000093 (triangle)
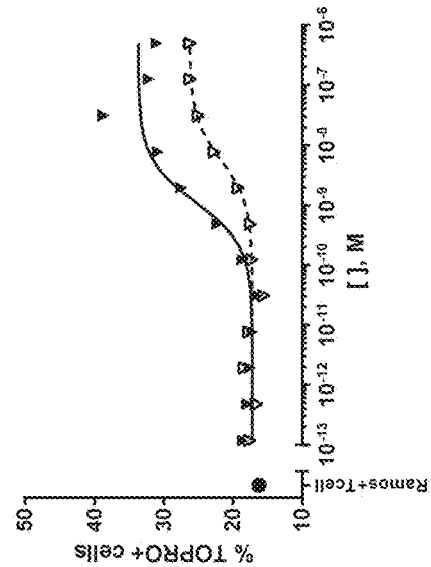
FIG. 16B. T017000093 in the absence (full line) or presence of 30μM HSA (open symbol - dotted line)
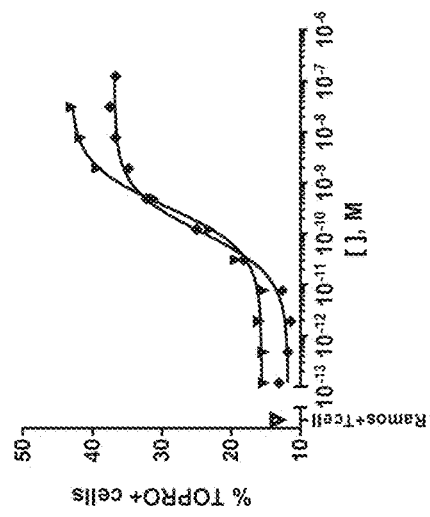
FIG. 16C. T017000068 (square) vs T017000095 (triangle)
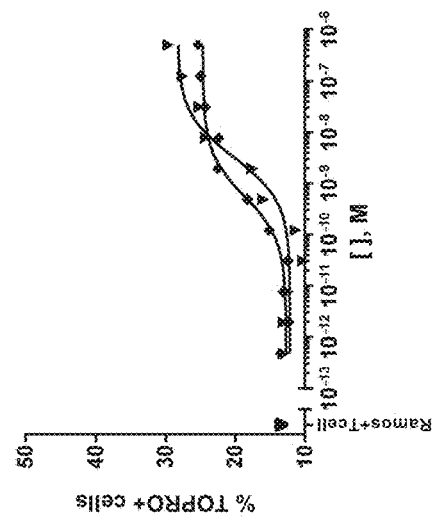
FIG. 16D. T017000095 in the absence (full line) or presence of 30μM HSA (open symbol - dotted line)

FIG. 17
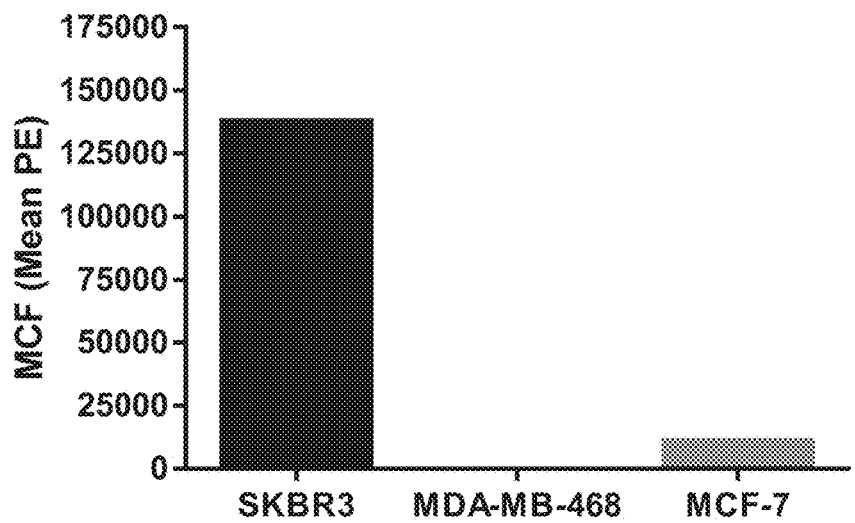
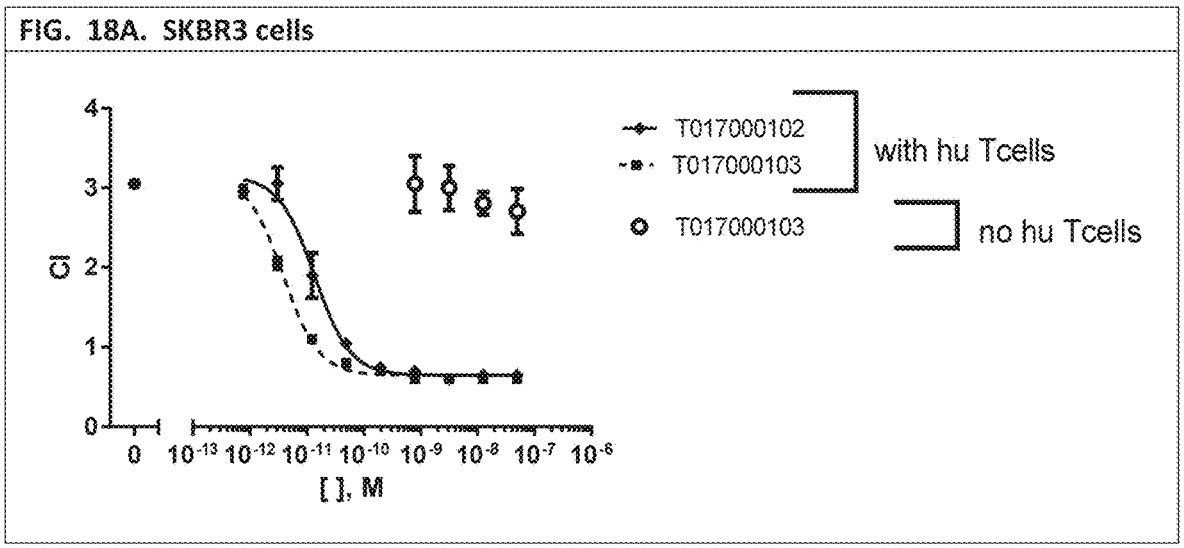

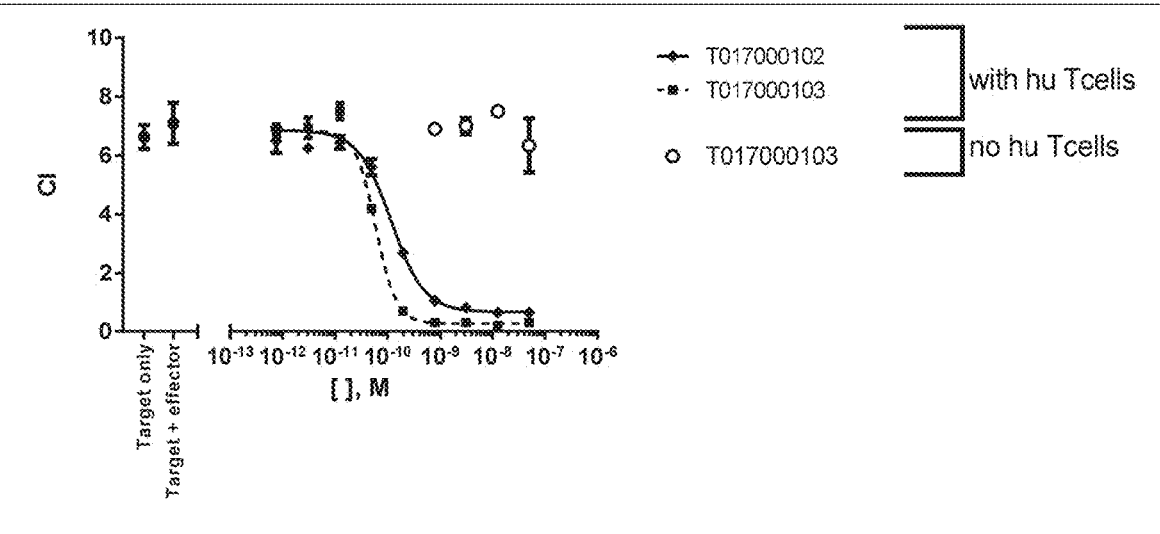
FIG. 18B. MCF-7 cells
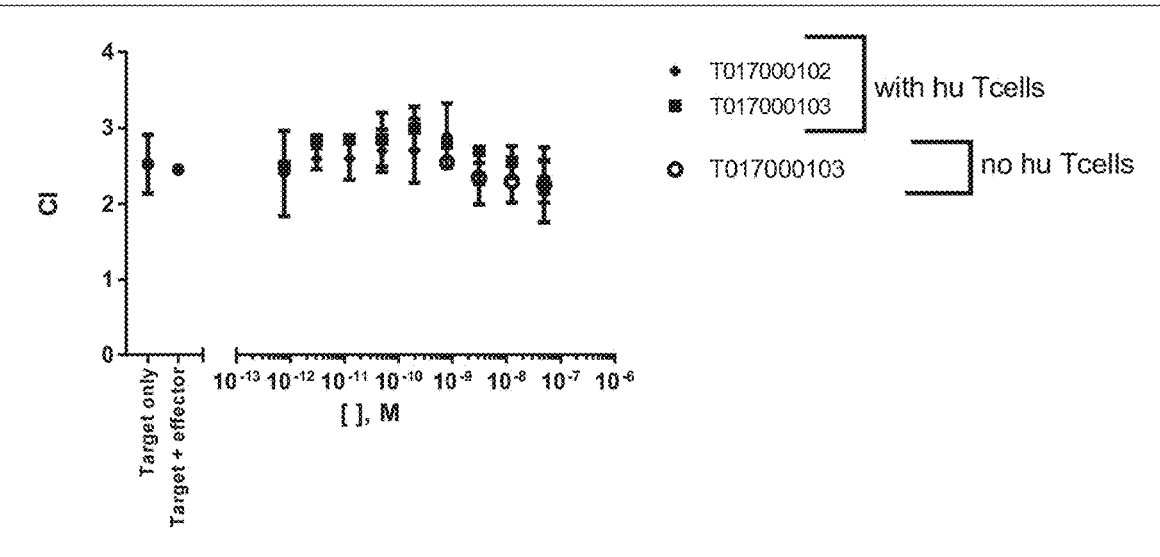
FIG. 18C. MDA-MB-468 cells

Figure 20:
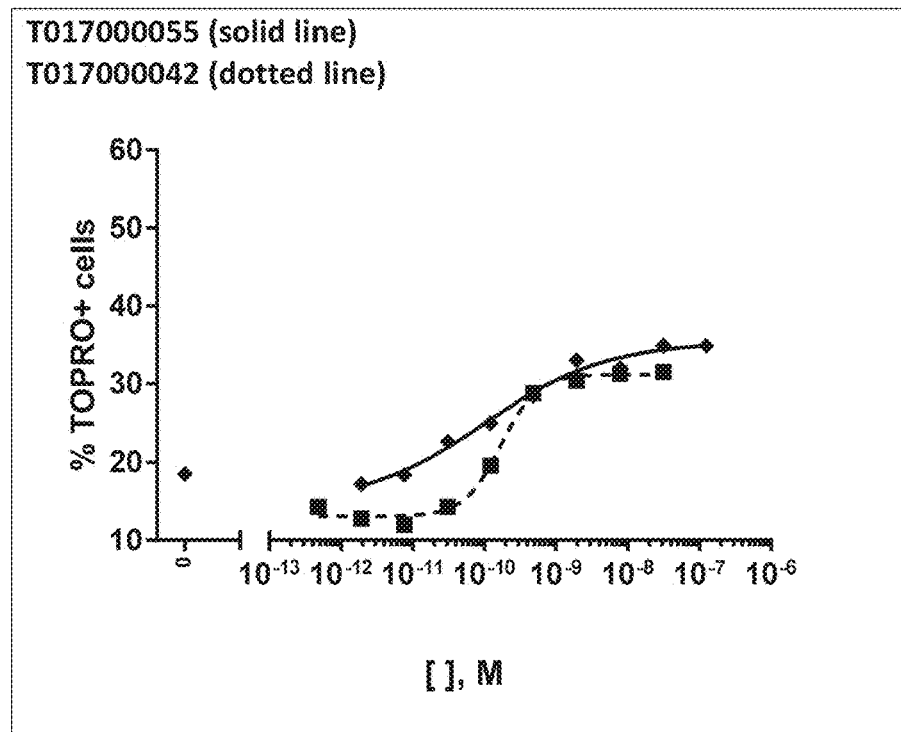

FIG. 20 cont'
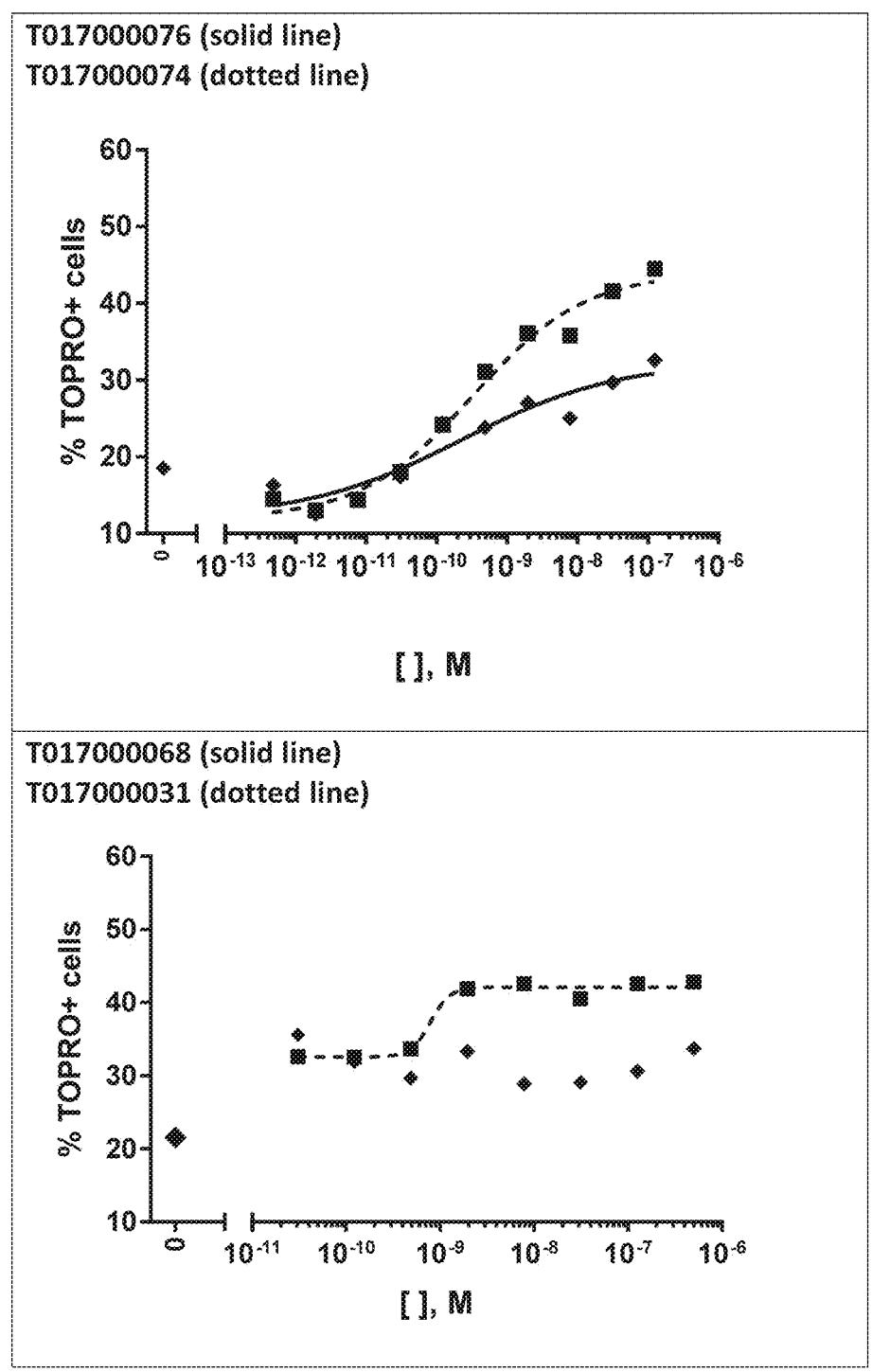

Figure 21:
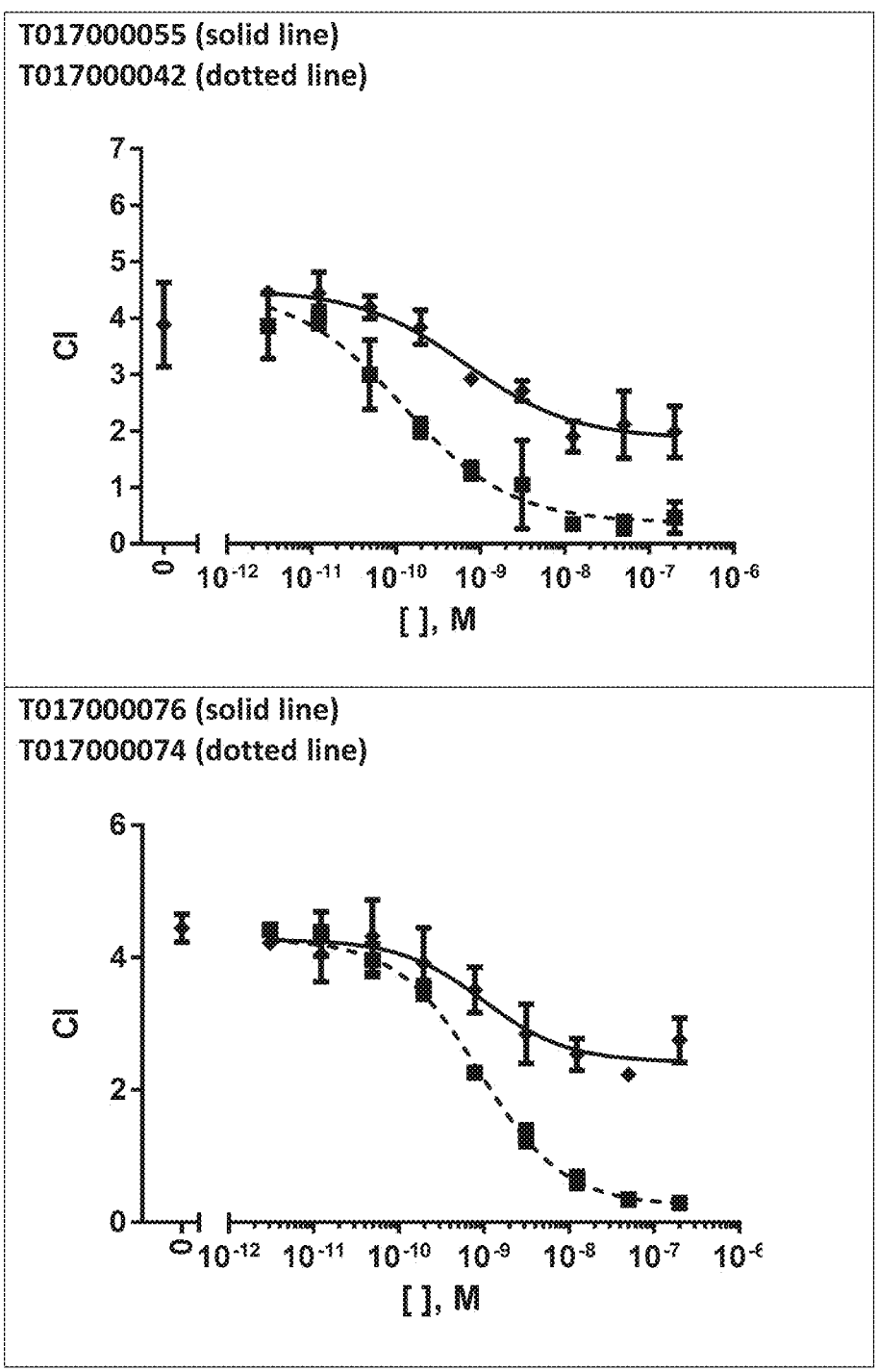

FIG. 21 cont'
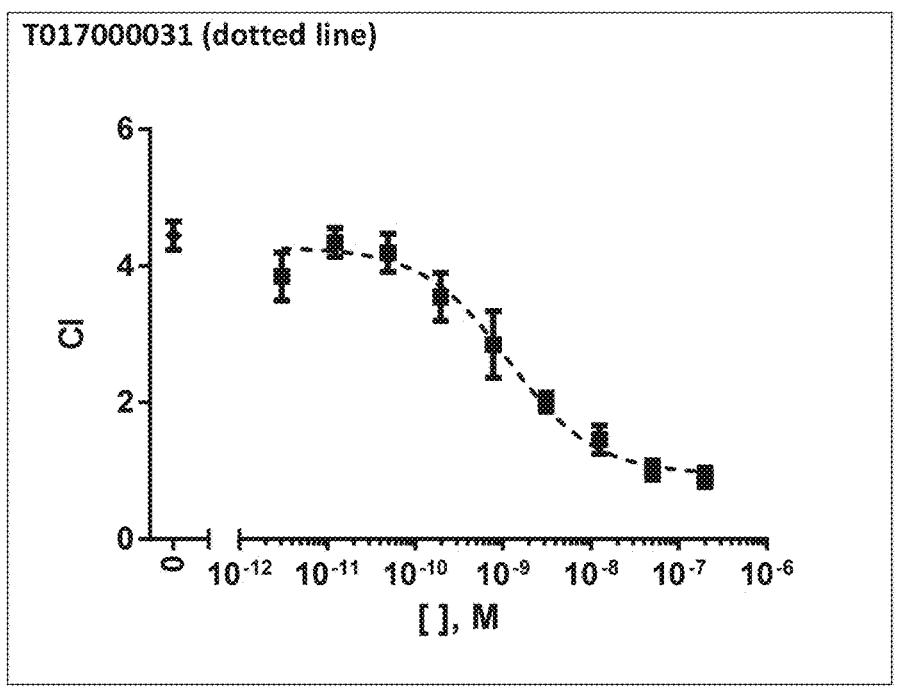
FIG. 22
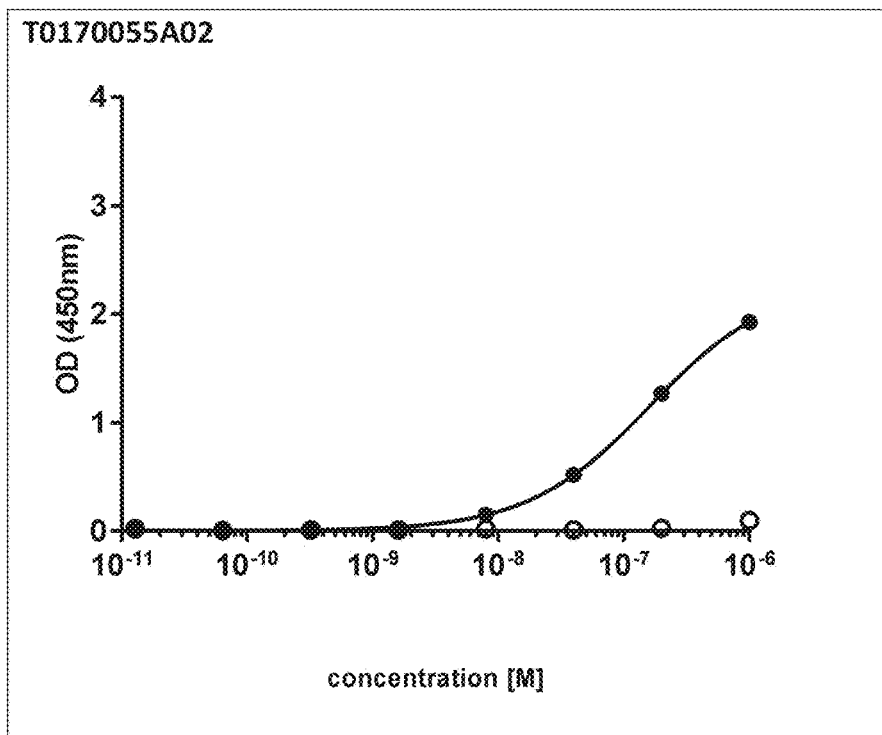

FIG. 22 cont'
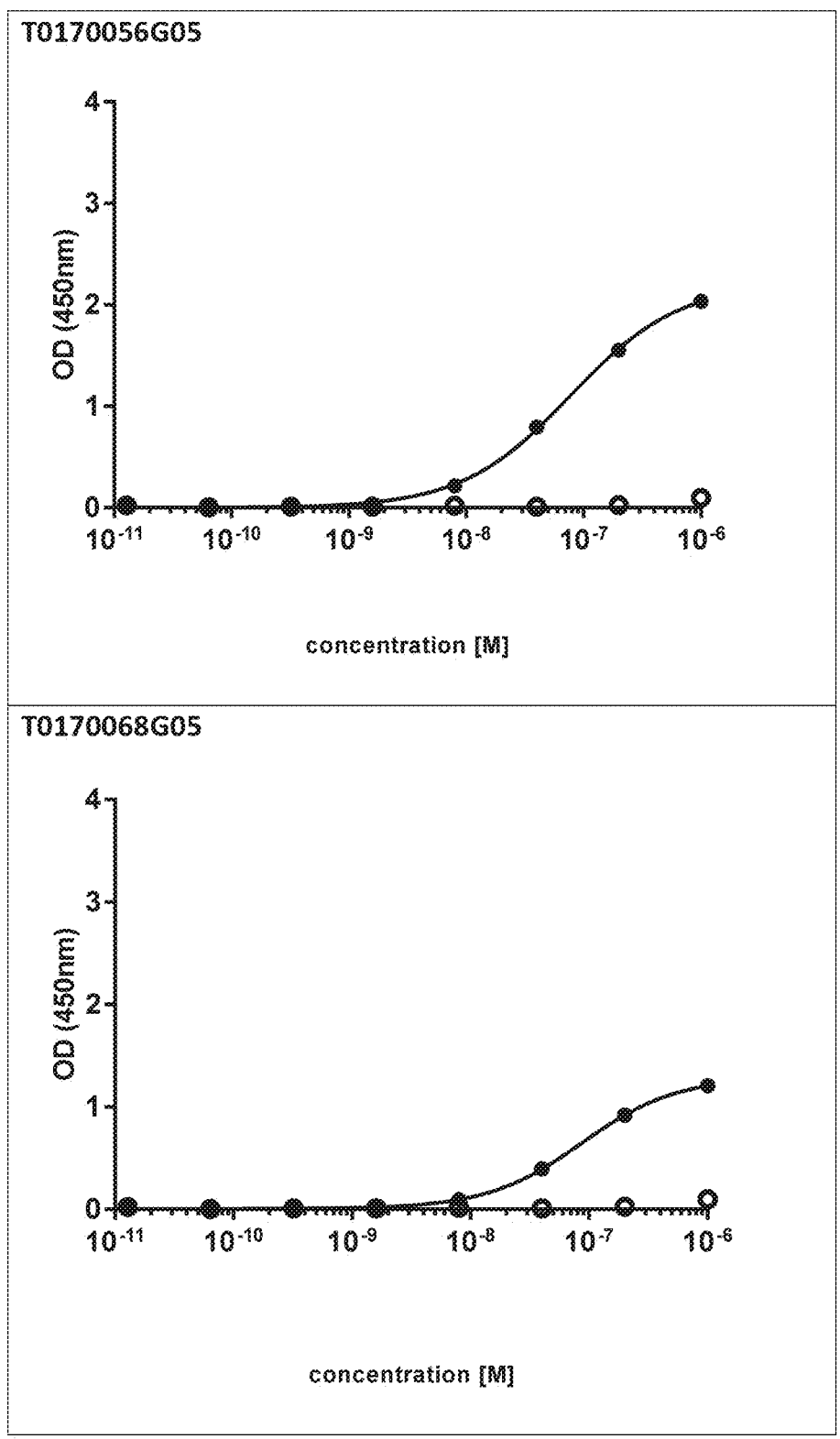

*FIG. 22 cont'*
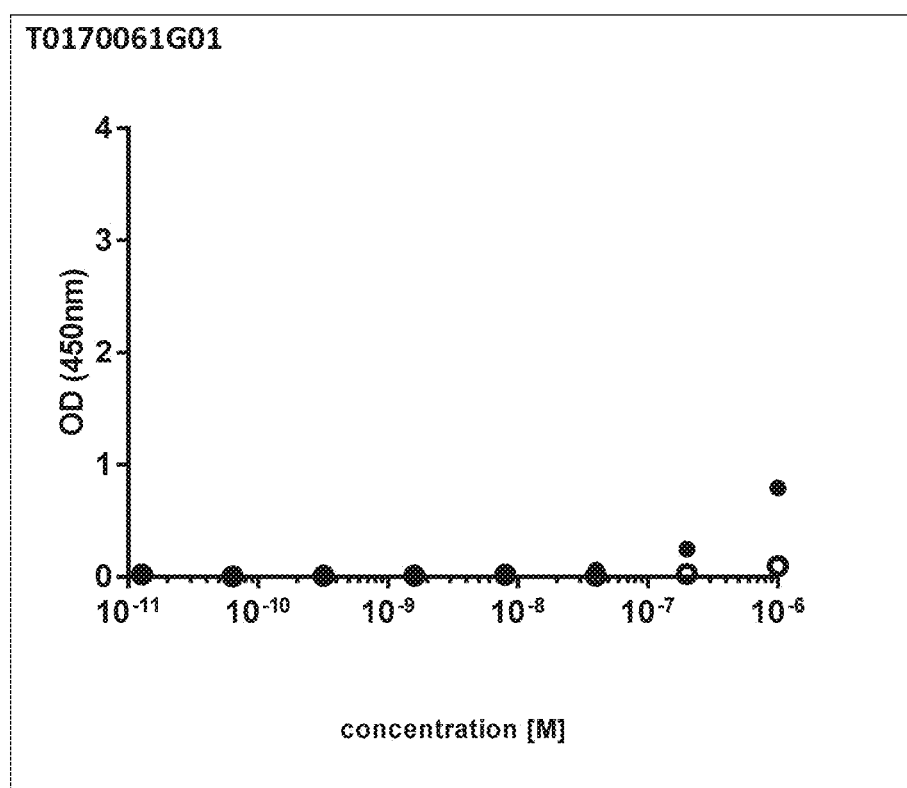

FIG. 24A. T017000076 (square) vs T017000093 (triangle) in the absence of HSA
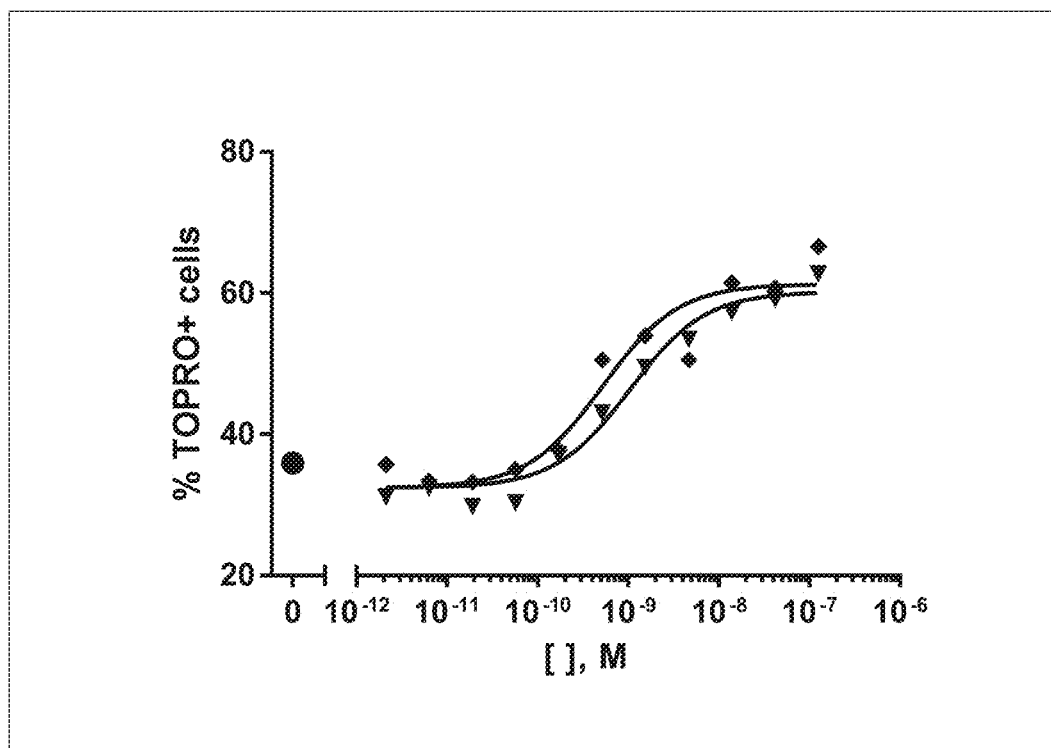
FIG. 24B. T017000093 in presence of 30µM HSA (open triangle)
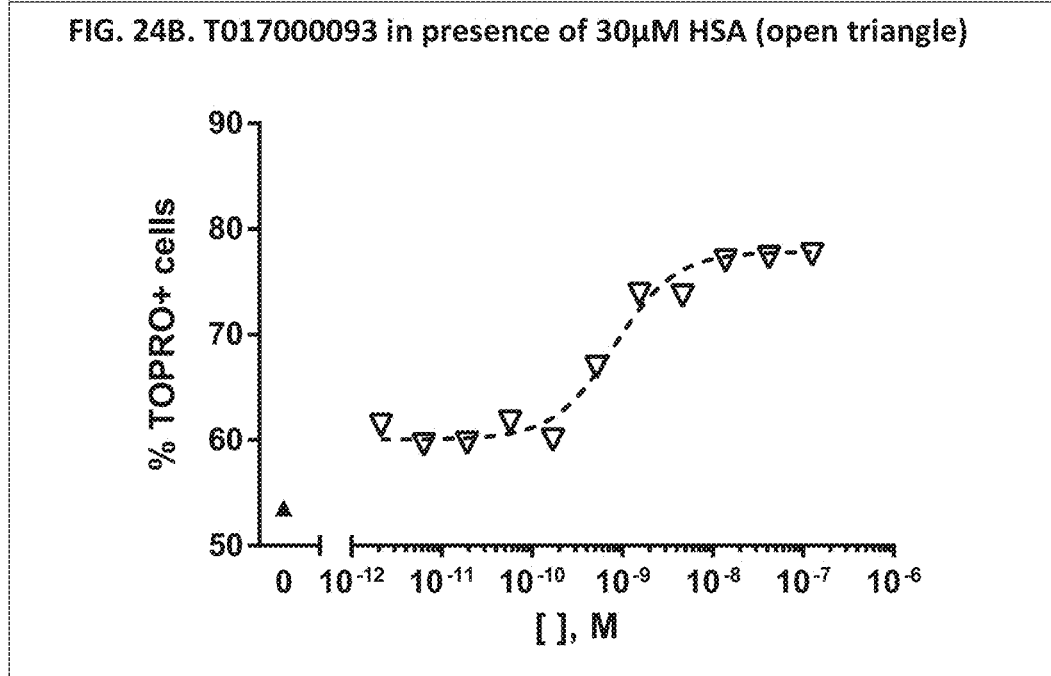

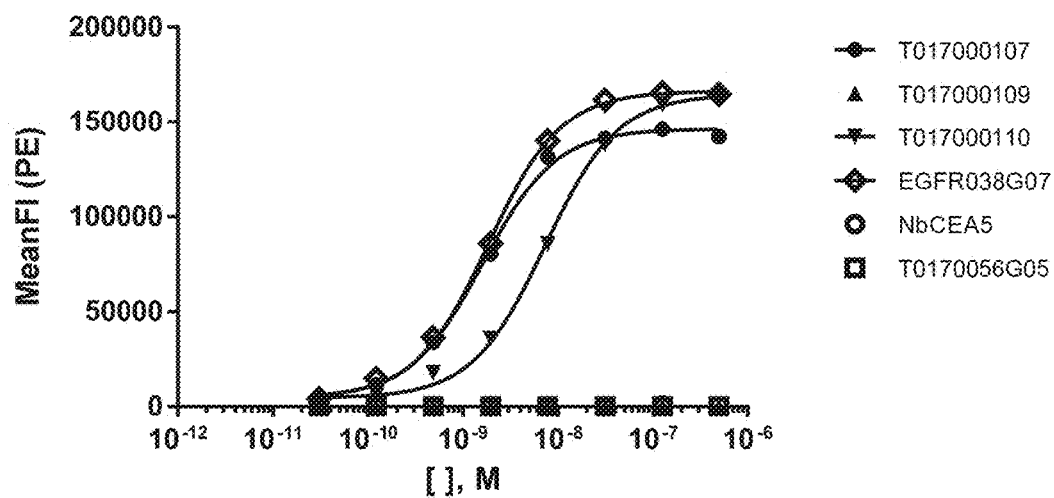
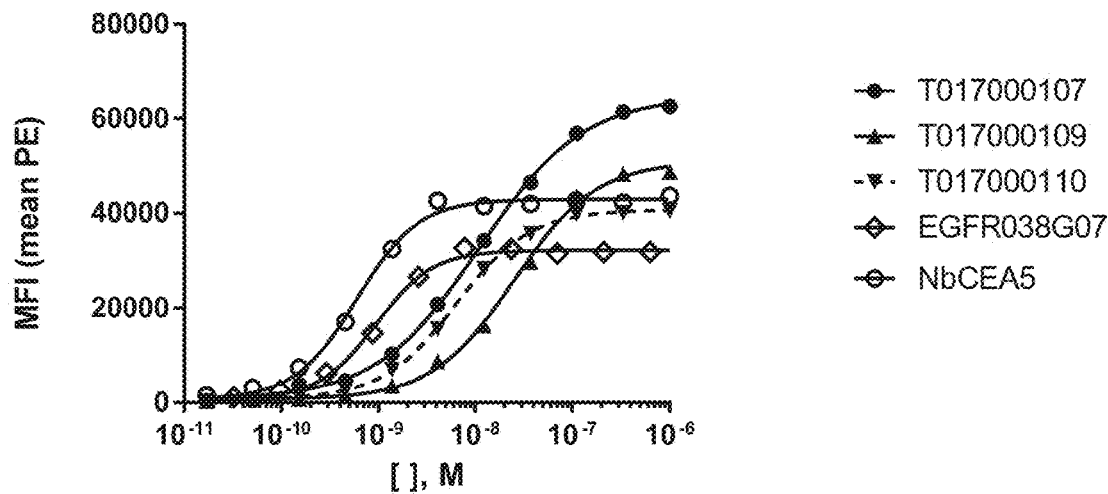

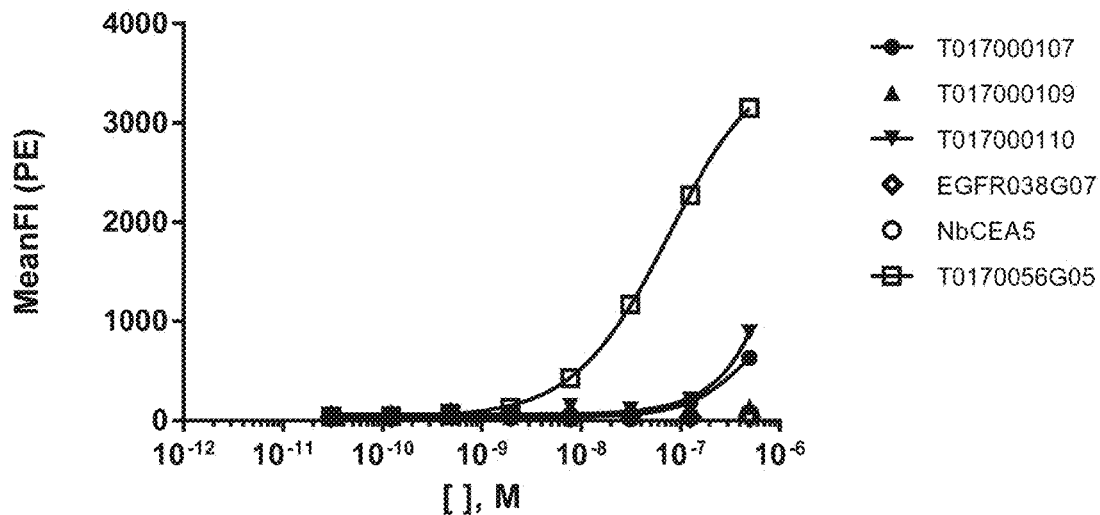
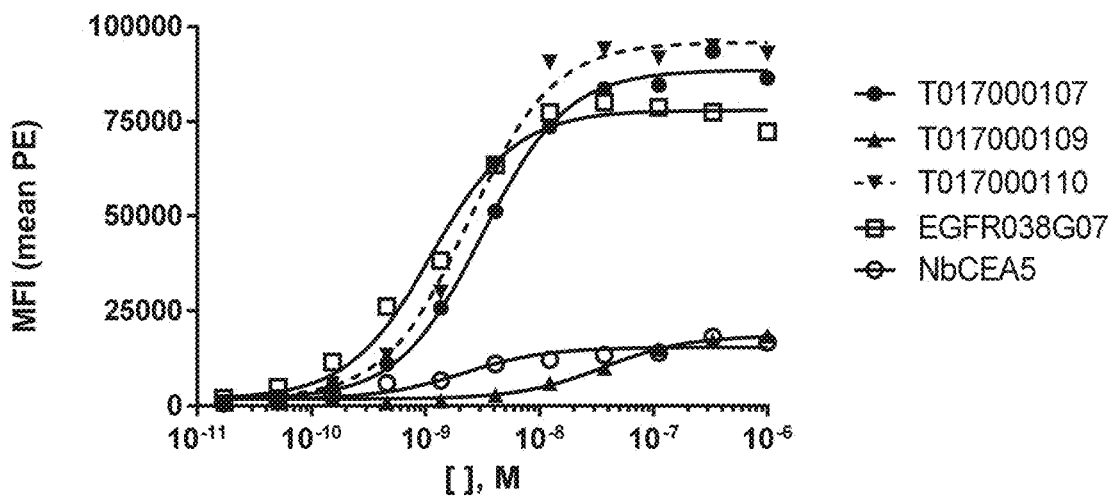

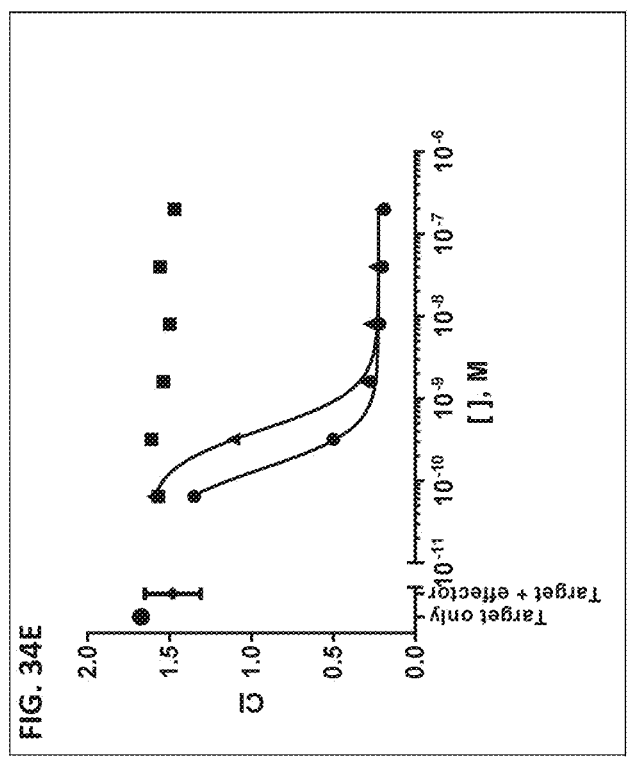

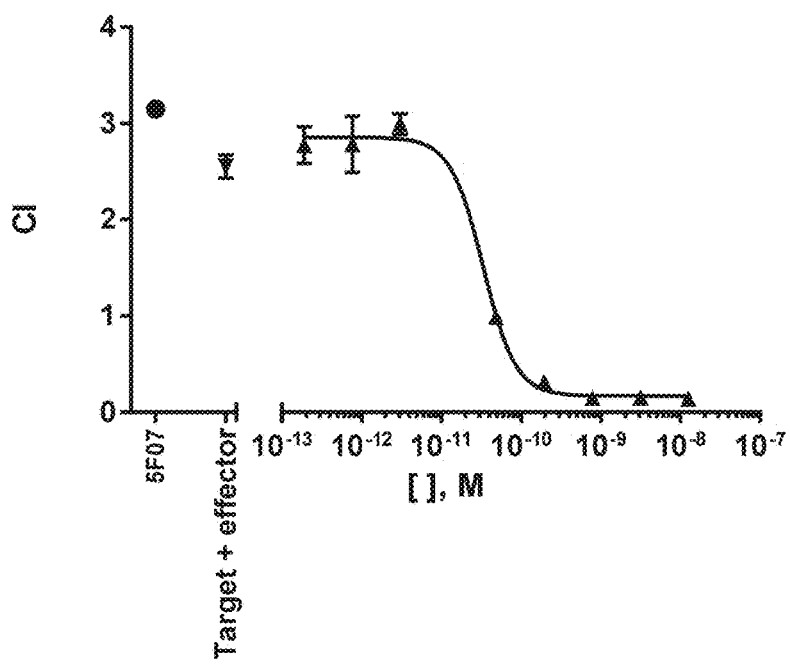

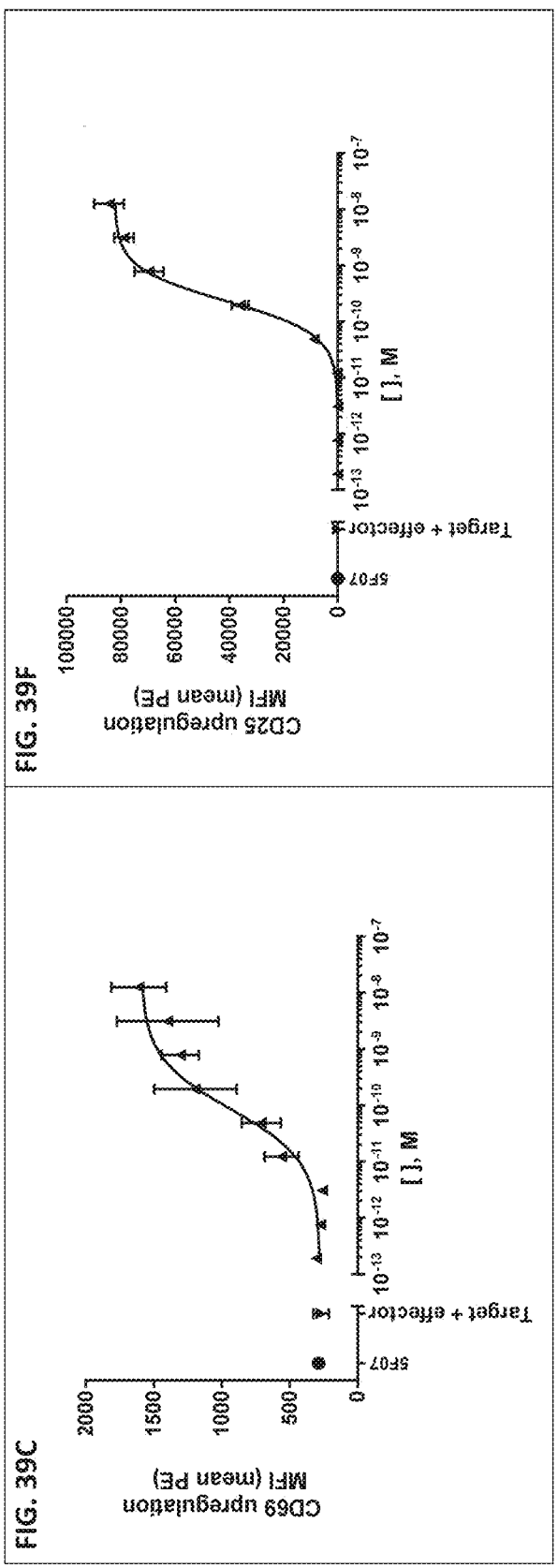

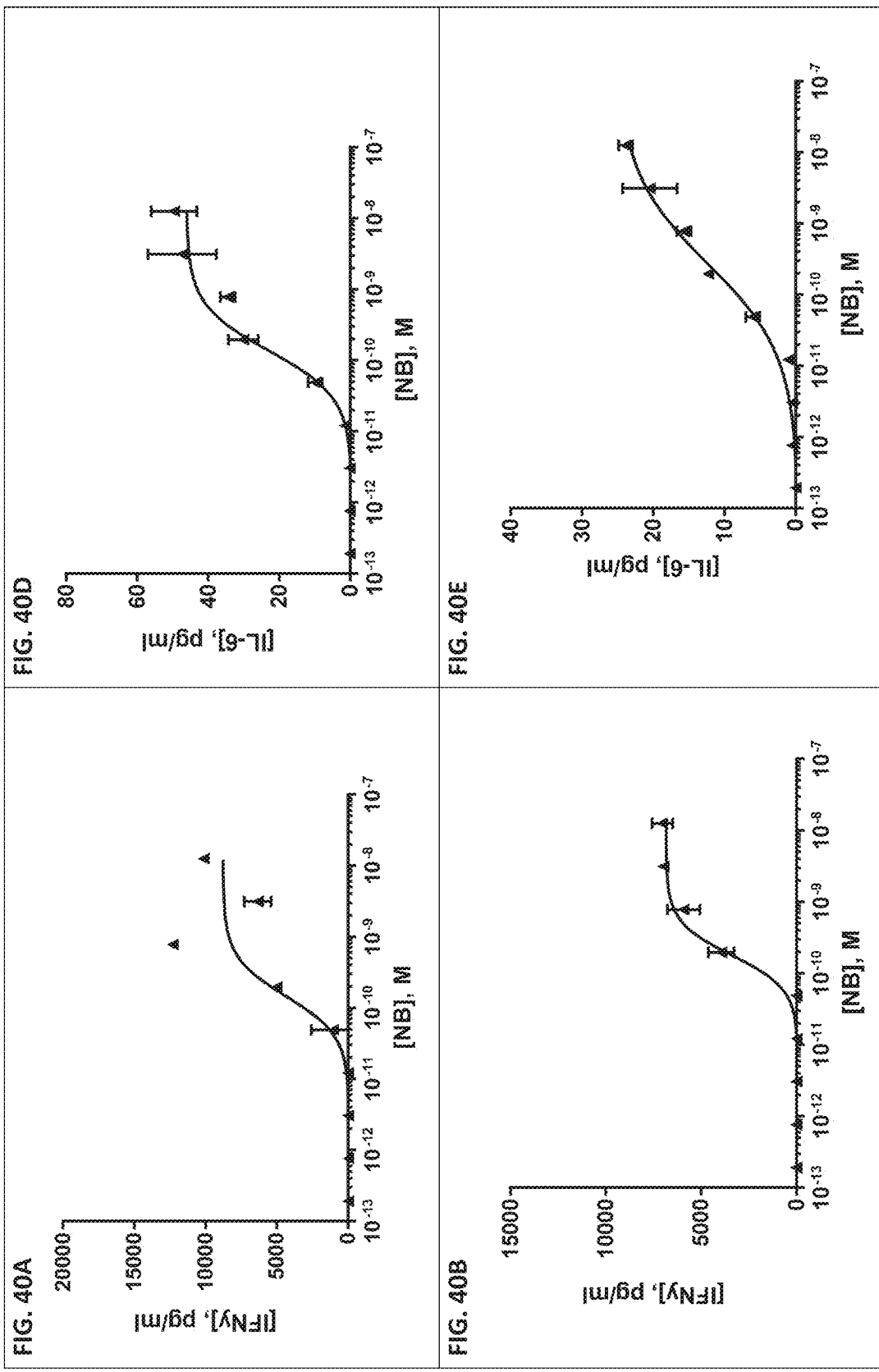

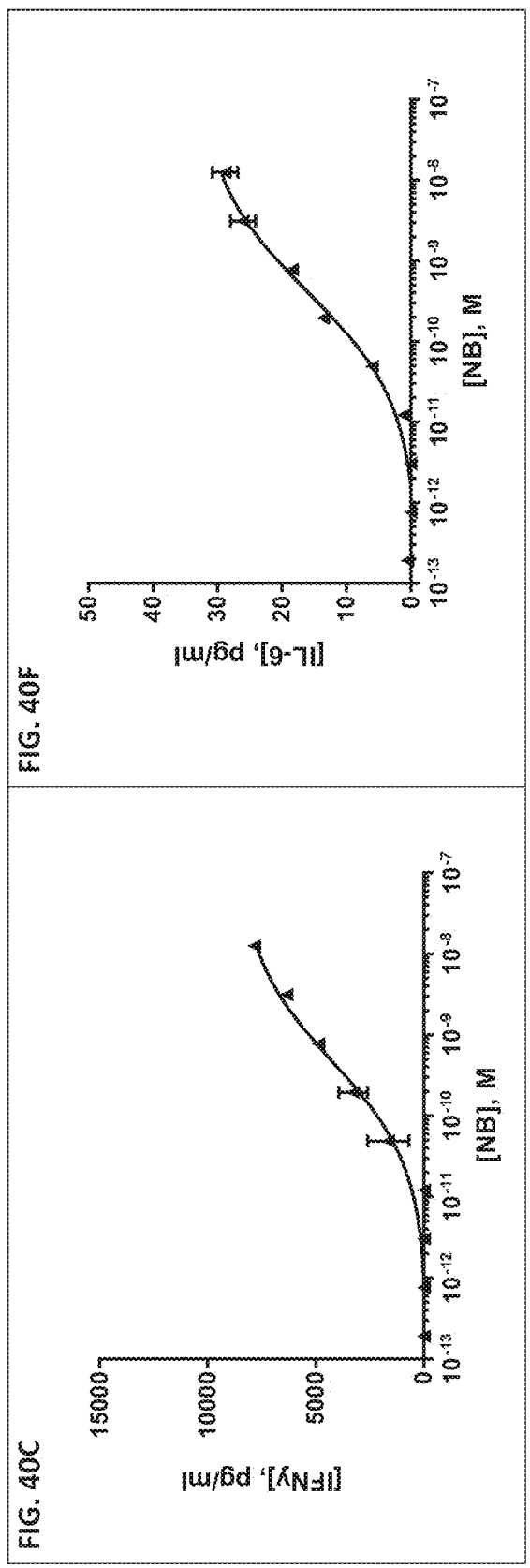

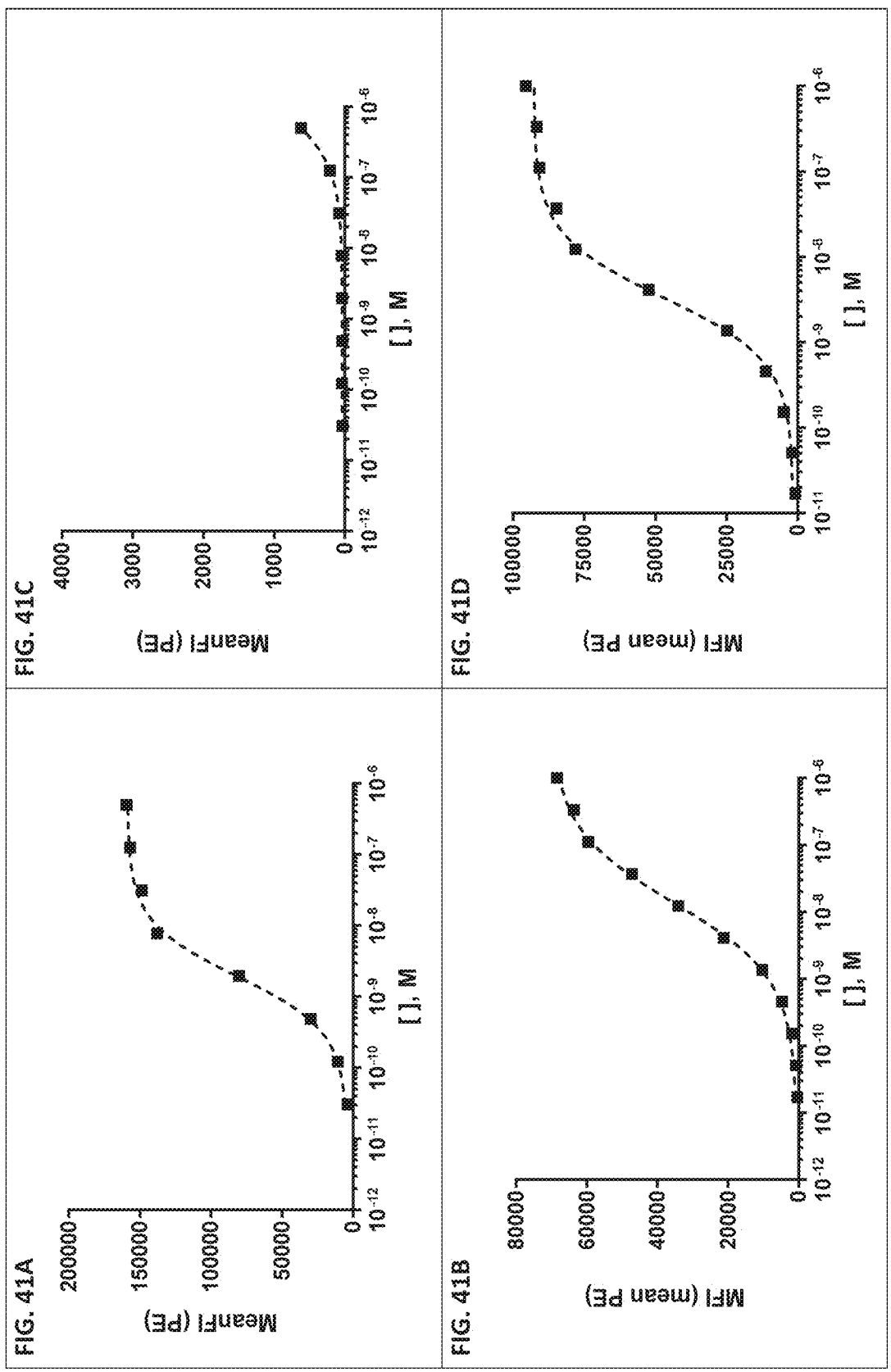

T CELL RECRUITING POLYPEPTIDES BASED ON TCR ALPHA/BETA REACTIVITY

RELATED APPLICATIONS

This application is a national stage filing under 35 U.S.C. § 371 of International Application No. PCT/EP2016/060859, filed May 13, 2016, and claims the benefit under 35 U.S.C. § 119(e) of U.S. provisional application Ser. No. 62/319,486, filed Apr. 7, 2016, and of U.S. provisional application Ser. No. 62/160,757, filed May 13, 2015, the entire contents of each of which is incorporated by reference herein in its entirety.

FIELD OF THE INVENTION

The present invention provides multispecific T cell recruiting polypeptides binding the constant domain of TCR on a T cell and at least one antigen on a target cell. The present invention also relates to the monovalent T cell recruiting polypeptides for use in these multispecific polypeptides. The invention also provides methods for treatment and kits providing the same.

BACKGROUND

Cancer takes an enormous human toll around the world. It is nowadays the world's leading cause of death, followed by heart disease and stroke. Cancers figure among the leading causes of morbidity and mortality worldwide, with approximately 14 million new cases and 8.2 million cancer related deaths in 2012. The number of new cases is expected to rise by about 70% over the next 2 decades (source: WHO Cancer). The total economic impact of premature death and disability from cancer worldwide was about $900 billion in 2008, representing 1.5% of the world's gross domestic product.

Available treatment regimens for solid tumours typically include a combination of surgical resection chemotherapy and radiotherapy. In 40 years of clinical experience little progress has been achieved, especially in advanced stages of cancer.

New therapies combatting cancer are eagerly awaited.

Antibody therapy is now an important part of the physician's armamentarium to battle diseases and especially cancer. Monoclonal antibodies have been established as a key therapeutic approach for a range of diseases already for several years. All of the contemporaneously approved antibody therapies rely on monospecific monoclonal antibodies (mAbs). Until today, most of the targets of the mAbs require either an agonistic or an antagonistic approach. Whereas targeting of cell-surface antigens themselves can mediate antitumour activity through the induction of apoptosis, most mAb-based activity against hematologic malignancies is reliant on either Fc-mediated effector functions such as complement dependent cytotoxicity (CDC) and antibody-dependent cell-mediated cytotoxicity (ADCC).

Immunotherapy has emerged as a rapidly growing area of cancer research. Immunotherapy is directing the body's immune surveillance system, and in particular T cells, to cancer cells.

Cytotoxic T cells (CTL) are T lymphocytes that kill cancer cells, cells that are infected (particularly with viruses), or cells that are damaged in other ways. T lymphocytes (or T cells) express the T cell receptor or TCR molecule and the CD3 receptor on the cell surface. The αβ TCR-CD3 complex (or "TCR complex") is composed of six different type I single-spanning transmembrane proteins: the TCRα and TCRβ chains that form the TCR heterodimer responsible for ligand recognition, and the non-covalently associated CD3γ, CD3δ, CD3ε and ζ chains, which bear cytoplasmic sequence motifs that are phosphorylated upon receptor activation and recruit a large number of signalling components (Call et al. 2004, Molecular Immunology 40: 1295-1305).

Both α and β chains of the T cell receptor consist of a constant domain and a variable domain. Physiologically, the αβ chains of the T cell receptor recognize the peptide loaded MHC complex and couple upon engagement to the CD3 chains. These CD3 chains subsequently transduce the engagement signal to the intracellular environment.

Considering the potential of naturally occurring cytotoxic T lymphocytes (CTLs) to mediate cell lysis, various strategies have been explored to recruit immune cells to mediate tumour cell killing. Since T lymphocytes lack the expression of Fc receptors, they are not recruited to a tumour site through the Fc tail of an anti-tumour monoclonal. As an alternative, the patient's T cells were modified with a second TCR of known specificity for a defined tumour antigen. This adoptive cell transfer is by nature highly personalized and labour intensive. However, the main problem of T cell therapies remains the large number of immune escape mechanisms known to occur in cancer patients (Nagorsen et al. 2012, Pharmacology & Therapeutics 136: 334-342).

Rather than eliciting specific T cell responses, which rely on expression by cancer cells of MHC molecules and the presence, generation, transport and display of specific peptide antigens, more recent developments have attempted to combine the advantages of immunotherapy with antibody therapy by engaging all T cells of a patient in a polyclonal fashion via recombinant antibody based technologies: "bispecifics".

Bispecific antibodies have been engineered that have a tumour recognition part on the one arm (target-binding arm) whereas the other arm of the molecule has specificity for a T cell antigen (effector-binding arm), mostly CD3. Through the simultaneous binding of the two arms to their respective antigens, T lymphocytes are directed towards and activated at the tumour cell where they can exert their cytolytic function.

The concept of using bispecific antibodies to activate T cells against tumour cells was described more than 20 years ago, but manufacturing problems and clinical failures sent the field into stagnation. Smaller format bispecifics were developed, which more easily penetrate tissues and tumours than conventional antibodies. In addition, the smaller format is better at creating the cytolytic synapses, which kill the target cell. It was thought that the smaller format bispecifics would be easier to manufacture and less immunogenic than conventional antibodies. However, the smaller bispecific BiTE molecules, consisting of two single chain variable fragments (scFvs) joined by a 5 amino acid peptide linker, presented a lack of stability (scFvs tend to aggregate), low expression titres and poor solubility. Moreover, the first clinical trials of Blinatumomab (a BiTE molecule), which recognizes CD3 chains, were prematurely stopped due to neurologic adverse events, cytokine release syndrome and infections on the one hand and the absence of objective clinical responses or robust signs of biological activity on the other hand. Efficacy aside, BiTEs must be continuously infused—probably due to the lack of an Fc domain—which does not contribute to patient compliance. The same problem holds true for DARTs (dual affinity retargeting molecules developed by MacroGenics), in which the heavy chain variable domain from one antibody (Ab) is linked with the light chain variable domain of another Ab. MacroGenics now attempts to solve this problem by fusing an Fc domain onto its next generation DARTs, which makes the molecule not only bigger, but also results in manufacturing problems and importation of other Fc functions. The larger format with Fc is expected to have a better PK, but re-introduces the risk of off-target activity. (Garber 2014, Nature reviews 13: 799-801)

Hence, there remains a need for alternative bispecific formats.

SUMMARY OF THE INVENTION

The invention solves this problem by providing multispecific polypeptides comprising a first and at least one further immunoglobulin single variable domain (ISV), wherein said first ISV has a high affinity for/binds to a constant domain of the T cell receptor (TCR); said at least one second ISV has a high affinity for/binds to an antigen present on a target cell. In a particular aspect, the binding of the first ISV will activate the inherent cytolytic potential of the T cell against a target cell independently of MHC.

Thus, in a first aspect the present invention provides a polypeptide comprising a first and a second immunoglobulin single variable domain (ISV), wherein
  said first ISV has high affinity for/binds to the constant domain of the T cell receptor (TCR) present on a T cell;
  said second ISV has high affinity for/binds to a first antigen on a target cell;
  wherein said first antigen is different from said TCR; and
  wherein said target cell is different from said T cell.

In a further aspect, the present invention provides a polypeptide as described herein, wherein said polypeptide directs the T cell to the target cell.

In a further aspect, the present invention provides a polypeptide as described herein, wherein said polypeptide induces T cell activation.

In a further aspect, the present invention provides a polypeptide as described herein, wherein said T cell activation is independent from MHC recognition.

In a further aspect, the present invention provides a polypeptide as described herein, wherein said T cell activation depends on presenting said polypeptide bound to said first antigen on a target cell to a T cell.

In a further aspect, the present invention provides a polypeptide as described herein, wherein said T cell activation causes one or more cellular response of said T cell, wherein said cellular response is selected from the group consisting of proliferation, differentiation, cytokine secretion, cytotoxic effector molecule release, cytotoxic activity, expression of activation markers and redirected target cell lysis.

In a further aspect, the present invention provides a polypeptide as described herein, wherein said T cell activation causes inhibition of an activity of said target cell by more than about 10%, such as 20%, 30%, or 40% or even more than 50%, such as more than 60%, such as 70%, 80%, or even more than 90%, such as 100%.

In a further aspect, the present invention provides a polypeptide as described herein, wherein said first ISV binds to the constant domain of a T cell receptor α (TCR-α) (SEQ ID NO: 348) and/or the constant domain of the T cell receptor β (TCR-β) (SEQ ID NO: 349), or polymorphic variants or isoforms thereof.

Alternatively, the present invention provides a polypeptide as described herein, wherein said first ISV binds to the constant domain of a T cell receptor α (TCR-α) (SEQ ID NO: 484) and/or the constant domain of the T cell receptor β (TCR-β) (SEQ ID NO: 485), or polymorphic variants or isoforms thereof.

In a further aspect, the present invention provides a polypeptide as described herein, wherein said polypeptide and/or first ISV has an on rate constant (Kon) for binding to said TCR selected from the group consisting of at least about $10^2$ $M^{-1}s^{-1}$, at least about $10^3$ $M^{-1}s^{-1}$, at least about $10^4$ $M^{-1}s^{-1}$, at least about $10^5$ $M^{-1}s^{-1}$, at least about $10^6$ $M^{-1}s^{-1}$, $10^7$ $M^{-1}s^{-1}$, at least about $10^8$ $M^{-1}s^{-1}$, at least about $10^9$ $M^{-1}s^{-1}$, and at least about $10^{10}$ $M^{-1}s^{-1}$, preferably as measured by surface plasmon resonance or BLI.

In a further aspect, the present invention provides a polypeptide as described herein, wherein said polypeptide and/or first ISV has an off rate constant (Koff) for binding to said TCR selected from the group consisting of at most about $10^{-3}s^{-1}$, at most about $10^{-4}s^{-1}$, at most about $10^{-5}s^{-1}$, at most about $10^{-6}s^{-1}$, at most about $10^{-7}s^{-1}$, at most about $10^{-8}s^{-1}$, at most about $10^{-9}s^{-1}$, and at most about $10^{-10}s^{-1}$, preferably as measured by surface plasmon resonance or BLI.

In a further aspect, the present invention provides a polypeptide as described herein, wherein said first ISV binds to said TCR with an EC50 value of between 100 nM and 1 pM, such as at an average EC50 value of 100 nM or less, even more preferably at an average EC50 value of 90 nM or less, such as less than 80, 70, 60, 50, 40, 30, 20, 10, 5 nM or even less, such as less than 4, 3, 2, or 1 nM or even less, such as less than 500, 400, 300, 200, 100, 90, 80, 70, 60, 50, 40, 30, 20, 10, 5 pM, or even less, such as less than 4 pM, preferably as measured by flow cytometry.

In a further aspect, the present invention provides a polypeptide as described herein, wherein said first ISV binds to said TCR with an average KD value of between 100 nM and 10 pM, such as at an average KD value of 90 nM or less, even more preferably at an average KD value of 80 nM or less, such as less than 70, 60, 50, 40, 30, 20, 10, 5 nM or even less, such as less than 4, 3, 2, or 1 nM, such as less than 500, 400, 300, 200, 100, 90, 80, 70, 60, 50, 40, 30, 20 pM, or even less, such as less than 10 pM. Preferably, the KD is determined by Kinexa, BLI or SPR, for instance as determined by Proteon.

In a further aspect, the present invention provides a polypeptide as described herein, wherein said first ISV essentially consists of 4 framework regions (FR1 to FR4, respectively) and 3 complementarity determining regions (CDR1 to CDR3, respectively), in which:
(i) CDR1 is chosen from the group consisting of:
  (a) SEQ ID NOs: 119-133; or (b) amino acid sequences that have 4, 3, 2, or 1 amino acid(s) difference with the amino acid sequence of SEQ ID NO: 123 or with any of SEQ ID NOs: 199-133, provided that the polypeptide comprising the CDR1 with 4, 3, 2, or 1 amino acid(s) difference binds TCR with about the same or a higher affinity compared to the binding by the polypeptide comprising the CDR1 without the 4, 3, 2, or 1 amino acid(s) difference, said affinity as measured by surface plasmon resonance; and/or
(ii) CDR2 is chosen from the group consisting of:
  (c) SEQ ID NOs: 134-163; or (d) amino acid sequences that have 4, 3, 2, or 1 amino acid(s) difference with the amino acid sequence of SEQ ID NO: 153 or with any of SEQ ID NOs: 134-163, provided that the polypeptide comprising the CDR2 with 4, 3, 2, or 1 amino acid(s) difference binds TCR with about the same or a higher affinity compared to the binding by the polypeptide comprising the CDR2 without the 4, 3, 2, or 1 amino acid(s) difference, said affinity as measured by surface plasmon resonance; and/or (iii) CDR3 is chosen from the group consisting of:

(e) SEQ ID NOs: 164-174; or (f) amino acid sequences that have 4, 3, 2, or 1 amino acid(s) difference with the amino acid sequence of SEQ ID NO: 170 or with any of SEQ ID NOs: 164-174, provided that the polypeptide comprising the CDR3 with 4, 3, 2, or 1 amino acid(s) difference binds TCR with about the same or a higher affinity compared to the binding by the polypeptide comprising the CDR3 without the 4, 3, 2, or 1 amino acid(s) difference, said affinity as measured by surface plasmon resonance.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which CDR1 is chosen from the group consisting of (a) SEQ ID NO: 123; and (b) amino acid sequences that have 1, 2 or 3 amino acid difference(s) with SEQ ID NO: 123, wherein
at position 2 the D has been changed into A, S, E or G;
at position 4 the H has been changed into Y;
at position 5 the K has been changed into L;
at position 6 the I has been changed into L;
at position 8 the F has been changed into I or V; and/or
at position 10 the G has been changed into S.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which CDR2 is chosen from the group consisting of (a) SEQ ID NO: 153; and (b) amino acid sequences that have 1, 2, 3, 4 or 5 amino acid difference(s) with SEQ ID NO: 153, wherein
at position 1 the H has been changed into T or R;
at position 3 the S has been changed into T or A;
at position 5 the G has been changed into S or A;
at position 7 the Q has been changed into D, E, T, A or V;
at position 8 the T has been changed into A or V; and/or
at position 9 the D has been changed into A, Q, N, V or S.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which CDR3 is chosen from the group consisting of (a) SEQ ID NO: 170; and (b) amino acid sequences that have 1, 2 or 3 amino acid difference(s) with SEQ ID NO: 170, wherein
at position 1 the F has been changed into Y, L or G;
at position 4 the I has been changed into L;
at position 5 the Y has been changed into W; and/or
at position 8 the D has been changed into N or S.

Preferably, the polypeptide comprising the one or more CDRs with 5, 4, 3, 2, or 1 amino acid(s) difference binds TCR with about the same or a higher affinity compared to the binding by the polypeptide comprising the CDRs without the 5, 4, 3, 2, or 1 amino acid(s) difference, said affinity as measured by surface plasmon resonance.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which (i) CDR1 is chosen from the group consisting of (a) SEQ ID NO: 123; and (b) amino acid sequences that have 1, 2, or 3 amino acid difference(s) with SEQ ID NO: 123, wherein
at position 2 the D has been changed into A, 5, E or G;
at position 4 the H has been changed into Y;
at position 5 the K has been changed into L;
at position 6 the I has been changed into L;
at position 8 the F has been changed into I or V; and/or
at position 10 the G has been changed into S, provided that the polypeptide comprising the CDR1 with 3, 2, or 1 amino acid(s) difference binds TCR with about the same or a higher affinity compared to the binding by the polypeptide comprising the CDR1 without the 3, 2, or 1 amino acid(s) difference, said affinity as measured by surface plasmon resonance;

and in which (ii) CDR2 is chosen from the group consisting of (a) SEQ ID NO: 153; and (b) amino acid sequences that have 1, 2, 3, 4, or 5 amino acid difference(s) with SEQ ID NO: 153, wherein
at position 1 the H has been changed into T or R;
at position 3 the S has been changed into T or A;
at position 5 the G has been changed into S or A;
at position 7 the Q has been changed into D, E, T, A or V;
at position 8 the T has been changed into A or V; and/or
at position 9 the D has been changed into A, Q, N, V or S, provided that the polypeptide comprising the CDR2 with 5, 4, 3, 2, or 1 amino acid(s) difference binds TCR with about the same or a higher affinity compared to the binding by the polypeptide comprising the CDR2 without the 5, 4, 3, 2, or 1 amino acid(s) difference, said affinity as measured by surface plasmon resonance;

and in which (iii) CDR3 is chosen from the group consisting of (a) SEQ ID NO: 170; and (b) amino acid sequences that have 1, 2, or 3 amino acid difference(s) with SEQ ID NO: 170, wherein
at position 1 the F has been changed into Y, L or G;
at position 4 the I has been changed into L;
at position 5 the Y has been changed into W; and/or
at position 8 the D has been changed into N or S, provided that the polypeptide comprising the CDR3 with 3, 2, or 1 amino acid(s) difference binds TCR with about the same or a higher affinity compared to the binding by the polypeptide comprising the CDR3 without the 3, 2, or 1 amino acid(s) difference, said affinity as measured by surface plasmon resonance.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which CDR1 is chosen from the group consisting of (a) SEQ ID NO: 124; and (b) amino acid sequences that have 1, or 2 amino acid difference(s) with SEQ ID NO: 124, wherein
at position 2 the E has been changed into Q; and/or
at position 6 the I has been changed into V.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which CDR2 is chosen from the group consisting of
  (a) SEQ ID NO: 145; and
  (b) amino acid sequence that has 1 amino acid difference with SEQ ID NO: 145, wherein
    at position 9 the N has been changed into D.

In a further aspect the present invention provides a polypeptide as described herein, in which said first ISV essentially consists of 4 framework regions (FR1 to FR4, respectively) and 3 complementarity determining regions (CDR1 to CDR3, respectively), in which CDR3 is chosen from the group consisting of
  (a) SEQ ID NO: 167; and
  (b) amino acid sequence that has 1 amino acid difference with SEQ ID NO: 167, wherein
    at position 4 the L has been changed into I.

Preferably, the polypeptide comprising the one or more CDRs with 2 or 1 amino acid(s) difference binds TCR with about the same or a higher affinity compared to the binding by the polypeptide comprising the CDRs without the 2, or 1 amino acid(s) difference, said affinity as measured by surface plasmon resonance.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which
(i) CDR1 is chosen from the group consisting of
  (a) SEQ ID NO: 124; and
  (b) amino acid sequences that have 1, or 2 amino acid difference(s) with SEQ ID NO: 124, wherein
    at position 2 the E has been changed into Q; and/or
    at position 6 the I has been changed into V,
  provided that the polypeptide comprising the CDR1 with 2, or 1 amino acid(s) difference binds TCR with about the same or a higher affinity compared to the binding by the polypeptide comprising the CDR1 without the 2, or 1 amino acid(s) difference, said affinity as measured by surface plasmon resonance;
and in which
(ii) CDR2 is chosen from the group consisting of
  (a) SEQ ID NO: 145; and
  (b) amino acid sequence that has 1 amino acid difference with SEQ ID NO: 145, wherein
    at position 9 the N has been changed into D,
  provided that the polypeptide comprising the CDR2 with 1 amino acid(s) difference binds TCR with about the same or a higher affinity compared to the binding by the polypeptide comprising the CDR2 without the 1 amino acid(s) difference, said affinity as measured by surface plasmon resonance;
and in which
(iii) CDR3 is chosen from the group consisting of
  (a) SEQ ID NO: 167; and
  (b) amino acid sequence that has 1 amino acid difference with SEQ ID NO: 167, wherein
    at position 4 the L has been changed into I,
  provided that the polypeptide comprising the CDR3 with 1 amino acid(s) difference binds TCR with about the same or a higher affinity compared to the binding by the polypeptide comprising the CDR3 without the 1 amino acid(s) difference, said affinity as measured by surface plasmon resonance.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which CDR1 is SEQ ID NO: 130.

In a further, aspect the present invention provides a polypeptide as described herein, in which said first ISV essentially consists of 4 framework regions (FR1 to FR4, respectively) and 3 complementarity determining regions (CDR1 to CDR3, respectively), in which CDR2 is chosen from the group consisting of
  (a) SEQ ID NO: 157; and
  (b) amino acid sequence that has 1 amino acid difference with SEQ ID NO: 157, wherein
    at position 8 the T has been changed into I.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which CDR3 is SEQ ID NO: 172.

Preferably, the polypeptide comprising the CDR with 1 amino acid difference binds TCR with about the same or a higher affinity compared to the binding by the polypeptide comprising the CDRs without the 1 amino acid difference, said affinity as measured by surface plasmon resonance.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which
(i) CDR1 is SEQ ID NO: 130;
and in which
(ii) CDR2 is chosen from the group consisting of
  (a) SEQ ID NO: 157; and
  (b) amino acid sequence that has 1 amino acid difference with SEQ ID NO: 157, wherein
    at position 8 the T has been changed into I,
  provided that the polypeptide comprising the CDR2 with 1 amino acid difference binds TCR with about the same or a higher affinity compared to the binding by the polypeptide comprising the CDR2 without the 1 amino acid difference, said affinity as measured by surface plasmon resonance;
and in which
(iii) CDR3 is SEQ ID NO: 172.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 119-123, 125-127, 129, 132 and 133; and
    (b) amino acid sequences that have 4, 3, 2, or 1 amino acid(s) difference with the amino acid sequence of SEQ ID NO: 123; and/or
  (ii) CDR2 is chosen from the group consisting of:
    (c) SEQ ID NOs: 134-141, 143-144, 146-156, 159-163; and
    (d) amino acid sequences that have 4, 3, 2, or 1 amino acid(s) difference with the amino acid sequence of SEQ ID NO: 153; and/or
  (iii) CDR3 is chosen from the group consisting of:
    (e) SEQ ID NOs: 164-166, 169-171, 173-174; and
    (f) amino acid sequences that have 4, 3, 2, or 1 amino acid(s) difference with the amino acid sequence of SEQ ID NO: 170.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which:
(i) CDR1 is chosen from the group consisting of:
(a) SEQ ID NOs: 119-123, 125-127, 129, 132 and 133; and
(b) amino acid sequences that have 4, 3, 2, or 1 amino acid(s) difference with the amino acid sequence of SEQ ID NO: 123, provided that the polypeptide comprising the CDR1 with 4, 3, 2, or 1 amino acid(s) difference binds TCR with about the same or a higher affinity compared to the binding by the polypeptide comprising the CDR1 without the 4, 3, 2, or 1 amino acid(s) difference, said affinity as measured by surface plasmon resonance; and/or
(ii) CDR2 is chosen from the group consisting of:
(c) SEQ ID NOs: 134-141, 143-144, 146-156, 159-163; and
(d) amino acid sequences that have 4, 3, 2, or 1 amino acid(s) difference with the amino acid sequence of SEQ ID NO: 153, provided that the polypeptide comprising the CDR2 with 4, 3, 2, or 1 amino acid(s) difference binds TCR with about the same or a higher affinity compared to the binding by the polypeptide comprising the CDR2 without the 4, 3, 2, or 1 amino acid(s) difference, said affinity as measured by surface plasmon resonance; and/or
(iii) CDR3 is chosen from the group consisting of:
(e) SEQ ID NOs: 164-166, 169-171, 173-174; and
(f) amino acid sequences that have 4, 3, 2, or 1 amino acid(s) difference with the amino acid sequence of SEQ ID NO: 170, provided that the polypeptide comprising the CDR3 with 4, 3, 2, or 1 amino acid(s) difference binds TCR with about the same or a higher affinity compared to the binding by the polypeptide comprising the CDR3 without the 4, 3, 2, or 1 amino acid(s) difference, said affinity as measured by surface plasmon resonance.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which: CDR1 is represented by SEQ ID NO: 123, CDR2 is represented by SEQ ID NO: 153, and CDR3 is represented by SEQ ID NO: 170.

In a further aspect, the present invention provides a polypeptide as described herein, in which said first ISV is chosen from the group consisting of SEQ ID NOs: 1-104.

In a further aspect, the present invention provides a polypeptide as described herein, in which said first ISV cross-blocks the binding to the constant domain of the T cell receptor (TCR) by at least one of the polypeptides with SEQ ID NOs: 1-104.

In a further aspect, the present invention provides a polypeptide as described herein, in which said first ISV is cross-blocked from binding to the constant domain of the T cell receptor (TCR) by at least one of the polypeptides with SEQ ID NOs: 1-104.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which:
(i) CDR1 is chosen from the group consisting of:
(a) SEQ ID NOs: 124, 128 and 131; and
(b) amino acid sequences that have 4, 3, 2, or 1 amino acid(s) difference with the amino acid sequence of SEQ ID NO: 124; and/or
(ii) CDR2 is chosen from the group consisting of:
(c) SEQ ID NOs: 142 and 145; and
(d) amino acid sequences that have 4, 3, 2, or 1 amino acid(s) difference with the amino acid sequence of SEQ ID NO: 145; and/or
(iii) CDR3 is chosen from the group consisting of:
(e) SEQ ID NOs: 167 and 168; and
(f) amino acid sequences that have 4, 3, 2, or 1 amino acid(s) difference with the amino acid sequence of SEQ ID NO: 167.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which:
(i) CDR1 is chosen from the group consisting of:
(a) SEQ ID NOs: 124, 128 and 131; and
(b) amino acid sequences that have 4, 3, 2, or 1 amino acid(s) difference with the amino acid sequence of SEQ ID NO: 124, provided that the polypeptide comprising the CDR1 with 4, 3, 2, or 1 amino acid(s) difference binds TCR with about the same or a higher affinity compared to the binding by the polypeptide comprising the CDR1 without the 4, 3, 2, or 1 amino acid(s) difference, said affinity as measured by surface plasmon resonance; and/or
(ii) CDR2 is chosen from the group consisting of:
(c) SEQ ID NOs: 142 and 145; and
(d) amino acid sequences that have 4, 3, 2, or 1 amino acid(s) difference with the amino acid sequence of SEQ ID NO: 145, provided that the polypeptide comprising the CDR2 with 4, 3, 2, or 1 amino acid(s) difference binds TCR with about the same or a higher affinity compared to the binding by the polypeptide comprising the CDR2 without the 4, 3, 2, or 1 amino acid(s) difference, said affinity as measured by surface plasmon resonance; and/or
(iii) CDR3 is chosen from the group consisting of:
(e) SEQ ID NOs: 167 and 168; and
(f) amino acid sequences that have 4, 3, 2, or 1 amino acid(s) difference with the amino acid sequence of SEQ ID NO: 167, provided that the polypeptide comprising the CDR3 with 4, 3, 2, or 1 amino acid(s) difference binds TCR with about the same or a higher affinity compared to the binding by the polypeptide comprising the CDR3 without the 4, 3, 2, or 1 amino acid(s) difference, said affinity as measured by surface plasmon resonance.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which: CDR1 is represented by SEQ ID NO: 124, CDR2 is represented by SEQ ID NO: 145, and CDR3 is represented by SEQ ID NO: 167.

In a further aspect, the present invention provides a polypeptide as described herein, in which said first ISV is chosen from the group consisting of SEQ ID NOs: 105-115.

In a further aspect, the present invention provides a polypeptide as described herein, in which said first ISV cross-blocks the binding to the constant domain of the T cell receptor (TCR) by at least one of the polypeptides with SEQ ID NOs: 105-115.

In a further aspect, the present invention provides a polypeptide as described herein, in which the first ISV is cross-blocked from binding to the constant domain of the T cell receptor (TCR) by at least one of the polypeptides with SEQ ID NOs: 105-115.

In a further aspect the present invention provides a polypeptide as described herein, in which said first ISV essentially consists of 4 framework regions (FR1 to FR4, respectively) and 3 complementarity determining regions (CDR1 to CDR3, respectively), in which:
(i) CDR1 is chosen from the group consisting of
   (a) SEQ ID NO: 130; and
   (b) amino acid sequences that have 4, 3, 2, or 1 amino acid(s) difference with the amino acid sequence of SEQ ID NO: 130; and/or
(ii) CDR2 is chosen from the group consisting of:
   (c) SEQ ID NOs: 157-158; and
   (d) amino acid sequences that have 4, 3, 2, or 1 amino acid(s) difference with the amino acid sequence of SEQ ID NO: 157; and/or
(iii) CDR3 is chosen from the group consisting of:
   (e) SEQ ID NO: 172; and
   (f) amino acid sequences that have 4, 3, 2, or 1 amino acid(s) difference with the amino acid sequence of SEQ ID NO: 172.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which:
(i) CDR1 is chosen from the group consisting of
   (a) SEQ ID NO: 130; and
   (b) amino acid sequences that have 4, 3, 2, or 1 amino acid(s) difference with the amino acid sequence of SEQ ID NO: 130, provided that the polypeptide comprising the CDR1 with 4, 3, 2, or 1 amino acid(s) difference binds TCR with about the same or a higher affinity compared to the binding by the polypeptide comprising the CDR1 without the 4, 3, 2, or 1 amino acid(s) difference, said affinity as measured by surface plasmon resonance; and/or
(ii) CDR2 is chosen from the group consisting of:
   (c) SEQ ID NOs: 157-158; and
   (d) amino acid sequences that have 4, 3, 2, or 1 amino acid(s) difference with the amino acid sequence of SEQ ID NO: 157, provided that the polypeptide comprising the CDR2 with 4, 3, 2, or 1 amino acid(s) difference binds TCR with about the same or a higher affinity compared to the binding by the polypeptide comprising the CDR2 without the 4, 3, 2, or 1 amino acid(s) difference, said affinity as measured by surface plasmon resonance; and/or
(iii) CDR3 is chosen from the group consisting of:
   (e) SEQ ID NO: 172; and
   (f) amino acid sequences that have 4, 3, 2, or 1 amino acid(s) difference with the amino acid sequence of SEQ ID NO: 172, provided that the polypeptide comprising the CDR3 with 4, 3, 2, or 1 amino acid(s) difference binds TCR with about the same or a higher affinity compared to the binding by the polypeptide comprising the CDR3 without the 4, 3, 2, or 1 amino acid(s) difference, said affinity as measured by surface plasmon resonance.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which: CDR1 is represented by SEQ ID NO: 130, CDR2 is represented by SEQ ID NO: 157, and CDR3 is represented by SEQ ID NO: 172.

In a further aspect, the present invention provides a polypeptide as described herein, in which said first ISV is chosen from the group consisting of SEQ ID NOs: 116-118.

In a further aspect, the present invention provides a polypeptide as described herein, in which said first ISV cross-blocks the binding to the constant domain of the T cell receptor (TCR) by at least one of the polypeptides with SEQ ID NOs: 116-118.

In a further aspect, the present invention provides a polypeptide as described herein in which said first ISV is cross-blocked from binding to the constant domain of the T cell receptor (TCR) by at least one of the polypeptides with SEQ ID NOs: 116-118.

In a further aspect, the present invention provides a polypeptide as described herein, further comprising a third ISV, which has high affinity for/binds to a second antigen on a target cell, wherein said second antigen is different from said first antigen.

In a further aspect, the present invention provides a polypeptide as described herein, wherein said first antigen on a target cell is a tumour antigen, preferably a tumour associated antigen (TAA).

In a further aspect, the present invention provides a polypeptide as described herein, wherein said second antigen on a target cell is a tumour antigen, preferably a tumour associated antigen (TAA).

In a further aspect, the present invention provides a polypeptide as described herein, wherein said first antigen and said second antigen are present on the same target cell.

In a further aspect, the present invention provides a polypeptide as described herein, wherein said first antigen and said second antigen are present on different target cells.

In a further aspect, the present invention provides a polypeptide as described herein, wherein said TAA's are independently chosen from the group consisting of Melanoma-associated Chondroitin Sulfate Proteoglycan (MCSP), Epidermal Growth Factor Receptor (EGFR), Fibroblast Activation Protein (FAP), MART-1, carcinoembryonic antigen (CEA), gp100, MAGE-1, HER-2, Lewis$^Y$ antigens, CD123, CD44, CLL-1, CD96, CD47, CD32, CXCR4, Tim-3, CD25, TAG-72, Ep-CAM, PSMA, PSA, GD2, GD3, CD4, CD5, CD19, CD20, CD22, CD33, CD36, CD45, CD52, CD147, growth factor receptors including ErbB3 and ErbB4, Cytokine receptors including Interleukin-2 receptor gamma chain (CD132 antigen), Interleukin-10 receptor alpha chain (IL-10R-A), Interleukin-10 receptor beta chain (IL-10R-B), Interleukin-12 receptor beta-1 chain (IL-12R-beta1), Interleukin-12 receptor beta-2 chain (IL-12 receptor beta-2), Interleukin-13 receptor alpha-1 chain (IL-13R-alpha-1) (CD213a1 antigen), Interleukin-13 receptor alpha-2 chain (Interleukin-13 binding protein), Interleukin-17 receptor (IL-17 receptor), Interleukin-17B receptor (IL-17B receptor), Interleukin 21 receptor precursor (IL-21R), Interleukin-1 receptor type I (IL-1R-1) (CD121a); Interleukin-1 receptor type II (IL-1R-beta) (CDw121b), Interleukin-1 receptor antagonist protein (IL-1ra), Interleukin-2 receptor alpha chain (CD25 antigen, Interleukin-2 receptor beta chain (CD122 antigen), Interleukin-3 receptor alpha chain (IL-3R-alpha) (CD123 antigen), CD30, IL23R, IGF-1R, IL5R, IgE, CD248 (endosialin), CD44v6, gpA33, Ron, Trop2, PSCA, claudin 6, claudin 18.2, CLEC12A, CD38, ephA2, c-Met, CD56, MUC16, EGFRvIII, AGS-16, CD27L, Nectin-4, SLITRK6, mesothelin, folate receptor, tissue factor, axl, glypican-3, CA9, Cripto, CD138, CD37, MUC1, CD70, gastrin releasing peptide receptor, PAP, CEACAM5, CEACAM6, CXCR7, N-cadherin, FXYD2 gamma a, CD21, CD133, Na/K-ATPase, mIgM (membrane-bound IgM), mIgA (membrane-bound IgA), Mer, Tyro2, CD120, CD95, CA 195, DR5, DR6, DcR3 and CAIX, including related polymorphic variants and isoforms.

In a further aspect, the present invention provides a polypeptide as described herein, wherein said TAA is CD20 (UniProt 11836), HER2 (Uniprot P04626), EGFR, CEA, polymorphic variants or isoforms thereof.

In a further aspect, the present invention provides a polypeptide as described herein, wherein said first antigen and said second antigen are chosen from the group consisting of:
  EGFR as a first antigen and CEA as a second antigen;
  CD19 as a first antigen and CD20 as a second antigen;
  CD19 as a first antigen and CD22 as a second antigen;
  CD123 as a first antigen and Tim-3 as a second antigen;
  CD123 as a first antigen and CD69 as a second antigen.

In a further aspect, the present invention provides a polypeptide as described herein, further comprising a serum protein binding moiety.

In a further aspect, the present invention provides a polypeptide as described herein, wherein said serum protein binding moiety binds serum albumin.

In a further aspect, the present invention provides a polypeptide as described herein, wherein said serum protein binding moiety is an ISV binding serum albumin.

In a further aspect, the present invention provides a polypeptide as described herein, wherein said ISV binding serum albumin essentially consists of 4 framework regions (FR1 to FR4, respectively) and 3 complementarity determining regions (CDR1 to CDR3 respectively), in which CDR1 is SFGMS (SEQ ID NO: 481), CDR2 is SIS-GSGSDTLYADSVKG (SEQ ID NO: 482) and CDR3 is GGSLSR (SEQ ID NO: 475), CDR determined according to Kabat definition; and/or in which CDR1 is GFTFSSFGMS (SEQ ID NO: 472) or GFTFRSFGMS (SEQ ID NO: 473), CDR2 is SISGSGSDTL (SEQ ID NO: 474) and CDR3 is GGSLSR (SEQ ID NO: 475), CDR determined according to Kontermann 2010.

In a further aspect, the present invention provides a polypeptide as described herein, wherein said ISV binding serum albumin is selected from Alb8, Alb23, Alb129, Alb132, Alb11, Alb11 (S112K)-A, Alb82, Alb82-A, Alb82-AA, Alb82-AAA, Alb82-G, Alb82-GG and Alb82-GGG (SEQ ID NOs: 400 to 412).

In a further aspect, the present invention provides a polypeptide as described herein, wherein said ISVs are directly linked to each other or are linked via a linker.

In a further aspect, the present invention provides a polypeptide as described herein, wherein said first ISV and/or said second ISV and/or possibly said third ISV and/or possibly said ISV binding serum albumin are linked via a linker.

In a further aspect, the present invention provides a polypeptide as described herein, wherein said linker is chosen from the group consisting of linkers of 5GS, 7GS, 9GS, 10GS, 15GS, 18GS, 20GS, 25GS, 30GS and 35GS (SEQ ID NOs: 376 to 385).

In a further aspect, the present invention provides a polypeptide as described herein, wherein said serum protein binding moiety is a non-antibody based polypeptide.

In a further aspect, the present invention provides a polypeptide as described herein, further comprising PEG.

In a further aspect, the present invention provides a polypeptide as described herein, wherein said ISV is a Nanobody, a $V_{HH}$, a humanized $V_{HH}$, or a camelized $V_H$.

In a further aspect, the present invention provides a polypeptide wherein said first ISV is chosen from the group consisting of SEQ ID NOs: 1 to 118.

In a further aspect, the present invention provides a polypeptide as described herein, wherein said first ISV is chosen from the group consisting of SEQ ID NOs: 1 to 118, and wherein said second ISV is chosen from the group consisting of SEQ ID NOs: 350-358.

In a further aspect, the present invention provides a polypeptide chosen from the group consisting of SEQ ID NOs: 292, 295-296, 299-300, 303, 306-343, 387-388, 390, 414, 417-418, 421-422, 425, 428-464, 467-468, 470-471 and 486-487.

In a further aspect, the present invention provides a polypeptide that specifically binds the constant domain of the T cell receptor (TCR) and that comprises or essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 119-133; or
    (b) amino acid sequences that have 4, 3, 2, or 1 amino acid(s) difference with the amino acid sequence of any of SEQ ID NOs: 119-133, provided that the polypeptide comprising the CDR1 with 4, 3, 2, or 1 amino acid(s) difference binds TCR with about the same or a higher affinity compared to the binding by the polypeptide comprising the CDR1 without the 4, 3, 2, or 1 amino acid(s) difference, said affinity as measured by surface plasmon resonance; and/or
  (ii) CDR2 is chosen from the group consisting of:
    (c) SEQ ID NOs: 134-163; or
    (d) amino acid sequences that have 4, 3, 2, or 1 amino acid(s) difference with the amino acid sequence of any of SEQ ID NOs: 134-163, provided that the polypeptide comprising the CDR2 with 4, 3, 2, or 1 amino acid(s) difference binds TCR with about the same or a higher affinity compared to the binding by the polypeptide comprising the CDR2 without the 4, 3, 2, or 1 amino acid(s) difference, said affinity as measured by surface plasmon resonance; and/or
  (iii) CDR3 is chosen from the group consisting of:
    (e) SEQ ID NOs: 164-174; or
    (f) amino acid sequences that have 4, 3, 2, or 1 amino acid(s) difference with the amino acid sequence of any of SEQ ID NOs: 164-174, provided that the polypeptide comprising the CDR3 with 4, 3, 2, or 1 amino acid(s) difference binds TCR with about the same or a higher affinity compared to the binding by the polypeptide comprising the CDR3 without the 4, 3, 2, or 1 amino acid(s) difference, said affinity as measured by surface plasmon resonance.

The present invention also provides a polypeptide as described herein, in which:
  (i) CDR1 is chosen from the group consisting of:
    (a) SEQ ID NOs: 119-123, 125-127, 129, 132 and 133; and
    (b) amino acid sequences that have 4, 3, 2, or 1 amino acid(s) difference with the amino acid sequence of SEQ ID NO: 123, provided that the polypeptide comprising the CDR1 with 4, 3, 2, or 1 amino acid(s) difference binds TCR with about the same or a higher affinity compared to the binding by the polypeptide comprising the CDR1 without the 4, 3, 2, or 1 amino acid(s) difference, said affinity as measured by surface plasmon resonance; and/or
(ii) CDR2 is chosen from the group consisting of:
(c) SEQ ID NOs: 134-141, 143-144, 146-156, 159-163; and
(d) amino acid sequences that have 4, 3, 2, or 1 amino acid(s) difference with the amino acid sequence of SEQ ID NO: 153, provided that the polypeptide comprising the CDR2 with 4, 3, 2, or 1 amino acid(s) difference binds TCR with about the same or a higher affinity compared to the binding by the polypeptide comprising the CDR2 without the 4, 3, 2, or 1 amino acid(s) difference, said affinity as measured by surface plasmon resonance; and/or
(iii) CDR3 is chosen from the group consisting of:
(e) SEQ ID NOs: 164-166, 169-171, 173-174; and
(f) amino acid sequences that have 4, 3, 2, or 1 amino acid(s) difference with the amino acid sequence of SEQ ID NO: 170, provided that the polypeptide comprising the CDR3 with 4, 3, 2, or 1 amino acid(s) difference binds TCR with about the same or a higher affinity compared to the binding by the polypeptide comprising the CDR3 without the 4, 3, 2, or 1 amino acid(s) difference, said affinity as measured by surface plasmon resonance.

In a further aspect, the present invention provides a polypeptide as described herein, in which CDR1 is chosen from the group consisting of
(a) SEQ ID NO: 123; and
(b) amino acid sequences that have 1, 2, 3 or 4 amino acid difference(s) with SEQ ID NO: 123, wherein
at position 2 the D has been changed into A, 5, E or G;
at position 4 the H has been changed into Y;
at position 5 the K has been changed into L;
at position 6 the I has been changed into L;
at position 8 the F has been changed into I or V; and/or
at position 10 the G has been changed into S.

In a further aspect, the present invention provides a polypeptide as described herein, in which CDR2 is chosen from the group consisting of
(a) SEQ ID NO: 153; and
(b) amino acid sequences that have 1, 2, 3, 4 or 5 amino acid difference(s) with SEQ ID NO: 153, wherein
at position 1 the H has been changed into T or R;
at position 3 the S has been changed into T or A;
at position 5 the G has been changed into S or A;
at position 7 the Q has been changed into D, E, T, A or V;
at position 8 the T has been changed into A or V; and/or
at position 9 the D has been changed into A, Q, N, V or S.

In a further aspect, the present invention provides a polypeptide as described herein, in which CDR3 is chosen from the group consisting of
(a) SEQ ID NO: 170; and
(b) amino acid sequences that have 1, 2, 3 or 4 amino acid difference(s) with SEQ ID NO: 170, wherein
at position 1 the F has been changed into Y, L or G;
at position 4 the I has been changed into L;
at position 5 the Y has been changed into W; and/or
at position 8 the D has been changed into N or S.

In a further aspect, the present invention provides a polypeptide as described herein, in which CDR1 is represented by SEQ ID NO: 123, CDR2 is represented by SEQ ID NO: 153, and CDR3 is represented by SEQ ID NO: 170.

In a further aspect, the present invention provides a polypeptide as described herein, in which:
(i) CDR1 is chosen from the group consisting of:
(a) SEQ ID NOs: 124, 128 and 131; and
(b) amino acid sequences that have 4, 3, 2, or 1 amino acid(s) difference with the amino acid sequence of SEQ ID NO: 124, provided that the polypeptide comprising the CDR1 with 4, 3, 2, or 1 amino acid(s) difference binds TCR with about the same or a higher affinity compared to the binding by the polypeptide comprising the CDR1 without the 4, 3, 2, or 1 amino acid(s) difference, said affinity as measured by surface plasmon resonance; and/or
(ii) CDR2 is chosen from the group consisting of:
(c) SEQ ID NOs: 142 and 145; and
(d) amino acid sequences that have 4, 3, 2, or 1 amino acid(s) difference with the amino acid sequence of SEQ ID NO: 145, provided that the polypeptide comprising the CDR2 with 4, 3, 2, or 1 amino acid(s) difference binds TCR with about the same or a higher affinity compared to the binding by the polypeptide comprising the CDR2 without the 4, 3, 2, or 1 amino acid(s) difference, said affinity as measured by surface plasmon resonance; and/or
(iii) CDR3 is chosen from the group consisting of:
(e) SEQ ID NOs: 167 and 168; and
(f) amino acid sequences that have 4, 3, 2, or 1 amino acid(s) difference with the amino acid sequence of SEQ ID NO: 167, provided that the polypeptide comprising the CDR3 with 4, 3, 2, or 1 amino acid(s) difference binds TCR with about the same or a higher affinity compared to the binding by the polypeptide comprising the CDR3 without the 4, 3, 2, or 1 amino acid(s) difference, said affinity as measured by surface plasmon resonance.

In a further aspect, the present invention provides a polypeptide as described herein, in which CDR1 is chosen from the group consisting of
(a) SEQ ID NO: 124; and
(b) amino acid sequences that have 1, or 2 amino acid difference(s) with SEQ ID NO: 124, wherein
at position 2 the E has been changed into Q; and/or
at position 6 the I has been changed into V.

In a further aspect, the present invention provides a polypeptide as described herein, in which CDR2 is chosen from the group consisting of
(a) SEQ ID NO: 145; and
(b) amino acid sequence that has 1 amino acid difference with SEQ ID NO: 145, wherein
at position 9 the N has been changed into D.

In a further aspect, the present invention provides a polypeptide as described herein, in which CDR3 is chosen from the group consisting of
(a) SEQ ID NO: 167; and
(b) amino acid sequence that has 1 amino acid difference with SEQ ID NO: 167, wherein
at position 4 the L has been changed into I.

In a further aspect, the present invention provides a polypeptide as described herein, in which CDR1 is represented by SEQ ID NO: 124, CDR2 is represented by SEQ ID NO: 145, and CDR3 is represented by SEQ ID NO: 167.

In a further aspect, the present invention provides a polypeptide as described herein, in which:
(i) CDR1 is chosen from the group consisting of
(a) SEQ ID NO: 130; and
(b) amino acid sequences that have 4, 3, 2, or 1 amino acid(s) difference with the amino acid sequence of SEQ ID NO: 130, provided that the polypeptide comprising the CDR1 with 4, 3, 2, or 1 amino acid(s)

difference binds TCR with about the same or a higher affinity compared to the binding by the polypeptide comprising the CDR1 without the 4, 3, 2, or 1 amino acid(s) difference, said affinity as measured by surface plasmon resonance; and/or
(ii) CDR2 is chosen from the group consisting of:
  (c) SEQ ID NOs: 157-158; and
  (d) amino acid sequences that have 4, 3, 2, or 1 amino acid(s) difference with the amino acid sequence of SEQ ID NO: 157, provided that the polypeptide comprising the CDR2 with 4, 3, 2, or 1 amino acid(s) difference binds TCR with about the same or a higher affinity compared to the binding by the polypeptide comprising the CDR2 without the 4, 3, 2, or 1 amino acid(s) difference, said affinity as measured by surface plasmon resonance; and/or
(iii) CDR3 is chosen from the group consisting of:
  (e) SEQ ID NO: 172; and
  (f) amino acid sequences that have 4, 3, 2, or 1 amino acid(s) difference with the amino acid sequence of SEQ ID NO: 172, provided that the polypeptide comprising the CDR3 with 4, 3, 2, or 1 amino acid(s) difference binds TCR with about the same or a higher affinity compared to the binding by the polypeptide comprising the CDR3 without the 4, 3, 2, or 1 amino acid(s) difference, said affinity as measured by surface plasmon resonance.

In a further aspect, the present invention provides a polypeptide as described herein, in which CDR1 is chosen from SEQ ID NO: 130.

In a further aspect, the present invention provides a polypeptide as described herein, in which CDR2 is chosen from the group consisting of
  (a) SEQ ID NO: 157; and
  (b) amino acid sequence that has 1 amino acid difference with SEQ ID NO: 157, wherein
    at position 8 the T has been changed into I.

In a further aspect, the present invention provides a polypeptide as described herein, in which CDR3 is chosen from SEQ ID NO: 172.

In a further aspect, the present invention provides a polypeptide as described herein, in which CDR1 is represented by SEQ ID NO: 130, CDR2 is represented by SEQ ID NO: 157, and CDR3 is represented by SEQ ID NO: 172.

In another aspect, the invention provides a polypeptide that specifically binds carcinoembryonic antigen (CEA) and that comprises or essentially consists of 4 framework regions (FR1 to FR4, respectively) and 3 complementarity determining regions (CDR1 to CDR3, respectively), in which:
(i) CDR1 is chosen from the group consisting of:
  (a) SEQ ID NO: 361 (GDTYGSYWMG); or
  (b) amino acid sequences that have 4, 3, 2, or 1 amino acid(s) difference with the amino acid sequence of SEQ ID NO: 361, provided that the polypeptide comprising the CDR1 with 4, 3, 2, or 1 amino acid(s) difference binds CEA with about the same or a higher affinity compared to the binding by the polypeptide comprising the CDR1 without the 4, 3, 2, or 1 amino acid(s) difference, said affinity as measured by surface plasmon resonance; and/or
(ii) CDR2 is chosen from the group consisting of:
  (c) SEQ ID NO: 363 (AINRGGGYTV); or
  (d) amino acid sequences that have 4, 3, 2, or 1 amino acid(s) difference with the amino acid sequence of SEQ ID NO: 363, provided that the polypeptide comprising the CDR2 with 4, 3, 2, or 1 amino acid(s) difference binds CEA with about the same or a higher affinity compared to the binding by the polypeptide comprising the CDR2 without the 4, 3, 2, or 1 amino acid(s) difference, said affinity as measured by surface plasmon resonance; and/or
(iii) CDR3 is chosen from the group consisting of:
  (e) SEQ ID NO: 365 (SGVLGGLHEDWFNY); or
  (f) amino acid sequences that have 4, 3, 2, or 1 amino acid(s) difference with the amino acid sequence of SEQ ID NO: 365, provided that the polypeptide comprising the CDR3 with 4, 3, 2, or 1 amino acid(s) difference binds CEA with about the same or a higher affinity compared to the binding by the polypeptide comprising the CDR3 without the 4, 3, 2, or 1 amino acid(s) difference, said affinity as measured by surface plasmon resonance.

In a further aspect, the present invention provides a polypeptide as described herein, in which CDR1 is represented by SEQ ID NO: 361, CDR2 is represented by SEQ ID NO: 363, and CDR3 is represented by SEQ ID NO: 365.

In another aspect, the invention provides a polypeptide that specifically binds CD20 and that comprises or essentially consists of 4 framework regions (FR1 to FR4, respectively) and 3 complementarity determining regions (CDR1 to CDR3, respectively), in which:
(i) CDR1 is chosen from the group consisting of:
  (a) SEQ ID NO: 362 (GGTFSSYTMG); or
  (b) amino acid sequences that have 4, 3, 2, or 1 amino acid(s) difference with the amino acid sequence of SEQ ID NO: 362, provided that the polypeptide comprising the CDR1 with 4, 3, 2, or 1 amino acid(s) difference binds CD20 with about the same or a higher affinity compared to the binding by the polypeptide comprising the CDR1 without the 4, 3, 2, or 1 amino acid(s) difference, said affinity as measured by surface plasmon resonance; and/or
(ii) CDR2 is chosen from the group consisting of:
  (c) SEQ ID NO: 364 (EVRWGGVTT); or
  (d) amino acid sequences that have 4, 3, 2, or 1 amino acid(s) difference with the amino acid sequence of SEQ ID NO: 364, provided that the polypeptide comprising the CDR2 with 4, 3, 2, or 1 amino acid(s) difference binds CD20 with about the same or a higher affinity compared to the binding by the polypeptide comprising the CDR2 without the 4, 3, 2, or 1 amino acid(s) difference, said affinity as measured by surface plasmon resonance; and/or
(iii) CDR3 is chosen from the group consisting of:
  (e) SEQ ID NO: 366 (VRQMYMTVVPDY); or
  (f) amino acid sequences that have 4, 3, 2, or 1 amino acid(s) difference with the amino acid sequence of SEQ ID NO: 366, provided that the polypeptide comprising the CDR3 with 4, 3, 2, or 1 amino acid(s) difference binds CD20 with about the same or a higher affinity compared to the binding by the polypeptide comprising the CDR3 without the 4, 3, 2, or 1 amino acid(s) difference, said affinity as measured by surface plasmon resonance.

In a further aspect, the present invention provides a polypeptide as described herein, in which CDR1 is represented by SEQ ID NO: 362, CDR2 is represented by SEQ ID NO: 364, and CDR3 is represented by SEQ ID NO: 366.

In a further aspect, the present invention provides a polypeptide as described herein, which is a Nanobody, a $V_H$, a humanized $V_{HH}$, or a camelized $V_H$.

In a further aspect, the present invention provides a polypeptide as described herein, further comprising a serum protein binding moiety.

In a further aspect, the present invention provides a polypeptide as described herein, wherein said serum protein binding moiety binds serum albumin.

In a further aspect, the present invention provides a polypeptide as described herein, wherein said serum protein binding moiety is an ISV that binds serum albumin.

In a further aspect, the present invention provides a polypeptide as described herein, wherein said ISV that binds serum albumin essentially consists of 4 framework regions (FR1 to FR4, respectively) and 3 complementarity determining regions (CDR1 to CDR3 respectively), in which CDR1 is SFGMS (SEQ ID NO: 481), CDR2 is SISGSGSDTLYADSVKG (SEQ ID NO: 482) and CDR3 is GGSLSR (SEQ ID NO: 475), CDR as determined according to Kabat definition; and/or in which CDR1 is GFTFSSFGMS (SEQ ID NO: 472) or GFTFRSFGMS (SEQ ID NO: 473), CDR2 is SISGSGSDTL (SEQ ID NO: 474) and CDR3 is GGSLSR (SEQ ID NO: 475); CDR as determined according to Kontermann 2010.

In a further aspect, the present invention provides a polypeptide as described herein, wherein said ISV that binds serum albumin is selected from Alb8, Alb23, Alb129, Alb132, Alb11, Alb11 (S112K)-A, Alb82, Alb82-A, Alb82-AA, Alb82-AAA, Alb82-G, Alb82-GG, and Alb82-GGG (SEQ ID NOs: 400 to 412).

In a further aspect, the present invention provides a polypeptide as described herein, wherein said ISV is directly linked or is linked via a linker.

In a further aspect, the present invention provides a polypeptide as described herein, wherein said linker is chosen from the group consisting of linkers of 5GS, 7GS, 9GS, 10GS, 15GS, 18GS, 20GS, 25GS, 30GS and 35GS (SEQ ID NOs:376 to 385).

In a further aspect, the present invention provides a polypeptide as described herein, further comprising a PEG moiety.

In a further aspect, the present invention provides a nucleic acid or nucleic acid sequence encoding a polypeptide as defined herein.

In a further aspect, the present invention provides a vector comprising a nucleic acid or nucleic acid sequence as defined herein.

In a further aspect, the present invention provides a host cell transformed or transfected with the nucleic acid or nucleic acid sequence as defined herein or with the vector as defined herein.

In a further aspect, the present invention provides a process for the production of the polypeptide as described herein, said process comprising culturing a host cell as defined herein under conditions allowing the expression of the polypeptide as defined herein and recovering the produced polypeptide from the culture.

In a further aspect, the present invention provides a pharmaceutical composition comprising the polypeptide as described herein, or, the polypeptide produced according to the process as described herein.

In a further aspect, the present invention provides a polypeptide as described herein, or produced according to the process as described herein, for use in treating a subject in need thereof.

In a further aspect, the present invention provides a method for delivering a prophylactic or therapeutic polypeptide to a specific location, tissue or cell type in the body, the method comprising the steps of administering to a subject a polypeptide as described herein, or produced according to the process as described herein.

In a further aspect, the present invention provides a polypeptide as described herein, or produced according to the process as described herein, for use in the prevention, treatment or amelioration of a disease selected from the group consisting of a proliferative disease, an inflammatory disease, an infectious disease and an autoimmune disease.

In a further aspect, the present invention provides a method for the prevention, treatment or amelioration of a disease selected from the group consisting of a proliferative disease, an inflammatory disease, an infectious disease and an autoimmune disease, comprising the step of administering to a subject in need thereof the polypeptide as described herein, or produced according to a process as described herein.

In a further aspect, the present invention provides a polypeptide for use in or a method for the prevention, treatment or amelioration of a disease as described herein, wherein said proliferative disease is cancer.

In a further aspect, the present invention provides a polypeptide for use in or a method for the prevention, treatment or amelioration of a disease as described herein, wherein said cancer is chosen from the group consisting of carcinomas, gliomas, mesotheliomas, melanomas, lymphomas, leukemias, adenocarcinomas: breast cancer, ovarian cancer, cervical cancer, glioblastoma, multiple myeloma (including monoclonal gammopathy of undetermined significance, asymptomatic and symptomatic myeloma), prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, vaginal cancer, uterine cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma, Kaposi's sarcoma, multicentric Castleman's disease or AIDS-associated primary effusion lymphoma, neuroectodermal tumors, rhabdomyosarcoma; as well as any metastasis of any of the above cancers, as well as non-cancer indications such as nasal polyposis.

In a further aspect, the present invention provides a polypeptide for use in or a method for the prevention, treatment or amelioration of a disease as described herein, wherein the treatment is a combination treatment.

In a further aspect, the present invention provides a kit comprising a polypeptide as defined herein, a nucleic acid or nucleic acid sequence as defined herein, a vector as defined herein, or a host cell as defined herein.

FIGURE LEGENDS

Figure 1:
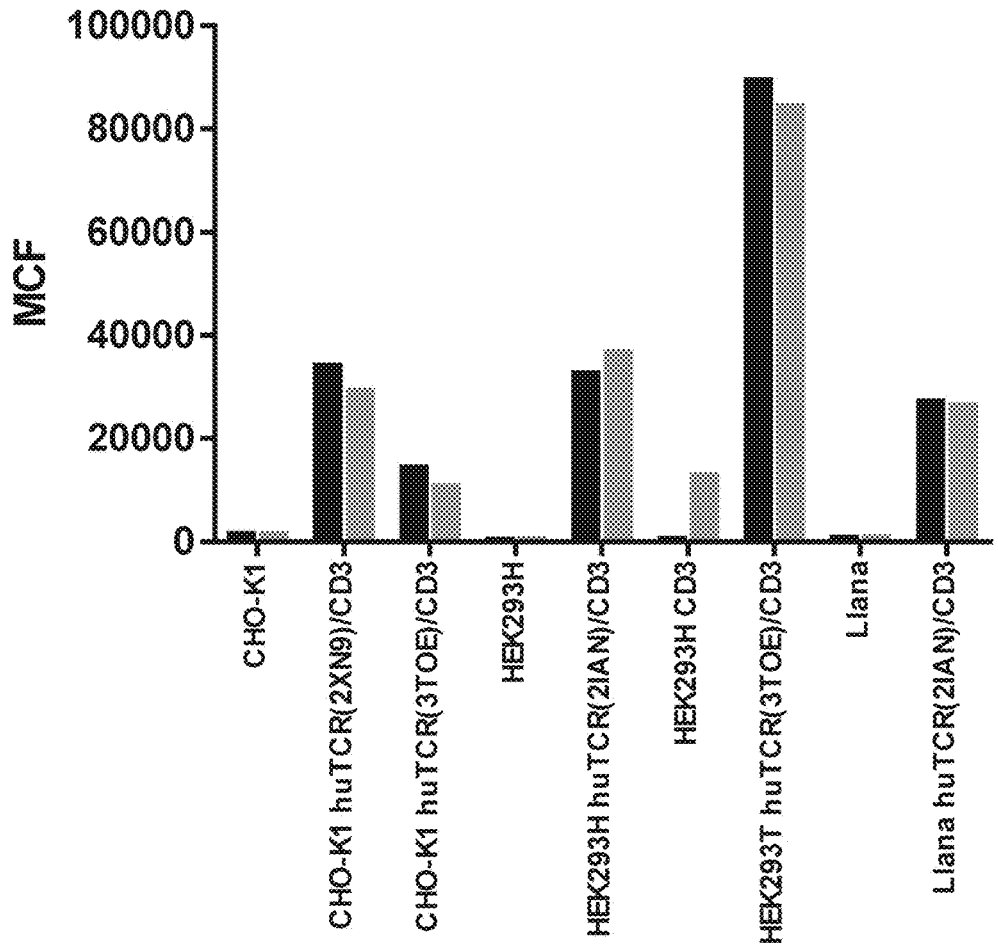

FIG. 1: Assessment of the expression of human TCR/CD3 and human CD3 on transfected CHO, HEK293 and Liana cell lines using 100 nM anti-human TCR α/β antibody (clone BW242/412) (black) and 100 nM anti-human CD3 antibody (clone OKT-3) (grey). The MCF value (mean channel fluorescence) was plotted for each cell line. The X-axis depicts the cell type and the transfected genes; CD3 indicates transfection with the CD3 complex (epsilon, delta, gamma and zeta chains), huTCR indicates transfection with the TCR α/β chains, wherein the variable domain used is between brackets.

Figure 2:
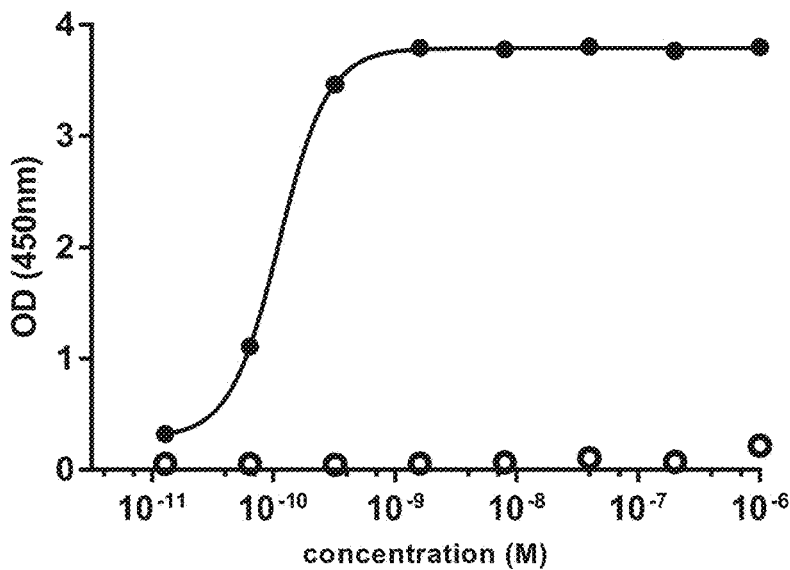

FIG. 2: Quality assessment of soluble recombinant cynomolgus TCR α/β proteins using anti-non-human primate/Rat TCRα/β antibody clone R73; anti-human TCR α/β antibodies (solid circles) and an irrelevant anti-egg lysozyme Nanobody (cAblys) (open circles). The OD value was plotted against the concentration of the Nanobody.

FIGS. 3A and 3B: Dose dependent binding of monovalent anti-TCR Nanobodies to human TCR/CD3 expressed on CHO-K1 cells (FIG. 3A) and to primary human T cells (FIG. 3B). The MCF value (mean channel fluorescence) was plotted against the concentration of the Nanobody.

FIG. 4: Dose dependent binding of monovalent anti-TCR Nanobodies to HEK293H human TCR(2IAN)/CD3 (closed circle), HEK293H human CD3 (cross) and to HEK293H reference cell line (open circles). The MCF value (mean channel fluorescence) was plotted against the concentration of the Nanobody.

FIG. 5: Dose dependent binding of monovalent anti-TCR Nanobodies (closed circles) and an irrelevant Nanobody (open circles) to soluble recombinant human TCR α/β (2XN9)-zipper protein. The OD at 450 nm was plotted against the concentration of the Nanobody.

Figure 6A:
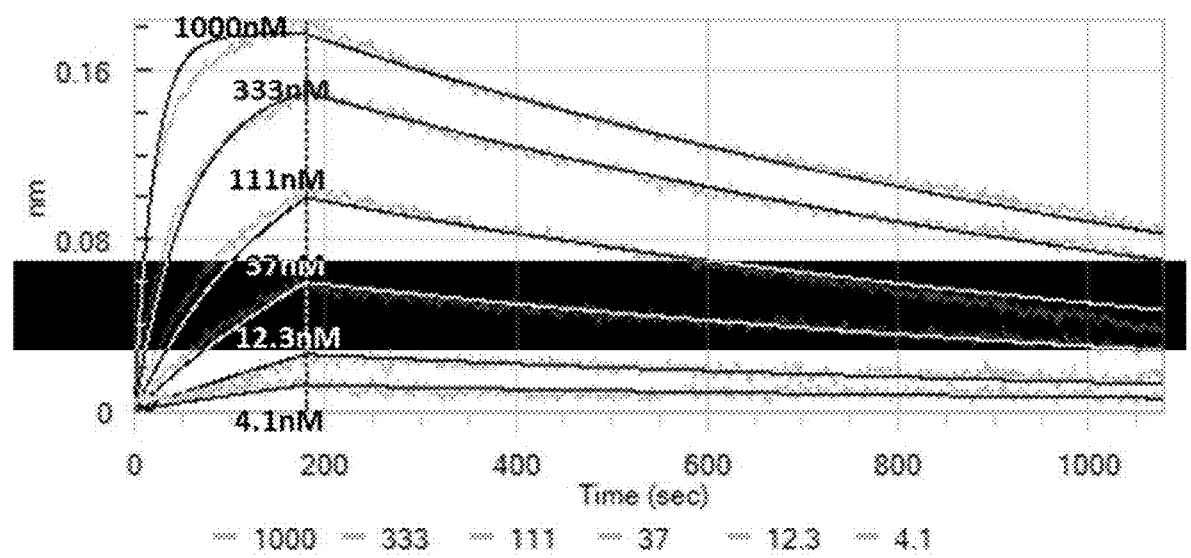
Figure 6B:
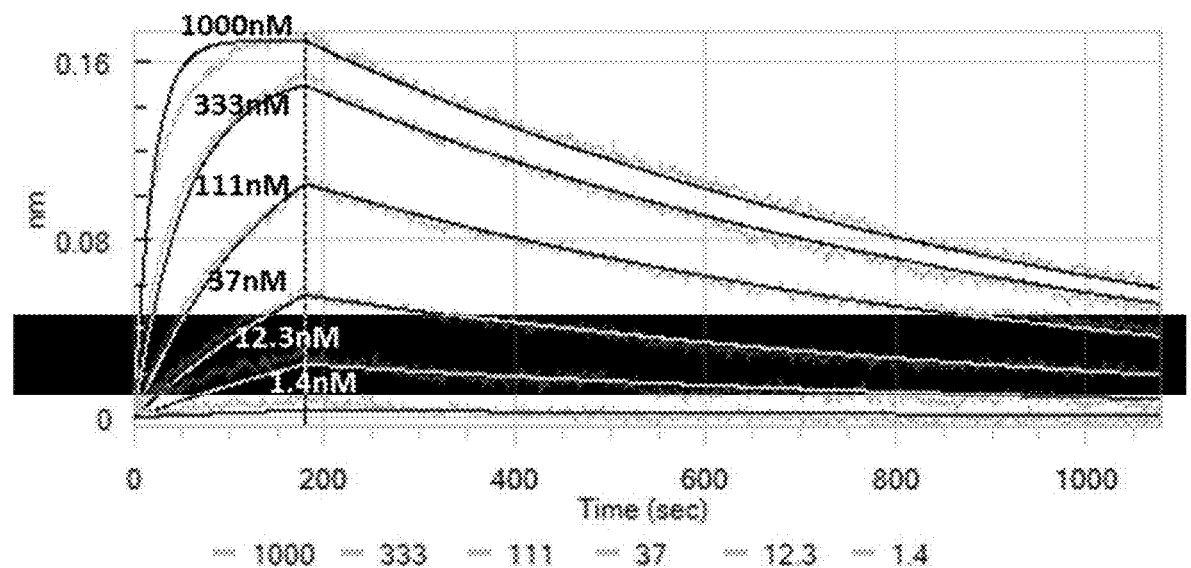

FIGS. 6A and 6B: Kinetic analysis of T01700055A02 (FIG. 6A) and T01700056G05 (FIG. 6B) on soluble recombinant human TCR α/β (2XN9)-zipper protein interaction via BioLayer Interferometry on an Octet RED384 instrument. Applied analyte concentrations were: 1000, 333, 111, 37, 12.3, 4.1 and 1.4 nM. Langmuir fits to the kinetic data are indicated with the black lines, whereas sensorgrams are presented by the grey lines.

Figure 7A:
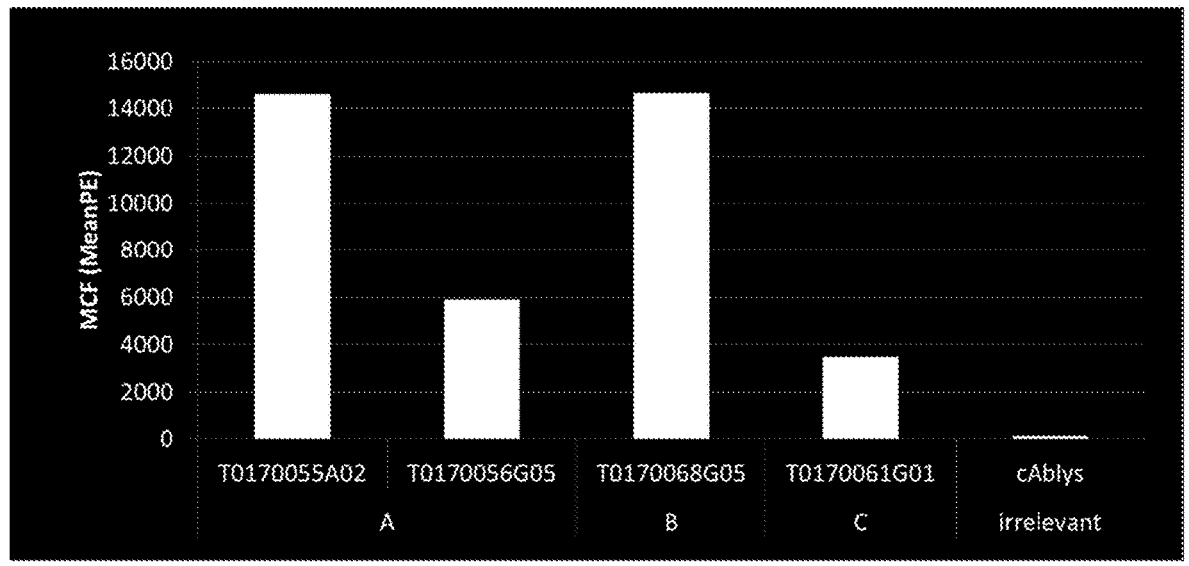
Figure 7B:
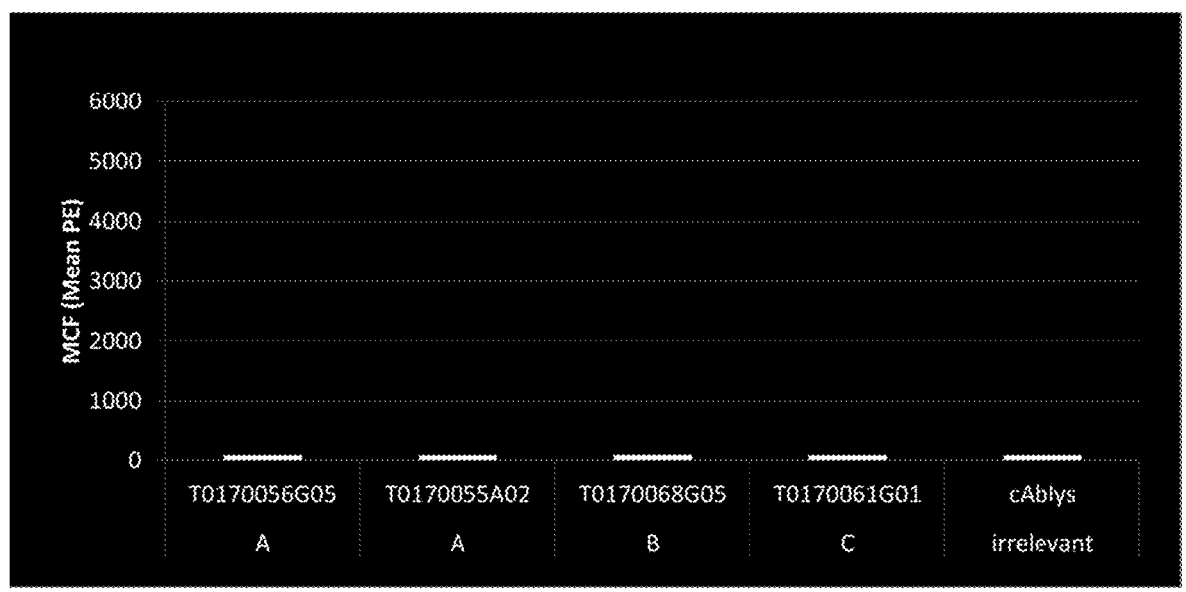

FIGS. 7A and 7B: T cell activation data of bead coupled monovalent anti-TCR Nanobodies (FIG. 7A). T cell activation data of monovalent anti-TCR Nanobodies presented in solution (FIG. 7B). Activation was measured by monitoring the CD69 upregulation on primary human T cells. The MCF value (mean channel fluorescence) was plotted for each Nanobody.

FIGS. 8A-C: Binding of a dilution series of CD20×TCR (full line) and TCR×CD20 (dotted line) multispecific polypeptides to human TCR/CD3 expressed on CHO-K1 cells (FIG. 8A), primary human T cells (FIG. 8B) and Ramos cells (FIG. 8C). The MCF value (mean channel fluorescence) was plotted against the concentration of the polypeptides.

FIGS. 9A and 9B: Dose-dependent killing effect of CD20×TCR (full line) binding and TCR×CD20 (dotted line) binding bispecific polypeptides in a flow cytometry based human T cell mediated Ramos B cell killing assay. The % cell death (% of TOPRO positive cells) is plotted against the concentration of the polypeptides (FIG. 9A). Dose-dependent killing effect of CD20×TCR (full line) binding bispecific polypeptides in a flow cytometry based human T cell mediated Raji B cell killing assay. The % cell death (% of TOPRO positive cells) was plotted against the concentration of the polypeptides (FIG. 9B).

Figure 10:
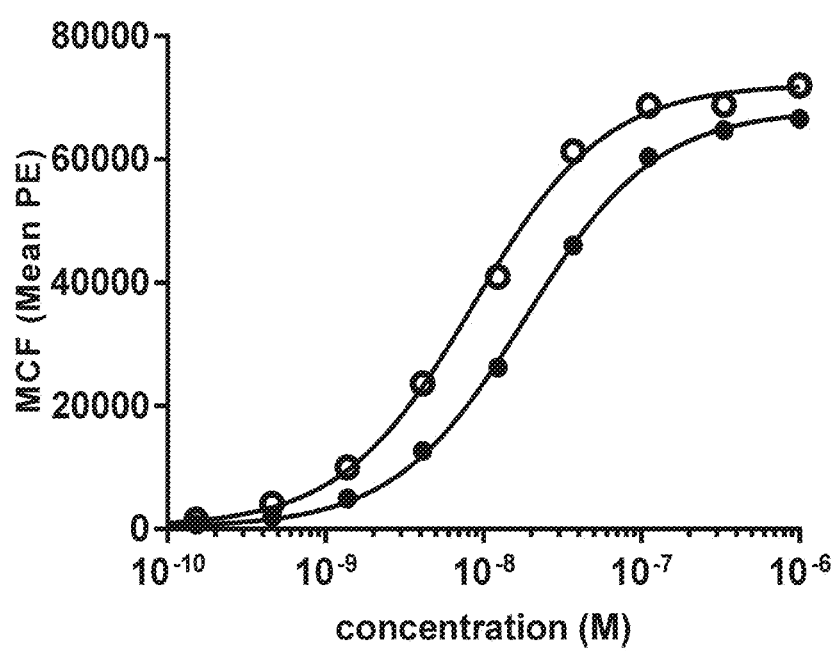

FIG. 10: Dose-dependent binding of the anti-CD20 Nanobody on human CD20 Ramos (open symbols) and Raji (closed symbols) cells. The MCF value (mean channel fluorescence) was plotted against the concentration of the Nanobody.

FIGS. 11A and 11B: Dose-dependent killing effect of CD20×TCR binding (full line) and TCR×CD20 binding (dotted line) bispecific polypeptides in the xCELLigence based assay using CHO-K1 human CD20 transfected cells (FIG. 11A). Dose-dependent killing effect of T017000055 in the xCELLigence based assay using CHO-K1 human CD20 transfected cells (full line, closed symbol) and CHO-K1 parental cell line (open circles) to illustrate TAA (CD20) dependent killing (FIG. 11B). The cell index (CI) was plotted against the concentration of polypeptides.

Figure 12:
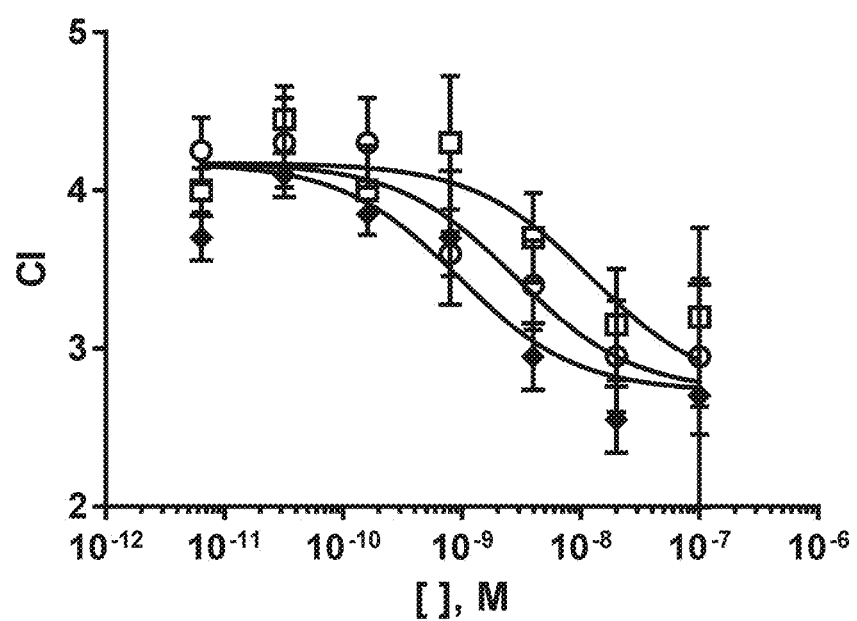

FIG. 12: Dose-dependent killing effect of CD20×TCR polypeptides using a 5GS linker (open squares), 9GS linker (open circles) and a 35GS linker (closed symbols) in a xCELLigence based killing assay using CHO-K1 human TCR(2XN9)/CD3 cells. The cell index (CI) was plotted against the concentration of polypeptides.

FIGS. 13A and 13B: Dose-dependent killing effect of T017000055 (FIG. 13A) and T017000076 (FIG. 13B) in a flow cytometry based human T cell mediated Ramos B cell killing assay using different effector (E) to target (T) ratio's (E:T ratio 10:1—closed circles, E:T ratio 5:1—open squares, E:T ratio 2:1—closed triangles and E:T ratio 1:1—open diamonds). The % cell death (% of TOPRO positive cells) was plotted against the concentration of the polypeptides.

Figure 14:
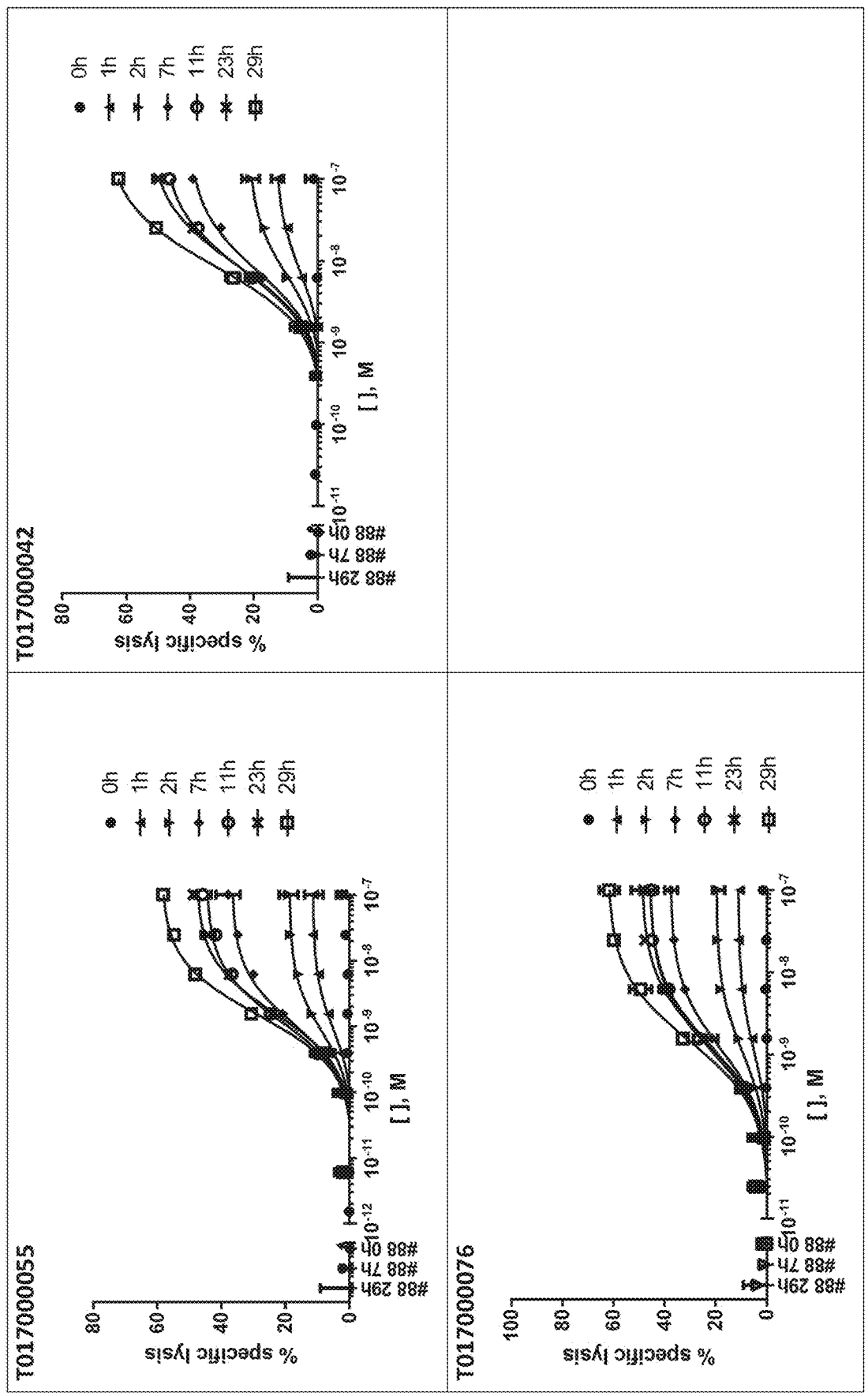

FIG. 14: Time-dependent cytolytic activity of CD20/TCR binding polypeptides in the purified primary human T cell mediated killing assay in xCELLigence using CHO-K1 human CD20 target cells. The % specific lysis was plotted against the concentration of the construct. The different curves represent the analysis time after addition of the T cells.

FIGS. 15A-15C: Binding of a serial dilution of half-life extended polypeptides to human TCR/CD3 expressed on CHO-K1 cells (FIG. 15A), primary human T cells (FIG. 15B) and Ramos cells (FIG. 15C). The MCF value (mean channel fluorescence) was plotted against the concentration of the polypeptides.

FIGS. 16A-16D: Dose-dependent killing effect of CD20×TCR binding multispecific polypeptides versus CD20×TCR×ALB11 binding polypeptides in a flow cytometry based human T cell mediated Ramos B cell killing assay (FIG. 16A, FIG. 16C). Dose-dependent killing effect of CD20×TCR×ALB11 binding polypeptides in the absence or presence of 30 μM HSA in a flow cytometry based human T cell mediated Ramos B cell killing assay (FIG. 16B, FIG. 16D). The % cell death (% of TOPRO positive cells) was plotted against the concentration of the polypeptides.

FIG. 17: Binding of 100 nM monovalent anti-HER2 Nanobody (5F07) to SKBR3, MCF-7 and MDA-MB-468 cell lines in flow cytometry to assess HER2 expression levels. The MCF value (mean channel fluorescence) was plotted for each cell line.

FIGS. 18A-18C: Dose-dependent killing effect of multispecific TCR×HER2 binding polypeptides (dotted line) and multispecific HER2×TCR binding polypeptides (full line) in an xCELLigence based human T cell mediated killing assay using SKBR-3 cells (FIG. 18A), MCF-7 cells (FIG. 18B) and MDA-MB-468 cells (FIG. 18C). Data were analysed after 18 h. The cell index (CI) was plotted against the concentration of the polypeptides.

Figure 19:
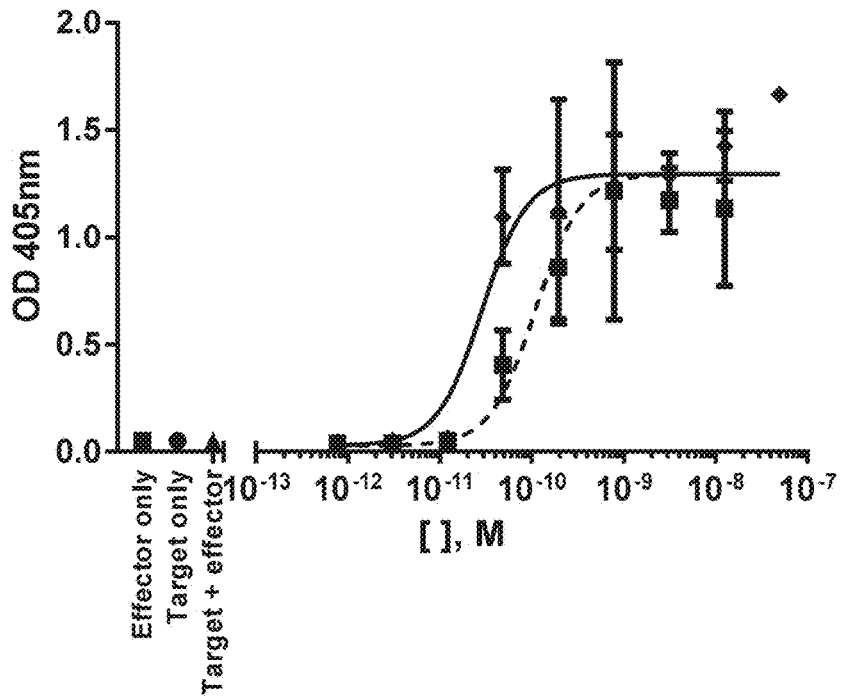

FIG. 19: Dose-dependent INF-γ production by human T cells after incubation of HER2-positive cells with multispecific TCR×HER2 binding polypeptides (dotted line) and multispecific HER2×TCR binding polypeptides (full line) in an xCELLigence based assay. Data were analysed after 72 h incubation. The OD was plotted against the concentration of the polypeptides.

FIG. 20: Dose-dependent killing effect of CD20×TCR binding (full line) and TCR×CD20 binding (dotted line) multispecific polypeptides in a flow cytometry based cynomolgus T cell mediated Ramos B cell killing assay. The % cell death (% of TOPRO positive cells) was plotted against the concentration of the polypeptides.

FIG. 21: Dose-dependent killing effect of CD20×TCR binding (full line) and TCR×CD20 binding (dotted line) bispecific polypeptides in the xCELLigence based cynomolgus T cell mediated CHO-K1 human CD20 killing assay. The CI was plotted against the concentration of polypeptides.

FIG. 22: Dose dependent binding of monovalent anti-TCR Nanobodies (closed circles) and an irrelevant Nanobody (open circles) to soluble recombinant cynomolgus TCR α/β-zipper protein. The OD at 450 nm was plotted against the concentration of the Nanobody.

Figure 23A:
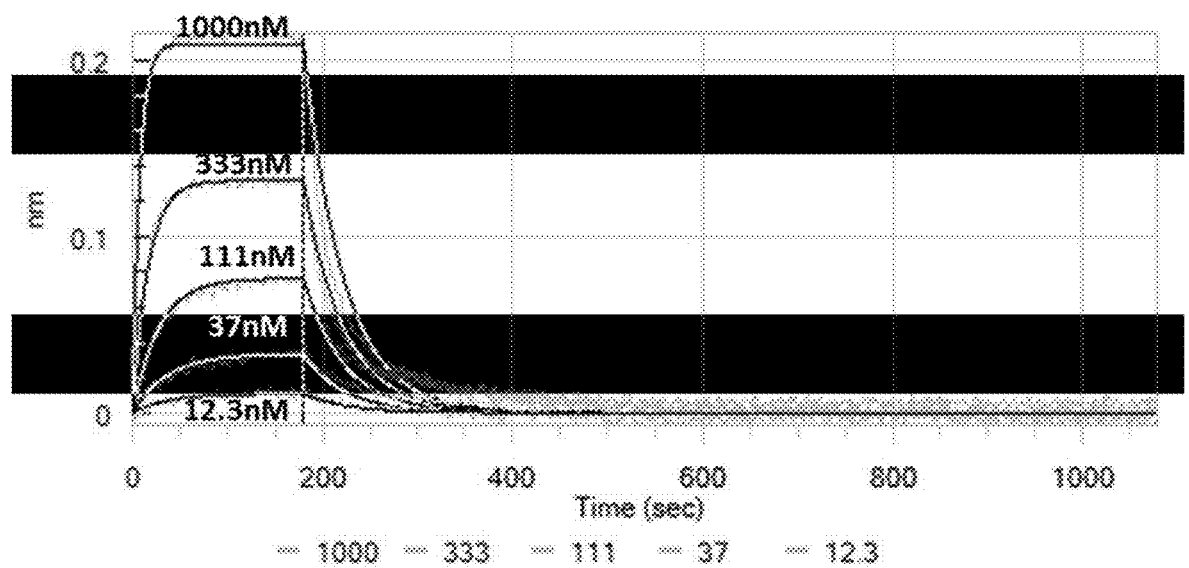
Figure 23B:
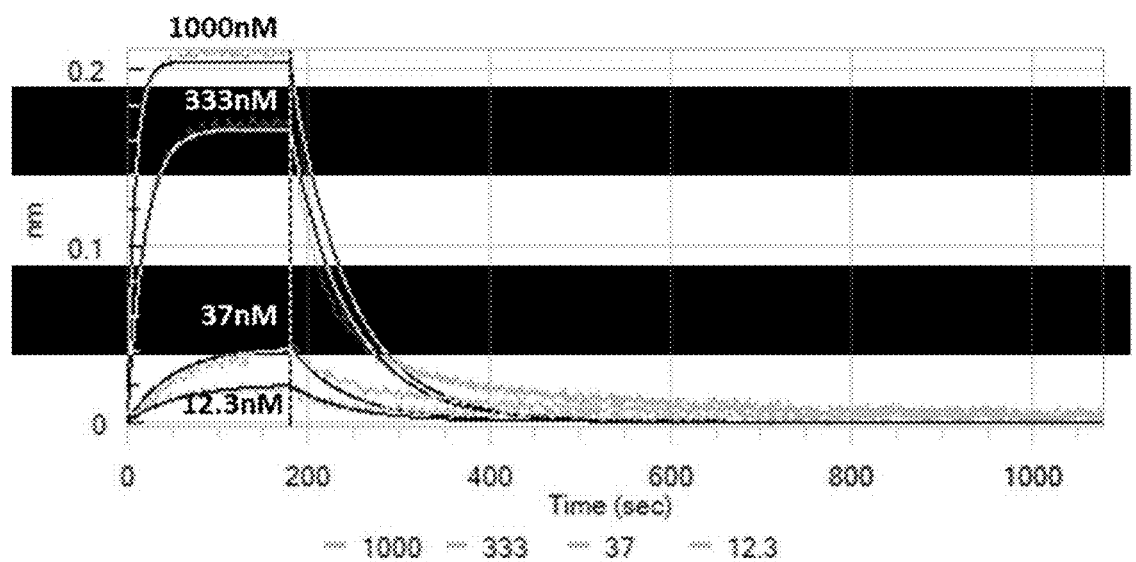

FIGS. 23A and 23B: Kinetic analysis of T0170055A02 (FIG. 23A) and T0170056G05 (FIG. 23B) on soluble recombinant cynomolgus TCRα/β-zipper protein interaction via BioLayer Interferometry on an Octet RED384 instrument. Applied analyte concentrations were: 1000, 333, 111, 37, 12.3, 4.1 and 1.4 nM. Langmuir fits to the kinetic data are indicated with the black lines, whereas sensorgrams are presented by the grey lines.

FIGS. 24A and 24B: Dose-dependent killing effect of T017000076 (CD20×TCR binding multispecific construct) versus T017000093 (CD20×TCR×ALB11 binding construct) in a flow cytometry based cynomolgus T cell mediated Ramos B cell killing assay (FIG. 24A). Dose-dependent killing of T017000093 in the presence of 30 µM HSA in a flow cytometry based cynomolgus T cell mediated Ramos B cell killing assay (FIG. 24B). The % cell death (% of TOPRO positive cells) was plotted against the concentration of the Nanobody.

Figure 25:
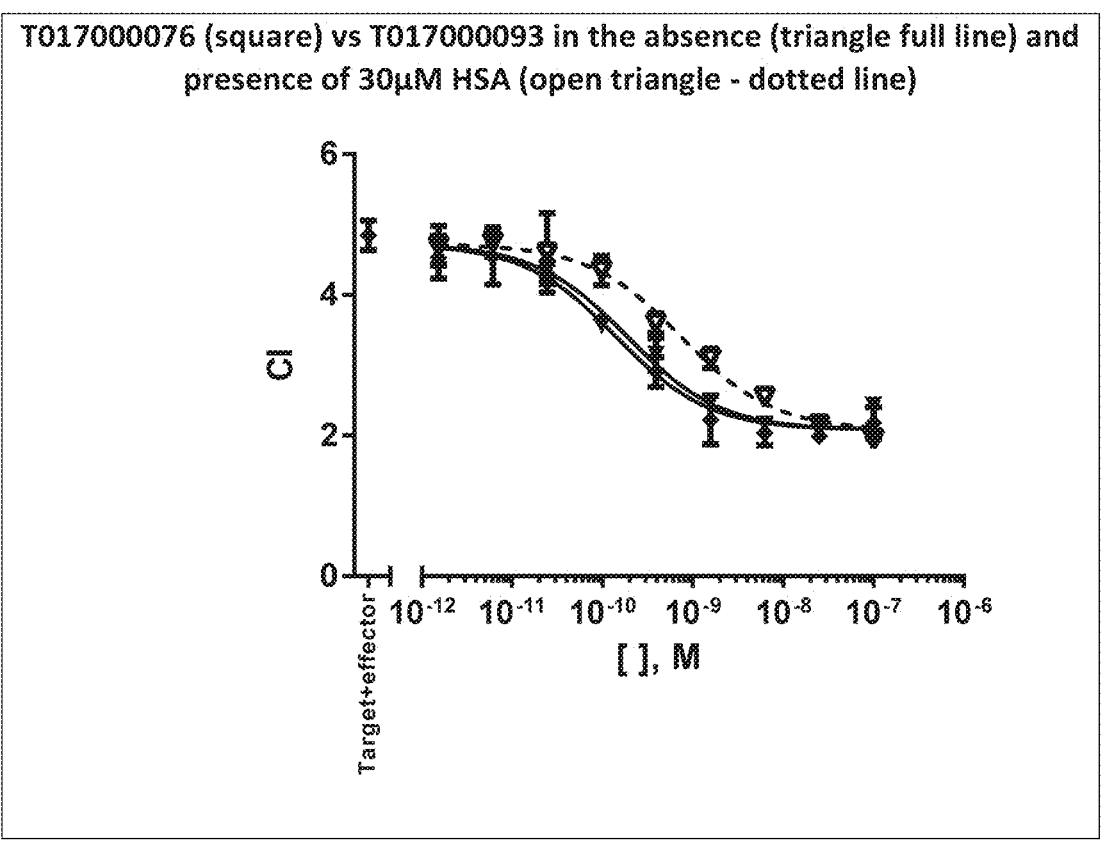

FIG. 25: Dose-dependent killing effect of CD20×TCR binding multispecific construct versus CD20×TCR×ALB11 binding construct and versus CD20×TCR×ALB11 binding construct in the presence of 30 µM HSA in a cynomolgus T cell mediated CHO-K1 human CD20 transfected cell xCELLigence based assay. The cell index (CI) ws plotted against the concentration of Nanobody.

Figure 26:
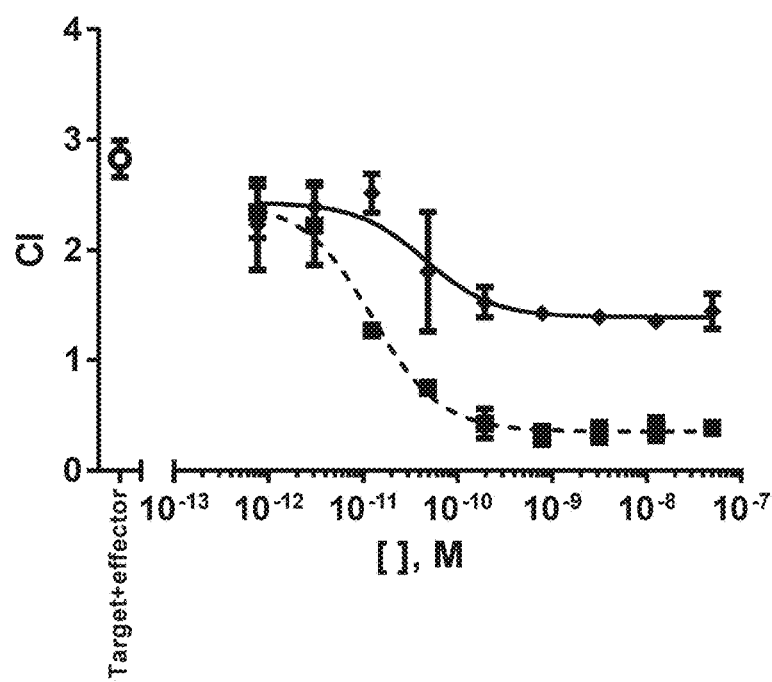

FIG. 26: Dose-dependent killing effect of multispecific TCR×HER2 binding polypeptides (dotted line) and multispecific HER2×TCR binding polypeptides (full line) in an xCELLigence based cynomolgus T cell mediated HER2-positive SKBR-3 tumour killing assay. Data were analysed after 40 h incubation. The cell index (CI) was plotted against the concentration of the Nanobody.

Figure 27:
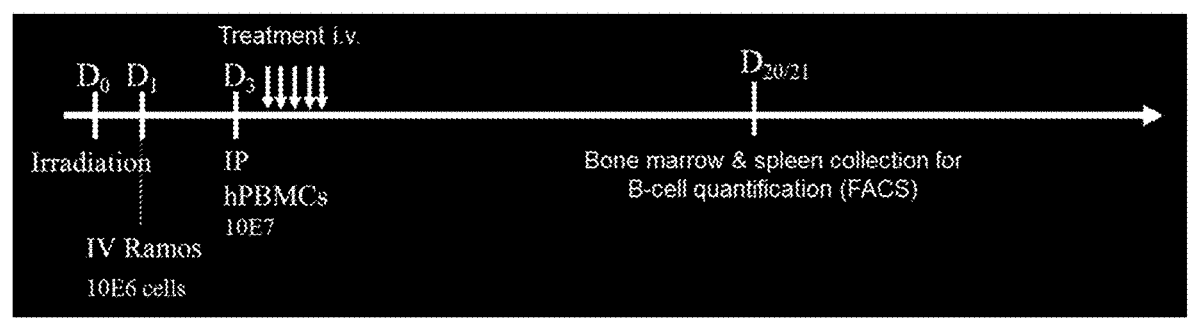

FIG. 27: Study design for Ramos model as described in Example 19. Ramos cells were injected intravenously in to mice on day 1 (D1). PBMCs were injected intraperitoneally in to animals on day 3(D3). Mice were treated from D3 to day 7 (D7) with T017000083 (TCR/CD20) IV once daily during 5 days (Q1Dx5) or T017000088 (irrelevant multispecific polypeptide) IV Q1Dx5.

Figure 28A:
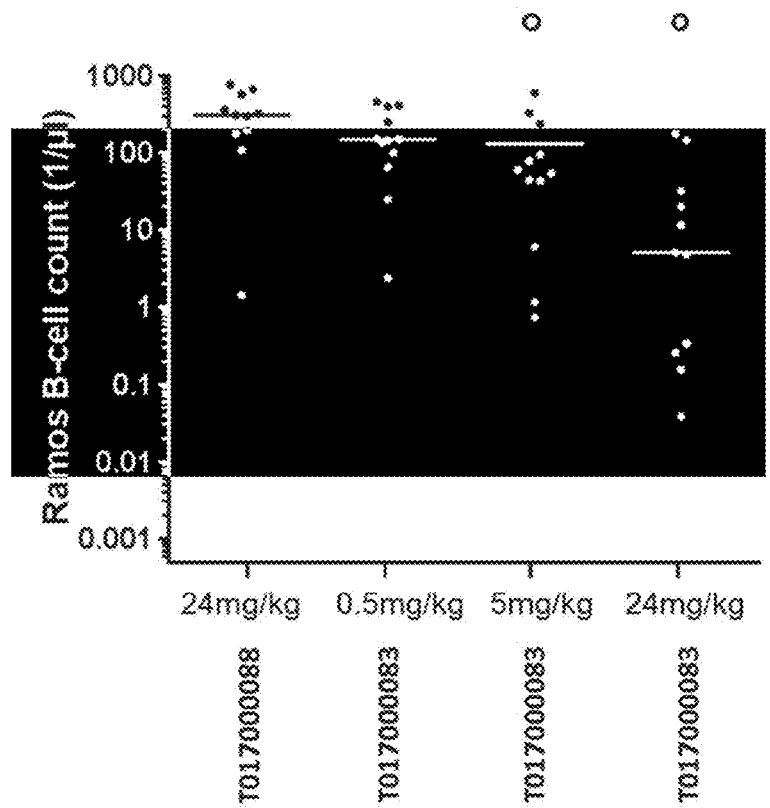
Figure 28B:
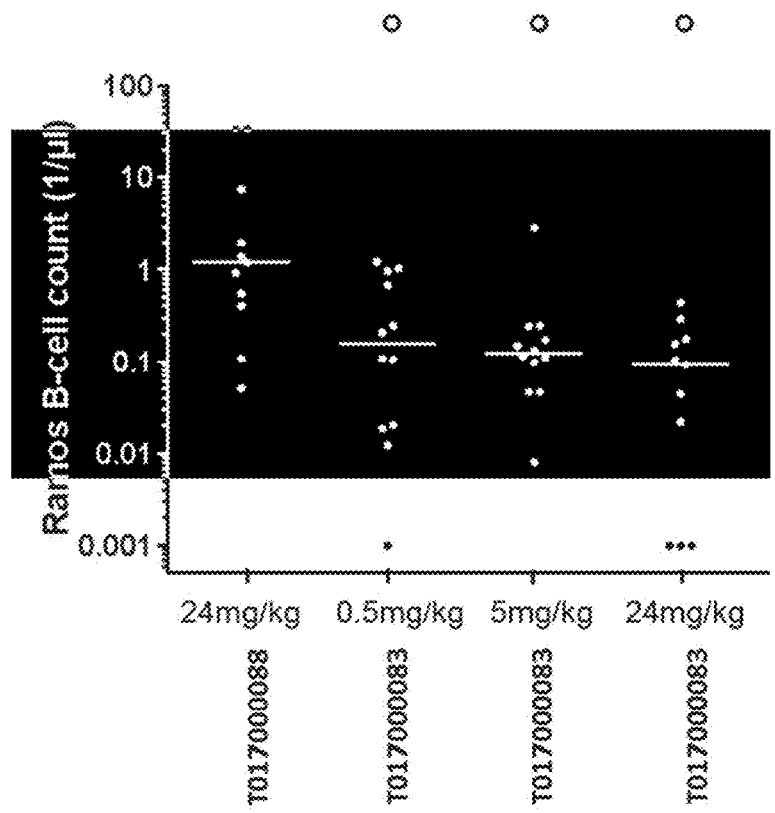
Figure 28C:
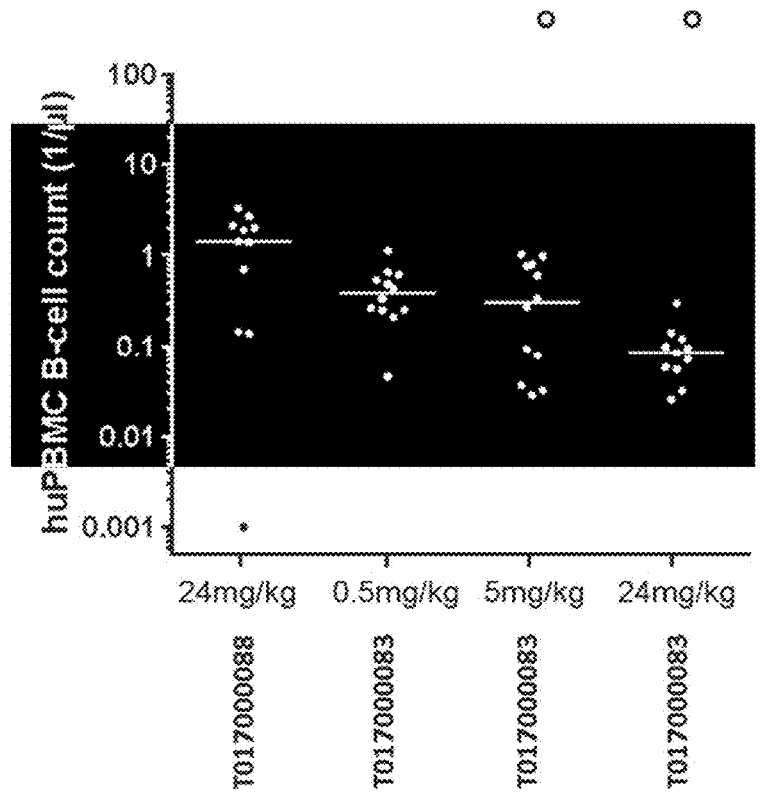
Figure 28D:
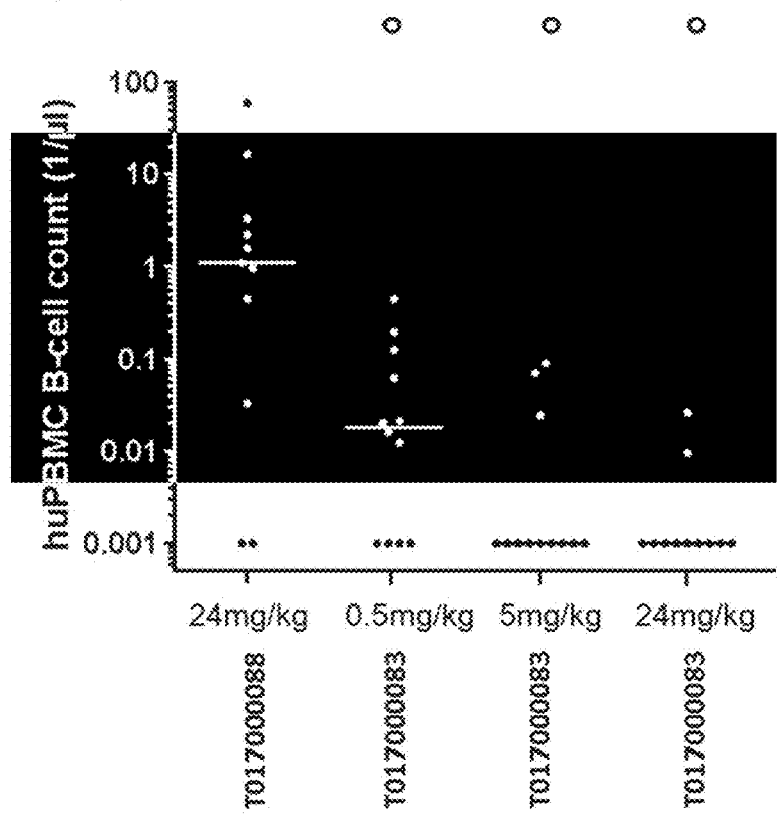

FIGS. 28A-28D: Absolute Ramos B cell count on log scale in bone marrow (FIG. 28A) and spleen (FIG. 28B). Absolute PBMC derived B cell count on log scale in bone marrow (FIG. 28C) and spleen (FIG. 28D). Individual animal results are depicted. The number of B cells is shown in function of the different treatment groups. The open circles on top of the graphs show which active doses were statistically significant different from the irrelevant polypeptide (T017000088) based on the F-tests from the mixed-effects ANOVA analysis. All effects in the spleen are statistically significant at the 5% level of significance. Notably, the Y-axis value of 0.001 signifies no cells counted.

Figure 29:
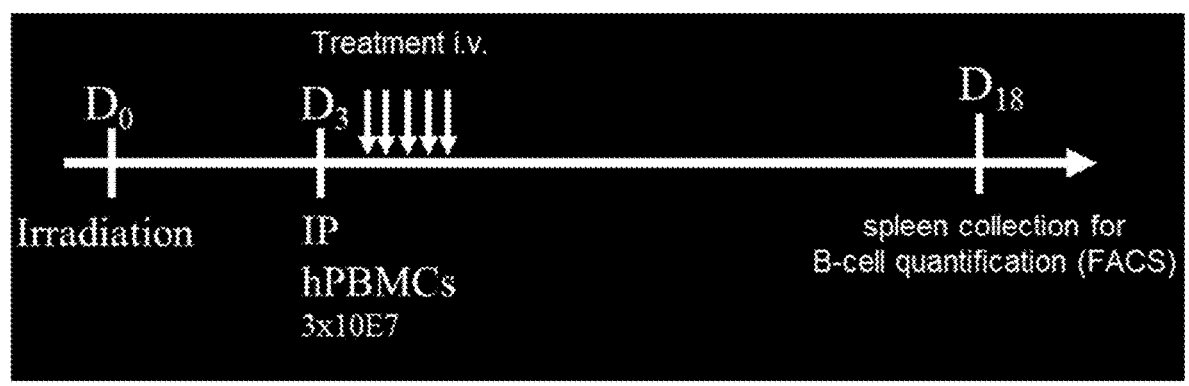

FIG. 29: Study design for PBMC B cell depletion model as described in Example 20. PBMCs were injected intraperitoneally to animals on day 3 (D3). Mice were treated from D3 to day 7 (D7) with T017000083 (TCR/CD20) IV once daily during 5 days (Q1Dx5) or T017000088 (irrelevant polypeptide) IV Q1Dx5.

Figure 30:
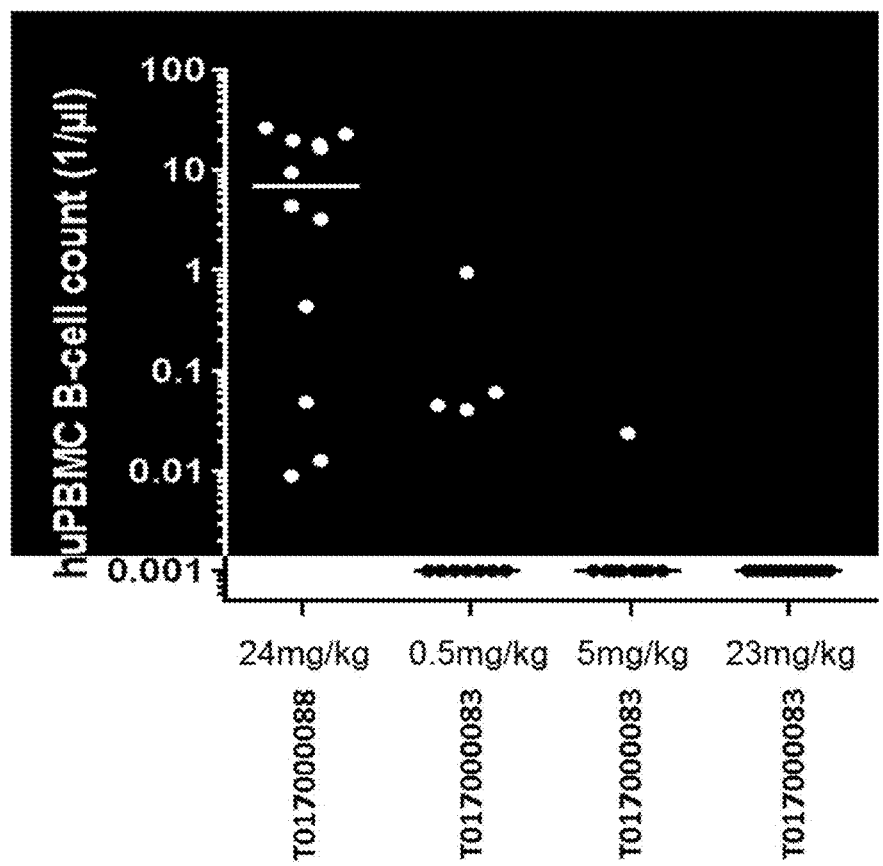

FIG. 30: Absolute PBMC-derived B cell count on log scale. Individual animal results are depicted. The number of B cells is shown in function of the different treatment groups. Notably, Y-axis value of 0.001 signifies no cells counted.

Figure 31A:
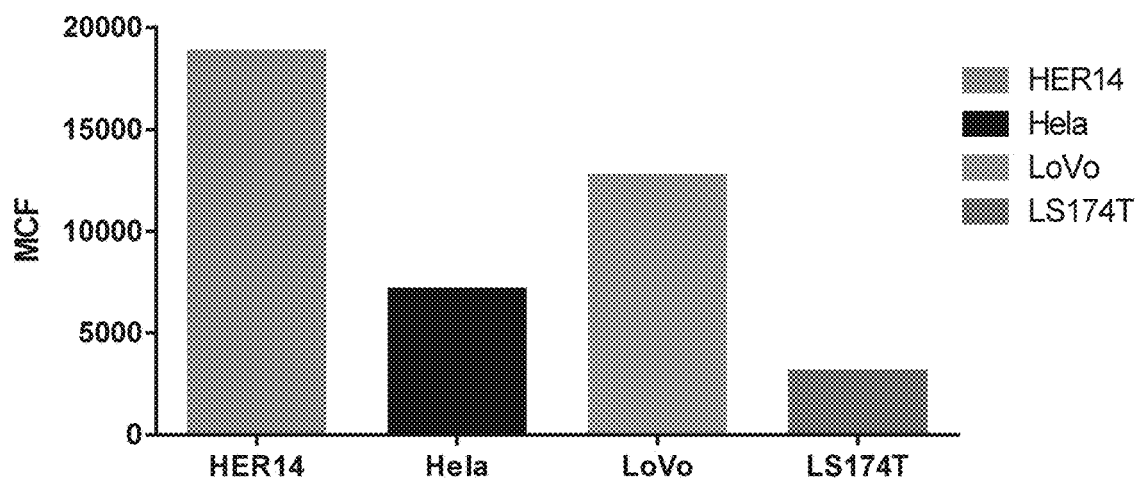
Figure 31B:
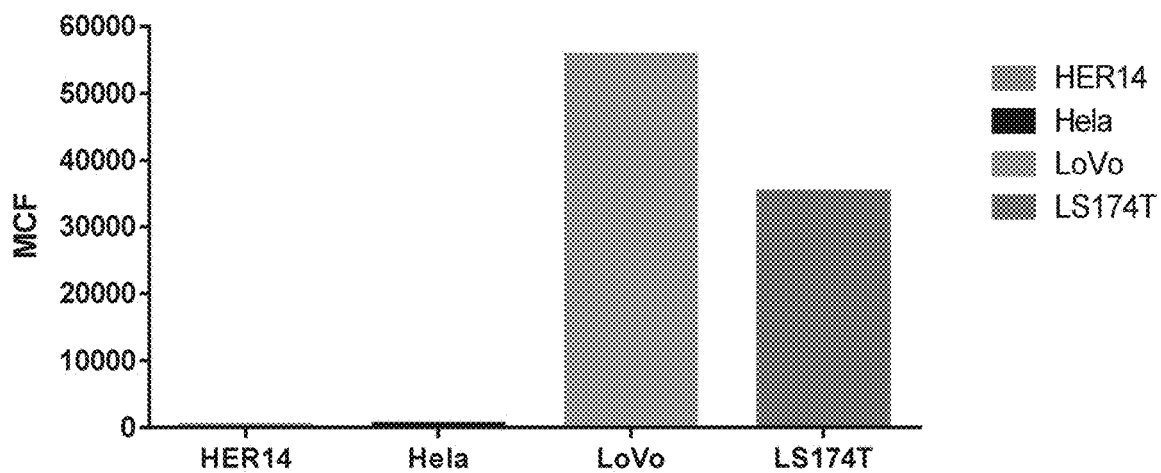

FIGS. 31A and 31B: Determination of EGFR (FIG. 31A; with anti-EGFR antibody; Santa Cruz, sc-120 PE) or CEACAM5 (FIG. 31B; with anti-CEACAM antibody; Sino Biological, 11077-MM02-P) expression level on HER14, Hela, LoVo and LS174-T cell lines in flow cytometry. The MCF value (mean channel fluorescence) was plotted for each cell line.

FIGS. 32A-32D: Dose-dependent binding of the monovalent Nanobodies and multispecific polypeptides to HER14 (FIG. 31A), LS174T (FIG. 31B), primary human T cells (FIG. 31C) and LoVo cells (FIG. 31D). The mean channel fluorescence intensity was plotted against the concentration.

Figure 33:
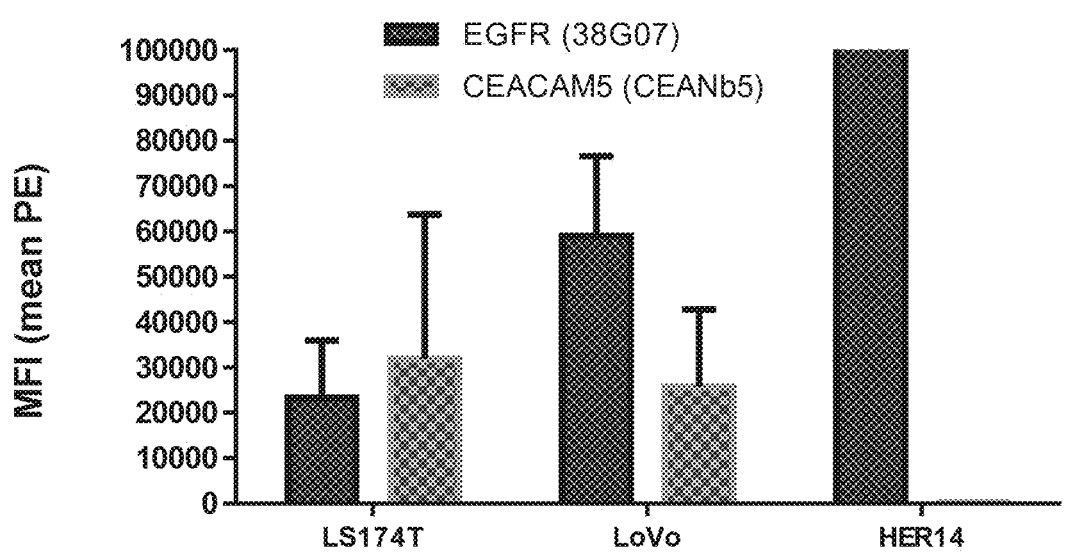
Figure 34A:
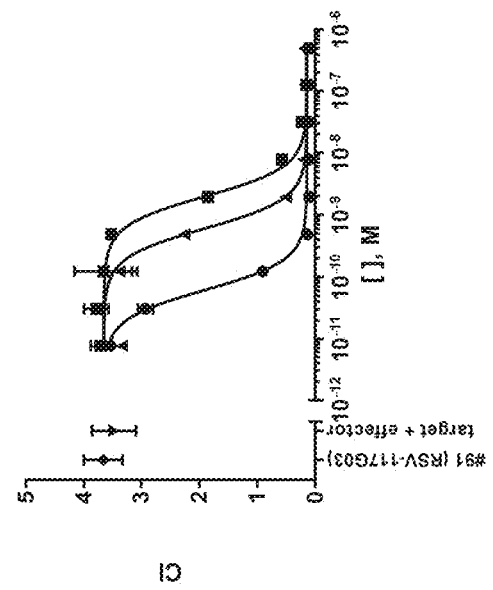
Figure 34B:
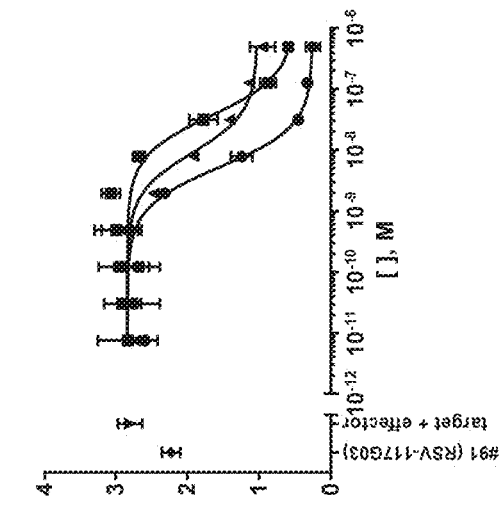
Figure 34C:
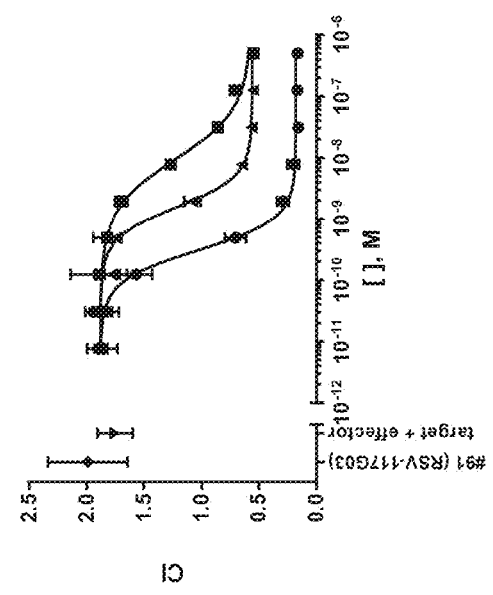
Figure 34D:
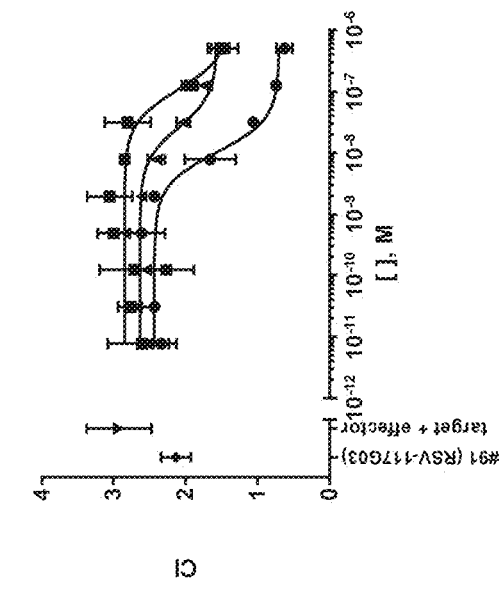

FIG. 33: Determination of EGFR and CEACAM5 expression levels of HER14, LoVo and LS174T cell lines using 100 nM of the EGFR and CEACAM Nanobodies in flow cytometry. The MFI value (mean fluorescence intensity) was plotted for each cell line.

FIGS. 34A-34E: Dose-dependent redirected LoVo(FIG. 34A, FIG. 34B), LST174T (FIG. 34C, FIG. 34D) and HER14 (FIG. 34E) target cell killing of multispecific polypeptides by human effector T cells in the xCELLigence based assay using an effector to target ratio of 15. The CI after an incubation time of 30 h-40 h (FIG. 34A, FIG. 34C) and 50 h-60 h (FIG. 34B, FIG. 34D, FIG. 34E) so was plotted against the concentration of the multispecific polypeptides. (T017000107=circle, T017000109=square, T017000110=triangle).

Figure 35:
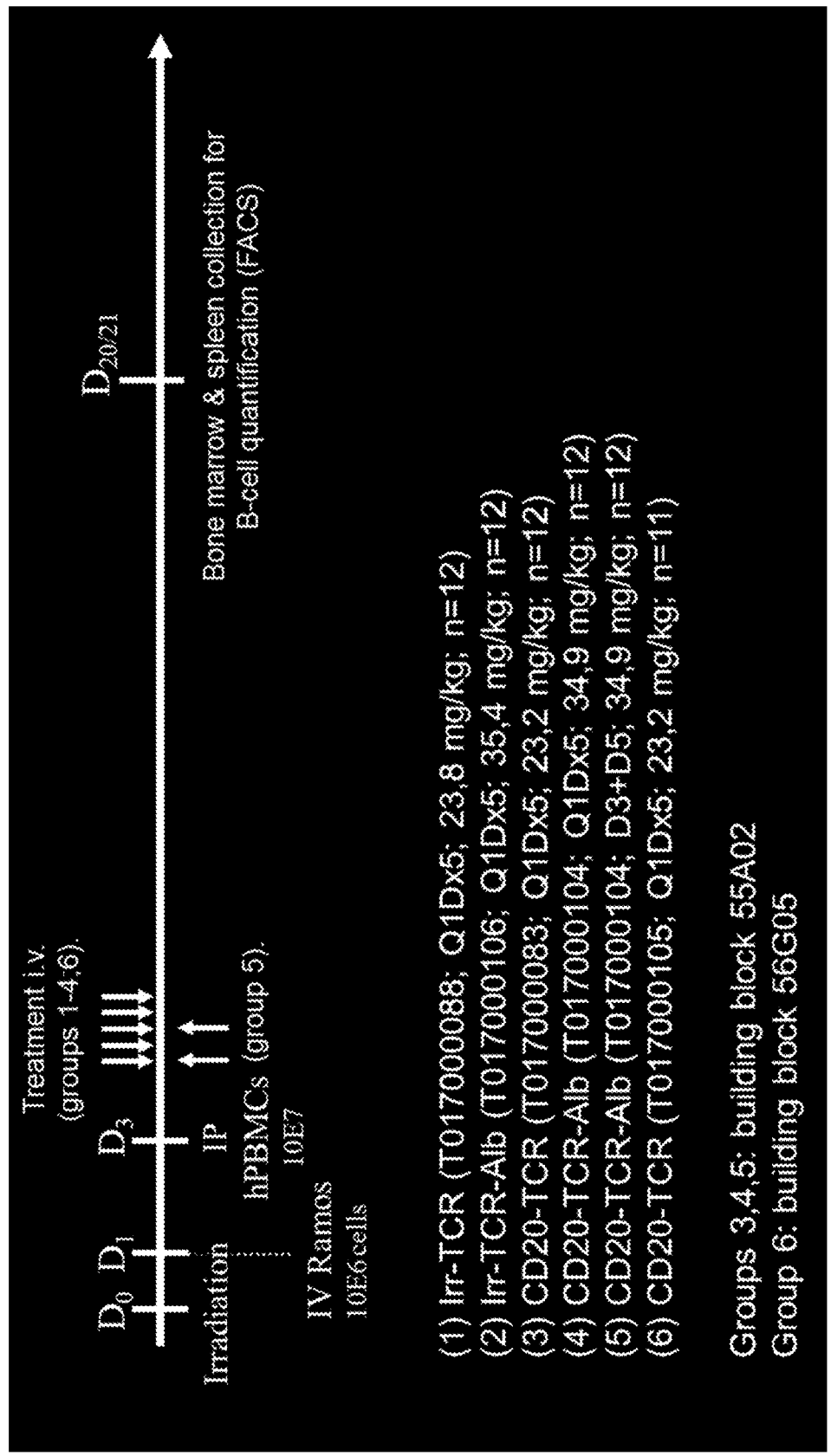

FIG. 35: Study design of the in vivo Ramos model used in Example 26. Ramos cells were injected intravenously into mice on day 1 (D1). PBMCs were injected intraperitoneally to animals on day 3 (D3). Mice were treated from D3 to day 7 (D7) with T017000088, T017000106, T017000083, T017000104 or T017000105.

Figure 36A:
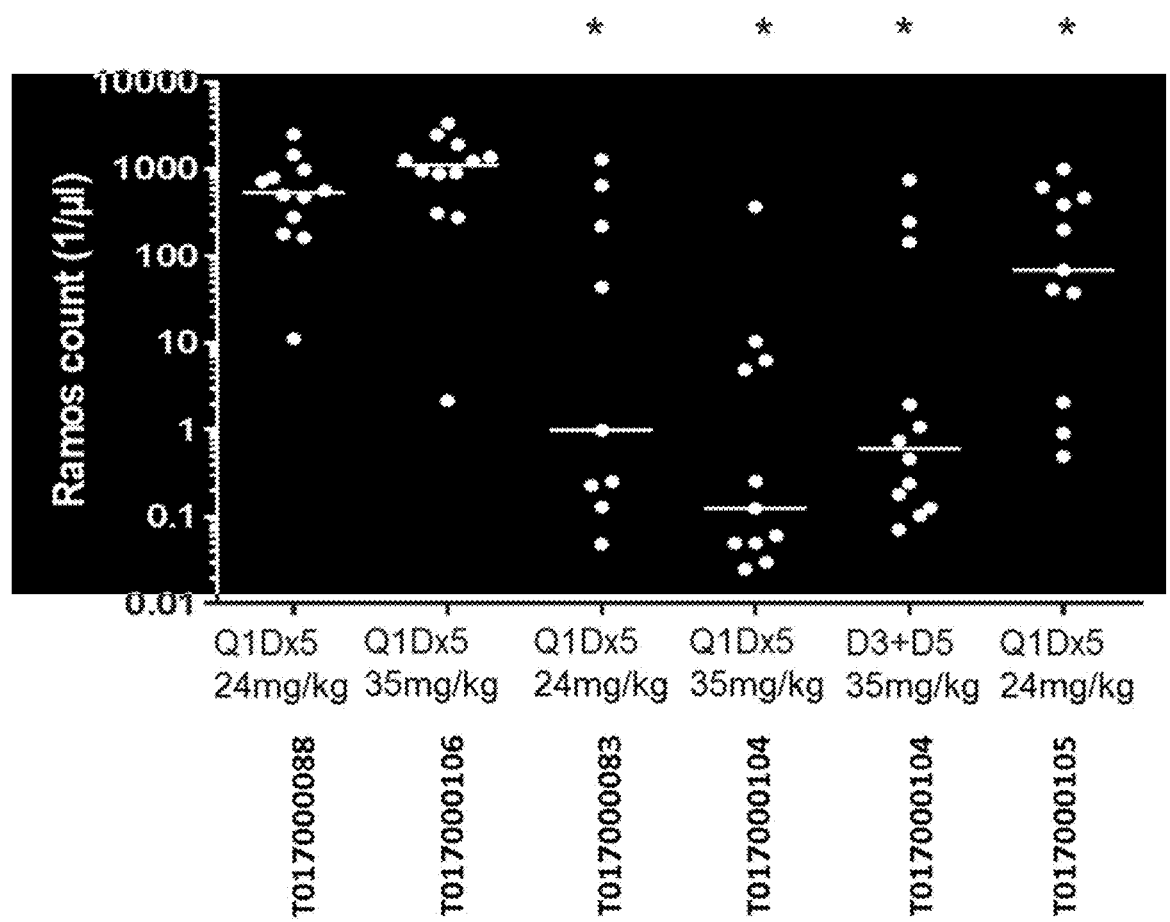
Figure 36B:
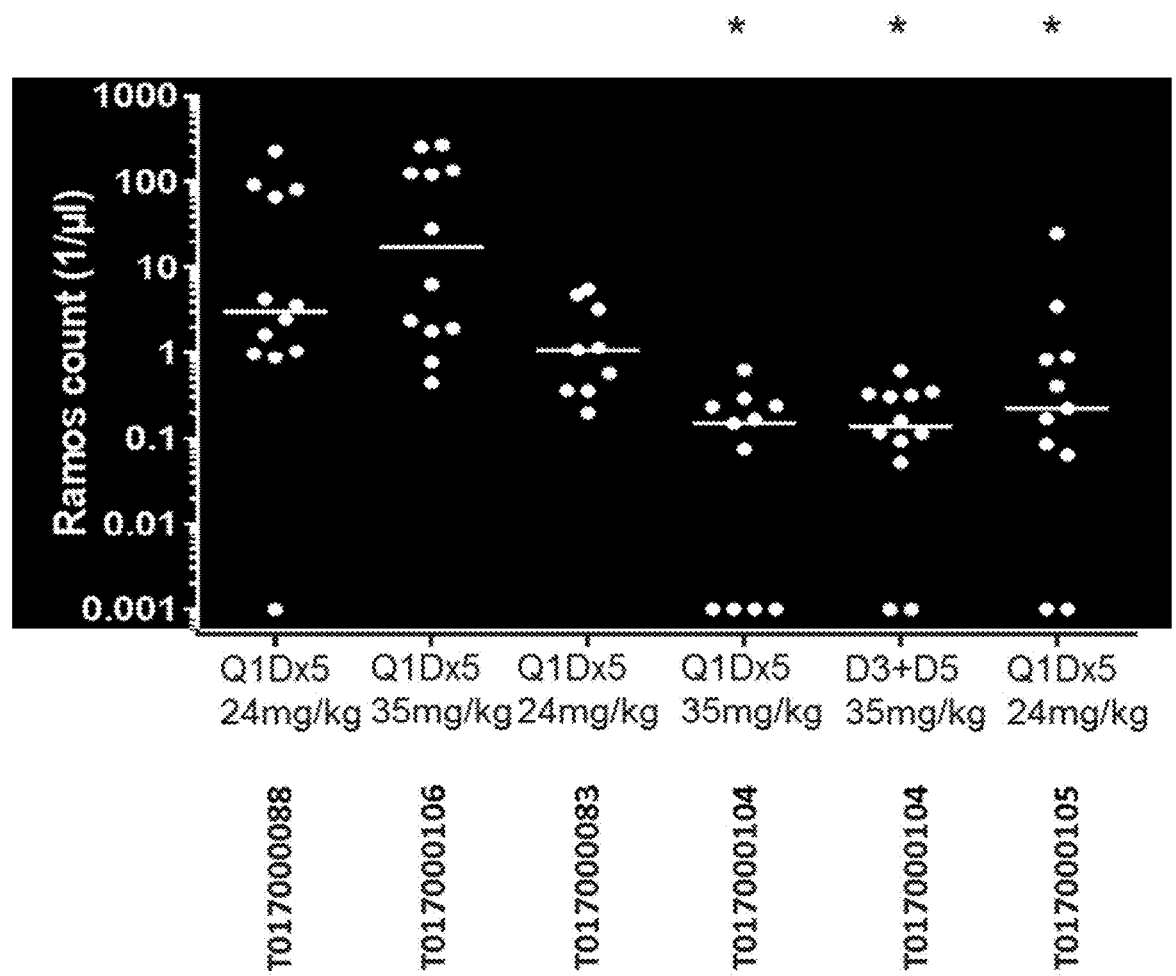

FIGS. 36A-36B: Absolute Ramos B cell count on log scale in bone marrow (FIG. 36A) and spleen (FIG. 36B). Individual animal results are depicted. The number of Ramos B cells are shown in function of the different treatment groups. The stars on top of the graph show which active doses were statistically significant different from the control Nanobody (T017000088 or T017000106) based on the F-tests from the mixed-effects ANOVA analysis. All effects are statistically significant at the 5% level of significance.

Figure 37A:
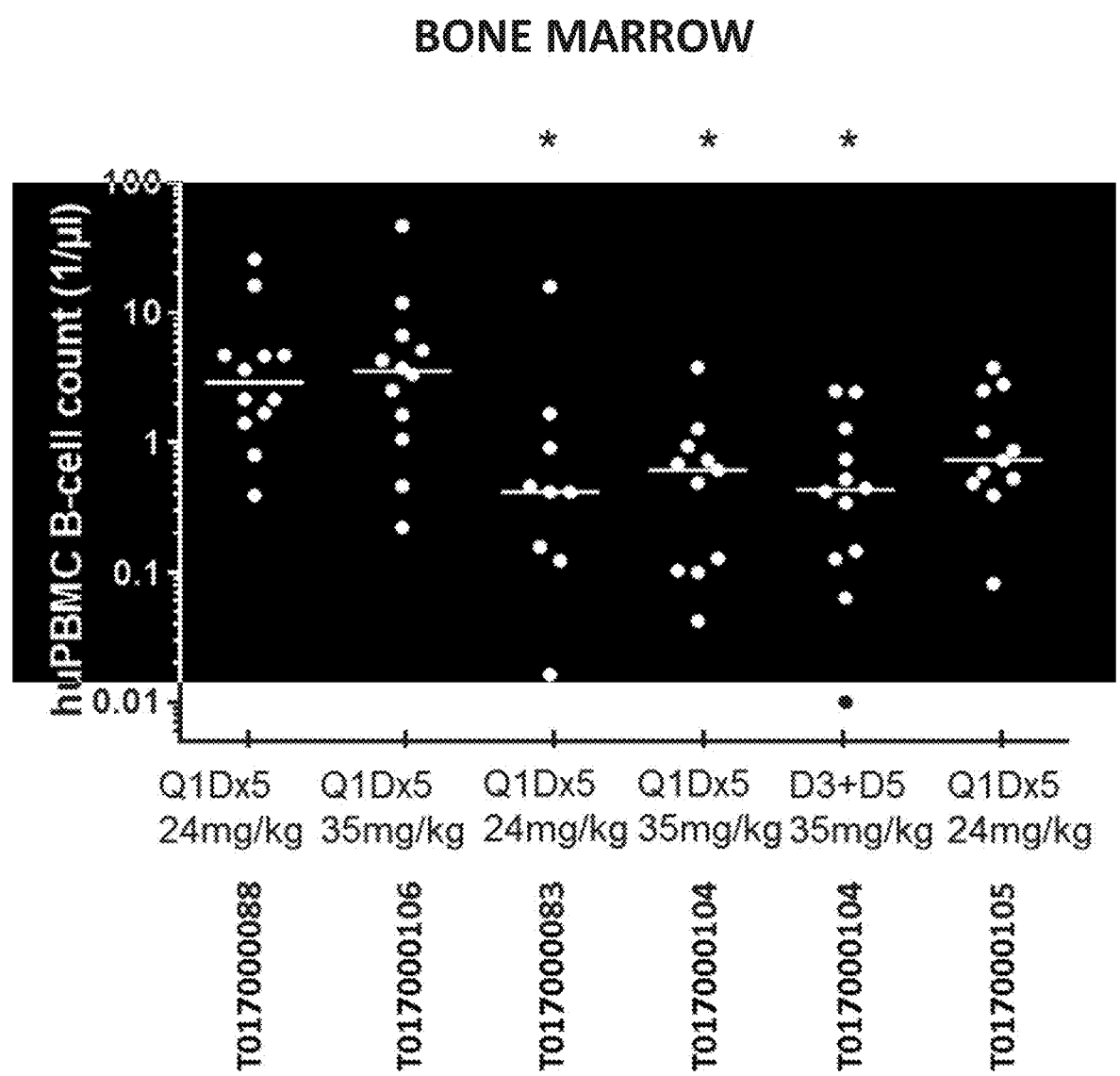
Figure 37B:
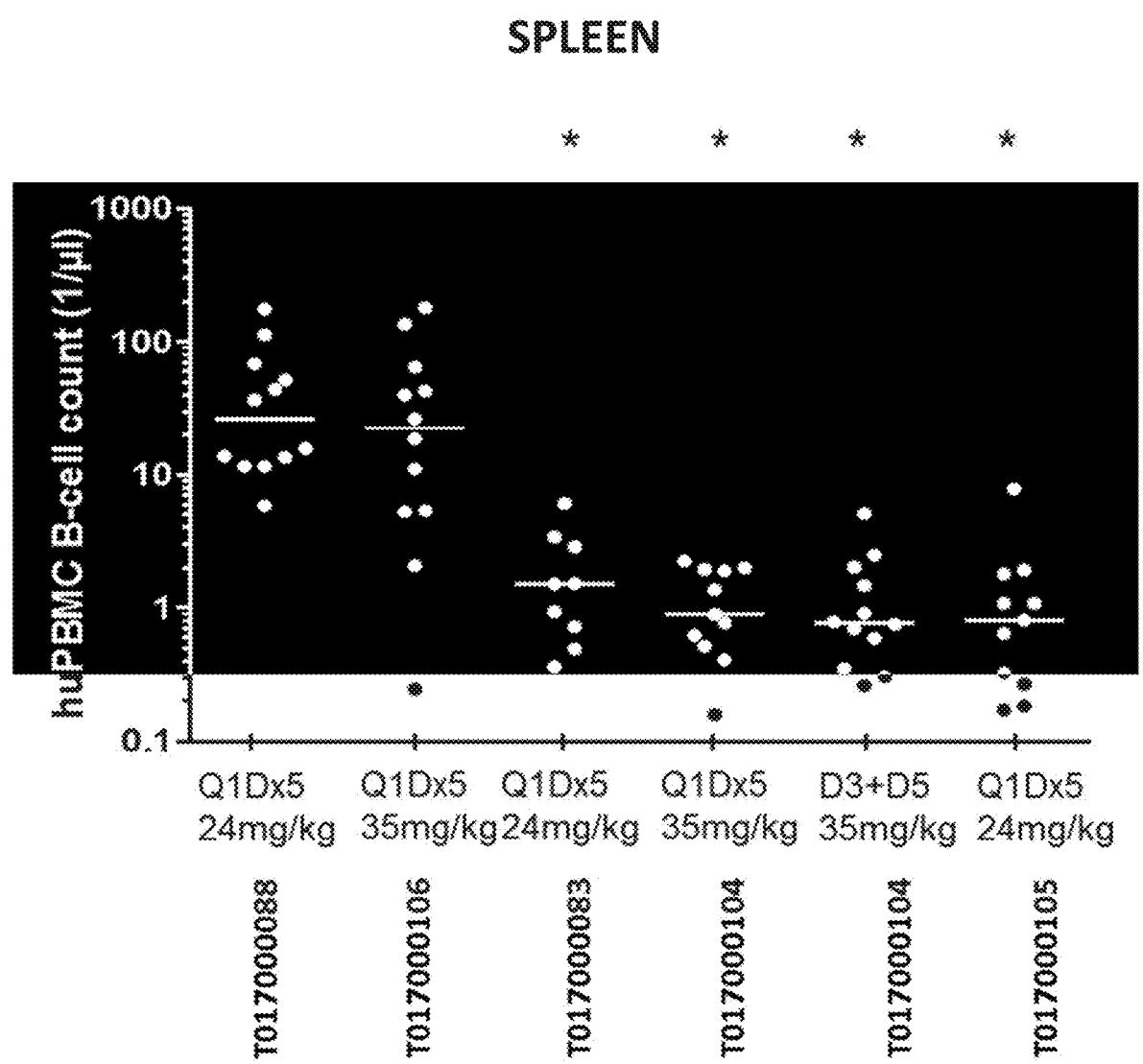

FIGS. 37A-37B: Absolute PBMC derived B cell count on log scale in bone marrow (FIG. 37A) and spleen (FIG. 37B). Individual animal results are depicted. The number of PBMC derived B cells are shown in function of the different treatment groups. The stars on top of the graph show which active doses were statistically significant different from the control Nanobody (T017000088 or T017000106) based on the F-tests from the mixed-effects ANOVA analysis. All effects are statistically significant at the 5% level of significance.

Figure 38A:
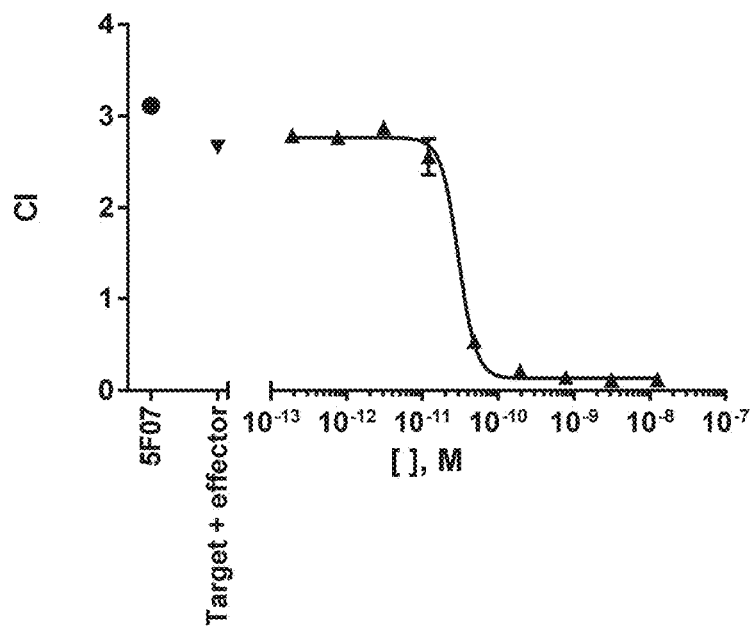
Figure 38B:
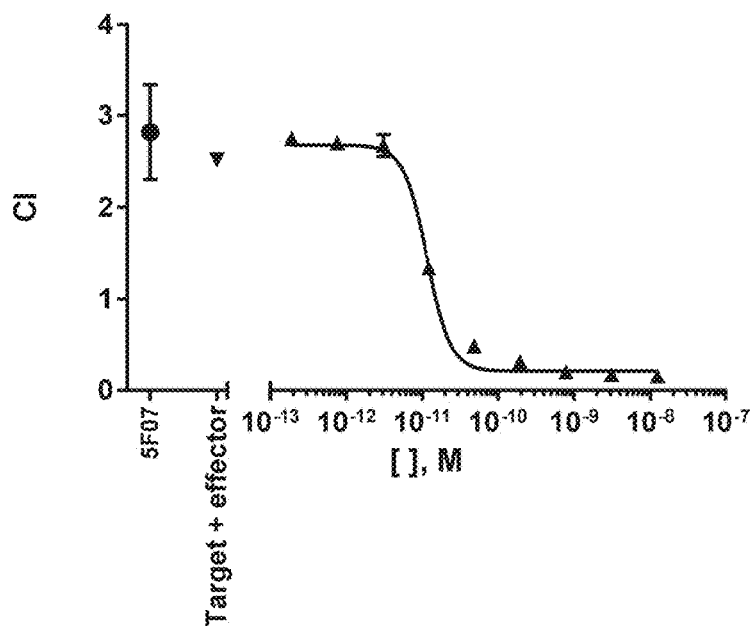
Figure 39A:
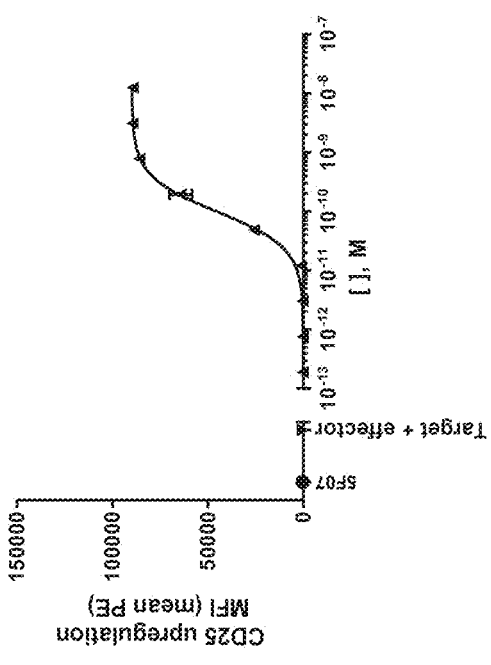
Figure 39D:
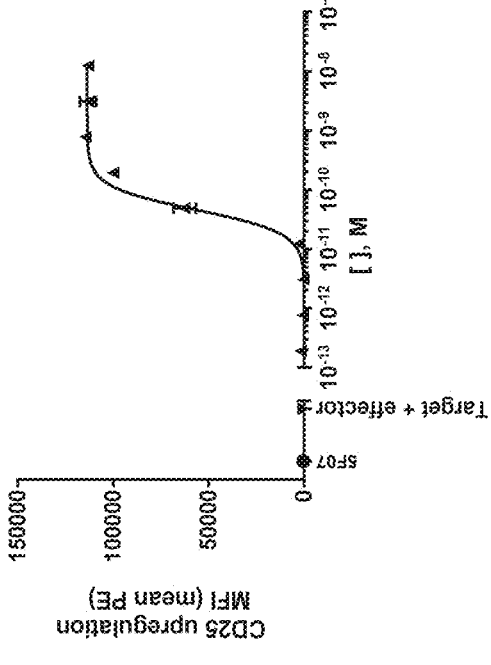
Figure 39B:
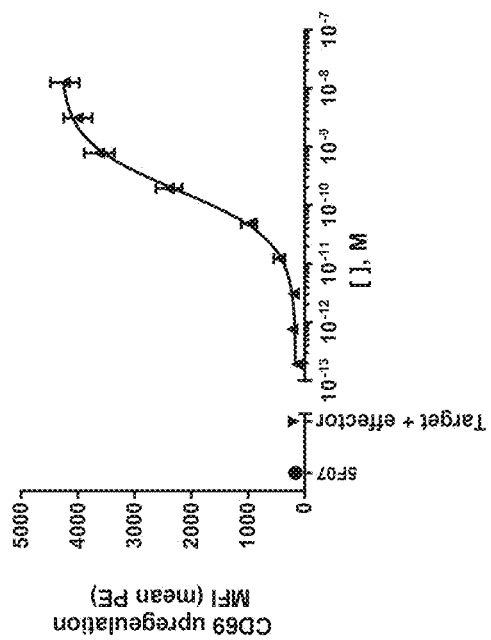
Figure 39E:
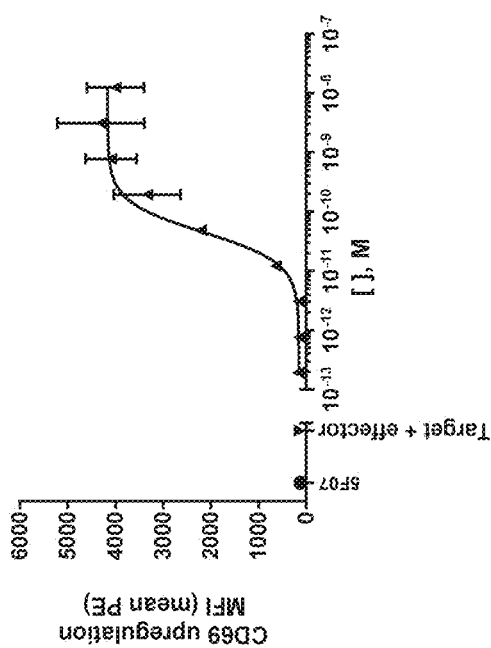

FIGS. 38A-38C: Dose-dependent redirected SKBR3 target cell killing of T017000102 by human effector T cells isolated from donor 932 (FIG. 38A), human CD4+ T cells isolated from donor 941 (FIG. 38B) and human CD8+ T cells isolated from donor 941 (FIG. 38C) in the xCELLigence based assay using an effector to target ratio of 15. The CI after an incubation time of 40 h was plotted against the concentration of the multispecific polypeptide.

FIGS. 39A-39F: Dose-dependent T cell activation of human effector T cells isolated from donor 932 (FIG. 39A, FIG. 39D), human CD4+ T cells isolated from donor 941 (FIG. 39B, FIG. 39E) and human CD8+ T cells isolated from donor 941 (FIG. 39C, FIG. 39F) by T017000102 in a redirected SKBR3 target cell killing setting. Activation was measured by monitoring the CD69 (FIG. 39A, FIG. 39B, FIG. 39C) upregulation and CD25 (FIG. 39D, FIG. 39E, FIG. 39F) upregulation. The mean fluorescence intensity (MFI) was plotted against the concentration.

FIGS. 40A-40F: Dose-dependent cytokine production by human effector T cells isolated from donor 932 (FIG. 40A, FIG. 40D), human CD4+ T cells isolated from donor 941 (FIG. 40B, FIG. 40E) and human CD8+ T cells isolated from donor 941 (FIG. 40C, FIG. 40F) by T017000102 in a redirected SKBR3 target cell killing setting. Human INF-γ production (FIG. 40A, FIG. 40B, FIG. 40C) and human IL-6 (FIG. 40D, FIG. 40E, FIG. 40F) was measured after 72 h of incubation. The measured concentration human INF-γ and human IL-6 (in pg/ml) was plotted against the concentration of the Nanobody.

FIGS. 41A-41D: Dose-dependent binding of HLE construct T017000108 to HER14 (FIG. 41A), LS174T (FIG. 41B), primary human T cells (FIG. 41C) and LoVo cells (FIG. 41D). The mean fluorescence intensity (MFI) was plotted against the concentration.

Figure 42:
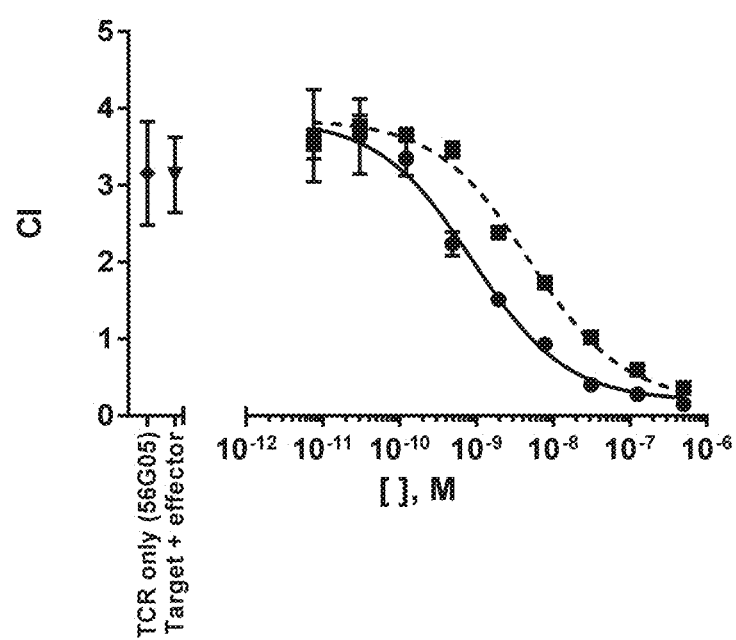

FIG. 42: Dose-dependent redirected LS174T target cell killing of T017000107 (solid line) and T017000108 (dotted line) by human effector T cells in the xCELLigence based assay using an effector to target ratio of 15. The CI after an incubation time of 48 h was plotted against the concentration of the multispecific polypeptides.

DETAILED DESCRIPTION OF THE INVENTION

The present inventors realized that formats bringing T cells and tumour cells together to induce an immune response should comply with various and frequently opposing requirements. The format should be broadly applicable. In particular, the format should preferably be useful in a broad range of patients and preferably also against a broad range of tumours. The format should preferably be safe and only target the intended cells. In addition, the format should preferably be small enough to easily penetrate tissues and tumours, while on the other hand the format should be patient friendly. For instance, the format should have an extended half-life, such that the format is not removed instantaneous upon administration by renal clearance. However, extending the half-life should preferably not introduce off-target activity and side effects or limit the penetration into tissues and tumours. Additionally, it was recognized that tumour cells often create escape mechanisms by the down-regulation of targeted antigens within a therapy. Accordingly, in a further preferred version, the format should simultaneously target multiple antigens.

The present invention realizes at least one of these requirements.

In particular, it was hypothesized that immunoglobulin single variable domains (ISVs) would in principle be ideal candidates, since they are small enough to easily penetrate (tumour) tissue and can be combined with other ISVs as building blocks. Next, ISVs directed against the constant TCR domains should have broad applicability. In contrast to the variable TCR domains, these constant TCR domains display less sequence variability, and consequently should be useful in a broad range of patients.

Unexpectedly, it turned out to be extremely difficult to generate ISVs via immunization in llamas against the constant domains of TCR. Either no significant immune response was mounted, or the so generated ISVs were directed against the variable TCR domains. Only by implementing a rigorously carried out immunization and screening method using different cells and sequences for immunization and boosting as well as using different screening proteins, the inventors were able to isolate ISVs against the constant TCR domains. Although only three clusters of related ISVs were identified, these ISVs had an unexpected range of advantageous features. First, the ISVs were unexpectedly broadly applicable, i.e. the TCR ISVs were able to bind to T cells from different donors with high affinity. Formatted in a multispecific polypeptide, the TCR ISVs enabled tumour cell killing with different tumour associated antigens. Hence, the TCR ISVs can be used against a multitude of cancers. In addition, the multispecific polypeptides comprising the TCR ISVs remained active when bound to albumin. This contributes to a favourable PK profile and patient compliance, while minimizing side effects. The polypeptides of the invention only showed effects when bound both to the T cell and the target cell, which is indicative of its safety.

The present inventors considered that the simultaneous targeting of multiple antigens reduces the probability of generating tumour escape variants, because of which the therapeutic activity of T cell engaging strategy is improved. Multispecific polypeptides are provided which comprise a TCR ISV combined with immunoglobulin single variable domains against different target antigens and/or different epitopes on a particular antigen (biparatopic).

Immunoglobulin sequences, such as antibodies and antigen binding fragments derived there from (e.g., immunoglobulin single variable domains or ISVs) are used to specifically target their respective antigens in research and therapeutic applications. The generation of immunoglobulin single variable domains such as e.g., VHHs or Nanobodies may involve the immunization of an experimental animal such as a Llama, construction of phage libraries from immune tissue, selection of phage displaying antigen binding immunoglobulin single variable domains and screening of said domains and engineered constructs thereof for the desired specificities (WO 94/04678). Alternatively, similar immunoglobulin single variable domains such as e.g., dAbs can be generated by selecting phage displaying antigen binding immunoglobulin single variable domains directly from naive or synthetic libraries and subsequent screening of said domains and engineered constructs thereof for the desired specificities (Ward et al., Nature, 1989, 341: 544-546; Holt et al., Trends Biotechnol., 2003, 21(11):484-490; as well as for example WO 06/030220, WO 06/003388 and other published patent applications of Domantis Ltd.). Unfortunately, the use of monoclonal and/or heavily engineered antibodies also carries a high manufacturing cost and may result in suboptimal tumor penetration compared to other strategies.

The present invention provides multispecific polypeptides that specifically bind to the T cell receptor (TCR), with an unexpected range of advantageous features. First, the polypeptides are easy to manufacture. Moreover, the ISVs are unexpectedly broadly applicable, i.e. the TCR ISVs were able to bind to T cells from different donors with high affinity. Formatted in a multispecific polypeptide, the TCR ISVs enabled tumour cell killing with different tumour associated antigens. In contrast, no killing was observed when the polypeptides were not bound to T cells and target cell which underscores the safety of the polypeptides of the invention. Hence, the TCR ISVs can be used against a multitude of cancers. Moreover, the TCR ISVs can be considered as safe. In addition, the multispecific polypeptides comprising the TCR ISVs remained active when bound to albumin. This will contribute to a favourable PK profile and patient compliance, while minimizing side effects.

Accordingly, the present invention relates to a polypeptide comprising a first and a second immunoglobulin single variable domain (ISV), wherein the first ISV has high affinity for/binds to the constant domain of the T cell receptor (TCR) and the second ISV has high affinity for/binds to an antigen on a cell (target cell), preferably a tumour cell. The antigen is preferably specific for said target cell, such as e.g. a tumour associated antigen (TAA). The multispecific polypeptide of the invention directs the T cell to the cell, e.g. a tumour cell and induces T cell activation in order to allow said T cell to inhibit or kill said target cell, e.g. said tumour cell.

Definitions:
a) Unless indicated or defined otherwise, all terms used have their usual meaning in the art, which will be clear to the skilled person. Reference is for example made to the standard handbooks mentioned in paragraph a) on page 46 of WO 08/020079.
b) The term "immunoglobulin single variable domain", interchangeably used with "single variable domain" and "ISV", defines molecules wherein the antigen binding site is present on, and formed by, a single immunoglobulin domain. This sets immunoglobulin single variable domains apart from "conventional" immunoglobulins or their fragments (such as Fabs, scFvs, etc.), wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation. In contrast, the binding site of an immunoglobulin single variable domain is formed by a single VH or VL domain. Hence, the antigen binding site of an immunoglobulin single variable domain is formed by no more than three CDRs.

The terms "immunoglobulin single variable domain", "single variable domain", and "ISV" hence do not comprise conventional immunoglobulins or their fragments which require interaction of at least two variable domains for the formation of an antigen binding site. However, these terms do comprise fragments of conventional immunoglobulins wherein the antigen binding site is formed by a single variable domain.

The term "immunoglobulin single variable domain" or "ISV" includes (without being limiting) antigen-binding domains or fragments such as $V_{HH}$ domains or $V_H$ or $V_L$ domains, respectively. The terms antigen-binding molecules or antigen-binding protein are used interchangeably and include also the term Nanobodies. The immunoglobulin single variable domains can be light chain variable domain sequences (e.g., a $V_L$-sequence), or heavy chain variable domain sequences (e.g., a $V_H$-sequence); more specifically, they can be heavy chain variable domain sequences that are derived from a conventional four-chain antibody or heavy chain variable domain sequences that are derived from a heavy chain antibody. Accordingly, the immunoglobulin single variable domains can be domain antibodies, or immunoglobulin sequences that are suitable for use as domain antibodies, single domain antibodies, or immunoglobulin sequences that are suitable for use as single domain antibodies, "dAbs", or immunoglobulin sequences that are suitable for use as dAbs, or Nanobodies, including but not limited to $V_{HH}$ sequences, humanized VHH sequences or camelized VH sequences. The invention includes immunoglobulin sequences of different origin, comprising mouse, rat, rabbit, donkey, human and camelid immunoglobulin sequences. The immunoglobulin single variable domain includes fully human, humanized, otherwise sequence optimized or chimeric immunoglobulin sequences. The immunoglobulin single variable domain and structure of an immunoglobulin single variable domain can be considered—without however being limited thereto—to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively. It is noted that the terms Nanobody or Nanobodies are registered trademarks of Ablynx N.V. and thus may also be referred to as Nanobody or Nanobodies, respectively.

c) Unless indicated otherwise, the terms "immunoglobulin sequence", "sequence", "nucleotide sequence" and "nucleic acid" are as described in paragraph b) on page 46 of WO 08/020079.
d) Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta 2006 (Adv. Drug Deliv. Rev. 58 (5-6):640-656), Levin and Weiss 2006 (Mol. Biosyst. 2(1):49-57), Irving et al. 2005 (J. Immunol. Methods 248(1-2):31-45), Schmitz et al. 2000 (Placenta 21 Suppl. A: 5106-112, Gonzales et al. 2005 (Tumour Biol. 26(1):31-43), which describe techniques for protein engineering, such as affinity maturation and other techniques for improving the specificity and other desired properties of proteins such as immunoglobulins.
e) Amino acid residues will be indicated according to the standard three-letter or one-letter amino acid code. Reference is made to Table A-2 on page 48 of the International application WO 08/020079 of Ablynx N.V. entitled "Immunoglobulin single variable domains directed against IL-6R and polypeptides comprising the same for the treatment of diseases and disorders associated with 11-6 mediated signalling".
f) For the purposes of comparing two or more nucleotide sequences, the percentage of "sequence identity" between a first nucleotide sequence and a second nucleotide sequence may be calculated or determined as described in paragraph e) on page 49 of WO 08/020079 (incorporated herein by reference), such as by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position); or using a suitable computer algorithm or technique, again as described in paragraph e) on pages 49 of WO 08/020079 (incorporated herein by reference).

g) For the purposes of comparing two or more immunoglobulin single variable domains or other amino acid sequences such e.g. the polypeptides of the invention etc., the percentage of "sequence identity" between a first amino acid sequence and a second amino acid sequence (also referred to herein as "amino acid identity") may be calculated or determined as described in paragraph f) on pages 49 and 50 of WO 08/020079 (incorporated herein by reference), such as by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e., as an "amino acid difference" as defined herein; or using a suitable computer algorithm or technique, again as described in paragraph f) on pages 49 and 50 of WO 08/020079 (incorporated herein by reference).

Also, in determining the degree of sequence identity between two immunoglobulin single variable domains, the skilled person may take into account so-called "conservative" amino acid substitutions, as described on page 50 of WO 08/020079.

Any amino acid substitutions applied to the polypeptides described herein may also be based on the analysis of the frequencies of amino acid variations between homologous proteins of different species developed by Schulz et al. 1978 (Principles of Protein Structure, Springer-Verlag), on the analyses of structure forming potentials developed by Chou and Fasman 1975 (Biochemistry 13: 211) and 1978 (Adv. Enzymol. 47: 45-149), and on the analysis of hydrophobicity patterns in proteins developed by Eisenberg et al. 1984 (Proc. Natl. Acad. Sci. USA 81: 140-144), Kyte & Doolittle 1981 (J Molec. Biol. 157: 105-132), and Goldman et al. 1986 (Ann. Rev. Biophys. Chem. 15: 321-353), all incorporated herein in their entirety by reference. Information on the primary, secondary and tertiary structure of Nanobodies is given in the description herein and in the general background art cited above. Also, for this purpose, the crystal structure of a $V_{HH}$ domain from a llama is for example given by Desmyter et al. 1996 (Nature Structural Biology, 3: 803), Spinelli et al. 1996 (Natural Structural Biology 3: 752-757), and Decanniere et al. 1999 (Structure, 7: 361). Further information about some of the amino acid residues that in conventional $V_H$ domains form the $V_H/V_L$ interface and potential camelizing substitutions on these positions can be found in the prior art cited above.

h) Immunoglobulin single variable domains and nucleic acid sequences are said to be "exactly the some" if they have 100% sequence identity (as defined herein) over their entire length.

i) When comparing two immunoglobulin single variable domains, the term "amino acid difference" refers to an insertion, deletion or substitution of a single amino acid residue on a position of the first sequence, compared to the second sequence; it being understood that two immunoglobulin single variable domains can contain one, two or more such amino acid differences.

j) When a nucleotide sequence or amino acid sequence is said to "comprise" another nucleotide sequence or amino acid sequence, respectively, or to "essentially consist of" another nucleotide sequence or amino acid sequence, this has the meaning given in paragraph i) on pages 51-52 of WO 08/020079.

k) The term "in essentially isolated form" has the meaning given to it in paragraph j) on pages 52 and 53 of WO 08/020079.

l) The terms "domain" and "binding domain" have the meanings given to it in paragraph k) on page 53 of WO 08/020079.

m) The terms "antigenic determinant" and "epitope", which may also be used interchangeably herein, have the meanings given to it in paragraph I) on page 53 of WO 08/020079.

n) As further described in paragraph m) on page 53 of WO 08/020079, an amino acid sequence (such as an antibody, a polypeptide of the invention, or generally an antigen-binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

o) The term "specificity" refers to the number of different types of antigens or antigenic determinants to which a particular antigen-binding molecule or antigen-binding protein (such as an ISV, Nanobody or a polypeptide of the invention) can bind. The specificity of an antigen-binding protein can be determined based on affinity and/or avidity. The affinity, represented by the equilibrium constant for the dissociation of an antigen with an antigen-binding protein ($K_D$ or KD), is a measure for the binding strength between an antigenic determinant, i.e. the target, and an antigen-binding site on the antigen-binding protein, i.e. the ISV or Nanobody: the lesser the value of the $K_D$, the stronger the binding strength between an antigenic determinant and the antigen-binding molecule (alternatively, the affinity can also be expressed as the affinity constant ($K_A$), which is $1/K_D$). As will be clear to the skilled person (for example on the basis of the further disclosure herein), affinity can be determined in a manner known per se, depending on the specific antigen of interest.

Avidity is the affinity of the polypeptide, i.e. the ligand is able to bind via two (or more) pharmacophores (ISV) in which the multiple interactions synergize to enhance the "apparent" affinity. Avidity is the measure of the strength of binding between the polypeptide of the invention and the pertinent antigens. The polypeptide of the invention is able to bind via its two (or more) building blocks, such as ISVs or Nanobodies, to the at least two targets, in which the multiple interactions, e.g. the first building block, ISV or Nanobody binding to the first target and the second building block, ISV, or Nanobody binding to the second target, synergize to enhance the "apparent" affinity. Avidity is related to both the affinity between an antigenic determinant and its antigen binding site on the antigen-binding molecule and the number of pertinent binding sites present on the antigen-binding molecules. For example, and without limitation, polypeptides that contain two or more building blocks, such as ISVs or Nanobodies directed against different targets on a cell may (and usually will) bind with higher avidity than each of the individual monomers or individual building blocks, such as, for instance, the monovalent ISVs or Nanobodies, comprised in the polypeptides of the invention.

Any $K_D$ value greater than $10^4$ mol/liter (or any $K_A$ value lower than $10^4$ $M^{-1}$) liters/mol is generally considered to indicate non-specific binding.

The polypeptides of the invention comprise a first and a second building block, e.g. a first and a second ISV, or a first and a second Nanobody. Preferably the affinity of each building block, e.g. ISV or Nanobody, is determined individually. In other words, the affinity is determined for the monovalent building block, ISV or Nanobody, independent of avidity effects due to the other building block, ISV or Nanobody, which might or might not be present. The affinity for a monovalent building block, ISV or Nanobody can be determined on the monovalent building block, ISV or Nanobody per se, i.e. when said monovalent building block, ISV or Nanobody is not comprised in the polypeptide of the invention. In the alternative or in addition, the affinity for a monovalent building block, ISV or Nanobody can be determined on one target while the other target is absent.

The binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

The dissociation constant may be the actual or apparent dissociation constant, as will be clear to the skilled person. Methods for determining the dissociation constant will be clear to the skilled person, and for example include the techniques mentioned herein. In this respect, it will also be clear that it may not be possible to measure dissociation constants of more than $10^{-4}$ moles/liter or $10^{-3}$ moles/liter (e.g., of $10^{-2}$ moles/liter). Optionally, as will also be clear to the skilled person, the (actual or apparent) dissociation constant may be calculated on the basis of the (actual or apparent) association constant ($K_A$), by means of the relationship $[K_D=1/K_A]$.

The affinity denotes the strength or stability of a molecular interaction. The affinity is commonly given as by the $K_D$, or dissociation constant, which has units of mol/liter (or M). The affinity can also be expressed as an association constant, $K_A$, which equals $1/K_D$ and has units of $(mol/liter)^{-1}$ (or $M^{-1}$). In the present specification, the stability of the interaction between two molecules (such as an amino acid sequence, Nanobody or polypeptide of the invention and its intended target) will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$ value characterizes the strength of a molecular interaction also in a thermodynamic sense as it is related to the free energy (DG) of binding by the well known relation $DG=RT.ln(K_D)$ (equivalently $DG=-RT.ln(K_A)$), where R equals the gas constant, T equals the absolute temperature and ln denotes the natural logarithm.

The $K_D$ for biological interactions which are considered meaningful (e.g. specific) are typically in the range of $10^{-10}M$ (0.1 nM) to $10^{-5}M$ (10000 nM). The stronger an interaction is, the lower is its $K_D$.

The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has units $s^{-1}$ (where s is the SI unit notation of second). The on-rate $k_{on}$ has units $M^{-1}s^{-1}$. The on-rate may vary between $10^2$ $M^{-1}s^{-1}$ to about $10^7$ $M^{-1}s^{-1}$, approaching the diffusion-limited association rate constant for biomolecular interactions. The off-rate is related to the half-life of a given molecular interaction by the relation $t_{1/2}=ln(2)/k_{off}$. The off-rate may vary between $10^{-6}s^{-1}$ (near irreversible complex with a $t_{1/2}$ of multiple days) to $1s^{-1}$ ($t_{1/2}=0.69s$).

The affinity of a molecular interaction between two molecules can be measured via different techniques known per se, such as the well-known surface plasmon resonance (SPR) biosensor technique (see for example Ober et al. 2001, Intern. Immunology, 13: 1551-1559). The term "surface plasmon resonance", as used herein, refers to an optical phenomenon that allows for the analysis of real-time biospecific interactions by detection of alterations in protein concentrations within a biosensor matrix, where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIAcore® system (BIAcore International AB, a GE Healthcare company, Uppsala, Sweden and Piscataway, N.J.). For further descriptions, see Jonsson et al. 1993 (Ann. Biol. Clin. 51: 19-26), Jonsson et al. 1991 (Biotechniques 11: 620-627), Johnsson, et al. 1995 (J. Mol. Recognit. 8: 125-131), and Johnnson, et al. 1991 (Anal. Biochem. 198: 268-277).

Another well-known biosensor technique to determine affinities of biomolecular interactions is bio-layer interferometry (BLI) (see for example Abdiche et al. 2008, Anal. Biochem. 377: 209-217). The term "bio-layer Interferometry" or "BLI", as used herein, refers to a label-free optical technique that analyzes the interference pattern of light reflected from two surfaces: an internal reference layer (reference beam) and a layer of immobilized protein on the biosensor tip (signal beam). A change in the number of molecules bound to the tip of the biosensor causes a shift in the interference pattern, reported as a wavelength shift (nm), the magnitude of which is a direct measure of the number of molecules bound to the biosensor tip surface. Since the interactions can be measured in real-time, association and dissociation rates and affinities can be determined. BLI can for example be performed using the well-known Octet® Systems (ForteBio, a division of Pall Life Sciences, Menlo Park, USA).

Alternatively, affinities can be measured in Kinetic Exclusion Assay (KinExA) (see for example Drake et al. 2004, Anal. Biochem., 328: 35-43), using the KinExA® platform (Sapidyne Instruments Inc, Boise, USA). The term "KinExA", as used herein, refers to a solution-based method to measure true equilibrium binding affinity and kinetics of unmodified molecules. Equilibrated solutions of an antibody/antigen complex are passed over a column with beads precoated with antigen (or antibody), allowing the free antibody (or antigen) to bind to the coated molecule. Detection of the antibody (or antigen) thus captured is accomplished with a fluorescently labeled protein binding the antibody (or antigen).

It will also be clear to the skilled person that the measured $K_D$ may correspond to the apparent $K_D$ if the measuring process somehow influences the intrinsic binding affinity of the implied molecules for example by artefacts related to the coating on the biosensor of one molecule. Also, an apparent $K_D$ may be measured if one molecule contains more than one recognition site for the other molecule. In such situation the measured affinity may be affected by the avidity of the interaction by the two molecules.

Another approach that may be used to assess affinity is the 2-step ELISA (Enzyme-Linked Immunosorbent Assay) procedure of Friguet et al. 1985 (J. Immunol. Methods, 77: 305-19). This method establishes a solution phase binding equilibrium measurement and avoids possible artefacts relating to adsorption of one of the molecules on a support such as plastic.

However, the accurate measurement of $K_D$ may be quite labour-intensive, and as consequence, often apparent $K_D$ values are determined to assess the binding strength of two molecules. It should be noted that as long as all measurements are made in a consistent way (e.g. keeping the assay conditions unchanged) apparent $K_D$ measurements can be used as an approximation of the true $K_D$ and hence, in the present document, $K_D$ and apparent $K_D$ should be treated with equal importance or relevance.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an IC50 value is obtained corresponding to the concentration of A at which the signal measured for C in absence of A is halved. Provided $K_{D\ ref}$, the $K_D$ of the reference molecule, is known, as well as the total concentration $c_{ref}$ of the reference molecule, the apparent $K_D$ for the interaction A-B can be obtained from following formula: $K_D=IC50/(1+c_{ref}/K_{D\ ref})$. Note that if $c_{ref} \ll K_{D\ ref}$, $K_D \approx IC50$. Provided the measurement of the IC50 is performed in a consistent way (e.g. keeping $c_{ref}$ fixed) for the binders that are compared, the strength or stability of a molecular interaction can be assessed by the IC50 and this measurement is judged as equivalent to $K_D$ or to apparent $K_D$ throughout this text.

p) The half-life of an amino acid sequence, compound or polypeptide of the invention can generally be defined as described in paragraph o) on page 57 of WO 08/020079 and as mentioned therein refers to the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally be as described in paragraph o) on page 57 of WO 08/020079. As also mentioned in paragraph o) on page 57 of WO 08/020079, the half-life can be expressed using parameters such as the t1/2-alpha, t1/2-beta and the area under the curve (AUC). Reference is for example made to the Experimental Part below, as well as to the standard handbooks, such as Kenneth et al. 1996 (Chemical Stability of Pharmaceuticals: A Handbook for Pharmacists) and Peters et al. 1996 (Pharmacokinete analysis: A Practical Approach). Reference is also made to Gibaldi & Perron 1982 (Pharmacokinetics, Dekker M, 2nd Rev. edition). The terms "increase in half-life" or "increased half-life" are as defined in paragraph o) on page 57 of WO 08/020079 and in particular refer to an increase in the t1/2-beta, either with or without an increase in the t1/2-alpha and/or the AUC or both.

q) In respect of a target or antigen, the term "interaction site" on the target or antigen means a site, epitope, antigenic determinant, part, domain or stretch of amino acid residues on the target or antigen that is a site for binding to a ligand, receptor or other binding partner, a catalytic site, a cleavage site, a site for allosteric interaction, a site involved in multimerisation (such as homomerization or heterodimerization) of the target or antigen; or any other site, epitope, antigenic determinant, part, domain or stretch of amino acid residues on the target or antigen that is involved in a biological action or mechanism of the target or antigen. More generally, an "interaction site" can be any site, epitope, antigenic determinant, part, domain or stretch of amino acid residues on the target or antigen to which an amino acid sequence or polypeptide of the invention can bind such that the target or antigen (and/or any pathway, interaction, signalling, biological mechanism or biological effect in which the target or antigen is involved) is modulated.

r) An immunoglobulin single variable domain or polypeptide is said to be "specific for" a first target or antigen compared to a second target or antigen when it binds to the first antigen with an affinity/avidity (as described above, and suitably expressed as a $K_D$ value, $K_A$ value, $K_{off}$ rate and/or $K_{on}$ rate) that is at least 10 times, such as at least 100 times, and preferably at least 1000 times, and up to 10.000 times or more better than the affinity with which said amino acid sequence or polypeptide binds to the second target or polypeptide. For example, the first antigen may bind to the target or antigen with a $K_D$ value that is at least 10 times less, such as at least 100 times less, and preferably at least 1000 times less, such as 10.000 times less or even less than that, than the $K_D$ with which said amino acid sequence or polypeptide binds to the second target or polypeptide. Preferably, when an immunoglobulin single variable domain or polypeptide is "specific for" a first target or antigen compared to a second target or antigen, it is directed against (as defined herein) said first target or antigen, but not directed against said second target or antigen.

s) The terms "cross-block", "cross-blocked" and "cross-blocking" are used interchangeably herein to mean the ability of an immunoglobulin single variable domain or polypeptide to interfere with the binding of the natural ligand to its receptor(s). The extent to which an immunoglobulin single variable domain or polypeptide of the invention is able to interfere with the binding of another compound such as the natural ligand to its target and therefore whether it can be said to cross-block according to the invention, can be determined using competition binding assays. One particularly suitable quantitative cross-blocking assay uses a FACS- or an ELISA-based approach or Alphascreen to measure competition between the labelled (e.g., His tagged or biotinylated) immunoglobulin single variable domain or polypeptide according to the invention and the other binding agent in terms of their binding to the target. The experimental part generally describes suitable FACS-, ELISA- or Alphascreen-displacement-based assays for determining whether a binding molecule cross-blocks or is capable of cross-blocking an immunoglobulin single variable domain or polypeptide according to the invention. It will be appreciated that the assay can be used with any of the immunoglobulin single variable domains or other binding agents described herein. Thus, in general, a cross-blocking amino acid sequence or other binding agent according to the invention is for example one which will bind to the target in the above cross-blocking assay such that, during the assay and in the presence of a second amino acid sequence or other binding agent of the invention, the recorded displacement of the immunoglobulin single variable domain or polypeptide according to the invention is between 60% and 100% (e.g., in ELISA/Alphascreen based competition assay) or between 80% to 100% (e.g., in FACS based competition assay) of the maximum theoretical displacement (e.g. displacement by cold (e.g., unlabeled) immunoglobulin single variable domain or polypeptide that needs to be cross-blocked) by the to be tested potentially cross-blocking agent that is present in an amount of 0.01 mM or less (cross-blocking agent may be another conventional monoclonal antibody such as IgG, classic monovalent antibody fragments (Fab, scFv) and engineered variants (e.g., diabodies, triabodies, minibodies, VHHs, dAbs, VHs, VLs)).

t) An amino acid sequence such as e.g. an immunoglobulin single variable domain or polypeptide according to the invention is said to be a "VHH1 type immunoglobulin single variable domain" or "VHH type 1 sequence", if said VHH1 type immunoglobulin single variable domain or VHH type 1 sequence has 85% identity (using the VHH1 consensus sequence as the query sequence and use the blast algorithm with standard setting, i.e., blosom62 scoring matrix) to the VHH1 consensus sequence (QVQLVESGGGLVQPGGSLRLS-CAASGFTLDYYAIGWFRQAPGKEREGVSCISSSD GSTYYADSVKGRFTISRD-NAKNTVYLQMNSLKPEDTAVYYCAA) (SEQ ID NO: 483), and mandatorily has a cysteine in position 50, i.e., C50 (using Kabat numbering).

u) An amino acid sequence such as e.g., an immunoglobulin single variable domain or polypeptide according to the invention is said to be "cross-reactive" for two different antigens or antigenic determinants (such as serum albumin from two different species of mammal, such as human serum albumin and cynomolgus monkey serum albumin) if it is specific for (as defined herein) both these different antigens or antigenic determinants.

v) As further described in paragraph q) on pages 58 and 59 of WO 08/020079 (incorporated herein by reference), the amino acid residues of an immunoglobulin single variable domain are numbered according to the general numbering for $V_H$ domains given by Kabat et al. ("Sequence of proteins of immunological interest", US Public Health Services, NIH Bethesda, Md., Publication No. 91), as applied to $V_{HH}$ domains from Camelids in the article of Riechmann and Muyldermans, 2000 (J. Immunol. Methods 240 (1-2): 185-195; see for example FIG. 2 of this publication). It should be noted that—as is well known in the art for $V_H$ domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. The total number of amino acid residues in a VH domain and a VHH domain will usually be in the range of from 110 to 120, often between 112 and 115. It should however be noted that smaller and longer sequences may also be suitable for the purposes described herein.

Determination of CDR regions may also be done according to different methods. In the CDR determination according to Kabat, FR1 of an immunoglobulin single variable domain comprises the amino acid residues at positions 1-30, CDR1 of an immunoglobulin single variable domain comprises the amino acid residues at positions 31-35, FR2 of an immunoglobulin single variable domain comprises the amino acids at positions 36-49, CDR2 of an immunoglobulin single variable domain comprises the amino acid residues at positions 50-65, FR3 of an immunoglobulin single variable domain comprises the amino acid residues at positions 66-94, CDR3 of an immunoglobulin single variable domain comprises the amino acid residues at positions 95-102, and FR4 of an immunoglobulin single variable domain comprises the amino acid residues at positions 103-113.

In the present application, however, unless indicated otherwise, CDR sequences were determined according to Kontermann and Dubel (Eds. 2010, Antibody Engineering, vol 2, Springer Verlag Heidelberg Berlin, Martin, Chapter 3, pp. 33-51). According to this method, FR1 comprises the amino acid residues at positions 1-25, CDR1 comprises the amino acid residues at positions 26-35, FR2 comprises the amino acids at positions 36-49, CDR2 comprises the amino acid residues at positions 50-58, FR3 comprises the amino acid residues at positions 59-94, CDR3 comprises the amino acid residues at positions 95-102, and FR4 comprises the amino acid residues at positions 103-113.

w) The Figures, Sequence Listing and the Experimental Part/Examples are only given to further illustrate the invention and should not be interpreted or construed as limiting the scope of the invention and/or of the appended claims in any way, unless explicitly indicated otherwise herein.

x) The half maximal inhibitory concentration (IC50) is a measure of the effectiveness of a compound in inhibiting a biological or biochemical function, e.g. a pharmacological effect. This quantitative measure indicates how much of the ISV or Nanobody (inhibitor) is needed to inhibit a given biological process (or component of a process, i.e. an enzyme, cell, cell receptor, chemotaxis, anaplasia, metastasis, invasiveness, etc) by half. In other words, it is the half maximal (50%) inhibitory concentration (IC) of a substance (50% IC, or IC50). The IC50 of a drug can be determined by constructing a dose-response curve and examining the effect of different concentrations of antagonist such as the ISV or Nanobody of the invention on reversing agonist activity. IC50 values can be calculated for a given antagonist such as the ISV or Nanobody of the invention by determining the concentration needed to inhibit half of the maximum biological response of the agonist.

The term half maximal effective concentration (EC50) refers to the concentration of a compound which induces a response halfway between the baseline and maximum after a specified exposure time. In the present context it is used as a measure of a polypeptide's, ISV's or Nanobody's potency. The EC50 of a graded dose response curve represents the concentration of a compound where 50% of its maximal effect is observed. Concentration is preferably expressed in molar units.

In biological systems, small changes in ligand concentration typically result in rapid changes in response, following a sigmoidal function. The inflection point at which the increase in response with increasing ligand concentration begins to slow is the EC50. This can be determined mathematically by derivation of the best-fit line. Relying on a graph for estimation is convenient in most cases. In case the EC50 is provided in the examples section, the experiments were designed to reflect the KD as accurate as possible. In other words, the EC50 values may then be considered as KD values. The term "average KD" relates to the average KD value obtained in at least 1, but preferably more than 1, such as at least 2 experiments. The term "average" refers to the mathematical term "average" (sums of data divided by the number of items in the data).

It is also related to IC50 which is a measure of a compound's inhibition (50% inhibition). For competition binding assays and functional antagonist assays, IC50 is the most common summary measure of the dose-response curve. For agonist/stimulator assays the most common summary measure is the EC50.

y) It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 15%, more preferably within 10%, and most preferably within 5% of a given value or range.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

The present invention relates to a polypeptide comprising at least a first and at least one further immunoglobulin single variable domain (ISV), wherein said at least first ISV has high affinity for/binds to the constant domain of the T cell receptor (TCR) and said at least one further ISV has high affinity for/binds to an antigen on a target cell.

Typically, the multispecific polypeptides of the invention combine high affinity antigen recognition on the target cell with T cell activation, resulting in an activation that is independent of the T cells' natural specificity. The mode of action of the binding molecules that bind both to a cell surface molecule on a target cell such as a tumour antigen and to the T cell TCR is commonly known. Bringing a T cell in close vicinity to a target cell, i.e., engaging said T cell and clustering of the TCR complex results in killing of the target cell by the T cell. In the present invention this process is exploited in fighting against proliferative disease, inflammatory disease, infectious disease and autoimmune disease. Generally T cells are equipped with granules containing a deadly combination of pore-forming proteins, called perforins, and cell death-inducing proteases, called granzymes. Preferably, these proteins are delivered into target cells via a cytolytic synapse that forms if T cells are in close vicinity with a target cell that is aimed to be killed. Normally, close vicinity between a T cell and a target cell is achieved by the T cell binding to an MHC/peptide complex using its matching T cell receptor. The polypeptides of the invention bring a T cell into such close vicinity to a target cell in the absence of T cell receptor/MHC interaction.

Accordingly, the present invention relates to a polypeptide as described herein, wherein said polypeptide directs the T cell to the target cell.

With one arm (first ISV), the multispecific polypeptide has high affinity for/binds to the constant domain of the TCR subunit, a protein component of the signal-transducing complex of the T cell receptor on T cells. With another arm (second ISV and/or third ISV, etc.), the multispecific polypeptide recognizes, has high affinity for/binds an antigen(s) on target cells. Preferably, T cell activation is only seen when the multispecific polypeptides are presented to T cells on the surface of target cells. Antigen dependence on target cells for activation results in a favourable safety profile. In an embodiment, the multispecific polypeptides transiently tether T cells and target cells. Preferably, the multispecific polypeptide can induce resting polyclonal T cells, such as $CD4^+$ and/or $CD8^+$ T cells into activation, for highly potent redirected lysis of target cells. Preferably, the T cell is directed to a next target cell after lysis of the first target cell.

Proteins and polypeptides that comprise or essentially consist of two or more immunoglobulin single variable domains (such as at least two immunoglobulin single variable domains of the invention) will be referred to herein as "multivalent" proteins or polypeptides or as "multivalent constructs". Some non-limiting examples of such multivalent constructs will become clear from the further description herein. The polypeptides of the invention are "multivalent", i.e. comprising two or more building blocks or ISVs of which at least the first building block, ISV or Nanobody and the second building block, ISV or Nanobody are different, and directed against different targets, such as antigens or antigenic determinants. Polypeptides of the invention that contain at least two building blocks, ISVs or Nanobodies, in which at least one building block, ISV or Nanobody is directed against a first antigen (i.e., against the first target, such as e.g. the constant domain of a TCR) and at least one building block, ISV or Nanobody is directed against a second antigen (i.e., against the second target which is different from the first target, such as e.g. a TAA, such as CD20 or HER2), will also be referred to as "multispecific" polypeptides of the invention, and the building blocks, ISVs or Nanobodies present in such polypeptides will also be referred to herein as being in a "multivalent format" or "multispecific format". Thus, for example, a "bispecific" polypeptide of the invention is a polypeptide that comprises at least one building block, ISV or Nanobody directed against a first target (e.g. TCR) and at least one further building block, ISV or Nanobody directed against a second target (i.e., directed against a second target different from said first target, such as e.g. a TAA, e.g. CD20 or HER2), whereas a "trispecific" polypeptide of the invention is a polypeptide that comprises at least one building block, ISV or Nanobody directed against a first target (e.g., TCR), a second building block, ISV or Nanobody directed against a second target different from said first target (e.g. a TAA, e.g. CD20 or HER2) and at least one further building block, ISV or Nanobody directed against a third antigen (i.e., different from both the first and the second target, such as another TAA); etc. As will be clear from the description, the invention is not limited to bispecific polypeptides, in the sense that a multispecific polypeptide of the invention may comprise at least a first building block, ISV or Nanobody against a first target, a second building block, ISV or Nanobody against a second target and any number of building blocks, ISVs or Nanobodies directed against one or more targets, which may be the same or different from the first and/or second target, respectively. The building blocks, ISVs or Nanobodies can optionally be linked via linker sequences.

The terms bispecific polypeptide, bispecific format, bispecific construct, bispecific Nanobody construct, bispecific and bispecific antibody are used interchangeably herein.

As will be clear from the further description above and herein, the immunoglobulin single variable domains of the invention can be used as "building blocks" to form polypeptides of the invention, e.g., by suitably combining them with other groups, residues, moieties or binding units, in order to form compounds or constructs as described herein (such as, without limitations, the bi-/tri-/tetra-/multivalent and bi-/tri-/tetra-/multispecific polypeptides of the invention described herein) which combine within one molecule one or more desired properties or biological functions.

It will be appreciated (as is also demonstrated in the Example section) that the ISV binding TCR and the ISV binding the antigen on a target cell can be positioned in any order in the polypeptide of the invention. More particularly, in one embodiment, the ISV binding TCR is positioned N-terminally and the ISV binding the antigen on a target cell is positioned C-terminally. In another embodiment, the ISV binding the antigen on a target cell is positioned N-terminally and the ISV binding TCR is positioned C-terminally.

In a preferred aspect, the polypeptide of the invention comprises at least a first, at least a second and at least a third immunoglobulin single variable domain (ISV), wherein said at least a first ISV has high affinity for/binds to the constant domain of the T cell receptor (TCR); said at least a second ISV has high affinity for/binds to a first antigen on a target cell, and said at least a third ISV has high affinity for/binds to a second antigen on a target cell, wherein said second antigen is different from said first antigen. Said first antigen and said second antigen can be on the same or on different target cells.

It will be appreciated (as is also demonstrated in the Example section) that the ISV binding TCR and the ISVs binding the first and second antigen on a target cell can be positioned in any order in the polypeptide of the invention. More particularly, in one embodiment, the ISV binding TCR is positioned N-terminally, the ISV binding the first antigen on a target cell is positioned centrally and the ISV binding the second antigen on a target cell is positioned C-terminally. In another embodiment, the ISV binding TCR is positioned N-terminally, the ISV binding the second antigen on a target cell is positioned centrally and the ISV binding the first antigen on a target cell is positioned C-terminally. In another embodiment, the ISV binding the first antigen on a target cell is positioned N-terminally, the ISV binding the second antigen on a target cell is positioned centrally and the ISV binding the TCR is positioned C-terminally. In another embodiment, the ISV binding the first antigen on a target cell is positioned N-terminally, the ISV binding the TCR is positioned centrally and the ISV binding the second antigen on a target cell is positioned C-terminally. In another embodiment, the ISV binding the second antigen on a target cell is positioned N-terminally, the ISV binding the TCR is positioned centrally and the ISV binding the first antigen on a target cell is positioned C-terminally. In another embodiment, the ISV binding the second antigen on a target cell is positioned N-terminally, the ISV binding the first antigen on a target cell is positioned centrally and the ISV binding the TCR is positioned C-terminally.

The invention further relates to compounds or constructs, and in particular proteins or polypeptides that comprise or essentially consist of one or more ISVs or polypeptides of the invention, and optionally further comprise one or more other groups, residues, moieties or binding units. As will become clear to the skilled person from the further disclosure herein, such further groups, residues, moieties, binding units or amino acid sequences may or may not provide further functionality to the polypeptide of the invention (and/or to the compound or construct in which it is present) and may or may not modify the properties of the polypeptide of the invention.

The compounds, constructs or polypeptides of the invention can generally be prepared by a method which comprises at least one step of suitably linking the one or more immunoglobulin single variable domains of the invention to the one or more further groups, residues, moieties or binding units, optionally via one or more suitable linkers, so as to provide the compound, construct or polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

The process of designing/selecting and/or preparing a compound, construct or polypeptide of the invention, starting from an amino acid sequence of the invention, is also referred to herein as "formatting" said amino acid sequence of the invention; and an amino acid of the invention that is made part of a compound, construct or polypeptide of the invention is said to be "formatted" or to be "in the format of" said compound, construct or polypeptide of the invention. Examples of ways in which an amino acid sequence of the invention can be formatted and examples of such formats will be clear to the skilled person based on the disclosure herein; and such formatted immunoglobulin single variable domains or polypeptides form a further aspect of the invention.

For example, such further groups, residues, moieties or binding units may be one or more additional immunoglobulin single variable domains, such that the compound or construct is a (fusion) protein or (fusion) polypeptide. In a preferred but non-limiting aspect, said one or more other groups, residues, moieties or binding units are immunoglobulin sequences. Even more preferably, said one or more other groups, residues, moieties or binding units are chosen from the group consisting of domain antibodies, immunoglobulin single variable domains that are suitable for use as a domain antibody, single domain antibodies, immunoglobulin single variable domains (ISVs) that are suitable for use as a single domain antibody, "dAb'"s, immunoglobulin single variable domains that are suitable for use as a dAb, or Nanobodies. Alternatively, such groups, residues, moieties or binding units may for example be chemical groups, residues, moieties, which may or may not by themselves be biologically and/or pharmacologically active. For example, and without limitation, such groups may be linked to the one or more immunoglobulin single variable domains or polypeptides of the invention so as to provide a "derivative" of an ISV or polypeptide of the invention, as further described herein.

Also within the scope of the present invention are compounds or constructs, which comprise or essentially consist of one or more derivatives as described herein, and optionally further comprise one or more other groups, residues, moieties or binding units, optionally linked via one or more linkers. Preferably, said one or more other groups, residues, moieties or binding units are immunoglobulin single variable domains. In the compounds or constructs described above, the one or more immunoglobulin single variable domains of the invention and the one or more groups, residues, moieties or binding units may be linked directly to each other and/or via one or more suitable linkers or spacers. For example, when the one or more groups, residues, moieties or binding units are immunoglobulin single variable domains, the linkers may also be immunoglobulin single variable domains, so that the resulting compound or construct is a fusion protein or fusion polypeptide.

In some embodiments, the polypeptides comprise at least two or more immunoglobulin single variable domains disclosed herein. In some embodiments, the polypeptides essentially consist of two or more immunoglobulin single variable domains disclosed herein. A polypeptide that "essentially consists of" two or more immunoglobulin single variable domains, is a polypeptide that in addition to the two or more immunoglobulin single variable domains disclosed herein does not have additional immunoglobulin single variable domains. For instance, a polypeptide that essentially consists of two immunoglobulin single variable domains does not include any additional immunoglobulin single variable domains. However, it should be appreciated that a polypeptide that essentially consists of two or more immunoglobulin single variable domains may include additional functionalities, such as a label, a toxin, one or more linkers, a binding sequence, etc. These additional functionalities include both amino acid based and non-amino acid based groups. In some embodiments, the polypeptides consist of one or more immunoglobulin single variable domains disclosed herein. It should be appreciated that the terms "polypeptide construct" and "polypeptide" can be used interchangeably herein (unless the context clearly dictates otherwise).

In some embodiments, the polypeptides include multivalent or multispecific constructs comprising immunoglobulin single variable domains disclosed herein. In some embodiments, the polypeptides comprise one or more antibody based-scaffolds and/or non-antibody based scaffolds disclosed herein. In some embodiments, the polypeptides comprise a serum binding protein moiety. In some embodiments, the serum binding protein moiety is an immunoglobulin single variable domain. In some embodiments, the immunoglobulin single variable domain is a Nanobody.

It will be appreciated that the order of the building blocks, such as e.g. a first building block, a second building block, a third building block etc., on the polypeptide (orientation) can be chosen according to the needs of the person skilled in the art, as well as the relative affinities which may depend on the location of these building blocks in the polypeptide. Whether the polypeptide comprises a linker, is a matter of design choice. However, some orientations, with or without linkers, may provide preferred binding characteristics in comparison to other orientations. For instance, the order of a first and a second building block in the polypeptide of the invention can be (from N-terminus to C-terminus): (i) first building block (e.g. a first ISV such as a first Nanobody)—[linker]—second building block (e.g. a second ISV such as a second Nanobody); or (ii) second building block (e.g. a second ISV such as a second Nanobody)—[linker]—first building block (e.g. a first ISV such as a first Nanobody); (wherein the linker is optional). All orientations are encompassed by the invention. Polypeptides that contain an orientation of building blocks that provides desired (binding) characteristics can be easily identified by routine screening, for instance as exemplified in the experimental section.

The first immunoglobulin single variable domain (ISV) of the polypeptide of the invention has high affinity for/binds to an effector cell, preferably the TCR of said effector cell, and even more preferably the constant domain of the T cell receptor (TCR).

An effector cell is a cell comprising a TCR complex, preferably an immune cell, such as a T cell, preferably a CD4$^+$ T-helper cell (also known as CD4 cell, T-helper cell or T4 cell), more preferably a Cytotoxic T cell (also known as $T_c$ cell, CTL or CD8$^+$ T cells) or Natural Killer T cells (NKT cells). In some embodiments, the cell is present in vivo. In some embodiments, the cell is present in vitro. The effector cell of the invention relates in particular to mammalian cells, preferably to primate cells, and even more preferably to human cells.

As used herein, the terms "TCR complex" or "αβ TCR-CD3 complex" refers to the T cell receptor complex presented on the surface of T cells (see Kuhns et al. 2006, Immunity 24: 133-139). The TCR complex is composed of six different type I single-spanning transmembrane proteins: the TCRα and TCRβ chains that form the TCR heterodimer responsible for ligand recognition, and the non-covalently associated CD3γ, CD3δ, CD3ε and ζ chains, which bear cytoplasmic sequence motifs that are phosphorylated upon receptor activation and recruit a large number of signalling components. Both α and β chains of the T cell receptor consist of a constant domain and a variable domain. The sequences for the human CD3 and the human TCRα/β constant domains are provided in Table A-6 (SEQ ID NOs: 344-349; cf. UniProt identifiers: CD3 delta: P04234, CD3 gamma: P09693, CD3 epsilon: P07766, CD3 zeta: P20963, TCR alpha: P01848 and TCR beta: related to P01850).

In an embodiment, the present invention relates to a polypeptide as described herein, wherein said first ISV binds to the constant domain of a T cell receptor α (TCR-α) (SEQ ID NO: 348) and/or the constant domain of the T cell receptor β (TCR-β) (SEQ ID NO: 349), or polymorphic variants or isoforms thereof.

Alternatively, the present invention relates to a polypeptide as described herein, wherein said first ISV binds to the constant domain of a T cell receptor α (TCR-α) (SEQ ID NO: 484) and/or the constant domain of the T cell receptor β (TCR-β) (SEQ ID NO: 485), or polymorphic variants or isoforms thereof.

Isoforms are alternative protein sequences that can be generated from the same gene by a single or by the combination of biological events such as alternative promoter usage, alternative splicing, alternative initiation and ribosomal frameshifting, all as known in the art.

"T cell activation" as used herein refers to one or more cellular response(s) of a T cell, e.g. a cytotoxic T cell, such as selected from: proliferation, differentiation, cytokine secretion, cytotoxic effector molecule release, cytotoxic activity, expression of activation markers, and redirected target cell lysis. The polypeptides of the invention are capable of inducing T cell activation. Suitable assays to measure T cell activation are known in the art described herein, for instance as described in WO 99/54440 or by Schlereth et al. 2005 (Cancer Immunol. Immunother. 20: 1-12), or as exemplified in the examples or below.

In an embodiment, the present invention relates to a polypeptide as described herein, wherein said polypeptide induces T cell activation. Preferably, the polypeptide of the invention induces T cell activation only when said second and/or further ISV is bound to an antigen on a target cell.

In an embodiment, the present invention relates to a polypeptide as described herein, wherein said T cell activation depends on presenting said polypeptide bound to said first antigen on a target cell to a T cell.

T cell activation by the polypeptides of the invention can be monitored by upregulation of CD69, CD25 and various cell adhesion molecules, de novo expression and/or release of cytokines (e.g., IFN-γ, TNF-α, IL-6, IL-2, IL-4 and IL-10), upregulation of granzyme and perforin expression, and/or cell proliferation, membrane blebbing, activation of procaspases 3 and/or 7, fragmentation of nuclear DNA and/or cleavage of caspase substrate poly (ADPribose) polymerase. Preferably, redirected lysis of target cells by multispecific polypeptides is independent of T cell receptor specificity, presence of MHC class I and/or 12 microglobulin, and/or of any co-stimulatory stimuli.

In an embodiment, the present invention relates to a polypeptide as described herein, wherein said T cell activation is independent from MHC recognition.

The polypeptides of the invention show redirected lysis in vitro with previously unstimulated peripheral polyclonal CD8$^+$ and CD4$^+$-positive T cells. The redirected lysis of target cells via the recruitment of T cells by the polypeptides of the invention involves cytolytic synapse formation and delivery of perforin and granzymes. Cell lysis by T cells has been described, e.g. by Atkinson and Bleackley 1995 (Crit. Rev. Immunol 15(3-4):359-384). Preferably, the engaged T cells are capable of serial target cell lysis, and are not affected by immune escape mechanisms interfering with peptide antigen processing and presentation, or clonal T cell differentiation (see, for example, WO 2007/042261). In vitro, redirected lysis is seen at low picomolar concentrations, suggesting that very low numbers of the polypeptides of the invention need to be bound to target cells for triggering T cells. As demonstrated in the examples, the low effector to target ratio might be indicative for serial target cell lysis. Accordingly, the present invention relates to potent polypeptides. Preferably, the polypeptide of the invention mediates killing of target cells, e.g. cancer cells, such as stimulating T cells in pore formation and delivering pro-apoptotic components of cytotoxic T cell granules.

In an embodiment, the present invention relates to a polypeptide as described herein, wherein said T cell activation causes one or more cellular response of said T cell, wherein said cellular response is selected from the group consisting of proliferation, differentiation, cytokine secretion, cytotoxic effector molecule release, cytotoxic activity, expression of activation markers and redirected target cell lysis.

As used herein, the term "potency" is a measure of the biological activity of an agent, such as a polypeptide, ISV or Nanobody. Potency of an agent can be determined by any suitable method known in the art, such as for instance as described in the experimental section. Cell culture based potency assays are often the preferred format for determining biological activity since they measure the physiological response elicited by the agent and can generate results within a relatively short period of time. Various types of cell based assays, based on the mechanism of action of the product, can be used, including but not limited to proliferation assays, cytotoxicity assays, cell killing assays, reporter gene assays, cell surface receptor binding assays, and assays to measure induction/inhibition of functionally essential proteins or other signal molecules (such as phosphorylated proteins, enzymes, cytokines, cAMP and the like), Ramos B cell depletion model, T cell mediated tumour cell killing assay (for instance as set out in the Examples section), all well known in the art. Results from cell based potency assays can be expressed as "relative potency" as determined by comparison of the multispecific polypeptide of the invention to the response obtained for the corresponding reference monovalent ISV, e.g. a polypeptide comprising only one ISV or one Nanobody, optionally further comprising an irrelevant Nanobody (cf. experimental section).

In an embodiment, the present invention relates to a polypeptide as described herein, wherein said T cell activation causes inhibition of an activity of said target cell, such as to delay or minimize the spread of the target cell, to inhibit or delay growth and/or proliferation of the target cell, and/or to kill the target cell (e.g., cause regression of the disorder and/or symptoms) by more than about 10%, such as 20%, 30%, or 40% or even more than 50%, such as more than 60%, such as 70%, 80%, or even more than 90%, such as 100%.

The first building block, ISV, Nanobody or VHH of the invention has a high affinity for its—the constant domain of TCR—target. The first building block, ISV or Nanobody of the invention may for example be directed against an antigenic determinant, epitope, part, domain, subunit or confirmation (where applicable) of said first target. The first building block, e.g. the first ISV, Nanobody or VHH, is preferably chosen for its high affinity for its target per se, disregarding the influence of any avidity effects.

Accordingly, the present invention relates to a polypeptide as described herein, wherein said first ISV binds to the constant domain of the T cell receptor (TCR) with an average KD value of between 100 nM and 10 pM, such as at an average KD value of 90 nM or less, even more preferably at an average KD value of 80 nM or less, such as less than 70, 60, 50, 40, 30, 20, 10, 5 nM or even less, such as less than 4, 3, 2, or 1 nM, such as less than 500, 400, 300, 200, 100, 90, 80, 70, 60, 50, 40, 30, 20 pM, or even less, such as less than 10 pM. Preferably, the KD is determined by Kinexa, BLI or SPR, for instance as determined by Proteon. For instance, said KD is determined as set out in the Examples section.

Accordingly, the present invention relates to a polypeptide as described herein, wherein said first ISV has a high affinity when measured as a monovalent. Preferably said average KD is measured by surface plasmon resonance (SPR) on recombinant protein.

Accordingly, the present invention relates to a polypeptide as described herein, wherein said polypeptide has a dissociation constant ($K_D$) to (or for binding) said TCR selected from the group consisting of: at most about $10^{-5}$ M, at most about $10^{-6}$ M, at most about $10^{-7}$ M, at most about $10^{-8}$ M, at most about $10^{-9}$ M, at most about $10^{-10}$ M, at most about $10^{-11}$ M, and at most about $10^{-12}$ M, preferably as measured by surface plasmon resonance.

The present invention also relates to a polypeptide as described herein, wherein said first ISV binds to said TCR with an EC50 value of between 100 nM and 1 pM, such as at an average EC50 value of 100 nM or less, even more preferably at an average EC50 value of 90 nM or less, such as less than 80, 70, 60, 50, 40, 30, 20, 10, 5 nM or even less, such as less than 4, 3, 2, or 1 nM or even less, such as less than 500, 400, 300, 200, 100, 90, 80, 70, 60, 50, 40, 30, 20, 10, 5 pM, or even less, such as less than 4 pM.

Accordingly, the present invention relates to a polypeptide as described herein, wherein said average KD is determined by FACS, Biacore, ELISA, on a monovalent first ISV, such as a Nanobody, or a polypeptide comprising a monovalent first ISV, such as a Nanobody, for instance said EC50 is determined as set out in the Examples section.

It has been shown in the examples that the KD correlates well with the EC50.

In an embodiment, the present invention relates to a polypeptide as described herein, wherein said polypeptide has an on rate constant (Kon) to (or for binding) said TCR selected from the group consisting of at least about $10^{2}$ $M^{-1}s^{-1}$, at least about $10^{3}$ $M^{-1}s^{-1}$, at least about $10^{4}$ $M^{-1}s^{-1}$, at least about $10^{5}$ $M^{-1}s^{-1}$, at least about $10^{6}$ $M^{-1}s^{-1}$, $10^{7}$ $M^{-1}s^{-1}$, at least about $10^{8}$ $M^{-1}s^{-1}$, at least about $10^{9}$ $M^{-1}s^{-1}$, and at least about $10^{10}$ $M^{-1}s^{-1}$, preferably as measured by surface plasmon resonance or as performed in the examples section.

In an embodiment, the present invention relates to a polypeptide as described herein, wherein said polypeptide has an off rate constant (Koff) to (or for binding) said TCR selected from the group consisting of at most about $10^{-3}s^{-1}$, at most about $10^{-4}s^{-1}$, at most about $10^{-5}s^{-1}$, at most about $10^{-6}s^{-1}$, at most about $10^{-7}s^{-1}$, at most about $10^{-8}s^{-1}$, at most about $10^{-9}s^{-1}$, and at most about $10^{-10}s^{-1}$, preferably as measured by surface plasmon resonance or as performed in the examples section.

Amino acid sequence modifications of the binding molecules, ISVs, or polypeptides described herein are contemplated. For example, it may be desirable to improve the binding affinity and/or other biological properties of the antibody or ISV. Amino acid sequence variants of the binding molecules, ISVs, or polypeptides are prepared by introducing appropriate nucleotide changes into the binding molecules, ISVs, or polypeptides nucleic acid, or by peptide synthesis.

Such modifications include, for example, deletions from, and/or insertions into, and/or substitutions of, residues within the amino acid sequences of the binding molecules, ISVs or polypeptides. Any combination of deletion, insertion, and substitution is made to arrive at the final construct, provided that the final construct possesses the desired characteristics. The amino acid changes also may alter post-translational processes of the binding molecules, such as changing the number or position of glycosylation sites. Preferably, 1, 2, 3, 4, 5, 6, 7, 8, 9, or 10 amino acids may be substituted in a CDR, while 1, 2, 3, 4, 5, 6, 7, 8, 9, 10, 11, 12, 13, 14, 15, 16, 17, 18, 19, 20, or 25 amino acids may be substituted in the framework regions (FRs). The substitutions are preferably conservative substitutions as described herein. Additionally or alternatively, 1, 2, 3, 4, 5, or 6 amino acids may be inserted or deleted in each of the CDRs (of course, dependent on their length), while 1, 2, 3, 4, 5, 6, 7, 8, 9, 10, 11, 12, 13, 14, 15, 16, 17, 18, 19, 20, or 25 amino acids may be inserted or deleted in each of the FRs.

A useful method for identification of certain residues or regions of the binding molecules, ISVs or polypeptides, that are preferred locations for mutagenesis is called "alanine scanning mutagenesis" as described by Cunningham and Wells 1989 (Science 244: 1081-1085). Here, a residue or group of target residues within the binding molecule is/are identified (e.g. charged residues such as Arg, Asp, His, Lys, and Glu) and replaced by a neutral or negatively charged amino acid (most preferably alanine or polyalanine) to affect the interaction of the amino acids with the epitope. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se needs not to be predetermined. For example, to analyze the performance of a mutation at a given site, ala scanning or random mutagenesis is conducted at a target codon or region and the expressed binding molecule variants are screened for the desired activity.

Preferably, amino acid sequence insertions include amino- and/or carboxyl-terminal fusions ranging in length from 1, 2, 3, 4, 5, 6, 7, 8, 9 or 10 residues to polypeptides containing a hundred or more residues.

Another type of variant is an amino acid substitution variant. These variants have preferably at least 1, 2, 3, 4, 5, 6, 7, 8, 9 or 10 amino acid residues in the binding molecule, ISV or polyptide replaced by a different residue. The sites of greatest interest for substitution mutagenesis include the CDRs, in particular the hypervariable regions, but FR alterations are also contemplated. For example, if a CDR sequence encompasses 6 amino acids, it is envisaged that one, two or three of these amino acids are substituted. Similarly, if a CDR sequence encompasses 15 amino acids it is envisaged that one, two, three, four, five or six of these amino acids are substituted.

Generally, if amino acids are substituted in one or more or all of the CDRs, it is preferred that the then-obtained "substituted" sequence is at least 60%, more preferably 65%, even more preferably 70%, particularly preferably 75%, more particularly preferably 80% or even more than 90% identical to the "original" CDR sequence. This means that it is dependent of the length of the CDR to which degree it is identical to the "substituted" sequence. For example, a CDR having 5 amino acids is preferably 80% identical to its substituted sequence in order to have at least one amino acid substituted. Accordingly, the CDRs of the binding molecule may have different degrees of identity to their substituted sequences, e.g., CDR1 may have 80%, while CDR3 may have 90%.

Preferred substitutions (or replacements) are conservative substitutions. However, any substitution (including non-conservative substitution or one or more from the "exemplary substitutions" listed in Table B-1 below) is envisaged as long as the polypeptide retains its capability to bind to the constant domain of the T cell receptor (TCR) present on a T cell via the first ISV and to a first antigen on a target cell via the second ISV and/or its CDRs have an identity to the then substituted sequence (at least 60%, more preferably 65%, even more preferably 70%, particularly preferably 75%, more particularly preferably 80% identical to the "original" CDR sequence).

Conservative substitutions are shown in Table B-1 below.

As indicated before, only after rigorous immunization and screening and selection methods, the present inventors were able to identify ISVs binding to the constant domains of TCR. Accordingly, the present invention relates to polypeptides comprising a first ISV chosen from the group consisting of SEQ ID NOs: 1-118 (cf. Table A-4). Sequence analysis further demonstrated that all ISVs binding to TCR comprised a very similar CDR3. Accordingly, the present invention relates to a polypeptide according to the invention in which said first ISV essentially consists of 4 framework regions (FR1 to FR4, respectively) and 3 complementarity determining regions (CDR1 to CDR3, respectively), in which CDR3 has the amino acid sequence $X_1SR X_2X_3PYX_4Y$, in which $X_1$ is F, Y, G, L or K, $X_2$ is I or L, $X_3$ is Y or W, and $X_4$ is D, N or S.

Sequence analysis further revealed that there are only a limited number of sequence variations in the CDRs (cf. Example 4.2 and Tables A-1 to A-3).

TABLE B-1

| Amino Acid Substitutions | | |
| --- | --- | --- |
| Original | Exemplary Substitutions | Preferred Substitutions |
| Ala (A) | val, leu, ile | val |
| Arg (R) | lys, gln, asn | lys |
| Asn (N) | gln, his, asp, lys, arg | gln |
| Asp (D) | glu, asn | glu |
| Cys (C) | ser, ala | ser |
| Gln (Q) | asn, glu | asn |
| Glu (E) | asp, gln | asp |
| Gly (G) | ala | ala |
| His (H) | asn, gln, lys, arg | arg |
| Ile (I) | leu, val, met, ala, phe | leu |
| Leu (L) | norleucine, ile, val, met, ala | ile |
| Lys (K) | arg, gln, asn | arg |
| Met (M) | leu, phe, ile | leu |
| Phe (F) | leu, val, ile, ala, tyr | tyr |
| Pro (P) | ala | ala |
| Ser (S) | thr | thr |
| Thr (T) | ser | ser |
| Trp (W) | tyr, phe | tyr |

TABLE B-1-continued

| Amino Acid Substitutions | | |
| --- | --- | --- |
| Original | Exemplary Substitutions | Preferred Substitutions |
| Tyr (Y) | trp, phe, thr, ser | phe |
| Val (V) | ile, leu, met, phe, ala | leu |

Accordingly, the present invention relates to a polypeptide as described herein, wherein said first ISV essentially consists of 4 framework regions (FR1 to FR4, respectively) and 3 complementarity determining regions (CDR1 to CDR3, respectively), in which:

(i) CDR1 is chosen from the group consisting of:
  (a) SEQ ID NOs: 119-133; or
  (b) amino acid sequences that have 4, 3, 2, or 1 amino acid(s) difference with the amino acid sequence of SEQ ID NO: 123 or with any of SEQ ID NOs: 119-133; and/or (ii) CDR2 is chosen from the group consisting of:
  (c) SEQ ID NOs: 134-163; or
  (d) amino acid sequences that have 4, 3, 2, or 1 amino acid(s) difference with the amino acid sequence of SEQ ID NO: 153 or with any of SEQ ID NOs: 134-163; and/or (iii) CDR3 is chosen from the group consisting of:
  (e) SEQ ID NOs: 164-174; or
  (f) amino acid sequences that have 4, 3, 2, or 1 amino acid(s) difference with the amino acid sequence of SEQ ID NO: 170 or with any of SEQ ID NOs: 164-174.

Further preferred CDR sequences are depicted in Table A-4.

Generally, the combinations of CDR's listed in Table A-4 (i.e. those mentioned on the same line in Table A-4) are preferred. Thus, it is generally preferred that, when a CDR in an ISV is a CDR sequence mentioned in Table A-4 or suitably chosen from the group consisting of CDR sequences that have 4, 3, 2 or only 1 amino acid difference(s) with a CDR sequence listed in Table A-4, that at least one and preferably both of the other CDR's are suitably chosen from the CDR sequences that belong to the same combination in Table A-4 (i.e. mentioned on the same line in Table A-4) or are suitably chosen from the group consisting of CDR sequences that have 4, 3, 2 or only 1 amino acid difference(s) with the CDR sequence(s) belonging to the same combination.

Sequence analysis of the resulting binders further resulted in the identification of 3 distinct clusters. Corresponding alignments are provided (see Table A-1, Table A-2 and Table A-3). Clustering was based on sequence similarities and differences in CDR2 and CDR3. Cluster A is the most prominent comprising 104 clones (SEQ ID NOs: 1-104), cluster B comprises 11 clones (SEQ ID NOs: 105-115), and cluster C is represented by only 3 clones (SEQ ID NOs: 116-118). The clustering based on the structural similarities and differences in the amino acid sequence translated into functional similarities and differences as revealed by the examples. Representatives of all clusters were isolated based on high affinity binding to the constant domain of the TCR (Examples 3 & 4) and human T cell activation (Example 4.2). In general cluster A representatives demonstrated the best EC50 values. In addition, cluster A representatives were cross-reactive with the constant domain of cynomolgus TCR (cf. Example 18). Although cluster C representatives had somewhat less favourable EC50 values than cluster B representatives, cluster C representatives had lower IC50 values in a flow cytometry based T cell mediated Ramos killing assay (cf. Example 10).

Accordingly, the present invention relates to a polypeptide as described herein, in which said first ISV essentially consists of 4 framework regions (FR1 to FR4, respectively) and 3 complementarity determining regions (CDR1 to CDR3, respectively), in which CDR1 is chosen from the group consisting of
- (a) SEQ ID NO: 123; and
- (b) amino acid sequences that have 1, 2, 3 or 4 amino acid difference(s) with SEQ ID NO: 123, wherein
  at position 2 the D has been changed into A, S, E or G;
  at position 4 the H has been changed into Y;
  at position 5 the K has been changed into L;
  at position 6 the I has been changed into L;
  at position 8 the F has been changed into I or V; and/or
  at position 10 the G has been changed into S.

Accordingly, the present invention relates to a polypeptide as described herein, in which said first ISV essentially consists of 4 framework regions (FR1 to FR4, respectively) and 3 complementarity determining regions (CDR1 to CDR3, respectively), in which CDR2 is chosen from the group consisting of
- (a) SEQ ID NO: 153; and
- (b) amino acid sequences that have 1, 2, 3 or 4 amino acid difference(s) with SEQ ID NO: 153, wherein
  at position 1 the H has been changed into T or R;
  at position 3 the S has been changed into T or A;
  at position 5 the G has been changed into S or A;
  at position 7 the Q has been changed into D, E, T, A or V;
  at position 8 the T has been changed into A or V; and/or
  at position 9 the D has been changed into A, Q, N, V or S.

Accordingly, the present invention relates to a polypeptide as described herein, in which said first ISV essentially consists of 4 framework regions (FR1 to FR4, respectively) and 3 complementarity determining regions (CDR1 to CDR3, respectively), in which CDR3 is chosen from the group consisting of
- (a) SEQ ID NO: 170; and
- (b) amino acid sequences that have 1, 2, 3 or 4 amino acid difference(s) with SEQ ID NO: 170, wherein
  at position 1 the F has been changed into Y, L or G;
  at position 4 the I has been changed into L;
  at position 5 the Y has been changed into W; and/or
  at position 8 the D has been changed into N or S.

In an embodiment, the invention relates to a polypeptide as described herein, in which said first ISV essentially consists of 4 framework regions (FR1 to FR4, respectively) and 3 complementarity determining regions (CDR1 to CDR3, respectively), in which:
- (i) CDR1 is chosen from the group consisting of:
  - (a) SEQ ID NOs: 119-123, 125-127, 129, 132 and 133; and
  - (b) amino acid sequences that have 4, 3, 2, or 1 amino acid(s) difference with the amino acid sequence of SEQ ID NO: 123; and/or
- (ii) CDR2 is chosen from the group consisting of:
  - (c) SEQ ID NOs: 134-141, 143-144, 146-156, 159-163; and
  - (d) amino acid sequences that have 4, 3, 2, or 1 amino acid(s) difference with the amino acid sequence of SEQ ID NO: 153; and/or
- (iii) CDR3 is chosen from the group consisting of:
  - (e) SEQ ID NOs: 164-166, 169-171, 173-174; and
  - (f) amino acid sequences that have 3, 2, or 1 amino acid(s) difference with the amino acid sequence of SEQ ID NO: 170.

In an embodiment, the invention relates to a polypeptide as described herein, in which said first ISV essentially consists of 4 framework regions (FR1 to FR4, respectively) and 3 complementarity determining regions (CDR1 to CDR3, respectively), in which: CDR1 is represented by SEQ ID NO: 123, CDR2 is represented by SEQ ID NO: 153, and CDR3 is represented by SEQ ID NO: 170.

Nanobodies of cluster B show relatively limited sequence variability in the CDRs.

Accordingly, the present invention relates to a polypeptide as described herein, in which said first ISV essentially consists of 4 framework regions (FR1 to FR4, respectively) and 3 complementarity determining regions (CDR1 to CDR3, respectively), in which CDR1 is chosen from the group consisting of
- (a) SEQ ID NO: 124; and
- (b) amino acid sequences that have 1, or 2 amino acid difference(s) with SEQ ID NO: 124, wherein
  at position 2 the E has been changed into Q; and/or
  at position 6 the I has been changed into V.

Accordingly, the present invention relates to a polypeptide as described herein, in which said first ISV essentially consists of 4 framework regions (FR1 to FR4, respectively) and 3 complementarity determining regions (CDR1 to CDR3, respectively), in which CDR2 is chosen from the group consisting of
- (a) SEQ ID NO: 145; and
- (b) amino acid sequence that has 1 amino acid difference with SEQ ID NO: 145, wherein
  at position 9 the N has been changed into D.

Accordingly, the present invention relates to a polypeptide as described herein, in which said first ISV essentially consists of 4 framework regions (FR1 to FR4, respectively) and 3 complementarity determining regions (CDR1 to CDR3, respectively), in which CDR3 is chosen from the group consisting of
- (a) SEQ ID NO: 167; and
- (b) amino acid sequence that has 1 amino acid difference with SEQ ID NO: 167, wherein
  at position 4 the L has been changed into I.

Accordingly, the present invention relates to a polypeptide as described herein, in which said first ISV essentially consists of 4 framework regions (FR1 to FR4, respectively) and 3 complementarity determining regions (CDR1 to CDR3, respectively), in which:
- (i) CDR1 is chosen from the group consisting of:
  - (a) SEQ ID NOs: 124, 128 and 131; and
  - (b) amino acid sequences that have 4, 3, 2, or 1 amino acid(s) difference with the amino acid sequence of SEQ ID NO: 124; and/or
- (ii) CDR2 is chosen from the group consisting of:
  - (c) SEQ ID NOs: 142 and 145; and
  - (d) amino acid sequences that have 4, 3, 2, or 1 amino acid(s) difference with the amino acid sequence of SEQ ID NO: 145; and/or
- (iii) CDR3 is chosen from the group consisting of:
  - (e) SEQ ID NOs: 167 and 168; and
  - (f) amino acid sequences that have 3, 2, or 1 amino acid(s) difference with the amino acid sequence of SEQ ID NO: 167.

Accordingly, the present invention relates to a polypeptide as described herein, in which said first ISV essentially consists of 4 framework regions (FR1 to FR4, respectively) and 3 complementarity determining regions (CDR1 to CDR3, respectively), in which: CDR1 is represented by SEQ ID NO: 124, CDR2 is represented by SEQ ID NO: 145, and CDR3 is represented by SEQ ID NO: 167.

In Cluster C, the sequence variation is even more limited than within the other clusters.

Accordingly, the present invention relates to a polypeptide as described herein, in which said first ISV essentially consists of 4 framework regions (FR1 to FR4, respectively) and 3 complementarity determining regions (CDR1 to CDR3, respectively), in which CDR2 is chosen from the group consisting of
- (a) SEQ ID NO: 157; and
- (b) amino acid sequence that has 1 amino acid difference with SEQ ID NO: 157, wherein
  at position 8 the T has been changed into I.

Accordingly, the present invention relates to a polypeptide as described herein, in which said first ISV essentially consists of 4 framework regions (FR1 to FR4, respectively) and 3 complementarity determining regions (CDR1 to CDR3, respectively), in which:
- (i) CDR1 is chosen from the group consisting of
  - (a) SEQ ID NO: 130; and
  - (b) amino acid sequences that have 4, 3, 2, or 1 amino acid(s) difference with the amino acid sequence of SEQ ID NO: 130; and/or
- (ii) CDR2 is chosen from the group consisting of:
  - (c) SEQ ID NOs: 157-158; and
  - (d) amino acid sequences that have 4, 3, 2, or 1 amino acid(s) difference with the amino acid sequence of SEQ ID NO: 157; and/or
- (iii) CDR3 is chosen from the group consisting of:
  - (e) SEQ ID NO: 172; and
  - (f) amino acid sequences that have 3, 2, or 1 amino acid(s) difference with the amino acid sequence of SEQ ID NO: 172.

In an aspect, the present invention relates to a polypeptide as described herein, in which said first ISV essentially consists of 4 framework regions (FR1 to FR4, respectively) and 3 complementarity determining regions (CDR1 to CDR3, respectively), in which: CDR1 is represented by SEQ ID NO: 130, CDR2 is represented by SEQ ID NO: 157, and CDR3 is represented by SEQ ID NO: 172.

The second immunoglobulin single variable domain (ISV) of the polypeptide of the invention has a high affinity for/binds to an antigen on a target cell, preferably a cancer cell. A "target cell" as referred to herein, is a cell that presents a particular antigen on its surface. In a preferred aspect, the "target cell" is a cancer cell.

The membrane (also called plasma membrane or phospholipid bilayer) surrounds the cytoplasm of a cell, which is the outer boundary of the cell, i.e. the membrane is the surface of the cell. This membrane serves to separate and protect a cell from its surrounding environment and is made mostly from a double layer of phospholipids. Embedded within this membrane is a variety of protein molecules, such as channels, pumps and cellular receptors. Since the membrane is fluid, the protein molecules can travel within the membrane. The term "antigen on a target cell" as used herein denotes a molecule, which is displayed on the surface of a cell. In most cases, this molecule will be located in or on the plasma membrane of the cell such that at least part of this molecule remains accessible from outside the cell in tertiary form. A non-limiting example of a cell surface molecule, which is located in the plasma membrane, is a transmembrane protein comprising, in its tertiary conformation, regions of hydrophilicity and hydrophobicity. Here, at least one hydrophobic region allows the cell surface molecule to be embedded, or inserted in the hydrophobic plasma membrane of the cell while the hydrophilic regions extend on either side of the plasma membrane into the cytoplasm and extracellular space, respectively.

Said antigen can be any target on a cell, e.g. a tumour antigen. In a preferred embodiment, said antigen is specific for said target cell, e.g. cancer cell, such as a tumour associated antigen (TAA) on said cancer cell.

The term "tumour antigen" as used herein may be understood as those antigens that are presented on tumour cells. These antigens can be presented on the cell surface with an extracellular part, which is often combined with a transmembrane and cytoplasmic part of the molecule. These antigens can sometimes be presented only by tumour cells and never by a normal or healthy cell. Tumour antigens can be exclusively expressed on tumour cells or might represent a tumour specific mutation compared to normal cells. In this case, they are called tumour-specific antigens. However, this will not be the case generally. More common are antigens that are presented by tumour cells and normal cells, and they are called "tumour-associated antigens (TAA)". These tumour-associated antigens can be overexpressed on tumour cells compared to normal cells or are better accessible for antibody binding in tumour cells due to the less compact structure of the tumour tissue compared to normal tissue. TAA are preferably antigens that are expressed on cells of particular tumours, but that are preferably not expressed in normal cells. Often, TAA are antigens that are normally expressed in cells only at particular points in an organism's development (such as during fetal development) and that are being inappropriately expressed in the organism at the present point of development, or are antigens not expressed in normal tissues or cells of an organ now expressing the antigen.

In an embodiment, said first antigen on a target cell is a tumour antigen, preferably a tumour associated antigen (TAA).

In an embodiment, said second antigen on a target cell is a tumour antigen, preferably a tumour associated antigen (TAA).

In an embodiment, said antigen is present more abundantly on a cancer cell than on a normal cell. The antigen on a target cell is preferably a tumor-associated antigen (TAA). Preferred TAAs include MART-1, carcinoembryonic antigen ("CEA"), gp100, MAGE-1, HER-2, CD20, Lewis$^Y$ antigens, Melanoma-associated Chondroitin Sulfate Proteoglycan (MCSP), Epidermal Growth Factor Receptor (EGFR), Fibroblast Activation Protein (FAP), CD19 and CD33.

Cell surface antigens that are preferentially expressed on AML LSC compared with normal hematopoietic stem cells, and thus preferred as TAA, include CD123, CD44, CLL-1, CD96, CD47, CD32, CXCR4, Tim-3 and CD25.

Other tumor-associated antigens suitable as an antigen on a target cell for binding by the second ISV within the polypeptides of the invention include: TAG-72, Ep-CAM, PSMA, PSA, glycolipids such as GD2 and GD3.

The TAA of the invention include also hematopoietic differentiation antigens, i.e. glycoproteins usually associated with cluster differentiation (CD) grouping, such as CD4, CD5, CD19, CD20, CD22, CD33, CD36, CD45, CD52, CD69 and CD147; growth factor receptors, including HER2, ErbB3 and ErbB4; Cytokine receptors, including Interleukin-2 receptor gamma chain (CD132 antigen), Interleukin-10 receptor alpha chain (IL-10R-A), Interleukin-10 receptor beta chain (IL-10R-B), Interleukin-12 receptor beta-1 chain (IL-12R-beta1), Interleukin-12 receptor beta-2 chain (IL-12 receptor beta-2), Interleukin-13 receptor alpha-1 chain (IL-13R-alpha-1) (CD213a1 antigen), Interleukin-13 receptor alpha-2 chain (Interleukin-13 binding protein), Interleukin-17 receptor (IL-17 receptor), Interleukin-17B receptor (IL-17B receptor), Interleukin 21 receptor precursor (IL-21R), Interleukin-1 receptor type I (IL-1R-1) (CD121a), Interleukin-1 receptor type II (IL-1R-beta) (CDw121b), Interleukin-1 receptor antagonist protein (IL-1ra), Interleukin-2 receptor alpha chain (CD25 antigen), Interleukin-2 receptor beta chain (CD122 antigen), Interleukin-3 receptor alpha chain (IL-3R-alpha) (CD123 antigen); as well as others, such as CD30, IL23R, IGF-1R, IL5R, IgE, CD248 (endosialin), CD44v6, gpA33, Ron, Trop2, PSCA, claudin 6, claudin 18.2, CLEC12A, CD38, ephA2, c-Met, CD56, MUC16, EGFRvIII, AGS-16, CD27L, Nectin-4, SLITRK6, mesothelin, folate receptor, tissue factor, axl, glypican-3, CA9, Cripto, CD138, CD37, MUC1, CD70, gastrin releasing peptide receptor, PAP, CEACAM5, CEACAM6, CXCR7, N-cadherin, FXYD2 gamma a, CD21, CD133, Na/K-ATPase, mIgM (membrane-bound IgM), mIgA (membrane-bound IgA), Mer, Tyro2, CD120, CD95, CA 195, DR5, DR6, DcR3 and CAIX.

Accordingly the present invention relates to a polypeptide as described herein, wherein said TAA is chosen from the group consisting of Melanoma-associated Chondroitin Sulfate Proteoglycan (MCSP), Epidermal Growth Factor Receptor (EGFR), Fibroblast Activation Protein (FAP), MART-1, carcinoembryonic antigen ("CEA"), gp100, MAGE-1, HER-2, Lewis' antigens, CD123, CD44, CLL-1, CD96, CD47, CD32, CXCR4, Tim-3, CD25, TAG-72, EpCAM, PSMA, PSA, GD2, GD3, CD4, CD5, CD19, CD20, CD22, CD33, CD36, CD45, CD52, CD147; growth factor receptors, including ErbB3 and ErbB4; Cytokine receptors, including Interleukin-2 receptor gamma chain (CD132 antigen), Interleukin-10 receptor alpha chain (IL-10R-A), Interleukin-10 receptor beta chain (IL-10R-B), Interleukin-12 receptor beta-1 chain (IL-12R-beta1), Interleukin-12 receptor beta-2 chain (IL-12 receptor beta-2), Interleukin-13 receptor alpha-1 chain (IL-13R-alpha-1) (CD213a1 antigen), Interleukin-13 receptor alpha-2 chain (Interleukin-13 binding protein), Interleukin-17 receptor (IL-17 receptor), Interleukin-17B receptor (IL-17B receptor), Interleukin 21 receptor precursor (IL-21R), Interleukin-1 receptor type I (IL-1R-1) (CD121a), Interleukin-1 receptor type II (IL-1R-beta) (CDw121b), Interleukin-1 receptor antagonist protein (IL-1ra), Interleukin-2 receptor alpha chain (CD25 antigen), Interleukin-2 receptor beta chain (CD122 antigen), Interleukin-3 receptor alpha chain (IL-3R-alpha) (CD123 antigen), CD30, IL23R, IGF-1R, IL5R, IgE, CD248 (endosialin), CD44v6, gpA33, Ron, Trop2, PSCA, claudin 6, claudin 18.2, CLEC12A, CD38, ephA2, c-Met, CD56, MUC16, EGFRvIII, AGS-16, CD27L, Nectin-4, SLITRK6, mesothelin, folate receptor, tissue factor, axl, glypican-3, CA9, Cripto, CD138, CD37, MUC1, CD70, gastrin releasing peptide receptor, PAP, CEACAM5, CEACAM6, CXCR7, N-cadherin, FXYD2 gamma a, CD21, CD133, Na/K-ATPase, mIgM (membrane-bound IgM), mIgA (membrane-bound IgA), Mer, Tyro2, CD120, CD95, CA 195, DR5, DR6, DcR3 and CAIX, and related polymorphic variants and isoforms, preferably said TAA is CD20 (UniProt 11836), HER2 (Uniprot P04626), EGFR, or CEACAM, polymorphic variants and/or isoforms thereof.

The second building block, ISV, Nanobody or VHH of the invention has a high affinity for its antigen. The second building block, ISV or Nanobody of the invention may, for example, be directed against an antigenic determinant, epitope, part, domain, subunit or confirmation (where applicable) of said antigen on a target cell.

The target cell of the invention relates in particular to mammalian cells, preferably to primate cells, and even more preferably to human cells. The target cell is preferably a hyperproliferative cell such as e.g. a cancer cell.

The present invention relates to a polypeptide as described herein, wherein said second or further ISV binds to an antigen on a target cell with an average KD value of between 100 nM and 10 pM, such as at an average KD value of 90 nM or less, even more preferably at an average KD value of 80 nM or less, such as less than 70, 60, 50, 40, 30, 20, 10, 5 nM or even less, such as less than 4, 3, 2, or 1 nM, such as less than 500, 400, 300, 200, 100, 90, 80, 70, 60, 50, 40, 30, 20 pM, or even less, such as less than 10 pM. Preferably, the KD is determined by Kinexa, BLI or SPR, for instance as determined by a Proteon.

Accordingly, the present invention relates to a polypeptide as described herein, wherein said second or further ISV has a high affinity for its antigen when measured as a monovalent.

Accordingly, the present invention relates to a polypeptide as described herein, wherein said average KD is measured by surface plasmon resonance (SPR) and/or KinExA or Proteon, for instance on recombinant protein, such as described in the Examples section.

The present invention also relates to a polypeptide as described herein, wherein said second or further ISV binds to an antigen on a target cell with an EC50 value of between 100 nM and 1 pM, such as at an average EC50 value of 100 nM or less, even more preferably at an average EC50 value of 90 nM or less, such as less than 80, 70, 60, 50, 40, 30, 20, 10, 5 nM or even less, such as less than 4, 3, 2, or 1 nM or even less, such as less than 500, 400, 300, 200, 100, 90, 80, 70, 60, 50, 40, 30, 20, 10, 5 pM, or even less, such as less than 4 pM.

Accordingly, the present invention relates to a polypeptide as described herein, wherein said average EC50 is determined by FACS or ELISA, on a monovalent second ISV, such as a Nanobody, or a polypeptide comprising a monovalent second ISV, such as a Nanobody.

It has been shown in the examples that the KD correlates well with the EC50.

Simultaneous targeting of multiple antigens can reduce the probability of generating tumour escape variants, because of which the therapeutic activity of T cell engaging strategy is improved. The present invention provides multispecific polypeptides which comprise a TCR ISV combined with immunoglobulin single variable domains against different (target) antigens (on a target cell). Preferred combinations of first and second antigens are provided below (it will be appreciated that the ISVs binding said antigens can be positioned in any order in the polypeptide of the invention):

| first antigen | second antigen |
| --- | --- |
| EGFR (OMIM: 131550) | CD20 (OMIM: 112210) |
| EGFR (OMIM: 131550) | CEA (OMIM: 114890) |
| EGFR (OMIM: 131550) | HER2 (OMIM: 164870) |
| HER2 (OMIM: 164870) | CD20 (OMIM: 112210) |
| HER2 (OMIM: 164870) | CEA (OMIM: 114890) |
| CD20 (OMIM: 112210) | CEA (OMIM: 114890) |

Similarly, simultaneous targeting of multiple epitopes, antigenic determinants, parts, domains, subunits or conformations of a protein or antigen on a target cell can reduce the probability of generating tumour escape variants, because of which the therapeutic activity of T cell engaging strategy is improved (cf. Example 22). The present invention provides polypeptides which comprise an anti-TCR ISV combined with immunoglobulin single variable domains against different epitopes, antigenic determinants, parts, domains, subunits or conformations of an antigen on a target cell (also referred to as biparatopic constructs). Preferred combinations of first and second TAA ISVs are provided below (it will be appreciated that the ISVs binding said antigens can be positioned in any order in the polypeptide of the invention):

| TAA1 ISV | name | SEQ ID NO: | TAA2 ISV | name | SEQ ID NO: |
|---|---|---|---|---|---|
| EGFR-1 | 7D12 | 355 | EGFR-2 | 9G08 | 352 |
| HER2-1 | 5F07 | 350 | HER2-2 | 47D05 | 351 |
| CEA-1 | CEA#1 | 353 | CEA-2 | CEA#5 | 354 |

The polypeptides and compositions of the present invention can be used for the prevention and/or treatment of diseases and disorders of the present invention (herein also "diseases and disorders of the present invention") which include, but are not limited to cancer. The term "cancer" refers to the pathological condition in mammals that is typically characterized by dysregulated cellular proliferation or survival. Examples of cancer include, but are not limited to, carcinomas, gliomas, mesotheliomas, melanomas, lymphomas, leukemias, adenocarcinomas: breast cancer, ovarian cancer, cervical cancer, glioblastoma, multiple myeloma (including monoclonal gammopathy of undetermined significance, asymptomatic and symptomatic myeloma), prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, vaginal cancer, uterine cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma, Kaposi's sarcoma, multicentric Castleman's disease or AIDS-associated primary effusion lymphoma, neuroectodermal tumors, rhabdomyosarcoma (see e.g., Cancer, Principles and practice (DeVita et al. eds 1997) for additional cancers); as well as any metastasis of any of the above cancers, as well as non-cancer indications such as nasal polyposis, as well as other disorders and diseases described herein.

For a general description of immunoglobulin single variable domains, reference is made to the further description below, as well as to the prior art cited herein. In this respect, it should however be noted that this description and the prior art mainly describes immunoglobulin single variable domains of the so-called "$V_H3$ class" (i.e., immunoglobulin single variable domains with a high degree of sequence homology to human germline sequences of the $V_H3$ class such as DP-47, DP-51 or DP-29), which form a preferred aspect of this invention. It should, however, be noted that the invention in its broadest sense generally covers any type of immunoglobulin single variable domains and for example also covers the immunoglobulin single variable domains belonging to the so-called "$V_H4$ class" (i.e., immunoglobulin single variable domains with a high degree of sequence homology to human germline sequences of the $V_H4$ class such as DP-78), as for example described in WO 07/118670.

Generally, immunoglobulin single variable domains (in particular $V_{HH}$ sequences and sequence optimized immunoglobulin single variable domains) can in particular be characterized by the presence of one or more "Hallmark residues" (as described for example in Table B2) in one or more of the framework sequences (again as further described herein).

TABLE B-2

Hallmark Residues in VHHs

| Position | Human $V_H3$ | Hallmark Residues |
|---|---|---|
| 11 | L, V; predominantly L | L, S, V, M, W, F, T, Q, E, A, R, G, K, Y, N, P, I; preferably L |
| 37 | V, I, F; usually V | $F^{(1)}$, Y, V, L, A, H, S, I, W, C, N, G, D, T, P, preferably $F^{(1)}$ or Y |
| 44$^{(8)}$ | G | $E^{(3)}$, $Q^{(3)}$, $G^{(2)}$, D, A, K, R, L, P, S, V, H, T, N, W, M, I; preferably $G^{(2)}$, $E^{(3)}$ or $Q^{(3)}$; most preferably $G^{(2)}$ or $Q^{(3)}$. |
| 45$^{(8)}$ | L | $L^{(2)}$, $R^{(3)}$, P, H, F, G, Q, S, E, T, Y, C, I, D, V; preferably $L^{(2)}$ or $R^{(3)}$ |
| 47$^{(8)}$ | W, Y | $F^{(1)}$, $L^{(1)}$ or $W^{(2)}$ G, I, S, A, V, M, R, Y, E, P, T, C, H, K, Q, N, D; preferably $W^{(2)}$, $L^{(1)}$ or $F^{(1)}$ |
| 83 | R or K; usually R | R, $K^{(5)}$, T, $E^{(5)}$, Q, N, S, I, V, G, M, L, A, D, Y, H; preferably K or R; most preferably K |
| 84 | A, T, D; predominantly A | $P^{(5)}$, S, H, L, A, V, I, T, F, D, R, Y, N, Q, G, E; preferably P |
| 103 | W | $W^{(4)}$, $R^{(6)}$, G, S, K, A, M, Y, L, F, T, N, V, Q, $P^{(6)}$, E, C; preferably W |
| 104 | G | G, A, S, T, D, P, N, E, C, L; preferably G |
| 108 | L, M or T; predominantly L | Q, $L^{(7)}$, R, P, E, K, S, T, M, A, H; preferably Q or $L^{(7)}$ |

Notes:
$^{(1)}$In particular, but not exclusively, in combination with KERE or KQRE at positions 43-46.
$^{(2)}$Usually as GLEW at positions 44-47.
$^{(3)}$Usually as KERE or KQRE at positions 43-46, e.g. as KEREL, KEREF, KQREL, KQREF, KEREG, KOREW or KQREG at positions 43-47. Alternatively, also sequences such as TERE (for example TEREL), TQRE (for example TQREL), KECE (for example KECEL or KECER), KQCE (for example KQCEL), RERE (for example REREG), RQRE (for example RQREL, RQREF or RQREW), QERE (for example QEREG), QQRE, (for example QQREW, QQREL or QQREF), KGRE (for example KGREG), KDRE (for example KDREV) are possible. Some other possible, but less preferred sequences include for example DECKL and NVCEL.
$^{(4)}$With both GLEW at positions 44-47 and KERE or KQRE at positions 43-46.
$^{(5)}$Often as KP or EP at positions 83-84 of naturally occurring VHH domains.
$^{(6)}$In particular, but not exclusively, in combination with GLEW at positions 44-47.
$^{(7)}$With the proviso that when positions 44-47 are GLEW, position 108 is always Q in (non-humanized) $V_{HH}$ sequences that also contain a W at 103.
$^{(8)}$ The GLEW group also contains GLEW-like sequences at positions 44-47, such as for example GVEW, EPEW, GLER, DQEW, DLEW, GIEW, ELEW, GPEW, EWLP, and GPER.

The immunoglobulins of the invention may also contain a C-terminal extension (X)n (in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I)), for which reference is made to WO 12/175741 and WO 15/060643.

Apart from this and/or in addition, the immunoglobulin of the invention may have certain preferred amino acid residues at positions 11, 89, 110 and/or 112 as is described in further detail in WO 15/060643 (which is incorporated herein as reference).

Again, such immunoglobulin single variable domains may be derived in any suitable manner and from any suitable source, and may for example be naturally occurring $V_{HH}$ sequences (i.e., from a suitable species of Camelid, e.g., llama) or synthetic or semi-synthetic VHs or VLs (e.g., from human). Such immunoglobulin single variable domains may include "humanized" or otherwise "sequence optimized" VHHs, "camelized" immunoglobulin sequences (and in particular camelized heavy chain variable domain sequences, i.e., camelized VHs), as well as human VHs, human VLs, camelid VHHs that have been altered by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein. As mentioned herein, a particularly preferred class of immunoglobulin single variable domains of the invention comprises immunoglobulin single variable domains with an amino acid sequence that corresponds to the amino acid sequence of a naturally occurring $V_{HH}$ domain, but that has been "humanized", i.e. by replacing one or more amino acid residues in the amino acid sequence of said naturally occurring $V_{HH}$ sequence (and in particular in the framework sequences) by one or more of the amino acid residues that occur at the corresponding position(s) in a $V_H$ domain from a conventional 4-chain antibody from a human being (e.g. indicated above). This can be performed in a manner known per se, which will be clear to the skilled person, for example on the basis of the further description herein and the prior art on humanization referred to herein. Again, it should be noted that such humanized immunoglobulin single variable domains of the invention can be obtained in any suitable manner known per se and thus are not strictly limited to polypeptides that have been obtained using a polypeptide that comprises a naturally occurring $V_{HH}$ domain as a starting material.

Another particularly preferred class of immunoglobulin single variable domains of the invention comprises immunoglobulin single variable domains with an amino acid sequence that corresponds to the amino acid sequence of a naturally occurring $V_H$ domain, but that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a heavy chain antibody. This can be performed in a manner known per se, which will be clear to the skilled person, for example on the basis of the description herein. Such "camelizing" substitutions are preferably inserted at amino acid positions that form and/or are present at the $V_H$-$V_L$ interface, and/or at the so-called Camelidae hallmark residues, as defined herein (see also for example WO 94/04678 and Davies and Riechmann 1994 (FEBS letters 339: 285-290) and 1996 (Protein Engineering 9: 531-537)). Preferably, the $V_H$ sequence that is used as a starting material or starting point for generating or designing the camelized immunoglobulin single variable domains is preferably a $V_H$ sequence from a mammal, more preferably the $V_H$ sequence of a human being, such as a $V_H3$ sequence. However, it should be noted that such camelized immunoglobulin single variable domains of the invention can be obtained in any suitable manner known per se and thus are not strictly limited to polypeptides that have been obtained using a polypeptide that comprises a naturally occurring $V_H$ domain as a starting material.

For example, again as further described herein, both "humanization" and "camelization" can be performed by providing a nucleotide sequence that encodes a naturally occurring $V_{HH}$ domain or $V_H$ domain, respectively, and then changing, in a manner known per se, one or more codons in said nucleotide sequence in such a way that the new nucleotide sequence encodes a "humanized" or "camelized" immunoglobulin single variable domain of the invention, respectively. This nucleic acid can then be expressed in a manner known per se, so as to provide the desired immunoglobulin single variable domains of the invention. Alternatively, based on the amino acid sequence of a naturally occurring $V_{HH}$ domain or $V_H$ domain, respectively, the amino acid sequence of the desired humanized or camelized immunoglobulin single variable domains of the invention, respectively, can be designed and then synthesized de novo using techniques for peptide synthesis known per se. Also, based on the amino acid sequence or nucleotide sequence of a naturally occurring $V_{HH}$ domain or $V_H$ domain, respectively, a nucleotide sequence encoding the desired humanized or camelized immunoglobulin single variable domains of the invention, respectively, can be designed and then synthesized de novo using techniques for nucleic acid synthesis known per se, after which the nucleic acid thus obtained can be expressed in a manner known per se, so as to provide the desired immunoglobulin single variable domains of the invention.

Accordingly, the present invention relates to a polypeptide as described herein, wherein said ISV is a Nanobody, a $V_{HH}$, a humanized $V_{HH}$, or a camelized $V_H$.

Generally, proteins or polypeptides that comprise or essentially consist of a single building block, single immunoglobulin single variable domain or single Nanobody will be referred to herein as "monovalent" proteins or polypeptides, as "monovalent constructs", as "monovalent building block", as "monovalent immunoglobulin single variable domain", or as "monovalent Nanobody", respectively.

In this respect, the present invention also relates to the monovalent building blocks that make up the polypeptides of the invention.

Accordingly, the present invention relates to an ISV or polypeptide that specifically binds the constant domain of the T cell receptor (TCR) and that comprises or essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 119-133; or
    (b) amino acid sequences that have 4, 3, 2, or 1 amino acid(s) difference with the amino acid sequence of any of SEQ ID NOs: 119-133, provided that the polypeptide comprising the CDR1 with 4, 3, 2, or 1 amino acid(s) difference binds TCR with about the same or a higher affinity compared to the binding by the polypeptide comprising the CDR1 without the 4, 3, 2, or 1 amino acid(s) difference, said affinity as measured by surface plasmon resonance;

and/or (ii) CDR2 is chosen from the group consisting of:

(c) SEQ ID NOs: 134-163; or (d) amino acid sequences that have 4, 3, 2, or 1 amino acid(s) difference with the amino acid sequence of any of SEQ ID NOs: 134-163, provided that the polypeptide comprising the CDR2 with 4, 3, 2, or 1 amino acid(s) difference binds TCR with about the same or a higher affinity compared to the binding by the polypeptide comprising the CDR2 without the 4, 3, 2, or 1 amino acid(s) difference, said affinity as measured by surface plasmon resonance;

and/or (iii) CDR3 is chosen from the group consisting of:

(e) SEQ ID NOs: 164-174; or (f) amino acid sequences that have 4, 3, 2, or 1 amino acid(s) difference with the amino acid sequence of any of SEQ ID NOs: 164-174, provided that the polypeptide comprising the CDR3 with 4, 3, 2, or 1 amino acid(s) difference binds TCR with about the same or a higher affinity compared to the binding by the polypeptide comprising the CDR3 without the 4, 3, 2, or 1 amino acid(s) difference, said affinity as measured by surface plasmon resonance.

As discussed above, ISVs were isolated that belong to different clusters, based on structural similarities and differences in CDR2 and CDR3.

Immunoglobulin single variable domains belonging to cluster A are represented by polypeptides according in which:

(i) CDR1 is chosen from the group consisting of:

(a) SEQ ID NOs: 119-123, 125-127, 129, 132 and 133; and (b) amino acid sequences that have 4, 3, 2, or 1 amino acid(s) difference with the amino acid sequence of SEQ ID NO: 123, provided that the polypeptide comprising the CDR1 with 4, 3, 2, or 1 amino acid(s) difference binds TCR with about the same or a higher affinity compared to the binding by the polypeptide comprising the CDR1 without the 4, 3, 2, or 1 amino acid(s) difference, said affinity as measured by surface plasmon resonance;

and/or (ii) CDR2 is chosen from the group consisting of:

(c) SEQ ID NOs: 134-141, 143-144, 146-156, 159-163; and (d) amino acid sequences that have 4, 3, 2, or 1 amino acid(s) difference with the amino acid sequence of SEQ ID NO: 153, provided that the polypeptide comprising the CDR2 with 4, 3, 2, or 1 amino acid(s) difference binds TCR with about the same or a higher affinity compared to the binding by the polypeptide comprising the CDR2 without the 4, 3, 2, or 1 amino acid(s) difference, said affinity as measured by surface plasmon resonance;

and/or (iii) CDR3 is chosen from the group consisting of:

(e) SEQ ID NOs: 164-166, 169-171, 173-174; and (f) amino acid sequences that have 4, 3, 2, or 1 amino acid(s) difference with the amino acid sequence of SEQ ID NO: 170, provided that the polypeptide comprising the CDR3 with 4, 3, 2, or 1 amino acid(s) difference binds TCR with about the same or a higher affinity compared to the binding by the polypeptide comprising the CDR3 without the 4, 3, 2, or 1 amino acid(s) difference, said affinity as measured by surface plasmon resonance.

In another aspect, in the polypeptides belonging to cluster A, CDR1 is chosen from the group consisting of (a) SEQ ID NO: 123; and (b) amino acid sequences that have 1, 2, or 3 amino acid difference(s) with SEQ ID NO: 123, wherein at position 2 the D has been changed into A, S, E or G;

at position 4 the H has been changed into Y;

at position 5 the K has been changed into L;

at position 6 the I has been changed into L;

at position 8 the F has been changed into I or V; and/or at position 10 the G has been changed into S.

In another aspect, in the polypeptides belonging to cluster A, CDR2 is chosen from the group consisting of (a) SEQ ID NO: 153; and (b) amino acid sequences that have 1, 2, 3, 4 or 5 amino acid difference(s) with SEQ ID NO: 153, wherein at position 1 the H has been changed into T or R;

at position 3 the S has been changed into T or A;

at position 5 the G has been changed into S or A;

at position 7 the Q has been changed into D, E, T, A or V;

at position 8 the T has been changed into A or V; and/or at position 9 the D has been changed into A, Q, N, V or S.

In another aspect, in the polypeptides belonging to cluster A, CDR3 is chosen from the group consisting of (a) SEQ ID NO: 170; and (b) amino acid sequences that have 1, 2, or 3 amino acid difference(s) with SEQ ID NO: 170, wherein at position 1 the F has been changed into Y, L or G;

at position 4 the I has been changed into L;

at position 5 the Y has been changed into W; and/or at position 8 the D has been changed into N or S.

Accordingly, the present invention relates to an ISV or polypeptide that specifically binds the constant domain of the T cell receptor (TCR) and that comprises or essentially consists of 4 framework regions (FR1 to FR4, respectively) and 3 complementarity determining regions (CDR1 to CDR3, respectively), in which:

(i) CDR1 is chosen from the group consisting of:

(a) SEQ ID NO: 123; and (b) amino acid sequences that have 1, 2, or 3 amino acid difference(s) with SEQ ID NO: 123, wherein at position 2 the D has been changed into A, S, E or G;

at position 4 the H has been changed into Y;

at position 5 the K has been changed into L;

at position 6 the I has been changed into L;

at position 8 the F has been changed into I or V; and/or at position 10 the G has been changed into S;

and (ii) CDR2 is chosen from the group consisting of:

(a) SEQ ID NO: 153; and (b) amino acid sequences that have 1, 2, 3, 4 or 5 amino acid difference(s) with SEQ ID NO: 153, wherein at position 1 the H has been changed into T or R;

at position 3 the S has been changed into T or A;

at position 5 the G has been changed into S or A;

at position 7 the Q has been changed into D, E, T, A or V;

at position 8 the T has been changed into A or V; and/or at position 9 the D has been changed into A, Q, N, V or S;

and (iii) CDR3 is chosen from the group consisting of:
(a) SEQ ID NO: 170; and
(b) amino acid sequences that have 1, 2, or 3 amino acid difference(s) with SEQ ID NO: 170, wherein
at position 1 the F has been changed into Y, L or G;
at position 4 the I has been changed into L;
at position 5 the Y has been changed into W; and/or
at position 8 the D has been changed into N or S.

In another aspect, the invention relates to a polypeptide in which CDR1 is represented by SEQ ID NO: 123, CDR2 is represented by SEQ ID NO: 153, and CDR3 is represented by SEQ ID NO: 170. Preferably the polypeptide is selected from any of SEQ ID NOs: 1 to 104.

Immunoglobulin single variable domains belonging to cluster B are represented by polypeptides according in which:

(i) CDR1 is chosen from the group consisting of:
(a) SEQ ID NOs: 124, 128 and 131; and
(b) amino acid sequences that have 4, 3, 2, or 1 amino acid(s) difference with the amino acid sequence of SEQ ID NO: 124, provided that the polypeptide comprising the CDR1 with 4, 3, 2, or 1 amino acid(s) difference binds TCR with about the same or a higher affinity compared to the binding by the polypeptide comprising the CDR1 without the 4, 3, 2, or 1 amino acid(s) difference, said affinity as measured by surface plasmon resonance;

and/or (ii) CDR2 is chosen from the group consisting of:
(c) SEQ ID NOs: 142 and 145; and
(d) amino acid sequences that have 4, 3, 2, or 1 amino acid(s) difference with the amino acid sequence of SEQ ID NO: 145, provided that the polypeptide comprising the CDR2 with 4, 3, 2, or 1 amino acid(s) difference binds TCR with about the same or a higher affinity compared to the binding by the polypeptide comprising the CDR2 without the 4, 3, 2, or 1 amino acid(s) difference, said affinity as measured by surface plasmon resonance;

and/or (iii) CDR3 is chosen from the group consisting of:
(e) SEQ ID NOs: 167 and 168; and
(f) amino acid sequences that have 4, 3, 2, or 1 amino acid(s) difference with the amino acid sequence of SEQ ID NO: 167, provided that the polypeptide comprising the CDR3 with 4, 3, 2, or 1 amino acid(s) difference binds TCR with about the same or a higher affinity compared to the binding by the polypeptide comprising the CDR3 without the 4, 3, 2, or 1 amino acid(s) difference, said affinity as measured by surface plasmon resonance.

In another aspect, in the polypeptides belonging to cluster B, CDR1 is chosen from the group consisting of
(a) SEQ ID NO: 124; and
(b) amino acid sequences that have 1, or 2 amino acid difference(s) with SEQ ID NO: 124, wherein
at position 2 the E has been changed into Q; and/or
at position 6 the I has been changed into V.

In another aspect, in the polypeptides belonging to cluster B, CDR2 is chosen from the group consisting of
(a) SEQ ID NO: 145; and
(b) amino acid sequence that has 1 amino acid difference with SEQ ID NO: 145, wherein
at position 9 the N has been changed into D.

In another aspect, in the polypeptides belonging to cluster B, CDR3 is chosen from the group consisting of
(a) SEQ ID NO: 167; and
(b) amino acid sequence that has 1 amino acid difference with SEQ ID NO: 167, wherein
at position 4 the L has been changed into I.

Accordingly, the present invention relates to an ISV or polypeptide that specifically binds the constant domain of the T cell receptor (TCR) and that comprises or essentially consists of 4 framework regions (FR1 to FR4, respectively) and 3 complementarity determining regions (CDR1 to CDR3, respectively), in which:

(i) CDR1 is chosen from the group consisting of:
(a) SEQ ID NO: 124; and
(b) amino acid sequences that have 1, or 2 amino acid difference(s) with SEQ ID NO: 124, wherein
at position 2 the E has been changed into Q; and/or
at position 6 the I has been changed into V;

and (ii) CDR2 is chosen from the group consisting of:
(a) SEQ ID NO: 145; and
(b) amino acid sequence that has 1 amino acid difference with SEQ ID NO: 145, wherein
at position 9 the N has been changed into D;

and (iii) CDR3 is chosen from the group consisting of:
(a) SEQ ID NO: 167; and
(b) amino acid sequence that has 1 amino acid difference with SEQ ID NO: 167, wherein
at position 4 the L has been changed into I.

In another aspect, the invention relates to a polypeptide in which CDR1 is represented by SEQ ID NO: 124, CDR2 is represented by SEQ ID NO: 145, and CDR3 is represented by SEQ ID NO: 167. Preferably the polypeptide is selected from any of SEQ ID NOs: 105-115.

Immunoglobulin single variable domains belonging to cluster C are represented by polypeptides according in which:

(i) CDR1 is chosen from the group consisting of:
(a) SEQ ID NO: 130; and
(b) amino acid sequences that have 4, 3, 2, or 1 amino acid(s) difference with the amino acid sequence of SEQ ID NO: 130, provided that the polypeptide comprising the CDR1 with 4, 3, 2, or 1 amino acid(s) difference binds TCR with about the same or a higher affinity compared to the binding by the polypeptide comprising the CDR1 without the 4, 3, 2, or 1 amino acid(s) difference, said affinity as measured by surface plasmon resonance;

and/or (ii) CDR2 is chosen from the group consisting of:
(c) SEQ ID NOs: 157-158; and
(d) amino acid sequences that have 4, 3, 2, or 1 amino acid(s) difference with the amino acid sequence of SEQ ID NO: 157, provided that the polypeptide comprising the CDR2 with 4, 3, 2, or 1 amino acid(s) difference binds TCR with about the same or a higher affinity compared to the binding by the polypeptide comprising the CDR2 without the 4, 3, 2, or 1 amino acid(s) difference, said affinity as measured by surface plasmon resonance;

and/or
(iii) CDR3 is chosen from the group consisting of:
(e) SEQ ID NO: 172; and
(f) amino acid sequences that have 4, 3, 2, or 1 amino acid(s) difference with the amino acid sequence of SEQ ID NO: 172, provided that the polypeptide comprising the CDR3 with 4, 3, 2, or 1 amino acid(s) difference binds TCR with about the same or a higher affinity compared to the binding by the polypeptide comprising the CDR3 without the 4, 3, 2, or 1 amino acid(s) difference, said affinity as measured by surface plasmon resonance.

In another aspect, in the polypeptides belonging to cluster C, CDR1 is chosen from SEQ ID NO: 130.

In another aspect, in the polypeptides belonging to cluster C, CDR2 is chosen from the group consisting of
(a) SEQ ID NO: 157; and
(b) amino acid sequence that has 1 amino acid difference with SEQ ID NO: 157, wherein
at position 8 the T has been changed into I.

In another aspect, in the polypeptides belonging to cluster C, CDR3 is chosen from SEQ ID NO: 172.

Accordingly, the present invention relates to an ISV or polypeptide that specifically binds the constant domain of the T cell receptor (TCR) and that comprises or essentially consists of 4 framework regions (FR1 to FR4, respectively) and 3 complementarity determining regions (CDR1 to CDR3, respectively), in which:
(i) CDR1 is chosen from SEQ ID NO: 130; and
(ii) CDR2 is chosen from the group consisting of:
(a) SEQ ID NO: 157; and
(b) amino acid sequence that has 1 amino acid difference with SEQ ID NO: 157, wherein
at position 8 the T has been changed into I; and
(iii) CDR3 is chosen from SEQ ID NO: 172.

In another aspect, the invention relates to a polypeptide in which CDR1 is represented by SEQ ID NO: 130, CDR2 is represented by SEQ ID NO: 157, and CDR3 is represented by SEQ ID NO: 172. Preferably the polypeptide is selected from any of SEQ ID NOs: 116-118.

In a further aspect, the invention relates to polypeptides that cross-block the binding to the constant domain of the T cell receptor (TCR) by at least one of the ISVs or polypeptides belonging to Cluster A, B or C.

Accordingly, the present invention relates to polypeptides that cross-block the binding to the constant domain of the T cell receptor (TCR) by at least one of the ISVs or polypeptides with SEQ ID NOs: 1-104.

In another aspect, the present invention relates to ISVs or polypeptides that cross-block the binding to the constant domain of the T cell receptor (TCR) by at least one of the ISVs or polypeptides with SEQ ID NOs: 105-115.

In yet another aspect, the present invention relates to ISVs or polypeptides that cross-block the binding to the constant domain of the T cell receptor (TCR) by at least one of the ISVs or polypeptides with SEQ ID NOs: 116-118.

In a further aspect, the invention relates to polypeptides that are cross-blocked from binding to the constant domain of the T cell receptor (TCR) by at least one of the ISVs or polypeptides belonging to Cluster A, B or C.

Accordingly, the present invention relates to polypeptides that are cross-blocked from binding to the constant domain of the T cell receptor (TCR) by at least one of the ISVs or polypeptides belonging to SEQ ID NOs: 1-104.

In another aspect, the present invention relates to polypeptides that are cross-blocked from binding to the constant domain of the T cell receptor (TCR) by at least one of the ISVs or polypeptides belonging to SEQ ID NOs: 105-115.

In another aspect, the present invention relates to polypeptides that are cross-blocked from binding to the constant domain of the T cell receptor (TCR) by at least one of the ISVs or polypeptides belonging to SEQ ID NOs: 116-118.

The present invention also relates to an ISV or polypeptide that specifically binds carcinoembryonic antigen (CEA) and that comprises or essentially consists of 4 framework regions (FR1 to FR4, respectively) and 3 complementarity determining regions (CDR1 to CDR3, respectively), in which:
(i) CDR1 is chosen from the group consisting of:
(a) SEQ ID NO: 361 (GDTYGSYWMG); or
(b) amino acid sequences that have 4, 3, 2, or 1 amino acid(s) difference with the amino acid sequence of SEQ ID NO: 361, provided that the polypeptide comprising the CDR1 with 4, 3, 2, or 1 amino acid(s) difference binds CEA with about the same or a higher affinity compared to the binding by the polypeptide comprising the CDR1 without the 4, 3, 2, or 1 amino acid(s) difference, said affinity as measured by surface plasmon resonance;
and/or
(ii) CDR2 is chosen from the group consisting of:
(c) SEQ ID NO: 363 (AINRGGGYTV); or
(d) amino acid sequences that have 4, 3, 2, or 1 amino acid(s) difference with the amino acid sequence of any of SEQ ID NO: 363, provided that the polypeptide comprising the CDR2 with 4, 3, 2, or 1 amino acid(s) difference binds CEA with about the same or a higher affinity compared to the binding by the polypeptide comprising the CDR2 without the 4, 3, 2, or 1 amino acid(s) difference, said affinity as measured by surface plasmon resonance;
and/or
(iii) CDR3 is chosen from the group consisting of:
(e) SEQ ID NO: 365 (SGVLGGLHEDWFNY); or
(f) amino acid sequences that have 4, 3, 2, or 1 amino acid(s) difference with the amino acid sequence of any of SEQ ID NO: 365, provided that the polypeptide comprising the CDR3 with 4, 3, 2, or 1 amino acid(s) difference binds CEA with about the same or a higher affinity compared to the binding by the polypeptide comprising the CDR3 without the 4, 3, 2, or 1 amino acid(s) difference, said affinity as measured by surface plasmon resonance.

In another aspect, the invention relates to a polypeptide in which CDR1 is represented by SEQ ID NO: 361, CDR2 is represented by SEQ ID NO: 363, and CDR3 is represented by SEQ ID NO: 365. Preferred polypeptides include SEQ ID NOs: 353 and 354.

In a further aspect, the invention relates to polypeptides that cross-block the binding to carcinoembryonic antigen (CEA) by at least one of the ISVs or polypeptides with SEQ ID NOs: 353 or 354.

In a further aspect, the invention relates to polypeptides that are cross-blocked from binding to carcinoembryonic antigen (CEA) by at least one of the ISVs or polypeptides with SEQ ID NOs: 353 or 354.

The present invention also relates to an ISV or polypeptide that specifically binds CD20 and that comprises or essentially consists of 4 framework regions (FR1 to FR4, respectively) and 3 complementarity determining regions (CDR1 to CDR3, respectively), in which:

(i) CDR1 is chosen from the group consisting of:
   (a) SEQ ID NO: 362 (GGTFSSYTMG); or
   (b) amino acid sequences that have 4, 3, 2, or 1 amino acid(s) difference with the amino acid sequence of SEQ ID NO: 362, provided that the polypeptide comprising the CDR1 with 4, 3, 2, or 1 amino acid(s) difference binds CD20 with about the same or a higher affinity compared to the binding by the polypeptide comprising the CDR1 without the 4, 3, 2, or 1 amino acid(s) difference, said affinity as measured by surface plasmon resonance;
and/or
(ii) CDR2 is chosen from the group consisting of:
   (c) SEQ ID NO: 364 (EVRWGGVTT); or
   (d) amino acid sequences that have 4, 3, 2, or 1 amino acid(s) difference with the amino acid sequence of any of SEQ ID NO: 364, provided that the polypeptide comprising the CDR2 with 4, 3, 2, or 1 amino acid(s) difference binds CD20 with about the same or a higher affinity compared to the binding by the polypeptide comprising the CDR2 without the 4, 3, 2, or 1 amino acid(s) difference, said affinity as measured by surface plasmon resonance;
and/or
(iii) CDR3 is chosen from the group consisting of:
   (e) SEQ ID NO: 366 (VRQMYMTVVPDY); or
   (f) amino acid sequences that have 4, 3, 2, or 1 amino acid(s) difference with the amino acid sequence of any of SEQ ID NO: 366, provided that the polypeptide comprising the CDR3 with 4, 3, 2, or 1 amino acid(s) difference binds CD20 with about the same or a higher affinity compared to the binding by the polypeptide comprising the CDR3 without the 4, 3, 2, or 1 amino acid(s) difference, said affinity as measured by surface plasmon resonance.

In another aspect, the invention relates to a polypeptide in which CDR1 is represented by SEQ ID NO: 362, CDR2 is represented by SEQ ID NO: 364, and CDR3 is represented by SEQ ID NO: 366. A preferred polypeptide includes SEQ ID NO: 357.

In a further aspect, the invention relates to polypeptides that cross-block the binding to CD20 by the ISV or polypeptide with SEQ ID NO: 357.

In a further aspect, the invention relates to polypeptides that are cross-blocked from binding to CD20 by the ISV or polypeptide with SEQ ID NO: 357.

The invention further relates to compounds or constructs, and in particular proteins or polypeptides that comprise or essentially consist of one or more ISVs or polypeptides of the invention, and optionally further comprise one or more other groups, residues, moieties or binding units. As will become clear to the skilled person from the further disclosure herein, such further groups, residues, moieties, binding units or amino acid sequences may or may not provide further functionality to the polypeptide of the invention (and/or to the compound or construct in which it is present) and may or may not modify the properties of the polypeptide of the invention.

In a specific, but non-limiting aspect of the invention, which will be further described herein, the ISVs and polypeptides of the invention may have an increased half-life in serum (as further described herein) compared to the immunoglobulin single variable domain or polypeptide from which they have been derived. For example, an immunoglobulin single variable domain or polypeptide of the invention may be linked (chemically or otherwise) to one or more groups or moieties that extend the half-life (such as PEG), so as to provide a derivative of the ISV or polypeptide of the invention with increased half-life.

In a specific aspect of the invention, a compound or construct of the invention or a polypeptide of the invention may have an increased half-life, compared to the corresponding ISV or polypeptide of the invention. Some preferred, but non-limiting examples of such compounds, constructs and polypeptides will become clear to the skilled person based on the further disclosure herein, and for example comprise immunoglobulin single variable domains or polypeptides of the invention that have been chemically modified to increase the half-life thereof (for example, by means of pegylation); immunoglobulin single variable domains or polypeptides of the invention that comprise at least one additional binding site for binding to a serum protein (such as serum albumin); or constructs or polypeptides of the invention which comprise at least ISV or polypeptide of the invention that is linked to at least one moiety (and in particular at least one amino acid sequence) which increases the half-life of the ISV or polypeptide of the invention. Examples of ISVs or polypeptides of the invention which comprise such half-life extending moieties or immunoglobulin single variable domains will become clear to the skilled person based on the further disclosure herein; and for example include, without limitation, polypeptides in which the one or more immunoglobulin single variable domains or polypeptide of the invention are suitably linked to one or more serum proteins or fragments thereof (such as (human) serum albumin or suitable fragments thereof) or to one or more binding units that can bind to serum proteins (such as, for example, domain antibodies, immunoglobulin single variable domains that are suitable for use as a domain antibody, single domain antibodies, immunoglobulin single variable domains that are suitable for use as a single domain antibody, "dAb"'s, immunoglobulin single variable domains that are suitable for use as a dAb, or Nanobodies that can bind to serum proteins such as serum albumin (such as human serum albumin), serum immunoglobulins such as IgG, or transferrin; reference is made to the further description and references mentioned herein); ISVs or polypeptides in which an ISV or polypeptide of the invention is linked to an Fc portion (such as a human Fc) or a suitable part or fragment thereof; or polypeptides in which the one or more immunoglobulin single variable domains or polypeptide of the invention are suitable linked to one or more small proteins or peptides that can bind to serum proteins, such as, without limitation, the proteins and peptides described in WO 91/01743, WO 01/45746, WO 02/076489, WO 08/068280, WO 09/127691 and WO 11/095545.

Generally, the compounds, constructs or polypeptides of the invention with increased half-life preferably have a half-life that is at least 1.5 times, preferably at least 2 times, such as at least 5 times, for example at least 10 times or more than 20 times, greater than the half-life of the corresponding ISV or polypeptide of the invention per se. For example, the compounds, constructs or polypeptides of the invention with increased half-life may have a half-life e.g., in humans that is increased with more than 1 hours, preferably more than 2 hours, more preferably more than 6 hours, such as more than 12 hours, or even more than 24, 48 or 72 hours, compared to the corresponding ISV or polypeptide of the invention per se.

In a preferred, but non-limiting aspect of the invention, such compounds, constructs or polypeptides of the invention have a serum half-life e.g. in humans that is increased with more than 1 hours, preferably more than 2 hours, more preferably more than 6 hours, such as more than 12 hours, or even more than 24, 48 or 72 hours, compared to the corresponding ISV or polypeptide of the invention per se.

In another preferred, but non-limiting aspect of the invention, such compounds, constructs or polypeptides of the invention exhibit a serum half-life in human of at least about 12 hours, preferably at least 24 hours, more preferably at least 48 hours, even more preferably at least 72 hours or more. For example, compounds, constructs or polypeptides of the invention may have a half-life of at least 5 days (such as about 5 to 10 days), preferably at least 9 days (such as about 9 to 14 days), more preferably at least about 10 days (such as about 10 to 15 days), or at least 11 days (such as about 11 to 16 days), more preferably at least about 12 days (such as about 12 to 18 days or more), or more than 14 days (such as about 14 to 19 days).

lacks not only the active mechanism to overcome the cell membrane barrier, but also the ability to penetrate into tumour tissues (Qianqian Guo et al. 2013, Polym. Chem. 4: 4584-4587).

In a particularly preferred but non-limiting aspect of the invention, the invention provides a polypeptide of the invention comprising a first and a second immunoglobulin single variable domain (ISV); and further comprising one or more (preferably one) serum albumin binding immunoglobulin single variable domain as described herein, e.g. the serum albumin binding immunoglobulin single variable domain referred to as Alb8, Alb23, Alb129, Alb132, Alb11, Alb11 (S112K)-A, Alb82, Alb82-A, Alb82-AA, Alb82-AAA, Alb82-G, Alb82-GG, Alb82-GGG (Table B-3).

TABLE B-3

Immunoglobulin single variable domains for use in HLE of the ISVs and polypeptides of the invention

| ISV | Sequence | SEQ ID NO |
|---|---|---|
| Alb8 | EVQLVESGGGLVQPGNSLRLSCAASGFTFSSFGMSWVRQAPGKGLEWVSSISGSGSDT LYADSVKGRFTISRDNAKTTLYLQMNSLRPEDTAVYYCTIGGSLSRSSQGTINTVSS | 400 |
| Alb23 | EVQLLESGGGLVQPGGSLRLSCAASGFTFRSFGMSWVRQAPGKGPEWVSSISGSGSDT LYADSVKGRFTISRDNSKNTLYLQMNSLRPEDTAVYYCTIGGSLSRSSQGTLVTVSS | 401 |
| Alb129 | EVQIVESGGGVVQPGNSLRSCAASGFTFSSFGMSWVRQAPGKGLEWVSSISGSGSDT LYADSVKGRFTISRDNAKTTLYLQMNSLRPEDTATYYCTIGGSLSRSSQGTLVTVSSA | 402 |
| Alb132 | EVQLVESGGGVVQPGGSLRLSCAASGETFRSFGMSWVRQAPGKGPEWVSSISGSGSD TLYADSVKGRFTISRDNSKNTLYLQMNSLRPEDTATYYCTIGGSLSRSSQGTLVTVSSA | 403 |
| Alb11 | EVQLVESGGGLVQPGNSLRLSCAASGFTFSSFGMSWVRQAPGKGLEWVSSISGSGSDT LYADSVKGRFTISRDNAKTTLYLQMNSLRPEDTAVYYCTIGGSLSRSSQGTLVTVSS | 404 |
| Alb11 (S112K)-A | EVQLVESGGGLVQPGNSLRLSCAASGFTFSSFGMSWVRQAPGKGLEWVSSISGSGSDT LYADSVKGRFTISRDNAKTTLYLQMNSLRPEDTAVYYCTIGGSLSRSSQGTLVKVSSA | 405 |
| Alb82 | EVQIVESGGGVVQPGNSLRLSCAASGFTFSSFGMSWVRQAPGKGLEWVSSISGSGSDT LYADSVKGRFTISRDNAKTTLYLQMNSLRPEDTALYYCTIGGSLSRSSQGTLVTVSS | 406 |
| Alb82-A | EVQLVESGGGVVQPGNSLRLSCAASGFTFSSFGMSWVRQAPGKGLEWVSSISGSGSDT LYADSVKGRFTISRDNAKTTLYLQMNSLRPEDTALYYCTIGGSLSRSSQGTLVTVSSA | 407 |
| Alb82-AA | EVQLVESGGGVVQPGNSLRLSCAASGFTFSSFGMSWVRQAPGKGLEWVSSISGSGSDT LYADSVKGRFTISRDNAKTTLYLQMNSLRPEDTALYYCTIGGSLSRSSQGTLVTVSSAA | 408 |
| Alb82-AAA | EVQLVESGGGVVQPGNSLRLSCAASGFTESSFGMSWVRQAPGKGLEWVSSISGSGSDT LYADSVKGRFTISRDNAKTTLYLQMNSLRPEDTALYYCTIGGSLSRSSQGTLVTVSSAAA | 409 |
| Alb82-G | EVQIVESGGGVVQPGNSLRLSCAASGFTFSSFGMSWVRQAPGKGLEWVSSISGSGSDT LYADSVKGRFTISRDNAKTTLYLQMNSLRPEDTALYYCTIGGSLSRSSQGTLVTVSSG | 410 |
| Alb82-GG | EVQILVESGGGVVQPGNSLRLSCAASGFTFSSFGMSWVRQAPGKGLEWVSSISGSGSDT LYADSVKGRFTISRDNAKTTLYLQMNSLRPEDTALYYCTIGGSLSRSSQGTLVTVSSGG | 411 |
| Alb82-GGG | EVQLVESGGGVVQPGNSLRLSCAASGFTFSSFGMSWVRQAPGKGLEWVSSISGSGSDT LYADSVKGRFTISRDNAKTTLYLQMNSLRPEDTALYYCTIGGSLSRSSQGTLVTVSSGGG | 412 |

In the present invention, it was demonstrated that the inclusion of an albumin targeting binding unit in the construct as such did not have an essential impact on the obtained potency or efficacy. Although a minor loss of efficacy/potency was observed in the presence of HSA, the half-life extended TCR binding multispecific polypeptides were still potent in tumour cell killing. Albumin-based drug delivery has been demonstrated to be useful for achieving improved cancer therapy, largely due to its passive target toward tumour via the enhanced permeability and retention effect and the increased demand for albumin by tumour cells as source of energy and amino acids. However, albumin Accordingly, the present invention relates to a polypeptide as described herein, further comprising a serum protein binding moiety.

The present invention relates to a polypeptide as described herein, wherein said serum protein binding moiety binds serum albumin.

The present invention relates to a polypeptide as described herein, wherein said serum protein binding moiety is an immunoglobulin single variable domain binding serum albumin.

The present invention relates to a polypeptide as described herein, wherein said ISV binding serum albumin essentially consists of 4 framework regions (FR1 to FR4, respectively) and 3 complementarity determining regions (CDR1 to CDR3 respectively), in which CDR1 is SFGMS (SEQ ID NO: 481), CDR2 is SISGSGSDTLYADSVKG (SEQ ID NO: 482), and in which CDR3 is GGSLSR (SEQ ID NO: 475), CDR determined according to Kabat definition; and/or in which CDR1 is GFTFSSFGMS (SEQ ID NO: 472) or GFTFRSFGMS (SEQ ID NO: 473), CDR2 is SISGSGSDTL (SEQ ID NO: 474) and CDR3 is GGSLSR (SEQ ID NO: 475), CDR determined according to Kontermann 2010.

The present invention relates to a polypeptide as described herein, wherein said ISV binding serum albumin comprises Alb8, Alb23, Alb129, Alb132, Alb11, Alb11 (5112K)-A, Alb82, Alb82-A, Alb82-AA, Alb82-AAA, Alb82-G, Alb82-GG, Alb82-GGG (Table-B3).

In the polypeptides of the invention, the two or more building blocks, ISVs or Nanobodies and the optionally one or more polypeptides, one or more other groups, drugs, agents, residues, moieties or binding units may be directly linked to each other (as for example described in WO 99/23221) and/or may be linked to each other via one or more suitable spacers or linkers, or any combination thereof.

Suitable spacers or linkers for use in multivalent and multispecific polypeptides will be clear to the skilled person, and may generally be any linker or spacer used in the art to link amino acid sequences. Preferably, said linker or spacer is suitable for use in constructing proteins or polypeptides that are intended for pharmaceutical use.

Some particularly preferred spacers include the spacers and linkers that are used in the art to link antibody fragments or antibody domains. These include the linkers mentioned in the general background art cited above, as well as for example linkers that are used in the art to construct diabodies or ScFv fragments (in this respect, however, it should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each ISV or Nanobody by itself forms a complete antigen-binding site).

For example, a linker may be a suitable amino acid sequence, and in particular amino acid sequences of between 1 and 50, preferably between 1 and 30, such as between 1 and 10 amino acid residues. Some preferred examples of such amino acid sequences include gly-ser linkers, for example of the type $(gly_x ser_y)_z$, such as (for example $(gly_4 ser)_3$ or $(gly_3 ser_2)_3$, as described in WO 99/42077, and the GS530, GS515, GS9 and GS57 linkers described in the applications by Ablynx mentioned herein (see for example WO 06/040153 and WO 06/122825), as well as hinge-like regions, such as the hinge regions of naturally occurring heavy chain antibodies or similar sequences (such as described in WO 94/04678). Preferred linkers are depicted in Table B-4.

TABLE B-4

Linkers

| Linker | Sequence | SEQ ID NO |
|---|---|---|
| 5GS | GGGGS | 376 |
| 7GS | SGGSGGS | 377 |
| 9GS | GGGGSGGGS | 378 |
| 10GS | GGGGSGGGGS | 379 |
| 15G5 | GGGGSGGGGSGGGGS | 380 |
| 18G5 | GGGGSGGGSGGGGGGS | 381 |
| 20GS | GGGGSGGGGSGGGGSGGGGS | 382 |
| 25G5 | GGGGSGGGGSGGGGSGGGGSGGGGS | 383 |
| 30GS | GGGGSGGGGSGGGGSGGGGSGGGGSGGGGS | 384 |
| 35GS | GGGGSGGGGSGGGGSGGGGSGGGGSGGGGSGGGGS | 385 |
| Poly-A | AAA | 386 |

Some other particularly preferred linkers are poly-alanine (such as AAA), as well as the linkers GS530 (SEQ ID NO: 85 in WO 06/122825) and GS59 (SEQ ID NO: 84 in WO 06/122825).

Other suitable linkers generally comprise organic compounds or polymers, in particular those suitable for use in proteins for pharmaceutical use. For instance, poly(ethyleneglycol) moieties have been used to link antibody domains, see for example WO 04/081026.

It is encompassed within the scope of the invention that the length, the degree of flexibility and/or other properties of the linker(s) used (although not critical, as it usually is for linkers used in ScFv fragments) may have some influence on the properties of the final polypeptide of the invention, including but not limited to the affinity, specificity or avidity for the TCR, or for one or more of the other antigens. Based on the disclosure herein, the skilled person will be able to determine the optimal linker(s) for use in a specific polypeptide of the invention, optionally after some limited routine experiments.

For example, in multivalent polypeptides of the invention that comprise building blocks, ISVs or Nanobodies directed against a first and second target, the length and flexibility of the linker are preferably such that it allows each building block, ISV or Nanobody of the invention present in the polypeptide to bind to its cognate target, e.g. the antigenic determinant on each of the targets. Again, based on the disclosure herein, the skilled person will be able to determine the optimal linker(s) for use in a specific polypeptide of the invention, optionally after some limited routine experiments.

It is also within the scope of the invention that the linker(s) used confer one or more other favourable properties or functionality to the polypeptides of the invention, and/or provide one or more sites for the formation of derivatives and/or for the attachment of functional groups (e.g. as described herein for the derivatives of the ISVs, Nanobodies, or polypeptides of the invention). For example, linkers containing one or more charged amino acid residues can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after some limited routine experiments.

Finally, when two or more linkers are used in the polypeptides of the invention, these linkers may be the same or different. Again, based on the disclosure herein, the skilled person will be able to determine the optimal linkers for use in a specific polypeptide of the invention, optionally after some limited routine experiments.

Usually, for ease of expression and production, a polypeptide of the invention will be a linear polypeptide. However, the invention in its broadest sense is not limited thereto. For example, when a polypeptide of the invention comprises three or more building blocks, ISVs or Nanobodies, it is possible to link them by use of a linker with three or more "arms", with each "arm" being linked to a building block, ISV or Nanobody, so as to provide a "star-shaped" construct. It is also possible, although usually less preferred, to use circular constructs.

Accordingly, the present invention relates to a polypeptide as described herein, wherein said first ISV and said second ISV and possibly said third ISV and/or said ISV binding serum albumin are directly linked to each other or are linked via a linker.

The present invention relates to a polypeptide as described herein, wherein said linker is chosen from the group consisting of linkers of 5GS, 7GS, 9GS, 10GS, 15GS, 18GS, 20GS, 25GS, 30GS and 35GS.

The present invention relates to a polypeptide as described herein, wherein said serum protein binding moiety is a non-antibody based polypeptide (e.g. PEG).

The invention also relates to methods for preparing the ISVs, polypeptides and constructs described herein. The ISVs, polypeptides and constructs of the invention can be prepared in a manner known per se, as will be clear to the skilled person from the further description herein. For example, the ISVs, polypeptides and constructs of the invention can be prepared in any manner known per se for the preparation of antibodies and in particular for the preparation of antibody fragments (including but not limited to (single) domain antibodies and ScFv fragments). Some preferred, but non-limiting methods for preparing the polypeptides and constructs include the methods and techniques described herein.

The method for producing an ISV, polypeptide or protein construct of the invention may comprise the following steps:
the expression, in a suitable host cell or host organism (also referred to herein as a "host of the invention") or in another suitable expression system of a nucleic acid that encodes said ISV, polypeptide or protein construct of the invention,
optionally followed by:
isolating and/or purifying the ISV, polypeptide or protein construct of the invention thus obtained.
In particular, such a method may comprise the steps of:
cultivating and/or maintaining a host of the invention under conditions that are such that said host of the invention expresses and/or produces at least one ISV, polypeptide or protein construct of the invention;
optionally followed by:
isolating and/or purifying the ISV, polypeptide or protein construct of the invention thus obtained.

Accordingly, the present invention also relates to a nucleic acid or nucleotide sequence that encodes an ISV, polypeptide or protein construct of the invention (also referred to as "nucleic acid of the invention" or "nucleotide sequence of the invention"). A nucleic acid of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one embodiment of the invention, the nucleic acid of the invention is in essentially isolated from, as defined herein. The nucleic acid of the invention may also be in the form of, be present in and/or be part of a vector, such as for example a plasmid, cosmid or YAC, which again may be in essentially isolated form.

The nucleic acids of the invention can be prepared or obtained in a manner known per se, based on the information on the polypeptides or protein constructs of the invention given herein, and/or can be isolated from a suitable natural source. Also, as will be clear to the skilled person, to prepare a nucleic acid of the invention, also several nucleotide sequences, such as at least one nucleotide sequence encoding an immunoglobulin single variable domain of the invention and for example nucleic acids encoding one or more linkers can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers. These and other techniques will be clear to the skilled person, and reference is again made to the standard handbooks, such as Sambrook et al. and Ausubel et al., mentioned herein, as well as the Examples below.

The nucleic acid of the invention may also be in the form of, be present in and/or be part of a genetic construct, as will be clear to the person skilled in the art. Such genetic constructs generally comprise at least one nucleic acid of the invention that is optionally linked to one or more elements of genetic constructs known per se, such as for example one or more suitable regulatory elements (such as a suitable promoter(s), enhancer(s), terminator(s), etc.) and the further elements of genetic constructs referred to herein. Such genetic constructs comprising at least one nucleic acid of the invention will also be referred to herein as "genetic constructs of the invention".

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting embodiment, a genetic construct of the invention comprises
a) at least one nucleic acid of the invention; operably connected to b) one or more regulatory elements, such as a promoter and optionally a suitable terminator;

and optionally also c) one or more further elements of genetic constructs known per se;

in which the terms "regulatory element", "promoter", "terminator" and "operably connected" have their usual meaning in the art (as further described herein); and in which said "further elements" present in the genetic constructs may for example be 3'- or 5'-UTR sequences, leader sequences, selection markers, expression markers/reporter genes, and/or elements that may facilitate or increase (the efficiency of) transformation or integration. These and other suitable elements for such genetic constructs will be clear to the skilled person, and may for instance depend upon the type of construct used; the intended host cell or host organism; the manner in which the nucleotide sequences of the invention of interest are to be expressed (e.g. via constitutive, transient or inducible expression); and/or the transformation technique to be used. For example, regulatory sequences, promoters and terminators known per se for the expression and production of antibodies and antibody fragments (including but not limited to (single) domain antibodies and ScFv fragments) may be used in an essentially analogous manner.

Preferably, in the genetic constructs of the invention, said at least one nucleic acid of the invention and said regulatory elements, and optionally said one or more further elements, are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promoter). Generally, when two nucleotide sequences are operably linked, they will be in the same orientation and usually also in the same reading frame. They will usually also be essentially contiguous, although this may also not be required.

The nucleic acids of the invention and/or the genetic constructs of the invention may be used to transform a host cell or host organism, i.e. for expression and/or production of the polypeptide or protein construct of the invention. The host is preferably a non-human host. Suitable hosts or host cells will be clear to the skilled person, and may for example be any suitable fungal, prokaryotic or eukaryotic cell or cell line or any suitable fungal, prokaryotic or eukaryotic organism, for example:

a bacterial strain, including but not limited to gram-negative strains such as strains of *Escherichia coli*; of *Proteus*, for example of *Proteus mirabilis*; of *Pseudomonas*, for example of *Pseudomonas fluorescens*; and gram-positive strains such as strains of *Bacillus*, for example of *Bacillus subtilis* or of *Bacillus brevis*; of *Streptomyces*, for example of *Streptomyces lividans*; of *Staphylococcus*, for example of *Staphylococcus carnosus*; and of *Lactococcus*, for example of *Lactococcus lactis*;

a fungal cell, including but not limited to cells from species of *Trichoderma*, for example from *Trichoderma reesei*; of *Neurospora*, for example from *Neurospora crassa*; of *Sordaria*, for example from *Sordoria macrospora*; of *Aspergillus*, for example from *Aspergillus niger* or from *Aspergillus sojae*; or from other filamentous fungi;

a yeast cell, including but not limited to cells from species of *Saccharomyces*, for example of *Saccharomyces cerevisiae*; of *Schizosacchoromyces*, for example of *Schizosaccharomyces pombe*; of *Pichia*, for example of *Pichia pastoris* or of *Pichia methanolica*; of *Hansenula*, for example of *Hansenula polymorpha*; of *Kluyveromyces*, for example of *Kluyveromyces lactis*; of *Arxula*, for example of *Arxula adeninivorans*; of *Yarrowia*, for example of *Yarrowia lipolytica;* an amphibian cell or cell line, such as *Xenopus* oocytes;

an insect-derived cell or cell line, such as cells/cell lines derived from lepidoptera, including but not limited to *Spodoptera* SF9 and Sf21 cells or cells/cell lines derived from *Drosophila*, such as Schneider and Kc cells;

a plant or plant cell, for example in tobacco plants; and/or a mammalian cell or cell line, for example a cell or cell line derived from a human, a cell or a cell line from mammals including but not limited to CHO-cells, BHK-cells (for example BHK-21 cells) and human cells or cell lines such as HeLa, COS (for example COS-7) and PER.C6 cells;

as well as all other hosts or host cells known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457; WO 96/34103; WO 99/42077; Frenken et al. 1998 (Res. Immunol. 149: 589-99); Riechmann and Muyldermans 1999 (J. Immunol. Met. 231: 25-38); van der Linden 2000 (J. Biotechnol. 80: 261-70); Joosten et al. 2003 (Microb. Cell Fact. 2: 1); Joosten et al. 2005 (Appl. Microbiol. Biotechnol. 66: 384-92); and the further references cited herein.

For expression of the ISVs, polypeptides or constructs in a cell, they may also be expressed as so-called "intrabodies", as for example described in WO 94/02610, WO 95/22618 and U.S. Pat. No. 7,004,940; WO 03/014960; in Cattaneo and Biocca 1997 (Intracellular Antibodies: Development and Applications. Landes and Springer-Verlag); and in Kontermann 2004 (Methods 34: 163-170).

According to one preferred, but non-limiting embodiment of the invention, the ISV, polypeptide or protein construct of the invention is produced in a bacterial cell, in particular a bacterial cell suitable for large scale pharmaceutical production, such as cells of the strains mentioned above.

According to another preferred, but non-limiting embodiment of the invention, the ISV, polypeptide or protein construct of the invention is produced in a yeast cell, in particular a yeast cell suitable for large scale pharmaceutical production, such as cells of the species mentioned above.

According to yet another preferred, but non-limiting embodiment of the invention, the ISV, polypeptide or construct of the invention is produced in a mammalian cell, in particular in a human cell or in a cell of a human cell line, and more in particular in a human cell or in a cell of a human cell line that is suitable for large scale pharmaceutical production, such as the cell lines mentioned hereinabove.

Suitable techniques for transforming a host or host cell of the invention will be clear to the skilled person and may depend on the intended host cell/host organism and the genetic construct to be used. Reference is again made to the handbooks and patent applications mentioned above.

After transformation, a step for detecting and selecting those host cells or host organisms that have been successfully transformed with the nucleotide sequence/genetic construct of the invention may be performed. This may for instance be a selection step based on a selectable marker present in the genetic construct of the invention or a step involving the detection of the polypeptide of the invention, e.g. using specific antibodies.

The transformed host cell (which may be in the form or a stable cell line) or host organisms (which may be in the form of a stable mutant line or strain) form further aspects of the present invention.

Preferably, these host cells or host organisms are such that they express, or are (at least) capable of expressing (e.g. under suitable conditions), an ISV, polypeptide or protein construct of the invention (and in case of a host organism: in at least one cell, part, tissue or organ thereof). The invention also includes further generations, progeny and/or offspring of the host cell or host organism of the invention, for instance obtained by cell division or by sexual or asexual reproduction.

Accordingly, in another aspect, the invention relates to a host or host cell that expresses (or that under suitable circumstances is capable of expressing) an ISV, polypeptide or protein construct of the invention; and/or that contains a nucleic acid encoding the same. Some preferred but non-limiting examples of such hosts or host cells can be as generally described in WO 04/041867, WO 04/041865 or WO 09/068627. For example, ISVs, polypeptides and protein constructs of the invention may with advantage be expressed, produced or manufactured in a yeast strain, such as a strain of *Pichia pastoris*. Reference is also made to WO 04/25591, WO 10/125187, WO 11/003622, and WO 12/056000 which also describes the expression/production in *Pichia* and other hosts/host cells of immunoglobulin single variable domains and polypeptides comprising the same.

To produce/obtain expression of the ISVs, polypeptides or protein constructs of the invention, the transformed host cell or transformed host organism may generally be kept, maintained and/or cultured under conditions such that the (desired) ISV, polypeptide or protein construct of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

Generally, suitable conditions may include the use of a suitable medium, the presence of a suitable source of food and/or suitable nutrients, the use of a suitable temperature, and optionally the presence of a suitable inducing factor or compound (e.g. when the nucleotide sequences of the invention are under the control of an inducible promoter); all of which may be selected by the skilled person. Again, under such conditions, the ISVs, polypeptides or protein constructs of the invention may be expressed in a constitutive manner, in a transient manner, or only when suitably induced.

It will also be clear to the skilled person that the ISV, polypeptide or protein construct of the invention may (first) be generated in an immature form (as mentioned above), which may then be subjected to post-translational modification, depending on the host cell/host organism used. Also, the ISV, polypeptide or protein construct of the invention may be glycosylated, again depending on the host cell/host organism used.

The ISV, polypeptide or protein construct of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the polypeptide or construct of the invention) and/or preparative immunological techniques (i.e. using antibodies against the amino acid sequence to be isolated).

The constructs of the invention can generally be prepared by a method which comprises at least the step of suitably linking ISVs or polypeptides of the invention to the one or more further groups, residues, moieties or binding units, optionally via the one or more suitable linkers, so as to provide the constructs of the invention. The ISVs, polypeptides and constructs of the invention can then further be modified, and in particular by chemical and/or biological (e.g. enzymatical) modification, of one or more of the amino acid residues that form the polypeptides or constructs of the invention, to obtain derivatives of the polypeptides or constructs of the invention.

The invention also relates to a pharmaceutical composition comprising the ISV, polypeptide, compound or construct of the invention.

In the above methods, the amino acid sequences, ISVs, Nanobodies, polypeptides, compounds or constructs of the invention and/or the compositions comprising the same can be administered in any suitable manner, depending on the specific pharmaceutical formulation or composition to be used. Thus, the amino acid sequences, ISVs, Nanobodies, polypeptides, compounds or constructs of the invention and/or the compositions comprising the same can for example be administered orally, intraperitoneally (e.g. intravenously, subcutaneously, intramuscularly, or via any other route of administration that circumvents the gastrointestinal tract), intranasally, transdermally, topically, by means of a suppository, by inhalation, again depending on the specific pharmaceutical formulation or composition to be used. The clinician will be able to select a suitable route of administration and a suitable pharmaceutical formulation or composition to be used in such administration, depending on the disease or disorder to be prevented or treated and other factors well known to the clinician.

As used herein, the term "therapeutic agent" refers to any agent that can be used in the treatment and/or management of a hyperproliferative cell disorder, e.g., cancer, or one or more symptoms thereof. In certain embodiments, the term "therapeutic agent" refers to a multispecific polypeptide of the invention. Preferably, a therapeutic agent is an agent which is known to be useful for, or has been or is currently being used for the treatment, prevention and/or management of a hyperproliferative cell disorder, e.g., cancer, or one or more symptoms thereof.

As used herein, a "therapeutically effective amount" in the context of cancer refers to the amount of a therapy alone, or in combination with other therapies, that provides a therapeutic benefit in the treatment and/or management of cancers. In one aspect, a therapeutically effective amount refers to the amount of a therapy sufficient to destroy, modify, control or remove primary, regional or metastatic cancer tissue. In another aspect, a therapeutically effective amount refers to the amount of a therapy sufficient to reduce the symptoms of a cancer. In another aspect, a therapeutically effective amount refers to the amount of a therapy sufficient to delay or minimize the spread of cancer. In a specific embodiment, a therapeutically effective amount of a therapy is an amount of a therapy sufficient to inhibit growth or proliferation of cancer cells, kill existing cancer cells (e.g., cause regression of the cancer), and/or prevent the spread of cancer cells to other tissues or areas (e.g., prevent metastasis). In another specific embodiment, a therapeutically effective amount of a therapy is the amount of a therapy sufficient to inhibit the growth of a tumor by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% as measured by a standard method known in the art. Used in connection with an amount of a multi-specific polypeptide of the invention, the term can encompass an amount that improves overall therapy, reduces or avoids unwanted effects, or enhances the therapeutic efficacy of or synergies with another therapy. In one embodiment, a therapeutically effective amount of a therapy reduces or avoids unwanted effects, or enhances the therapeutic efficacy of or synergies with another therapy by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to a control (e.g., a negative control such as phosphate buffered saline) in an assay known in the art or described herein.

As used herein, a "therapeutically effective amount" in the context of a non-cancer hyperproliferative cell disorder refers to the amount of a therapy alone, or in combination with other therapies, that provides a therapeutic benefit in the treatment and/or management of said disorder. In one aspect, a therapeutically effective amount refers to the amount of a therapy sufficient to destroy, modify, control or remove cells affected by a non-cancer hyperproliferative cell disorder. In another aspect, a therapeutically effective amount refers to the amount of a therapy sufficient to reduce the symptoms of a non-cancer hyperproliferative cell disorder. In another aspect, a therapeutically effective amount refers to the amount of a therapy sufficient to delay or minimize the spread of the non-cancer hyperproliferative cell disorder. In a specific embodiment, a therapeutically effective amount of a therapy is an amount of a therapy sufficient to inhibit growth or proliferation of the non-cancer hyperproliferative cell disorder, kill existing non-cancer hyperproliferative cells (e.g., cause regression of the disorder). In another specific embodiment, a therapeutically effective amount of a therapy is the amount of a therapy sufficient to inhibit the growth of the non-cancer hyperproliferative cells by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% as measured by a standard method known in the art. Used in connection with an amount of a multispecific polypeptide of the invention, the term can encompass an amount that improves overall therapy, reduces or avoids unwanted effects, or enhances the therapeutic efficacy of or synergies with another therapy. In one embodiment, a therapeutically effective amount of a therapy reduces or avoids unwanted effects, or enhances the therapeutic efficacy of or synergies with another therapy by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to a control (e.g., a negative control such as phosphate buffered saline) in an assay known in the art.

As used herein, the term "therapy" refers to any protocol, method and/or agent that can be used in the treatment, prevention and/or management of a hyperproliferative cell disorder, e.g., cancer. In certain embodiments, the terms "therapies" and "therapy" refer to a biological therapy, supportive therapy, and/or other therapies useful in the treatment, prevention and/or management of a hyperproliferative cell disorder, e.g., cancer, or one or more symptoms thereof known to one of skill in the art such as medical personnel.

As used herein, the terms "treat", "treatment" and "treating" in the context of administering (a) therapy(ies) to a subject refer to the reduction or amelioration of the progression, severity, and/or duration of a disorder associated with a hyperproliferative cell disorder, e.g., cancer, and/or the amelioration of one or more symptoms thereof resulting from the administration of one or more therapies (including, but not limited to, the administration of one or more prophylactic or therapeutic agents). In specific embodiments, the terms "treat", "treatment" and "treating" in the context of administering (a) therapy(ies) to a subject refer to the reduction or amelioration of the progression, severity, and/or duration of a hyperproliferative cell disorder, e.g., cancer, refers to a reduction in cancer cells by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to a control (e.g., a negative control such as phosphate buffered saline). In other embodiments, the terms "treat", "treatment" and "treating" in the context of administering (a) therapy(ies) to a subject refer to the reduction or amelioration of the progression, severity, and/or duration of a hyperproliferative cell disorder, e.g., cancer, refers to no change in cancer cell number, a reduction in hospitalization time, a reduction in mortality, or an increase in survival time of the subject with cancer.

The amino acid sequences, ISVs, Nanobodies, polypeptides, compounds and/or constructs of the invention and/or the compositions comprising the same are administered according to a regime of treatment that is suitable for preventing and/or treating the hyperproliferative cell disorder, e.g., cancer, to be prevented or treated. The clinician will generally be able to determine a suitable treatment regimen, depending on factors such as the stage of the hyperproliferative cell disorder, e.g., cancer, to be treated, the severity of the hyperproliferative cell disorder, e.g., cancer, to be treated and/or the severity of the symptoms thereof, the specific amino acid sequence, ISV, Nanobody, polypeptide, compound and/or construct of the invention to be used, the specific route of administration and pharmaceutical formulation or composition to be used, the age, gender, weight, diet, general condition of the patient, and similar factors well known to the clinician.

Generally, the treatment regimen will comprise the administration of one or more amino acid sequences, ISVs, Nanobodies, polypeptides, compounds and/or constructs of the invention, or of one or more compositions comprising the same, in one or more pharmaceutically effective amounts or doses. The specific amount(s) or doses to be administered can be determined by the clinician, again based on the factors cited above.

Generally, for the prevention and/or treatment of a hyperproliferative cell disorder, e.g., cancer, mentioned herein and depending on the type of hyperproliferative cell disorder, e.g., cancer, and stage of the disease to be treated, the potency of the specific amino acid sequence, ISV, Nanobody, polypeptide, compound or construct of the invention to be used, the specific route of administration and the specific pharmaceutical formulation or composition used, the amino acid sequences, ISVs, Nanobodies, polypeptides, compounds or constructs of the invention will generally be administered in an amount between 1 gram and 0.01 milligram per kg body weight per day, preferably between 0.1 gram and 0.01 milligram per kg body weight per day, such as about 0.1, 1, 10, 100 or 1000 milligram per kg body weight per day, e.g. from 0.1 mg per kg to 25 mg per kg of the subject's body weight; either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

Usually, in the above method, a single amino acid sequence, ISV, Nanobody, polypeptide, compound or construct of the invention will be used. It is however within the scope of the invention to use two or more amino acid sequences, ISVs, Nanobodies, polypeptides compounds and/or constructs of the invention in combination.

The ISVs, Nanobodies, amino acid sequences, polypeptides, compounds and/or constructs of the invention may also be used in combination with one or more further pharmaceutically active compounds or principles, i.e. as a combined treatment regimen, which may or may not lead to a synergistic effect. Again, the clinician will be able to select such further compounds or principles, as well as a suitable combined treatment regimen, based on the factors cited above and his expert judgement.

In particular, the amino acid sequences, ISVs, Nanobodies, polypeptides, compounds and/or constructs of the invention may be used in combination with other pharmaceutically active compounds or principles that are or can be used for the prevention and/or treatment of the hyperproliferative cell disorder, e.g., cancer, disease and/or disorder cited herein, as a result of which a synergistic effect may or may not be obtained. Examples of such compounds and principles, as well as routes, methods and pharmaceutical formulations or compositions for administering them will be clear to the clinician.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

In one aspect, the disclosure provides methods for the administration of immunoglobulin single variable domains and polypeptide constructs thereof comprising one or more immunoglobulin single variable domains, polypeptides, compounds and/or constructs. In some embodiments, the immunoglobulin single variable domain, polypeptide, compound and/or construct is administered as a pharmaceutical composition. The pharmaceutical composition, in addition to the immunoglobulin single variable domains and polypeptide constructs thereof includes a pharmaceutically-acceptable carrier.

As described in detail, the pharmaceutical compositions of the disclosure may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Formulations of the disclosure include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient (e.g., immunoglobulin single variable domain or polypeptide constructs thereof) which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%.

In certain embodiments, a formulation comprises an excipient selected from the group consisting of cyclodextrins, liposomes, micelle forming agents, e.g., bile acids, and polymeric carriers, e.g., polyesters and polyanhydrides. In certain embodiments, an aforementioned formulation renders orally bioavailable an immunoglobulin single variable domain or polypeptide construct.

Methods of preparing these formulations or compositions include the step of bringing into association an immunoglobulin single variable domain or polypeptide construct with the carrier and, optionally, one or more accessory ingredients. In general, the formulations are prepared by uniformly and intimately bringing into association an immunoglobulin single variable domain or polypeptide construct with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an immunoglobulin single variable domain or polypeptide construct as an active ingredient. An immunoglobulin single variable domain or polypeptide construct invention may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and nonionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxy-propylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets, and other solid dosage forms of the pharmaceutical compositions, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal or vaginal administration may be presented as a suppository, which may be prepared by mixing an immunoglobulin single variable domain or polypeptide construct with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations suitable for vaginal administration also include pessaries, tampons, creams, gels, pastes, foams or spray formulations containing such carriers as are known in the art to be appropriate.

Dosage forms for the topical or transdermal administration of an immunoglobulin single variable domain or polypeptide construct include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of an immunoglobulin single variable domain or polypeptide construct to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this disclosure.

Pharmaceutical compositions suitable for parenteral administration comprise one or more an immunoglobulin single variable domains or polypeptide constructs in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and non-aqueous carriers, which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly-(anhydrides). Depot injectable formulations are also prepared by entrapping the drug in liposomes or microemulsions, which are compatible with body tissue.

In another aspect, kits are provided comprising a binding molecule of the invention, a nucleic acid molecule of the invention, a vector of the invention, or a host cell of the invention. The kit may comprise one or more vials containing the binding molecule and instructions for use. The kit may also contain means for administering the binding molecule of the present invention such as a syringe, pump, infuser or the like.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

The invention will now be further described by means of the following non-limiting preferred aspects, examples and figures.

The entire contents of all of the references (including literature references, issued patents, published patent applications, and co-pending patent applications) cited throughout this application are hereby expressly incorporated by reference, in particular for the teaching that is referenced hereinabove.

EXAMPLES

Example 1: Material and Methods 1.1 TCR αβ/CD3 Transfected Cell Lines

Transient and stable CHO-K1 (ATCC: CCL-61), HEK293H (Life technologies 11631-017), Llana (Fibroblast cells from llama Navel cord cells) cell lines with recombinant overexpression of all 6 chains of the full human T cell Receptor complex were generated. For this, the coding sequences of the TCR alpha (a) and TCR beta (0) chain were cloned in a pcDNA3.1-derived vector, downstream of a CMV promotor and a 2A-like viral peptide sequence was inserted between both chains to induce ribosomal skipping during translation of the polyprotein. In the same vector, the coding sequences of the epsilon, delta, gamma and zeta chains of the CD3 complex were cloned downstream of an additional CMV promotor, also using 2A-like viral peptide sequences between the respective chains. In addition, a stable HEK293H clone with recombinant overexpression of the 4 chains of the human CD3 was generated as described above using a single gene vector.

The used sequences for the human CD3 and the human TCRα/β constant domains were derived from UniProtKB (CD3 delta: P04234, CD3 gamma: P09693, CD3 epsilon: P07766, CD3 zeta: P20963, TCR α: P01848 and TCR β: P01850; SEQ ID NOs: 344 to 349, respectively). The sequences for the human TCRα/β variable domains were derived from crystal structure sequences (PDB codes: 2IAN, 2XN9 and 3TOE) (human TCR α variable domains derived from 2IAN, 2XN9 and 3TOE with SEQ ID NOs: 393 to 395, respectively; human TCR β variable domains derived from 2IAN, 2XN9 and 3TOE with SEQ ID NOs: 476 to 478, respectively).

The cell surface expression of the human T cell receptor complex was confirmed by flow cytometry using a functional mouse IgG2b anti-human TCRα/β antibody, clone BW242/412 (Miltenyi 130-098-219) and a functional mouse IgG2a anti-CD3 PE labelled antibody, clone OKT-3 (eBioscience 12-0037) (FIG. 1).

1.2 Soluble Recombinant TCR α/β Proteins

Soluble human and cynomolgus/rhesus monkey TCR α/β proteins were generated in house. The sequences for the extracellular part of the human TCRα/β constant domain were derived from UniProtKB (TCR α: P01848 and TCR β: P01850; SEQ ID NOs: 479 and 480, respectively). The human TCR α/β variable domains were derived from crystal structure sequence (PDB code: 2XN9, SEQ ID NOs: 394 and 477, respectively for a and 3 chain).

The sequences for the extracellular part of the cynomolgus/rhesus monkey TCR α/β constant domains were derived from GenBank files EHH63463 and AEA41868 respectively (SEQ ID NOs: 396 and 397). The sequences for the cynomolgus/rhesus monkey TCR α/β variable domains were derived from AEA41865 and AEA41866 (SEQ ID NOs: 398 and 399, respectively for α and β chain).

The extracellular domains of human TCR α/β (2XN9) or cynomolgus/rhesus monkey TCR α/β were fused to a zipper protein coding sequence (O'Shea et al. 1993 Curr. Biol. 3(10): 658-667), produced by CHOK1SV cells (Lonza) using Lonza's GS Gene Expression System™ and subsequently purified.

Quality of the TCR α/β zipper proteins was assessed in an ELISA binding assay. Maxisorp 96-well ELISA plates (Nunc) were coated with 2 µg/mL soluble recombinant human TCR α/β (2XN9)-zipper protein or soluble recombinant cynomolgus TCR α/β-zipper protein. After an overnight incubation, plates were washed and blocked with PBS+1% casein for 1 h at room temperature. Next, plates were incubated with serial dilutions of either a functional flag tagged Nanobody or the functional mouse IgG anti-non-human primate/Rat TCRα/β antibody, clone R73 (eBioscience 16-5960) for 1 h at room temperature while shaking, washed again and incubated with mouse anti-flag-HRP (Sigma, #A8592) respectively rabbit anti-mouse-HRP (Dako, # P0260). After 1 h, TMB One Solution (Promega #G7431) was added. The reaction was stopped with 2M $H_2SO_4$ and the dose dependent binding was determined by measuring the OD at 450 nm using the Tecan sunrise 4 (FIG. 2).

Example 2: Immunization of Llamas with TCR/CD3, Cloning of the Heavy Chain-Only Antibody Fragment Repertoires and Preparation of Phages 2.1 Immunization It was set out to generate heavy chain only antibodies in camelidae (e.g. llama and alpaca) against T cell receptor (TCR) α and/or β constant chains. Although the native T cell receptor complex consists of both CD3 (gamma, delta, epsilon and zeta) chains, as well as TCR α- and β-chains, it was hypothesized that the absence of CD3 chains would facilitate access to the constant domains of the TCR. Especially since the CD3 chains laterally surround, and limit access to the constant domains of the TCR α- and β-chains. Contrary to our experience with other targets, the obtaining of an immune response against TCR α- or β-chains was not as straight forward as expected.

In a final approach, after approval of the Ethical Committee (CRIA, LA1400575, Belgium—EC2012#1), the inventors attempted a complex immunization protocol with DNA encoding for T cell complex. In short, 3 additional llamas were immunized with a pVAX1-human TCR(2IAN)/CD3 (described in Example 1.2) plasmid vector (Invitrogen, Carlsbad, Calif., USA) and with a pVAX1-human TCR (2XN9)/CD3 (described in Example 1.2) plasmid vector (Invitrogen, Carlsbad, Calif., USA) according to standard protocols. Two llamas received additionally 1 subcutaneous injection of primary human T cells. Human T cells were collected from Buffy Coat blood, from healthy volunteers (Blood bank Gent) using RosetteSep (StemCell Technologies, #15061) followed by enriching on Ficoll-Paque™ PLUS (GE Healthcare #17-1440-03) according to manufactures instructions and stored in liquid nitrogen. After thawing, cells were washed, and re-suspended in D-PBS from Gibco and kept on ice prior to injection.

2.2 Cloning of the Heavy Chain-Only Antibody Fragment Repertoires and Preparation of Phages Per animal, blood samples were collected after the injection of one type of immunization antigen. From these blood samples, PBMC were prepared using Ficoll-Hypaque according to the manufacturer's instructions (Amersham Biosciences, Piscataway, N.J., USA). For each immunized to llama, libraries were constructed by pooling the total RNA isolated from samples originating from a certain subset of the immunization schedule, i.e. after one type of immunization antigen.

In short, the PCR-amplified VHH repertoire was cloned via specific restriction sites into a vector designed to facilitate phage display of the VHH library. The vector was derived from pUC119. In frame with the VHH coding sequence, the vector encodes a C-terminal 3×FLAG and His6 tag. Phages were prepared according to standard protocols (see for example WO 04/041865, WO 04/041863, WO 04/062551, WO 05/044858 and other prior art and applications filed by Ablynx N.V. cited herein).

Example 3: Selection of TCR/CD3 Specific VHHs Via Phage Display

The vast majority of selected VHHs were directed against the variable regions of either the TCR α or TCR β chain. Therefore different selection and counter-selection strategies had to be devised by the inventors.

In short, VHH repertoires obtained from all llamas and cloned as phage library were used in different selection strategies, applying a multiplicity of selection conditions. Selections using human TCR/CD3 transfected cell lines with the same variable domain as used during immunization resulted in only variable domain binders. Therefore, tools containing a different variable TCRα/β domain (transfected cells (described in Example 1.1), soluble protein (described in Example 1.2), or human primary T cells (isolated as described in Example 2.1)) were used during selections and proved to be crucial in identification of constant domain binders. Additional variables during selections included the antigen presentation method (in solution when using cells or coated onto plates when proteins), the antigen concentration, the orthologue used (human or cynomolgus recombinant TCR α/β protein), and the number of selection rounds. All solid coated phase selections were done in Maxisorp 96-well plates (Nunc, Wiesbaden, Germany).

Selections were performed as follows: TCRα/β-CD3 antigen preparations for solid and solution phase selection formats were presented as described above at multiple concentrations. After 2 h incubation with the phage libraries, followed by extensive washing, bound phages were eluted with trypsin (1 mg/mL) for 15 minutes. The trypsin protease activity was immediately neutralized by applying 0.8 mM protease inhibitor ABSF. As control, selections without antigen were performed in parallel.

Phage outputs were used to infect *E. coli* for analysis of individual VHH clones. Periplasmic extracts were prepared according to standard protocols (see for example WO 03/035694, WO 04/041865, WO 04/041863, WO 04/062551 and other prior art and applications filed by Ablynx N.V. cited herein).

Example 4: Screening, Sequence Analysis and Purification 4.1 Screening for TCR/CD3 Binding Nanobodies in a Flow Cytometry Assay Periplasmic extracts were screened for cell expressed TCR/CD3 binding using human TCR/CD3 transfected CHO-K1 or HEK293H cells and the respective CHO-K1 or HEK293H reference cell line in a mixed cell line setup. To this end, a large batch of the reference cell lines were labelled with 8 µM PKH26 and frozen. $5 \times 10^4$ PKH labelled reference cells were mixed with $5 \times 10^4$ target cells and incubated with periplasmic extracts for 30 min at 4'C, and washed 3 times. Next, cells were incubated with 1 µg/ml monoclonal ANTI-FLAG® M2 antibody (Sigma-Aldrich, cat# F1804) for 30 min at 4'C, washed again, and incubated for 30 min at 4° C. with goat anti-mouse APC labelled antibody (Jackson Immunoresearch 115-135-164, 1:100). Samples were washed, resuspended in FACS Buffer (D-PBS from Gibco, with 10% FBS from Sigma and 0.05% sodium azide from Merck) and then analysed via a BD FACSArray. First a P1 population which represented more than 80% of the total cell population was selected based on FSC-SSC distribution. In this gate, 20,000 cells were counted during acquisition. Based on PKH26-SSC distribution, the PKH labelled parental population and the human TCR/CD3 unlabelled target population was selected. For these 2 populations the mean APC value was calculated.

4.2 Screening for TCR/CD3 Binding Nanobodies in a Human T Cell Activation Assay

After several attempts, it turned out that activation of purified human T cells by antibodies or Nanobodies according to standard protocols, i.e. coated onto a 96 well plate, was not sensitive enough (data not shown).

In order to assess activity, a different assay was developed, based on bead coupled T cell activation. In short, goat anti-mouse IgG dynabeads (Life technologies #11033) were coated with mouse anti-flag IgG antibodies (Sigma F1804), (15 µg/1E7beads). After an incubation period of 2 h at 4° C., beads were washed and incubated with 80 µl periplasmic extract for 20 min at 4° C. while shaking. Non-coupled Nanobodies were washed away before adding the bead complex together with soluble mouse anti-CD28 antibody (Pelicluster CD28—Sanquin #M1650) to purified primary human T cells (isolated as described in Example 2.1). As control condition, non-stimulated human T cells were used. In brief, goat anti-mouse IgG dynabeads coupled to mouse anti-flag IgG were incubated in 80 µl periplasmic extract containing irrelevant Nanobodies. After removal of the non-coupled Nanobodies during a wash step, the irrelevant Nanobody-bead complex was added to purified primary human T cells.

After an incubation of 24 h at 37° and 5% $CO_2$ the activation status of the human T cells was determined by measuring the CD69 expression level in flow cytometry using monoclonal mouse anti-human CD69PE (BD Biosciences #557050).

4.3 Sequence Analysis of the Obtained Nanobodies

Nanobodies which scored positive in the flow cytometric binding screen and the T cell activation assay were sequenced.

The sequence analysis demonstrated that all anti-TCR ISVs comprised a very similar CDR3. In particular, the CDR3 has the amino acid sequence $X_1SR\ X_2X_3PYX_4Y$, in which $X_1$ is F, Y, G, L or K, $X_2$ is I or L, $X_3$ is Y or W, and $X_4$ is D, N or S.

The sequence analysis further resulted in the identification of 3 distinct clusters. Corresponding alignments are provided (Table A-1, Table A-2, Table A-3). Clustering was based on sequence similarities and differences in CDR2 and CDR3. Cluster A is the most prominent comprising 104 clones (SEQ ID NOs: 1-104), cluster B comprises 11 clones (SEQ ID NOs: 105-115), and cluster C is represented by only 3 clones (SEQ ID NOs: 116-118).

Sequence variability of the CDRs was determined for the different clusters. For cluster A, the amino acid sequence of the CDRs of clone 56G05 was used as a reference, against which the CDRs of all other cluster A clones were compared. The sequence variability against 56G05 is depicted in the tables below.

| 56G05 | | | | | CDR1 | | | | | |
|---|---|---|---|---|---|---|---|---|---|---|
| Kabat numbering | 26 | 27 | 28 | 29 | 30 | 31 | 32 | 33 | 34 | 35 |
| absolute numbering | 1 | 2 | 3 | 4 | 5* | 6 | 7 | 8 | 9 | 10 |
| 56G05 sequence | G | D | V | H | K | I | N | F | L | G |
| variations | | A | | | Y | L | L | | I | | S |
| variations | | S | | | | | | | V | |
| variations | | E | | | | | | | | |
| variations | | G | | | | | | | | |

*in case position 5 is an L, then position 6 is also L

| 56G05 | | | | | CDR2 | | | | |
|---|---|---|---|---|---|---|---|---|---|
| Kabat numbering | 50 | 51 | 52 | 53 | 54 | 55 | 56 | 57 | 58 |
| absolute numbering | 1 | 2 | 3 | 4 | 5 | 6 | 7 | 8 | 9 |
| 56G05 sequence | H | I | S | I | G | D | Q | T | D |
| variations | T | | T | | S | | D | V | A |
| variations | R | | A | | A | | E | A | Q |
| variations | | | | | | | T | | N |
| variations | | | | | | | A | | V |
| variations | | | | | | | V | | S |

| 56G05 Kabat numbering | | | | CDR3 | | | | | |
|---|---|---|---|---|---|---|---|---|---|
| | 95 | 96 | 97 | 98 | 99 | 100 | 100a | 101 | 102 |
| absolute numbering | 1 | 2 | 3 | 4 | 5 | 6 | 7 | 8 | 9 |
| 56G05 sequence | F | S | R | I | Y | P | Y | D | Y |
| variations | Y | | | L | W | | | N | |
| variations | G | | | | | | | S | |
| variations | L | | | | | | | | |

For cluster B, the amino acid sequence of the CDRs of clone 55C07 was used as a reference, against which the CDRs of all other cluster B clones were compared. The sequence variability against 55C07 is depicted in the tables below.

| 55C07 Kabat numbering | | | | CDR1 | | | | | | |
|---|---|---|---|---|---|---|---|---|---|---|
| | 26 | 27 | 28 | 29 | 30 | 31 | 32 | 33 | 34 | 35 |
| absolute numbering | 1 | 2 | 3 | 4 | 5 | 6 | 7 | 8 | 9 | 10 |
| 55C07 sequence | G | E | T | F | K | I | N | I | W | G |
| variations | | Q | | | | V | | | | |

| 55C07 Kabat numbering | | | | CDR2 | | | | | |
|---|---|---|---|---|---|---|---|---|---|
| | 50 | 51 | 52 | 53 | 54 | 55 | 56 | 57 | 58 |
| absolute numbering | 1 | 2 | 3 | 4 | 5 | 6 | 7 | 8 | 9 |
| 55C07 sequence | S | L | T | I | G | G | A | T | N |
| variations | | | | | | | | | D |

| 55C07 Kabat numbering | | | | CDR3 | | | | | |
|---|---|---|---|---|---|---|---|---|---|
| | 95 | 96 | 97 | 98 | 99 | 100 | 100a | 101 | 102 |
| absolute numbering | 1 | 2 | 3 | 4 | 5 | 6 | 7 | 8 | 9 |
| 55C07 sequence | K | S | R | L | Y | P | Y | D | Y |
| variations | | | | | I | | | | |

For cluster C, the amino acid sequence of the CDRs of clone 61G01 was used as a reference, against which the CDRs of all other cluster C clones were compared. The sequence variability against 61G01 is depicted in the tables below.

| 61G01 Kabat numbering | | | | CDR1 | | | | | | |
|---|---|---|---|---|---|---|---|---|---|---|
| | 26 | 27 | 28 | 29 | 30 | 31 | 32 | 33 | 34 | 35 |
| absolute numbering | 1 | 2 | 3 | 4 | 5 | 6 | 7 | 8 | 9 | 10 |
| 61G01 sequence variations | G | E | I | G | R | I | N | F | Y | R |

| 61G01 Kabat numbering | | | | CDR2 | | | | | |
|---|---|---|---|---|---|---|---|---|---|
| | 50 | 51 | 52 | 53 | 54 | 55 | 56 | 57 | 58 |
| absolute numbering | 1 | 2 | 3 | 4 | 5 | 6 | 7 | 8 | 9 |
| 61G01 sequence | T | I | T | I | A | D | K | T | D |
| variations | | | | | | | | I | |

| 61G01 Kabat numbering | | | | CDR3 | | | | | |
|---|---|---|---|---|---|---|---|---|---|
| | 95 | 96 | 97 | 98 | 99 | 100 | 100a | 101 | 102 |
| absolute numbering | 1 | 2 | 3 | 4 | 5 | 6 | 7 | 8 | 9 |
| 61G01 sequence variations | G | S | R | L | Y | P | Y | D | Y |

The clustering based on the sequence transmuted into functional differences (see infro).

4.4 Purification of Monovalent Nanobodies

Representative Nanobodies for each cluster were selected and expressed in *E. coli* TG1 as triple Flag, His6-tagged proteins. Expression was induced by addition of 1 mM IPTG and allowed to continue for 4 hours at 37° C. After spinning the cell cultures, periplasmic extracts were prepared by freeze-thawing the pellets. These extracts were used as starting material and Nanobodies were purified via IMAC and size exclusion chromatography (SEC).

The Nanobodies were purified to 95% purity as assessed via SDS-PAGE (data not shown).

Example 5: Binding of Anti-TCR Nanobodies to Human TCR/CD3 Expressed on CHO-K1 Cells and to Purified Primary Human T Cells Binding of purified monovalent anti-TCR Nanobodies to human TCR(2XN9)/CD3 expressed on CHO-K1 cells and to purified primary human T cells was evaluated in flow cytometry as outlined in Example 4.1. Dilution series of Nanobodies 55A02 (cluster A), 56G05 (cluster A), 68G05 (cluster B) and 61G01 (cluster C) starting from 1 μM were applied to the cells.

The results are shown in FIG. 3.

Nanobodies clearly bound to human TCR/CD3 expressed on CHO-K1 cells. The cluster A representatives showed the best affinity, followed by the cluster B representative and the cluster C representative. Nanobodies bound to purified primary human T cells, although with slightly lower potency compared to the CHO-K1 human TCR(2XN9)/CD3 cells. The representatives of cluster A showed the best affinity for binding human primary T cells, in line with the data on the CHO-K1 (2XN9)/CD3. The EC50 values obtained from the dose response curve are represented in Table C-1.

TABLE C-1

EC50 (M) of anti-TCR monovalent Nanobodies for binding CHO-K1 human TCR(2XN9)/CD3 cells and for binding purified primary T cells as determined in flow cytometry.

| | | CHO-K1TCR(2XN9)/CD3 | | | Primary human T cells | | |
|---|---|---|---|---|---|---|---|
| Cluster | sample ID | EC50 (M) | 95% LCI | 95% UCI | EC50 (M) | 95% LCI | 95% UCI |
| A | T0170055A02 | 8.4E−09 | 7.2E−09 | 9.7E−09 | 9.1E−08 | 8.1E−08 | 1.0E−07 |
| A | T0170056G05 | 8.9E−09 | 8.3E−09 | 9.4E−09 | 9.1E−08 | 8.3E−08 | 9.9E−08 |
| B | T0170068G05 | 1.2E−08 | 1.0E−08 | 1.3E−08 | >1E−07 | / | / |
| C | T0170061G01 | 3.1E−08 | 2.8E−08 | 3.4E−08 | >1E−07 | / | / |

Example 6: Determination of Binding Epitope

Binding of purified monovalent anti-TCR Nanobodies to human TCR(2IAN)/CD3 expressed on HEK293H cells was evaluated and compared with the binding to HEK293H cells transfected with human CD3 in flow cytometry, as outlined in Example 5. Dilution series of anti-TCR Nanobodies starting from 1 µM were applied to the cells. The parental HEK293H cell line was included as TCR/CD3 negative cell line.

The results are shown in FIG. 4.

Nanobodies clearly bound to human TCR(2IAN)/CD3 expressed on HEK293H but not to the HEK293H cells transfected with human CD3 only, nor to the HEK293H parental cell line. The EC50 values obtained from the dose response curve are depicted in Table C-2.

TABLE C-2

EC50 (M) of anti-TCR monovalent Nanobodies for binding human TCR(2IAN)/CD3 or human CD3 expressed on HEK293H cells, as determined in flow cytometry.

| | | HEK293H wt | | HEK293H CD3 | | HEK293H TCR/CD3 | |
|---|---|---|---|---|---|---|---|
| cluster | Sample ID | EC50 | MCF at 1 µM | EC50 | MCF at 1 µM | EC50 | MCF at 1 µM |
| A | T0170055A02 | No fit | 246 | No fit | 1194 | 5.5E−08 | 91229 |
| A | T0170056G05 | No fit | 299 | No fit | 352 | 8.4E−08 | 86510 |
| B | T0170068G05 | No fit | 206 | No fit | 240 | >1E−07 | 31202 |
| C | T0170061G01 | No fit | 374 | No fit | 495 | >1E−07 | 10032 |

In conclusion, the clones were specific for binding to human TCR α/β. No binding was observed to human CD3.

Example 7: Binding of Anti-TCR Nanobodies to Soluble Recombinant Human TCR α/β Protein 7.1 Binding of Anti-TCR Nanobodies to Human T Cell Receptor Protein in ELISA Binding of purified monovalent TCR Nanobodies to soluble recombinant human TCR α/β protein was evaluated in ELISA (as described in Example 1.2) using 2 µg/ml directly coated soluble recombinant human TCR α/β protein.

The results are shown in FIG. 5. The EC50 values obtained from the dose response curve are depicted in Table C-3.

TABLE C-3

EC50 (M) of anti-TCR monovalent Nanobodies for binding soluble recombinant human TCR(2XN9) protein, as determined in ELISA.

| Cluster | sample ID | EC50 (M) | 95% LCI | 95% UCI |
|---|---|---|---|---|
| A | T0170055A02 | 1.9E−09 | 1.7E−09 | 2.2E−09 |
| A | T0170056G05 | 4.0E−09 | 3.5E−09 | 4.6E−09 |
| B | T0170068G05 | 1.6E−08 | 1.3E−08 | 1.9E−08 |
| C | T0170061G01 | 5.2E−08 | 4.2E−08 | 6.5E−08 |

In conclusion, representative clones of all clusters bind to soluble recombinant human TCR α/β protein.

7.2 Binding of Anti-TCR Nanobodies to Human T Cell Receptor Protein in BU

Binding affinities were measured using Bio-Layer Interferometry (BLI) on an Octet RED384 instrument (Pall ForteBio Corp.). Recombinant human soluble TCR(2XN9)-zipper protein was covalently immobilized on amine-reactive sensors (ForteBio) via NHS/EDC coupling chemistry. For kinetic analysis, sensors were first dipped into running buffer (10 mM Hepes, 150 mM NaCl, 0.05% p20, pH7.4 from GE Healthcare Life Sciences) to determine baseline setting. Subsequently, sensors were dipped into wells containing different concentrations of purified Nanobodies (range between 1.4 nM and 1 mM) for the association step (180 s) and transferred to wells containing running buffer for the dissociation (15 min) step. Affinity constants (KD) were calculated applying a 1:1 interaction model using the ForteBio Data Analysis software.

The results are depicted in FIG. 6. The binding characteristics are listed in Table C-4.

TABLE C-4

Kinetic analysis of anti-TCR monovalent Nanobodies for binding soluble recombinant human TCR(2XN9) protein as determined with the Octet RED384 instrument.

| | | Human sTCR (2XN9)-zipper | | |
|---|---|---|---|---|
| Cluster | sample ID | kon (1/Ms) | koff (1/s) | KD (M) |
| A | T0170055A02 | 4.9E+04 | 8.4E−04 | 1.7E−08 |
| A | T0170056G05 | 5.0E+04 | 1.2E−03 | 2.4E−08 |

In conclusion, the binding affinity for cluster A representatives determined using BLI on human soluble 2XN9 showed correlation with the affinities determined on CHO-K1(2XN9)/CD3 cells in flow cytometry (cf. Example 5).

Example 8: Determination of Purified Primary Human T Cell Activation Capacity Functionality of purified monovalent anti-TCR Nanobodies was evaluated in the human T cell activation assay. Goat anti-mouse IgG dynabeads (Life technologies #11033) were coated with mouse anti-Flag IgG antibodies (Sigma F1804), (15 µg/1E7beads). After an incubation period of 2 h at 4'C, beads were washed and incubated with a fixed (1 µg) amount of purified Flag tagged Nanobody for 20 min at 4° C. while shaking. Non-coupled Nanobodies were washed away before adding the bead complex together with soluble mouse anti-CD28 antibody (Pelicluster CD28—Sanquin #M1650) to purified primary human T cells isolated (isolated as described in Example 2.1) from distinct healthy donors.

In addition, the effect of monovalent TCR binding by the Nanobodies was evaluated by the incubation of the Nanobody with the purified primary human T cells without prior capture onto anti-mouse IgG dynabeads, in the presence of anti-CD28 antibody.

The activation status of the purified primary human T cells was monitored by measuring the CD69 expression in flow cytometry using monoclonal mouse anti-human CD69PE (BD Biosciences #557050) after an incubation of 24 h at 37° C. and 5% $CO_2$, as described in Example 4.2.

In conclusion, anti-TCR Nanobodies of all clusters showed clear CD69 upregulation after capturing onto anti-mouse IgG dynabeads. The irrelevant Nanobody did not show any CD69 upregulation (FIG. 7A). In addition, none of the Nanobodies presented in solution were able to activate purified primary human T cells as measured by increased expression of CD69 (FIG. 7B).

Example 9: Binding of Multispecific TCR Binding Polypeptides to Human T Cell Receptor Complex Expressed on Cells To demonstrate that redirection of engaged T cells to tumour cells is possible by the Nanobodies, the CD20 antigen was chosen as exemplary tumour target.

Different TCR binding building blocks (i.e. Nanobodies) were formatted into a multispecific construct with a human CD20 targeting Nanobody (see Table C-5). The effector and tumour Nanobodies were genetically linked with a 35GS linker and subsequently expressed in the yeast *Pichia* according to standard protocols (multispecific polypeptides).

Irrelevant constructs were generated by replacing the effector or tumour Nanobody with an irrelevant anti-egg lysozyme (cAblys) Nanobody (Table C-5)

TABLE C-5

Sample ID and description of multispecific constructs.

| Cluster | Sample ID | SEQ ID NO | Description |
|---|---|---|---|
| | | | Target Nanobody × Effector Nanobody |
| A | T017000014 | 300 | 20CD019C07-35GS-T0170028B01-FLAG3-HIS6 |
| A | T017000015 | 301 | cAbLys3(D1E)-35GS-T0170028B01-FLAG3-HIS6 |
| ctrl | T017000018 | 302 | 20CD019C07-35GS-cAbLys3-FLAG3-HIS6 |
| A | T017000054 | 321 | 20CD019C07-35GS-T0170055A03-FLAG3-HIS6 |
| A | T017000055 | 322 | 20CD019C07-35GS-T0170055A02-FLAG3-HIS6 |
| A | T017000058 | 323 | 20CD019C07-35GS-T0170040C01-FLAG3-HIS6 |
| A | T017000060 | 324 | 20CD019C07-35GS-T0170028B01-FLAG3-HIS6 |
| A | T017000076 | 334 | 20CD019C07-35GS-T0170056G05-FLAG3-HIS6 |
| A | T017000063 | 325 | 20CD019C07-35GS-T0170069B08-FLAG3-HIS6 |
| A | T017000064 | 326 | 20CD019C07-35GS-T0170068E08-FLAG3-HIS6 |
| B | T017000068 | 328 | 20CD019C07-35GS-T0170055C07-FLAG3-HIS6 |
| B | T017000070 | 330 | 20CD019C07-35GS-T0170055B06-FLAG3-HIS6 |
| A | T017000069 | 329 | 20CD019C07-35GS-T0170055B11-FLAG3-HIS6 |
| A | T017000050 | 319 | 20CD019C07-35GS-T0170069C08-FLAG3-HIS6 |
| A | T017000065 | 327 | 20CD019C07-35GS-T0170067E06-FLAG3-HIS6 |
| A | T017000078 | 336 | 20CD019C07-35GS-T0170069F05-FLAG3-HIS6 |
| A | T017000079 | 337 | 20CD019C07-35GS-T0170067D01-FLAG3-HIS6 |
| C | T017000051 | 320 | 20CD019C07-35GS-T0170061G01-FLAG3-HIS6 |
| A | T017000075 | 333 | 20CD019C07-35GS-T0170067E03-FLAG3-HIS6 |
| | | | Effector Nb × Target Nb |
| A | T017000019 | 303 | T0170028B01-35GS-20CD019C07-FLAG3-HIS6 |
| A | T017000025 | 305 | T0170028B01-35GS-cAbLys3-FLAG3-HIS6 |
| ctrl | T017000023 | 304 | cAbLys3(D1E)-35GS-20CD019C07-FLAG3-HIS6 |
| A | T017000041 | 314 | T0170055A03-35GS-20CD019C07-FLAG3-HIS6 |
| A | T017000042 | 315 | T0170055A02-35GS-20CD019C07-FLAG3-HIS6 |
| A | T017000044 | 316 | T0170040C01-35GS-20CD019C07-FLAG3-HIS6 |
| A | T017000046 | 317 | T0170028B01-35GS-20CD019C07-FLAG3-HIS6 |
| A | T017000074 | 332 | T0170056G05-35GS-20CD019C07-FLAG3-HIS6 |
| A | T017000029 | 306 | T0170069B08-35GS-20CD019C07-FLAG3-HIS6 |
| A | T017000035 | 311 | T0170068E08-35GS-20CD019C07-FLAG3-HIS6 |

TABLE C-5-continued

Sample ID and description of multispecific constructs.

| Cluster | Sample ID | SEQ ID NO | Description |
|---|---|---|---|
| B | T017000031 | 308 | T0170055C07-35GS-20CD019C07-FLAG3-HIS6 |
| B | T017000033 | 310 | T0170055B06-35GS-20CD019C07-FLAG3-HIS6 |
| A | T017000032 | 309 | T0170055B11-35GS-20CD019C07-FLAG3-HIS6 |
| A | T017000037 | 312 | T0170069C08-35GS-20CD019C07-FLAG3-HIS6 |
| A | T017000077 | 335 | T0170067E06-35GS-20CD019C07-FLAG3-HIS6 |
| A | T017000049 | 318 | T0170069F05-35GS-20CD019C07-FLAG3-HIS6 |
| A | T017000030 | 307 | T0170067D01-35GS-20CD019C07-FLAG3-HIS6 |
| C | T017000038 | 313 | T0170061G01-35GS-20CD019C07-FLAG3-HIS6 |
| A | T017000073 | 331 | T0170067E03-35GS-20CD019C07-FLAG3-HIS6 |

Binding of the multispecific constructs to human TCR/CD3 expressed on CHO-K1 cells, purified primary human T cells and CD20 positive Ramos cells (ATCC: CRL-1596) was evaluated in flow cytometry as outlined in Example 5. The results are presented in FIG. 8.

The EC50 values obtained from the dose response curve are depicted in Table C-6.

The data indicate similar binding of the TCR×CD20 multispecific polypeptides compared to their monovalent counterparts. However, a reduced binding of the CD20×TCR multispecific polypeptides to CHO-K1 human TCR (2XN9)/CD3 cells and purified primary human T cells was detected compared to their monovalent counterparts. On the human CD20 positive Ramos cell line, the multispecific polypeptide with the CD20 at the C terminus showed reduced binding in comparison to the polypeptides with the CD20 at the N terminus.

Example 10: Functional Characterization of Multispecific CD20×TCR Binding Polypeptides in a Flow Cytometry Based Killing Assay In order to assess whether multispecific polypeptides were able to kill tumour cells, cytotoxicity assays were performed with isolated human T cells as effector cells.

Human T cells were isolated as described in Example 2.1. The quality and purity of the purified human T cells was checked with anti-CD3 (eBioscience #12-0037-73), anti-CD8 (BD Biosciences #345775), anti-CD4 (BD Biosciences #345771), anti-CD45RO (BD Biosciences #555493), anti-CD45RA (BD Biosciences #550855), anti-CD19 (BD Biosciences #555413), anti-CD25 (BD Pharmigen #557138) and anti-CD69 (BD Pharmigen #557050) fluorescently labelled antibodies in a flow cytometric assay. Human CD20 expressing Ramos cells and human CD20 expressing Raji cells (ECACC: 85011429), labelled with the PKH-26 membrane dye as described above were used as target cells. $2.5\times10^5$ effector and $2.5\times10^4$ target cells were co-incubated in 96-well V-bottom plates at an effector versus target ratio of 10:1. For measurement of the concentration-dependent cell lysis, serial dilutions of multispecific polypeptides (Table C-5) were added to the samples and incubated for 18 h in a 5% $CO_2$ atmosphere at 37'C. After incubation, cells were pelleted by centrifugation and washed with FACS buffer. Subsequently, cells were resuspended in FACS buffer supplemented with 5 nM TOPRO3 (Molecular Probes cat# T3605) to distinguish live from dead cells. Cells were analysed using a FACS Array flow cytometer (BD Biosciences). Per sample, a total sample volume of 80 μl was acquired. Gating was set on PKH26 positive cells, and within this population the TOPRO3 positive cells were determined.

The CD20×TCR binding multispecific polypeptides showed dose dependent killing of the Ramos cells (FIG. 9A). T017000014 (cluster A, 20CD019C07-35GS-T0170028B01-FLAG3-HIS6) showed a dose dependent killing on both Ramos (FIG. 9A) and Raji (FIG. 9B) cells confirming that the observed cytotoxic effect was not restricted to a single tumour cell line. The expression level of the tumour antigen CD20 was determined for both cell lines (FIG. 10).

The IC50 values and the % lysis obtained from the dose response curve are depicted in Table C-7 (% lysis=% death cells at 500 nM of Nanobody minus % dead cells of the no Nanobody control).

These results demonstrate that the TCR multispecific polypeptides can induce T cell mediated killing of tumour target positive cell lines. When either the targeting Nanobody or the effector Nanobody was replaced by an irrelevant Nanobody, no effect on the viability of the Ramos cells could be observed. There was no clear preference of the orientation between the individual binding blocks in the multispecific polypeptide.

Example 11: Functional Characterization of Multispecific CD20×TCR Binding Polypeptides in an xCELLigence Based Killing Assay The TCR binding multispecific polypeptides were also tested for their cell toxicity on human CD20 transfected adherent target cells in the presence of human effector T cells using real-time electrical impedance based technique. Here, fluctuations in impedance induced by the adherence of cells to the surface of an electrode were measured. T cells are non-adherent and therefore do not impact the impedance measurements.

In brief, the xCELLigence station was placed in a 37° C. incubator at 5% $CO_2$. 50 μl of assay medium was added to each well of E-plate 96 (ACEA Biosciences; cat#05 232 368 001) and a blank reading on the xCELLigence system was performed to measure background impedance in absence of cells. Subsequently, human CD20 transfected CHO-K1 or CHO-K1 reference cells ($1\times10^4$) were seeded onto the E-plates 96, and 50l of a serial dilution of multispecific polypeptide was added. After 30 min at RT, 50 μl of human T cells were added per well ($3\times10^5$) to have an effector to target ratio of 30:1. The plate was placed in the xCELLigence station and impedance was measured every 15 min during 3 days. The data were analysed using a fixed time point indicated in the results.

The IC50 values are depicted in Table C-8.

TABLE C-8

IC50 (M) of the multispecific polypeptides in the xCELLigence based human T cell mediated CHO-K1 CD20 killing assay using an effector to target ratio of 30 to 1, analysed at 44 h after seeding.

| Cluster | ID monovalent Nanobody | sample ID (CD20 × TCR) | n | IC50 (M) | sample ID (TCR × CD20) | n | IC50 (M) |
|---|---|---|---|---|---|---|---|
| A | T0170055A02 | T017000055 | 2 | 1.4E−09 | T017000042 | 2 | 4.2E−09 |
| A | T0170056G05 | T017000076 | 3 | 3.6E−10 | T017000074 | 3 | 1.5E−09 |
| B | T0170055C07 | T017000068 | 1 | 1.3E−08 | T017000031 | 1 | 2.1E−09 |
| C | T0170061G01 | T017000051 | 1 | 2.7E−08 | T017000038 | 1 | 4.1E−09 |

The multispecific polypeptides showed tumour antigen dependent killing. The multispecific polypeptides were not able to induce T cell mediated killing of CHO-K1 reference cells, but induced dose dependent human T cell mediated killing of the CD20 transfected CHO-K1 cells. An example is shown in FIG. 11.

These results confirm the outcome obtained in the flow cytometry based killing assay of Example 10. In addition, only when the tumour target antigen is present T cell mediated killing was observed, indicating that the multispecific polypeptides are critically dependent on their target for induction of cytotoxicity.

Example 12: Linker Length Evaluation of the Multispecific Polypeptides

To evaluate the impact of the linker length used in the CD20/TCR binding multispecific polypeptides on the cytotoxic capacity, the effector and tumour building blocks were genetically linked with a 5GS (SEQ ID NO: 376), 9GS (SEQ ID NO: 378) or 35GS (SEQ ID NO: 385) linker and subsequently expressed in *Pichia* according to standard protocols (see Table C-9).

TABLE C-9

Sample ID and description of multispecific construct to evaluate impact of linker length.

| Cluster | Sample ID | SEQ ID NO | Description |
|---|---|---|---|
| | | | Target Nanobody × Effector Nanobody |
| A | T017000002 | 292 | 20CD019C07-5GS-T0170028B01-FLAG3-HIS6 |
| A | T017000008 | 296 | 20CD019C07-9GS-T0170028B01-FLAG3-HIS6 |
| A | T017000014 | 300 | 20CD019C07-35GS-T0170028B01-FLAG3-HIS6 |
| A | T017000060 | 324 | 20CD019C07-35GS-T0170028B01-FLAG3-HIS6 |
| | | | Effector Nanobody × Target Nanobody |
| A | T017000013 | 299 | T0170028B01-9GS-20CD019C07-FLAG3-HIS6 |
| A | T017000019 | 303 | T0170028B01-35GS-20CD019C07-FLAG3-HIS6 |
| A | T017000046 | 317 | T0170028B01-35GS-20CD019C07-FLAG3-HIS6 |
| | | | Control Polypeptides |
| ctrl | T017000003 | 293 | cAbLys3(D1E)-5GS-T0170028B01-FLAG3-HIS6 |
| ctrl | T017000006 | 294 | 20CD019C07-5GS-cAbLys3-FLAG3-HIS6 |
| ctrl | T017000009 | 297 | cAbLys3(D1E)-9GS-T0170028B01-FLAG3-HIS6 |
| ctrl | T017000012 | 298 | 20CD019C07-9GS-cAbLys3-FLAG3-HIS6 |
| ctrl | T017000015 | 301 | cAbLys3(D1E)-35GS-T0170028B01-FLAG3-HIS6 |
| ctrl | T017000018 | 302 | 20CD019C07-35GS-cAbLys3-FLAG3-HIS6 |
| ctrl | T017000023 | 304 | cAbLys3(D1E)-35GS-20CD019C07-FLAG3-HIS6 |
| ctrl | T017000025 | 305 | T0170028B01-35GS-cAbLys3-FLAG3-HIS6 |

The impact of the linker length used in the CD20/TCR binding multispecific polypeptides on the human primary effector T cell induced cellular toxicity on the adherent CHO-K1 human CD20 transfected target cells was evaluated using real-time electrical impedance based technique as described Example 11.

The results are summarized in FIG. 12.

All multispecific polypeptides, i.e. all linker lengths demonstrated specific cell killing. Unexpectedly, the TCR multispecific polypeptides with the longest linker (35GS linker) showed the best potency. In view of these results, further experiments were performed with multispecific polypeptides comprising the 35GS linker.

Example 13: Influence of Effector to Target Ratio on the Killing Effect of the Multispecific Polypeptides To evaluate the effect of different effector to target (E:T) ratios on the killing properties of the polypeptides, CD20× TCR binding multispecific polypeptides were incubated with $2.5\times10^4$ PKH labelled Ramos cells in the presence of respectively $2.5\times10^5$ (E:T=10:1), $1.25\times10^5$ (E:T=5:1), $5\times10^4$ (E:T=2:1) and $2.5\times10^4$ (E:T=1:1) human primary T cells as described in Example 10.

Exemplary results are shown in FIG. 13. The IC50 values are depicted in Table C-10.

TABLE C-10

IC50 (M) of the multispecific polypeptides in the flow cytometry based T cell mediated Ramos killing assay using different effector to target ratios.

| Cluster | ID monovalent Nanobody | sample ID (CD20 × TCR) | E:T | n | IC50 (M) | 95% LCI | 95% UCI | % lysis |
|---|---|---|---|---|---|---|---|---|
| A | T0170056G05 | T017000076 | 10 | 1 | 7.5E−10 | 5.2E−10 | 1.1E−09 | 25 |
| A | T0170056G05 | T017000076 | 5 | 1 | 8.9E−10 | 5.2E−10 | 1.5E−09 | 17 |
| A | T0170056G05 | T017000076 | 2 | 1 | 1.6E−09 | 6.1E−10 | 4.1E−09 | 10 |
| A | T0170056G05 | T017000076 | 1 | 1 | 4.6E−09 | 3.0E−10 | 6.9E−08 | 4 |
| A | T0170055A02 | T017000055 | 10 | 1 | 4.1E−09 | 3.1E−09 | 5.3E−09 | 28 |
| A | T0170055A02 | T017000055 | 5 | 1 | 2.5E−09 | 1.6E−09 | 4.0E−09 | 15 |
| A | T0170055A02 | T017000055 | 2 | 1 | 7.4E−10 | 3.4E−10 | 1.6E−09 | 9 |
| A | T0170055A02 | T017000055 | 1 | 1 | 3.4E−09 | 1.8E−10 | 6.4E−08 | 3 |

Both constructs were able to kill the human CD20 target cells at different E:T ratios, even at a ratio of 1:1, after an incubation time of 18 h with little difference in potency. Although there was an impact of the E:T ratio on the % lysis, this might also be linked to the incubation time (see below).

Example 14: Time Dependent Cytolytic Activity of CD20/TCR Binding Multispecific Constructs in the Purified Primary Human T Cell Mediated Assay in xCELLigence To evaluate the impact of incubation time on the killing properties of the CD20×TCR binding multispecific constructs, specific lysis of target cells was calculated for different time-points in xCELLigence. In brief, the xCELLigence station was placed in a 37° C. incubator at 5% $CO_2$. 50 µl of assay medium was added to each well of E-pate 96 (ACEA Biosciences; cat#05 232 368 001) and a blank reading on the xCELLigence system was performed to measure background impedance in absence of cells. Subsequently, human CD20 transfected CHO-K1 or CHO-K1 reference cells ($1\times10^4$) were seeded onto the E-plates 96. After 20 h, $3\times10^5$ purified primary human T cells (described supra) and 100 nM or 1.5 nM multispecific constructs were added, respectively. The cell index (CI) was measured every 15 min during 5 days. Using the normalized CI (the normalized cell index—NCI, is calculated by dividing the cell index value at a particular time point by the cell index value of the time-point when purified primary human T cells were added) specific lysis at different time points of the condition with constructs was calculated in relation to the condition lacking construct. (% specific lysis=$((NCI_{no\ construct} - NCI_{with\ construct})/NCI_{no\ construct}))\times100$.

The results are depicted in FIG. 14.

Already one hour after the addition of human primary T cells and the multispecific construct, an increase of cell lysis can be observed which clearly increased further upon longer incubation times. The maximal effect was clearly dependent on the incubation time but the obtained IC50 value did not change with increased incubation times. The irrelevant construct did not show any killing of the human CD20 transfected CHO-K1 cells.

Example 15: Exploration of Half-Life Extension (HLE)

It was hypothesized that HLE via albumin binding might be suitable to comply with various requirements, including (i) half-life extension (HLE) of the moiety; and (ii) efficacy of the multispecific polypeptide. Preferably, the HLE function would not impair the penetration of tumours and tissues.

Alb11 (SEQ ID NO: 404), a Nanobody binding to human serum albumin (HSA) was linked to the multispecific CD20×TCR binding polypeptides to increase the in vivo half-life of the formatted molecules (WO 06/122787). A number of formats were generated based on the CD20 tumour targeting building block at the N-terminus, the TCRα/β recruiting building blocks in the middle and the albumin targeting Nanobody at the C-terminus using a 35GS linker and expressed as indicated above. An overview of the explored formats is shown in Table C-11.

TABLE C-11

Sample ID and description of HLE constructs.

| Cluster | Sample ID | SEQ ID NO | Description |
|---|---|---|---|
| A | T017000093 | 340 | 20CD019C07-35GS-T0170056G05-35GS-ALB11-FLAG3-HIS6 |
| B | T017000095 | 341 | 20CD019C07-35GS-T0170055C07-35GS-ALB11-FLAG3-HIS6 |

As the addition of the Alb11 Nanobody might influence the affinity or potency of the construct and the binding of HSA to the Alb11 Nanobody might have an impact on the affinity or potency of the half-life extended constructs, the half-life extended constructs were characterized for binding to TCR overexpressing CHO-K1 and primary human T cells. In addition, the potency in the functional T cell dependent Ramos B cell killing assay was evaluated in the presence and absence of HSA (described in 15.1 and 15.2 below).

15.1 Impact of Alb11 Building Block on the Binding Properties

Analogous to the experiments described in Example 5, binding of half-life extended anti-TCR polypeptides to CHO-K1 human TCR(2XN9)/CD3 cells, primary human T cells and Ramos cells was evaluated in a flow cytometric assay in the absence of HSA.

The results are provided in FIG. 15. The EC50 values obtained in this assay are listed in Table C-12.

Comparison of the CD20-35GS-TCR HLE construct with the non-HLE constructs showed similar binding on all three cell lines tested. The data presented showed that coupling of the Alb11 building block did not influence the binding properties.

15.2 Impact of Human Serum Albumin on Potency in Human T Cell Mediated B Cell Killing Assay The functionality of half-life extended anti-TCR polypeptides was evaluated in the human T cell mediated Ramos killing assay as described in Example 10 in the presence and absence of 30 μM HSA and compared with the functionality of the non-HLE multispecific constructs.

The results are depicted in FIG. 16. The IC50 values obtained in this assay are listed in Table C-13.

TABLE C-13

IC50 (M) of and % lysis by the HLE polypeptides in the T cell dependent B cell (Ramos) killing assay to evaluate the effect of HLE.

| Cluster | sample ID | IC50 (M) | 95% LCI | 95% UCI | % lysis |
|---|---|---|---|---|---|
| A | T017000076 | 1.1E−10 | 7.6E−11 | 1.5E−10 | 25 |
| A | T017000093 | 3.4E−10 | 2.4E−10 | 4.9E−10 | 28 |
| A | T017000093 | 2.7E−10 | 2.1E−10 | 3.5E−10 | 26 |
| A | T017000093 + HSA | 1.6E−09 | 1.1E−09 | 2.2E−09 | 21 |
| B | T017000068 | 5.6E−10 | 2.7E−10 | 1.2E−09 | 12 |
| B | T017000095 | 3.3E−09 | 1.8E−09 | 5.8E−09 | 16 |
| B | T017000095 | 1.1E−09 | 6.5E−10 | 2.0E−09 | 16 |
| B | T017000095 + HSA | 5.7E−09 | 2.0E−09 | 1.6E−08 | 9 |

The results indicate that the inclusion of the albumin targeting Nanobody in the construct as such did not have an essential impact on the obtained potency or efficacy. Although a minor loss of efficacy/potency was observed in the presence of HSA, the half-life extended TCR multispecific polypeptides were still potent in tumour cell killing.

Example 16: Functional Characterization of Multispecific Polypeptides in an xCELLigence Based Human T Cell Mediated HER2-Positive Tumour Killing Assay In order to assess the general applicability of the TCR building blocks in directing T cells to tumour cells, TCR binding building blocks were combined with building block that binds a different TAA, in this case a Nanobody binding to HER2.

The anti-TCR building block was combined with a Nanobody that binds the HER2 solid tumour antigen in two orientations (Table C-14) and characterized in the xCELLigence based human T cell mediated HER2-positive tumour killing assay as described in Example 11 using two HER2 expressing cell lines (SKBR3 (ATCC: HTB-30), MCF-7 (ATCC: HTB-22)) and a HER2 negative reference cell line (MDA-MB-468 (ATCC HTB-132)) as target cell population. Human HER2 expression levels were confirmed using 100 nM of the monovalent anti-HER2 Nanobody HER2005F07 (SEQ ID NO: 350) in flow cytometry as described in Example 5. Results are shown in FIG. 17.

TABLE C-14

Sample ID and description of HER2/TCR binding polypeptides.

| Cluster | Sample ID | SEQ ID NO | Description |
|---|---|---|---|
| | | | Target Nb × Effector Nb |
| A | T017000102 | 342 | HER2005F07(Q108L)-35GS-T0170056G05-FLAG3-HIS6 |
| | | | Effector Nb × Target Nb |
| A | T017000103 | 343 | T0170056G05-35GS-HER2005F07(Q108L)-FLAG3-HIS6 |

In brief, SKBR3 ($4\times10^4$ cells/well), MDA-MB-468 ($4\times10^4$ cells/well) or MCF-7 ($2\times10^4$ cells/well) were seeded in 96 well E-plates and incubated with $6\times10^5$ cells or $3\times10^5$ cells human primary T cells (effector target ratio of 15 to 1) in the presence or absence of the multispecific constructs and followed over time. Data were analysed after 18 h and are shown in FIG. 18.

The IC50 values obtained in this assay are listed in Table C-15.

The data indicate specific killing of HER2-positive tumour cell lines by directing human primary T cells to the tumour cells via the anti-TCR Nanobody. Hence, the TCR binding building blocks are broadly applicable for directing cytotoxic T cells to tumours. Despite the large difference in tumour antigen density on SKBR3 and MCF-7 cells, both were efficiently killed by the addition of multispecific polypeptide constructs.

Example 17: Effect of HER2/TCR Binding Polypeptides on IFN-γ Release by Human T Cells in the HER2-Positive Tumour Cell Killing Assay To further evaluate the broad applicability of the TCR binding building blocks, the induction of cytokine release was monitored during the human T cell mediated SKBR3 killing assay based on xCELLigence. The release of the cytokine IFN-γ was measured by ELISA. Briefly, SKBR3 cells were seeded in 96 E-plate in the presence of purified human primary T cells with or without multispecific HER2/TCR binding or irrelevant polypeptides as described in Example 16. 72 h after the addition of the human primary T cells/polypeptides to the E-plates, IFN-γ production by the human primary T cells was measured. Maxisorp 96-well ELISA plates (Nunc) were coated with anti-human IFN-γ antibody (BD Biosciences #551221). After overnight incubation, plates were washed and blocked with PBS+2% BSA for 1 h at room temperature. Next, plates were incubated with 100l of the supernatants (2 fold diluted) and 1 μg/ml biotinylated anti-human IFN-γ antibody (BD Biosciences, #554550) for 2 h 30 min while shaking, washed again and incubated with streptavidin-HRP (Dakocytomation #P0397). After 30 min, TMB One Solution (Promega #G7431) was added. The reaction was stopped with 2M $H_2SO_4$ and the polypeptide dose dependent production of IFN-γ was determined by measurement of the OD at 405 nm using the Tecan sunrise 4.

The results are shown in FIG. 19. The EC50 values obtained in this assay are listed in Table C-16.

The multispecific HER2/TCR binding polypeptides induced a dose dependent production of the cytokine IFN-γ, indicating that the human T cells were activated only in presence of the relevant polypeptide.

Example 18: Cynomolgus Cross-Reactivity of Anti-TCR Nanobodies

The cross-reactivity of the TCR binding building blocks with cynomolgus monkey TCR was evaluated.

18.1 Functional Characterization of the Multispecific Polypeptides in a Cynomolgus T Cell Mediated Ramos CD20 Positive Tumour Killing Assay In a first experiment, a flow cytometric killing assay was set up, essentially as described in Example 10, using $2.5 \times 10^5$ primary cynomolgus T cells (isolated using Pan T Cell Isolation Kit MACS#130-091-993) as effector cells and $2.5 \times 10^4$ human CD20 positive Ramos cells as target cells.

The IC50 values and the % lysis obtained from the dose response curve are depicted in Table C-17. The results are shown in FIG. 20.

The TCR binding multispecific polypeptides that contained a TCR binding building block belonging to cluster A showed dose dependent killing of the Ramos cells using cynomolgus T cells.

18.2 Functional Characterization of the Multispecific Polypeptides in a Cynomolgus T Cell Mediated CHO-K1 Human CD20 Positive Cell Killing Assay To further assess the cross-reactivity of the TCR binding building blocks in the TCR/CD20 binding multispecific constructs, the xCELLigence based killing assay using purified primary cynomolgus T cells essentially as described in Example 11 was used.

The assay used an effector to target ratio of 30 to 1, i.e. $3 \times 10^5$ effector cynomolgus T cells (isolated using Pan T Cell Isolation Kit MACS#130-091-993) and $1 \times 10^4$ target CHO-K1 human CD20 cells.

The IC50 values obtained in this assay are listed in Table C-18. The results are summarized in FIG. 21.

It can be concluded that the TCR binding multispecific polypeptides that contain a TCR binding building block belonging to cluster A showed dose dependent killing of the CHO-K1 CD20 transfected cells using cynomolgus T cells. Hence, cluster A Nanobodies cross-react with primary cynomolgus T cells and can elicit potent killing based on these cynomolgus T cells.

18.3 Binding of Anti-TCR Nanobodies to cynomolgus T Cell Receptor Protein (ELISA)

Binding of purified monovalent anti-TCR Nanobodies to soluble recombinant cynomolgus TCR c/3 protein was evaluated in ELISA (as described in Example 1.2) using 2 µg/ml directly coated recombinant soluble cynomolgus TCR-α/β zipper protein.

The EC50 values obtained from the dose response curve are depicted in Table C-19.

An exemplary result is shown in FIG. 22.

TABLE C-19

EC50 (M) of anti-TCR monovalent Nanobodies for binding to soluble recombinant cynomolgus TCR/CD3 protein as determined in ELISA.

| Cluster | sample ID | EC50 (M) | 95% LCI | 95% UCI |
|---|---|---|---|---|
| A | T0170055A02 | 1.6E−07 | 1.5E−07 | 1.7E−07 |
| A | T0170056G05 | 7.7E−08 | 6.6E−08 | 9.1E−08 |
| B | T0170068G05 | 8.7E−08 | 8.5E−08 | 8.9E−08 |
| C | T0170061G01 | >1E7 | | |

The results indicate that the anti-TCR Nanobodies from cluster A and cluster B bind to the recombinant soluble cynomolgus TCR-α/β zipper protein.

18.4 Evaluation of Cynomolgus Cross-Reactivity in Bio-Layer Interferometry

Binding affinities of the monovalent anti-TCR Nanobodies were measured using Bio-Layer Interferometry (BLI) on an Octet RED384 instrument (Pall ForteBio Corp.) essentially as described in Example 7.1 using cynomolgus TCR α/β zipper. The results are depicted in FIG. 23, the binding characteristics of the anti-TCR Nanobodies are listed in Table C-20.

TABLE C-20

Binding characteristics of monovalent anti-TCR Nanobodies determined in Octet using directly coated cynoTCR-zipper protein.

| Cluster | sample ID | kon (1/Ms) | koff (1/s) | KD (M) |
|---|---|---|---|---|
| A | T0170055A02 | 1.1E+05 | 2.4E−02 | 2.1E−07 |
| A | T0170056G05 | 1.1E+05 | 1.6E−02 | 1.5E−07 |

The cluster A Nanobodies bind to the soluble recombinant cynomolgus TCR αβf zipper with a 10 fold lower affinity compared to soluble recombinant human TCR α/β zipper.

18.5 Functional Characterization of Half-Life Extended Multispecific Polypeptides in a Cynomolgus T Cell Mediated Ramos CD20 Positive Tumour Killing Assay Analogous to the set up described in Example 18.1, the half-life extended TCR binding polypeptides were evaluated in a cynomolgus T cell mediated Ramos killing assay.

The IC50 values obtained in this assay are listed in Table C-21. The results are depicted in FIG. 24.

TABLE C-21

IC50 of and % lysis by HLE multispecific polypeptides in the cynomolgus T cell dependent B cell (Ramos) killing assay to evaluate the effect of HLE.

| Cluster | sample ID | IC50 (M) | 95% LCI | 95% UCI | % lysis |
|---|---|---|---|---|---|
| A | T017000076 | 5.2E−10 | 2.9E−10 | 9.5E−10 | 29 |
| A | T017000093 | 1.0E−09 | 5.5E−10 | 2.0E−09 | 28 |
| A | T017000093 + HSA | 8.2E−10 | 4.7E−10 | 1.4E−09 | 18 |

The HLE extended TCR binding multispecific polypeptides that contain a TCR binding building block belonging to cluster A showed dose dependent killing of the Ramos cells using purified primary cynomolgus T cells. The inclusion of the ALB11 in the construct as such did not impact the potency (overlapping CI). Upon addition of HSA, a small drop in efficacy was observed while the potency was not affected.

18.6 Functional Characterization of Half-Life Extended CD20×TCR Binding Multispecific Polypeptides in a Cynomolgus T Cell Mediated CHO-CD20 Positive Tumour Cell Killing Assay To confirm the data in the flow cytometry based assay, the HLE constructs were tested in the xCELLigence based CHO-K1 human CD20 killing using purified primary cynomolgus T cells as described in Example 11.

The results are shown in FIG. 25. The IC50 values obtained from the dose response curve are depicted in Table C-22.

TABLE C-22

IC50 (M) of the TCR/CD20 binding multispecific and HLE constructs in the cynomolgus T cell mediated CHO-K1 human CD20 tumour killing assay to evaluate the effect of ALB11 and HSA.

| sample ID | IC50 (M) | 95% LCI | 95% UCI |
| --- | --- | --- | --- |
| T017000076 | 1.4E−10 | 9.5E−11 | 2.1E−10 |
| T017000093 | 1.9E−10 | 1.3E−10 | 2.8E−10 |
| T017000093 + HSA | 7.4E−10 | 5.0E−10 | 1.1E−09 |

The HLE TCR binding multispecific polypeptides showed dose dependent killing of CHO-K1 human CD20 transfected cells using cynomolgus T cells, confirming that the ALB11 has no impact on the cynomolgus cross-reactivity of the TCR binding building block.

18.7 Functional Characterization of Multispecific Polypeptides in a Cynomolgus T Cell Medicated HER2 Positive Tumour Cell Killing Assay The multispecific polypeptides were functionally characterized in a cynomolgus T cell mediated HER2 positive tumour cell killing assay. In short, the TCR/HER2 binding multispecific polypeptides were evaluated in a xCELLigence based killing assay essentially as described in Example 16, using 6×10$^5$ cynomolgus T cells as effector cells and 4×10$^4$ SKBR3 as target cells (effector to target of 30 to 1). Data were analysed after 18 h.

The results are depicted in FIG. 26. The IC50 values obtained in this assay are listed in Table C-23.

The cynomolgus cross-reactivity of the TCR binding building block was confirmed using the HER2/TCR binding multispecific constructs.

Example 19: In Vivo Proof-of-Concept in a Ramos B Cell Depletion Model

In this B cell depletion model, Ramos cells (a Burkitt's lymphoma cell line) and human PBMC were injected respectively intravenously and intraperitoneally in to NOG mice. Ramos B cell and PBMC-derived B cell killing by Nanobody-mediated recruitment of T cells present in the PBMC population was evaluated reflecting the potential of multispecific polypeptides to activate T cells by direct linkage of T cells via TCR to target B cells via CD20, resulting in target cell killing.

The in vivo efficacy of the bi-specific polypeptide T017000083 (CD20×TCR binding) on B cell depletion in a Ramos NOG mouse model was evaluated and compared with the irrelevant multispecific polypeptide T017000088 (irrelevant Nanobody+TCR binding Nanobody). The study demonstrated a statistically significant effect in bone marrow and spleen on Ramos B cell depletion and on PBMC derived B cell depletion in spleen.

In detail, the B cell depletion was evaluated in mice, intravenously injected with 10$^6$ Ramos cells in 200 µL of Roswell Park Memorial Institute (RPMI) medium 1640 at day one (D1). This injection took place 24 hours after a whole body irradiation of mice with a ɣ-source (1.44 Gy, 60Co) (D0). 10$^7$ PBMCs (500 µL in PBS) were injected on D3 (i.e. two days after tumor cell injection) after randomization of the mice into groups each of 24 animals. The treatment started on D3 one hour after PBMC injection and was repeated for 5 consecutive days in total until D7 (FIG. 27). Three dose levels of the TCR/CD20 binding polypeptides were tested (0.5 mg/kg, 5 mg/kg and 23 mg/kg).

On D20 or on D21, mice were sacrificed and spleen and bone marrow (femur) were collected for FACS analysis (mCD45, hCD45, hCD19, hCD20, hCD10) to analyze and quantify the presence of Ramos B cells (hCD19+ hCD20+ hCD45+ mCD45− hCD10+) and PBMC-derived B cells (hCD19+ hCD20+ hCD45+ mCD45− hCD10−).

Results for Ramos B cell depletion are represented in FIG. 28A and FIG. 28B. Mice treated with an irrelevant multispecific polypeptide were considered as control group for analyses. From FIG. 28A, a dose response pattern was seen in the bone marrow for T017000083 (CD20/TCR) versus the irrelevant multispecific polypeptide for reducing Ramos cell numbers. The 2 highest dose levels for the CD20/TCR binding multispecific polypeptide were statistically significantly different from the irrelevant multispecific polypeptide. Statistical analysis has been performed with F-tests from the mixed-effects ANOVA analysis. For the spleen, all tested dose levels of T017000083 were statistically significantly different from the irrelevant multispecific polypeptide, as depicted in FIG. 28B. The dose response pattern in spleen was less pronounced since all doses were close to or estimated to be on the maximum effect and thus very similar.

Results for PBMC-derived B cell depletion are represented in FIG. 28C and FIG. 28D. In bone marrow, a dose response pattern was seen for T017000083 as depicted in FIG. 28C. The estimated difference in human B cell numbers for T017000083 versus the irrelevant multispecific polypeptide for the 2 highest dose levels was statistically significantly different at the 5% level of significance. In the spleen, B cell counts were statistically significantly different from the irrelevant multispecific polypeptide-treated group in all the groups treated with T017000083, and this at all tested dose levels. The dose response pattern was less pronounced since all doses were close to or estimated to be on the maximum effect and thus very similar, although an increase in estimated difference with increasing dose was observed.

In conclusion, these results demonstrate that CD20/TCR multispecific polypeptides are able to significantly decrease Ramos B cells and PBMC-derived B cells in spleen and Ramos B cells in bone marrow in this model. This confirms the polypeptide-induced T cell activation by cross-linking T cells to target B cells and killing of the latter.

Example 20: In Vivo Proof-of-Concept in a PBMC B Cell Depletion Model

In this B cell depletion model, human PBMC were injected intraperitoneally in to NOG mice. PBMC-derived B cell killing by polypeptide-mediated recruitment of T cells present in the PBMC population was evaluated reflecting the potential of the polypeptides of the invention to activate T cells by direct linkage of T cells via TCR to target B cells via CD20, resulting in target cell killing.

The in vivo efficacy of the multispecific polypeptide T017000083 (CD20×TCR binding) on B cell depletion in a PBMC NOG mouse model was evaluated and compared with the irrelevant polypeptide T017000088. The study demonstrated a clear effect on PBMC derived B cell depletion in spleen.

In detail, the B cell depletion was evaluated in mice, intraperitoneally injected with 3×10⁷ PBMCs in 500 μL of PBS at day three (D3) after a whole body irradiation of mice with a ɣ-source (1.44 Gy, 60Co) (D0) and randomization of the mice into groups each of 12 animals. The treatment started on D3 one hour after PBMC injection and was repeated for 5 consecutive days, in total until day 7 (D7) (FIG. 29). Three dose levels of the CD20/TCR binding polypeptide were tested (0.5 mg/kg, 5 mg/kg and 23 mg/kg).

On day 18 (D18), mice were sacrificed and the spleen was collected for FACS analysis (mCD45, hCD45, hCD19, hCD20) to analyze and quantify the presence of PBMC-derived human B cells (hCD19+ hCD20+ hCD45+ mCD45−).

Results for PBMC-derived B cell depletion are represented in FIG. 30. In the spleen, B cell counts were clearly different from the irrelevant polypeptide-treated group in all the groups treated with T017000083 and this at all tested dose levels. The dose response pattern is not pronounced since all doses are close to or estimated to be on the maximum effect and thus very similar.

In conclusion, these results demonstrate that a CD20/TCR binding multispecific polypeptide is able to significantly decrease PBMC-derived B cells in spleen in this model. This confirms the polypeptide-induced T cell activation by cross-linking T cells to target B cells and killing of the latter.

Example 21: Targeting of Tumour Cells with Multispecific T Cell Engaging Polypeptides The therapeutic activity of T cell engaging strategy can be improved by the simultaneous targeting of multiple tumour associated antigens. Often tumour cells create an escape mechanism by the down-regulation of targeted antigens within a therapy. The simultaneous targeting of multiple antigens is likely to reduce the probability of generating tumour escape variants. The individual affinity of the respective tumour targeting Nanobodies may be varied such that preferable binding to either a single marker or simultaneous binding to both tumour markers is achieved. Antigens present on different cell populations can be combined or even soluble proteins can be targeted in combination with a tumour associated antigen.

As the Nanobody platform is ideally suited to combine different specificities into a multispecific format, the anti-TCR Nanobodies of the invention are combined into formats illustrating these concepts, i.e. with different tumour antigen binding Nanobodies in a multispecific polypeptide.

For the double tumour antigen targeting concept, a Nanobody reactive towards a first tumour antigen (TA1, e.g. CEA) is linked to a second Nanobody with different specificity (TA2, e.g. EGFR), different from TA1, in combination with a TCR reactive Nanobody. The specific order of the building blocks is varied within the format as well as the applied linker lengths in between the different building blocks. Combinations of TA1 and TA2 which are tested are depicted in Table C-24.

TABLE C-24

Combination of TCR, TA1, TA2 and Alb binding building blocks in multispecific polypeptides.

| T cell ISV | TA1 ISV | TA2 ISV | ALB-ISV |
|---|---|---|---|
| TCR | CEA | Irr | + |
| TCR | CEA | Irr | − |
| TCR | CEA | EGFR | + |
| TCR | CEA | EGFR | − |
| TCR | Irr | EGFR | + |
| TCR | Irr | EGFR | − |

In order to test half-life extension, an Alb Nanobody is included as well in the polypeptides as set out in Table C-24.

To demonstrate the specific killing, a mixed cell culture assay system is used where TA1 single positive (e.g. MC38-huCEA or MKN45) and TA2 single positive tumour cells (e.g. Hela or Her14) are co-incubated. The expression level of the respective tumour antigens was determined in different cell lines and is represented in FIG. 31. Upon addition of the polypeptides of the invention, primary human T cells and albumin if required, the T cell mediated cytotoxicity is monitored based on a cytometric read out. A comparison is made with respect to double negative cells or formats containing one or more irrelevant Nanobodies.

In order to verify the specific killing, the induced killing of double positive tumour (for TA1 and TA2, e.g. LS174T or LoVo) cells is compared with the induced killing of single positive tumour cells. For this, a T cell mediated cytotoxicity assay is used as described above with a single type of tumour cells positive for both markers (cf. Example 19).

Example 22: Targeting of Tumour Cells with Multispecific T Cell Engaging Polypeptides As mentioned above, the therapeutic activity of T cell engaging strategy can be improved by the simultaneous targeting of multiple tumour associated antigens. Not only do tumour cells create an escape mechanism by the down-regulation of targeted antigens within a therapy, but also by introducing (point-)mutations. Also in this case, simultaneous targeting of multiple epitopes on an antigen is likely to reduce the probability of generating tumour escape variants. Moreover, targeting multiple epitopes on a single antigen can increase the affinity of binding (avidity effect).

As the Nanobody platform is ideally suited to combine different specificities into a multivalent format, the anti-TCR Nanobodies of the invention are combined into formats illustrating these concepts, i.e. with different tumour antigen binding Nanobodies in a multispecific polypeptide.

For the multivalent tumour antigen targeting concept, two Nanobodies reactive towards an antigen are linked (TA1 and TA2, respectively), followed by a TCR reactive Nanobody. The specific order of the building blocks is varied within the format as well as the applied linker lengths in between the different building blocks. Combinations of TA1 and TA2 which are tested are depicted in Table C-25.

TABLE C-25

Combination of TCR, TA1, TA2 and Alb binding building blocks in multispecific polypeptides.

| T cell ISV | TA1 ISV | TA2 ISV | ALB-ISV |
|---|---|---|---|
| TCR | EGFR-1 (7D12) | EGFR-2 (9G08) | + |
| TCR | EGFR-1 (7D12) | EGFR-2 (9G08) | − |
| TCR | Her2-1 (5F07) | Her2-2 (47D05) | + |
| TCR | Her2-1 (5F07) | Her2-2 (47D05) | − |

In order to test half-life extension, an albumin binding Nanobody is included as well in the polypeptides as set out in Table C-25.

The potency and efficacy of these multivalent formats is evaluated and compared with the respective bispecific formats in an in vitro tumour cell killing assay comparable to the assay described in Example 10 but with the relevant cell lines (e.g. Hela, Her14, Ls174T, SKBR3, MCF7). Additionally, the effector-target ratio is varied such that an estimate is made whether a multivalent/multispecific polypeptide has a higher efficacy with lower effector target ratios.

Example 23: Binding of Monovalent Nanobodies and Multispecific Polypeptides to Cells in Flow Cytometry As described earlier, the therapeutic activity of T cell engaging strategy can be improved by the simultaneous targeting of multiple tumour associated antigens, as tumour cells often create an escape mechanism by the down-regulation of targeted antigens within a therapy. The simultaneous targeting of multiple antigens is likely to reduce the generation of tumour escape variants.

For this double tumour antigen targeting concept, a Nanobody reactive towards a first tumour antigen (EGFR) was linked to a second Nanobody with different specificity (CEACAM5), in combination with a TCR reactive Nanobody. The specific order of the building blocks was varied within the format. The effector and tumour Nanobodies were genetically linked with 35GS linker and subsequently expressed in the yeast *Pichia* according to standard protocols. Irrelevant constructs were generated by replacing the tumour Nanobody with an irrelevant anti-egg lysozyme (cAblys) Nanobody (Table C-26).

TABLE C-26

Sample ID and description of multispecific polypeptides.

| Sample ID | SEQ ID NO | TAA1 | TAA2 | T cell ISV | Description |
|---|---|---|---|---|---|
| T017000107 | 390 | EGFR | CEACAM5 | TCR | EGFR038G07-35GS-NbCEA5-35GS-T0170056G05-FLAG3-HIS6 |
| T017000109 | 391 | Irrelevant | CEACAM5 | TCR | cAbLys3(D1E,Q5V,A6E,Q108L)-35GS-NbCEA5-35GS-T0170056G05-FLAG3-HIS6 |
| T017000110 | 392 | EGFR | Irr | TCR | EGFR038G07-35GS-cAbLys3(D1E,Q5V,A6E,Q108L)-35GS-T0170056G05-FLAG3-HIS6 |

Dose-dependent binding of the monovalent Nanobodies and multispecific polypeptides to cancer cell lines expressing CEACAM5 and EGFR (LoVo; ATCC CCL-229 and LS174T; ECACC 87060401), a cell line expressing EGFR (HER14; NIH3T3 (ATCC CRL-1658) transfected with EGFR), and to purified primary human T cells (isolated as described in Example 2.1) was evaluated in flow cytometry as outlined in Example 5. The results are presented in FIG. 32.

The expression level of the respective tumour antigens on the different cells was determined in flow cytometry using 100 nM of a monovalent anti-EGFR Nanobody (EGFR038G07) and a monovalent anti-CEA Nanobody, as described in Example 5. Results are shown in FIG. 33.

The EC50 values obtained from the dose response curve for binding HER14 cells are depicted in Table C-27. The EC50 values obtained from the dose response curve for binding LS174T and LoVo cells are depicted in Table C-28.

TABLE C-27

EC50 (M) of monovalent Nanobodies and multispecific polypeptides for binding HER14 cells as determined in flow cytometry.

| sample ID | HER14 | | | |
|---|---|---|---|---|
| | EC50 (M) | 95% LCI | 95% UCI | Top |
| T017000107 | 1.6E−09 | 1.4E−09 | 1.9E−09 | 146111 |
| T017000109 | / | / | / | / |
| T017000110 | 7.3E−09 | 6.4E−09 | 8.3E−09 | 164582 |
| EGFR038G07 | 1.8E−09 | 1.6E−09 | 2.1E−09 | 166237 |
| NbCEA5 | / | / | / | | to the EGFR, CEACAM5 double positive cell lines LS174T and LoVo, as expected. There was also binding of the multispecific polypeptides to the human primary T cells. A drop in affinity of the multispecific polypeptides versus the monovalent TCR building block was observed due to the C-terminal position of the TCR building block.

Example 24: Binding of Monovalent Nanobodies to Human EGFR and CEACAM5 Protein (SPR)

Binding affinity of the purified EGFR monovalent Nanobody was evaluated by means of a surface plasmon resonance (SPR) based affinity determination on a Biacore T100 instrument. Thereto, hEGFR (Sino Biological, #10001-H08H) was immobilized onto a CM5 chip via amine coupling, using EDC and NHS chemistry. Purified Nanobodies were injected for 2 minutes at different concentrations (between 1.37 and 3000 nM) and allowed to dissociate for 15 min at a flow rate of 45 µl/min. In between sample injections, the surfaces were regenerated with 50 mM NaOH. HBS-EP+(Hepes buffer pH7.4) was used as running buffer.

Binding affinityies of the purified CEACAM5 monovalent Nanobody was evaluated by means of an SPR based affinity determination on a Biacore T100 instrument. Thereto, hCEACAM-5 (R&D Systems, #4128-CM) was immobilized onto a CM5 chip via amine coupling, using EDC and NHS chemistry. Purified Nanobodies were injected for 2 minutes at different concentrations (between 0.31 and 2000 nM) and allowed to dissociate for 15 min at a flow rate of 45 µl/min. In between sample injections, the

TABLE C-28

EC50 (M) of monovalent Nanobodies and multispecific polypeptides for binding LoVo and LS174T cells as determined in flow cytometry.

| sample ID | LS174T | | | | LoVo | | | |
|---|---|---|---|---|---|---|---|---|
| | EC50 (M) | 95% LCI | 95% UCI | Top | EC50 (M) | 95% LCI | 95% UCI | Top |
| T017000107 | 1.1E−08 | 9.7E−09 | 1.3E−08 | 64605 | 3.2E−09 | 2.7E−09 | 3.7E−09 | 88604 |
| T017000109 | 2.5E−08 | 2.2E−08 | 2.9E−08 | 50982 | 3.6E−08 | 1.4E−08 | 9.1E−08 | 18514 |
| T017000110 | 6.3E−09 | 5.5E−09 | 7.2E−09 | 40779 | 2.4E−09 | 2.1E−09 | 2.8E−09 | 95866 |
| EGFR038G07 | 9.3E−10 | 8.1E−10 | 1.1E−09 | 32191 | 5.4E−10 | 4.8E−10 | 6.2E−10 | 52268 |
| NbCEA5 | 5.9E−10 | 5.3E−10 | 6.6E−10 | 42978 | 1.2E−09 | 6.4E−10 | 2.4E−09 | 11238 |

The data showed binding of the EGFR monovalent Nanobody and of the multispecific polypeptides containing the EGFR building block to the HER14 cells, expressing only EGFR. No binding of the CEACAM monovalent Nanobody and the multispecific polypeptides containing only the CEACAM5 tumour anchor building block was observed. All monovalent and multispecific polypeptides showed binding surfaces were regenerated with 10 mM Glycine pH 1.5. HBS-EP+(Hepes buffer pH7.4) was used as running buffer.

The kinetic constants were calculated from the sensorgrams using the BIAEvaluation software (1:1 interaction). The affinity constants (KD) were calculated from resulting association and dissociation rate constants kon and koff, and are shown in Table C-29.

TABLE C-29

Affinity constant of monovalent Nanobodies for binding hEGFR and hCEACAM5, determined in Biacore using directly coated proteins.

| | hCEACAM5 | | | hEGFR ECD | | |
|---|---|---|---|---|---|---|
| | kon (1/Ms) | Koff (1/s) | KD (M) | kon (1/Ms) | koff (1/s) | KD (M) |
| EGFR038G07 | / | / | / | 5.58E+05 | 4.26E−04 | 7.63E−10 |
| NbCEA5 | 9.9E+05 | 5.1E−04 | 5.1E−10 | / | / | / |

Example 25: Redirected Cell Killing of Multispecific Polypeptides by Human Effector T Cells in the xCELLigence Based Assay The multispecific polypeptides were functionally characterized in a human T cell mediated EGFR/CEACAM positive tumour cell killing assay. In short, the multispecific constructs were evaluated in a xCELLigence based killing assay essentially as described in Example 16, using $6 \times 10^5$ human T cells as effector cells and $4 \times 10^4$ LS174T cells (ECACC 87060401) or LoVo cells (ATCC CCL-229) respectively as target cells (effector to target of 15 to 1). Data were analysed after 30-40 h and after 50-60 h.

The results are depicted in FIG. 34. The IC50 values obtained in this assay are listed in Tables 30 and 31.

TABLE 30

IC50 (M) of the multispecific polypeptides in the human T cell mediated xCELLigence based killing assay using an effector to target ratio of 15. Data were analysed after 30-40 h.

| | | LoVo | | | | LS174T | | |
|---|---|---|---|---|---|---|---|---|
| ID construct | n | IC50 (M) | 95% LCI | 95% UCI | n | IC50 (M) | 95% LCI | 95% UCI |
| T017000107 | 1 | 3.0E−10 | 2.6E−10 | 3.6E−10 | 1 | 1.0E−08 | 6.1E−09 | 1.7E−08 |
| T017000109 | 1 | 9.3E−09 | 6.7E−09 | 1.3E−08 | 1 | 1.0E−07 | 4.9E−08 | 2.2E−07 |
| T017000110 | 1 | 1.5E−09 | 1.3E−09 | 1.9E−09 | 1 | 2.6E−08 | 1.1E−08 | 6.0E−08 |

The data on the EGFR+/CEA+ LoVo cells showed a ~28 fold difference in potency between the CEACAM5 only and the EGFR-CEA multispecific constructs and a ~8 fold difference in potency between the EGFR only constructs and the EGFR-CEA multispecific constructs. On EGFR+/CEA+ LS174T cells, a ~7 fold difference in potency between the CEACAM5 only and the EGFR-CEA multispecific constructs was observed and ~2 fold difference between the EGFR only constructs and the EGFR-CEA multispecific constructs. These results showed that potency enhancements were obtained with multispecific constructs reactive against two different antigens present on a cell.

Example 26: In Vivo B Cell Depletion by Half-Life Extended (HLE) Polypeptides in a Ramos B Cell Depletion Model In this B cell depletion model, Burkitt's lymphoma Ramos cells and human PBMC were injected respectively intravenously and intraperitoneally in to mice after which Ramos B cell and PBMC-derived B cell killing by Nanobody-mediated recruitment of T cells present in PBMC population was evaluated: i.e. the potential of Nanobodies, HLE and non-HLE (NHLE), to activate T cells by direct linking of T cells via TCR to target B cells via CD20, resulting in target cell killing.

The polypeptides used in this study are described in Table 32:

TABLE 32

Sample ID and description of multispecific polypeptides used in in vivo study.

| Sample ID | SEQ ID NO | TAA | TCR ISV | HLE | Description |
|---|---|---|---|---|---|
| T017000083 | 338 | CD20 | TCR | NHLE | 20CD019C07(E1D)-35GS-T0170055A02-A |
| T017000088 | 339 | Irr | TCR | NHLE | RSV007B02(E1D)-35GS-T0170055A02-A |
| T017000104 | 387 | CD20 | TCR | HLE | 20CD019C07(E1D)-35GS-T0170055A02-35GS-ALB11-A |
| T017000105 | 388 | CD20 | TCR | NHLE | 20CD019C07(E1D)-35GS-T0170056G05-A |
| T017000106 | 389 | Irr | TCR | HLE | RSV007B02(E1D)-35GS-T0170055A02-35GS-ALB11-A |

The in vivo efficacy of a HLE bispecific Nanobody, T017000104 (TCR and CD20-specific coupled to an albumin targeting building block) in a Ramos NOG mouse model was evaluated and compared with the irrelevant Nanobody T017000106. The non-half-life extended (NHLE) Nanobody T017000105 (TCR and CD20-specific) and T0107000083 (TCR and CD20-specific) were compared to the NHLE irrelevant Nanobody T017000088 (irrelevant and TCR-specific). The study demonstrated a statistically significant effect in bone marrow and spleen on PBMC derived B cell depletion for T017000104 and T017000105 compared to their respective irrelevant control NBs. The Ramos cells were significantly reduced in T017000104 and T017000105 treated mice, both in spleen and bone marrow.

In detail, the B cell depletion was evaluated in the mice, intravenously injected with Ramos cells at day one (D1) and intraperitoneally with PBMCs at D3. Mice were treated from D3 to D7 (FIG. 35). Tumors were induced by intravenous injection of $10^6$ Ramos cells in 200 μL of Roswell Park Memorial Institute (RPMI) 1640 medium (D1) 24 hours after a whole body irradiation of mice with a γ-source (1.44 Gy, 60Co) (D0). PBMCs were injected on D3 (i.e. two days after tumor cell injection) after randomization of the mice into groups each of 12 animals (11 animals for group 6) based on body weight. The animals received one single intraperitoneal (IP) injection of $10^7$ PBMCs (500 μL in PBS). The treatment started on D3 one hour after PBMC injection and was repeated for 5 consecutive days in total for groups 1-4 and 6, whereas group 5 received only two injections (D3 and D5).

On D20 or on D21, the mice were sacrificed and spleen and bone marrow (femur) were collected for FACS analysis (mCD45, hCD45, hCD19, hCD20, hCD10) and analyzed for presence of Ramos B cells and PBMC-derived B cells.

Results for Ramos B cell depletion are represented in FIG. 36. Test items T017000083 and T017000105, and T017000104 were compared to their respective control groups (groups 1 and 2) based on presence/absence of HLE. In bone marrow, a statistically significant difference in Ramos B cell number between the control Nanobodies and the NHLE Nanobodies T017000083 and T017000105 was observed (FIG. 36A). In spleen the difference was significant only for T017000105 (FIG. 36B). The HLE Nanobody T017000104 significantly reduced the Ramos cells in spleen and bone marrow irrespective of the dosing frequency applied (FIGS. 36A and B). Statistical analysis has been performed with F-tests from the mixed-effects ANOVA analysis.

Results for PBMC-derived B cell depletion are represented in FIG. 37. In bone marrow, a reduction was observed in absolute B cell count in all treatment groups, compared to the irrelevant control Nanobody and this effect was significant for Nanobodies T017000083 and T017000104 (FIG. 37 A). In the spleen, the effect was more pronounced and significant for all treatment groups (FIG. 37 B).

In conclusion, these results demonstrate that both the anti-CD20/anti-TCR polypeptide and the HLE anti-CD20/anti-TCR polypeptide are able to significantly decrease Ramos B cells and PBMC-derived B cells in spleen and bone marrow in this B cell depletion model. This confirms the Nanobody-induced T cell activation by cross-linking T cells to target B cells and killing of the latter.

Example 27: Role of Human Effector CD4+ and CD8+ T Cells in T Cell Activation

To investigate the role of CD4+, respectively CD8+ human T cells in the redirected killing, targeting of tumour cells with multispecific T cell engaging polypeptides was performed using T cell subsets. In this case, the HER2-positive cell line SKBR3 and Nanobody T017000102 (targetting HER2 and TCR) were used.

27.1 Redirected Cell Killing of Multispecific Polypeptides by Human Effector CD4+ and CD8+ T Cells in the xCELLigence Based Assay Human T cells were collected as described in Example 2.1. After thawing, human CD4+, respectively CD8+ T cells were isolated using the CD4+(Miltenyi Biotec #130-096-533), respectively CD8+(Miltenyi Biotech #130-096-495) T cell isolation kit. SKBR3 cells, were seeded in 96 well E-plates ($2 \times 10^4$ cells/well) and incubated with $3 \times 10^5$ human primary effector T cells, human primary effector CD4+ T cells or human primary effector CD8+ T cells (effector target ratio of 15:1) in the presence or absence of multispecific constructs and followed over time, as described in Example 16. Data were analysed after 40 h.

Results are shown in FIG. 38. The IC50 values are depicted in Table 33.

TABLE 33

IC50 (M) of the multispecific polypeptides in the xCELLigence based human T cell mediated SKBR3 killing assay using an effector to target ratio of 15 to 1.

|  | IC50 (M) | 95% LCI | 95% UCI |
|---|---|---|---|
| T cells | 2.4E−11 | 1.9E−11 | 3.0E−11 |
| CD8+ T cells | 2.9E−11 | 2.1E−11 | 4.1E−11 |
| CD4+ T cells | 1.2E−11 | 1.1E−11 | 1.3E−11 |

The data showed dose dependent specific killing of HER2-positive tumour cell lines by directing human primary T cells, human CD4+ or human CD8+ T cells to the tumour cells via the TCR polypeptide.

27.2 Effect of HER2/TCR Binding Polypeptides on CD69 and CD25 Expression on Human Effector CD4+ and CD8+ T Cells in a HER2-Positive Tumour Cell Killing Assay Primary human T cells and CD4+ and CD8+ T cell subpopulations were isolated and a redirected HER2-positive tumour cell killing assay using SKBR3 cells was performed as described in Example 27.1. T cell activation was determined by measuring CD69 and CD25 upregulation after 24 h and 72 h of incubation respectively on the human primary T cells and on the CD4+ and CD8+ human T cell populations. CD69 and CD25 expression was measured in flow cytometry, using monoclonal mouse anti-human CD69PE (BD Biosciences #557050) and mouse anti-human CD25PE (BD Pharmigen #557138) antibody, for CD69 and CD25 measurement respectively.

Exemplary results are shown in FIG. 39.

The data showed dose dependent upregulation of CD69 and CD25 on human primary T cells, human CD4+ and human CD8+ T cells.

27.3 Effect of HER2/TCR Binding Polypeptides on IFN-γ and IL-6 Release by Human Effector CD4+ and CD8+ T Cells in a HER2-Positive Tumour Cell Killing Assay Primary human T cells and CD4+ and CD8+ T cell subpopulations were isolated and a redirected HER2-positive tumour cell killing assay using SKBR3 cells was performed as described in Example 27.1. The release of the cytokine IFN-γ was measured by ELISA as described in Example 17 and the release of IL-6 was measured in ELISA using the human IL-6 Quantikine ELISA Kit (R&D Systems, #D6050) according to manufactures instructions.

Exemplary results are shown in FIG. 40.

The data showed dose dependent IFN-γ and IL-6 release by human primary T cells, human CD4+ and human CD8+ T cells.

Example 28: Exploration of Half-Life Extension (HLE)

It was hypothesized that HLE via albumin binding might be suitable to comply with various requirements, including (i) half-life extension (HLE) of the moiety; and (ii) efficacy of the multispecific polypeptide. Preferably, the HLE function would not impair the penetration of tumours and tissues.

Alb11 (SEQ ID NO: 404), a Nanobody binding to human serum albumin (HSA) was linked to the multispecific EGFR×CEA×TCR binding polypeptide to increase the in vivo half-life of the formatted molecule (WO 06/122787). A format was generated with the albumin targeting Nanobody at the C-terminus using a 35GS linker and expressed as indicated above. The explored format is shown in Table 34.

TABLE 34

Sample ID and description of the multispecific HLE polypeptide.

| Sample ID | SEQ ID NO | Description |
| --- | --- | --- |
| T017000108 | 486 | EGFR038G07-35GS-NbCEA5-35GS-T0170056G05-35GS-ALB11-FLAG3-HIS6 |

As the addition of the Alb11 Nanobody might influence the affinity or potency of the construct, the half-life extended multispecific polypeptide was characterized for binding to EGFR and CEA expressing cell lines and primary human T cells. In addition, the potency in the functional T cell dependent LS174T killing assay was evaluated (described in 28.1 and 28.2 below).

28.1 Impact of the Alb11 Building Block on the Binding Properties

Dose-dependent binding of the HLE multispecific polypeptide to cancer cell lines expressing CEACAM5 and EGFR (LS174T and LoVo), a cell line expressing EGFR (HER14; NIH3T3 transfected with EGFR), and to purified primary human T cells (isolated as described in Example 2.1) was evaluated in flow cytometry as outlined in Example 5, in the absence of HSA.

The results are presented in FIG. 41. The EC50 value obtained from the dose response curve for binding to HER14 cells is depicted in Table 35. The EC50 values obtained from the dose response curves for binding to LS174T and LoVo cells are depicted in Table 36.

TABLE 35

EC50 (M) of T017000108 for binding to HER14 cells as determined in flow cytometry.

| | HER14 | | | |
| --- | --- | --- | --- | --- |
| sample ID | EC50 (M) | 95% LCI | 95% UCI | Top |
| T017000108 | 1.9E−09 | 1.7E−09 | 2.2E−09 | 158884 |

TABLE 36

EC50 (M) of T017000108 for binding to LoVo and LS174T as determined in flow cytometry.

| | LS174T | | | | LoVo | | | |
| --- | --- | --- | --- | --- | --- | --- | --- | --- |
| sample ID | EC50 (M) | 95% LCI | 95% UCI | Top | EC50 (M) | 95% LCI | 95% UCI | Top |
| T017000108 | 1.4E−08 | 1.2E−08 | 1.6E−08 | 70202 | 3.3E−09 | 2.9E−09 | 3.9E−09 | 92787 |

Comparison of the HLE construct with the non-HLE construct showed similar binding to all three cell lines tested. The data presented showed that coupling of the Alb11 building block did not influence the binding properties.

28.2 Impact of the Alb11 Nanobody in the Redirected Cell Killing by Human Effector T Cells in the xCELLigence Based Assay The functionality of the half-life extended multispecific polypeptide was evaluated in the absence of HSA in the human T cell mediated LS174T killing assay as described in Example 10 and compared with the functionality of the non-HLE multispecific constructs.

The results are depicted in FIG. 42. The obtained IC50 values are listed in Table 37.

TABLE 37

IC50 (M) of the multispecific polypeptides in the human T cell mediated xCELLigence based killing assay using an effector to target ratio of 15. Data were analysed after 40-50 h.

| sample ID | IC50 (M) | 95% LCI | 95% UCI |
|---|---|---|---|
| T017000107 | 7.9E−10 | 5.9E−10 | 1.1E−09 |
| T017000108 | 5.5E−09 | 4.1E−09 | 7.3E−09 |

The results indicate that the inclusion of the albumin targeting Nanobody in the construct as such did not have an essential impact on the obtained potency or efficacy.

TABLES

TABLE A-1

Sequence alignment of TCR cluster A binders - part 1

```
                  Kabat #:    1         10        20        30
                              |         |         |         |
SEQ ID NO: 50 T0170PMP056G05: EVQLVESGGGLVQPGGSLRLSCVASGDVHKINFLGWYRQ
SEQ ID NO:  8 T0170PMP053D01: ..................K...A...A............
SEQ ID NO: 60 T0170PMP067D01: ..................K...A...A............
SEQ ID NO: 47 T0170PMP056F01: ..................K.P.A...A............
SEQ ID NO: 76 T0170PMP069A06: ..................K...A...A............
SEQ ID NO: 65 T0170PMP067F02: ..................K...A...A............
SEQ ID NO: 66 T0170PMP068C03: ..................K...A...A............
SEQ ID NO: 26 T0170PMP055E05: ..................K...A...A............
SEQ ID NO: 19 T0170PMP055C02: ..................K...A...A............
SEQ ID NO: 61 T0170PMP067D06: ..................K...A...A............
SEQ ID NO: 50 T0170PMP069C08: ........................................
SEQ ID NO: 28 T0170PMP055F03: ................................I......
SEQ ID NO: 54 T0170PMP061A02: ................................I......
SEQ ID NO: 45 T0170PMP056D11: ................................I......
SEQ ID NO: 77 T0170PMP069B02: ......................R.........I......
SEQ ID NO: 96 T0170PMP070G02: ................................I......
SEQ ID NO:  2 T0170PMP028B01: ........................A...S...........
SEQ ID NO:  4 T0170PMP028G06: ........................A...S...........
SEQ ID NO: 29 T0170PMP055F06: ........................A...S...........
SEQ ID NO:  1 T0170PMP027A05: ........................A...S...........
SEQ ID NO:  6 T0170PMP040C01: ........................A...S...........
SEQ ID NO:  3 T0170PMP028F10: ..............R....P.A...S...........
SEQ ID NO:  5 T0170PMP029F08: ..........S.............A...S...........
SEQ ID NO: 13 T0170PMP055A08: ..........S.............A...S...........
SEQ ID NO: 32 T0170PMP055G09: ..........S.............A...S...........
SEQ ID NO: 69 T0170PMP068D05: ..........S.........P...A...S...........
SEQ ID NO: 75 T0170PMP068F08: ..........S.............A...S...........
SEQ ID NO: 95 T0170PMP070F11: ........................A...S..........C.
```

TABLE A-1-continued

Sequence alignment of TCR cluster A binders - part 1

| | |
|---|---|
| SEQ ID NO: 87 T0170PMP069E11: | .....................A...E.....I...... |
| SEQ ID NO: 99 T0170PMP084B07: | .....................A...E.....I...... |
| SEQ ID NO: 10 T0170PMP055A01: | ............R........A.........I...... |
| SEQ ID NO: 11 T0170PMP055A02: | .....................A.........I...... |
| SEQ ID NO: 22 T0170PMP055D03: | .....................A.........I...... |
| SEQ ID NO: 24 T0170PMP055D10: | .....................A.........I...... |

| | 40    50    60    70    78 |
|---|---|
| Kabat #: | \|      \|      \|      \|      \| |
| SEQ ID NO: 50 T0170PMP056G05: | APGKEREKVAHISIGDQTDYADSAKGRFTISRDESKNMV |
| SEQ ID NO: 8 T0170PMP053D01: | T.E....M..T.T...DV..............A.... |
| SEQ ID NO: 60 T0170PMP067D01: | T.E....M..T.T...EV..............A.... |
| SEQ ID NO: 47 T0170PMP056F01: | T.E....M..T.T...EV..............A.... |
| SEQ ID NO: 76 T0170PMP069A06: | T.E....M..T.T...EV..E...........A.... |
| SEQ ID NO: 65 T0170PMP067F02: | T.E....M..T.T...EV...H..........A.... |
| SEQ ID NO: 66 T0170PMP068C03: | T.E....M..T.T...EV..............A.... |
| SEQ ID NO: 26 T0170PMP055E05: | ..E....M..T.T...EV..............A.... |
| SEQ ID NO: 19 T0170PMP055C02: | T.E....M..T.T...EV..............A.... |
| SEQ ID NO: 61 T0170PMP067D06: | ..E....M..T.T...EV..............AT... |
| SEQ ID NO: 50 T0170PMP069C08: | ..................................... |
| SEQ ID NO: 28 T0170PMP055F03: | ...............S.....E............... |
| SEQ ID NO: 54 T0170PMP061A02: | ...............S.....E............... |
| SEQ ID NO: 45 T0170PMP056D11: | ...............S.....E............... |
| SEQ ID NO: 77 T0170PMP069B02: | ...............S.....E............... |
| SEQ ID NO: 96 T0170PMP070G02: | ...............S.....E............... |
| SEQ ID NO: 2 T0170PMP028B01: | ......GL..T.T...T.....Y..........AR... |
| SEQ ID NO: 4 T0170PMP028G06: | .......L..T.T...T.....Y..........AR... |
| SEQ ID NO: 29 T0170PMP055F06: | .......L..T.T...A.....Y..........AR... |
| SEQ ID NO: 1 T0170PMP027A05: | .......L..T.T...T...............A.... |
| SEQ ID NO: 6 T0170PMP040C01: | .......L..T.T...T...............A.... |
| SEQ ID NO: 3 T0170PMP028F10: | .......M..T.T...A...............A.... |
| SEQ ID NO: 5 T0170PMP029F08: | .......M..T.T...A...............A.... |
| SEQ ID NO: 13 T0170PMP055A08: | .......M..T.T...A...............A.... |
| SEQ ID NO: 32 T0170PMP055G09: | .......V..T.T...A...............A.... |
| SEQ ID NO: 69 T0170PMP068D05: | .......M..T.T...A...............A.... |
| SEQ ID NO: 75 T0170PMP068F08: | ......GM..T.T...A...............A.... |
| SEQ ID NO: 95 T0170PMP070F11: | .......M..T.T...A...............A.... |
| SEQ ID NO: 87 T0170PMP069E11: | C.....DM..T.T...A...............A.... |
| SEQ ID NO: 99 T0170PMP084B07: | ......DM..T.T...E.Q.............A.... |
| SEQ ID NO: 10 T0170PMP055A01: | ..A....M....T...A...............A.... |

TABLE A-1-continued

Sequence alignment of TCR cluster A binders - part 1

```
SEQ ID NO: 11 T0170PMP055A02:  ..A....M....T...A.................A....

SEQ ID NO: 22 T0170PMP055D03:  ..A....M....T...A.N...............A....

SEQ ID NO: 24 T0170PMP055D10:  ..A....M....T...A....G............A....
```

TABLE A-2

Sequence alignment of TCR cluster A binders - part 1 continued

```
                         79      90      100     110
              Kabat #:   |   ab  |       |a      |

SEQ ID NO: 50 T0170PMP056G05:  YLQMNSLKPEDTAVYFCRAFSRIYPYDYNGQGTLVTVSS

SEQ ID NO:  8 T0170PMP053D01:  ....T.........V...G..L...N............

SEQ ID NO: 60 T0170PMP067D01:  ....T.........V...G..L...N............

SEQ ID NO: 47 T0170PMP056F01:  ....T.........V...G..L...N............

SEQ ID NO: 76 T0170PMP069A06:  ....TG........V...G..L...N............

SEQ ID NO: 65 T0170PMP067F02:  ....T.........V...G..L...N......Q.....

SEQ ID NO: 66 T0170PMP068C03:  ....T.........V...G..L...N......Q.....

SEQ ID NO: 26 T0170PMP055E05:  ....T.......T.V...G..L...N......Q.....

SEQ ID NO: 19 T0170PMP055C02:  ....T..T......V...G..L...N......Q.....

SEQ ID NO: 61 T0170PMP067D06:  ....T.............G......N......Q.....

SEQ ID NO: 50 T0170PMP069C08:  ......................................

SEQ ID NO: 28 T0170PMP055F03:  ..............L........................

SEQ ID NO: 54 T0170PMP061A02:  ..............L........................

SEQ ID NO: 45 T0170PMP056D11:  ..............L........................

SEQ ID NO: 77 T0170PMP069B02:  ..............L.................Q.....

SEQ ID NO: 96 T0170PMP070G02:  ..........A...L.................Q.....

SEQ ID NO:  2 T0170PMP028B01:  ..................G..L...N......Q.....

SEQ ID NO:  4 T0170PMP028G06:  ..................G..L...N............

SEQ ID NO: 29 T0170PMP055F06:  ..................G..L...N............

SEQ ID NO:  1 T0170PMP027A05:  ..............H...G..L...N......Q.....

SEQ ID NO:  6 T0170PMP040C01:  ..................G..L...N......Q.....

SEQ ID NO:  3 T0170PMP028F10:  ..................G..L...N......Q.....

SEQ ID NO:  5 T0170PMP029F08:  ..................G..L...N............

SEQ ID NO: 13 T0170PMP055A08:  ......S...........G..L...N............

SEQ ID NO: 32 T0170PMP055G09:  ......S...........G..L...N......Q.....

SEQ ID NO: 69 T0170PMP068D05:  ......S...........G..L...N......Q.....

SEQ ID NO: 75 T0170PMP068F08:  ......S...........G..L...N......Q.....

SEQ ID NO: 95 T0170PMP070F11:  ......S...........G..L...N......Q.....

SEQ ID NO: 87 T0170PMP069E11:  ..................L..L...N............

SEQ ID NO: 99 T0170PMP084B07:  ..................L..L...N............

SEQ ID NO: 10 T0170PMP055A01:  ......................Y......N........
```

TABLE A-2-continued

Sequence alignment of TCR cluster A binders - part 1 continued

| | Kabat #: | 79<br>\|   ab | 90<br>\| | 100<br>\|   a | 110<br>\| |
|---|---|---|---|---|---|
| SEQ ID NO: 11 | T0170PMP055A02: | .................. | .Y..... | .N........... | |
| SEQ ID NO: 22 | T0170PMP055D03: | .................. | .Y..... | .N........... | |
| SEQ ID NO: 24 | T0170PMP055D10: | .................. | .Y..... | .N........... | |

TABLE A-3

Sequence alignment of TCR cluster A binders - part 2

| | Kabat #: | 1<br>\| | 10<br>\| | 20<br>\| | 30<br>\| | 40<br>\| | 50<br>\| | 60<br>\| | 70<br>\| | 78<br>\| |
|---|---|---|---|---|---|---|---|---|---|---|
| SEQ ID NO: 50 | T0170PMP056G05: | EVQLVESGGGLVQPGGSLRLSCVASGDVHKINFLGWYRQAPGKEREKVAHISIGDQTDYADSAKGRFTISRDESKNMV | | | | | | | | |
| SEQ ID NO: 71 | T0170PMP068E01: | ...............E.....A.........I........A....M....T...A.................A.... | | | | | | | | |
| SEQ ID NO: 101 | T0170PMP084E03: | ......................A.........I........A....M....T...A.................A.... | | | | | | | | |
| SEQ ID NO: 102 | T0170PMP084E05: | ......................A.........I...H....A....M....T...A.................A.... | | | | | | | | |
| SEQ ID NO: 30 | T0170PMP055F08: | ......................A.........I........A....M....T...A.........A.......A.... | | | | | | | | |
| SEQ ID NO: 37 | T0170PMP056C01: | ......................A...G.....I........A....M....T...A.................A.... | | | | | | | | |
| SEQ ID NO: 49 | T0170PMP056G02: | ..........A...........A.........I........A....M....T...A.................A.... | | | | | | | | |
| SEQ ID NO: 57 | T0170PMP067A03: | ......................A.........I........A..H.M....T...A.................A.... | | | | | | | | |
| SEQ ID NO: 59 | T0170PMP067C09: | ......................A.........I........A....M....T...A................AE.... | | | | | | | | |
| SEQ ID NO: 74 | T0170PMP068F06: | ......................A.........I........A....M....T...A.................A..V. | | | | | | | | |
| SEQ ID NO: 82 | T0170PMP069D02: | .........M............A.........I........A....M....T...A.................A.... | | | | | | | | |
| SEQ ID NO: 93 | T0170PMP070D07: | ......................A.........I........A....M....T...A.................A.... | | | | | | | | |
| SEQ ID NO: 100 | T0170PMP084C02: | ......................A.........I........A....M....T...A.................A.... | | | | | | | | |
| SEQ ID NO: 55 | T0170PMP061B04: | ......................A.........I........A....M....T...A.................A.... | | | | | | | | |
| SEQ ID NO: 83 | T0170PMP069D07: | ......................A.........I...V.A....M....T...A.................A.... | | | | | | | | |
| SEQ ID NO: 36 | T0170PMP056B11: | ...............A....T..A.........I........A....M....T...A.................A.... | | | | | | | | |
| SEQ ID NO: 104 | T0170PMP084F10: | .........W..A.........A.........I........A....M....T...A.................A.... | | | | | | | | |
| SEQ ID NO: 39 | T0170PMP056C03: | ......................A.........I........A....M....T...T.................A.... | | | | | | | | |
| SEQ ID NO: 80 | T0170PMP069C04: | ......................A.........I........A.G..M....T...A.................A.... | | | | | | | | |
| SEQ ID NO: 44 | T0170PMP056D02: | ......................A.........I........A....M....T...A.................A.... | | | | | | | | |

TABLE A-3-continued

Sequence alignment of TCR cluster A binders - part 2

|  | Kabat #: | 1 | 10 | 20 | 30 | 40 | 50 | 60 | 70 | 78 |
|---|---|---|---|---|---|---|---|---|---|---|
| SEQ ID NO: 56 | T0170PMP067A01: | ....................A.........I.......A...GM....T...A..................A.... |
| SEQ ID NO: 58 | T0170PMP067B06: | ....................A.........I.......AR...M....T...A..................A.... |
| SEQ ID NO: 88 | T0170PMP069F05: | ....................A.........I.......A....M....T...A..................A.... |
| SEQ ID NO: 103 | T0170PMP084F04: | ....................A.........I...H....A....M....T...A..................A.... |
| SEQ ID NO: 21 | T0170PMP055C10: | ....................A.........V.......A....M....T...A..................A.... |
| SEQ ID NO: 9 | T0170PMP053E10: | ....................R.........I.......A....M....T...A....E.............A.... |
| SEQ ID NO: 15 | T0170PMP055B01: | ....................R.........I.......A....M....T...A.V..E.............A.... |
| SEQ ID NO: 79 | T0170PMP069C01: | ....................R.........I.......A....MI..T...A....E.............A.... |
| SEQ ID NO: 62 | T0170PMP067D09: | ....................A.........I.......A....M....T...A.S..G.............A.... |
| SEQ ID NO: 63 | T0170PMP067E03: | ....................A.........I.......A....M....T...A.S................A.... |
| SEQ ID NO: 43 | T0170PMP056D01: | ........D..........A......................M....T.A.A....EF...........P.... |
| SEQ ID NO: 64 | T0170PMP067E06: | ........D..........A......................M....T.A.A....EF...........P.... |
| SEQ ID NO: 86 | T0170PMP069E09: | ...................A......................M....T.A.A....EF...........P.... |
| SEQ ID NO: 81 | T0170PMP069C05: | ........D..........A......................M....T.A.A....EF...........P.... |
| SEQ ID NO: 90 | T0170PMP070B08: | ........D..........A......................M....T.A.A....EF...........P.... |
| SEQ ID NO: 12 | T0170PMP055A03: | ..............................................T....A..................A.... |

TABLE A-4

Sequence alignment of TCR cluster A binders - part 2 continued

|  |  | Kabat #: | 79 ab | 90 | 100 a | 110 |
|---|---|---|---|---|---|---|
| SEQ ID NO: 50 | T0170PMP056G05: | YLQMNSLKPEDTAVYFCRAFSRIYPYDYWGQGTLVTVSS |
| SEQ ID NO: 71 | T0170PMP068E01: | ....................Y......N............ |
| SEQ ID NO: 101 | T0170PMP084E03: | .........G.........Y......N............ |
| SEQ ID NO: 102 | T0170PMP084E05: | ....................Y......N............ |
| SEQ ID NO: 30 | T0170PMP055F08: | ....................Y......N............ |
| SEQ ID NO: 37 | T0170PMP056C01: | ....................Y......N............ |
| SEQ ID NO: 49 | T0170PMP056G02: | ....................Y......N............ |
| SEQ ID NO: 57 | T0170PMP067A03: | ....................Y......N............ |

TABLE A-4-continued

Sequence alignment of TCR cluster A binders - part 2 continued

```
                              Kabat #:    79      90      100     110
                                          |  ab   |       |a      |
SEQ ID NO: 59   T0170PMP067C09:  .....................Y......N............
SEQ ID NO: 74   T0170PMP068F06:  .....................Y......N............
SEQ ID NO: 82   T0170PMP069D02:  .....................Y......N............
SEQ ID NO: 93   T0170PMP070D07:  ...........A.........Y......N............
SEQ ID NO: 100  T0170PMP084C02:  ....D................Y......N............
SEQ ID NO: 55   T0170PMP061B04:  .............A.......Y......N............
SEQ ID NO: 83   T0170PMP069D07:  .............A.......Y......N............
SEQ ID NO: 36   T0170PMP056B11:  .....................Y......N............
SEQ ID NO: 104  T0170PMP084F10:  .....................Y......N............
SEQ ID NO: 39   T0170PMP056C03:  .....................Y......N......Q.....
SEQ ID NO: 80   T0170PMP069C04:  .....................Y......N......Q.....
SEQ ID NO: 44   T0170PMP056D02:  .....................Y......N...R..Q.....
SEQ ID NO: 56   T0170PMP067A01:  .....................Y......N......Q.....
SEQ ID NO: 58   T0170PMP067B06:  .....................Y......N......Q.....
SEQ ID NO: 88   T0170PMP069F05:  ................L....Y......N......Q.....
SEQ ID NO: 103  T0170PMP084F04:  .............A.......Y......N......Q.....
SEQ ID NO: 21   T0170PMP055C10;  H....................Y......N......Q.....
SEQ ID NO: 9    T0170PMP053E10:  .....................Y......N......Q.....
SEQ ID NO: 15   T0170PMP055B01:  .....................Y......N......Q.....
SEQ ID NO: 79   T0170PMP069C01:  .....................Y......N......Q.....
SEQ ID NO: 62   T0170PMP067D09:  ...L.N...............Y......N............
SEQ ID NO: 63   T0170PMP067E03:  ...L.N...............Y......N............
SEQ ID NO: 43   T0170PMP056D01:  H...............L...G......N......Q.....
SEQ ID NO: 64   T0170PMP067E06:  ................L...G......N......Q.....
SEQ ID NO: 86   T0170PMP069E09:  ................L...G......N......Q.....
SEQ ID NO: 81   T0170PMP069C05:  ................L...G......S......Q.....
SEQ ID NO: 90   T0170PMP070B08:  .........V.....L...G......N...............
SEQ ID NO: 12   T0170PMP055A03:  ....................G.............Q.....
```

TABLE A-5

Sequence alignment of TCR cluster A binders - part 3

```
                          Kabat #:  1       10      20      30      40      50      60      70      78
                                    |       |       |       |       |       |       |       |       |
SEQ ID  T0170PMP056G05:  EVQLVESGGGLVQPGGSLRLSCVASGDVHKINFLGWYRQAPGKEREKVAHISIGDQTDYADSAKGRFTISRDESKNMV
NO: 50
SEQ ID  T0170PMP056C07:  ................................................T....A................A....
NO: 41
SEQ ID  T0170PMP070C09:  ................P...............................T....A................A....
NO: 92
```

TABLE A-5-continued

Sequence alignment of TCR cluster A binders - part 3

```
Kabat #:           1         10        20        30        40        50        60        70      78
                   |         |         |         |         |         |         |         |       |
SEQ ID NO: 98    (T0170PMP082B04): ....................p..................T..A..............A....
SEQ ID NO: 33    (T0170PMP056A02): ...................A..........................T..............A....
SEQ ID NO: 31    (T0170PMP055G05): ...................A..........H.............T...A............A....
SEQ ID NO: 78    (T0170PMP069B08): ...................A....Y.....H.............T...A............A....
SEQ ID NO: 20    (T0170PMP055C06): ..........H........A..........H..P...........T...V............A....
SEQ ID NO: 23    (T0170PMP055D06): ...................A..........H..............T...V............A....
SEQ ID NO: 25    (T0170PMP055E01): ...................A...E.Y..................T.A.VA....F......A....
SEQ ID NO: 27    (T0170PMP055F02): ...................A...E.Y..................T.A.VA....F......A....
SEQ ID NO: 38    (T0170PMP056C02): ...................A...E.Y..................T.A.VA....F.Q....A....
SEQ ID NO: 97    (T0170PMP070G06): ................P..A...E.Y..................T.A.VA....F......A....
SEQ ID NO: 89    (T0170PMP069G08): ...................A...E.Y......Q............T.A.VA....F......A....
SEQ ID NO: 94    (T0170PMP070E07): ...................A...E.Y..................T.A.VA....F......GA....
SEQ ID NO: 70    (T0170PMP068D07): ...................A...E.Y..................T.A.VA....F.......V....
SEQ ID NO: 51    (T0170PMP056G11): ...................A...E.Y..................T.A.VA....F......GA....
SEQ ID NO: 67    (T0170PMP068C07): ...................A...E.Y..................T.A.AA....F......A....
SEQ ID NO: 84    (T0170PMP069E02): ...................A...E.Y..................T.A.AA....F......A....
SEQ ID NO: 68    (T0170PMP068C11): ...................A...E.Y..................T.A.AA....F......A....
SEQ ID NO: 72    (T0170PMP068E08): ...................A...E.Y..................T.A.AA....F......A....
SEQ ID NO: 46    (T0170PMP056E02): ..............E....A...E.Y..................T.A.VA....F...L..A....
SEQ ID NO: 35    (T0170PMP056A10): ...................AV..S..LL..............GV....T.A.A...SHF..........A....
SEQ ID NO: 42    (T0170PMP056C10): ...................AV..S..LL.............M.T..T.A.A...SHF..........A....
SEQ ID NO: 16    (T0170PMP055B02): ...................A...S..LL........C.....M....T.A.A...SHF..........A....
SEQ ID NO: 34    (T0170PMP056A08): ...................A...S..LL..............M....T.A.A...SHF..........A....
SEQ ID NO: 40    (T0170PMP056C04): ...................A...S..LL..............M....T.A.A...SHF..........A....
SEQ ID NO: 53    (T0170PMP057D06): ...................A...S..LL..............M....T.A.A...SHF..........A....
```

TABLE A-5-continued

Sequence alignment of TCR cluster A binders - part 3

| Kabat #: | 1 | 10 | 20 | 30 | 40 | 50 | 60 | 70 | 78 |
|---|---|---|---|---|---|---|---|---|---|
| SEQ ID NO: 7 T0170PMP053A03: | .......... | .......... | ....AV..S. | .LL....... | .......... | .M....T.A. | A...SHF... | .......A.. | .. |
| SEQ ID NO: 85 T0170PMP069E07: | .......... | .......... | .....A...S | ..LL...... | .......... | .M....T.A. | A...SHF... | .......A.. | .. |
| SEQ ID NO: 18 T0170PMP055B11: | .......... | .......... | .....A...S | ..LL...... | .......... | .M....T.A. | A....HF... | .......A.. | .. |
| SEQ ID NO: 48 T0170PMP056F08: | .......... | .......... | ...G...A.. | .S..LL.... | .......... | .M....T.A. | A....HF... | .......A.. | .. |
| SEQ ID NO: 91 T0170PMP070B09: | .......... | .......... | .....A...S | ..LL...... | .......... | ......T.A. | A...SHF... | .......A.. | .. |
| SEQ ID NO: 73 T0170PMP068F04: | .......... | .......... | .....A...S | ..LL...... | .......... | .M....T.A. | A...SYF... | .......A.. | .. |
| SEQ ID NO: 14 T0170PMP055A10: | .......... | .......... | .....A...S | ..LL...... | .......... | .M....A.A. | ....HF.... | ......A... | .. |
| SEQ ID NO: 17 T0170PMP055B03: | .......... | .......... | ...P..A..S | ..LL...... | .......... | .M....T.A. | A....HF... | .......A.. | .. |
| SEQ ID NO: 52 T0170PMP057B02: | .........W | .......... | ......A... | S.Y.....S. | ......H...L | ..T.T...AA | .......... | .....AR... | .. |

TABLE A-6

Sequence alignment of TCR cluster A binders - part 3 continued

| Kabat #: | 79 ab | 90 | 100 a | 110 |
|---|---|---|---|---|
| SEQ ID NO: 50 T0170PMP056G05: | YLQMNSLKPEDTAVYFCRAFSRIYPYDYWGQGTLVTVSS | | | |
| SEQ ID NO: 41 T0170PMP056C07: | ................G.........R........ | | | |
| SEQ ID NO: 92 T0170PMP070C09: | ................G.................. | | | |
| SEQ ID NO: 98 T0170PMP082B04: | ................G.................. | | | |
| SEQ ID NO: 33 T0170PMP056A02: | ................G...W.......Q...... | | | |
| SEQ ID NO: 31 T0170PMP055G05: | ................G...........Q...... | | | |
| SEQ ID NO: 78 T0170PMP069B08: | ................G.................. | | | |
| SEQ ID NO: 20 T0170PMP055C06: | .....N..........G...........Q...... | | | |
| SEQ ID NO: 23 T0170PMP055D06: | F....N..........G...........Q...... | | | |
| SEQ ID NO: 25 T0170PMP055E01: | ................G...W.............. | | | |
| SEQ ID NO: 27 T0170PMP055F02: | ................G...W.............. | | | |
| SEQ ID NO: 38 T0170PMP056C02: | ................G...W.......Q...... | | | |
| SEQ ID NO: 97 T0170PMP070G06: | ................G...W.......Q...... | | | |
| SEQ ID NO: 89 T0170PMP069G08: | ................G...W.............. | | | |
| SEQ ID NO: 94 T0170PMP070E07: | ................G...W.............. | | | |
| SEQ ID NO: 70 T0170PMP068D07: | ................G...W.............. | | | |
| SEQ ID NO: 51 T0170PMP056G11: | ................G...W.......Q...... | | | |
| SEQ ID NO: 67 T0170PMP068C07: | ................G...W.......Q...... | | | |
| SEQ ID NO: 84 T0170PMP069E02: | ................G...W.............. | | | |

TABLE A-6-continued

Sequence alignment of TCR cluster A binders - part 3 continued

| Kabat #: | 79<br>\| ab | 90<br>\| | 100<br>\|a | 110<br>\| |
|---|---|---|---|---|
| SEQ ID NO: 68 T0170PMP068C11: | ................... | ........ | G...... | ......Q..... |
| SEQ ID NO: 72 T0170PMP068E08: | .......R.......... | ........ | G...W.. | ............ |
| SEQ ID NO: 46 T0170PMP056E02: | ................... | ........ | G...W.. | ............ |
| SEQ ID NO: 35 T0170PMP056A10: | .......R.......... | ........ | G...... | ......Q..... |
| SEQ ID NO: 42 T0170PMP056C10: | .......R.......... | ........ | G...... | ......Q..... |
| SEQ ID NO: 16 T0170PMP055B02: | .......R.......... | ........ | G...... | ............ |
| SEQ ID NO: 34 T0170PMP056A08: | .......R.......... | ........ | G...... | ............ |
| SEQ ID NO: 40 T0170PMP056C04: | .......R.......... | ........ | G...... | .H........ |
| SEQ ID NO: 53 T0170PMP057D06: | .......R.......... | ........ | G...... | ......Q..... |
| SEQ ID NO: 7 T0170PMP053A03: | .......R.......... | ........ | G...... | ............ |
| SEQ ID NO: 85 T0170PMP069E07: | .....G.R.......... | ........ | G...... | ............ |
| SEQ ID NO: 18 T0170PMP055B11: | .......R.......... | ........ | G...... | ............ |
| SEQ ID NO: 48 T0170PMP056F08: | .......R.......... | ........ | G...... | ............ |
| SEQ ID NO: 91 T0170PMP070B09: | .....N.R.......... | ........ | G...... | ............ |
| SEQ ID NO: 73 T0170PMP068F04: | .......R.......... | ........ | G...... | ......Q..... |
| SEQ ID NO: 14 T0170PMP055A10: | .......R.......... | ........ | G...... | .....R..Q..... |
| SEQ ID NO: 17 T0170PMP055B03: | .......R.......... | ........ | G...... | ......Q..... |
| SEQ ID NO: 52 T0170PMP057B02: | ...........L...H.G..L...N | ........ | ......Q | ............ |

TABLE A-7

Sequence alignment of TCR cluster B binders

| | Kabat #: | 1<br>\| | 10<br>\|a | 20<br>\| | 30<br>\| | 40<br>\| | 50<br>\| | 60<br>\| | 70<br>\| | 77<br>\| |
|---|---|---|---|---|---|---|---|---|---|---|
| SEQ ID NO: 106 | T0170PMP055C07: | EVQLVE-SGGGLVQPGGSLRLSCITSGETFKINIWGWYRQAPGKQRELVASLTIGGATNYADSVKGRFTISEDSAKNT |
| SEQ ID NO: 105 | T0170PMP055B06: | .....-...................................................D................ |
| SEQ ID NO: 115 | T0170PMP070C01: | .....-...................................................D. |
| SEQ ID NO: 108 | T0170PMP056B02: | .....-.............................T....................... |
| SEQ ID NO: 109 | T0170PMP056D07: | .....-.................Q................................... |
| SEQ ID NO: 112 | T0170PMP069E03: | .....-...................................................... |
| SEQ ID NO: 111 | T0170PMP068G05: | ......E...................................................... |
| SEQ ID NO: 114 | T0170PMP070A09: | .....-...................................................... |
| SEQ ID NO: 107 | T0170PMP055D01: | .....-...............................R...................... |

TABLE A-7-continued

Sequence alignment of TCR cluster B binders

| SEQ ID NO: 110 | T0170PMP068B03: | ......-....................V........G........................... |
| SEQ ID NO: 113 | T0170PMP069E06: | ......-...................L......V........G........................... |

|  | Kabat #: | 78<br>\| | abc | 90<br>\| | 100<br>\|a | 110<br>\| |
|---|---|---|---|---|---|---|
| SEQ ID NO: 106 | T0170PMP055C07: | VYLQMNSLKPEDTAVYFCNAKSRLYPYDYWGQGTLVTVSS |
| SEQ ID NO: 105 | T0170PMP055B06: | .........A.........................Q..... |
| SEQ ID NO: 115 | T0170PMP070C01: | ........................................ |
| SEQ ID NO: 108 | T0170PMP056B02: | ...................................Q..... |
| SEQ ID NO: 109 | T0170PMP056D07: | ...................................Q..... |
| SEQ ID NO: 112 | T0170PMP069E03: | ...............................D...Q..... |
| SEQ ID NO: 111 | T0170PMP068G05: | ............................I.......R..Q..... |
| SEQ ID NO: 114 | T0170PMP070A09: | ............................I.......R..Q..... |
| SEQ ID NO: 107 | T0170PMP055D01: | ............................I..........Q..... |
| SEQ ID NO: 110 | T0170PMP068B03: | .....................................R..Q..... |
| SEQ ID NO: 113 | T0170PMP069E06: | .....S..............................Q..... |

TABLE A-8

Sequence alignment of TCR cluster C binders

|  | Kabat #: | 1<br>\| | 10<br>\| | 20<br>\| | 30<br>\| | 40<br>\| | 50<br>\| | 60<br>\| | 70<br>\| | 78<br>\| |
|---|---|---|---|---|---|---|---|---|---|---|
| SEQ ID NO: 116 | T0170PMP061G01: | EVQLVESGGGLVQPGGSLRLSCAASGEIGRINFYRWYRQAPGNQREVVATITIADKTDYADSAKGRFTISRDESRNMV |
| SEQ ID NO: 118 | T0170PMP075D02: | ............................................................................ |
| SEQ ID NO: 117 | T0170PMP062D02: | ........................................G...........I..................... |

|  |  | 79<br>\| | abc | 90<br>\| | 100<br>\|a | 110<br>\| |
|---|---|---|---|---|---|---|
| SEQ ID NO: 116 | T0170PMP061G01: | YLQMSSLKPEDTAVYFCHAGSRLYPYDYWGQGTQVTVSS |
| SEQ ID NO: 118 | T0170PMP075D02: | ..........N............................ |
| SEQ ID NO: 117 | T0170PMP062D02: | .....G................................. |

TABLE A-4

Sequences for CDRs and frameworks, plus preferred combinations as provided in formula I, namely FR1-CDR1-FR2-CDR2-FR3-CDR3-FR4.

| SEQ | Nanobody | SEQ | FR1 | SEQ | CDR1 | SEQ | FR2 |
|---|---|---|---|---|---|---|---|
| 1 | T0170PMP027A05 | 175 | EVQLVESGGGLVQPGGSLRLSCAAS | 119 | GSVHKINFLG | 203 | WYRQAPGKERELVA |
| 2 | T0170PMP028B01 | 175 | EVQLVESGGGLVQPGGSLRLSCAAS | 119 | GSVHKINFLG | 204 | WYRQAPGKERGLVA |
| 3 | T0170PMP028F10 | 176 | EVQLVESGGGLVQPGRSLRLPCAAS | 119 | GSVHKINFLG | 205 | WYRQAPGKEREMVA |
| 4 | T0170PMP028G06 | 175 | EVQLVESGGGLVQPGGSLRLSCAAS | 119 | GSVHKINFLG | 203 | WYRQAPGKERELVA |
| 5 | T0170PMP029F08 | 175 | EVQLVESGGGLVQPGGSLRLSCAAS | 119 | GSVHKINFLG | 205 | WYRQAPGKEREMVA |
| 6 | T0170PMP040C01 | 175 | EVQLVESGGGLVQPGGSLRLSCAAS | 119 | GSVHKINFLG | 203 | WYRQAPGKERELVA |
| 7 | T0170PMP053A03 | 177 | EVQLVESGGGLVQPGGSLRLSCAVS | 120 | GSVHLLNFLG | 205 | WYRQAPGKEREMVA |
| 8 | T0170PMP053D01 | 178 | EVQLVESGGGLVQPGGSLKLSCAAS | 121 | GAVHKINFLG | 206 | WYRQTPEKEREMVA |
| 9 | T0170PMP053E10 | 179 | EVQLVESGGGLVQPGGSLRLSCRAS | 122 | GDVHKINILG | 207 | WYRQAPAKEREMVA |
| 10 | T0170PMP055A01 | 180 | EVQLVESGGGLVRPGGSLRLSCAAS | 122 | GDVHKINILG | 207 | WYRQAPAKEREMVA |
| 11 | T0170PMP055A02 | 175 | EVQLVESGGGLVQPGGSLRLSCAAS | 122 | GDVHKINILG | 207 | WYRQAPAKEREMVA |
| 12 | T0170PMP055A03 | 181 | EVQLVESGGGLVQPGGSLRLSCVAS | 123 | GDVHKINFLG | 208 | WYRQAPGKEREKVA |
| 13 | T0170PMP055A08 | 182 | EVQLVESGGGSVQPGGSLRLSCAAS | 119 | GSVHKINFLG | 205 | WYRQAPGKEREMVA |
| 14 | T0170PMP055A10 | 175 | EVQLVESGGGLVQPGGSLRLSCAAS | 120 | GSVHLLNFLG | 205 | WYRQAPGKEREMVA |
| 15 | T0170PMP055B01 | 179 | EVQLVESGGGLVQPGGSLRLSCRAS | 122 | GDVHKINILG | 207 | WYRQAPAKEREMVA |
| 16 | T0170PMP055B02 | 175 | EVQLVESGGGLVQPGGSLRLSCAAS | 120 | GSVHLLNFLG | 209 | WYRQCPGKEREMVA |
| 17 | T0170PMP055B03 | 183 | EVQLVESGGGLVQPGGSLRPSCAAS | 120 | GSVHLLNFLG | 205 | WYRQAPGKEREMVA |
| 18 | T0170PMP055B11 | 175 | EVQLVESGGGLVQPGGSLRLSCAAS | 120 | GSVHLLNFLG | 205 | WYRQAPGKEREMVA |
| 19 | T0170PMP055C02 | 178 | EVQLVESGGGLVQPGGSLRLSCAAS | 121 | GAVHKINFLG | 206 | WYRQTPEKEREMVA |
| 20 | T0170PMP055C06 | 185 | EVQLVESGGGLVHPGGSLRLSCAAS | 123 | GDVHKINFLG | 211 | WHRQPPGKEREKVA |
| 21 | T0170PMP055C10 | 175 | EVQLVESGGGLVQPGGSLRLSCAAS | 125 | GDVHKINVLG | 207 | WYRQAPAKEREMVA |
| 22 | T0170PMP055D03 | 175 | EVQLVESGGGLVQPGGSLRLSCAAS | 122 | GDVHKINILG | 207 | WYRQAPAKEREMVA |
| 23 | T0170PMP055D06 | 175 | EVQLVESGGGLVQPGGSLRLSCAAS | 123 | GDVHKINFLG | 213 | WHRQAPGKEREKVA |
| 24 | T0170PMP055D10 | 175 | EVQLVESGGGLVQPGGSLRLSCAAS | 122 | GDVHKINILG | 207 | WYRQAPAKEREMVA |
| 25 | T0170PMP055E01 | 175 | EVQLVESGGGLVQPGGSLRLSCAAS | 126 | GEVYKINFLG | 208 | WYRQAPGKEREKVA |

TABLE A-4-continued

Sequences for CDRs and frameworks, plus preferred combinations as provided in formula I, namely FR1-CDR1-FR2-CDR2-FR3-CDR3-FR4.

| # | ID | FR1 | CDR1 | FR2 |
|---|---|---|---|---|
| 26 | T0170PMP055E05 | 178 EVQLVESGGGLVQ PGGSLRLSCAAS | 121 GAVHKIN FLG | 214 WYRQAPEKE REMVA |
| 27 | T0170PMP055F02 | 175 EVQLVESGGGLVQ PGGSLRLSCAAS | 126 GEVYKIN FLG | 208 WYRQAPGKE REKVA |
| 28 | T0170PMP055F03 | 181 EVQLVESGGGLVQ PGGSLRLSCVAS | 122 GDVHKIN ILG | 208 WYRQAPGKE REKVA |
| 29 | T0170PMP055F06 | 175 EVQLVESGGGLVQ PGGSLRLSCAAS | 119 GSVHKIN FLG | 203 WYRQAPGKE RELVA |
| 30 | T0170PMP055F08 | 175 EVQLVESGGGLVQ PGGSLRLSCAAS | 122 GDVHKIN ILG | 207 WYRQAPAKE REMVA |
| 31 | T0170PMP055G05 | 175 EVQLVESGGGLVQ PGGSLRLSCAAS | 123 GDVHKIN FLG | 213 WHRQAPGKE REKVA |
| 32 | T0170PMP055G09 | 182 EVQLVESGGGSVQ PGGSLRLSCAAS | 119 GSVHKIN FLG | 215 WYRQAPGKE REVVA |
| 33 | T0170PMP056A02 | 186 EVQLVESGGGLVQ PGGSARLSCVAS | 123 GDVHKIN FLG | 208 WYRQAPGKE REKVA |
| 34 | T0170PMP056A08 | 175 EVQLVESGGGLVQ PGGSLRLSCAAS | 120 GSVHLLN FLG | 205 WYRQAPGKE REMVA |
| 35 | T0170PMP056A10 | 177 EVQLVESGGGLVQ PGGSLRLSCAVS | 120 GSVHLLN FLG | 216 WYRQAPGKE RGVVA |
| 36 | T0170PMP056B11 | 187 EVQLVESGGGLVQ AGGSLTLSCAAS | 122 GDVHKIN ILG | 207 WYRQAPAKE REMVA |
| 37 | T0170PMP056C01 | 175 EVQLVESGGGLVQ PGGSLRLSCAAS | 127 GGVHKIN ILG | 207 WYRQAPAKE REMVA |
| 38 | T0170PMP056C02 | 175 EVQLVESGGGLVQ PGGSLRLSCAAS | 126 GEVYKIN FLG | 208 WYRQAPGKE REKVA |
| 39 | T0170PMP056C03 | 175 EVQLVESGGGLVQ PGGSLRLSCAAS | 122 GDVHKIN ILG | 207 WYRQAPAKE REMVA |
| 40 | T0170PMP056C04 | 175 EVQLVESGGGLVQ PGGSLRLSCAAS | 120 GSVHLLN FLG | 205 WYRQAPGKE REMVA |
| 41 | T0170PMP056C07 | 181 EVQLVESGGGLVQ PGGSLRLSCVAS | 123 GDVHKIN FLG | 208 WYRQAPGKE REKVA |
| 42 | T0170PMP056C10 | 177 EVQLVESGGGLVQ PGGSLRLSCAVS | 120 GSVHLLN FLG | 218 WYRQAPGKE REMVT |
| 43 | T0170PMP056D01 | 188 EVQLVESGGDLVQ PGGSLRLSCAAS | 123 GDVHKIN FLG | 205 WYRQAPGKE REMVA |
| 44 | T0170PMP056D02 | 175 EVQLVESGGGLVQ PGGSLRLSCAAS | 122 GDVHKIN ILG | 207 WYRQAPAKE REMVA |
| 45 | T0170PMP056D11 | 181 EVQLVESGGGLVQ PGGSLRLSCVAS | 122 GDVHKIN ILG | 208 WYRQAPGKE REKVA |
| 46 | T0170PMP056E02 | 189 EVQLVESGGGLVQ PEGSLRLSCAAS | 126 GEVYKIN FLG | 208 WYRQAPGKE REKVA |
| 47 | T0170PMP056F01 | 190 EVQLVESGGGLVQ PGGSLKLPCAAS | 121 GAVHKIN FLG | 206 WYRQTPEKE REMVA |
| 48 | T0170PMP056F08 | 191 EVQLVESGGGLVQ PGGSLGLSCAAS | 120 GSVHLLN FLG | 205 WYRQAPGKE REMVA |
| 49 | T0170PMP056G02 | 192 EVQLVESGGGLAQ PGGSLRLSCAAS | 122 GDVHKIN ILG | 207 WYRQAPAKE REMVA |
| 50 | T0170PMP056G05/ T0170PMP069C08 | 181 EVQLVESGGGLVQ PGGSLRLSCVAS | 123 GDVHKIN FLG | 208 WYRQAPGKE REKVA |

TABLE A-4-continued

Sequences for CDRs and frameworks, plus preferred combinations as provided in formula I, namely FR1-CDR1-FR2-CDR2-FR3-CDR3-FR4.

| # | ID | FR1 | CDR1 | FR2 |
|---|---|---|---|---|
| 51 | T0170PMP056G11 | 175 EVQLVESGGGLVQPGGSLRLSCAAS | 126 GEVYKINFLG | 208 WYRQAPGKEREKVA |
| 52 | T0170PMP057B02 | 193 EVQLVESGGGWVQPGGSLRLSCAAS | 129 GSVYKINFLS | 219 WYRQAPGHERELVA |
| 53 | T0170PMP057D06 | 175 EVQLVESGGGLVQPGGSLRLSCAAS | 120 GSVHLLNFLG | 205 WYRQAPGKEREMVA |
| 54 | T0170PMP061A02 | 181 EVQLVESGGGLVQPGGSLRLSCVAS | 122 GDVHKINILG | 208 WYRQAPGKEREKVA |
| 55 | T0170PMP061B04 | 175 EVQLVESGGGLVQPGGSLRLSCAAS | 122 GDVHKINILG | 207 WYRQAPAREREMVA |
| 56 | T0170PMP067A01 | 175 EVQLVESGGGLVQPGGSLRLSCAAS | 122 GDVHKINILG | 222 WYRQAPAKERGMVA |
| 57 | T0170PMP067A03 | 175 EVQLVESGGGLVQPGGSLRLSCAAS | 122 GDVHKINILG | 223 WYRQAPAKEHEMVA |
| 58 | T0170PMP067B06 | 175 EVQLVESGGGLVQPGGSLRLSCAAS | 122 GDVHKINILG | 224 WYRQAPAREREMVA |
| 59 | T0170PMP067C09 | 175 EVQLVESGGGLVQPGGSLRLSCAAS | 122 GDVHKINILG | 207 WYRQAPAKEREMVA |
| 60 | T0170PMP067D01 | 178 EVQLVESGGGLVQPGGSLRLSCAAS | 121 GAVHKINFLG | 206 WYRQTPEKEREMVA |
| 61 | T0170PMP067D06 | 178 EVQLVESGGGLVQPGGSLRLSCAAS | 121 GAVHKINFLG | 214 WYRQAPEREREMVA |
| 62 | T0170PMP067D09 | 175 EVQLVESGGGLVQPGGSLRLSCAAS | 122 GDVHKINILG | 207 WYRQAPAREREMVA |
| 63 | T0170PMP067E03 | 175 EVQLVESGGGLVQPGGSLRLSCAAS | 122 GDVHKINILG | 207 WYRQAPAKEREMVA |
| 64 | T0170PMP067E06 | 188 EVQLVESGGDLVQPGGSLRLSCAAS | 123 GDVHKINFLG | 205 WYRQAPGREREMVA |
| 65 | T0170PMP067F02 | 178 EVQLVESGGGLVQPGGSLRLSCAAS | 121 GAVHKINFLG | 206 WYRQTPEKEREMVA |
| 66 | T0170PMP068C03 | 178 EVQLVESGGGLVQPGGSLRLSCAAS | 121 GAVHKINFLG | 206 WYRQTPEKEREMVA |
| 67 | T0170PMP068C07 | 175 EVQLVESGGGLVQPGGSLRLSCAAS | 126 GEVYRINFLG | 208 WYRQAPGKEREKVA |
| 68 | T0170PMP068C11 | 175 EVQLVESGGGLVQPGGSLRLSCAAS | 126 GEVYRINFLG | 208 WYRQAPGREREKVA |
| 69 | T0170PMP068D05 | 194 EVQLVESGGGSVQPGGSLRPSCAAS | 119 GSVHKINFLG | 205 WYRQAPGREREMVA |
| 70 | T0170PMP068D07 | 175 EVQLVESGGGLVQPGGSLRLSCAAS | 126 GEVYKINFLG | 208 WYRQAPGKEREKVA |
| 71 | T0170PMP068E01 | 195 EVQLVESGGGLVQPGESLRLSCAAS | 122 GDVHKINILG | 207 WYRQAPAKEREMVA |
| 72 | T0170PMP068E08 | 175 EVQLVESGGGLVQPGGSLRLSCAAS | 126 GEVYKINFLG | 208 WYRQAPGKEREKVA |
| 73 | T0170PMP068F04 | 175 EVQLVESGGGLVQPGGSLRLSCAAS | 120 GSVHLLNFLG | 205 WYRQAPGKEREMVA |
| 74 | T0170PMP068F06 | 175 EVQLVESGGGLVQPGGSLRLSCAAS | 122 GDVHKINILG | 207 WYRQAPAKEREMVA |
| 75 | T0170PMP068F08 | 182 EVQLVESGGGSVQPGGSLRLSCAAS | 119 GSVHKINFLG | 226 WYRQAPGKERGMVA |

TABLE A-4-continued

Sequences for CDRs and frameworks, plus preferred combinations as provided in formula I, namely FR1-CDR1-FR2-CDR2-FR3-CDR3-FR4.

| | | | | | |
|---|---|---|---|---|---|
| 76 | T0170PMP069A06 | 178 EVQLVESGGGLVQPGGSLRLSCAAS | 121 GAVHKINFLG | 206 WYRQTPEKEREMVA | |
| 77 | T0170PMP069B02 | 197 EVQLVESGGGLVRPGGSLRLSCVAS | 122 GDVHKINILG | 208 WYRQAPGKEREKVA | |
| 78 | T0170PMP069B08 | 175 EVQLVESGGGLVQPGGSLRLSCAAS | 132 GDVYKINFLG | 213 WHRQAPGKEREKVA | |
| 79 | T0170PMP069C01 | 179 EVQLVESGGGLVQPGGSLRLSCRAS | 122 GDVHKINILG | 227 WYRQAPAKEREMIA | |
| 80 | T0170PMP069C04 | 175 EVQLVESGGGLVQPGGSLRLSCAAS | 122 GDVHKINILG | 228 WYRQAPAKGREMVA | |
| 81 | T0170PMP069C05 | 188 EVQLVESGGDLVQPGGSLRLSCAAS | 123 GDVHKINFLG | 205 WYRQAPGKEREMVA | |
| 82 | T0170PMP069D02 | 198 EVQLVESGGGMVQPGGSLRLSCAAS | 122 GDVHKINILG | 207 WYRQAPAKEREMVA | |
| 83 | T0170PMP069D07 | 175 EVQLVESGGGLVQPGGSLRLSCAAS | 122 GDVHKINILG | 229 WYRQVPAKEREMVA | |
| 84 | T0170PMP069E02 | 175 EVQLVESGGGLVQPGGSLRLSCAAS | 126 GEVYKINFLG | 208 WYRQAPGKEREKVA | |
| 85 | T0170PMP069E07 | 175 EVQLVESGGGLVQPGGSLRLSCAAS | 120 GSVHLLNFLG | 205 WYRQAPGKEREMVA | |
| 86 | T0170PMP069E09 | 175 EVQLVESGGGLVQPGGSLRLSCAAS | 123 GDVHKINFLG | 205 WYRQAPGKEREMVA | |
| 87 | T0170PMP069E11 | 175 EVQLVESGGGLVQPGGSLRLSCAAS | 133 GEVHKINILG | 230 WYRQCPGKERDMVA | |
| 88 | T0170PMP069F05 | 175 EVQLVESGGGLVQPGGSLRLSCAAS | 122 GDVHKINILG | 207 WYRQAPAKEREMVA | |
| 89 | T0170PMP069G08 | 175 EVQLVESGGGLVQPGGSLRLSCAAS | 126 GEVYKINFLG | 231 WQRQAPGKEREKVA | |
| 90 | T0170PMP070B08 | 188 EVQLVESGGDLVQPGGSLRLSCAAS | 123 GDVHKINFLG | 205 WYRQAPGKEREMVA | |
| 91 | T0170PMP070B09 | 175 EVQLVESGGGLVQPGGSLRLSCAAS | 120 GSVHLLNFLG | 208 WYRQAPGKEREKVA | |
| 92 | T0170PMP070C09 | 200 EVQLVESGGGLVQPGGSPRLSCVAS | 123 GDVHKINFLG | 208 WYRQAPGKEREKVA | |
| 93 | T0170PMP070D07 | 175 EVQLVESGGGLVQPGGSLRLSCAAS | 122 GDVHKINILG | 207 WYRQAPAKEREMVA | |
| 94 | T0170PMP070E07 | 175 EVQLVESGGGLVQPGGSLRLSCAAS | 126 GEVYKINFLG | 208 WYRQAPGKEREKVA | |
| 95 | T0170PMP070F11 | 182 EVQLVESGGGSVQPGGSLRLSCAAS | 119 GSVHKINFLG | 232 WYCQAPGKEREMVA | |
| 96 | T0170PMP070G02 | 181 EVQLVESGGGLVQPGGSLRLSCVAS | 122 GDVHKINILG | 208 WYRQAPGKEREKVA | |
| 97 | T0170PMP070G06 | 183 EVQLVESGGGLVQPGGSLRPSCAAS | 126 GEVYKINFLG | 208 WYRQAPGKEREKVA | |
| 98 | T0170PMP082B04 | 201 EVQLVESGGGLVQPGGSLRPSCVAS | 123 GDVHKINFLG | 208 WYRQAPGKEREKVA | |
| 99 | T0170PMP084B07 | 175 EVQLVESGGGLVQPGGSLRLSCAAS | 133 GEVHKINILG | 233 WYRQAPGKERDMVA | |
| 100 | T0170PMP084C02 | 175 EVQLVESGGGLVQPGGSLRLSCAAS | 122 GDVHKINILG | 207 WYRQAPAKEREMVA | |

TABLE A-4-continued

Sequences for CDRs and frameworks, plus preferred combinations as provided in formula I, namely FR1-CDR1-FR2-CDR2-FR3-CDR3-FR4.

| # | ID | SEQ FR1 | SEQ CDR1 | SEQ FR2 |
|---|---|---|---|---|
| 101 | T0170PMP084E03 | 175 EVQLVESGGGLVQPGGSLRLSCAAS | 122 GDVHKINILG | 207 WYRQAPAKEREMVA |
| 102 | T0170PMP084E05 | 175 EVQLVESGGGLVQPGGSLRLSCAAS | 122 GDVHKINILG | 234 WHRQAPAKEREMVA |
| 103 | T0170PMP084F04 | 175 EVQLVESGGGLVQPGGSLRLSCAAS | 122 GDVHKINILG | 234 WHRQAPAKEREMVA |
| 104 | T0170PMP084F10 | 202 EVQLVESGGGWVQAGGSLRLSCAAS | 122 GDVHKINILG | 207 WYRQAPAKEREMVA |
| 105 | T0170PMP055B06 | 184 EVQLVESGGGLVQPGGSLRLSCITS | 124 GETFKINIWG | 210 WYRQAPGKQRELVA |
| 106 | T0170PMP055C07 | 184 EVQLVESGGGLVQPGGSLRLSCITS | 124 GETFKINIWG | 210 WYRQAPGKQRELVA |
| 107 | T0170PMP055D01 | 184 EVQLVESGGGLVQPGGSLRLSCITS | 124 GETFKINIWG | 212 WYRQAPGKRRELVA |
| 108 | T0170PMP056B02 | 184 EVQLVESGGGLVQPGGSLRLSCITS | 124 GETFKINIWG | 217 WYRQTPGKQRELVA |
| 109 | T0170PMP056D07 | 184 EVQLVESGGGLVQPGGSLRLSCITS | 128 GQTFKINIWG | 210 WYRQAPGKQRELVA |
| 110 | T0170PMP068B03 | 184 EVQLVESGGGLVQPGGSLRLSCITS | 131 GETFKVNIWG | 225 WYRQGPGKQRELVA |
| 111 | T0170PMP068G05 | 196 EVQLVEESGGGLVQPGGSLRLSCITS | 124 GETFKINIWG | 210 WYRQAPGKQRELVA |
| 112 | T0170PMP069E03 | 184 EVQLVESGGGLVQPGGSLRLSCITS | 124 GETFKINIWG | 210 WYRQAPGKQRELVA |
| 113 | T0170PMP069E06 | 199 EVQLVESGGGLVQPGGSLRLSCLTS | 131 GETFKVNIWG | 225 WYRQGPGKQRELVA |
| 114 | T0170PMP070A09 | 184 EVQLVESGGGLVQPGGSLRLSCITS | 124 GETFKINIWG | 210 WYRQAPGKQRELVA |
| 115 | T0170PMP070C01 | 184 EVQLVESGGGLVQPGGSLRLSCITS | 124 GETFKINIWG | 210 WYRQAPGKQRELVA |
| 116 | T0170PMP061G01 | 175 EVQLVESGGGLVQPGGSLRLSCAAS | 130 GEIGRINFYR | 220 WYRQAPGNQREVVA |
| 117 | T0170PMP062D02 | 175 EVQLVESGGGLVQPGGSLRLSCAAS | 130 GEIGRINFYR | 221 WYRQAPGNQRGVVA |
| 118 | T0170PMP075D02 | 175 EVQLVESGGGLVQPGGSLRLSCAAS | 130 GEIGRINFYR | 220 WYRQAPGNQREVVA |

| SEQ CDR2 | SEQ FR3 | SEQ CDR3 | SEQ FR4 |
|---|---|---|---|
| 134 TITIGDTTD | 235 YADSAKGRFTISRDEAKNMVYLQMNSLKPEDTAVHFCRA | 164 GSRLYPYNY | 285 WGQGTQVTVSS |
| 134 TITIGDTTD | 236 YADYAKGRFTISRDEARNMVYLQMNSLKPEDTAVYFCRA | 164 GSRLYPYNY | 285 WGQGTQVTVSS |
| 135 TITIGDATD | 237 YADSAKGRFTISRDEAKNMVYLQMNSLKPEDTAVYFCRA | 164 GSRLYPYNY | 285 WGQGTQVTVSS |
| 134 TITIGDTTD | 236 YADYAKGRFTISRDEARNMVYLQMNSLKPEDTAVYFCRA | 164 GSRLYPYNY | 286 WGQGTLVTVSS |
| 135 TITIGDATD | 237 YADSAKGRFTISRDEAKNMVYLQMNSLKPEDTAVYFCRA | 164 GSRLYPYNY | 286 WGQGTLVTVSS |
| 134 TITIGDTTD | 237 YADSAKGRFTISRDEAKNMVYLQMNSLKPEDTAVYFCRA | 164 GSRLYPYNY | 285 WGQGTQVTVSS |
| 136 HITIADATD | 238 YSHFAKGRFTISRDEAKNMVYLQMNSLRPEDTAVYFCRA | 165 GSRIYPYDY | 286 WGQGTLVTVSS |

TABLE A-4-continued

Sequences for CDRs and frameworks, plus preferred
combinations as provided in formula I, namely
FR1-CDR1-FR2-CDR2-FR3-CDR3-FR4.

| | | | | |
|---|---|---|---|---|
| 137 | TITIGD DVD | 239 YADSAKGRFTISRDEAKNMV YLQMTSLKPEDTAVYVCRA | 164 GSRLYPYNY | 286 WGQGTL VTVSS |
| 138 | HITIGD ATD | 240 YAESAKGRFTISRDEAKNMV YLQMNSLKPEDTAVYFCRA | 166 YSRIYPYNY | 285 WGQGTQ VTVSS |
| 138 | HITIGD ATD | 237 YADSAKGRFTISRDEAKNMV YLQMNSLKPEDTAVYFCRA | 166 YSRIYPYNY | 286 WGQGTL VTVSS |
| 138 | HITIGD ATD | 237 YADSAKGRFTISRDEAKNMV YLQMNSLKPEDTAVYFCRA | 166 YSRIYPYNY | 286 WGQGTL VTVSS |
| 139 | HITIGD QAD | 237 YADSAKGRFTISRDEAKNMV YLQMNSLKPEDIAVYFCRA | 165 GSRIYPYDY | 285 WGQGTQ VTVSS |
| 135 | TITIGD ATD | 241 YADSAKGRFTISRDEAKNMV YLQMNSLSPEDIAVYFCRA | 164 GSRLYPYNY | 286 WGQGTL VTVSS |
| 140 | HISIAD ATD | 242 YAHFAKGRFTISRDEAKNMV YLQMNSLRPEDTAVYFCRA | 165 GSRIYPYDY | 287 WGRGTQ VTVSS |
| 141 | HITIGD ATV | 240 YAESAKGRFTISRDEAKNMV YLQMNSLKPEDTAVYFCRA | 166 YSRIYPYNY | 285 WGQGTQ VTVSS |
| 136 | HITIAD ATD | 238 YSHFAKGRFTISRDEAKNMV YLQMNSLRPEDTAVYFCRA | 165 GSRIYPYDY | 286 WGQGTL VTVSS |
| 136 | HITIAD ATD | 242 YAHFAKGRFTISRDEAKNMV YLQMNSLRPEDTAVYFCRA | 165 GSRIYPYDY | 285 WGQGTQ VTVSS |
| 136 | HITIAD ATD | 242 YAHFAKGRFTISRDEAKNMV YLQMNSLRPEDTAVYFCRA | 165 GSRIYPYDY | 286 WGQGTL VTVSS |
| 143 | HITIGD EVD | 244 YADSAKGRFTISRDEAKNMV YLQMTSLTPEDTAVYVCRA | 164 GSRLYPYNY | 285 WGQGTQ VTVSS |
| 144 | HITIGD VID | 245 YADSAKGRFTISRDEAKNMV YLQMNNLKPEDTAVYFCRA | 165 GSRIYPYDY | 285 WGQGTQ VTVSS |
| 138 | HITIGD ATD | 247 YADSAKGRFTISRDEAKNMV HLQMNSLKPEDTAVYFCRA | 166 YSRIYPYNY | 285 WGQGTQ VTVSS |
| 146 | HITIGD ATN | 237 YADSAKGRFTISRDEAKNMV YLQMNSLKPEDIAVYFCRA | 166 YSRIYPYNY | 286 WGQGTL VTVSS |
| 144 | HITIGD VTD | 248 YADSAKGRFTISRDEAKNMV FLQMNNLKPEDTAVYFCRA | 165 GSRIYPYDY | 285 WGQGTQ VTVSS |
| 138 | HITIGD ATD | 249 YAGSAKGRFTISRDEAKNMV YLQMNSLKPEDTAVYFCRA | 166 YSRIYPYNY | 286 WGQGTL VTVSS |
| 147 | HITIAD VAD | 250 YADFAKGRFTISRDEAKNMV YLQMNSLKPEDTAVYFCRA | 169 GSRIWPYDY | 285 WGQGTQ VTVSS |
| 148 | TITIGD EVD | 251 YADSAKGRFTISRDEAKNMV YLQMTSLKPEDTTVYVCRA | 164 GSRLYPYNY | 285 WGQGTQ VTVSS |
| 147 | HITIAD VAD | 250 YADFAKGRFTISRDEAKNMV YLQMNSLKPEDTAVYFCRA | 169 GSRIWPYDY | 286 WGQGTL VTVSS |
| 149 | HISISD QTD | 252 YAESAKGRFTISRDESKNMV YLQMNSLKPEDTAVYLCRA | 170 FSRIYPYDY | 286 WGQGTL VTVSS |
| 135 | TITIGD ATD | 236 YADYAKGRFTISRDEARNMV YLQMNSLKPEDTAVYFCRA | 164 GSRLYPYNY | 286 WGQGTL VTVSS |
| 138 | HITIGD ATD | 253 YADSAKGRFAISRDEAKNMV YLQMNSLKPEDTAVYFCRA | 166 YSRIYPYNY | 286 WGQGTL VTVSS |
| 138 | HITIGD ATD | 237 YADSAKGRFTISRDEAKNMV YLQMNSLKPEDTAVYFCRA | 165 GSRIYPYDY | 285 WGQGTQ VTVSS |
| 135 | TITIGD ATD | 241 YADSAKGRFTISRDEAKNMV YLQMNSLSPEDTAVYFCRA | 164 GSRLYPYNY | 285 WGQGTQ VTVSS |

TABLE A-4-continued

Sequences for CDRs and frameworks, plus preferred combinations as provided in formula I, namely FR1-CDR1-FR2-CDR2-FR3-CDR3-FR4.

| | | | |
|---|---|---|---|
| 150 HITIGDQID | 237 YADSAKGRFTISRDEAKNMVYLQMNSLKPEDTAVYFCRA | 169 GSRIWPYDY | 285 WGQGTQVTVSS |
| 136 HITIADATD | 238 YSHFAKGRFTISRDEAKNMVYLQMNSLRPEDTAVYFCRA | 165 GSRIYPYDY | 286 WGQGTLVTVSS |
| 136 HITIADATD | 238 YSHFAKGRFTISRDEAKNMVYLQMNSLRPEDTAVYECRA | 165 GSRIYPYDY | 285 WGQGTQVTVSS |
| 138 HITIGDATD | 237 YADSAKGRFTISRDEAKNMVYLQMNSLKPEDTAVYFCRA | 166 YSRIYPYNY | 286 WGQGTLVTVSS |
| 138 HITIGDATD | 237 YADSAKGRFTISRDEAKNMVYLQMNSLKPEDTAVYFCRA | 166 YSRIYPYNY | 286 WGQGTLVTVSS |
| 147 HITIADVAD | 254 YADFAQGRFTISRDEAKNMVYLQMNSLKPEDTAVYFCRA | 169 GSRIWPYDY | 285 WGQGTQVTVSS |
| 151 HITIGDTID | 237 YADSAKGRFTISRDEAKNMVYLQMNSLKPEDTAVYFCRA | 166 YSRIYPYNY | 285 WGQGTQVTVSS |
| 136 HITIADATD | 238 YSHFAKGRFTISRDEAKNMVYLQMNSLRPEDIAVYFCRA | 165 GSRIYPYDY | 288 WGHGTLVTVSS |
| 139 HITIGDQAD | 237 YADSAKGRFTISRDEAKNMVYLQMNSLKPEDTAVYFCRA | 165 GSRIYPYDY | 289 WGRGTLVTVSS |
| 136 HITIADATD | 238 YSHFAKGRFTISRDEAKNMVYLQMNSLRPEDTAVYFCRA | 165 GSRIYPYDY | 285 WGQGTQVTVSS |
| 136 HITIADATD | 255 YAEFAKGRFTISRDEPKNMVHLQMNSLKPEDTAVYLCRA | 171 GSRIYPYNY | 285 WGQGTQVTVSS |
| 138 HITIGDATD | 237 YADSAKGRFTISRDEAKNMVYLQMNSLKPEDTAVYFCRA | 166 YSRIYPYNY | 287 WGRGTQVTVSS |
| 152 RISISDQTD | 252 YAESAKGRFTISRDESKNMVYLQMNSLKPEDTAVYLCRA | 170 FSRIYPYDY | 286 WGQGTLVTVSS |
| 147 HITIADVAD | 256 YADFAKGRLTISRDEAKNMVYLQMNSLKPEDTAVYFCRA | 169 GSRIWPYDY | 286 WGQGTLVTVSS |
| 148 TITIGDEVD | 239 YADSAKGRFTISRDEAKNMVYLQMTSLKPEDTAVYVCRA | 164 GSRLYPYNY | 286 WGQGTLVTVSS |
| 136 HITIADATD | 242 YAHFAKGRFTISRDEAKNMVYLQMNSLRPEDTAVYFCRA | 165 GSRIYPYDY | 286 WGQGTLVTVSS |
| 138 HITIGDATD | 237 YADSAKGRFTISRDEAKNMVYLQMNSLKPEDTAVYFCRA | 166 YSRIYPYNY | 286 WGQGTLVTVSS |
| 153 HISIGDQTD | 257 YADSAKGRFTISRDESKNMVYLQMNSLKPEDTAVYFCRA | 170 FSRIYPYDY | 286 WGQGTLVTVSS |
| 154 HITIADAAD | 258 YADFAKGRFTISRDGAKNMVYLQMNSLKPEDTAVYFCRA | 169 GSRIWPYDY | 285 WGQGTQVTVSS |
| 155 TITIGDAAD | 259 YADSAKGRFTISRDEARNMVYLQMNSLKPEDTALYFCHA | 164 GSRLYPYNY | 285 WGQGTQVTVSS |
| 136 HITIADATD | 238 YSHFAKGRFTISRDEAKNMVYLQMNSLRPEDTAVYFCRA | 165 GSRIYPYDY | 285 WGQGTQVTVSS |
| 156 HIAISDQTD | 252 YAESAKGRFTISRDESKNMVYLQMNSLKPEDTAVYLCRA | 170 FSRIYPYDY | 286 WGQGTLVTVSS |
| 138 HITIGDATD | 260 YADSAKGRFTISRDEAKNMVYLQMNSLKPEDTAAYFCRA | 166 YSRIYPYNY | 286 WGQGTLVTVSS |
| 138 HITIGDATD | 237 YADSAKGRFTISRDEAKNMVYLQMNSLKPEDTAVYFCRA | 166 YSRIYPYNY | 285 WGQGTQVTVSS |
| 138 HITIGDATD | 237 YADSAKGRFTISRDEAKNMVYLQMNSLKPEDIAVYFCRA | 166 YSRIYPYNY | 286 WGQGTLVTVSS |

TABLE A-4-continued

Sequences for CDRs and frameworks, plus preferred combinations as provided in formula I, namely FR1-CDR1-FR2-CDR2-FR3-CDR3-FR4.

| FR1-CDR1-FR2 | CDR2 | FR3 | CDR3 | FR4 |
|---|---|---|---|---|
| 138 HITIGD ATD | 237 YADSAKGRFTISRDEAKNMV YLQMNSLKPEDTAVYFCRA | 166 YSRIYPYNY | 285 WGQGTQ VTVSS | |
| 138 HITIGD ATD | 263 YADSAKGRFTISRDEAENMV YLQMNSLKPEDTAVYFCRA | 166 YSRIYPYNY | 286 WGQGTL VTVSS | |
| 148 TITIGD EVD | 239 YADSAKGRFTISRDEAKNMV YLQMTSLKPEDTAVYVCRA | 164 GSRLYPYNY | 286 WGQGTL VTVSS | |
| 148 TITIGD EVD | 264 YADSAKGRFTISRDEATNMV YLQMTSLKPEDTAVYFCRA | 171 GSRIYPYNY | 285 WGQGTQ VTVSS | |
| 159 HITIGD ATS | 265 YAGSARGRFTISRDEAKNMV YLQLNNLKPEDTAVYFCRA | 166 YSRIYPYNY | 286 WGQGTL VTVSS | |
| 159 HITIGD ATS | 266 YADSAKGRFTISRDEARNMV YLQLNNLKPEDTAVYFCRA | 166 YSRIYPYNY | 286 WGQGTL VTVSS | |
| 136 HITIAD ATD | 267 YAEFAKGRFTISRDEPRNMV YLQMNSLRPEDTAVYLCRA | 171 GSRIYPYNY | 285 WGQGTQ VTVSS | |
| 148 TITIGD EVD | 268 YAHSARGRFTISRDEARNMV YLQMTSLRPEDTAVYVCRA | 164 GSRLYPYNY | 285 WGQGTQ VTVSS | |
| 160 TITIGD EVA | 239 YADSARGRFTISRDEARNMV YLQMTSLKPEDTAVYVCRA | 164 GSRLYPYNY | 285 WGQGTQ VTVSS | |
| 154 HITIAD AAD | 250 YADFARGRFTISRDEARNMV YLQMNSLKPEDTAVYFCRA | 169 GSRIWPYDY | 285 WGQGTQ VTVSS | |
| 154 HITIAD AAD | 250 YADFARGRFTISRDEARNMV YLQMNSLKPEDTAVYFCRA | 165 GSRIYPYDY | 285 WGQGTQ VTVSS | |
| 135 TITIGD ATD | 241 YADSARGRFTISRDEARNMV YLQMNSLSPEDTAVYFCRA | 164 GSRLYPYNY | 285 WGQGTQ VTVSS | |
| 147 HITIAD VAD | 269 YADFAKGRFTISRDEVKNMV YLQMNSLKPEDTAVYFCRA | 169 GSRIWPYDY | 286 WGQGTL VTVSS | |
| 138 HITIGD ATD | 237 YADSAKGRFTISRDEAKNMV YLQMNSLKPEDTAVYFCRA | 166 YSRIYPYNY | 286 WGQGTL VTVSS | |
| 154 HITIAD AAD | 270 YADFAKGRFTISRDEAKNMV YLQMNSLRPEDTAVYFCRA | 169 GSRIWPYDY | 285 WGQGTQ VTVSS | |
| 161 HITIAD VTD | 271 YSYFAKGRFTISRDEAKNMV YLQMNSLRPEDTAVYFCRA | 165 GSRIYPYDY | 285 WGQGTQ VTVSS | |
| 138 HITIGD ATD | 272 YADSAKGRFTISRDEAKNVV YLQMNSLKPEDTAVYFCRA | 166 YSRIYPYNY | 286 WGQGTL VTVSS | |
| 135 TITIGD ATD | 241 YADSAKGRFTISRDEAKNMV YLQMNSLSPEDTAVYFCRA | 164 GSRLYPYNY | 285 WGQGTQ VTVSS | |
| 148 TITIGD EVD | 273 YEDSAKGRFTISRDEAKNMV YLQMTGLKPEDTAVYVCRA | 164 GSRLYPYNY | 286 WGQGTL VTVSS | |
| 149 HISISD QTD | 252 YAESAKGRFTISRDESKNMV YLQMNSLKPEDTAVYLCRA | 170 FSRIYPYDY | 285 WGQGTQ VTVSS | |
| 138 HITIGD ATD | 237 YADSAKGRFTISRDEAKNMV YLQMNSLKPEDTAVYFCRA | 165 GSRIYPYDY | 286 WGQGTL VTVSS | |
| 138 HITIGD ATD | 240 YAESAKGRFTISRDEAKNMV YLQMNSLKPEDTAVYFCRA | 166 YSRIYPYNY | 285 WGQGTQ VTVSS | |
| 138 HITIGD ATD | 237 YADSAKGRFTISRDEAKNMV YLQMNSLKPEDTAVYFCRA | 166 YSRIYPYNY | 285 WGQGTQ VTVSS | |
| 136 HITIAD ATD | 267 YAEFAKGRFTISRDEPKNMV YLQMNSLKPEDTAVYLCRA | 173 GSRIYPSY | 285 WGQGTQ VTVSS | |
| 138 HITIGD ATD | 237 YADSAKGRFTISRDEAKNMV YLQMNSLKPEDTAVYFCRA | 166 YSRIYPYNY | 286 WGQGTL VTVSS | |

TABLE A-4-continued

Sequences for CDRs and frameworks, plus preferred combinations as provided in formula I, namely FR1-CDR1-FR2-CDR2-FR3-CDR3-FR4.

| FR1 | CDR1 | FR2 | CDR2 | FR3 | CDR3 | FR4 |
|---|---|---|---|---|---|---|
| 138 | HITIGDATD | 260 | YADSAKGRFTISRDEAKNMVYLQMNSLKPEDTAAYFCRA | 166 | YSRIYPYNY | 286 WGQGTLVTVSS |
| 154 | HITIADAAD | 250 | YADFAKGRFTISRDEAKNMVYLQMNSLKPEDTAVYFCRA | 169 | GSRIWPYDY | 286 WGQGTLVTVSS |
| 136 | HITIADATD | 275 | YSHFAKGRFTISRDEAKNMVYLQMNGLRPEDTAVYFCRA | 165 | GSRIYPYDY | 286 WGQGTLVTVSS |
| 136 | HITIADATD | 267 | YAEFAKGRFTISRDEPKNMVYLQMNSLKPEDTAVYLCRA | 171 | GSRIYPYNY | 285 WGQGTQVTVSS |
| 135 | TITIGDATD | 237 | YADSAKGRFTISRDEAKNMVYLQMNSLKPEDTAVYFCRA | 174 | LSRLYPYNY | 286 WGQGTLVTVSS |
| 138 | HITIGDATD | 276 | YADSAKGRFTISRDEAKNMVYLQMNSLKPEDTAVYLCRA | 166 | YSRIYPYNY | 285 WGQGTQVTVSS |
| 147 | HITIADVAD | 250 | YADFAKGRFTISRDEAKNMVYLQMNSLKPEDTAVYFCRA | 169 | GSRIWPYDY | 286 WGQGTLVTVSS |
| 136 | HITIADATD | 277 | YAEFAKGRFTISRDEPKNMVYLQMNSLKPVPTAVYLCRA | 171 | GSRIYPYNY | 286 WGQGTLVTVSS |
| 136 | HITIADATD | 278 | YSHFAKGRFTISRDEAKNMVYLQMNNLRPEDTAVYFCRA | 165 | GSRIYPYDY | 286 WGQGTLVTVSS |
| 139 | HITIGDQAD | 237 | YADSAKGRFTISRDEAKNMVYLQMNSLKPEDTAVYFCRA | 165 | GSRIYPYDY | 286 WGQGTLVTVSS |
| 138 | HITIGDATD | 280 | YADSAKGRFTISRDEAKNMVYLQMNSLKPEDAAVYFCRA | 166 | YSRIYPYNY | 286 WGQGTLVTVSS |
| 147 | HITIADVAD | 258 | YADFAKGRFTISRDGAKNMVYLQMNSLKPEDTAVYFCRA | 169 | GSRIWPYDY | 286 WGQGTLVTVSS |
| 135 | TITIGDATD | 241 | YADSAKGRFTISRDEAKNMVYLQMNSLSPEDTAVYFCRA | 164 | GSRLYPYNY | 285 WGQGTQVTVSS |
| 149 | HISISDQTD | 281 | YAESAKGRFTISRDESKNMVYLQMNSLKPEDAAVYLCRA | 170 | FSRIYPYDY | 285 WGQGTQVTVSS |
| 147 | HITIADVAD | 250 | YADFAKGRFTISRDEAKNMVYLQMNSLKPEDTAVYFCRA | 169 | GSRIWPYDY | 285 WGQGTQVTVSS |
| 162 | HITIADQAD | 237 | YADSAKGRFTISRDEAKNMVYLQMNSLKPEDTAVYFCRA | 165 | GSRIYPYDY | 286 WGQGTLVTVSS |
| 163 | TITIGDETQ | 237 | YADSAKGRFTISRDEAKNMVYLQMNSLKPEDTAVYFCRA | 174 | LSRLYPYNY | 286 WGQGTLVTVSS |
| 138 | HITIGDATD | 283 | YADSAKGRFTISRDEAKNMVYLQMDSLKPEDTAVYFCRA | 166 | YSRIYPYNY | 286 WGQGTLVTVSS |
| 138 | HITIGDATD | 284 | YADSAKGRFTISRDEAKNMVYLQMNSLKPGDTAVYFCRA | 166 | YSRIYPYNY | 286 WGQGTLVTVSS |
| 138 | HITIGDATD | 237 | YADSAKGRFTISRDEAKNMVYLQMNSLKPEDTAVYFCRA | 166 | YSRIYPYNY | 286 WGQGTLVTVSS |
| 138 | HITIGDATD | 260 | YADSAKGRFTISRDEAKNMVYLQMNSLKPEDTAAYFCRA | 166 | YSRIYPYNY | 285 WGQGTQVTVSS |
| 138 | HITIGDATD | 237 | YADSAKGRFTISRDEAKNMVYLQMNSLKPEDTAVYFCRA | 166 | YSRIYPYNY | 286 WGQGTLVTVSS |
| 142 | SLTIGGATD | 243 | YADSVKGRFTISEDSAKNTVYLQMNSLKAEDTAVYFCNA | 167 | KSRLYPYDY | 285 WGQGTQVTVSS |
| 145 | SLTIGGATN | 246 | YADSVKGRFTISEDSAKNTVYLQMNSLKPEDTAVYFCNA | 167 | KSRLYPYDY | 286 WGQGTLVTVSS |
| 145 | SLTIGGATN | 246 | YADSVKGRFTISEDSAKNTVYLQMNSLKPEDTAVYFCNA | 168 | KSRIYPYDY | 285 WGQGTQVTVSS |

TABLE A-4-continued

Sequences for CDRs and frameworks, plus preferred combinations as provided in formula I, namely FR1-CDR1-FR2-CDR2-FR3-CDR3-FR4.

| | | | |
|---|---|---|---|
| 145 SLTIGGATN | 246 YADSVKGRFTISEDSAKNTVYLQMNSLKPEDTAVYFCNA | 167 KSRLYPYDY | 285 WGQGTQVTVSS |
| 145 SLTIGGATN | 246 YADSVKGRFTISEDSAKNTVYLQMNSLKPEDTAVYFCNA | 167 KSRLYPYDY | 285 WGQGTQVTVSS |
| 145 SLTIGGATN | 246 YADSVKGRFTISEDSAKNTVYLQMNSLKPEDTAVYFCNA | 167 KSRLYPYDY | 287 WGRGTQVTVSS |
| 145 SLTIGGATN | 246 YADSVKGRFTISEDSAKNTVYLQMNSLKPEDIAVYFCNA | 168 KSRIYPYDY | 287 WGRGTQVTVSS |
| 145 SLTIGGATN | 246 YADSVKGRFTISEDSAKNTVYLQMNSLKPEDTAVYFCNA | 167 KSRLYPYDY | 290 WDQGTQVTVSS |
| 145 SLTIGGATN | 274 YADSVKGRFTISEDSAKNTVYLQMSSLKPEDTAVYFCNA | 167 KSRLYPYDY | 285 WGQGTQVTVSS |
| 145 SLTIGGATN | 246 YADSVKGRFTISEDSAKNTVYLQMNSLKPEDTAVYFCNA | 168 KSRIYPYDY | 287 WGRGTQVTVSS |
| 145 SLTIGGATN | 279 YADSVKGRFTISEDSAKDTVYLQMNSLKPEDTAVYFCNA | 167 KSRLYPYDY | 286 WGQGTLVTVSS |
| 157 TITIADKTD | 261 YADSAKGRFTISRDESRNMVYLQMSSLKPEDTAVYFCHA | 172 GSRLYPYDY | 285 WGQGTQVTVSS |
| 158 TITIADKID | 262 YADSAKGRFTISRDESRNMVYLQMGSLKPEDTAVYFCHA | 172 GSRLYPYDY | 285 WGQGTQVTVSS |
| 157 TITIADKTD | 282 YADSAKGRFTISRDESRNMVYLQMSSLKPENTAVYFCHA | 172 GSRLYPYDY | 285 WGQGTQVTVSS |

"SEQ" refers to the given SEQ ID NO.
The first column refers to the SEQ ID NO of the complete ISV, i.e. FR1-CDR1-FR2-CDR2-FR3-CDR3-FR4.
CDR1, CDR2 and CDR3 were determined according to Kontermann, 2010.

TABLE A-5

Sequences of multispecific polypeptides (with and without tags).

| SEQID | Sequence |
|---|---|
| 291 T017000001 | EVQLVESGGGLVQGGGSLSLSCAASGRTFSSYAMAWFRQPPGKEREFVASISWSGENTNYRNSVKGRFTISRDNAKNTVYLQMNSLKP EDTAVYYCAAKIAKTYPDNWYWTKSNNYNYWGQGTLVTVSSGGGGSGGGGSGGGGSGGGGSGGGGSGGGGSGGGGSEVQLVESGGGLV QGGGSLSLSCAASGRTFSSYAMAWFRQPPGKEREFVASISWSGENTNYRNSVKGRFTISRDNAKNTVYLQMNSLKPEDTAVYYCAAKI AKTYPDNWYWTKSNNYNYWGQGTLVTVSSGAADYKDHDGDYKDHDIDYKDDDDKGAAHHHHHH |
| 292 T017000002 | EVQLVESGGGLVQPGGSLRLSCTFSGGTFSSYTMGWFRQAPGKEREFVAEVRWGGVTTYSNSLKDRFSISEDSVKNAVYLQMNSLKPE DTAVYYCAAVRQMYMTVVPDYWGQGTLVTVSSGGGGSEVQLVESGGGLVQPGGSLRLSCAASGSVHKINFLGWYRQAPGKERGLVATI TIGDTTDYADYAKGRFTISRDEARNMVYLQMNSLKPEDTAVYFCRAGSRLYPYNYWGQGTLVTVSSGAADYKDHDGDYKDHDIDYKDD DDKGAAHHHHHH |
| 293 T017000003 | EVQLQASGGGSVQAGGSLRLSCAASGYTIGPYCMGWFRQAPGKEREGVAAINMGGGITYYADSVKGRFTISQDNAKNTVYLLMNSLEP EDTAIYYCAADSTIYASYYECGHGLSTGGYGYDSWGQGTQVTVSSGGGGSEVQLVESGGGLVQPGGSLRLSCAASGSVHKINFLGWYR QAPGKERGLVATITIGDTTDYADYAKGRFTISRDEARNMVYLQMNSLKPEDTAVYFCRAGSRLYPYNYWGQGTLVTVSSGAADYKDHD GDYKDHDIDYKDDDDKGAAHHHHHH |
| 294 T017000006 | EVQLVESGGGLVQPGGSLRLSCTFSGGTFSSYTMGWFRQAPGKEREFVAEVRWGGVTTYSNSLKDRFSISEDSVKNAVYLQMNSLKPE DTAVYYCAAVRQMYMTVVPDYWGQGTLVTVSSGGGGSDVQLQASGGGSVQAGGSLRLSCAASGYTIGPYCMGWFRQAPGKEREGVAAI NMGGGITYYADSVKGRFTISQDNAKNTVYLLMNSLEPEDTAIYYCAADSTIYASYYECGHGLSTGGYGYDSWGQGTQVTVSSGAADYK DHDGDYKDHDIDYKDDDDKGAAHHHHHH |
| 295 T017000007 | EVQLVESGGGLVQPGGSLRLSCAASGSVHKINFLGWYRQAPGKERGLVATITIGDTTDYADYAKGRFTISRDEARNMVYLQMNSLKPE DTAVYFCRAGSRLYPYNYWGQGTLVTVSSGGGGSEVQLVESGGGLVQPGGSLRLSCTFSGGTFSSYTMGWFRQAPGKEREFVAEVRWG GVTTYSNSLKDRFSISEDSVKNAVYLQMNSLKPEDTAVYYCAAVRQMYMTVVPDYWGQGTLVTVSSGAADYKDHDGDYKDHDIDYKDD DDKGAAHHHHHH |
| 296 T017000008 | EVQLVESGGGLVQPGGSLRLSCTFSGGTFSSYTMGWFRQAPGKEREFVAEVRWGGVTTYSNSLKDRFSISEDSVKNAVYLQMNSLKPE DTAVYYCAAVRQMYMTVVPDYWGQGTLVTVSSGGGGSGGGGSEVQLVESGGGLVQPGGSLRLSCAASGSVHKINFLGWYRQAPGKERGL VATITIGDTTDYADYAKGRFTISRDEARNMVYLQMNSLKPEDTAVYFCRAGSRLYPYNYWGQGTLVTVSSGAADYKDHDGDYKDHDID YKDDDDKGAAHHHHHH |

TABLE A-5-continued

Sequences of multispecific polypeptides (with and without tags).

| SEQID | Sequence |
|---|---|
| 297 T017000009 | EVQLQASGGGLVQAGGSLRLSCAASGYTIGPYCMGWFRQAPGKEREGVAAINMGGGITYYADSVKGRFTISQDNAKNTVYLLMNSLEP EDTAIYY.CAADSTIYASYYECGHGLSTGGYGYDSWGQGTQVTVSSGGGGSGGGGSEVQLVESGGGLVQPGGSLRLSCAASGSVHKINF LGWYRQAPGKERGLVATITIGDYTDYADYAKGRFTISRDEARNMVYLQMNSLKPEDTAVYFCRAGSRLYPYNYWGQGTLVTVSSGAAD YKDHDGDYKDHDIDYKDDDDKGAAHHHHHH |
| 298 T017000012 | EVQLVESGGGLVQPGGSLRLSCTFSGGTFSSYTMGWFRQAPGKEREFVAEVRWGGVTTYSNSLKDRFSISEDSVKNAVYLQMNSLKPE DTAVYYCAAVRQMYMTVVPDYWGQGTLVTVSSGGGGSGGGGSDVQLQASGGGSVQAGGSLRLSCAASGYTIGPYCMGWFRQAPGKEREG VAAINMGGGITYYADSVKGRFTISQDNAKNTVYLLMNSLEPEDTAIYYCAADSTIYASYYECGHGLSTGGYGYDSWGQGTQVTVSSGA ADYKDHDGDYKDHDIDYKDDDDKGAAHHHHHH |
| 299 T017000013 | EVQLVESGGGLVQPGGSLRLSCAASGSVHKINFLGWYRQAPGKERGLVATITIGDTTDYADYAKGRFTISRDEARNMVYLQMNSLKPE DTAVYFCRAGSRLYPYNYWGQGTLVTVSSGGGGSGGGGSEVQLVESGGGLVQPGGSLRLSCTFSGGTFSSYTMGWFRQAPGKEREFVAE VRWGGVTTYSNSLKDRFSISEDSVKNAVYLQMNSLKPEDTAVYYCAAVRQMYMTVVPDYWGQGTLVTVSSGAADYKDHDGDYKDHDID YKDDDDKGAAHHHHHH |
| 300 T017000014 | EVQLVESGGGLVQPGGSLRLSCTFSGGTFSSYTMGWFRQAPGKEREFVAEVRWGGVTTYSNSLKDRFSISEDSVKNAVYLQMNSLKPE DTAVYYCAAVRQMYMTVVPDYWGQGTLVTVSSGGGGSGGGGSGGGGSGGGGSGGGGSGGGGSGGGGSEVQLVESGGGLVQPGGSLRLS CAASGSVHKINFLGWYRQAPGKERGLVATITIGDTTDYADYAKGRFTISRDEARNMVYLQMNSLKPEDTAVYFCRAGSRLYPYNYWGQ GTLVTVSSGAADYKDHDGDYKDHDIDYKDDDDKGAAHHHHHH |
| 301 T017000015 | EVQLQASGGGSVQAGGSLRLSCAASGYTIGPYCMGWFRQAPGKEREGVAAINMGGGITYYADSVKGRFTISQDNAKNTVYLLMNSLEP EDTAIYYCAADSTIYASYYECGHGLSTGGYGYDSWGQGTQVTVSSGGGGSGGGGSGGGGSGGGGSGGGGSGGGGSGGGGSEVQLVESG GGLVQPGGSLRLSCAASGSVHKINFLGWYRQAPGKERGLVATITIGDTTDYADYAKGRFTISRDEARNMVYLQMNSLKPEDTAVYFCR AGSRLYPYNYWGQGTLVTVSSGAADYKDHDGDYKDHDIDYKDDDDKGAAHHHHHH |
| 302 T017000018 | EVQLVESGGGLVQPGGSLRLSCTFSGGTFSSYTMGWFRQAPGKEREFVAEVRWGGVTTYSNSLKDRFSISEDSVKNAVYLQMNSLKPE DTAVYYCAAVRQMYMTVVPDYWGQGTLVTVSSGGGGSGGGGSGGGGSGGGGSGGGGSGGGGSGGGGSDVQLQASGGGSVQAGGSLRLS CAASGYTIGPYCMGWFRQAPGKEREGVAAINMGGGITYYADSVKGRFTISQDNAKNTVYLLMNSLEPEDTAIYYCAADSTIYASYYEC GHGLSTGGYGYDSWGQGTQVTVSSGAADYKDHDGDYKDHDIDYKDDDDKGAAHHHHHH |
| 303 T017000019 | EVQLVESGGGLVQPGGSLRLSCAASGSVHKINFLGWYRQAPGKERGLVATITIGDTTDYADYAKGRFTISRDEARNMVYLQMNSLKPE DTAVYFCRAGSRLYPYNYWGQGTLVTVSSGGGGSGGGGSGGGGSGGGGSGGGGSGGGGSGGGGSEVQLVESGGGLVQPGGSLRLSCTF SGGTFSSYTMGWFRQAPGKEREFVAEVRWGGVTTYSNSLKDRFSISEDSVKNAVYLQMNSLKPEDTAVYYCAAVRQMYMTVVPDYWGQ GTLVTVSSGAADYKDHDGDYKDHDIDYKDDDDKGAAHHHHHH |
| 304 T017000023 | EVQLQASGGGSVQAGGSLRLSCAASGYTIGPYCMGWFRQAPGKEREGVAAINMGGGITYYADSVKGRFTISQDNAKNTVYLLMNSLEP EDTAIYYCAADSTIYASYYECGHGLSTGGYGYDSWGQGTQVTVSSGGGGSGGGGSGGGGSGGGGSGGGGSGGGGSEVQLVESG GGLVQPGGSLRLSCTFSGGTFSSYTMGWFRQAPGKEREFVAEVRWGGVTTYSNSLKDRFSISEDSVKNAVYLQMNSLKPEDTAVYYCA AVRQMYMTVVPDYWGQGTLVTVSSGAADYKDHDGDYKDHDIDYKDDDDKGAAHHHHHH |
| 305 T017000025 | EVQLVESGGGLVQPGGSLRLSCAASGSVHKINFLGWYRQAPGKERGLVATITIGDTTDYADYAKGRFTISRDEARNMVYLQMNSLKPE DTAVYFCRAGSRLYPYNYWGQGTLVTVSSGGGGSGGGGSGGGGSGGGGSGGGGSGGGGSGGGGSDVQLQASGGGSVQAGGSLRLSCAA SGYTIGPYCMGWFRQAPGKEREGVAAINMGGGITYYADSVKGRFTISQDNAKNTVYLLMNSLEPEDTAIYYCAADSTIYASYYECGHG LSTGGYGYDSWGQGTQVTVSSGAADYKDHDGDYKDHDIDYKDDDDKGAAHHHHHH |
| 306 T017000029 | EVQLVESGGGLVQPGGSLRLSCAASGDVYKINFLGWHRQAPGKEREKVAHITIGDATDYADSAKGRFTISRDEAKNMVYLQMNSLKPE DTAVYFCRAGSRIYPYDYWGQGTLVTVSSGGGGSGGGGSGGGGSGGGGSGGGGSGGGGSGGGGSEVQLVESGGGLVQPGGSLRLSCTF SGGTFSSYTMGWFRQAPGKEREFVAEVRWGGVTTYSNSLKDRFSISEDSVKNAVYLQMNSLKPEDTAVYYCAAVRQMYMTVVPDYWGQ GTLVTVSSGAADYKDHDGDYKDHDIDYKDDDDKGAAHHHHHH |
| 307 T017000030 | EVQLVESGGGLVQPGGSLKLSCAASGAVHKINFLGWYRQTPEKEREMVATITIGDEVDYADSAKGRFTISRDEAKNMVYLQMTSLKPE DTAVYVCRAGSRLYPYNYWGQGTLVTVSSGGGGSGGGGSGGGGSGGGGSGGGGSGGGGSGGGGSEVQLVESGGGLVQPGGSLRLSCTF SGGTFSSYTMGWFRQAPGKEREFVAEVRWGGVTTYSNSLKDRFSISEDSVKNAVYLQMNSLKPEDTAVYYCAAVRQMYMTVVPDYWGQ GTLVTVSSGAADYKDHDGDYKDHDIDYKDDDDKGAAHHHHHH |
| 308 T017000031 | EVQLVESGGGLVQPGGSLRLSCITSGETFKINIWGWYRQAPGKQRELVASLTIGGATNYADSVKGRFTISEDSAKNTVYLQMNSLKPE DTAVYFCNAKSRLYPYDYWGQGTLVTVSSGGGGSGGGGSGGGGSGGGGSGGGGSGGGGSGGGGSEVQLVESGGGLVQPGGSLRLSCTF SGGTFSSYTMGWFRQAPGKEREFVAEVRWGGVTTYSNSLKDRFSISEDSVKNAVYLQMNSLKPEDTAVYYCAAVRQMYMTVVPDYWGQ GTLVTVSSGAADYKDHDGDYKDHDIDYKDDDDKGAAHHHHHH |
| 309 T017000032 | EVQLVESGGGLVQPGGSLRLSCAASGSVHLLNFLGWYRQAPGKEREMVAHITIADATDYAHFAKGRFTISRDEAKNMVYLQMNSLRPE DTAVYFCRAGSRIYPYDYWGQGTLVTVSSGGGGSGGGGSGGGGSGGGGSGGGGSGGGGSGGGGSEVQLVESGGGLVQPGGSLRLSCTF SGGTFSSYTMGWFRQAPGKEREFVAEVRWGGVTTYSNSLKDRFSISEDSVKNAVYLQMNSLKPEDTAVYYCAAVRQMYMTVVPDYWGQ GTLVTVSSGAADYKDHDGDYKDHDIDYKDDDDKGAAHHHHHH |
| 310 T017000033 | EVQLVESGGGLVQPGGSLRLSCITSGETFKINIWGWYRQAPGKQRELVASLTIGGATDYADSVKGRFTISEDSAKNTVYLQMNSLKAE DTAVYFCNAKSRLYPYDYWGQGTLVTVSSGGGGSGGGGSGGGGSGGGGSGGGGSGGGGSGGGGSEVQLVESGGGLVQPGGSLRLSCTF SGGTFSSYTMGWFRQAPGKEREFVAEVRWGGVTTYSNSLKDRFSISEDSVKNAVYLQMNSLKPEDTAVYYCAAVRQMYMTVVPDYWGQ GTLVTVSSGAADYKDHDGDYKDHDIDYKDDDDKGAAHHHHHH |
| 311 T017000035 | EVQLVESGGGLVQPGGSLRLSCAASGEVYKINFLGWYRQAPGKEREKVAHITIADAADYADFAKGRFTISRDEAKNMVYLQMNSLRPE DTAVYFCRAGSRIWPYDYWGQGTLVTVSSGGGGSGGGGSGGGGSGGGGSGGGGSGGGGSGGGGSEVQLVESGGGLVQPGGSLRLSCTF SGGTFSSYTMGWFRQAPGKEREFVAEVRWGGVTTYSNSLKDRFSISEDSVKNAVYLQMNSLKPEDTAVYYCAAVRQMYMTVVPDYWGQ GTLVTVSSGAADYKDHDGDYKDHDIDYKDDDDKGAAHHHHHH |

TABLE A-5-continued

Sequences of multispecific polypeptides (with and without tags).

| SEQID | Sequence |
|---|---|
| 312 T017000037 | EVQLVESGGGLVQPGGSLRLSCVASGDVHKINFLGWYRQAPGKEREKVAHISIGDQTDYADSAKGRFTISRDESKNMVYLQMNSLKPE<br>DTAVYFCRAFSRIYPYDYWGQGTLVTVSSGGGGSGGGGSGGGGSGGGGSGGGGSGGGGSGGGGSEVQLVESGGGLVQPGGSLRLSCTF<br>SGGTFSSYTMGWFRQAPGKEREFVAEVRWGGVTTYSNSLKDRFSISEDSVKNAVYLQKNSLKPEDTAVYYCAAVRQMYMTVVPDYWGQ<br>GTLVTVSSGAADYKDHDGDYKDHDIDYKDDDDKGAAHHHHHH |
| 313 T017000038 | EVQLVESGGGLVQPGGSLRLSCAASGEIGRINFYRWYRQAPGNQREVVATITIADKTDYADSAKGRFTISRDESRNMVYLQMSSLKPE<br>DTAVYFCHAGSRLYPYDYWGQGTLVTVSSGGGGSGGGGSGGGGSGGGGSGGGGSGGGGSGGGGSEVQLVESGGGLVQPGGSLRLSCTF<br>SGGTFSSYTMGWFRQAPGKEREFVAEVRWGGVTTYSNSLKDRFSISEDSVKNAVYLQMNSLKPEDTAVYYCAAVRQMYMTVVPDYWGQ<br>GTLVTVSSGAADYKDHDGDYKDHDIDYKDDDDKGAAHHHHHH |
| 314 T017000041 | EVQLVESGGGLVQPGGSLRLSCVASGDVHKINFLGWYRQAPGKEREKVAHITIGDQADYADSAKGRFTISRDEAKNMVYLQMNSLKPE<br>DTAVYFCRAGSRIYPYDYWGQGTLVTVSSGGGGSGGGGSGGGGSGGGGSGGGGSGGGGSGGGGSEVQLVESGGGLVQPGGSLRLSCTF<br>SGGTFSSYTMGWFRQAPGKEREFVAEVRWGGVTTYSNSLKDRFSISEDSVKNAVYLQMNSLKPEDTAVYYCAAVRQMYMTVVPDYWGQ<br>GTLVTVSSGAADYKDHDGDYKDHDIDYKDDDDKGAAHHHHHH |
| 315 T017000042 | EVQLVESGGGLVQPGGSLRLSCAASGDVHKINILGWYRQAPAKEREMVAHITIGDATDYADSAKGRFTISRDEAKNMVYLQMNSLKPE<br>DTAVYFCRAYSRIYPYNYWGQGTLVTVSSGGGGSGGGGSGGGGSGGGGSGGGGSGGGGSGGGGSEVQLVESGGGLVQPGGSLRLSCTF<br>SGGTFSSYTMGWFRQAPGKEREFVAEVRWGGVTTYSNSLKDRFSISEDSVKNAVYLQMNSLKPEDTAVYYCAAVRQMYMTVVPDYWGQ<br>GTLVTVSSGAADYKDHDGDYKDHDIDYKDDDDKGAAHHHHHH |
| 316 T017000044 | EVQLVESGGGLVQPGGSLRLSCAASGSVHKINFLGWYRQAPGKERELVATITIGDTTDYADSAKGRFTISRDEAKNMVYLQMNSLKPE<br>DTAVYFCRAGSRLYPYNYWGQGTLVTVSSGGGGSGGGGSGGGGSGGGGSGGGGSGGGGSGGGGSEVQLVESGGGLVQPGGSLRLSCTF<br>SGGTFSSYTMGWFRQAPGKEREFVAEVRWGGVTTYSNSLKDRFSISEDSVKNAVYLQMNSLKPEDTAVYYCAAVRQMYMTVVPDYWGQ<br>GTLVTVSSGAADYKDHDGDYKDHDIDYKDDDDKGAAHHHHHH |
| 317 T017000046 | EVQLVESGGGLVQPGGSLRLSCAASGSVHKINFLGWYRQAPGKERGLVATITIGDTTDYADYAKGRFTISRDEARNMVYLQMNSLKPE<br>DTAVYFCRAGSRLYPYNYWGQGTLVTVSSGGGGSGGGGSGGGGSGGGGSGGGGSGGGGSGGGGSEVQLVESGGGLVQPGGSLRLSCTF<br>SGGTFSSYTMGWFRQAPGKEREFVAEVRWGGVTTYSNSLKDRFSISEDSVKNAVYLQMNSLKPEDTAVYYCAAVRQMYMTVVPDYWGQ<br>GTLVTVSSGAADYKDHDGDYKDHDIDYKDDDDKGAAHHHHHH |
| 318 T017000049 | EVQLVESGGGLVQPGGSLRLSCAASGDVHKINILGWYRQAPAKEREMVAHITIGDATDYADSAKGRFTISRDEAKNMVYLQMNSLKPE<br>DTAVYLCRAYSRIYPYNYWGQGTLVTVSSGGGGSGGGGSGGGGSGGGGSGGGGSGGGGSGGGGSEVQLVESGGGLVQPGGSLRLSCTF<br>SGGTFSSYTMGWFRQAPGKEREFVAEVRWGGVTTYSNSLKDRFSISEDSVKNAVYLQMNSLKPEDTAVYYCAAVRQMYMTVVPDYWGQ<br>GTLVTVSSGAADYKDHDGDYKDHDIDYKDDDDKGAAHHHHHH |
| 319 T017000050 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CVASGDVHKINFLGWYRQAPGKEREKVAHISIGDQTDYADSAKGRFTISRDESKNMVYLQMNSLKPEDTAVYFCRAFSRIYPYDYWGQ<br>GTLVTVSSGAADYKDHDGDYKDHDIDYKDDDDKGAAHHHHHH |
| 320 T017000051 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CAASGEIGRINFYRWYRQAPGNQREVVATITIADKTDYADSAKGRFTISRDESRNMVYLQMSSLKPEDTAVYFCHAGSRLYPYDYWGQ<br>GTLVTVSSGAADYKDHDGDYKDHDIDYKDDDDKGAAHHHHHH |
| 321 T017000054 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CVASGDVHKINFLGWYRQAPGKEREKVAHITIGDQADYADSAKGRFTISRDEAKNMVYLQMNSLKPEDTAVYFCRAGSRIYPYDYWGQ<br>GTLVTVSSGAADYKDHDGDYKDHDIDYKDDDDKGAAHHHHHH |
| 322 T017000055 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CAASGDVHKINILGWYRQAPAKEREMVAHITIGDATDYADSAKGRFTISRDEAKNMVYLQMNSLKPEDTAVYFCRAYSRIYPYNYWGQ<br>GTLVTVSSGAADYKDHDGDYKDHDIDYKDDDDKGAAHHHHHH |
| 323 T017000058 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CAASGSVHKINFLGWYRQAPGKERELVATITIGDTTDYADSAKGRFTISRDEAKNMVYLQMNSLKPEDTAVYFCRAGSRLYPYNYWGQ<br>GTLVTVSSGAADYKDHDGDYKDHDIDYKDDDDKGAAHHHHHH |
| 324 T017000060 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CAASGSVHKINFLGWYRQAPGKERGLVATITIGDTTDYADYAKGRFTISRDEARNMVYLQMNSLKPEDTAVYFCRAGSRLYPYNYWGQ<br>GTLVTVSSGAADYKDHDGDYKDHDIDYKDDDDKGAAHHHHHH |
| 325 T017000063 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CAASGDVYKINFLGWHRQAPGKEREKVAHITIGDATDYADSAKGRFTISRDEAKNMVTLQMNSLKPEDTAVYFCRAGSRIYPYDYWGQ<br>GTLVTVSSGAADYKDHDGDYKDHDIDYKDDDDKGAAHHHHHH |
| 326 T017000064 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CAASGEVYKINFLGWYRQAPGKEREKVAHITIADAADYADFAKGRFTISRDEAKNMVYLQMNSLRPEDTAVYFCRAGSRIWPYDYWGQ<br>GTLVTVSSGAADYKDHDGDYKDHDIDYKDDDDKGAAHHHHHH |

TABLE A-5-continued

Sequences of multispecific polypeptides (with and without tags).

| SEQID | Sequence |
|---|---|
| 327 T017000065 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGDLVQPGGSLRLS<br>CAASGDVHKINFLGWYRQAPGKEREMVAHITIADATDYAEFAKGRFTISRDEPKNMVYLQMNSLKPEDTAVYLCRAGSRIYPYNYWGQ<br>GTLVTVSSGAADYKDHDGDYKDHDIDYKDDDDKGAAHHHHHH |
| 328 T017000068 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CITSGETFKINIWGWYRQAPGKQRELVASLTIGGATNYADSVKGRFTISEDSAKNTVYLQMNSLKPEDTAVYFCNAKSRLYPYDYWGQ<br>GTLVTVSSGAADYKDHDGDYKDHDIDYKDDDDKGAAHHHHHH |
| 329 T017000069 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CAASGSVHLLNFLGWYRQAPGKEREMVAHITIADATDYAHFAKGRFTISRDEAKNMVYLQMNSLRPEDTAVYFCRAGSRIYPYDYWGQ<br>GTLVTVSSGAADYKDHDGDYKDHDIDYKDDDDKGAAHHHHHH |
| 330 T017000070 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CITSGETFKINIWGWYRQAPGKQRELVASLTIGGATDYADSVKGRFTISEDSAKNTVYLQMNSLKAEDTAVYFCNAKSRLYPYDYWGQ<br>GTLVTVSSGAADYKDHDGDYKDHDIDYKDDDDKGAAHHHHHH |
| 331 T017000073 | EVQLVESGGGLVQPGGSLRLSCAASGDVHKINILGWYRQAPAKEREMVAHITIGDATSYADSAKGRFTISRDEAKNMVYLQLNNLKPE<br>DTAVYFCRAYSRIYPYNYWGQGTLVTVSSGGGGSGGGGSGGGGSGGGGSGGGGSGGGGSGGGGSEVQLVESGGGLVQPGGSLRLSCTF<br>SGGTFSSYTMGWFRQAPGKEREFVAEVRWGGVTTYSNSLKDRFSISEDSVKNAVYLQMNSLKPEDTAVYYCAAVRQMYMTVVPDYWGQ<br>GTLVTVSSGAADYKDHDGDYKDHDIDYKDDDDKGAAHHHHHH |
| 332 T017000074 | EVQLVESGGGLVQPGGSLRLSCVASGDVHKINFLGWYRQAPGKEREKVAHISIGDQTDYADSAKGRFTISRDESKNMVYLQMNSLKPE<br>DTAVYFCRAFSRIYPYDYWGQGTLVTVSSGGGGSGGGGSGGGGSGGGGSGGGGSGGGGSGGGGSEVQLVESGGGLVQPGGSLRLSCTF<br>SGGTFSSYTMGWFRQAPGKEREFVAEVRWGGVTTYSNSLKDRFSISEDSVKNAVYLQMNSLKPEDTAVYYCAAVRQMYMTVVPDYWGQ<br>GTLVTVSSGAADYKDHDGDYKDHDIDYKDDDDKGAAHHHHHH |
| 333 T017000075 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CAASGDVHKINILGWYRQAPAKEREMVAHITIGDATSYADSAKGRFTISRDEAKNMVYLQLNNLKPEDTAVYFCRAYSRIYPYNYWGQ<br>GTLVTVSSGAADYKDHDGDYKDHDIDYKDDDDKGAAHHHHHH |
| 334 T017000076 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CVASGDVHKINFLGWYRQAPGKEREKVAHISIGDQTDYADSAKGRFTISRDESKNMVYLQMNSLKPEDTAVYFCRAFSRIYPYDYWGQ<br>GTLVTVSSGAADYKDHDGDYKDHDIDYKDDDDKGAAHHHHHH |
| 335 T017000077 | EVQLVESGGDLVQPGGSLRLSCAASGDVHKINFLGWYRQAPGKEREMVAHITIADATDYAEFAKGRFTISRDEPKNMVYLQMNSLKPE<br>DTAVYLCRAGSRIYPYNYWGQGTLVTVSSGGGGSGGGGSGGGGSGGGGSGGGGSGGGGSGGGGSEVQLVESGGGLVQPGGSLRLSCTF<br>SGGTFSSYTMGWFRQAPGKEREFVAEVRWGGVTTYSNSLKDRFSISEDSVKNNAVYLQMNSLKPEDTAVYYCAAVRQMYMTVVPDYWG<br>QGTLVTVSSGAADYKDHDGDYKDHDIDYKDDDDKGAAHHHHHH |
| 336 T017000078 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CAASGDVHKINILGWYRQAPAKEREMVAHITIGDATDYADSAKGRFTISRDEAKNMVYLQMNSLKPEDTAVYLCRAYSRIYPYNYWGQ<br>GTLVTVSSGAADYKDHDGDYKDHDIDYKDDDDKGAAHHHHHH |
| 337 T017000079 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLKLS<br>CAASGAVHKINFLGWYRQTPEKEREMVATITIGDEVDYADSAKGRFTISRDEAKNMVYLQMTSLKPEDTAVYVCRAGSRLYPYNYWGQ<br>GTLVTVSSGAADYKDHDGDYKDHDIDYKDDDDKGAAHHHHHH |
| 338 T017000083 | DVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CAASGDVHKINILGWYRQAPAKEREMVAHITIGDATDYADSAKGRFTISRDEAKNMVYLQMNSLKPEDTAVYFCRAYSRIYPYNYWGQ<br>GTLVTVSSA |
| 339 T017000088 | DVQLVESGGGLVQAGDSLRLSCAASGRTFSSYAMGWFRQAPGKEREFVAAISWSDGSTYYADSVKGRFTISRDNAKNTVYLQMNSLKP<br>EDTAVYYCAADLTSTNPGSYIYIWAYDYWGQGTQVTVSSGGGGSGGGGSGGGGSGGGGSGGGGSGGGGSGGGGSEVQLVESGGGLVQP<br>GGSLRLSCAASGDVHKINILGWYRQAPAKEREMVAHITIGDATDYADSAKGRFTISRDEAKNMVYLQMNSLKPEDTAVYFCRAYSRIY<br>PYNYWGQGTLVTVSSA |
| 340 T017000093 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CVASGDVHKINFLGWYRQAPGKEREKVAHISIGDQTDYADSAKGRFTISRDESKNMVYLQMNSLKPEDTAVYFCRAFSRIYPYDYWGQ<br>GTLVTVSSGGGGSGGGGSGGGGSGGGGSGGGGSGGGGSGGGGSEVQLVESGGGLVQPGNSLRLSCAASGFTFSSFGMSWVRQAPGKGL<br>EWVSSISGSGSDTLYADSVKGRFTISRDNAKTTLYLQMNSLRPEDTAVYYCTIGGSLSRSSQGTLVTVSSGAADYKDHDGDYKDHDID<br>YKDDDDKGAAHHHHHH |
| 341 T017000095 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CITSGETFKINIWGWYRQAPGKQRELVASLTIGGATNYADSVKGRFTISEDSAKNTVYLQMNSLKPEDTAVYFCNAKSRLYPYDYWGQ |

TABLE A-5-continued

Sequences of multispecific polypeptides (with and without tags).

| SEQID | | Sequence |
|---|---|---|
| | | GTLVTVSSGGGGSGGGGSGGGGSGGGGSGGGGSGGGGSEVQLVESGGGLVQPGNSLRLSCAASGFTFSSFGMSWVRQAPGKGL<br>EWVSSISGSGSDTLYADSVKGRFTISRDNAKTTLYLQMNSLRPEDTAVYYC-<br>TIGGSLSRSSQGTLVTVSSGAADYKDHDGDYKDHDIDYKDDDDKGAAHHHHHH |
| 342 | T017000102 | EVQLVESGGGLVQAGGSLRLSCAASGITFSINTMGWYRQAPGKQRELVALISSIGDTYYADSVKGRFTISRDNAKNTVYLQMNSLKPE<br>DTAVYYCKRFRTAAQGTDYWGQGTLVTVSSGGGGSGGGGSGGGGSGGGGSGGGGSGGGGSGGGGSEVQLVESGGGLVQPGGSLRLSCV<br>ASGDVHKINFLGWYRQAPGKEREKVAHISIGDQTDYADSAKGRFTISRDESKNMVYLQMNSLKPEDTAVYFCRAFSRIYPYDYWGQGT<br>LVTVSSGAADYKDHDGDYKDHDIDYKDDDDKGAAHHHHHH |
| 343 | T017000103 | EVQLVESGGGLVQPGGSLRLSCVASGDVHKINFLGWYRQAPGKEREKVAHISIGDQTDYADSAKGRFTISRDESKNMVYLQMNSLKPE<br>DTAVYFCRAFSRIYPYDYWGQGTLVTVSSGGGGSGGGGSGGGGSGGGGSGGGGSGGGGSGGGGSEVQLVESGGGLVQAGGSLRLSCAA<br>SGITFSINTMGWYRQAPGKQRELVALISSIGDTYYADSVKGRFTISRDNAKNTVYLQMNSLKPEDTAVYYCKRFRTAAQGTDYWGQGT<br>LVTVSSGAADYKDHDGDYKDHDIDYKDDDDKGAAHHHHHH |
| 387 | T017000104 | DVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSEVQLVESGGGLVQPGGSLRLS<br>CAASGDVHKINILGWYRQAPAKEREMVAHITIGDATDYADSAKGRFTISRDEAKNMVYLQMNSLKPEDTAVYFCRAYSRIYPYNYWGQ<br>GTLVTVSSGGGGSGGGGSGGGGSGGGGSGGGGSGGGGSEVQLVESGGGLVQPGNSLRLSCAASGFTFSSFGMSWVRQAPGKGL<br>EWVSSISGSGSDTLYADSVKGRFTISRDNAKTTLYLQMNSLRPEDTAVYYCTIGGSLSRSSQGTLVTVSSA |
| 388 | T017000105 | DVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CVASGDVHKINFLGWYRQAPGKEREKVAHISIGDQTDYADSAKGRFTISRDESKNMVYLQMNSLKPEDTAIVYFCRAFSRIYPYDYWG<br>QGTLVTVSSA |
| 389 | T017000106 | DVQLVESGGGLVQAGDSLRLSCAASGRTFSSYAMGWFRQAPGKEREFVAAISWSDGSTYYADSVKGRFIISRDNAKNTVYLQMNSLKP<br>EDTAVYYCAADLTSTNPGSYIYIWAYDYWGQGTQVTVSSGGGGSGGGGSGGGGSGGGGSGGGGSGGGGSGGGGSEVQLVESGGGLVQP<br>GGSLRLSCAASGDVHKINILGWYRQAPAKEREMVAHITIGDATDYADSAKGRFTISRDEAKNMVYLQMNSLKPEDTAVYFCRAYSRIY<br>PYNYWGQGTLVTVSSGGGGSGGGGSGGGGSGGGGSGGGGSGGGGSGGGGSEVQLVESGGGLVQPGNSLRLSCAASGFTFSSFGMSWVR<br>QAPGKGLEWVSSISGSGSDTLYADSVKGRFTISRDNAKTTLYLQMNSLRPEDTAVYYCTIGGSLSRSSQGTLVTVSSA |
| 390 | T017000107 | EVQLVESGGGLVQAGGSLRLSCAASGRTFSSYVMGWFRQATGKEREFVATIAWDSGSTYYADSVKGRFTISRDNAKNTVHLQMNSLKP<br>EDTAVYYCAASYNVYYNNYYYPISRDEYDYWGQGTLVTVSSGGGGSGGGGSGGGGSGGGGSGGGGSGGGGSEVQLVESGGGSV<br>QAGGSLRLSCAASGDTYGSYWMGWFRQAPGKEREGVAAINRGGYTVYADSVKGRFTISRDTAKNTVYLQMNSLRPDDTADYYCAASG<br>VLGGLHEDWFNYWGQGTLVTVSSGGGGSGGGGSGGGGSGGGGSGGGGSGGGGSGGGGSEVQLVESGGGLVQPGGSLRLSCVASGDVHK<br>INFLGWYRQAPGKEREKVAHISIGDQTDYADSAKGRFTISRDESKNMVYLQMNSLKPEDTAVYFCRAFSRIYPYDYWGQGTLVTVSSG<br>AADYKDHDGDYKDHDIDYKDDDDKGAAHHHHHH |
| 391 | T017000109 | EVQLVESGGGSVQAGGSLRLSCAASGYTIGPYCMGWFRQAPGKEREGVAAINMGGGITYYADSVTCGRFTISQDNAKNTWLLMNSLEP<br>EDTAIYYCAADSTIYASYYECGHGLSTGGYGYDSWGQGTLVTVSSGGGGSGGGGSGGGGSGGGGSGGGGSGGGGSGGGGSEVQLVESG<br>GGSVQAGGSLRLSCAASGDTYGSYWMGWFRQAPGKEREGVAAINRGGGYTVYADSVKGRFTISRDTAKNTVYLQMNSLRPDDTADYYC<br>AASGVLGGLHEDWFNYWGQGTLVTVSSGGGGSGGGGSGGGGSGGGGSGGGGSGGGGSEVQLVESGGGLVQPGGSLRLSCVASG<br>DVHKINFLGWYRQAPGKEREKVAHISIGDQTDYADSAKGRFTISRDESKNMVYLQMNSLKPEDTAVYFCRAFSRIYPYDYWGQGTLVT<br>VSSGAADYKDHDGDYKDHDIDYKDDDDKGAAHHHHHH |
| 392 | T017000110 | EVQLVESGGGLVQAGGSLRLSCAASGRTFSSYVMGWFRQATGKEREFVATIAWDSGSTYYADSVKGRFTISRDNAKNTVHLQMNSLKP<br>EDTAVYYCAASYNVYYNNYYYPISRDEYDYWGQGTLVTVSSGGGGSGGGGSGGGGSGGGGSGGGGSGGGGSGGGGSEVQLVESGGGSV<br>QAGGSLRLSCAASGYTIGPYCMGWFRQAPGKEREGVAAINMGGGITYYADSVKGRFTISQDNAKNTVYLLMNSLEPEDTAIYYCAADS<br>TIYASYYECGHGLSTGGYGYDSWGQGTLVTVSSGGGGSGGGGSGGGGSGGGGSGGGGSGGGGSGGGGSEVQLVESGGGLVQPGGSLRL<br>SCVASGDVHKINFLGWYRQAPGKEREKVAHISIGDQTDYADSAKGRFTISRDESKNMVYLQMNSLKPEDTAVYFCRAFSRIYPYDYWG<br>QGTLVTVSSGAADYKDHDGDYKDHDIDYKDDDDKGAAHHHHHH |
| 413 | T017000001 | EVQLVESGGGLVQGGGSLSLSCAASGRTFSSYAMAWFRQPPGKEREFVASISWSGENTNYRNSVKGRFTISRDNAKNTVYLQMNSLKP<br>EDTAVYYCAAKIAKTYPDNWYWTKSNNYNYWGQGTLVTVSSGGGGSGGGGSGGGGSGGGGSGGGGSGGGGSGGGGSEVQLVESGGGLV<br>QGGGSLSLSCAASGRTFSSYAMAWFRQPPGKEREFVASISWSGENTNYRNSVKGRFTISRDNAKNTVYLQMNSLKPEDTAVYYCAAKI<br>AKTYPDNWYWTKSNNYNYWGQGTLVTVSS |
| 414 | T017000002 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSEVQLVESGGGLVQPGGSLRLSCAASGSVHKINFLGWYRQAPGKERGLVATI<br>TIGDTTDYADYAKGRFTISRDEARNMVYLQMNSLKPEDTAVYFCRAGSRLYPYNYWGQGTLVTVSS |
| 415 | T017000003 | EVQLQASGGGSVQAGGSLRLSCAASGYTIGPYCMGWFRQAPGKEREGVAAINMGGGITYYADSVKGRFTISQDNAKNTVYLLMNSLEP<br>EDTAIYYCAADSTIYASYYECGHGLSTGGYGYDSWGQGTQVTVSSGGGGSEVQLVESGGGLVQPGGSLRLSCAASGSVHKINFLGWYR<br>QAPGKERGLVATITIGDTTDYADYAKGRFTISRDEARNMVYLQMNSLKPEDTAVYFCRAGSRLYPYNYWGQGTLVTVSS |
| 416 | T017000006 | EVQLVESGGGLVQPGGSLRLSCTFSGGTFSSYIMGWFRQAPGKEREFVIAEVRWGGVTTYSNSLKDRFSISEDSVKNAVYLQMNSLKP<br>EDTAVYYCAAVRQMYMTVVPDYWGQGTLVTVSSGGGGSDVQLQASGGGSVQAGGSLRLSCAASGYTIGPYCMGWFRQAPGKEREGVAA<br>INMGGGITYYADSVKGRFTISQDNAKNTVYLLMNSLEPEDTAIYYCAADSTIYASYYECGHGLSTGGYGYDSWGQGTQVTVSS |
| 417 | T017000007 | EVQLVESGGGLVQPGGSLRLSCAASGSVHKINFLGWYRQAPGKERGLVATITIGDTTDYADYAKGRFTISRDEARNMVYLQMNSLKPE<br>DTAVYFCRAGSRLYPYNYWGQGTLVTVSSGGGGSEVQLVESGGGLVQPGGSLRLSCTFSGGTFSSYTMGWFRQAPGKEREFVAEVRWG<br>GVTTYSNSLKDRFSISEDSVKNAVYLQMNSLKPEDTAVYYCAAVRQMYMTVVPDYWGQGTLVTVSS |
| 418 | T017000008 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSEVQLVESGGGLVQPGGSLRLSCAASGSVHKINFLGWYRQAPGKERGL<br>VATITIGDTTDYADYAKGRFTISRDEARNMVYLQMNSLKPEDTAVYFCRAGSRLYPYNYWGQGTLVTVSS |

TABLE A-5-continued

Sequences of multispecific polypeptides (with and without tags).

| SEQID | Sequence |
|---|---|
| 419 T017000009 | EVQLQASGGGSVQAGGSLRLSCAASGYTIGPYCMGWFRQAPGKEREGVAAINMGGGITYYADSVKGRFIISQDNAKNTVYLLMNSLEP<br>EDTAIYYCAADSTIYASYYECGHGLSTGGYGYDSWGQGTQVTVSSGGGGSGGGSEVQLVESGGGLVQPGGSLRLSCAASGSVHKINFL<br>GWYRQAPGKERGLVATITIGDTTDYADYAKGRFTISRDEARNMVYLQMNSLKPEDTAVYFCRAGSRLYPYNYWGQGTLVTVSS |
| 420 T017000012 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSDVQLQASGGGSVQAGGSLRLSCAASGYTIGPYCMGWFRQAPGKEREG<br>VAAINMGGGITYYADSVKGRFTISQDNAKNTVYLLMNSLEPEDTAIYYCAADSTIYASYYECGHGLSTGGYGYDSWGQGTQVTVSS |
| 421 T017000013 | EVQLVESGGGLVQPGGSLRLSCAASGSVHKINFLGWYRQAPGKERGLVATITIGDTTDYADYAKGRFTISRDEARNMVYLQMNSLKPE<br>DTAVYFCRAGSRLYPYNYWGQGTLVTVSSGGGGSGGGSEVQLVESGGGLVQPGGSLRLSCTFSGGTFSSYTMGWFRQAPGKEREFVAE<br>VRWGGVTTYSNSLKDRFSISEDSVKMAVYLQMNSLKPEDTAVYYCAAVRQMYMTVVPDYWGQGTLVTVSS |
| 422 T017000014 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CAASGSVHKINFLGWYRQAPGKERGLVATITIGDTTDYADYAKGRFTISRDEARNMVYLQMNSLKPEDTAVYFCRAGSRLYPYNYWGQ<br>GTLVTVSS |
| 423 T017000015 | EVQLQASGGGSVQAGGSLRLSCAASGYTIGPYCMGWFRQAPGKEREGVAAINMGGGITYYADSVKGRFTISQDNAKNTVYLLMNSLEP<br>EDTAIYYCAADSTIYASYYECGHGLSTGGYGYDSWGQGTQVTVSSGGGGSGGGGSGGGGSGGGGSGGGGSGGGGSGGGGSEVQLVESG<br>GGLVQPGGSLRLSCAASGSVHKINFLGWYRQAPGKERGLVATITIGDTTDYADYAKGRFTISRDEARNMVYLQMNSLKPEDTAVYFCR<br>AGSRLYPYNYWGQGTLVTVSS |
| 424 T017000018 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSDVQLQASGGGSVQAGGSLRLS<br>CAASGYTIGPYCMGWFRQAPGKEREGVAAINMGGGITYYADSVKGRFTISQDNAKNTVYLLMNSLEPEDTAIYYCAADSTIYASYYEC<br>GHGLSTGGYGYDSWGQGTQVTVSS |
| 425 T017000019 | EVQLVESGGGLVQPGGSLRLSCAASGSVHKINFLGWYRQAPGKERGLVATITIGDTTDYADYAKGRFTISRDEARNMVYLQMNSLKPE<br>DTAVYFCRAGSRLYPYNYWGQGTLVTVSSGGGGSGGGGSGGGGSGGGGSGGGGSGGGGSGGGGSEVQLVESGGGLVQPGGSLRLSCTF<br>SGGTFSSYTMGWFRQAPGKEREFVAEVRWGGVTTYSNSLKDRFSISEDSVKNAVYLQMNSLKPEDTAVYYCAAVRQMYMTVVPDYWGQ<br>GTLVTVSS |
| 426 T017000023 | EVQLQASGGGSVQAGGSLRLSCAASGYTIGPYCMGWFRQAPGKEREGVAAINMGGGITYYADSVKGRFTISQDNAKNTVYLLMNSLEP<br>EDTAIYYCAADSTIYASYYECGHGLSTGGYGYDSWGQGTQVTVSSGGGGSGGGGSGGGGSGGGGSGGGGSGGGGSGGGGSEVQLVESG<br>GGLVQPGGSLRLSCTFSGGTFSSYTMGWFRQAPGKEREFVAEVRWGGVTTYSNSLKDRFSISEDSVKNAVYLQMNSLKPEDTAVYYCA<br>AVRQMYMTVVPDYWGQGTLVTVSS |
| 427 T017000025 | EVQLVESGGGLVQPGGSLRLSCAASGSVHKINFLGWYRQAPGKERGLVATITIGDTTDYADYAKGRFTISRDEARNMVYLQMNSLKPE<br>DTAVYFCRAGSRLYPYNYWGQGTLVTVSSGGGGSGGGGSGGGGSGGGGSGGGGSGGGGSGGGGSDVQLQASGGGSVQAGGSLRLSCAA<br>SGYTIGPYCMGWFRQAPGKEREGVAAINMGGGITYYADSVKGRFTISQDNAKNTVYLLMNSLEPEDTAIYYCAADSTIYASYYECGHG<br>LSTGGYGYDSWGQGTQVTVSS |
| 428 T017000029 | EVQLVESGGGLVQPGGSLRLSCAASGDVYKINFLGWHRQAPGKEREKVAHITIGDATDYADSAKGRFTISRDEAKNMVYLQMNSLKPE<br>DTAVYFCRAGSRIYPYDYWGQGTLVTVSSGGGGSGGGGSGGGGSGGGGSGGGGSGGGGSGGGGSEVQLVESGGGLVQPGGSLRLSCTF<br>SGGTFSSYTMGWFRQAPGKEREFVAEVRWGGVTTYSNSLKDRFSISEDSVKNAVYLQMNSLKPEDTAVYYCAAVRQMYMTVVPDYWGQ<br>GTLVTVSS |
| 429 T017000030 | EVQLVESGGGLVQPGGSLKLSCAASGAVHKINFLGWYRQTPEKEREMVATITIGDEVDYADSAKGRFTISRDEAKNMVYLQMTSLKPE<br>DTAVYFCRAGSRLYPYNYWGQGTLVTVSSGGGGSGGGGSGGGGSGGGGSGGGGSGGGGSGGGGSEVQLVESGGGLVQPGGSLRLSCTF<br>SGGTFSSYTMGWFRQAPGKEREFVAEVRWGGVTTYSNSLKDRFSISEDSVKNAVYLQMNSLKPEDTAVYYCAAVRQMYMTVVPDYWGQ<br>GTLVTVSS |
| 430 T017000031 | EVQLVESGGGLVQPGGSLRLSCITSGETFKINIWGWYRQAPGKQRELVASLTIGGATNYADSVKGRFTISEDSAKNTVYLQMNSLKPE<br>DTAVYFCNAKSRLYPYDYWGQGTLVTVSSGGGGSGGGGSGGGGSGGGGSGGGGSGGGGSGGGGSEVQLVESGGGLVQPGGSLRLSCTF<br>SGGTFSSYTMGWFRQAPGKEREFVAEVRWGGVTTYSNSLKDRFSISEDSVKNAVYLQMNSLKPEDTAVYYCAAVRQMYMTVVPDYWGQ<br>GTLVTVSS |
| 431 T017000032 | EVQLVESGGGLVQPGGSLRLSCAASGSVHLLNFLGWYRQAPGKEREMVAHITIADATDYAHFAKGRFTISRDEAKNMVYLQMNSLRPE<br>DTAVYFCRAGSRIYPYDYWGQGTLVTVSSGGGGSGGGGSGGGGSGGGGSGGGGSGGGGSGGGGSEVQLVESGGGLVQPGGSLRLSCTF<br>SGGTFSSYTMGWFRQAPGKEREFVAEVRWGGVTTYSNSLKDRFSISEDSVKNAVYLQMNSLKPEDTAVYYCAAVRQMYMTVVPDYWGQ<br>GTLVTVSS |
| 432 T017000033 | EVQLVESGGGLVQPGGSLRLSCITSGETFKINIWGWYRQAPGKQRELVASLTIGGATDYADSVKGRFTISEDSAKNTVYLQMNSLKAE<br>DTAVYFCNAKSRLYPYDYWGQGTLVTVSSGGGGSGGGGSGGGGSGGGGSGGGGSGGGGSGGGGSEVQLVESGGGLVQPGGSLRLSCTF<br>SGGTFSSYTMGWFRQAPGKEREFVAEVRWGGVTTYSNSLKDRFSISEDSVKNAVYLQMNSLKPEDTAVYYCAAVRQMYMTVVPDYWGQ<br>GTLVTVSS |
| 433 T017000035 | EVQLVESGGGLVQPGGSLRLSCAASGEVYKINFLGWYRQAPGKEREKVAHITIADAADYADFAKGRFTISRDEAKNMVYLQMNSLRPE<br>DTAVYFCRAGSRIWPYDYWGQGTLVTVSSGGGGSGGGGSGGGGSGGGGSGGGGSGGGGSGGGGSEVQLVESGGGLVQPGGSLRLSCTF<br>SGGTFSSYTMGWFRQAPGKEREFVAEVRWGGVTTYSNSLKDRFSISEDSVKNAVYLQMNSLKPEDTAVYYCAAVRQMYMTVVPDYWGQ<br>GTLVTVSS |
| 434 T017000037 | EVQLVESGGGLVQPGGSLRLSCVASGDVHKINFLGWYRQAPGKEREKVAHISIGDQTDYADSAKGRFTISRDESKNMVYLQMNSLKPE<br>DTAVYFCRAFSRIYPYDYWGQGTLVTVSSGGGGSGGGGSGGGGSGGGGSGGGGSGGGGSGGGGSEVQLVESGGGLVQPGGSLRLSCTF |

TABLE A-5-continued

Sequences of multispecific polypeptides (with and without tags).

| SEQID | Sequence |
|---|---|
| | SGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSS |
| 435 T017000038 | EVQLVESGGGLVQPGGSLRLSCAASGEIGRINFYRWYRQAPGNQREVVATITIADKTDYADSAKGRFTISRDESRNMVYLQMSSLKPEDTAVYFCHAGSRLYPYDYWGQGTLVTVSSGGGGSGGGGSGGGGSGGGGSGGGGSGGGGSGGGGSEVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSS |
| 436 T017000041 | EVQLVESGGGLVQPGGSLRLSCVASGDVHKINFLGWYRQAPGKEREKVAHITIGDQADYADSAKGRFTISRDEAKNMVYLQMNSLKPEDTAVYFCRAGSRIYPYDYWGQGTLVTVSSGGGGSGGGGSGGGGSGGGGSGGGGSGGGGSGGGGSEVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSS |
| 437 T017000042 | EVQLVESGGGLVQPGGSLRLSCAASGDVHKINILGWYRQAPAKEREMVAHITIGDATDYADSAKGRFTISRDEAKNMVYLQMNSLKPEDTAVYFCRAYSRIYPYNYWGQGTLVTVSSGGGGSGGGGSGGGGSGGGGSGGGGSGGGGSGGGGSEVQLVESGGGLVQPGGSLRLSCTFSGGTFSSYTMGWFRQAPGKEREFVAEVRWGGVTTYSNSLKDRFSISEDSVKNAVYLQKNSLKPEDTAVYYCAAVRQMYMTVVPDYWGQGTLVTVSS |
| 438 T017000044 | EVQLVESGGGLVQPGGSLRLSCAASGSVHKINFLGWYRQAPGKERELVATITIGDTTDYADSAKGRFTISRDEAKNMVYLQMNSLKPEDTAVYFCRAGSRLYPYNYWGQGTLVTVSSGGGGSGGGGSGGGGSGGGGSGGGGSGGGGSGGGGSEVQLVESGGGLVQPGGSLRLSCTFSGGTFSSYTMGWFRQAPGKEREFVAEVRWGGVTTYSNSLKDRFSISEDSVKNAVYLQKNSLKPEDTAVYYCAAVRQMYMTVVPDYWGQGTLVTVSS |
| 439 T017000046 | EVQLVESGGGLVQPGGSLRLSCAASGSVHKINFLGWYRQAPGKERGLVATITIGDTTDYADYAKGRFTISRDEARNMVYLQMNSLKPEDTAVYFCRAGSRLYPYNYWGQGTLVTVSSGGGGSGGGGSGGGGSGGGGSGGGGSGGGGSGGGGSEVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSS |
| 440 T017000049 | EVQLVESGGGLVQPGGSLRLSCAASGDVHKINILGWYRQAPAKEREMVAHITIGDATDYADSAKGRFTISRDEAKNMVYLQMNSLKPEDTAVYLCRAYSRIYPYNYWGQGTLVTVSSGGGGSGGGGSGGGGSGGGGSGGGGSGGGGSGGGGSEVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSS |
| 441 T017000050 | EVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSSGGGGSGGGGSGGGGSGGGGSGGGGSGGGGSGGGGSEVQLVESGGGLVQPGGSLRLSCVASGDVHKINFLGWYRQAPGKEREKVAHISIGDQTDYADSAKGRFTISRDESKNMVYLQMNSLKPEDTAVYFCRAFSRIYPYDYWGQGTLVTVSS |
| 442 T017000051 | EVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSSGGGGSGGGGSGGGGSGGGGSGGGGSGGGGSGGGGSEVQLVESGGGLVQPGGSLRLSCAASGEIGRINFYRWYRQAPGNQREVVATITIADKTDYADSAKGRFTISRDESRNMVYLQMSSLKPEDTAVYFCHAGSRLYPYDYWGQGTLVTVSS |
| 443 T017000054 | EVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSSGGGGSGGGGSGGGGSGGGGSGGGGSGGGGSGGGGSEVQLVESGGGLVQPGGSLRLSCVASGDVHKINFLGWYRQAPGKEREKVAHITIGDQADYADSAKGRFTISRDEAKNMVYLQMNSLKPEDTAVYFCRAGSRIYPYDYWGQGTLVTVSS |
| 444 T017000055 | EVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSSGGGGSGGGGSGGGGSGGGGSGGGGSGGGGSGGGGSEVQLVESGGGLVQPGGSLRLSCAASGDVHKINILGWYRQAPAKEREMVAHITIGDATDYADSAKGRFTISRDEAKNMVYLQMNSLKPEDTAVYFCRAYSRIYPYNYWGQGTLVTVSS |
| 445 T017000058 | EVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSSGGGGSGGGGSGGGGSGGGGSGGGGSGGGGSGGGGSEVQLVESGGGLVQPGGSLRLSCAASGSVHKINFLGWYRQAPGKERELVATITIGDTTDYADSAKGRFTISRDEAKNMVYLQMNSLKPEDTAVYFCRAGSRLYPYNYWGQGTLVTVSS |
| 446 T017000060 | EVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSSGGGGSGGGGSGGGGSGGGGSGGGGSGGGGSGGGGSEVQLVESGGGLVQPGGSLRLSCAASGSVHKINFLGWYRQAPGKERGLVATITIGDTTDYADYAKGRFTISRDEARNMVYLQMNSLKPEDTAVYFCRAGSRLYPYNYWGQGTLVTVSS |
| 447 T017000063 | EVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSSGGGGSGGGGSGGGGSGGGGSGGGGSGGGGSGGGGSEVQLVESGGGLVQPGGSLRLSCAASGDVYKINFLGWHRQAPGKEREKVAHITIGDATDYADSAKGRFTISRDEAKNMVYLQMNSLKPEDTAVYFCRAGSRIYPYDYWGQGTLVTVSS |
| 448 T017000064 | EVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSSGGGGSGGGGSGGGGSGGGGSGGGGSGGGGSGGGGSEVQLVESGGGLVQPGGSLRLSCAASGEVYKINFLGWYRQAPGKEREKVAHITIADAADYADFAKGRFTISRDEAKNMVYLQMNSLRPEDTAVYFCRAGSRIWPYDYWGQGTLVTVSS |
| 449 T017000065 | EVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSSGGGGSGGGGSGGGGSGGGGSGGGGSGGGGSGGGGSEVQLVESGGDLVQPGGSLRLS |

TABLE A-5-continued

Sequences of multispecific polypeptides (with and without tags).

| SEQID | Sequence |
|---|---|
| | CAASGDVHKINFLGWYRQAPGKEREMVAHITIADATDYAEFAKGRFTISRDEPKNMVYLQMNSLKPEDTAVYLCRAGSRIYPYNYWGQ<br>GTLVTVSS |
| 450 T017000068 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CITSGETFKINIWGWYRQAPGKQRELVASLTIGGATNYADSVKGRFTISEDSAKNTVYLQMNSLKPEDTAVYFCNAKSRLYPYDYWGQ<br>GTLVTVSS |
| 451 T017000069 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CAASGSVHLLNFLGWYRQAPGKEREMVAHITIADATDYAHFAKGRFTISRDEAKNMVYLQMNSLRPEDTAVYFCRAGSRIYPYDYWGQ<br>GTLVTVSS |
| 452 T017000070 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CITSGETFKINIWGWYRQAPGKQRELVASLTIGGATDYADSVKGRFTISEDSAKNTVYLQMNSLKAEDTAVYFCNAKSRLYPYDYWGQ<br>GTLVTVSS |
| 453 T017000073 | EVQLVESGGGLVQPGGSLRLSCAASGDVHKINILGWYRQAPAKEREMVAHITIGDATSYADSAKGRFTISRDEAKNMVYLQLNNLKPE<br>DTAVYFCRAYSRIYPYNYWGQGTLVTVSSGGGGSGGGGSGGGGSGGGGSGGGGSGGGGSGGGGSEVQLVESGGGLVQPGGSLRLSCTF<br>SGGTFSSYTMGWFRQAPGKEREFVAEVRWGGVTTYSNSLKDRFSISEDSVKNAVYLQMNSLKPEDTAVYYCAAVRQMYMTVVPDYWGQ<br>GTLVTVSS |
| 454 T017000074 | EVQLVESGGGLVQPGGSLRLSCVASGDVHKINFLGWYRQAPGKEREKVAHISIGDQTDYADSAKGRFTISRDESKNMVYLQMNSLKPE<br>DTAVYFCRAFSRIYPYDYWGQGTLVTVSSGGGGSGGGGSGGGGSGGGGSGGGGSGGGGSGGGGSEVQLVESGGGLVQPGGSLRLSCTF<br>SGGTFSSYTMGWFRQAPGKEREFVAEVRWGGVTTYSNSLKDRFSISEDSVKNAVYLQMNSLKPEDTAVYYCAAVRQMYMTVVPDYWGQ<br>GTLVTVSS |
| 455 T017000075 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CAASGDVHKINILGWYRQAPAKEREMVAHITIGDATSYADSAKGRFTISRDEAKNMVYLQLNNLKPEDTAVYFCRAYSRIYPYNYWGQ<br>GTLVTVSS |
| 456 T017000076 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CVASGDVHKINFLGWYRQAPGKEREKVAHISIGDQTDYADSAKGRFTISRDESKNMVYLQMNSLKPEDTAVYFCRAFSRIYPYDYWGQ<br>GTLVTVSS |
| 457 T017000077 | EVQLVESGGDLVQPGGSLRLSCAASGDVHKINFLGWYRQAPGKEREMVAHITIADATDYAEFAKGRFTISRDEPKNMVYLQMNSLKPE<br>DTAVYLCRAGSRIYPYNYWGQGTLVTVSSGGGGSGGGGSGGGGSGGGGSGGGGSGGGGSGGGGSEVQLVESGGGLVQPGGSLRLSCTF<br>SGGTFSSYTMGWFRQAPGKEREFVAEVRWGGVTTYSNSLKDRFSISEDSVKNAVYLQMNSLKPEDTAVYYCAAVRQMYMTVVPDYWGQ<br>GTLVTVSS |
| 458 T017000078 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CAASGDVHKINILGWYRQAPAKEREMVAHITIGDATDYADSAKGRFTISRDEAKNMVYLQMNSLKPEDTAVYLCRAYSRIYPYNYWGQ<br>GTLVTVSS |
| 459 T017000079 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLKLS<br>CAASGAVHKINFLGWYRQTPEKEREMVATITIGDEVDYADSAKGRFTISRDEAKNMVYLQMTSLKPEDTAVYVCRAGSRLYPYNYWGQ<br>GTLVTVSS |
| 460 T017000093 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CVASGDVHKINFLGWYRQAPGKEREKVAHISIGDQTDYADSAKGRFTISRDESKNMVYLQMNSLKPEDTAVYFCRAFSRIYPYDYWGQ<br>GTLVTVSSGGGGSGGGGSGGGGSGGGGSGGGGSGGGGSGGGGSEVQLVESGGGLVQPGNSLRLSCAASGFTFSSFGMSWVRQAPGKGL<br>EWVSSISGSGSDTLYADSVKGRFTISRDNAKTTLYLQMNSLRPEDTAVYYCTIGGSLSRSSQGTLVTVSS |
| 461 T017000095 | EVQLVESGGGLVQPGGSLRLSCTFSGGTFSSYTMGWFRQAPGKEREFVAEVRWGGVTTYSNSLKDRFSISEDSVKNAVYLQMNSLKPE<br>DTAVYYCAAVRQMYMTVVPDYWGQGTLVTVSSGGGGSGGGGSGGGGSGGGGSGGGGSGGGGSGGGGSEVQLVESGGGLVQPGGSLRLS<br>CITSGETFKINIWGWYRQAPGKQRELVASLTIGGATNYADSVKGRFTISEDSAKNTVYLQMNSLKPEDTAVYFCNAKSRLYPYDYWGQ<br>GTLVTVSSGGGGSGGGGSGGGGSGGGGSGGGGSGGGGSGGGGSEVQLVESGGGLVQPGNSLRLSCAASGFTFSSFGMSWVRQAPGKGL<br>EWVSSISGSGSDTLYADSVKGRFTISRDNAKTTLYLQMNSLRPEDTAVYYCTIGGSLSRSSQGTLVTVSS |
| 462 T017000102 | EVQLVESGGGLVQAGGSLRLSCAASGITFSINTMGWYRQAPGKQRELVALISSIGDTYYADSVKGRFTISRDNAKNTVYLQMNSLKPE<br>DTAVYYCKRFRTAAQGTDYWGQGTLVTVSSGGGGSGGGGSGGGGSGGGGSGGGGSGGGGSGGGGSEVQLVESGGGLVQPGGSLRLSCV<br>ASGDVHKINFLGWYRQAPGKEREKVAHISIGDQTDYADSAKGRFTISRDESKNMVYLQMNSLKPEDTAVYFCRAFSRIYPYDYWGQGT<br>LVTVSS |
| 463 T017000103 | EVQLVESGGGLVQPGGSLRLSCVASGDVHKINFLGWYRQAPGKEREKVAHISIGDQTDYADSAKGRFTISRDESKNMVYLQMNSLKPE<br>DTAVYFCRAFSRIYPYDYWGQGTLVTVSSGGGGSGGGGSGGGGSGGGGSGGGGSGGGGSGGGGSEVQLVESGGGLVQAGGSLRLSCAA<br>SGITFSINTMGWYRQAPGKQRELVALISSIGDTYYADSVKGRFTISRDNAKNTVYLQMNSLKPEDTAVYYCKRFRTAAQGTDYWGQGT<br>LVTVSS |

TABLE A-5-continued

Sequences of multispecific polypeptides (with and without tags).

| SEQID | Sequence |
|---|---|
| 464 T017000107 | EVQLVESGGGLVQAGGSLRLSCAASGRTFSSYVMGWFRQATGKEREFVATIAWDSGSTYYADSVKGRFTISRDNAKNTVHLQMNSLKP EDTAVYYCAASYNVYYNNYYYPISRDEYDYWGQGTLVTVSSGGGGSGGGGSGGGGSGGGGSGGGGSGGGGSGGGGSEVQLVESGGGSV QAGGSLRLSCAASGDTYGSYWMGWFRQAPGKEREGVAAINRGGGYTVYADSVKGRFTISRDTAKNTVYLQMNSLRPDDTADYYCAASG VLGGLHEDWFNYWGQGTLVTVSSGGGGSGGGGSGGGGSGGGGSGGGGSGGGGSGGGGSEVQLVESGGGLVQPGGSLRLSCVASGDVHK INFLGWYRQAPGKEREKVAHISIGDQTDYADSAKGRFTISRDESKNMVYLQMNSLKPEDTAVYFCRAFSRIYPYDYWGQGTLVTVSS |
| 465 T017000109 | EVQLVESGGGSVQAGGSLRLSCAASGYTIGPYCMGWFRQAPGKEREGVAAINMGGGITYYADSVKGRFTISQDNAKNTVYLLMNSLEP EDTAIYYCAADSTIYASYYECGHGLSTGGYGYDSWGQGTLVTVSSGGGGSGGGGSGGGGSGGGGSGGGGSGGGGSGGGGSEVQLVESG GGSVQAGGSLRLSCAASGDTYGSYWMGWFRQAPGKEREGVAAINRGGGYTVYADSVKGRFTISRDTAKNTVYLQMNSLRPDDTADYYC AASGVLGGLHEDWFNYWGQGTLVTVSSGGGGSGGGGSGGGGSGGGGSGGGGSGGGGSGGGGSEVQLVESGGGLVQPGGSLRLSCVASG DVHKINFLGWYRQAPGKEREKVAHISIGDQTDYADSAKGRFTISRDESKNMVYLQKNSLKPEDTAVYFGRAFSRIYPYDYWGQGTLVT VSS |
| 466 T017000110 | EVQLVESGGGLVQAGGSLRLSCAASGRTFSSYVMGWFRQATGKEREFVATIAWDSGSTYYADSVKGRFTISRDNAKNTVHLQMNSLKP EDTAVYYCAASYNVYYNNYYYPISRDEYDYWGQGTLVTVSSGGGGSGGGGSGGGGSGGGGSGGGGSGGGGSGGGGSEVQLVESGGGSV QAGGSLRLSCAASGYTIGPYCMGWFRQAPGKEREGVAAINMGGGITYYADSVKGRFTISQDNAKNTVYLLMNSLEPEDTAIYYCAADS TIYASYYECGHGLSTGGYGYDSWGQGTLVTVSSGGGGSGGGGSGGGGSGGGGSGGGGSGGGGSGGGGSEVQLVESGGGLVQPGGSLRL SCVASGDVHKINFLGWYRQAPGKEREKVAHISIGDQTDYADSAKGRFTISRDESKNMVYLQMNSLKPEDTAVYFCRAFSRIYPYDYWG QGTLVTVSS |
| 467 T017000104 | DVQLVESGGGLVQPGGSLRLSCTFSGGTFSSYTMGWFRQAPGKEREFVAEVRWGGVTTYSNSLKDRFSISEDSVKNAVYLQMNSLKPE DTAVYYCAAVRQMYMTVVPDYWGQGTLVTVSSGGGGSGGGGSGGGGSGGGGSGGGGSGGGGSGGGGSEVQLVESGGGLVQPGGSLRLS CAASGDVHKINILGWYRQAPAKEREMVAHITIGDATDYADSAKGRFTISRDEAKNMVYLQMNSLKPEDTAVYFCRAYSRIYPYNYWGQ GTLVTVSSGGGGSGGGGSGGGGSGGGGSGGGGSGGGGSGGGGSEVQLVESGGGLVQPGNSLRLSCAASGFTFSSFGMSWVRQAPGKGL EWVSSISGSGSDTLYADSVKGRFTISRDNAKTTLYLQMNSLRPEDTAVYYCTIGGSLSRSSQGTLVTVSS |
| 468 T017000105 | DVQLVESGGGLVQPGGSLRLSCTFSGGTFSSYTMGWFRQAPGKEREFVAEVRWGGVTTYSNSLKDRFSISEDSVKNAVYLQMNSLKPE DTAVYYCAAVRQMYMTVVPDYWGQGTLVTVSSGGGGSGGGGSGGGGSGGGGSGGGGSGGGGSGGGGSEVQLVESGGGLVQPGGSLRLS CVASGDVHKINFLGWYRQAPGKEREKVAHISIGDQTDYADSAKGRFTISRDESKNMVYLQMNSLKPEDTAVYFCRAFSRIYPYDYWGQ GTLVTVSS |
| 469 T017000106 | DVQLVESGGGLVQAGDSLRLSCAASGRTFSSYAMGWFRQAPGKEREFVAAISWSDGSTYYADSVKGRFTISRDNAKNTVYLQMNSLKP EDTAVYYCAADLTSTNPGSYIYIWAYDYWGQGTQVTVSSGGGGSGGGGSGGGGSGGGGSGGGGSGGGGSGGGGSEVQLVESGGGLVQP GGSLRLSCAASGDVHKINILGWYRQAPAKEREMVAHITIGDATDYADSAKGRFTISRDEAKNMVYLQMNSLKPEDTAVYFCRAYSRIY PYNYWGQGTLVTVSSGGGGSGGGGSGGGGSGGGGSGGGGSGGGGSGGGGSEVQLVESGGGLVQPGNSLRLSCAASGFTFSSFGMSWVR QAPGKGLEWVSSISGSGSDTLYADSVKGRFTISRDNAKTTLYLQMNSLRPEDTAVYYCTIGGSLSRSSQGTLVTVSS |
| 470 T017000083 | DVQLVESGGGLVQPGGSLRLSCTFSGGTFSSYTMGWFRQAPGKEREFVAEVRWGGVTTYSNSLKDRFSISEDSVKNAVYLQMNSLKPE DTAVYYCAAVRQMYMTVVPDYWGQGTLVTVSSGGGGSGGGGSGGGGSGGGGSGGGGSGGGGSGGGGSEVQLVESGGGLVQPGGSLRLS CAASGDVHKINILGWYRQAPAKEREMVAHITIGDATDYADSAKGRFTISRDEAKNMVYLQMNSLKPEDTAVYFCRAYSRIYPYNYWGQ GTLVTVSS |
| 471 T017000088 | DVQLVESGGGLVQAGDSLRLSCAASGRTFSSYAMGWFRQAPGKEREFVAAISWSDGSTYYADSVKGRFTISRDNAKNTVYLQMNSLKP EDTAVYYCAADLTSTNPGSYIYIWAYDYWGQGTQVTVSSGGGGSGGGGSGGGGSGGGGSGGGGSGGGGSGGGGSEVQLVESGGGLVQP GGSLRLSCAASGDVHKINILGWYRQAPAKEREMVAHITIGDATDYADSAKGRFTISRDEAKNMVYLQMNSLKPEDTAVYFCRAYSRIY PYNYWGQGTLVTVSS |
| 486 T017000108 | EVQLVESGGGLVQAGGSLRLSCAASGRTFSSYVMGWFRQATGKEREFVATIAWDSGSTYYADSVKGRFTISRDNAKNTVHLQMNSLKP EDTAVYYCAASYNVYYNNYYYPISRDEYDYWGQGTLVTVSSGGGGSGGGGSGGGGSGGGGSGGGGSGGGGSGGGGSEVQLVESGGGSV QAGGSLRLSCAASGDTYGSYWMGWFRQAPGKEREGVAAINRGGGYTVYADSVKGRFTISRDTAKNTVYLQMNSLRPDDTADYYCAASG VLGGLHEDWFNYWGQGTLVTVSSGGGGSGGGGSGGGGSGGGGSGGGGSGGGGSGGGGSEVQLVESGGGLVQPGGSLRLSCVASGDVHK INFLGWYRQAPGKEREKVAHISIGDQTDYADSAKGRFTISRDESKNMVYLQMNSLKPEDTAVYFCRAFSRIYPYDYWGQGTLVTVSSG GGGSGGGGSGGGGSGGGGSGGGGSGGGGSGGGGSEVQLVESGGGLVQPGNSLRLSCAASGFTFSSFGMSWVRQAPGKGLEWVSSISGS GSDTLYADSVKGRFTISRDNAKTTLYLQMNSLRPEDTAVYYCTIGGSLSRSSQGTLVTVSSGAADYKDHDGDYKDHDIDYKDDDDKGA AHHHHHH |
| 487 T017000108 | EVQLVESGGGLVQAGGSLRLSCAASGRTFSSYVMGWFRQATGKEREFVATIAWDSGSTYYADSVKGRFTISRDNAKNTVHLQMNSLKP EDTAVYYCAASYNVYYNNYYYPISRDEYDYWGQGTLVTVSSGGGGSGGGGSGGGGSGGGGSGGGGSGGGGSGGGGSEVQLVESGGGSV QAGGSLRLSCAASGDTYGSYWMGWFRQAPGKEREGVAAINRGGGYTVYADSVKGRFTISRDTAKNTVYLQMNSLRPDDTADYYCAASG VLGGLHEDWFNYWGQGTLVTVSSGGGGSGGGGSGGGGSGGGGSGGGGSGGGGSGGGGSEVQLVESGGGLVQPGGSLRLSCVASGDVHK INFLGWYRQAPGKEREKVAHISIGDQTDYADSAKGRFTISRDESKNMVYLQMNSLKPEDTAVYFCRAFSRIYPYDYWGQGTLVTVSSG GGGSGGGGSGGGGSGGGGSGGGGSGGGGSGGGGSEVQLVESGGGLVQPGNSLRLSCAASGFTFSSFGMSWVRQAPGKGLEWVSSISGS GSDTLYADSVKGRFTISRDNAKTTLYLQMNSLRPEDTAVYYCTIGGSLSRSSQGTLVTVSS |

"SEQ" refers to the given SEQ ID NO;
"ID" refers to identification name;
"Sequence" denotes amino acid sequence

TABLE A-6

Sequences of components of TCR complex.

| SEQID | SEQUENCE |
|---|---|
| 344 Human CD3 delta (P04234) | MEHSTFLSGLVLATLLSQVSPFKIPIEELEDRVFVNCNTSITWVEGTVGTLLSDITRLDLGKRILDPRGIYRCNGTDIYKDKE STVQVHYRMCQSCVELDPATVAGIIVTDVIATLLLALGVFCFAGHETGRLSGAADTQALLRNDQVYQPLRDRDDAQYSHLGGN WARNK |
| 345 Human CD3 gamma (P09693) | MEQGKGLAVLILAIILLQGTLAQSIKGNHLVKVYDYQEDGSVLLTCDAEAKNITWFKDGKMIGFLTEDKKKWNLGSNAKDPRG MYQCKGSQNKSKPLQVYYRMCQNCIELNAATISGFLFAEIVSIFVLAVGVYFIAGQDGVRQSRASDKQTLLPNDQLYQPLKDR EDDQYSHLQGNQLRRN |
| 346 Human CD3 epsilon (P07766) | MQSGTHWRVLGLCLLSVGVWGQDGNEEMGGITQTPYKVSISGTTVILTCPQYPGSEILWQHNDKNIGGDEDDKNIGSDEDHLS LKEFSELEQSGYYVCYPRGSKPEDANFYLYLRARVCENCMEMDVMSVATIVIVDICITGGLLLLVYYWSKNRKAKAKPVTRGA GAGGRQRGQNKERPPPVPNPDYEPIRKGQRDLYSGLNQRRI |
| 347 Human CD3 zeta (P20963) | MKWKALFTAAILQAQLPITEAQSFGLLDPKLCYLLDGILFIYGVILTALFLRVKFSRSADAPAYQQGQNQLYNELNLGRREEY DVLDKRRGRDPEMGGKPQRRKNPQEGLYNELQKDKMAEAYSEIGMKGERRRGKGHDGLYQGLSTATKDTYDALHMQALPPR |
| 348 Human TCR alpha constant domain (P01848) | PNIQNPDPAVYQLRDSKSSDKSVCLFTDFDSQTNVSQSKDSDVYITDKTVLDMRSMDFKSNSAVAWSNKSDFACANAFNNSII PEDTFFPSPESSCDVKLVEKSFETDTNFRILLLKVAGFNLLMTLRLWSSLNFQNLSVIG |
| 349 Human TCR beta constant domain (P01850) | EDLNKVFPPEVAVFEPSEAEISHTQKATLVCLATGFFPDHVELSWWVNGKEVHSGVSTDPQPLKEQPALNDSRYCLSSRLRVS ATFWQNPRNHFRCQVQFYGLSENDEWTVSAEAWGRADCGFTSVSYQQGVLSATILYEILLGKATLYAVLVSALVLMAMVKRKD FQDRAKPVTQI |
| 393 Human TCR alpha variable domain derived from 2IAN | IQVEQSPPDLILQEGANSTLRCNFSDSVNNLQWFHQNPWGQLINLFYIPSGTKQNGRLSATTVATERYSLLYISSSQTTDSGV YFCAALIQGAQKLVFGQGTRLTIN |
| 476 Human TCR beta variable domain derived from 2IAN | NAGVTQTPKFRILKIGQSMTLQCTQDMNHNYMYWYRQDPGMGLKLIYYSVGAGITDKGEVPNGYNVSRSTTEDFPLRLELAAP SQTSVYFCASTYHGTGYFGEGSWLTVV |
| 394 Human TCR alpha variable domain derived from 2XN9 | QLLEQSPQFLSIQEGENLTVYCNSSSVFSSLQWYRQEPGEGPVLLVTVVTGGEVKKLKRLTFQFGDARKDSSLHITAAQPGDT GLYLCAGAGSQGNLIFGKGTKLSVK |
| 477 Human TCR beta variable domain derived from 2XN9 | DGGITQSPKYLFRKEGQNVTLSCEQNLNHDAMYWYRQDPGQGLRLIYYSQIVNDFQKGDIAEGYSVSREKKESFPLTVTSAQK NPTAFYLCASSSRSSYEQYFGPGTRLTVT |
| 395 Human TCR alpha variable domain derived from 3TOE | GDAKTTQPNSMESNEEEPVHLPCNHSTISGTDYIHWYRQLPSQGPEYVIHGLTSNVNNRMASLAIAEDRKSSTLILHRATLRD AAVYYCTVYGGATNKLIFGTGTLLAVQ |
| 478 Human TCR beta variable domain derived from 3TOE | VVSQHPSWVIAKSGTSVKIECRSLDFQATTMFWYRQFPKQSLMLMATSNEGSKATYEQGVEKDKFLINHASLTLSTLTVTSAH PEDSSFYICSARGGSYNSPLHFGNGTRLTVT |
| 396 Cyno TCR alpha constant domain | PYIQNPDPAVYQLRGSKSNDTSVCLFTDFDSVMNVSQSKDSDVHITDKTVLDMRSMDFKSNGAVAWSNKSDFACTSAFKDSVI PADTFFPSPESSC |

TABLE A-6-continued

Sequences of components of TCR complex.

| SEQID | SEQUENCE |
|---|---|
| 397 Rhesus TCR beta constant domain | EDLKKVFPPKVAVFEPSEAEISHTQKATLVCLATGFYPDHVELSWWVNGKEVHSGVSTDPQPLKEQPALEDSRYSLSSRLRVS ATFWHNPRNHFRCQVQFYGLSEDDEWTEDRDKPITQKISAEAWGRADC |
| 398 Rhesus TCR alpha variable domain | QQIMQIPQYQHVQEGEDFTTYCNSSTTLSNIQWYKQRPGGHPVFLIMLVKSGEVKKQKRLIFQFGEAKKNSSLHITATQTTDV GTYFCATTGVNNLFFGTGTRLTVL |
| 399 Rhesus TCR beta variable domain | AGPVNAGVTQTPKFQVLKTGQSMTLQCAQDMNHDYMYWYRQDPGMGLRLIHYSVGEGSTEKGEVPDGYNVTRSNTEDFPLRLE SAAPSQTSVYFCASSYWTGRSYEQYFGPGTRLTVI |
| 479 Huriian TCR alpha constant domain | PNIQNPDPAVYQLRDSKSSDKSVCLFTDFDSQTNVSQSKDSDVYITDKSVLDMRSMDFKSNSAVAWSNKSDFACANAFNNSII PEDTFFPSPESSC |
| 480 Human TCR beta constant domain | EDLNKVFPPEVAVFEPSEAEISHTQKATLVCLATGFYPDHVELSWWVNGKEVHSGVSTDPQPLKEQPALNDSRYSLSSRLRVS ATFWQNPRNHFRCQVQFYGLSENDEWTQDRAKPVTQIVSAEAWGRADC |
| 484 Human TCR alpha constant domain (P01848) | PNIQNPDPAVYQLRDSKSSDKSVCLFTDFDSQTNVSQSKDSDVYITDKTVLDMRSMDFKSNSAVAWSNKSDFACANAFNNSII PEDTFFPSPESSCDVKLVEKSFETDTNLNFQNLSVTGFRILLLLKVAGFNLLMTLRLWSS |
| 485 Human TCP beta constant domain | EDLNKVFPPEVAVFEPSEAEISHTQKATLVCLATGFFPDHVELSWWVNGKEVHSGVSTDPQPLKEQPALNDSRYCLSSRLRVS ATFWQNPRNHFRCQVQFYGLSENDEWTQDRAKPVTQIVSAEAWGRADCGFTSVSYQQGVLSATILYEILLGKATLYAVLVSAL VLMAMVKRKDF |

"SEQ" refers to the given SEQ ID NO;
"ID" refers to identification name;
"Sequence" denotes amino acid sequence

TABLE A-7

Sequences of TAA binding building blocks and control Nanobodies.

| SEQID | SEQUENCE |
|---|---|
| 350 HER2005F07 (Q108L) | EVQLVESGGGLVQAGGSLRLSCAASGITFSINTMGWYRQAPGKQRELVALISSIGDTYYADSVKGRFTISRDNAKNTVYLQMNSLKPE DTAVYYCKRFRTAAQGTDYWGQGTLVTVSS |
| 351 HER2047D05 (L108Q) | EVQLVESGGGLVQPGGSLRLSCAASGSIFGFNDMAWYRQAPGKQRELVALISRVGVTSSADSVKGRFTISRVNAKDTVYLQMNSLKPE DIAVYYCYMDQRLDGSTLAYWGQGTQVTVSS |
| 352 EGFR009G08 | EVQLVESGGGLVQAGGSLRLSCAASGRTFSSYAMGWFRQAPGKEREFVVAINWSSGSTYYADSVKGRFTISRDNAKNTMYLQMNSLKP EDTAVYYCAAGYQINSGNYNFKDYEYDYWGQGTQVTVSS |
| 353 NbCEA5 (CEA#1) | EVQLVESGGGSVQAGGSLRLSCAASGDTYGSYWMGWFRQAPGKEREGVAAINRGGGYTVYADSVKGRFTISRDTAKNTVYLQMNSLRP DDTADYYCAASGVLGGLHEDWFNYWGQGTLVTVSS |
| 354 T023200005 (CEA#5) | EVQLVESGGGSVQAGGSLRLSCAASGDTYGSYWMGWFRQAPGQEREAVAAINRGGGYTVYADSVKGRFTISRDNAKNTLYLQMNSLRP DDTADYYCAASGVLGGLHEDWFNYWGQGTLVTVSS |
| 355 7D12 (EGFR#1) | EVQLVESGGGSVQTGGSLRLTCAASGRTSRSYGMGWFRQAPGKEREFVSGISWRGDSTGYADSVKGRFTISRDNAKNTVDLQMNSLKP EDTAIYYCAAAAGSAWYGTLYEYDYWGQGTLVTVSS |
| 356 T023200033 (EGFR#33) | EVQLVESGGGSVQAGGSLRLTCAASGSTSRSYGMGWFRQAPGKEREFVSGISWRGDSTGYADSVKGRFTISRDNAKNTVDLQMNSLKP EDTAIYYCAAAAGSTWYGTLYEYDYWGQGTLVTVSS |
| 357 20CD019C07 | EVQLVESGGGLVQPGGSLRLSCTFSGGTFSSYTMGWFRQAPGKEREFVAEVRWGGVTTYSNSLKDRFSISEDSVKNAVYLQMNSLKPE DTAVYYCAAVRQMYMTVVPDYWGQGTLVTVSS |
| 358 EGFR038G07 | EVQLVESGGGLVQAGGSLRLSCAASGRTFSSYVMGWFRQATGKEREFVATIAWDSGSTYYADSVKGRFTISRDNAKNTVHLQMNSLKP EDTAVYYCAASYNVYYNNYYYPISRDEYDYWGQGTLVTVSS |

TABLE A-7-continued

Sequences of TAA binding building blocks and control Nanobodies.

| SEQID | SEQUENCE |
|---|---|
| 359cAblys3 | DVQLQASGGGSVQAGGSLRLSCAASGYTIGPYCMGWFRQAPGKEREGVAAINMGGGITYYADSVKGRFTISQDNAKNTVYLLMNSLEP EDTAIYYCAADSTIYASYYECGHGLSTGGYGYDSWGQGTQVTVSS |
| 360RSV007B02 | EVQLVESGGGLVQAGDSLRLSCAASGRTFSSYAMGWFRQAPGKEREFVAAISWSDGSTYYADSVKGRFTISRDNAKNTVYLQMNSLKP EDTAVYYCAADLTSTNPGSYIYIWAYDYWGQGTQVTVSS |

"SEQ" refers to a given SEQ ID NO;
"ID" refers to identification name;
"Sequence" denotes amino acid sequence

TABLE A-8

Sequences for CDRs and frameworks of TAA binding building blocks, plus preferred combinations as provided in formula I, namely FR1-CDR1-FR2-CDR2-FR3-CDR3-FR4.

| SEQNanobody | SEQFR1 | SEQCDR1 | SEQFR2 | SEQCDR2 |
|---|---|---|---|---|
| 353 NBCEA5 (CEA#1) | 367 EVQLVESGGGSVQ AGGSLRLSCAAS | 361 GDTYGSY WMG | 369 WFRQAPGKE REGVA | 363 AINRGG GYTV |
| 354 T023200005 (CEA#5) | 367 EVQLVESGGGSVQ AGGSLRLSCAAS | 361 GDTYGSY WMG | 370 WFRQAPGQE REAVA | 363 AINRGG GYTV |
| 357 20CD019C07 | 368 EVQLVESGGGLVQ PGGSLRLSCTFS | 362 GGTFSSY TMG | 371 WFRQAPGKE REFVA | 364 EVRWGG VTT |

| SEQFR3 | SEQCDR3 | SEQFR4 |
|---|---|---|
| 372 YADSVKGRFTISRDTAKNTV YLQMNSLRPDDTADYYCAA | 365 SGVLGGLHED WFNY | 375 WGQGTL VTVSS |
| 373 YADSVKGRFTISRDNAKNTL YLQMNSLRPDDTADYYCAA | 365 SGVLGGLHED WFNY | 375 WGQGTL VTVSS |
| 374 YSNSLKDRFSISEDSVKNAV YLQMNSLKPEDTAVYYCAA | 366 VRQMYMTVVP DY | 375 WGQGTL VTVSS |

"SEQ" refers to the given SEQ ID NO.
The first column refers to the SEQ ID NO of the complete ISV, i.e. FR1-CDR1-FR2-CDR2-FR3-CDR3-FR4.
CDR1, CDR2 and CDR3 were determined according to Kontermann, 2010.

TABLE C-6

EC50 (M) of multispecific TCR binding polypeptides for binding to CHO-K1 human TCR(2XN9)/CD3, purified primary human T cells and Ramos cells as determined in flow cytometry.

| | | CHO-K1 huTCR(2XN9)/CD3 | | | human T cells | | | Ramos cells | | |
|---|---|---|---|---|---|---|---|---|---|---|
| Cluster | sample ID | EC50 (M) | 95% LCI | 95% UCI | EC50 (M) | 95% LCI | 95% UCI | EC50 (M) | 95% LCI | 95% UCI |
| A | T017000055 | 1.1E-07 | 9.8E-08 | 1.3E-07 | 1.3E-07 | 3.0E-08 | 5.6E-07 | 1.8E-09 | 1.6E-09 | 1.9E-09 |
| A | T017000042 | 1.7E-08 | 1.4E-08 | 1.9E-08 | 2.3E-07 | 2.0E-07 | 2.6E-07 | 2.0E-08 | 1.8E-08 | 2.2E-08 |
| A | T017000076 | 7.8E-08 | 7.1E-08 | 8.6E-08 | 1.3E-07 | 1.3E-08 | 1.3E-06 | 1.8E-09 | 1.7E-09 | 2.0E-09 |
| A | T017000074 | 1.6E-08 | 1.5E-08 | 1.7E-08 | 1.9E-07 | 1.7E-07 | 2.1E-07 | 1.6E-08 | 1.4E-08 | 1.7E-08 |
| B | T017000068 | 1.9E-07 | 1.5E-07 | 2.3E-07 | 6.2E-09 | 4.2E-09 | 8.9E-09 | 1.8E-09 | 1.7E-09 | 2.0E-09 |
| B | T017000031 | 2.0E-08 | 1.8E-08 | 2.3E-08 | 3.5E-07 | 3.1E-07 | 4.0E-07 | 2.3E-08 | 2.0E-08 | 2.5E-08 |
| C | T017000051 | 4.6E-07 | 4.1E-07 | 5.1E-07 | >1E-07 | / | / | 2.7E-09 | 2.4E-09 | 2.9E-09 |
| C | T017000038 | 1.7E-08 | 1.6E-08 | 1.9E-08 | >1E-07 | / | / | 2.1E-08 | 1.9E-08 | 2.3E-08 |

TABLE C-7

IC50 (M) of the multispecific polypeptides in the flow cytometry based T cell mediated Ramos killing assay using an effector to target ratio of 10 to 1.

| Cluster | ID monovalent Nanobody | ID construct (CD20 × TCR) | n | IC50 (M) | % lysis | % lysis (stdev) | ID construct (TCR × CD20) | n | IC50 (M) | % lysis | % lysis (stdev) |
|---|---|---|---|---|---|---|---|---|---|---|---|
| A | T0170056G05 | T017000076 | 8 | 3.0E−10 | 25 | 14 | T017000074 | 6 | 9.2E−10 | 18 | 11 |
| A | T0170055A02 | T017000055 | 19 | 5.3E−10 | 29 | 13 | T017000042 | 5 | 5.7E−09 | 17 | 11 |
| B | T0170055C07 | T017000068 | 7 | 1.0E−09 | 22 | 7 | T017000031 | 3 | 1.1E−09 | 29 | 9 |
| C | T0170061G01 | T017000051 | 2 | 5.7E−10 | 16 | 2 | T017000038 | 2 | 2.7E−09 | 27 | 4 |

TABLE C-12

EC50 values of the half-life extended polypeptides in cell based binding to CHO-K1 human TCR(2XN9)/CD3, primary human T cells and Ramos cells as determined in flow cytometry.

| | | CHO-K1-K1 huTCR (2XN9)/CD3 | | | human T cells | | | Ramos cells | | |
|---|---|---|---|---|---|---|---|---|---|---|
| Cluster | sample ID | EC50 (M) | 95% LCI | 95% UCI | EC50 (M) | 95% LCI | 95% UCI | EC50 (M) | 95% LCI | 95% UCI |
| A | T017000093 | 7.7E−08 | 7.0E−08 | 8.4E−08 | 4.8E−07 | 4.8E−08 | 4.8E−06 | 1.5E−09 | 1.3E−09 | 1.6E−09 |
| B | T017000095 | 2.7E−07 | 2.2E−07 | 3.4E−07 | 2.2E−07 | 5.1E−08 | 9.8E−07 | 3.7E−09 | 3.3E−09 | 4.1E−09 |

TABLE C-15

IC50 values of the HER2/TCR binding polypeptides in the T cell mediated HER2-positive tumour killing assay.

| | | xCELLigence based cytotoxicity (readout 18 h) - SKBR3 (E/T = 15:1) | | | | | | | | |
|---|---|---|---|---|---|---|---|---|---|---|
| Cluster | ID monovalent Nb | ID construct (HER2 × TCR) | n | IC50 (M) | 95% LCI | 95% UCI | ID construct (TCR × HER2) | n | IC50 (M) | 95% LCI | 95% UCI |
| A | T0170056G05 | T017000102 | 1 | 1.4E−11 | 1.1E−11 | 1.7E−11 | T017000103 | 1 | 3.8E−12 | 3.2E−12 | 4.7E−12 |

| Cluster | ID monovalent Nb | ID construct (HER2 × TCR) | n | EC50 (M) | 95% LCI2 | 95% UCI2 | ID construct (TCR × HER2) | n | IC50 (M) | 95% LCI | 95% UCI |
|---|---|---|---|---|---|---|---|---|---|---|---|
| | | xCELLigence based cytotoxicity (readout 18 h) - MCF-7 (E/T = 15:1) | | | | | | | | | |
| A | T0170056G05 | T017000102 | 1 | 1.2E−10 | 9.0E−11 | 1.0E−10 | T017000103 | 1 | 5.9E−11 | 5.0E−11 | 7.0E−11 |
| | | xCELLigence based cytotoxicity (readout 18 h) - MDA-MB-468(E/T = 15:1) | | | | | | | | | |
| A | T0170056G05 | T017000102 | 1 | No fit | | | T017000103 | 1 | No fit | | |

TABLE C-16

IC50 (M) of the HER2/TCR binding polypeptides for IFN-γ secretion by human T cells in the human T cell mediated xCELLigence based HER2 dependent killing assay.

| ID monovalent Nb | ID construct (HER2 × TCR) | n | IC50 (M) | 95% LCI | 95% UCI | ID construct (TCR × HER2) | n | IC50 (M) | 95% LCI | 95% UCI |
|---|---|---|---|---|---|---|---|---|---|---|
| T0170056G05 | T017000102 | 1 | 2.8E−11 | 1.4E−11 | 5.6E−11 | T017000103 | 1 | 1.1E−10 | 5.6E−11 | 2.2E−10 |

TABLE C-17

IC50 (M) of and % lysis by the TCR/CD20 binding multispecific constructs in the cynomolgus T cell mediated B cell (Ramos) killing assay to evaluate the cynomolgus functionality of the TCR building block.

| Cluster | ID monovalent Nb | ID construct (CD20 × TCR) | n | IC50 (M) | % lysis | % lysis (stdev) | ID construct (TCR × CD20) | n | IC50 (M) | % lysis | % lysis (stdev) |
|---|---|---|---|---|---|---|---|---|---|---|---|
| A | T0170055A02 | T017000055 | 2 | 5.69E−10 | 17 | 6 | T017000042 | 1 | 1.7E−10 | 18 | |
| A | T0170056G05 | T017000076 | 2 | 3.09E−10 | 20 | 1 | T017000074 | 2 | 2.4E−10 | 31 | 2.21 |
| B | T0170055C07 | T017000068 | 1 | | | | T017000031 | 1 | 7.9E−10 | 10 | |

TABLE C-18

IC50 (M) of the TCR/CD20 binding multispecific polypeptides in the cynomolgus T cell mediated xCELLigence based CHO-K1 human CD20 killing assay.

| Cluster | ID monovalent Nb | ID construct (CD20 × TCR) | n | IC50 (M) | 95% LCI | 95% UCI | ID construct (TCR × CD20) | n | IC50 (M) | 95% LCI | 95% UCI |
|---|---|---|---|---|---|---|---|---|---|---|---|
| A | T0170055A02 | T017000055 | 1 | 9.9E−10 | 4.2E−10 | 2.3E−09 | T017000042 | 1 | 8.9E−10 | 6.0E−10 | 1.3E−09 |
| A | T0170056G05 | T017000076 | 1 | 6.7E−10 | 2.2E−10 | 2.0E−09 | T017000074 | 1 | 1.2E−10 | 6.4E−11 | 2.3E−10 |
| B | T0170055C07 | T017000068 | 1 | ND | ND | ND | T017000031 | 1 | 1.2E−09 | 7.2E−10 | 1.9E−09 |

TABLE C-23

IC50 (M) of the TCR/Her2 binding multispecific polypeptides in the cynomolgus T cell mediated xCELLigence based SKBR3 killing assay.

| ID monovalent Nb | ID construct (HER2 × TCR) | n | IC50 (M) | 95% LCI | 95% UCI | ID construct (TCR × HER2) | n | IC50 (M) | 95% LCI | 95% UCI |
|---|---|---|---|---|---|---|---|---|---|---|
| T0170056G05 | T017000102 | 1 | 4.6E−11 | 1.3E−11 | 1.7E−10 | T017000103 | 1 | 1.2E−11 | 7.3E−12 | 2.1E−11 |

TABLE 31

IC50 (M) of the multispecific polypeptides in the human T cell mediated xCELLigence based killing assay using an effector to target ratio of 15. Data were analysed after 50-60 h.

| | LoVo | | | | LS174T | | | | HER14 | | | |
|---|---|---|---|---|---|---|---|---|---|---|---|---|
| ID construct | n | IC50 (M) | 95% LCI | 95% UCI | n | IC50 (M) | 95% LCI | 95% UCI | n | IC50 (M) | 95% LCI | 95% UCI |
| T017000107 | 1 | 6.1E−11 | 5.4E−11 | 7.0E−11 | 1 | 5.3E−09 | 4.2E−09 | 6.6E−09 | 1 | 1.4E−10 | 1.2E−10 | 1.6E−10 |
| T017000109 | 1 | 2.0E−09 | 1.8E−09 | 2.2E−09 | 1 | 3.6E−08 | 2.7E−08 | 4.9E−08 | 1 | / | / | / |
| T017000110 | 1 | 6.0E−10 | 5.3E−10 | 6.8E−10 | 1 | 8.9E−09 | 5.8E−09 | 1.4E−08 | 1 | 4.2E−10 | 3.7E−10 | 4.7E−10 |

The invention claimed is:

1. Polypeptide comprising a first and a second immunoglobulin single variable domain (ISV), wherein
   said first ISV specifically binds to the constant domain of the T cell receptor (TCR) present on a T cell;
   said second ISV specifically binds to a first antigen on a target cell;
   wherein said first antigen is different from said TCR;
   wherein said target cell is different from said T cell, and
   wherein said first ISV essentially consists of 4 framework regions (FR1 to FR4, respectively) and 3 complementarity determining regions (CDR1 to CDR3, respectively), in which:
   (i) CDR1 is chosen from the group consisting of:
      (a) SEQ ID NOs: 119-123, 125-127, 129, 132 and 133, or
      (b) amino acid sequences that have 2 or 1 amino acid(s) difference with the amino acid sequence of SEQ ID NO: 123; and
   (ii) CDR2 is chosen from the group consisting of:
      (c) SEQ ID NOs: 134-141, 143-144, 146-156, and 159-163, or
      (d) amino acid sequences that have 2 or 1 amino acid(s) difference with the amino acid sequence of SEQ ID NO:153; and
   (iii) CDR3 is chosen from the group consisting of:
      (e) SEQ ID NOs: 164-166, 169-171, 173-174, or
      (f) amino acid sequences that have 2 or 1 amino acid(s) difference with the amino acid sequence of SEQ ID NO: 170.

2. The polypeptide according to claim 1, wherein said first ISV binds to the constant domain of a T cell receptor α (TCR-α) (SEQ ID NO: 348 and/or SEQ ID NO: 484) and/or the constant domain of the T cell receptor β (TCR-β) (SEQ ID NO: 349 and/or SEQ ID NO: 485), or polymorphic variants or isoforms thereof.

3. The polypeptide according to claim 1, wherein:
   (i) CDR1 is chosen from the group consisting of:
      (a) SEQ ID NO: 123; or
      (b) amino acid sequences that have 2 or 1 amino acid(s) difference with the amino acid sequence of SEQ ID NO: 123; and
   (ii) CDR2 is chosen from the group consisting of:
      (c) SEQ ID NO: 153; or
      (d) amino acid sequences that have 2 or 1 amino acid(s) difference with the amino acid sequence of SEQ ID NO: 153; and
   (iii) CDR3 is chosen from the group consisting of:
      (e) SEQ ID NOs: 170; or
      (f) amino acid sequences that have 2 or 1 amino acid(s) difference with the amino acid sequence of SEQ ID NO: 170.

4. The polypeptide according to claim 1, further comprising a third ISV, which specifically binds to a second antigen on a target cell, wherein said second antigen is different from said first antigen.

5. The polypeptide according to claim 1, wherein said first antigen on a target cell is a tumour antigen, preferably a tumour associated antigen (TAA).

6. The polypeptide according to claim 4, wherein said second antigen on a target cell is a tumour antigen, preferably a tumour associated antigen (TAA).

7. The polypeptide according to claim 4, wherein said first antigen and said second antigen are present on the same target cell.

8. The polypeptide according to claim 4, wherein said first antigen and said second antigen are present on different target cells.

9. The polypeptide according to claim 1, further comprising a serum protein binding moiety.

10. The polypeptide according to claim 9, wherein said serum protein binding moiety is an ISV binding serum albumin.

11. The polypeptide according to claim 1, wherein said first ISV and said second ISV are linked via a linker.

12. The polypeptide according to claim 11, wherein said linker is chosen from the group consisting of linkers of 5GS, 7GS, 9GS, 10GS, 15GS, 18GS, 20GS, 25GS, 30GS and 35GS (SEQ ID NOs: 376 to 385).

13. The polypeptide according to claim 1, wherein said ISV is a Nanobody, a $V_{HH}$, a humanized $V_{HH}$, or a camelized $V_H$.

14. A polypeptide that specifically binds the constant domain of the T cell receptor (TCR) and that comprises or essentially consists of 4 framework regions (FR1 to FR4, respectively) and 3 complementarity determining regions (CDR1 to CDR3, respectively), in which:
(i) CDR1 is chosen from the group consisting of:
  (a) SEQ ID NOs: 119-123, 125-127, 129, 132 and 133; or
  (b) amino acid sequences that have 2 or 1 amino acid(s) difference with the amino acid sequence of SEQ ID NO: 123; and
(ii) CDR2 is chosen from the group consisting of:
  (c) SEQ ID NOs: 134-141, 143-144, 146-156, and 159-163; or
  (d) amino acid sequences that have 2 or 1 amino acid(s) difference with the amino acid sequence of SEQ ID NO: 153; and
(iii) CDR3 is chosen from the group consisting of:
  (e) SEQ ID NOs: 164-166, 169-171, 173-174; or
  (f) amino acid sequences that have 2 or 1 amino acid(s) difference with the amino acid sequence of SEQ ID NO: 170.

15. The polypeptide according to claim 14, which is a Nanobody, a $V_{HH}$, a humanized $V_{HH}$, or a camelized $V_H$.

16. The polypeptide according to claim 14, further comprising a serum protein binding moiety.

17. The polypeptide according to claim 16, wherein said serum protein binding moiety is an ISV that binds serum albumin.

18. A nucleic acid or nucleic acid sequence encoding the polypeptide as defined in claim 1.

19. A pharmaceutical composition comprising the polypeptide according to claim 1.

20. The polypeptide according to claim 14, wherein:
(i) CDR1 is chosen from the group consisting of:
  (a) SEQ ID NO: 123; or
  (b) amino acid sequences that have 2 or 1 amino acid(s) difference with the amino acid sequence of SEQ ID NO: 123; and
(ii) CDR2 is chosen from the group consisting of:
  (c) SEQ ID NO: 153; or
  (d) amino acid sequences that have 2 or 1 amino acid(s) difference with the amino acid sequence of SEQ ID NO: 153; and
(iii) CDR3 is chosen from the group consisting of:
  (e) SEQ ID NOs: 170; or
  (f) amino acid sequences that have 2 or 1 amino acid(s) difference with the amino acid sequence of SEQ ID NO: 170.

* * * * *

SEQUENCE LISTING

<160> NUMBER OF SEQ ID NOS: 487

<210> SEQ ID NO 1
<211> LENGTH: 117
<212> TYPE: PRT
<213> ORGANISM: Artificial Sequence
<220> FEATURE:
<223> OTHER INFORMATION: Nanobody sequence

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Lys Ile Asn
```

```
                    20                  25                  30

Phe Leu Gly Trp Tyr Arg Gln Ala Pro Gly Lys Glu Arg Glu Leu Val
            35                  40                  45

Ala Thr Ile Thr Ile Gly Asp Thr Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val His Phe Cys Arg
                85                  90                  95

Ala Gly Ser Arg Leu Tyr Pro Tyr Asn Tyr Trp Gly Gln Gly Thr Gln
            100                 105                 110

Val Thr Val Ser Ser
        115

<210> SEQ ID NO 2
<211> LENGTH: 117
<212> TYPE: PRT
<213> ORGANISM: Artificial Sequence
<220> FEATURE:
<223> OTHER INFORMATION: Nanobody sequence

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Lys Ile Asn
            20                  25                  30

Phe Leu Gly Trp Tyr Arg Gln Ala Pro Gly Lys Glu Arg Gly Leu Val
            35                  40                  45

Ala Thr Ile Thr Ile Gly Asp Thr Thr Asp Tyr Ala Asp Tyr Ala Lys
    50                  55                  60

Gly Arg Phe Thr Ile Ser Arg Asp Glu Ala Arg Asn Met Val Tyr Leu
65                  70                  75                  80

Gln Met Asn Ser Leu Lys Pro Glu Asp Thr Ala Val Tyr Phe Cys Arg
                85                  90                  95

Ala Gly Ser Arg Leu Tyr Pro Tyr Asn Tyr Trp Gly Gln Gly Thr Gln
            100                 105                 110

Val Thr Val Ser Ser
        115

<210> SEQ ID NO 3
<211> LENGTH: 117
<212> TYPE: PRT
<213> ORGANISM: Artificial Sequence
<220> FEATURE:
<223> OTHER INFORMATION: Nanobody sequence

<400> SEQUENCE: 3

Glu Val Gln Leu Val Glu Ser Gly Gly Gly Leu Val Gln Pro Gly Arg
1               5                   10                  15

Ser Leu Arg Leu Pro Cys Ala Ala Ser Gly Ser Val His Lys Ile Asn
            20                  25                  30

Phe Leu Gly Trp Tyr Arg Gln Ala Pro Gly Lys Glu Arg Glu Met Val
            35                  40                  45

Ala Thr Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80
```

```
Gln Met Asn Ser Leu Lys Pro Glu Asp Thr Ala Val Tyr Phe Cys Arg
            85                  90                  95

Ala Gly Ser Arg Leu Tyr Pro Tyr Asn Tyr Trp Gly Gln Gly Thr Gln
            100                 105                 110

Val Thr Val Ser Ser
        115

<210> SEQ ID NO 4
<211> LENGTH: 117
<212> TYPE: PRT
<213> ORGANISM: Artificial Sequence
<220> FEATURE:
<223> OTHER INFORMATION: Nanobody sequence

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Lys Ile Asn
            20                  25                  30

Phe Leu Gly Trp Tyr Arg Gln Ala Pro Gly Lys Glu Arg Glu Leu Val
        35                  40                  45

Ala Thr Ile Thr Ile Gly Asp Thr Thr Asp Tyr Ala Asp Tyr Ala Lys
    50                  55                  60

Gly Arg Phe Thr Ile Ser Arg Asp Glu Ala Arg Asn Met Val Tyr Leu
65                  70                  75                  80

Gln Met Asn Ser Leu Lys Pro Glu Asp Thr Ala Val Tyr Phe Cys Arg
            85                  90                  95

Ala Gly Ser Arg Leu Tyr Pro Tyr Asn Tyr Trp Gly Gln Gly Thr Leu
            100                 105                 110

Val Thr Val Ser Ser
        115

<210> SEQ ID NO 5
<211> LENGTH: 117
<212> TYPE: PRT
<213> ORGANISM: Artificial Sequence
<220> FEATURE:
<223> OTHER INFORMATION: Nanobody sequence

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Lys Ile Asn
            20                  25                  30

Phe Leu Gly Trp Tyr Arg Gln Ala Pro Gly Lys Glu Arg Glu Met Val
        35                  40                  45

Ala Thr Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
            85                  90                  95

Ala Gly Ser Arg Leu Tyr Pro Tyr Asn Tyr Trp Gly Gln Gly Thr Leu
            100                 105                 110

Val Thr Val Ser Ser
        115

<210> SEQ ID NO 6
```

```
<211> LENGTH: 117
<212> TYPE: PRT
<213> ORGANISM: Artificial Sequence
<220> FEATURE:
<223> OTHER INFORMATION: Nanobody sequence

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Lys Ile Asn
            20                  25                  30

Phe Leu Gly Trp Tyr Arg Gln Ala Pro Gly Lys Glu Arg Glu Leu Val
        35                  40                  45

Ala Thr Ile Thr Ile Gly Asp Thr Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
            85                  90                  95

Ala Gly Ser Arg Leu Tyr Pro Tyr Asn Tyr Trp Gly Gln Gly Thr Gln
            100                 105                 110

Val Thr Val Ser Ser
            115

<210> SEQ ID NO 7
<211> LENGTH: 117
<212> TYPE: PRT
<213> ORGANISM: Artificial Sequence
<220> FEATURE:
<223> OTHER INFORMATION: Nanobody sequence

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Val Ser Gly Ser Val His Leu Leu Asn
            20                  25                  30

Phe Leu Gly Trp Tyr Arg Gln Ala Pro Gly Lys Glu Arg Glu Met Val
        35                  40                  45

Ala His Ile Thr Ile Ala Asp Ala Thr Asp Tyr Ser His Phe Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Arg Pro Glu Asp Thr Ala Val Tyr Phe Cys Arg
            85                  90                  95

Ala Gly Ser Arg Ile Tyr Pro Tyr Asp Tyr Trp Gly Gln Gly Thr Leu
            100                 105                 110

Val Thr Val Ser Ser
            115

<210> SEQ ID NO 8
<211> LENGTH: 117
<212> TYPE: PRT
<213> ORGANISM: Artificial Sequence
<220> FEATURE:
<223> OTHER INFORMATION: Nanobody sequence

<400> SEQUENCE: 8

Glu Val Gln Leu Val Glu Ser Gly Gly Gly Leu Val Gln Pro Gly Gly
1               5                   10                  15
```

```
Ser Leu Lys Leu Ser Cys Ala Ala Ser Gly Ala Val His Lys Ile Asn
            20                  25                  30

Phe Leu Gly Trp Tyr Arg Gln Thr Pro Glu Lys Glu Arg Glu Met Val
        35                  40                  45

Ala Thr Ile Thr Ile Gly Asp Asp Val Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Thr Ser Leu Lys Pro Glu Asp Thr Ala Val Tyr Val Cys Arg
            85                  90                  95

Ala Gly Ser Arg Leu Tyr Pro Tyr Asn Tyr Trp Gly Gln Gly Thr Leu
            100                 105                 110

Val Thr Val Ser Ser
        115

<210> SEQ ID NO 9
<211> LENGTH: 117
<212> TYPE: PRT
<213> ORGANISM: Artificial Sequence
<220> FEATURE:
<223> OTHER INFORMATION: Nanobody sequence

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Arg Ala Ser Gly Asp Val His Lys Ile Asn
            20                  25                  30

Ile Leu Gly Trp Tyr Arg Gln Ala Pro Ala Lys Glu Arg Glu Met Val
        35                  40                  45

Ala His Ile Thr Ile Gly Asp Ala Thr Asp Tyr Ala Glu Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
            85                  90                  95

Ala Tyr Ser Arg Ile Tyr Pro Tyr Asn Tyr Trp Gly Gln Gly Thr Gln
            100                 105                 110

Val Thr Val Ser Ser
        115

<210> SEQ ID NO 10
<211> LENGTH: 117
<212> TYPE: PRT
<213> ORGANISM: Artificial Sequence
<220> FEATURE:
<223> OTHER INFORMATION: Nanobody sequence

<400> SEQUENCE: 10

Glu Val Gln Leu Val Glu Ser Gly Gly Gly Leu Val Arg Pro Gly Gly
1               5                   10                  15

Ser Leu Arg Leu Ser Cys Ala Ala Ser Gly Asp Val His Lys Ile Asn
            20                  25                  30

Ile Leu Gly Trp Tyr Arg Gln Ala Pro Ala Lys Glu Arg Glu Met Val
        35                  40                  45

Ala His Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80
```

Gln Met Asn Ser Leu Lys Pro Glu Asp Thr Ala Val Tyr Phe Cys Arg
                85                  90                  95

Ala Tyr Ser Arg Ile Tyr Pro Tyr Asn Tyr Trp Gly Gln Gly Thr Leu
            100                 105                 110

Val Thr Val Ser Ser
        115

<210> SEQ ID NO 11
<211> LENGTH: 117
<212> TYPE: PRT
<213> ORGANISM: Artificial Sequence
<220> FEATURE:
<223> OTHER INFORMATION: Nanobody sequence

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Val His Lys Ile Asn
            20                  25                  30

Ile Leu Gly Trp Tyr Arg Gln Ala Pro Ala Lys Glu Arg Glu Met Val
        35                  40                  45

Ala His Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Tyr Ser Arg Ile Tyr Pro Tyr Asn Tyr Trp Gly Gln Gly Thr Leu
            100                 105                 110

Val Thr Val Ser Ser
        115

<210> SEQ ID NO 12
<211> LENGTH: 117
<212> TYPE: PRT
<213> ORGANISM: Artificial Sequence
<220> FEATURE:
<223> OTHER INFORMATION: Nanobody sequence

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Val Ala Ser Gly Asp Val His Lys Ile Asn
            20                  25                  30

Phe Leu Gly Trp Tyr Arg Gln Ala Pro Gly Lys Glu Arg Glu Lys Val
        35                  40                  45

Ala His Ile Thr Ile Gly Asp Gln Ala Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Gly Ser Arg Ile Tyr Pro Tyr Asp Tyr Trp Gly Gln Gly Thr Gln
            100                 105                 110

Val Thr Val Ser Ser
        115

-continued

```
<210> SEQ ID NO 13
<211> LENGTH: 117
<212> TYPE: PRT
<213> ORGANISM: Artificial Sequence
<220> FEATURE:
<223> OTHER INFORMATION: Nanobody sequence

<400> SEQUENCE: 13
```

Glu Val Gln Leu Val Glu Ser Gly Gly Gly Val Gln Pro Gly Gly
1               5                   10                  15

Ser Leu Arg Leu Ser Cys Ala Ala Ser Gly Ser Val His Lys Ile Asn
            20                  25                  30

Phe Leu Gly Trp Tyr Arg Gln Ala Pro Gly Lys Glu Arg Glu Met Val
        35                  40                  45

Ala Thr Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Ser Pro Glu Asp Thr Ala Val Tyr Phe Cys Arg
                85                  90                  95

Ala Gly Ser Arg Leu Tyr Pro Tyr Asn Tyr Trp Gly Gln Gly Thr Leu
            100                 105                 110

Val Thr Val Ser Ser
        115

```
<210> SEQ ID NO 14
<211> LENGTH: 117
<212> TYPE: PRT
<213> ORGANISM: Artificial Sequence
<220> FEATURE:
<223> OTHER INFORMATION: Nanobody sequence

<400> SEQUENCE: 14
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Leu Leu Asn
            20                  25                  30

Phe Leu Gly Trp Tyr Arg Gln Ala Pro Gly Lys Glu Arg Glu Met Val
        35                  40                  45

Ala His Ile Ser Ile Ala Asp Ala Thr Asp Tyr Ala His Phe Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Arg Pro Glu Asp Thr Ala Val Tyr Phe Cys Arg
                85                  90                  95

Ala Gly Ser Arg Ile Tyr Pro Tyr Asp Tyr Trp Gly Arg Gly Thr Gln
            100                 105                 110

Val Thr Val Ser Ser
        115

```
<210> SEQ ID NO 15
<211> LENGTH: 117
<212> TYPE: PRT
<213> ORGANISM: Artificial Sequence
<220> FEATURE:
<223> OTHER INFORMATION: Nanobody sequence

<400> SEQUENCE: 15
```

Glu Val Gln Leu Val Glu Ser Gly Gly Gly Leu Val Gln Pro Gly Gly
1               5                   10                  15

```
Ser Leu Arg Leu Ser Cys Arg Ala Ser Gly Asp Val His Lys Ile Asn
            20                  25                  30

Ile Leu Gly Trp Tyr Arg Gln Ala Pro Ala Lys Glu Arg Glu Met Val
        35                  40                  45

Ala His Ile Thr Ile Gly Asp Ala Thr Val Tyr Ala Glu Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Tyr Ser Arg Ile Tyr Pro Tyr Asn Tyr Trp Gly Gln Gly Thr Gln
            100                 105                 110

Val Thr Val Ser Ser
            115

<210> SEQ ID NO 16
<211> LENGTH: 117
<212> TYPE: PRT
<213> ORGANISM: Artificial Sequence
<220> FEATURE:
<223> OTHER INFORMATION: Nanobody sequence

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Leu Leu Asn
            20                  25                  30

Phe Leu Gly Trp Tyr Arg Gln Cys Pro Gly Lys Glu Arg Glu Met Val
        35                  40                  45

Ala His Ile Thr Ile Ala Asp Ala Thr Asp Tyr Ser His Phe Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Arg Pro Glu Asp Thr Ala Val Tyr Phe Cys Arg
                85                  90                  95

Ala Gly Ser Arg Ile Tyr Pro Tyr Asp Tyr Trp Gly Gln Gly Thr Leu
            100                 105                 110

Val Thr Val Ser Ser
            115

<210> SEQ ID NO 17
<211> LENGTH: 117
<212> TYPE: PRT
<213> ORGANISM: Artificial Sequence
<220> FEATURE:
<223> OTHER INFORMATION: Nanobody sequence

<400> SEQUENCE: 17

Glu Val Gln Leu Val Glu Ser Gly Gly Gly Leu Val Gln Pro Gly Gly
1               5                   10                  15

Ser Leu Arg Pro Ser Cys Ala Ala Ser Gly Ser Val His Leu Leu Asn
            20                  25                  30

Phe Leu Gly Trp Tyr Arg Gln Ala Pro Gly Lys Glu Arg Glu Met Val
        35                  40                  45

Ala His Ile Thr Ile Ala Asp Ala Thr Asp Tyr Ala His Phe Ala Lys
    50                  55                  60

Gly Arg Phe Thr Ile Ser Arg Asp Glu Ala Lys Asn Met Val Tyr Leu
```

Gln Met Asn Ser Leu Arg Pro Glu Asp Thr Ala Val Tyr Phe Cys Arg
                    85                  90                  95

Ala Gly Ser Arg Ile Tyr Pro Tyr Asp Tyr Trp Gly Gln Gly Thr Gln
                100                 105                 110

Val Thr Val Ser Ser
            115

<210> SEQ ID NO 18
<211> LENGTH: 117
<212> TYPE: PRT
<213> ORGANISM: Artificial Sequence
<220> FEATURE:
<223> OTHER INFORMATION: Nanobody sequence

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Leu Leu Asn
                20                  25                  30

Phe Leu Gly Trp Tyr Arg Gln Ala Pro Gly Lys Glu Arg Glu Met Val
            35                  40                  45

Ala His Ile Thr Ile Ala Asp Ala Thr Asp Tyr Ala His Phe Ala Lys
        50                  55                  60

Gly Arg Phe Thr Ile Ser Arg Asp Glu Ala Lys Asn Met Val Tyr Leu
65                  70                  75                  80

Gln Met Asn Ser Leu Arg Pro Glu Asp Thr Ala Val Tyr Phe Cys Arg
                    85                  90                  95

Ala Gly Ser Arg Ile Tyr Pro Tyr Asp Tyr Trp Gly Gln Gly Thr Leu
                100                 105                 110

Val Thr Val Ser Ser
            115

<210> SEQ ID NO 19
<211> LENGTH: 117
<212> TYPE: PRT
<213> ORGANISM: Artificial Sequence
<220> FEATURE:
<223> OTHER INFORMATION: Nanobody sequence

<400> SEQUENCE: 19

Glu Val Gln Leu Val Glu Ser Gly Gly Gly Leu Val Gln Pro Gly Gly
1               5                   10                  15

Ser Leu Lys Leu Ser Cys Ala Ala Ser Gly Ala Val His Lys Ile Asn
                20                  25                  30

Phe Leu Gly Trp Tyr Arg Gln Thr Pro Glu Lys Glu Arg Glu Met Val
            35                  40                  45

Ala His Ile Thr Ile Gly Asp Glu Val Asp Tyr Ala Asp Ser Ala Lys
        50                  55                  60

Gly Arg Phe Thr Ile Ser Arg Asp Glu Ala Lys Asn Met Val Tyr Leu
65                  70                  75                  80

Gln Met Thr Ser Leu Thr Pro Glu Asp Thr Ala Val Tyr Val Cys Arg
                    85                  90                  95

Ala Gly Ser Arg Leu Tyr Pro Tyr Asn Tyr Trp Gly Gln Gly Thr Gln
                100                 105                 110

Val Thr Val Ser Ser
            115

<210> SEQ ID NO 20
<211> LENGTH: 117
<212> TYPE: PRT
<213> ORGANISM: Artificial Sequence
<220> FEATURE:
<223> OTHER INFORMATION: Nanobody sequence

<400> SEQUENCE: 20

Glu Val Gln Leu Val Glu Ser Gly Gly Gly Leu Val His Pro Gly Gly
1               5                   10                  15

Ser Leu Arg Leu Ser Cys Ala Ala Ser Gly Asp Val His Lys Ile Asn
            20                  25                  30

Phe Leu Gly Trp His Arg Gln Pro Pro Gly Lys Glu Arg Glu Lys Val
        35                  40                  45

Ala His Ile Thr Ile Gly Asp Val Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Asn Leu Lys Pro Glu Asp Thr Ala Val Tyr Phe Cys Arg
                85                  90                  95

Ala Gly Ser Arg Ile Tyr Pro Tyr Asp Tyr Trp Gly Gln Gly Thr Gln
            100                 105                 110

Val Thr Val Ser Ser
        115

<210> SEQ ID NO 21
<211> LENGTH: 117
<212> TYPE: PRT
<213> ORGANISM: Artificial Sequence
<220> FEATURE:
<223> OTHER INFORMATION: Nanobody sequence

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Val His Lys Ile Asn
            20                  25                  30

Val Leu Gly Trp Tyr Arg Gln Ala Pro Ala Lys Glu Arg Glu Met Val
        35                  40                  45

Ala His Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val His Leu
65                  70                  75                  80

Gln Met Asn Ser Leu Lys Pro Glu Asp Thr Ala Val Tyr Phe Cys Arg
                85                  90                  95

Ala Tyr Ser Arg Ile Tyr Pro Tyr Asn Tyr Trp Gly Gln Gly Thr Gln
            100                 105                 110

Val Thr Val Ser Ser
        115

<210> SEQ ID NO 22
<211> LENGTH: 117
<212> TYPE: PRT
<213> ORGANISM: Artificial Sequence
<220> FEATURE:
<223> OTHER INFORMATION: Nanobody sequence

<400> SEQUENCE: 22

Glu Val Gln Leu Val Glu Ser Gly Gly Gly Leu Val Gln Pro Gly Gly

```
               1               5                  10                 15
            Ser Leu Arg Leu Ser Cys Ala Ala Ser Gly Asp Val His Lys Ile Asn
                            20                  25                  30

Ile Leu Gly Trp Tyr Arg Gln Ala Pro Ala Lys Glu Arg Glu Met Val
                        35                  40                  45

Ala His Ile Thr Ile Gly Asp Ala Thr Asn Tyr Ala Asp Ser Ala Lys
                    50                  55                  60

Gly Arg Phe Thr Ile Ser Arg Asp Glu Ala Lys Asn Met Val Tyr Leu
            65                  70                  75                  80

Gln Met Asn Ser Leu Lys Pro Glu Asp Thr Ala Val Tyr Phe Cys Arg
                            85                  90                  95

Ala Tyr Ser Arg Ile Tyr Pro Tyr Asn Tyr Trp Gly Gln Gly Thr Leu
                            100                 105                 110

Val Thr Val Ser Ser
                    115

<210> SEQ ID NO 23
<211> LENGTH: 117
<212> TYPE: PRT
<213> ORGANISM: Artificial Sequence
<220> FEATURE:
<223> OTHER INFORMATION: Nanobody sequence

<400> SEQUENCE: 23

Glu Val Gln Leu Val Glu Ser Gly Gly Gly Leu Val Gln Pro Gly Gly
            1               5                   10                  15

Ser Leu Arg Leu Ser Cys Ala Ala Ser Gly Asp Val His Lys Ile Asn
                            20                  25                  30

Phe Leu Gly Trp His Arg Gln Ala Pro Gly Lys Glu Arg Glu Lys Val
                        35                  40                  45

Ala His Ile Thr Ile Gly Asp Val Thr Asp Tyr Ala Asp Ser Ala Lys
                    50                  55                  60

Gly Arg Phe Thr Ile Ser Arg Asp Glu Ala Lys Asn Met Val Phe Leu
            65                  70                  75                  80

Gln Met Asn Asn Leu Lys Pro Glu Asp Thr Ala Val Tyr Phe Cys Arg
                            85                  90                  95

Ala Gly Ser Arg Ile Tyr Pro Tyr Asp Tyr Trp Gly Gln Gly Thr Gln
                            100                 105                 110

Val Thr Val Ser Ser
                    115

<210> SEQ ID NO 24
<211> LENGTH: 117
<212> TYPE: PRT
<213> ORGANISM: Artificial Sequence
<220> FEATURE:
<223> OTHER INFORMATION: Nanobody sequence

<400> SEQUENCE: 24

Glu Val Gln Leu Val Glu Ser Gly Gly Gly Leu Val Gln Pro Gly Gly
            1               5                   10                  15

Ser Leu Arg Leu Ser Cys Ala Ala Ser Gly Asp Val His Lys Ile Asn
                            20                  25                  30

Ile Leu Gly Trp Tyr Arg Gln Ala Pro Ala Lys Glu Arg Glu Met Val
                        35                  40                  45

Ala His Ile Thr Ile Gly Asp Ala Thr Asp Tyr Ala Gly Ser Ala Lys
                    50                  55                  60
```

```
Gly Arg Phe Thr Ile Ser Arg Asp Glu Ala Lys Asn Met Val Tyr Leu
 65                  70                  75                  80

Gln Met Asn Ser Leu Lys Pro Glu Asp Thr Ala Val Tyr Phe Cys Arg
                 85                  90                  95

Ala Tyr Ser Arg Ile Tyr Pro Tyr Asn Tyr Trp Gly Gln Gly Thr Leu
            100                 105                 110

Val Thr Val Ser Ser
            115

<210> SEQ ID NO 25
<211> LENGTH: 117
<212> TYPE: PRT
<213> ORGANISM: Artificial Sequence
<220> FEATURE:
<223> OTHER INFORMATION: Nanobody sequence

<400> SEQUENCE: 25

Glu Val Gln Leu Val Glu Ser Gly Gly Gly Leu Val Gln Pro Gly Gly
 1               5                   10                  15

Ser Leu Arg Leu Ser Cys Ala Ala Ser Gly Glu Val Tyr Lys Ile Asn
                 20                  25                  30

Phe Leu Gly Trp Tyr Arg Gln Ala Pro Gly Lys Glu Arg Glu Lys Val
             35                  40                  45

Ala His Ile Thr Ile Ala Asp Val Ala Asp Tyr Ala Asp Phe Ala Lys
         50                  55                  60

Gly Arg Phe Thr Ile Ser Arg Asp Glu Ala Lys Asn Met Val Tyr Leu
 65                  70                  75                  80

Gln Met Asn Ser Leu Lys Pro Glu Asp Thr Ala Val Tyr Phe Cys Arg
                 85                  90                  95

Ala Gly Ser Arg Ile Trp Pro Tyr Asp Tyr Trp Gly Gln Gly Thr Gln
            100                 105                 110

Val Thr Val Ser Ser
            115

<210> SEQ ID NO 26
<211> LENGTH: 117
<212> TYPE: PRT
<213> ORGANISM: Artificial Sequence
<220> FEATURE:
<223> OTHER INFORMATION: Nanobody sequence

<400> SEQUENCE: 26

Glu Val Gln Leu Val Glu Ser Gly Gly Gly Leu Val Gln Pro Gly Gly
 1               5                   10                  15

Ser Leu Lys Leu Ser Cys Ala Ala Ser Gly Ala Val His Lys Ile Asn
                 20                  25                  30

Phe Leu Gly Trp Tyr Arg Gln Ala Pro Glu Lys Glu Arg Glu Met Val
             35                  40                  45

Ala Thr Ile Thr Ile Gly Asp Glu Val Asp Tyr Ala Asp Ser Ala Lys
         50                  55                  60

Gly Arg Phe Thr Ile Ser Arg Asp Glu Ala Lys Asn Met Val Tyr Leu
 65                  70                  75                  80

Gln Met Thr Ser Leu Lys Pro Glu Asp Thr Thr Val Tyr Val Cys Arg
                 85                  90                  95

Ala Gly Ser Arg Leu Tyr Pro Tyr Asn Tyr Trp Gly Gln Gly Thr Gln
            100                 105                 110

Val Thr Val Ser Ser
            115
```

<210> SEQ ID NO 27
<211> LENGTH: 117
<212> TYPE: PRT
<213> ORGANISM: Artificial Sequence
<220> FEATURE:
<223> OTHER INFORMATION: Nanobody sequence

<400> SEQUENCE: 27

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Glu Val Tyr Lys Ile Asn
            20                  25                  30

Phe Leu Gly Trp Tyr Arg Gln Ala Pro Gly Lys Glu Arg Glu Lys Val
        35                  40                  45

Ala His Ile Thr Ile Ala Asp Val Ala Asp Tyr Ala Asp Phe Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Gly Ser Arg Ile Trp Pro Tyr Asp Tyr Trp Gly Gln Gly Thr Leu
            100                 105                 110

Val Thr Val Ser Ser
        115
```

<210> SEQ ID NO 28
<211> LENGTH: 117
<212> TYPE: PRT
<213> ORGANISM: Artificial Sequence
<220> FEATURE:
<223> OTHER INFORMATION: Nanobody sequence

<400> SEQUENCE: 28

```
Glu Val Gln Leu Val Glu Ser Gly Gly Gly Leu Val Gln Pro Gly Gly
1               5                   10                  15

Ser Leu Arg Leu Ser Cys Val Ala Ser Gly Asp Val His Lys Ile Asn
            20                  25                  30

Ile Leu Gly Trp Tyr Arg Gln Ala Pro Gly Lys Glu Arg Glu Lys Val
        35                  40                  45

Ala His Ile Ser Ile Ser Asp Gln Thr Asp Tyr Ala Glu Ser Ala Lys
    50                  55                  60

Gly Arg Phe Thr Ile Ser Arg Asp Glu Ser Lys Asn Met Val Tyr Leu
65                  70                  75                  80

Gln Met Asn Ser Leu Lys Pro Glu Asp Thr Ala Val Tyr Leu Cys Arg
                85                  90                  95

Ala Phe Ser Arg Ile Tyr Pro Tyr Asp Tyr Trp Gly Gln Gly Thr Leu
            100                 105                 110

Val Thr Val Ser Ser
        115
```

<210> SEQ ID NO 29
<211> LENGTH: 117
<212> TYPE: PRT
<213> ORGANISM: Artificial Sequence
<220> FEATURE:
<223> OTHER INFORMATION: Nanobody sequence

<400> SEQUENCE: 29

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Lys Ile Asn
            20                  25                  30

Phe Leu Gly Trp Tyr Arg Gln Ala Pro Gly Lys Glu Arg Glu Leu Val
            35                  40                  45

Ala Thr Ile Thr Ile Gly Asp Ala Thr Asp Tyr Ala Asp Tyr Ala Lys
50                      55                  60

Gly Arg Phe Thr Ile Ser Arg Asp Glu Ala Arg Asn Met Val Tyr Leu
65                      70                  75                  80

Gln Met Asn Ser Leu Lys Pro Glu Asp Thr Ala Val Tyr Phe Cys Arg
            85                  90                  95

Ala Gly Ser Arg Leu Tyr Pro Tyr Asn Tyr Trp Gly Gln Gly Thr Leu
            100                 105                 110

Val Thr Val Ser Ser
            115
```

<210> SEQ ID NO 30
<211> LENGTH: 117
<212> TYPE: PRT
<213> ORGANISM: Artificial Sequence
<220> FEATURE:
<223> OTHER INFORMATION: Nanobody sequence

<400> SEQUENCE: 30

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Val His Lys Ile Asn
            20                  25                  30

Ile Leu Gly Trp Tyr Arg Gln Ala Pro Ala Lys Glu Arg Glu Met Val
            35                  40                  45

Ala His Ile Thr Ile Gly Asp Ala Thr Asp Tyr Ala Asp Ser Ala Lys
50                      55                  60

Gly Arg Phe Ala Ile Ser Arg Asp Glu Ala Lys Asn Met Val Tyr Leu
65                      70                  75                  80

Gln Met Asn Ser Leu Lys Pro Glu Asp Thr Ala Val Tyr Phe Cys Arg
            85                  90                  95

Ala Tyr Ser Arg Ile Tyr Pro Tyr Asn Tyr Trp Gly Gln Gly Thr Leu
            100                 105                 110

Val Thr Val Ser Ser
            115
```

<210> SEQ ID NO 31
<211> LENGTH: 117
<212> TYPE: PRT
<213> ORGANISM: Artificial Sequence
<220> FEATURE:
<223> OTHER INFORMATION: Nanobody sequence

<400> SEQUENCE: 31

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Val His Lys Ile Asn
            20                  25                  30

Phe Leu Gly Trp His Arg Gln Ala Pro Gly Lys Glu Arg Glu Lys Val
            35                  40                  45

Ala His Ile Thr Ile Gly Asp Ala Thr Asp Tyr Ala Asp Ser Ala Lys
50                      55                  60
```

```
Gly Arg Phe Thr Ile Ser Arg Asp Glu Ala Lys Asn Met Val Tyr Leu
 65                  70                  75                  80

Gln Met Asn Ser Leu Lys Pro Glu Asp Thr Ala Val Tyr Phe Cys Arg
                 85                  90                  95

Ala Gly Ser Arg Ile Tyr Pro Tyr Asp Tyr Trp Gly Gln Gly Thr Gln
            100                 105                 110

Val Thr Val Ser Ser
            115

<210> SEQ ID NO 32
<211> LENGTH: 117
<212> TYPE: PRT
<213> ORGANISM: Artificial Sequence
<220> FEATURE:
<223> OTHER INFORMATION: Nanobody sequence

<400> SEQUENCE: 32

Glu Val Gln Leu Val Glu Ser Gly Gly Gly Ser Val Gln Pro Gly Gly
 1               5                  10                  15

Ser Leu Arg Leu Ser Cys Ala Ala Ser Gly Ser Val His Lys Ile Asn
                20                  25                  30

Phe Leu Gly Trp Tyr Arg Gln Ala Pro Gly Lys Glu Arg Glu Val Val
            35                  40                  45

Ala Thr Ile Thr Ile Gly Asp Ala Thr Asp Tyr Ala Asp Ser Ala Lys
         50                  55                  60

Gly Arg Phe Thr Ile Ser Arg Asp Glu Ala Lys Asn Met Val Tyr Leu
 65                  70                  75                  80

Gln Met Asn Ser Leu Ser Pro Glu Asp Thr Ala Val Tyr Phe Cys Arg
                 85                  90                  95

Ala Gly Ser Arg Leu Tyr Pro Tyr Asn Tyr Trp Gly Gln Gly Thr Gln
            100                 105                 110

Val Thr Val Ser Ser
            115

<210> SEQ ID NO 33
<211> LENGTH: 117
<212> TYPE: PRT
<213> ORGANISM: Artificial Sequence
<220> FEATURE:
<223> OTHER INFORMATION: Nanobody sequence

<400> SEQUENCE: 33

Glu Val Gln Leu Val Glu Ser Gly Gly Gly Leu Val Gln Pro Gly Gly
 1               5                  10                  15

Ser Ala Arg Leu Ser Cys Val Ala Ser Gly Asp Val His Lys Ile Asn
                20                  25                  30

Phe Leu Gly Trp Tyr Arg Gln Ala Pro Gly Lys Glu Arg Glu Lys Val
            35                  40                  45

Ala His Ile Thr Ile Gly Asp Gln Thr Asp Tyr Ala Asp Ser Ala Lys
         50                  55                  60

Gly Arg Phe Thr Ile Ser Arg Asp Glu Ala Lys Asn Met Val Tyr Leu
 65                  70                  75                  80

Gln Met Asn Ser Leu Lys Pro Glu Asp Thr Ala Val Tyr Phe Cys Arg
                 85                  90                  95

Ala Gly Ser Arg Ile Trp Pro Tyr Asp Tyr Trp Gly Gln Gly Thr Gln
            100                 105                 110

Val Thr Val Ser Ser
```

<210> SEQ ID NO 34
<211> LENGTH: 117
<212> TYPE: PRT
<213> ORGANISM: Artificial Sequence
<220> FEATURE:
<223> OTHER INFORMATION: Nanobody sequence

<400> SEQUENCE: 34

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Ser Val His Leu Leu Asn
            20                  25                  30

Phe Leu Gly Trp Tyr Arg Gln Ala Pro Gly Lys Glu Arg Glu Met Val
        35                  40                  45

Ala His Ile Thr Ile Ala Asp Ala Thr Asp Tyr Ser His Phe Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Arg Pro Glu Asp Thr Ala Val Tyr Phe Cys Arg
                85                  90                  95

Ala Gly Ser Arg Ile Tyr Pro Tyr Asp Tyr Trp Gly Gln Gly Thr Leu
            100                 105                 110

Val Thr Val Ser Ser
        115
```

<210> SEQ ID NO 35
<211> LENGTH: 117
<212> TYPE: PRT
<213> ORGANISM: Artificial Sequence
<220> FEATURE:
<223> OTHER INFORMATION: Nanobody sequence

<400> SEQUENCE: 35

```
Glu Val Gln Leu Val Glu Ser Gly Gly Gly Leu Val Gln Pro Gly Gly
 1               5                  10                  15

Ser Leu Arg Leu Ser Cys Ala Val Ser Gly Ser Val His Leu Leu Asn
            20                  25                  30

Phe Leu Gly Trp Tyr Arg Gln Ala Pro Gly Lys Glu Arg Gly Val Val
        35                  40                  45

Ala His Ile Thr Ile Ala Asp Ala Thr Asp Tyr Ser His Phe Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Arg Pro Glu Asp Thr Ala Val Tyr Phe Cys Arg
                85                  90                  95

Ala Gly Ser Arg Ile Tyr Pro Tyr Asp Tyr Trp Gly Gln Gly Thr Gln
            100                 105                 110

Val Thr Val Ser Ser
        115
```

<210> SEQ ID NO 36
<211> LENGTH: 117
<212> TYPE: PRT
<213> ORGANISM: Artificial Sequence
<220> FEATURE:
<223> OTHER INFORMATION: Nanobody sequence

<400> SEQUENCE: 36

```
Glu Val Gln Leu Val Glu Ser Gly Gly Gly Leu Val Gln Ala Gly Gly
1               5                   10                  15

Ser Leu Thr Leu Ser Cys Ala Ala Ser Gly Asp Val His Lys Ile Asn
            20                  25                  30

Ile Leu Gly Trp Tyr Arg Gln Ala Pro Ala Lys Glu Arg Glu Met Val
        35                  40                  45

Ala His Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Tyr Ser Arg Ile Tyr Pro Tyr Asn Tyr Trp Gly Gln Gly Thr Leu
            100                 105                 110

Val Thr Val Ser Ser
        115
```

<210> SEQ ID NO 37
<211> LENGTH: 117
<212> TYPE: PRT
<213> ORGANISM: Artificial Sequence
<220> FEATURE:
<223> OTHER INFORMATION: Nanobody sequence

<400> SEQUENCE: 37

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Val His Lys Ile Asn
            20                  25                  30

Ile Leu Gly Trp Tyr Arg Gln Ala Pro Ala Lys Glu Arg Glu Met Val
        35                  40                  45

Ala His Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Tyr Ser Arg Ile Tyr Pro Tyr Asn Tyr Trp Gly Gln Gly Thr Leu
            100                 105                 110

Val Thr Val Ser Ser
        115
```

<210> SEQ ID NO 38
<211> LENGTH: 117
<212> TYPE: PRT
<213> ORGANISM: Artificial Sequence
<220> FEATURE:
<223> OTHER INFORMATION: Nanobody sequence

<400> SEQUENCE: 38

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Glu Val Tyr Lys Ile Asn
            20                  25                  30

Phe Leu Gly Trp Tyr Arg Gln Ala Pro Gly Lys Glu Arg Glu Lys Val
        35                  40                  45

Ala His Ile Thr Ile Ala Asp Val Ala Asp Tyr Ala Asp Phe Ala Gln
```

```
                    50                  55                  60
Gly Arg Phe Thr Ile Ser Arg Asp Glu Ala Lys Asn Met Val Tyr Leu
 65                  70                  75                  80

Gln Met Asn Ser Leu Lys Pro Glu Asp Thr Ala Val Tyr Phe Cys Arg
                 85                  90                  95

Ala Gly Ser Arg Ile Trp Pro Tyr Asp Tyr Trp Gly Gln Gly Thr Gln
                100                 105                 110

Val Thr Val Ser Ser
            115

<210> SEQ ID NO 39
<211> LENGTH: 117
<212> TYPE: PRT
<213> ORGANISM: Artificial Sequence
<220> FEATURE:
<223> OTHER INFORMATION: Nanobody sequence

<400> SEQUENCE: 39

Glu Val Gln Leu Val Glu Ser Gly Gly Gly Leu Val Gln Pro Gly Gly
 1               5                  10                  15

Ser Leu Arg Leu Ser Cys Ala Ala Ser Gly Asp Val His Lys Ile Asn
                20                  25                  30

Ile Leu Gly Trp Tyr Arg Gln Ala Pro Ala Lys Glu Arg Glu Met Val
             35                  40                  45

Ala His Ile Thr Ile Gly Asp Thr Thr Asp Tyr Ala Asp Ser Ala Lys
 50                  55                  60

Gly Arg Phe Thr Ile Ser Arg Asp Glu Ala Lys Asn Met Val Tyr Leu
 65                  70                  75                  80

Gln Met Asn Ser Leu Lys Pro Glu Asp Thr Ala Val Tyr Phe Cys Arg
                 85                  90                  95

Ala Tyr Ser Arg Ile Tyr Pro Tyr Asn Tyr Trp Gly Gln Gly Thr Gln
                100                 105                 110

Val Thr Val Ser Ser
            115

<210> SEQ ID NO 40
<211> LENGTH: 117
<212> TYPE: PRT
<213> ORGANISM: Artificial Sequence
<220> FEATURE:
<223> OTHER INFORMATION: Nanobody sequence

<400> SEQUENCE: 40

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ser Val His Leu Leu Asn
                20                  25                  30

Phe Leu Gly Trp Tyr Arg Gln Ala Pro Gly Lys Glu Arg Glu Met Val
             35                  40                  45

Ala His Ile Thr Ile Ala Asp Ala Thr Asp Tyr Ser His Phe Ala Lys
 50                  55                  60

Gly Arg Phe Thr Ile Ser Arg Asp Glu Ala Lys Asn Met Val Tyr Leu
 65                  70                  75                  80

Gln Met Asn Ser Leu Arg Pro Glu Asp Thr Ala Val Tyr Phe Cys Arg
                 85                  90                  95

Ala Gly Ser Arg Ile Tyr Pro Tyr Asp Tyr Trp Gly His Gly Thr Leu
                100                 105                 110
```

```
Val Thr Val Ser Ser
        115

<210> SEQ ID NO 41
<211> LENGTH: 117
<212> TYPE: PRT
<213> ORGANISM: Artificial Sequence
<220> FEATURE:
<223> OTHER INFORMATION: Nanobody sequence

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Val Ala Ser Gly Asp Val His Lys Ile Asn
            20                  25                  30

Phe Leu Gly Trp Tyr Arg Gln Ala Pro Gly Lys Glu Arg Glu Lys Val
        35                  40                  45

Ala His Ile Thr Ile Gly Asp Gln Ala Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Gly Ser Arg Ile Tyr Pro Tyr Asp Tyr Trp Gly Arg Gly Thr Leu
            100                 105                 110

Val Thr Val Ser Ser
        115

<210> SEQ ID NO 42
<211> LENGTH: 117
<212> TYPE: PRT
<213> ORGANISM: Artificial Sequence
<220> FEATURE:
<223> OTHER INFORMATION: Nanobody sequence

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Val Ser Gly Ser Val His Leu Leu Asn
            20                  25                  30

Phe Leu Gly Trp Tyr Arg Gln Ala Pro Gly Lys Glu Arg Glu Met Val
        35                  40                  45

Thr His Ile Thr Ile Ala Asp Ala Thr Asp Tyr Ser His Phe Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Arg Pro Glu Asp Thr Ala Val Tyr Phe Cys Arg
                85                  90                  95

Ala Gly Ser Arg Ile Tyr Pro Tyr Asp Tyr Trp Gly Gln Gly Thr Gln
            100                 105                 110

Val Thr Val Ser Ser
        115

<210> SEQ ID NO 43
<211> LENGTH: 117
<212> TYPE: PRT
<213> ORGANISM: Artificial Sequence
<220> FEATURE:
<223> OTHER INFORMATION: Nanobody sequence
```

<400> SEQUENCE: 43

Glu Val Gln Leu Val Glu Ser Gly Gly Asp Leu Val Gln Pro Gly Gly
1               5                   10                  15

Ser Leu Arg Leu Ser Cys Ala Ala Ser Gly Asp Val His Lys Ile Asn
            20                  25                  30

Phe Leu Gly Trp Tyr Arg Gln Ala Pro Gly Lys Glu Arg Glu Met Val
        35                  40                  45

Ala His Ile Thr Ile Ala Asp Ala Thr Asp Tyr Ala Glu Phe Ala Lys
    50                  55                  60

Gly Arg Phe Thr Ile Ser Arg Asp Glu Pro Lys Asn Met Val His Leu
65              70                  75                  80

Gln Met Asn Ser Leu Lys Pro Glu Asp Thr Ala Val Tyr Leu Cys Arg
            85                  90                  95

Ala Gly Ser Arg Ile Tyr Pro Tyr Asn Tyr Trp Gly Gln Gly Thr Gln
        100                 105                 110

Val Thr Val Ser Ser
        115

<210> SEQ ID NO 44
<211> LENGTH: 117
<212> TYPE: PRT
<213> ORGANISM: Artificial Sequence
<220> FEATURE:
<223> OTHER INFORMATION: Nanobody sequence

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Val His Lys Ile Asn
            20                  25                  30

Ile Leu Gly Trp Tyr Arg Gln Ala Pro Ala Lys Glu Arg Glu Met Val
        35                  40                  45

Ala His Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val Tyr Leu
65              70                  75                  80

Gln Met Asn Ser Leu Lys Pro Glu Asp Thr Ala Val Tyr Phe Cys Arg
            85                  90                  95

Ala Tyr Ser Arg Ile Tyr Pro Tyr Asn Tyr Trp Gly Arg Gly Thr Gln
        100                 105                 110

Val Thr Val Ser Ser
        115

<210> SEQ ID NO 45
<211> LENGTH: 117
<212> TYPE: PRT
<213> ORGANISM: Artificial Sequence
<220> FEATURE:
<223> OTHER INFORMATION: Nanobody sequence

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Val Ala Ser Gly Asp Val His Lys Ile Asn
            20                  25                  30

Ile Leu Gly Trp Tyr Arg Gln Ala Pro Gly Lys Glu Arg Glu Lys Val
        35                  40                  45

```
Ala Arg Ile Ser Ile Ser Asp Gln Thr Asp Tyr Ala Glu Ser Ala Lys
 50                  55                  60

Gly Arg Phe Thr Ile Ser Arg Asp Glu Ser Lys Asn Met Val Tyr Leu
 65                  70                  75                  80

Gln Met Asn Ser Leu Lys Pro Glu Asp Thr Ala Val Tyr Leu Cys Arg
                 85                  90                  95

Ala Phe Ser Arg Ile Tyr Pro Tyr Asp Tyr Trp Gly Gln Gly Thr Leu
            100                 105                 110

Val Thr Val Ser Ser
            115

<210> SEQ ID NO 46
<211> LENGTH: 117
<212> TYPE: PRT
<213> ORGANISM: Artificial Sequence
<220> FEATURE:
<223> OTHER INFORMATION: Nanobody sequence

<400> SEQUENCE: 46

Glu Val Gln Leu Val Glu Ser Gly Gly Gly Leu Val Gln Pro Glu Gly
 1               5                  10                  15

Ser Leu Arg Leu Ser Cys Ala Ala Ser Gly Glu Val Tyr Lys Ile Asn
             20                  25                  30

Phe Leu Gly Trp Tyr Arg Gln Ala Pro Gly Lys Glu Arg Glu Lys Val
         35                  40                  45

Ala His Ile Thr Ile Ala Asp Val Ala Asp Tyr Ala Asp Phe Ala Lys
 50                  55                  60

Gly Arg Leu Thr Ile Ser Arg Asp Glu Ala Lys Asn Met Val Tyr Leu
 65                  70                  75                  80

Gln Met Asn Ser Leu Lys Pro Glu Asp Thr Ala Val Tyr Phe Cys Arg
                 85                  90                  95

Ala Gly Ser Arg Ile Trp Pro Tyr Asp Tyr Trp Gly Gln Gly Thr Leu
            100                 105                 110

Val Thr Val Ser Ser
            115

<210> SEQ ID NO 47
<211> LENGTH: 117
<212> TYPE: PRT
<213> ORGANISM: Artificial Sequence
<220> FEATURE:
<223> OTHER INFORMATION: Nanobody sequence

<400> SEQUENCE: 47

Glu Val Gln Leu Val Glu Ser Gly Gly Gly Leu Val Gln Pro Gly Gly
 1               5                  10                  15

Ser Leu Lys Leu Pro Cys Ala Ala Ser Gly Ala Val His Lys Ile Asn
             20                  25                  30

Phe Leu Gly Trp Tyr Arg Gln Thr Pro Glu Lys Glu Arg Glu Met Val
         35                  40                  45

Ala Thr Ile Thr Ile Gly Asp Glu Val Asp Tyr Ala Asp Ser Ala Lys
 50                  55                  60

Gly Arg Phe Thr Ile Ser Arg Asp Glu Ala Lys Asn Met Val Tyr Leu
 65                  70                  75                  80

Gln Met Thr Ser Leu Lys Pro Glu Asp Thr Ala Val Tyr Val Cys Arg
                 85                  90                  95

Ala Gly Ser Arg Leu Tyr Pro Tyr Asn Tyr Trp Gly Gln Gly Thr Leu
            100                 105                 110
```

Val Thr Val Ser Ser
        115

<210> SEQ ID NO 48
<211> LENGTH: 117
<212> TYPE: PRT
<213> ORGANISM: Artificial Sequence
<220> FEATURE:
<223> OTHER INFORMATION: Nanobody sequence

<400> SEQUENCE: 48

Glu Val Gln Leu Val Glu Ser Gly Gly Gly Leu Val Gln Pro Gly Gly
1               5                   10                  15

Ser Leu Gly Leu Ser Cys Ala Ala Ser Gly Ser Val His Leu Leu Asn
            20                  25                  30

Phe Leu Gly Trp Tyr Arg Gln Ala Pro Gly Lys Glu Arg Glu Met Val
        35                  40                  45

Ala His Ile Thr Ile Ala Asp Ala Thr Asp Tyr Ala His Phe Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Arg Pro Glu Asp Thr Ala Val Tyr Phe Cys Arg
                85                  90                  95

Ala Gly Ser Arg Ile Tyr Pro Tyr Asp Tyr Trp Gly Gln Gly Thr Leu
            100                 105                 110

Val Thr Val Ser Ser
        115

<210> SEQ ID NO 49
<211> LENGTH: 117
<212> TYPE: PRT
<213> ORGANISM: Artificial Sequence
<220> FEATURE:
<223> OTHER INFORMATION: Nanobody sequence

<400> SEQUENCE: 49

Glu Val Gln Leu Val Glu Ser Gly Gly Gly Leu Ala Gln Pro Gly Gly
1               5                   10                  15

Ser Leu Arg Leu Ser Cys Ala Ala Ser Gly Asp Val His Lys Ile Asn
            20                  25                  30

Ile Leu Gly Trp Tyr Arg Gln Ala Pro Ala Lys Glu Arg Glu Met Val
        35                  40                  45

Ala His Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Tyr Ser Arg Ile Tyr Pro Tyr Asn Tyr Trp Gly Gln Gly Thr Leu
            100                 105                 110

Val Thr Val Ser Ser
        115

<210> SEQ ID NO 50
<211> LENGTH: 117
<212> TYPE: PRT
<213> ORGANISM: Artificial Sequence
<220> FEATURE:
<223> OTHER INFORMATION: Nanobody sequence

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Val Ala Ser Gly Asp Val His Lys Ile Asn
            20                  25                  30

Phe Leu Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
    50                  55                  60

Gly Arg Phe Thr Ile Ser Arg Asp Glu Ser Lys Asn Met Val Tyr Leu
65                  70                  75                  80

Gln Met Asn Ser Leu Lys Pro Glu Asp Thr Ala Val Tyr Phe Cys Arg
            85                  90                  95

Ala Phe Ser Arg Ile Tyr Pro Tyr Asp Tyr Trp Gly Gln Gly Thr Leu
        100                 105                 110

Val Thr Val Ser Ser
        115

<210> SEQ ID NO 51
<211> LENGTH: 117
<212> TYPE: PRT
<213> ORGANISM: Artificial Sequence
<220> FEATURE:
<223> OTHER INFORMATION: Nanobody sequence

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Glu Val Tyr Lys Ile Asn
            20                  25                  30

Phe Leu Gly Trp Tyr Arg Gln Ala Pro Gly Lys Glu Arg Glu Lys Val
        35                  40                  45

Ala His Ile Thr Ile Ala Asp Ala Ala Asp Tyr Ala Asp Phe Ala Lys
    50                  55                  60

Gly Arg Phe Thr Ile Ser Arg Asp Gly Ala Lys Asn Met Val Tyr Leu
65                  70                  75                  80

Gln Met Asn Ser Leu Lys Pro Glu Asp Thr Ala Val Tyr Phe Cys Arg
            85                  90                  95

Ala Gly Ser Arg Ile Trp Pro Tyr Asp Tyr Trp Gly Gln Gly Thr Gln
        100                 105                 110

Val Thr Val Ser Ser
        115

<210> SEQ ID NO 52
<211> LENGTH: 117
<212> TYPE: PRT
<213> ORGANISM: Artificial Sequence
<220> FEATURE:
<223> OTHER INFORMATION: Nanobody sequence

<400> SEQUENCE: 52

Glu Val Gln Leu Val Glu Ser Gly Gly Gly Trp Val Gln Pro Gly Gly
1               5                   10                  15

Ser Leu Arg Leu Ser Cys Ala Ala Ser Gly Ser Val Tyr Lys Ile Asn
            20                  25                  30

Phe Leu Ser Trp Tyr Arg Gln Ala Pro Gly His Glu Arg Glu Leu Val
        35                  40                  45

Ala Thr Ile Thr Ile Gly Asp Ala Asp Tyr Ala Asp Ser Ala Lys
        50                  55                  60

Gly Arg Phe Thr Ile Ser Arg Asp Glu Ala Arg Asn Met Val Tyr Leu
65                  70                  75                  80

Gln Met Asn Ser Leu Lys Pro Glu Asp Thr Ala Leu Tyr Phe Cys His
                85                  90                  95

Ala Gly Ser Arg Leu Tyr Pro Tyr Asn Tyr Trp Gly Gln Gly Thr Gln
            100                 105                 110

Val Thr Val Ser Ser
            115

<210> SEQ ID NO 53
<211> LENGTH: 117
<212> TYPE: PRT
<213> ORGANISM: Artificial Sequence
<220> FEATURE:
<223> OTHER INFORMATION: Nanobody sequence

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Leu Leu Asn
            20                  25                  30

Phe Leu Gly Trp Tyr Arg Gln Ala Pro Gly Lys Glu Arg Glu Met Val
        35                  40                  45

Ala His Ile Thr Ile Ala Asp Ala Thr Asp Tyr Ser His Phe Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Arg Pro Glu Asp Thr Ala Val Tyr Phe Cys Arg
                85                  90                  95

Ala Gly Ser Arg Ile Tyr Pro Tyr Asp Tyr Trp Gly Gln Gly Thr Gln
            100                 105                 110

Val Thr Val Ser Ser
            115

<210> SEQ ID NO 54
<211> LENGTH: 117
<212> TYPE: PRT
<213> ORGANISM: Artificial Sequence
<220> FEATURE:
<223> OTHER INFORMATION: Nanobody sequence

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Val Ala Ser Gly Asp Val His Lys Ile Asn
            20                  25                  30

Ile Leu Gly Trp Tyr Arg Gln Ala Pro Gly Lys Glu Arg Glu Lys Val
        35                  40                  45

Ala His Ile Ala Ile Ser Asp Gln Thr Asp Tyr Ala Glu Ser Ala Lys
    50                  55                  60

Gly Arg Phe Thr Ile Ser Arg Asp Glu Ser Lys Asn Met Val Tyr Leu
65                  70                  75                  80

Gln Met Asn Ser Leu Lys Pro Glu Asp Thr Ala Val Tyr Leu Cys Arg
                85                  90                  95

Ala Phe Ser Arg Ile Tyr Pro Tyr Asp Tyr Trp Gly Gln Gly Thr Leu

-continued

```
                100                 105                 110
Val Thr Val Ser Ser
        115

<210> SEQ ID NO 55
<211> LENGTH: 117
<212> TYPE: PRT
<213> ORGANISM: Artificial Sequence
<220> FEATURE:
<223> OTHER INFORMATION: Nanobody sequence

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Val His Lys Ile Asn
            20                  25                  30

Ile Leu Gly Trp Tyr Arg Gln Ala Pro Ala Lys Glu Arg Glu Met Val
        35                  40                  45

Ala His Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Ala Tyr Phe Cys Arg
                85                  90                  95

Ala Tyr Ser Arg Ile Tyr Pro Tyr Asn Tyr Trp Gly Gln Gly Thr Leu
            100                 105                 110

Val Thr Val Ser Ser
        115

<210> SEQ ID NO 56
<211> LENGTH: 117
<212> TYPE: PRT
<213> ORGANISM: Artificial Sequence
<220> FEATURE:
<223> OTHER INFORMATION: Nanobody sequence

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Val His Lys Ile Asn
            20                  25                  30

Ile Leu Gly Trp Tyr Arg Gln Ala Pro Ala Lys Glu Arg Gly Met Val
        35                  40                  45

Ala His Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Tyr Ser Arg Ile Tyr Pro Tyr Asn Tyr Trp Gly Gln Gly Thr Gln
            100                 105                 110

Val Thr Val Ser Ser
        115

<210> SEQ ID NO 57
<211> LENGTH: 117
<212> TYPE: PRT
<213> ORGANISM: Artificial Sequence
<220> FEATURE:
```

<223> OTHER INFORMATION: Nanobody sequence

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Val His Lys Ile Asn
            20                  25                  30

Ile Leu Gly Trp Tyr Arg Gln Ala Pro Ala Lys Glu His Glu Met Val
        35                  40                  45

Ala His Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Tyr Ser Arg Ile Tyr Pro Tyr Asn Tyr Trp Gly Gln Gly Thr Leu
            100                 105                 110

Val Thr Val Ser Ser
        115

<210> SEQ ID NO 58
<211> LENGTH: 117
<212> TYPE: PRT
<213> ORGANISM: Artificial Sequence
<220> FEATURE:
<223> OTHER INFORMATION: Nanobody sequence

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Val His Lys Ile Asn
            20                  25                  30

Ile Leu Gly Trp Tyr Arg Gln Ala Pro Ala Arg Glu Arg Glu Met Val
        35                  40                  45

Ala His Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Tyr Ser Arg Ile Tyr Pro Tyr Asn Tyr Trp Gly Gln Gly Thr Gln
            100                 105                 110

Val Thr Val Ser Ser
        115

<210> SEQ ID NO 59
<211> LENGTH: 117
<212> TYPE: PRT
<213> ORGANISM: Artificial Sequence
<220> FEATURE:
<223> OTHER INFORMATION: Nanobody sequence

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Val His Lys Ile Asn
            20                  25                  30

Ile Leu Gly Trp Tyr Arg Gln Ala Pro Ala Lys Glu Arg Glu Met Val

```
            35                  40                  45
Ala His Ile Thr Ile Gly Asp Ala Thr Asp Tyr Ala Asp Ser Ala Lys
    50                  55                  60
Gly Arg Phe Thr Ile Ser Arg Asp Glu Ala Glu Asn Met Val Tyr Leu
65                  70                  75                  80
Gln Met Asn Ser Leu Lys Pro Glu Asp Thr Ala Val Tyr Phe Cys Arg
                85                  90                  95
Ala Tyr Ser Arg Ile Tyr Pro Tyr Asn Tyr Trp Gly Gln Gly Thr Leu
            100                 105                 110
Val Thr Val Ser Ser
        115

<210> SEQ ID NO 60
<211> LENGTH: 117
<212> TYPE: PRT
<213> ORGANISM: Artificial Sequence
<220> FEATURE:
<223> OTHER INFORMATION: Nanobody sequence

<400> SEQUENCE: 60

Glu Val Gln Leu Val Glu Ser Gly Gly Gly Leu Val Gln Pro Gly Gly
1               5                   10                  15
Ser Leu Lys Leu Ser Cys Ala Ala Ser Gly Ala Val His Lys Ile Asn
            20                  25                  30
Phe Leu Gly Trp Tyr Arg Gln Thr Pro Glu Lys Glu Arg Glu Met Val
        35                  40                  45
Ala Thr Ile Thr Ile Gly Asp Glu Val Asp Tyr Ala Asp Ser Ala Lys
    50                  55                  60
Gly Arg Phe Thr Ile Ser Arg Asp Glu Ala Lys Asn Met Val Tyr Leu
65                  70                  75                  80
Gln Met Thr Ser Leu Lys Pro Glu Asp Thr Ala Val Tyr Val Cys Arg
                85                  90                  95
Ala Gly Ser Arg Leu Tyr Pro Tyr Asn Tyr Trp Gly Gln Gly Thr Leu
            100                 105                 110
Val Thr Val Ser Ser
        115

<210> SEQ ID NO 61
<211> LENGTH: 117
<212> TYPE: PRT
<213> ORGANISM: Artificial Sequence
<220> FEATURE:
<223> OTHER INFORMATION: Nanobody sequence

<400> SEQUENCE: 61

Glu Val Gln Leu Val Glu Ser Gly Gly Gly Leu Val Gln Pro Gly Gly
1               5                   10                  15
Ser Leu Lys Leu Ser Cys Ala Ala Ser Gly Ala Val His Lys Ile Asn
            20                  25                  30
Phe Leu Gly Trp Tyr Arg Gln Ala Pro Glu Lys Glu Arg Glu Met Val
        35                  40                  45
Ala Thr Ile Thr Ile Gly Asp Glu Val Asp Tyr Ala Asp Ser Ala Lys
    50                  55                  60
Gly Arg Phe Thr Ile Ser Arg Asp Glu Ala Thr Asn Met Val Tyr Leu
65                  70                  75                  80
Gln Met Thr Ser Leu Lys Pro Glu Asp Thr Ala Val Tyr Phe Cys Arg
                85                  90                  95
```

Ala Gly Ser Arg Ile Tyr Pro Tyr Asn Tyr Trp Gly Gln Gly Thr Gln
            100                 105                 110

Val Thr Val Ser Ser
        115

<210> SEQ ID NO 62
<211> LENGTH: 117
<212> TYPE: PRT
<213> ORGANISM: Artificial Sequence
<220> FEATURE:
<223> OTHER INFORMATION: Nanobody sequence

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Val His Lys Ile Asn
            20                  25                  30

Ile Leu Gly Trp Tyr Arg Gln Ala Pro Ala Lys Glu Arg Glu Met Val
        35                  40                  45

Ala His Ile Thr Ile Gly Asp Ala Thr Ser Tyr Ala Gly Ser Ala Lys
    50                  55                  60

Gly Arg Phe Thr Ile Ser Arg Asp Glu Ala Lys Asn Met Val Tyr Leu
65                  70                  75                  80

Gln Leu Asn Asn Leu Lys Pro Glu Asp Thr Ala Val Tyr Phe Cys Arg
            85                  90                  95

Ala Tyr Ser Arg Ile Tyr Pro Tyr Asn Tyr Trp Gly Gln Gly Thr Leu
            100                 105                 110

Val Thr Val Ser Ser
        115

<210> SEQ ID NO 63
<211> LENGTH: 117
<212> TYPE: PRT
<213> ORGANISM: Artificial Sequence
<220> FEATURE:
<223> OTHER INFORMATION: Nanobody sequence

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Val His Lys Ile Asn
            20                  25                  30

Ile Leu Gly Trp Tyr Arg Gln Ala Pro Ala Lys Glu Arg Glu Met Val
        35                  40                  45

Ala His Ile Thr Ile Gly Asp Ala Thr Ser Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Leu Asn Asn Leu Lys Pro Glu Asp Thr Ala Val Tyr Phe Cys Arg
            85                  90                  95

Ala Tyr Ser Arg Ile Tyr Pro Tyr Asn Tyr Trp Gly Gln Gly Thr Leu
            100                 105                 110

Val Thr Val Ser Ser
        115

<210> SEQ ID NO 64
<211> LENGTH: 117
<212> TYPE: PRT
<213> ORGANISM: Artificial Sequence

```
<220> FEATURE:
<223> OTHER INFORMATION: Nanobody sequence

<400> SEQUENCE: 64

Glu Val Gln Leu Val Glu Ser Gly Gly Asp Leu Val Gln Pro Gly Gly
1               5                   10                  15

Ser Leu Arg Leu Ser Cys Ala Ala Ser Gly Asp Val His Lys Ile Asn
            20                  25                  30

Phe Leu Gly Trp Tyr Arg Gln Ala Pro Gly Lys Glu Arg Glu Met Val
        35                  40                  45

Ala His Ile Thr Ile Ala Asp Ala Thr Asp Tyr Ala Glu Phe Ala Lys
    50                  55                  60

Gly Arg Phe Thr Ile Ser Arg Asp Glu Pro Lys Asn Met Val Tyr Leu
65              70                  75                  80

Gln Met Asn Ser Leu Lys Pro Glu Asp Thr Ala Val Tyr Leu Cys Arg
                85                  90                  95

Ala Gly Ser Arg Ile Tyr Pro Tyr Asn Tyr Trp Gly Gln Gly Thr Gln
            100                 105                 110

Val Thr Val Ser Ser
        115

<210> SEQ ID NO 65
<211> LENGTH: 117
<212> TYPE: PRT
<213> ORGANISM: Artificial Sequence
<220> FEATURE:
<223> OTHER INFORMATION: Nanobody sequence

<400> SEQUENCE: 65

Glu Val Gln Leu Val Glu Ser Gly Gly Gly Leu Val Gln Pro Gly Gly
1               5                   10                  15

Ser Leu Lys Leu Ser Cys Ala Ala Ser Gly Ala Val His Lys Ile Asn
            20                  25                  30

Phe Leu Gly Trp Tyr Arg Gln Thr Pro Glu Lys Glu Arg Glu Met Val
        35                  40                  45

Ala Thr Ile Thr Ile Gly Asp Glu Val Asp Tyr Ala His Ser Ala Lys
    50                  55                  60

Gly Arg Phe Thr Ile Ser Arg Asp Glu Ala Lys Asn Met Val Tyr Leu
65              70                  75                  80

Gln Met Thr Ser Leu Lys Pro Glu Asp Thr Ala Val Tyr Val Cys Arg
                85                  90                  95

Ala Gly Ser Arg Leu Tyr Pro Tyr Asn Tyr Trp Gly Gln Gly Thr Gln
            100                 105                 110

Val Thr Val Ser Ser
        115

<210> SEQ ID NO 66
<211> LENGTH: 117
<212> TYPE: PRT
<213> ORGANISM: Artificial Sequence
<220> FEATURE:
<223> OTHER INFORMATION: Nanobody sequence

<400> SEQUENCE: 66

Glu Val Gln Leu Val Glu Ser Gly Gly Gly Leu Val Gln Pro Gly Gly
1               5                   10                  15

Ser Leu Lys Leu Ser Cys Ala Ala Ser Gly Ala Val His Lys Ile Asn
            20                  25                  30
```

```
Phe Leu Gly Trp Tyr Arg Gln Thr Pro Glu Lys Glu Arg Glu Met Val
             35                  40                  45

Ala Thr Ile Thr Ile Gly Asp Glu Val Ala Tyr Ala Asp Ser Ala Lys
 50                  55                  60

Gly Arg Phe Thr Ile Ser Arg Asp Glu Ala Lys Asn Met Val Tyr Leu
 65                  70                  75                  80

Gln Met Thr Ser Leu Lys Pro Glu Asp Thr Ala Val Tyr Val Cys Arg
             85                  90                  95

Ala Gly Ser Arg Leu Tyr Pro Tyr Asn Tyr Trp Gly Gln Gly Thr Gln
            100                 105                 110

Val Thr Val Ser Ser
            115

<210> SEQ ID NO 67
<211> LENGTH: 117
<212> TYPE: PRT
<213> ORGANISM: Artificial Sequence
<220> FEATURE:
<223> OTHER INFORMATION: Nanobody sequence

<400> SEQUENCE: 67

Glu Val Gln Leu Val Glu Ser Gly Gly Gly Leu Val Gln Pro Gly Gly
 1               5                  10                  15

Ser Leu Arg Leu Ser Cys Ala Ala Ser Gly Glu Val Tyr Lys Ile Asn
             20                  25                  30

Phe Leu Gly Trp Tyr Arg Gln Ala Pro Gly Lys Glu Arg Glu Lys Val
             35                  40                  45

Ala His Ile Thr Ile Ala Asp Ala Asp Tyr Ala Asp Phe Ala Lys
 50                  55                  60

Gly Arg Phe Thr Ile Ser Arg Asp Glu Ala Lys Asn Met Val Tyr Leu
 65                  70                  75                  80

Gln Met Asn Ser Leu Lys Pro Glu Asp Thr Ala Val Tyr Phe Cys Arg
             85                  90                  95

Ala Gly Ser Arg Ile Trp Pro Tyr Asp Tyr Trp Gly Gln Gly Thr Gln
            100                 105                 110

Val Thr Val Ser Ser
            115

<210> SEQ ID NO 68
<211> LENGTH: 117
<212> TYPE: PRT
<213> ORGANISM: Artificial Sequence
<220> FEATURE:
<223> OTHER INFORMATION: Nanobody sequence

<400> SEQUENCE: 68

Glu Val Gln Leu Val Glu Ser Gly Gly Gly Leu Val Gln Pro Gly Gly
 1               5                  10                  15

Ser Leu Arg Leu Ser Cys Ala Ala Ser Gly Glu Val Tyr Lys Ile Asn
             20                  25                  30

Phe Leu Gly Trp Tyr Arg Gln Ala Pro Gly Lys Glu Arg Glu Lys Val
             35                  40                  45

Ala His Ile Thr Ile Ala Asp Ala Ala Asp Tyr Ala Asp Phe Ala Lys
 50                  55                  60

Gly Arg Phe Thr Ile Ser Arg Asp Glu Ala Lys Asn Met Val Tyr Leu
 65                  70                  75                  80

Gln Met Asn Ser Leu Lys Pro Glu Asp Thr Ala Val Tyr Phe Cys Arg
             85                  90                  95
```

Ala Gly Ser Arg Ile Tyr Pro Tyr Asp Tyr Trp Gly Gln Gly Thr Gln
            100                 105                 110

Val Thr Val Ser Ser
        115

<210> SEQ ID NO 69
<211> LENGTH: 117
<212> TYPE: PRT
<213> ORGANISM: Artificial Sequence
<220> FEATURE:
<223> OTHER INFORMATION: Nanobody sequence

<400> SEQUENCE: 69

Glu Val Gln Leu Val Glu Ser Gly Gly Gly Ser Val Gln Pro Gly Gly
1               5                   10                  15

Ser Leu Arg Pro Ser Cys Ala Ala Ser Gly Ser Val His Lys Ile Asn
            20                  25                  30

Phe Leu Gly Trp Tyr Arg Gln Ala Pro Gly Lys Glu Arg Glu Met Val
        35                  40                  45

Ala Thr Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Ser Pro Glu Asp Thr Ala Val Tyr Phe Cys Arg
                85                  90                  95

Ala Gly Ser Arg Leu Tyr Pro Tyr Asn Tyr Trp Gly Gln Gly Thr Gln
            100                 105                 110

Val Thr Val Ser Ser
        115

<210> SEQ ID NO 70
<211> LENGTH: 117
<212> TYPE: PRT
<213> ORGANISM: Artificial Sequence
<220> FEATURE:
<223> OTHER INFORMATION: Nanobody sequence

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Glu Val Tyr Lys Ile Asn
            20                  25                  30

Phe Leu Gly Trp Tyr Arg Gln Ala Pro Gly Lys Glu Arg Glu Lys Val
        35                  40                  45

Ala His Ile Thr Ile Ala Asp Val Ala Asp Tyr Ala Asp Phe Ala Lys
    50                  55                  60

Gly Arg Phe Thr Ile Ser Arg Asp Glu Val Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Gly Ser Arg Ile Trp Pro Tyr Asp Tyr Trp Gly Gln Gly Thr Leu
            100                 105                 110

Val Thr Val Ser Ser
        115

<210> SEQ ID NO 71
<211> LENGTH: 117
<212> TYPE: PRT

```
<213> ORGANISM: Artificial Sequence
<220> FEATURE:
<223> OTHER INFORMATION: Nanobody sequence

<400> SEQUENCE: 71

Glu Val Gln Leu Val Glu Ser Gly Gly Gly Leu Val Gln Pro Gly Glu
1               5                   10                  15

Ser Leu Arg Leu Ser Cys Ala Ala Ser Gly Asp Val His Lys Ile Asn
            20                  25                  30

Ile Leu Gly Trp Tyr Arg Gln Ala Pro Ala Lys Glu Arg Glu Met Val
        35                  40                  45

Ala His Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Tyr Ser Arg Ile Tyr Pro Tyr Asn Tyr Trp Gly Gln Gly Thr Leu
            100                 105                 110

Val Thr Val Ser Ser
        115

<210> SEQ ID NO 72
<211> LENGTH: 117
<212> TYPE: PRT
<213> ORGANISM: Artificial Sequence
<220> FEATURE:
<223> OTHER INFORMATION: Nanobody sequence

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Glu Val Tyr Lys Ile Asn
            20                  25                  30

Phe Leu Gly Trp Tyr Arg Gln Ala Pro Gly Lys Glu Arg Glu Lys Val
        35                  40                  45

Ala His Ile Thr Ile Ala Asp Ala Ala Asp Tyr Ala Asp Phe Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Arg Pro Glu Asp Thr Ala Val Tyr Phe Cys Arg
                85                  90                  95

Ala Gly Ser Arg Ile Trp Pro Tyr Asp Tyr Trp Gly Gln Gly Thr Gln
            100                 105                 110

Val Thr Val Ser Ser
        115

<210> SEQ ID NO 73
<211> LENGTH: 117
<212> TYPE: PRT
<213> ORGANISM: Artificial Sequence
<220> FEATURE:
<223> OTHER INFORMATION: Nanobody sequence

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Leu Leu Asn
            20                  25                  30
```

Phe Leu Gly Trp Tyr Arg Gln Ala Pro Gly Lys Glu Arg Glu Met Val
                35                  40                  45

Ala His Ile Thr Ile Ala Asp Val Thr Asp Tyr Ser Tyr Phe Ala Lys
 50                  55                  60

Gly Arg Phe Thr Ile Ser Arg Asp Glu Ala Lys Asn Met Val Tyr Leu
 65                  70                  75                  80

Gln Met Asn Ser Leu Arg Pro Glu Asp Thr Ala Val Tyr Phe Cys Arg
                85                  90                  95

Ala Gly Ser Arg Ile Tyr Pro Tyr Asp Tyr Trp Gly Gln Gly Thr Gln
                100                 105                 110

Val Thr Val Ser Ser
            115

<210> SEQ ID NO 74
<211> LENGTH: 117
<212> TYPE: PRT
<213> ORGANISM: Artificial Sequence
<220> FEATURE:
<223> OTHER INFORMATION: Nanobody sequence

<400> SEQUENCE: 74

Glu Val Gln Leu Val Glu Ser Gly Gly Gly Leu Val Gln Pro Gly Gly
 1               5                   10                  15

Ser Leu Arg Leu Ser Cys Ala Ala Ser Gly Asp Val His Lys Ile Asn
                20                  25                  30

Ile Leu Gly Trp Tyr Arg Gln Ala Pro Ala Lys Glu Arg Glu Met Val
                35                  40                  45

Ala His Ile Thr Ile Gly Asp Ala Thr Asp Tyr Ala Asp Ser Ala Lys
 50                  55                  60

Gly Arg Phe Thr Ile Ser Arg Asp Glu Ala Lys Asn Val Val Tyr Leu
 65                  70                  75                  80

Gln Met Asn Ser Leu Lys Pro Glu Asp Thr Ala Val Tyr Phe Cys Arg
                85                  90                  95

Ala Tyr Ser Arg Ile Tyr Pro Tyr Asn Tyr Trp Gly Gln Gly Thr Leu
                100                 105                 110

Val Thr Val Ser Ser
            115

<210> SEQ ID NO 75
<211> LENGTH: 117
<212> TYPE: PRT
<213> ORGANISM: Artificial Sequence
<220> FEATURE:
<223> OTHER INFORMATION: Nanobody sequence

<400> SEQUENCE: 75

Glu Val Gln Leu Val Glu Ser Gly Gly Gly Ser Val Gln Pro Gly Gly
 1               5                   10                  15

Ser Leu Arg Leu Ser Cys Ala Ala Ser Gly Ser Val His Lys Ile Asn
                20                  25                  30

Phe Leu Gly Trp Tyr Arg Gln Ala Pro Gly Lys Glu Arg Gly Met Val
                35                  40                  45

Ala Thr Ile Thr Ile Gly Asp Ala Thr Asp Tyr Ala Asp Ser Ala Lys
 50                  55                  60

Gly Arg Phe Thr Ile Ser Arg Asp Glu Ala Lys Asn Met Val Tyr Leu
 65                  70                  75                  80

Gln Met Asn Ser Leu Ser Pro Glu Asp Thr Ala Val Tyr Phe Cys Arg

```
                    85                  90                  95
Ala Gly Ser Arg Leu Tyr Pro Tyr Asn Tyr Trp Gly Gln Gly Thr Gln
                100                 105                 110

Val Thr Val Ser Ser
        115

<210> SEQ ID NO 76
<211> LENGTH: 117
<212> TYPE: PRT
<213> ORGANISM: Artificial Sequence
<220> FEATURE:
<223> OTHER INFORMATION: Nanobody sequence

<400> SEQUENCE: 76

Glu Val Gln Leu Val Glu Ser Gly Gly Gly Leu Val Gln Pro Gly Gly
1               5                   10                  15

Ser Leu Lys Leu Ser Cys Ala Ala Ser Gly Ala Val His Lys Ile Asn
            20                  25                  30

Phe Leu Gly Trp Tyr Arg Gln Thr Pro Glu Lys Glu Arg Glu Met Val
        35                  40                  45

Ala Thr Ile Thr Ile Gly Asp Glu Val Asp Tyr Glu Asp Ser Ala Lys
    50                  55                  60

Gly Arg Phe Thr Ile Ser Arg Asp Glu Ala Lys Asn Met Val Tyr Leu
65                  70                  75                  80

Gln Met Thr Gly Leu Lys Pro Glu Asp Thr Ala Val Tyr Val Cys Arg
                85                  90                  95

Ala Gly Ser Arg Leu Tyr Pro Tyr Asn Tyr Trp Gly Gln Gly Thr Leu
                100                 105                 110

Val Thr Val Ser Ser
        115

<210> SEQ ID NO 77
<211> LENGTH: 117
<212> TYPE: PRT
<213> ORGANISM: Artificial Sequence
<220> FEATURE:
<223> OTHER INFORMATION: Nanobody sequence

<400> SEQUENCE: 77

Glu Val Gln Leu Val Glu Ser Gly Gly Gly Leu Val Arg Pro Gly Gly
1               5                   10                  15

Ser Leu Arg Leu Ser Cys Val Ala Ser Gly Asp Val His Lys Ile Asn
            20                  25                  30

Ile Leu Gly Trp Tyr Arg Gln Ala Pro Gly Lys Glu Arg Glu Lys Val
        35                  40                  45

Ala His Ile Ser Ile Ser Asp Gln Thr Asp Tyr Ala Glu Ser Ala Lys
    50                  55                  60

Gly Arg Phe Thr Ile Ser Arg Asp Glu Ser Lys Asn Met Val Tyr Leu
65                  70                  75                  80

Gln Met Asn Ser Leu Lys Pro Glu Asp Thr Ala Val Tyr Leu Cys Arg
                85                  90                  95

Ala Phe Ser Arg Ile Tyr Pro Tyr Asp Tyr Trp Gly Gln Gly Thr Gln
                100                 105                 110

Val Thr Val Ser Ser
        115

<210> SEQ ID NO 78
<211> LENGTH: 117
```

```
<212> TYPE: PRT
<213> ORGANISM: Artificial Sequence
<220> FEATURE:
<223> OTHER INFORMATION: Nanobody sequence

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Val Tyr Lys Ile Asn
            20                  25                  30

Phe Leu Gly Trp His Arg Gln Ala Pro Gly Lys Glu Arg Glu Lys Val
        35                  40                  45

Ala His Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Gly Ser Arg Ile Tyr Pro Tyr Asp Tyr Trp Gly Gln Gly Thr Leu
            100                 105                 110

Val Thr Val Ser Ser
        115

<210> SEQ ID NO 79
<211> LENGTH: 117
<212> TYPE: PRT
<213> ORGANISM: Artificial Sequence
<220> FEATURE:
<223> OTHER INFORMATION: Nanobody sequence

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Arg Ala Ser Gly Asp Val His Lys Ile Asn
            20                  25                  30

Ile Leu Gly Trp Tyr Arg Gln Ala Pro Ala Lys Glu Arg Glu Met Ile
        35                  40                  45

Ala His Ile Thr Ile Gly Asp Ala Thr Asp Tyr Ala Glu Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Tyr Ser Arg Ile Tyr Pro Tyr Asn Tyr Trp Gly Gln Gly Thr Gln
            100                 105                 110

Val Thr Val Ser Ser
        115

<210> SEQ ID NO 80
<211> LENGTH: 117
<212> TYPE: PRT
<213> ORGANISM: Artificial Sequence
<220> FEATURE:
<223> OTHER INFORMATION: Nanobody sequence

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Val His Lys Ile Asn
```

```
                20                  25                  30
Ile Leu Gly Trp Tyr Arg Gln Ala Pro Ala Lys Gly Arg Glu Met Val
            35                  40                  45

Ala His Ile Thr Ile Gly Asp Ala Thr Asp Tyr Ala Asp Ser Ala Lys
        50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Tyr Ser Arg Ile Tyr Pro Tyr Asn Tyr Trp Gly Gln Gly Thr Gln
            100                 105                 110

Val Thr Val Ser Ser
        115

<210> SEQ ID NO 81
<211> LENGTH: 117
<212> TYPE: PRT
<213> ORGANISM: Artificial Sequence
<220> FEATURE:
<223> OTHER INFORMATION: Nanobody sequence

<400> SEQUENCE: 81

Glu Val Gln Leu Val Glu Ser Gly Gly Asp Leu Val Gln Pro Gly Gly
1               5                   10                  15

Ser Leu Arg Leu Ser Cys Ala Ala Ser Gly Asp Val His Lys Ile Asn
            20                  25                  30

Phe Leu Gly Trp Tyr Arg Gln Ala Pro Gly Lys Glu Arg Glu Met Val
        35                  40                  45

Ala His Ile Thr Ile Ala Asp Ala Thr Asp Tyr Ala Glu Phe Ala Lys
    50                  55                  60

Gly Arg Phe Thr Ile Ser Arg Asp Glu Pro Lys Asn Met Val Tyr Leu
65                  70                  75                  80

Gln Met Asn Ser Leu Lys Pro Glu Asp Thr Ala Val Tyr Leu Cys Arg
                85                  90                  95

Ala Gly Ser Arg Ile Tyr Pro Tyr Ser Tyr Trp Gly Gln Gly Thr Gln
            100                 105                 110

Val Thr Val Ser Ser
        115

<210> SEQ ID NO 82
<211> LENGTH: 117
<212> TYPE: PRT
<213> ORGANISM: Artificial Sequence
<220> FEATURE:
<223> OTHER INFORMATION: Nanobody sequence

<400> SEQUENCE: 82

Glu Val Gln Leu Val Glu Ser Gly Gly Gly Met Val Gln Pro Gly Gly
1               5                   10                  15

Ser Leu Arg Leu Ser Cys Ala Ala Ser Gly Asp Val His Lys Ile Asn
            20                  25                  30

Ile Leu Gly Trp Tyr Arg Gln Ala Pro Ala Lys Glu Arg Glu Met Val
        35                  40                  45

Ala His Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80
```

Gln Met Asn Ser Leu Lys Pro Glu Asp Thr Ala Val Tyr Phe Cys Arg
            85                  90                  95

Ala Tyr Ser Arg Ile Tyr Pro Tyr Asn Tyr Trp Gly Gln Gly Thr Leu
            100                 105                 110

Val Thr Val Ser Ser
            115

<210> SEQ ID NO 83
<211> LENGTH: 117
<212> TYPE: PRT
<213> ORGANISM: Artificial Sequence
<220> FEATURE:
<223> OTHER INFORMATION: Nanobody sequence

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Val His Lys Ile Asn
            20                  25                  30

Ile Leu Gly Trp Tyr Arg Gln Val Pro Ala Lys Glu Arg Glu Met Val
        35                  40                  45

Ala His Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Ala Tyr Phe Cys Arg
            85                  90                  95

Ala Tyr Ser Arg Ile Tyr Pro Tyr Asn Tyr Trp Gly Gln Gly Thr Leu
            100                 105                 110

Val Thr Val Ser Ser
            115

<210> SEQ ID NO 84
<211> LENGTH: 117
<212> TYPE: PRT
<213> ORGANISM: Artificial Sequence
<220> FEATURE:
<223> OTHER INFORMATION: Nanobody sequence

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Glu Val Tyr Lys Ile Asn
            20                  25                  30

Phe Leu Gly Trp Tyr Arg Gln Ala Pro Gly Lys Glu Arg Glu Lys Val
        35                  40                  45

Ala His Ile Thr Ile Ala Asp Ala Asp Tyr Ala Asp Phe Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
            85                  90                  95

Ala Gly Ser Arg Ile Trp Pro Tyr Asp Tyr Trp Gly Gln Gly Thr Leu
            100                 105                 110

Val Thr Val Ser Ser
            115

<210> SEQ ID NO 85

<211> LENGTH: 117
<212> TYPE: PRT
<213> ORGANISM: Artificial Sequence
<220> FEATURE:
<223> OTHER INFORMATION: Nanobody sequence

<400> SEQUENCE: 85

Glu Val Gln Leu Val Glu Ser Gly Gly Gly Leu Val Gln Pro Gly Gly
1               5                   10                  15
Ser Leu Arg Leu Ser Cys Ala Ala Ser Gly Ser Val His Leu Leu Asn
            20                  25                  30
Phe Leu Gly Trp Tyr Arg Gln Ala Pro Gly Lys Glu Arg Glu Met Val
        35                  40                  45
Ala His Ile Thr Ile Ala Asp Ala Thr Asp Tyr Ser His Phe Ala Lys
    50                  55                  60
Gly Arg Phe Thr Ile Ser Arg Asp Glu Ala Lys Asn Met Val Tyr Leu
65                  70                  75                  80
Gln Met Asn Gly Leu Arg Pro Glu Asp Thr Ala Val Tyr Phe Cys Arg
                85                  90                  95
Ala Gly Ser Arg Ile Tyr Pro Tyr Asp Tyr Trp Gly Gln Gly Thr Leu
            100                 105                 110
Val Thr Val Ser Ser
        115

<210> SEQ ID NO 86
<211> LENGTH: 117
<212> TYPE: PRT
<213> ORGANISM: Artificial Sequence
<220> FEATURE:
<223> OTHER INFORMATION: Nanobody sequence

<400> SEQUENCE: 86

Glu Val Gln Leu Val Glu Ser Gly Gly Gly Leu Val Gln Pro Gly Gly
1               5                   10                  15
Ser Leu Arg Leu Ser Cys Ala Ala Ser Gly Asp Val His Lys Ile Asn
            20                  25                  30
Phe Leu Gly Trp Tyr Arg Gln Ala Pro Gly Lys Glu Arg Glu Met Val
        35                  40                  45
Ala His Ile Thr Ile Ala Asp Ala Thr Asp Tyr Ala Glu Phe Ala Lys
    50                  55                  60
Gly Arg Phe Thr Ile Ser Arg Asp Glu Pro Lys Asn Met Val Tyr Leu
65                  70                  75                  80
Gln Met Asn Ser Leu Lys Pro Glu Asp Thr Ala Val Tyr Leu Cys Arg
                85                  90                  95
Ala Gly Ser Arg Ile Tyr Pro Tyr Asn Tyr Trp Gly Gln Gly Thr Gln
            100                 105                 110
Val Thr Val Ser Ser
        115

<210> SEQ ID NO 87
<211> LENGTH: 117
<212> TYPE: PRT
<213> ORGANISM: Artificial Sequence
<220> FEATURE:
<223> OTHER INFORMATION: Nanobody sequence

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Ala Ala Ser Gly Glu Val His Lys Ile Asn
            20                  25                  30

Ile Leu Gly Trp Tyr Arg Gln Cys Pro Gly Lys Glu Arg Asp Met Val
        35                  40                  45

Ala Thr Ile Thr Ile Gly Asp Ala Thr Asp Tyr Ala Asp Ser Ala Lys
 50                  55                  60

Gly Arg Phe Thr Ile Ser Arg Asp Glu Ala Lys Asn Met Val Tyr Leu
 65                  70                  75                  80

Gln Met Asn Ser Leu Lys Pro Glu Asp Thr Ala Val Tyr Phe Cys Arg
            85                  90                  95

Ala Leu Ser Arg Leu Tyr Pro Tyr Asn Tyr Trp Gly Gln Gly Thr Leu
        100                 105                 110

Val Thr Val Ser Ser
        115

<210> SEQ ID NO 88
<211> LENGTH: 117
<212> TYPE: PRT
<213> ORGANISM: Artificial Sequence
<220> FEATURE:
<223> OTHER INFORMATION: Nanobody sequence

<400> SEQUENCE: 88

Glu Val Gln Leu Val Glu Ser Gly Gly Gly Leu Val Gln Pro Gly Gly
 1               5                  10                  15

Ser Leu Arg Leu Ser Cys Ala Ala Ser Gly Asp Val His Lys Ile Asn
            20                  25                  30

Ile Leu Gly Trp Tyr Arg Gln Ala Pro Ala Lys Glu Arg Glu Met Val
        35                  40                  45

Ala His Ile Thr Ile Gly Asp Ala Thr Asp Tyr Ala Asp Ser Ala Lys
 50                  55                  60

Gly Arg Phe Thr Ile Ser Arg Asp Glu Ala Lys Asn Met Val Tyr Leu
 65                  70                  75                  80

Gln Met Asn Ser Leu Lys Pro Glu Asp Thr Ala Val Tyr Leu Cys Arg
            85                  90                  95

Ala Tyr Ser Arg Ile Tyr Pro Tyr Asn Tyr Trp Gly Gly Thr Gln
        100                 105                 110

Val Thr Val Ser Ser
        115

<210> SEQ ID NO 89
<211> LENGTH: 117
<212> TYPE: PRT
<213> ORGANISM: Artificial Sequence
<220> FEATURE:
<223> OTHER INFORMATION: Nanobody sequence

<400> SEQUENCE: 89

Glu Val Gln Leu Val Glu Ser Gly Gly Gly Leu Val Gln Pro Gly Gly
 1               5                  10                  15

Ser Leu Arg Leu Ser Cys Ala Ala Ser Gly Glu Val Tyr Lys Ile Asn
            20                  25                  30

Phe Leu Gly Trp Gln Arg Gln Ala Pro Gly Lys Glu Arg Glu Lys Val
        35                  40                  45

Ala His Ile Thr Ile Ala Asp Val Ala Asp Tyr Ala Asp Phe Ala Lys
 50                  55                  60

Gly Arg Phe Thr Ile Ser Arg Asp Glu Ala Lys Asn Met Val Tyr Leu
 65                  70                  75                  80

```
Gln Met Asn Ser Leu Lys Pro Glu Asp Thr Ala Val Tyr Phe Cys Arg
            85                  90                  95

Ala Gly Ser Arg Ile Trp Pro Tyr Asp Tyr Trp Gly Gln Gly Thr Leu
            100                 105                 110

Val Thr Val Ser Ser
            115

<210> SEQ ID NO 90
<211> LENGTH: 117
<212> TYPE: PRT
<213> ORGANISM: Artificial Sequence
<220> FEATURE:
<223> OTHER INFORMATION: Nanobody sequence

<400> SEQUENCE: 90

Glu Val Gln Leu Val Glu Ser Gly Gly Asp Leu Val Gln Pro Gly Gly
1               5                   10                  15

Ser Leu Arg Leu Ser Cys Ala Ala Ser Gly Asp Val His Lys Ile Asn
            20                  25                  30

Phe Leu Gly Trp Tyr Arg Gln Ala Pro Gly Lys Glu Arg Glu Met Val
            35                  40                  45

Ala His Ile Thr Ile Ala Asp Ala Thr Asp Tyr Ala Glu Phe Ala Lys
        50                  55                  60

Gly Arg Phe Thr Ile Ser Arg Asp Glu Pro Lys Asn Met Val Tyr Leu
65                  70                  75                  80

Gln Met Asn Ser Leu Lys Pro Val Asp Thr Ala Val Tyr Leu Cys Arg
            85                  90                  95

Ala Gly Ser Arg Ile Tyr Pro Tyr Asn Tyr Trp Gly Gln Gly Thr Leu
            100                 105                 110

Val Thr Val Ser Ser
            115

<210> SEQ ID NO 91
<211> LENGTH: 117
<212> TYPE: PRT
<213> ORGANISM: Artificial Sequence
<220> FEATURE:
<223> OTHER INFORMATION: Nanobody sequence

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Leu Leu Asn
            20                  25                  30

Phe Leu Gly Trp Tyr Arg Gln Ala Pro Gly Lys Glu Arg Glu Lys Val
            35                  40                  45

Ala His Ile Thr Ile Ala Asp Ala Thr Asp Tyr Ser His Phe Ala Lys
        50                  55                  60

Gly Arg Phe Thr Ile Ser Arg Asp Glu Ala Lys Asn Met Val Tyr Leu
65                  70                  75                  80

Gln Met Asn Asn Leu Arg Pro Glu Asp Thr Ala Val Tyr Phe Cys Arg
            85                  90                  95

Ala Gly Ser Arg Ile Tyr Pro Tyr Asp Tyr Trp Gly Gln Gly Thr Leu
            100                 105                 110

Val Thr Val Ser Ser
            115
```

```
<210> SEQ ID NO 92
<211> LENGTH: 117
<212> TYPE: PRT
<213> ORGANISM: Artificial Sequence
<220> FEATURE:
<223> OTHER INFORMATION: Nanobody sequence

<400> SEQUENCE: 92
```

Glu Val Gln Leu Val Glu Ser Gly Gly Gly Leu Val Gln Pro Gly Gly
1               5                   10                  15

Ser Pro Arg Leu Ser Cys Val Ala Ser Gly Asp Val His Lys Ile Asn
            20                  25                  30

Phe Leu Gly Trp Tyr Arg Gln Ala Pro Gly Lys Glu Arg Glu Lys Val
        35                  40                  45

Ala His Ile Thr Ile Gly Asp Gln Ala Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Gly Ser Arg Ile Tyr Pro Tyr Asp Tyr Trp Gly Gln Gly Thr Leu
            100                 105                 110

Val Thr Val Ser Ser
        115

```
<210> SEQ ID NO 93
<211> LENGTH: 117
<212> TYPE: PRT
<213> ORGANISM: Artificial Sequence
<220> FEATURE:
<223> OTHER INFORMATION: Nanobody sequence

<400> SEQUENCE: 93
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Val His Lys Ile Asn
            20                  25                  30

Ile Leu Gly Trp Tyr Arg Gln Ala Pro Ala Lys Glu Arg Glu Met Val
        35                  40                  45

Ala His Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Ala Ala Val Tyr Phe Cys Arg
                85                  90                  95

Ala Tyr Ser Arg Ile Tyr Pro Tyr Asn Tyr Trp Gly Gln Gly Thr Leu
            100                 105                 110

Val Thr Val Ser Ser
        115

```
<210> SEQ ID NO 94
<211> LENGTH: 117
<212> TYPE: PRT
<213> ORGANISM: Artificial Sequence
<220> FEATURE:
<223> OTHER INFORMATION: Nanobody sequence

<400> SEQUENCE: 94
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Glu Val Tyr Lys Ile Asn
            20                  25                  30

Phe Leu Gly Trp Tyr Arg Gln Ala Pro Gly Lys Glu Arg Glu Lys Val
            35                  40                  45

Ala His Ile Thr Ile Ala Asp Val Ala Asp Tyr Ala Asp Phe Ala Lys
        50                  55                  60

Gly Arg Phe Thr Ile Ser Arg Asp Gly Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Gly Ser Arg Ile Trp Pro Tyr Asp Tyr Trp Gly Gln Gly Thr Leu
            100                 105                 110

Val Thr Val Ser Ser
            115

<210> SEQ ID NO 95
<211> LENGTH: 117
<212> TYPE: PRT
<213> ORGANISM: Artificial Sequence
<220> FEATURE:
<223> OTHER INFORMATION: Nanobody sequence

<400> SEQUENCE: 95

Glu Val Gln Leu Val Glu Ser Gly Gly Gly Ser Val Gln Pro Gly Gly
1               5                   10                  15

Ser Leu Arg Leu Ser Cys Ala Ala Ser Gly Ser Val His Lys Ile Asn
            20                  25                  30

Phe Leu Gly Trp Tyr Cys Gln Ala Pro Gly Lys Glu Arg Glu Met Val
            35                  40                  45

Ala Thr Ile Thr Ile Gly Asp Ala Thr Asp Tyr Ala Asp Ser Ala Lys
        50                  55                  60

Gly Arg Phe Thr Ile Ser Arg Asp Glu Ala Lys Asn Met Val Tyr Leu
65                  70                  75                  80

Gln Met Asn Ser Leu Ser Pro Glu Asp Thr Ala Val Tyr Phe Cys Arg
                85                  90                  95

Ala Gly Ser Arg Leu Tyr Pro Tyr Asn Tyr Trp Gly Gln Gly Thr Gln
            100                 105                 110

Val Thr Val Ser Ser
            115

<210> SEQ ID NO 96
<211> LENGTH: 117
<212> TYPE: PRT
<213> ORGANISM: Artificial Sequence
<220> FEATURE:
<223> OTHER INFORMATION: Nanobody sequence

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Val Ala Ser Gly Asp Val His Lys Ile Asn
            20                  25                  30

Ile Leu Gly Trp Tyr Arg Gln Ala Pro Gly Lys Glu Arg Glu Lys Val
            35                  40                  45

Ala His Ile Ser Ile Ser Asp Gln Thr Asp Tyr Ala Glu Ser Ala Lys
        50                  55                  60

Gly Arg Phe Thr Ile Ser Arg Asp Glu Ser Lys Asn Met Val Tyr Leu

```
                65                  70                  75                  80
Gln Met Asn Ser Leu Lys Pro Glu Asp Ala Val Tyr Leu Cys Arg
                    85                  90                  95

Ala Phe Ser Arg Ile Tyr Pro Tyr Asp Tyr Trp Gly Gln Gly Thr Gln
                100                 105                 110

Val Thr Val Ser Ser
            115

<210> SEQ ID NO 97
<211> LENGTH: 117
<212> TYPE: PRT
<213> ORGANISM: Artificial Sequence
<220> FEATURE:
<223> OTHER INFORMATION: Nanobody sequence

<400> SEQUENCE: 97

Glu Val Gln Leu Val Glu Ser Gly Gly Gly Leu Val Gln Pro Gly Gly
1               5                   10                  15

Ser Leu Arg Pro Ser Cys Ala Ala Ser Gly Glu Val Tyr Lys Ile Asn
                20                  25                  30

Phe Leu Gly Trp Tyr Arg Gln Ala Pro Gly Lys Glu Arg Glu Lys Val
            35                  40                  45

Ala His Ile Thr Ile Ala Asp Val Ala Asp Tyr Ala Asp Phe Ala Lys
        50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Gly Ser Arg Ile Trp Pro Tyr Asp Tyr Trp Gly Gln Gly Thr Gln
                100                 105                 110

Val Thr Val Ser Ser
            115

<210> SEQ ID NO 98
<211> LENGTH: 117
<212> TYPE: PRT
<213> ORGANISM: Artificial Sequence
<220> FEATURE:
<223> OTHER INFORMATION: Nanobody sequence

<400> SEQUENCE: 98

Glu Val Gln Leu Val Glu Ser Gly Gly Gly Leu Val Gln Pro Gly Gly
1               5                   10                  15

Ser Leu Arg Pro Ser Cys Val Ala Ser Gly Asp Val His Lys Ile Asn
                20                  25                  30

Phe Leu Gly Trp Tyr Arg Gln Ala Pro Gly Lys Glu Arg Glu Lys Val
            35                  40                  45

Ala His Ile Thr Ile Ala Asp Gln Ala Asp Tyr Ala Asp Ser Ala Lys
        50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Gly Ser Arg Ile Tyr Pro Tyr Asp Tyr Trp Gly Gln Gly Thr Leu
                100                 105                 110

Val Thr Val Ser Ser
            115
```

<210> SEQ ID NO 99
<211> LENGTH: 117
<212> TYPE: PRT
<213> ORGANISM: Artificial Sequence
<220> FEATURE:
<223> OTHER INFORMATION: Nanobody sequence

<400> SEQUENCE: 99

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Glu Val His Lys Ile Asn
            20                  25                  30

Ile Leu Gly Trp Tyr Arg Gln Ala Pro Gly Lys Glu Arg Asp Met Val
        35                  40                  45

Ala Thr Ile Thr Ile Gly Asp Glu Thr Gln Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Leu Ser Arg Leu Tyr Pro Tyr Asn Tyr Trp Gly Gln Gly Thr Leu
            100                 105                 110

Val Thr Val Ser Ser
        115
```

<210> SEQ ID NO 100
<211> LENGTH: 117
<212> TYPE: PRT
<213> ORGANISM: Artificial Sequence
<220> FEATURE:
<223> OTHER INFORMATION: Nanobody sequence

<400> SEQUENCE: 100

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Val His Lys Ile Asn
            20                  25                  30

Ile Leu Gly Trp Tyr Arg Gln Ala Pro Ala Lys Glu Arg Glu Met Val
        35                  40                  45

Ala His Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asp Ser Leu Lys Pro Glu Asp Thr Ala Val Tyr Phe Cys Arg
                85                  90                  95

Ala Tyr Ser Arg Ile Tyr Pro Tyr Asn Tyr Trp Gly Gln Gly Thr Leu
            100                 105                 110

Val Thr Val Ser Ser
        115
```

<210> SEQ ID NO 101
<211> LENGTH: 117
<212> TYPE: PRT
<213> ORGANISM: Artificial Sequence
<220> FEATURE:
<223> OTHER INFORMATION: Nanobody sequence

<400> SEQUENCE: 101

Glu Val Gln Leu Val Glu Ser Gly Gly Gly Leu Val Gln Pro Gly Gly

```
            1               5                  10                 15
Ser Leu Arg Leu Ser Cys Ala Ala Ser Gly Asp Val His Lys Ile Asn
                20                  25                  30

Ile Leu Gly Trp Tyr Arg Gln Ala Pro Ala Lys Glu Arg Glu Met Val
                35                  40                  45

Ala His Ile Thr Ile Gly Asp Ala Thr Asp Tyr Ala Asp Ser Ala Lys
        50                  55                  60

Gly Arg Phe Thr Ile Ser Arg Asp Glu Ala Lys Asn Met Val Tyr Leu
65                  70                  75                  80

Gln Met Asn Ser Leu Lys Pro Gly Asp Thr Ala Val Tyr Phe Cys Arg
                85                  90                  95

Ala Tyr Ser Arg Ile Tyr Pro Tyr Asn Tyr Trp Gly Gln Gly Thr Leu
                100                 105                 110

Val Thr Val Ser Ser
        115
```

<210> SEQ ID NO 102
<211> LENGTH: 117
<212> TYPE: PRT
<213> ORGANISM: Artificial Sequence
<220> FEATURE:
<223> OTHER INFORMATION: Nanobody sequence

<400> SEQUENCE: 102

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Val His Lys Ile Asn
                20                  25                  30

Ile Leu Gly Trp His Arg Gln Ala Pro Ala Lys Glu Arg Glu Met Val
                35                  40                  45

Ala His Ile Thr Ile Gly Asp Ala Thr Asp Tyr Ala Asp Ser Ala Lys
        50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Tyr Ser Arg Ile Tyr Pro Tyr Asn Tyr Trp Gly Gln Gly Thr Leu
                100                 105                 110

Val Thr Val Ser Ser
        115
```

<210> SEQ ID NO 103
<211> LENGTH: 117
<212> TYPE: PRT
<213> ORGANISM: Artificial Sequence
<220> FEATURE:
<223> OTHER INFORMATION: Nanobody sequence

<400> SEQUENCE: 103

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Val His Lys Ile Asn
                20                  25                  30

Ile Leu Gly Trp His Arg Gln Ala Pro Ala Lys Glu Arg Glu Met Val
                35                  40                  45

Ala His Ile Thr Ile Gly Asp Ala Thr Asp Tyr Ala Asp Ser Ala Lys
        50                  55                  60
```

```
Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Ala Tyr Phe Cys Arg
                85                  90                  95

Ala Tyr Ser Arg Ile Tyr Pro Tyr Asn Tyr Trp Gly Gln Gly Thr Gln
            100                 105                 110

Val Thr Val Ser Ser
        115

<210> SEQ ID NO 104
<211> LENGTH: 117
<212> TYPE: PRT
<213> ORGANISM: Artificial Sequence
<220> FEATURE:
<223> OTHER INFORMATION: Nanobody sequence

<400> SEQUENCE: 104

Glu Val Gln Leu Val Glu Ser Gly Gly Gly Trp Val Gln Ala Gly Gly
1               5                   10                  15

Ser Leu Arg Leu Ser Cys Ala Ala Ser Gly Asp Val His Lys Ile Asn
            20                  25                  30

Ile Leu Gly Trp Tyr Arg Gln Ala Pro Ala Lys Glu Arg Glu Met Val
        35                  40                  45

Ala His Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Tyr Ser Arg Ile Tyr Pro Tyr Asn Tyr Trp Gly Gln Gly Thr Leu
            100                 105                 110

Val Thr Val Ser Ser
        115

<210> SEQ ID NO 105
<211> LENGTH: 117
<212> TYPE: PRT
<213> ORGANISM: Artificial Sequence
<220> FEATURE:
<223> OTHER INFORMATION: Nanobody sequence

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ile Thr Ser Gly Glu Thr Phe Lys Ile Asn
            20                  25                  30

Ile Trp Gly Trp Tyr Arg Gln Ala Pro Gly Lys Gln Arg Glu Leu Val
        35                  40                  45

Ala Ser Leu Thr Ile Gly Gly Ala Thr Asp Tyr Ala Asp Ser Val Lys
    50                  55                  60

Gly Arg Phe Thr Ile Ser Glu Asp Ser Ala Lys Asn Thr Val Tyr Leu
65                  70                  75                  80

Gln Met Asn Ser Leu Lys Ala Glu Asp Thr Ala Val Tyr Phe Cys Asn
                85                  90                  95

Ala Lys Ser Arg Leu Tyr Pro Tyr Asp Tyr Trp Gly Gln Gly Thr Gln
            100                 105                 110

Val Thr Val Ser Ser
        115
```

<210> SEQ ID NO 106
<211> LENGTH: 117
<212> TYPE: PRT
<213> ORGANISM: Artificial Sequence
<220> FEATURE:
<223> OTHER INFORMATION: Nanobody sequence

<400> SEQUENCE: 106

Glu Val Gln Leu Val Glu Ser Gly Gly Gly Leu Val Gln Pro Gly Gly
1               5                   10                  15

Ser Leu Arg Leu Ser Cys Ile Thr Ser Gly Glu Thr Phe Lys Ile Asn
            20                  25                  30

Ile Trp Gly Trp Tyr Arg Gln Ala Pro Gly Lys Gln Arg Glu Leu Val
        35                  40                  45

Ala Ser Leu Thr Ile Gly Gly Ala Thr Asn Tyr Ala Asp Ser Val Lys
    50                  55                  60

Gly Arg Phe Thr Ile Ser Glu Asp Ser Ala Lys Asn Thr Val Tyr Leu
65                  70                  75                  80

Gln Met Asn Ser Leu Lys Pro Glu Asp Thr Ala Val Tyr Phe Cys Asn
                85                  90                  95

Ala Lys Ser Arg Leu Tyr Pro Tyr Asp Tyr Trp Gly Gln Gly Thr Leu
            100                 105                 110

Val Thr Val Ser Ser
        115

<210> SEQ ID NO 107
<211> LENGTH: 117
<212> TYPE: PRT
<213> ORGANISM: Artificial Sequence
<220> FEATURE:
<223> OTHER INFORMATION: Nanobody sequence

<400> SEQUENCE: 107

Glu Val Gln Leu Val Glu Ser Gly Gly Gly Leu Val Gln Pro Gly Gly
1               5                   10                  15

Ser Leu Arg Leu Ser Cys Ile Thr Ser Gly Glu Thr Phe Lys Ile Asn
            20                  25                  30

Ile Trp Gly Trp Tyr Arg Gln Ala Pro Gly Lys Arg Arg Glu Leu Val
        35                  40                  45

Ala Ser Leu Thr Ile Gly Gly Ala Thr Asn Tyr Ala Asp Ser Val Lys
    50                  55                  60

Gly Arg Phe Thr Ile Ser Glu Asp Ser Ala Lys Asn Thr Val Tyr Leu
65                  70                  75                  80

Gln Met Asn Ser Leu Lys Pro Glu Asp Thr Ala Val Tyr Phe Cys Asn
                85                  90                  95

Ala Lys Ser Arg Ile Tyr Pro Tyr Asp Tyr Trp Gly Gln Gly Thr Gln
            100                 105                 110

Val Thr Val Ser Ser
        115

<210> SEQ ID NO 108
<211> LENGTH: 117
<212> TYPE: PRT
<213> ORGANISM: Artificial Sequence
<220> FEATURE:
<223> OTHER INFORMATION: Nanobody sequence

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Ile Thr Ser Gly Glu Thr Phe Lys Ile Asn
            20                  25                  30

Ile Trp Gly Trp Tyr Arg Gln Thr Pro Gly Lys Gln Arg Glu Leu Val
        35                  40                  45

Ala Ser Leu Thr Ile Gly Gly Ala Thr Asn Tyr Ala Asp Ser Val Lys
    50                  55                  60

Gly Arg Phe Thr Ile Ser Glu Asp Ser Ala Lys Asn Thr Val Tyr Leu
65                  70                  75                  80

Gln Met Asn Ser Leu Lys Pro Glu Asp Thr Ala Val Tyr Phe Cys Asn
                85                  90                  95

Ala Lys Ser Arg Leu Tyr Pro Tyr Asp Tyr Trp Gly Gln Gly Thr Gln
            100                 105                 110

Val Thr Val Ser Ser
        115

<210> SEQ ID NO 109
<211> LENGTH: 117
<212> TYPE: PRT
<213> ORGANISM: Artificial Sequence
<220> FEATURE:
<223> OTHER INFORMATION: Nanobody sequence

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ile Thr Ser Gly Gln Thr Phe Lys Ile Asn
            20                  25                  30

Ile Trp Gly Trp Tyr Arg Gln Ala Pro Gly Lys Gln Arg Glu Leu Val
        35                  40                  45

Ala Ser Leu Thr Ile Gly Gly Ala Thr Asn Tyr Ala Asp Ser Val Lys
    50                  55                  60

Gly Arg Phe Thr Ile Ser Glu Asp Ser Ala Lys Asn Thr Val Tyr Leu
65                  70                  75                  80

Gln Met Asn Ser Leu Lys Pro Glu Asp Thr Ala Val Tyr Phe Cys Asn
                85                  90                  95

Ala Lys Ser Arg Leu Tyr Pro Tyr Asp Tyr Trp Gly Gln Gly Thr Gln
            100                 105                 110

Val Thr Val Ser Ser
        115

<210> SEQ ID NO 110
<211> LENGTH: 117
<212> TYPE: PRT
<213> ORGANISM: Artificial Sequence
<220> FEATURE:
<223> OTHER INFORMATION: Nanobody sequence

<400> SEQUENCE: 110

Glu Val Gln Leu Val Glu Ser Gly Gly Gly Leu Val Gln Pro Gly Gly
1               5                   10                  15

Ser Leu Arg Leu Ser Cys Ile Thr Ser Gly Glu Thr Phe Lys Val Asn
            20                  25                  30

Ile Trp Gly Trp Tyr Arg Gln Gly Pro Gly Lys Gln Arg Glu Leu Val
        35                  40                  45

Ala Ser Leu Thr Ile Gly Gly Ala Thr Asn Tyr Ala Asp Ser Val Lys
    50                  55                  60

```
Gly Arg Phe Thr Ile Ser Glu Asp Ser Ala Lys Asn Thr Val Tyr Leu
 65                  70                  75                  80

Gln Met Asn Ser Leu Lys Pro Glu Asp Thr Ala Val Tyr Phe Cys Asn
             85                  90                  95

Ala Lys Ser Arg Leu Tyr Pro Tyr Asp Tyr Trp Gly Arg Gly Thr Gln
            100                 105                 110

Val Thr Val Ser Ser
        115

<210> SEQ ID NO 111
<211> LENGTH: 118
<212> TYPE: PRT
<213> ORGANISM: Artificial Sequence
<220> FEATURE:
<223> OTHER INFORMATION: Nanobody sequence

<400> SEQUENCE: 111

Glu Val Gln Leu Val Glu Ser Gly Gly Gly Leu Val Gln Pro Gly
 1               5                  10                  15

Gly Ser Leu Arg Leu Ser Cys Ile Thr Ser Gly Glu Thr Phe Lys Ile
             20                  25                  30

Asn Ile Trp Gly Trp Tyr Arg Gln Ala Pro Gly Lys Gln Arg Glu Leu
         35                  40                  45

Val Ala Ser Leu Thr Ile Gly Gly Ala Thr Asn Tyr Ala Asp Ser Val
 50                  55                  60

Lys Gly Arg Phe Thr Ile Ser Glu Asp Ser Ala Lys Asn Thr Val Tyr
 65                  70                  75                  80

Leu Gln Met Asn Ser Leu Lys Pro Glu Asp Thr Ala Val Tyr Phe Cys
             85                  90                  95

Asn Ala Lys Ser Arg Ile Tyr Pro Tyr Asp Tyr Trp Gly Arg Gly Thr
            100                 105                 110

Gln Val Thr Val Ser Ser
        115

<210> SEQ ID NO 112
<211> LENGTH: 117
<212> TYPE: PRT
<213> ORGANISM: Artificial Sequence
<220> FEATURE:
<223> OTHER INFORMATION: Nanobody sequence

<400> SEQUENCE: 112

Glu Val Gln Leu Val Glu Ser Gly Gly Gly Leu Val Gln Pro Gly Gly
 1               5                  10                  15

Ser Leu Arg Leu Ser Cys Ile Thr Ser Gly Glu Thr Phe Lys Ile Asn
             20                  25                  30

Ile Trp Gly Trp Tyr Arg Gln Ala Pro Gly Lys Gln Arg Glu Leu Val
         35                  40                  45

Ala Ser Leu Thr Ile Gly Gly Ala Thr Asn Tyr Ala Asp Ser Val Lys
     50                  55                  60

Gly Arg Phe Thr Ile Ser Glu Asp Ser Ala Lys Asn Thr Val Tyr Leu
 65                  70                  75                  80

Gln Met Asn Ser Leu Lys Pro Glu Asp Thr Ala Val Tyr Phe Cys Asn
             85                  90                  95

Ala Lys Ser Arg Leu Tyr Pro Tyr Asp Tyr Trp Asp Gln Gly Thr Gln
            100                 105                 110

Val Thr Val Ser Ser
```

```
                 115

<210> SEQ ID NO 113
<211> LENGTH: 117
<212> TYPE: PRT
<213> ORGANISM: Artificial Sequence
<220> FEATURE:
<223> OTHER INFORMATION: Nanobody sequence

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Leu Thr Ser Gly Glu Thr Phe Lys Val Asn
            20                  25                  30

Ile Trp Gly Trp Tyr Arg Gln Gly Pro Gly Lys Gln Arg Glu Leu Val
        35                  40                  45

Ala Ser Leu Thr Ile Gly Gly Ala Thr Asn Tyr Ala Asp Ser Val Lys
    50                  55                  60

Gly Arg Phe Thr Ile Ser Glu Asp Ser Ala Lys Asn Thr Val Tyr Leu
65                  70                  75                  80

Gln Met Ser Ser Leu Lys Pro Glu Asp Thr Ala Val Tyr Phe Cys Asn
                85                  90                  95

Ala Lys Ser Arg Leu Tyr Pro Tyr Asp Tyr Trp Gly Gln Gly Thr Gln
            100                 105                 110

Val Thr Val Ser Ser
        115

<210> SEQ ID NO 114
<211> LENGTH: 117
<212> TYPE: PRT
<213> ORGANISM: Artificial Sequence
<220> FEATURE:
<223> OTHER INFORMATION: Nanobody sequence

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ile Thr Ser Gly Glu Thr Phe Lys Ile Asn
            20                  25                  30

Ile Trp Gly Trp Tyr Arg Gln Ala Pro Gly Lys Gln Arg Glu Leu Val
        35                  40                  45

Ala Ser Leu Thr Ile Gly Gly Ala Thr Asn Tyr Ala Asp Ser Val Lys
    50                  55                  60

Gly Arg Phe Thr Ile Ser Glu Asp Ser Ala Lys Asn Thr Val Tyr Leu
65                  70                  75                  80

Gln Met Asn Ser Leu Lys Pro Glu Asp Thr Ala Val Tyr Phe Cys Asn
                85                  90                  95

Ala Lys Ser Arg Ile Tyr Pro Tyr Asp Tyr Trp Gly Arg Gly Thr Gln
            100                 105                 110

Val Thr Val Ser Ser
        115

<210> SEQ ID NO 115
<211> LENGTH: 117
<212> TYPE: PRT
<213> ORGANISM: Artificial Sequence
<220> FEATURE:
<223> OTHER INFORMATION: Nanobody sequence

<400> SEQUENCE: 115
```

Glu Val Gln Leu Val Glu Ser Gly Gly Gly Leu Val Gln Pro Gly Gly
1               5                   10                  15

Ser Leu Arg Leu Ser Cys Ile Thr Ser Gly Glu Thr Phe Lys Ile Asn
            20                  25                  30

Ile Trp Gly Trp Tyr Arg Gln Ala Pro Gly Lys Gln Arg Glu Leu Val
            35                  40                  45

Ala Ser Leu Thr Ile Gly Gly Ala Thr Asn Tyr Ala Asp Ser Val Lys
    50                  55                  60

Gly Arg Phe Thr Ile Ser Glu Asp Ser Ala Lys Asp Thr Val Tyr Leu
65                  70                  75                  80

Gln Met Asn Ser Leu Lys Pro Glu Asp Thr Ala Val Tyr Phe Cys Asn
                85                  90                  95

Ala Lys Ser Arg Leu Tyr Pro Tyr Asp Tyr Trp Gly Gln Gly Thr Leu
            100                 105                 110

Val Thr Val Ser Ser
            115

<210> SEQ ID NO 116
<211> LENGTH: 117
<212> TYPE: PRT
<213> ORGANISM: Artificial Sequence
<220> FEATURE:
<223> OTHER INFORMATION: Nanobody sequence

<400> SEQUENCE: 116

Glu Val Gln Leu Val Glu Ser Gly Gly Gly Leu Val Gln Pro Gly Gly
1               5                   10                  15

Ser Leu Arg Leu Ser Cys Ala Ala Ser Gly Glu Ile Gly Arg Ile Asn
            20                  25                  30

Phe Tyr Arg Trp Tyr Arg Gln Ala Pro Gly Asn Gln Arg Glu Val Val
            35                  40                  45

Ala Thr Ile Thr Ile Ala Asp Lys Thr Asp Tyr Ala Asp Ser Ala Lys
    50                  55                  60

Gly Arg Phe Thr Ile Ser Arg Asp Glu Ser Arg Asn Met Val Tyr Leu
65                  70                  75                  80

Gln Met Ser Ser Leu Lys Pro Glu Asp Thr Ala Val Tyr Phe Cys His
                85                  90                  95

Ala Gly Ser Arg Leu Tyr Pro Tyr Asp Tyr Trp Gly Gln Gly Thr Gln
            100                 105                 110

Val Thr Val Ser Ser
            115

<210> SEQ ID NO 117
<211> LENGTH: 117
<212> TYPE: PRT
<213> ORGANISM: Artificial Sequence
<220> FEATURE:
<223> OTHER INFORMATION: Nanobody sequence

<400> SEQUENCE: 117

Glu Val Gln Leu Val Glu Ser Gly Gly Gly Leu Val Gln Pro Gly Gly
1               5                   10                  15

Ser Leu Arg Leu Ser Cys Ala Ala Ser Gly Glu Ile Gly Arg Ile Asn
            20                  25                  30

Phe Tyr Arg Trp Tyr Arg Gln Ala Pro Gly Asn Gln Arg Gly Val Val
            35                  40                  45

Ala Thr Ile Thr Ile Ala Asp Lys Ile Asp Tyr Ala Asp Ser Ala Lys

```
                50                  55                  60
Gly Arg Phe Thr Ile Ser Arg Asp Glu Ser Arg Asn Met Val Tyr Leu
 65                  70                  75                  80

Gln Met Gly Ser Leu Lys Pro Glu Asp Thr Ala Val Tyr Phe Cys His
                 85                  90                  95

Ala Gly Ser Arg Leu Tyr Pro Tyr Asp Tyr Trp Gly Gln Gly Thr Gln
            100                 105                 110

Val Thr Val Ser Ser
        115

<210> SEQ ID NO 118
<211> LENGTH: 117
<212> TYPE: PRT
<213> ORGANISM: Artificial Sequence
<220> FEATURE:
<223> OTHER INFORMATION: Nanobody sequence

<400> SEQUENCE: 118

Glu Val Gln Leu Val Glu Ser Gly Gly Gly Leu Val Gln Pro Gly Gly
  1               5                  10                  15

Ser Leu Arg Leu Ser Cys Ala Ala Ser Gly Glu Ile Gly Arg Ile Asn
             20                  25                  30

Phe Tyr Arg Trp Tyr Arg Gln Ala Pro Gly Asn Gln Arg Glu Val Val
         35                  40                  45

Ala Thr Ile Thr Ile Ala Asp Lys Thr Asp Tyr Ala Asp Ser Ala Lys
     50                  55                  60

Gly Arg Phe Thr Ile Ser Arg Asp Glu Ser Arg Asn Met Val Tyr Leu
 65                  70                  75                  80

Gln Met Ser Ser Leu Lys Pro Glu Asn Thr Ala Val Tyr Phe Cys His
                 85                  90                  95

Ala Gly Ser Arg Leu Tyr Pro Tyr Asp Tyr Trp Gly Gln Gly Thr Gln
            100                 105                 110

Val Thr Val Ser Ser
        115

<210> SEQ ID NO 119
<211> LENGTH: 10
<212> TYPE: PRT
<213> ORGANISM: Artificial Sequence
<220> FEATURE:
<223> OTHER INFORMATION: CDR1

<400> SEQUENCE: 119

Gly Ser Val His Lys Ile Asn Phe Leu Gly
  1               5                  10

<210> SEQ ID NO 120
<211> LENGTH: 10
<212> TYPE: PRT
<213> ORGANISM: Artificial Sequence
<220> FEATURE:
<223> OTHER INFORMATION: CDR1

<400> SEQUENCE: 120

Gly Ser Val His Leu Leu Asn Phe Leu Gly
  1               5                  10

<210> SEQ ID NO 121
<211> LENGTH: 10
<212> TYPE: PRT
<213> ORGANISM: Artificial Sequence
```

```
<220> FEATURE:
<223> OTHER INFORMATION: CDR1

<400> SEQUENCE: 121

Gly Ala Val His Lys Ile Asn Phe Leu Gly
1               5                   10

<210> SEQ ID NO 122
<211> LENGTH: 10
<212> TYPE: PRT
<213> ORGANISM: Artificial Sequence
<220> FEATURE:
<223> OTHER INFORMATION: CDR1

<400> SEQUENCE: 122

Gly Asp Val His Lys Ile Asn Ile Leu Gly
1               5                   10

<210> SEQ ID NO 123
<211> LENGTH: 10
<212> TYPE: PRT
<213> ORGANISM: Artificial Sequence
<220> FEATURE:
<223> OTHER INFORMATION: CDR1

<400> SEQUENCE: 123

Gly Asp Val His Lys Ile Asn Phe Leu Gly
1               5                   10

<210> SEQ ID NO 124
<211> LENGTH: 10
<212> TYPE: PRT
<213> ORGANISM: Artificial Sequence
<220> FEATURE:
<223> OTHER INFORMATION: CDR1

<400> SEQUENCE: 124

Gly Glu Thr Phe Lys Ile Asn Ile Trp Gly
1               5                   10

<210> SEQ ID NO 125
<211> LENGTH: 10
<212> TYPE: PRT
<213> ORGANISM: Artificial Sequence
<220> FEATURE:
<223> OTHER INFORMATION: CDR1

<400> SEQUENCE: 125

Gly Asp Val His Lys Ile Asn Val Leu Gly
1               5                   10

<210> SEQ ID NO 126
<211> LENGTH: 10
<212> TYPE: PRT
<213> ORGANISM: Artificial Sequence
<220> FEATURE:
<223> OTHER INFORMATION: CDR1

<400> SEQUENCE: 126

Gly Glu Val Tyr Lys Ile Asn Phe Leu Gly
1               5                   10

<210> SEQ ID NO 127
<211> LENGTH: 10
<212> TYPE: PRT
<213> ORGANISM: Artificial Sequence
<220> FEATURE:
```

<223> OTHER INFORMATION: CDR1

<400> SEQUENCE: 127

Gly Gly Val His Lys Ile Asn Ile Leu Gly
1               5                   10

<210> SEQ ID NO 128
<211> LENGTH: 10
<212> TYPE: PRT
<213> ORGANISM: Artificial Sequence
<220> FEATURE:
<223> OTHER INFORMATION: CDR1

<400> SEQUENCE: 128

Gly Gln Thr Phe Lys Ile Asn Ile Trp Gly
1               5                   10

<210> SEQ ID NO 129
<211> LENGTH: 10
<212> TYPE: PRT
<213> ORGANISM: Artificial Sequence
<220> FEATURE:
<223> OTHER INFORMATION: CDR1

<400> SEQUENCE: 129

Gly Ser Val Tyr Lys Ile Asn Phe Leu Ser
1               5                   10

<210> SEQ ID NO 130
<211> LENGTH: 10
<212> TYPE: PRT
<213> ORGANISM: Artificial Sequence
<220> FEATURE:
<223> OTHER INFORMATION: CDR1

<400> SEQUENCE: 130

Gly Glu Ile Gly Arg Ile Asn Phe Tyr Arg
1               5                   10

<210> SEQ ID NO 131
<211> LENGTH: 10
<212> TYPE: PRT
<213> ORGANISM: Artificial Sequence
<220> FEATURE:
<223> OTHER INFORMATION: CDR1

<400> SEQUENCE: 131

Gly Glu Thr Phe Lys Val Asn Ile Trp Gly
1               5                   10

<210> SEQ ID NO 132
<211> LENGTH: 10
<212> TYPE: PRT
<213> ORGANISM: Artificial Sequence
<220> FEATURE:
<223> OTHER INFORMATION: CDR1

<400> SEQUENCE: 132

Gly Asp Val Tyr Lys Ile Asn Phe Leu Gly
1               5                   10

<210> SEQ ID NO 133
<211> LENGTH: 10
<212> TYPE: PRT
<213> ORGANISM: Artificial Sequence
<220> FEATURE:
<223> OTHER INFORMATION: CDR1

<400> SEQUENCE: 133

Gly Glu Val His Lys Ile Asn Ile Leu Gly
1               5                   10

<210> SEQ ID NO 134
<211> LENGTH: 9
<212> TYPE: PRT
<213> ORGANISM: Artificial Sequence
<220> FEATURE:
<223> OTHER INFORMATION: CDR2

<400> SEQUENCE: 134

Thr Ile Thr Ile Gly Asp Thr Thr Asp
1               5

<210> SEQ ID NO 135
<211> LENGTH: 9
<212> TYPE: PRT
<213> ORGANISM: Artificial Sequence
<220> FEATURE:
<223> OTHER INFORMATION: CDR2

<400> SEQUENCE: 135

Thr Ile Thr Ile Gly Asp Ala Thr Asp
1               5

<210> SEQ ID NO 136
<211> LENGTH: 9
<212> TYPE: PRT
<213> ORGANISM: Artificial Sequence
<220> FEATURE:
<223> OTHER INFORMATION: CDR2

<400> SEQUENCE: 136

His Ile Thr Ile Ala Asp Ala Thr Asp
1               5

<210> SEQ ID NO 137
<211> LENGTH: 9
<212> TYPE: PRT
<213> ORGANISM: Artificial Sequence
<220> FEATURE:
<223> OTHER INFORMATION: CDR2

<400> SEQUENCE: 137

Thr Ile Thr Ile Gly Asp Asp Val Asp
1               5

<210> SEQ ID NO 138
<211> LENGTH: 9
<212> TYPE: PRT
<213> ORGANISM: Artificial Sequence
<220> FEATURE:
<223> OTHER INFORMATION: CDR2

<400> SEQUENCE: 138

His Ile Thr Ile Gly Asp Ala Thr Asp
1               5

<210> SEQ ID NO 139
<211> LENGTH: 9
<212> TYPE: PRT
<213> ORGANISM: Artificial Sequence
<220> FEATURE:
<223> OTHER INFORMATION: CDR2

```
<400> SEQUENCE: 139

His Ile Thr Ile Gly Asp Gln Ala Asp
1               5

<210> SEQ ID NO 140
<211> LENGTH: 9
<212> TYPE: PRT
<213> ORGANISM: Artificial Sequence
<220> FEATURE:
<223> OTHER INFORMATION: CDR2

<400> SEQUENCE: 140

His Ile Ser Ile Ala Asp Ala Thr Asp
1               5

<210> SEQ ID NO 141
<211> LENGTH: 9
<212> TYPE: PRT
<213> ORGANISM: Artificial Sequence
<220> FEATURE:
<223> OTHER INFORMATION: CDR2

<400> SEQUENCE: 141

His Ile Thr Ile Gly Asp Ala Thr Val
1               5

<210> SEQ ID NO 142
<211> LENGTH: 9
<212> TYPE: PRT
<213> ORGANISM: Artificial Sequence
<220> FEATURE:
<223> OTHER INFORMATION: CDR2

<400> SEQUENCE: 142

Ser Leu Thr Ile Gly Gly Ala Thr Asp
1               5

<210> SEQ ID NO 143
<211> LENGTH: 9
<212> TYPE: PRT
<213> ORGANISM: Artificial Sequence
<220> FEATURE:
<223> OTHER INFORMATION: CDR2

<400> SEQUENCE: 143

His Ile Thr Ile Gly Asp Glu Val Asp
1               5

<210> SEQ ID NO 144
<211> LENGTH: 9
<212> TYPE: PRT
<213> ORGANISM: Artificial Sequence
<220> FEATURE:
<223> OTHER INFORMATION: CDR2

<400> SEQUENCE: 144

His Ile Thr Ile Gly Asp Val Thr Asp
1               5

<210> SEQ ID NO 145
<211> LENGTH: 9
<212> TYPE: PRT
<213> ORGANISM: Artificial Sequence
<220> FEATURE:
<223> OTHER INFORMATION: CDR2

<400> SEQUENCE: 145
```

Ser Leu Thr Ile Gly Gly Ala Thr Asn
1               5

<210> SEQ ID NO 146
<211> LENGTH: 9
<212> TYPE: PRT
<213> ORGANISM: Artificial Sequence
<220> FEATURE:
<223> OTHER INFORMATION: CDR2

<400> SEQUENCE: 146

His Ile Thr Ile Gly Asp Ala Thr Asn
1               5

<210> SEQ ID NO 147
<211> LENGTH: 9
<212> TYPE: PRT
<213> ORGANISM: Artificial Sequence
<220> FEATURE:
<223> OTHER INFORMATION: CDR2

<400> SEQUENCE: 147

His Ile Thr Ile Ala Asp Val Ala Asp
1               5

<210> SEQ ID NO 148
<211> LENGTH: 9
<212> TYPE: PRT
<213> ORGANISM: Artificial Sequence
<220> FEATURE:
<223> OTHER INFORMATION: CDR2

<400> SEQUENCE: 148

Thr Ile Thr Ile Gly Asp Glu Val Asp
1               5

<210> SEQ ID NO 149
<211> LENGTH: 9
<212> TYPE: PRT
<213> ORGANISM: Artificial Sequence
<220> FEATURE:
<223> OTHER INFORMATION: CDR2

<400> SEQUENCE: 149

His Ile Ser Ile Ser Asp Gln Thr Asp
1               5

<210> SEQ ID NO 150
<211> LENGTH: 9
<212> TYPE: PRT
<213> ORGANISM: Artificial Sequence
<220> FEATURE:
<223> OTHER INFORMATION: CDR2

<400> SEQUENCE: 150

His Ile Thr Ile Gly Asp Gln Thr Asp
1               5

<210> SEQ ID NO 151
<211> LENGTH: 9
<212> TYPE: PRT
<213> ORGANISM: Artificial Sequence
<220> FEATURE:
<223> OTHER INFORMATION: CDR2

<400> SEQUENCE: 151

His Ile Thr Ile Gly Asp Thr Thr Asp
1               5

<210> SEQ ID NO 152
<211> LENGTH: 9
<212> TYPE: PRT
<213> ORGANISM: Artificial Sequence
<220> FEATURE:
<223> OTHER INFORMATION: CDR2

<400> SEQUENCE: 152

Arg Ile Ser Ile Ser Asp Gln Thr Asp
1               5

<210> SEQ ID NO 153
<211> LENGTH: 9
<212> TYPE: PRT
<213> ORGANISM: Artificial Sequence
<220> FEATURE:
<223> OTHER INFORMATION: CDR2

<400> SEQUENCE: 153

His Ile Ser Ile Gly Asp Gln Thr Asp
1               5

<210> SEQ ID NO 154
<211> LENGTH: 9
<212> TYPE: PRT
<213> ORGANISM: Artificial Sequence
<220> FEATURE:
<223> OTHER INFORMATION: CDR2

<400> SEQUENCE: 154

His Ile Thr Ile Ala Asp Ala Ala Asp
1               5

<210> SEQ ID NO 155
<211> LENGTH: 9
<212> TYPE: PRT
<213> ORGANISM: Artificial Sequence
<220> FEATURE:
<223> OTHER INFORMATION: CDR2

<400> SEQUENCE: 155

Thr Ile Thr Ile Gly Asp Ala Ala Asp
1               5

<210> SEQ ID NO 156
<211> LENGTH: 9
<212> TYPE: PRT
<213> ORGANISM: Artificial Sequence
<220> FEATURE:
<223> OTHER INFORMATION: CDR2

<400> SEQUENCE: 156

His Ile Ala Ile Ser Asp Gln Thr Asp
1               5

<210> SEQ ID NO 157
<211> LENGTH: 9
<212> TYPE: PRT
<213> ORGANISM: Artificial Sequence
<220> FEATURE:
<223> OTHER INFORMATION: CDR2

<400> SEQUENCE: 157

Thr Ile Thr Ile Ala Asp Lys Thr Asp

<210> SEQ ID NO 158
<211> LENGTH: 9
<212> TYPE: PRT
<213> ORGANISM: Artificial Sequence
<220> FEATURE:
<223> OTHER INFORMATION: CDR2

<400> SEQUENCE: 158

Thr Ile Thr Ile Ala Asp Lys Ile Asp
1               5

<210> SEQ ID NO 159
<211> LENGTH: 9
<212> TYPE: PRT
<213> ORGANISM: Artificial Sequence
<220> FEATURE:
<223> OTHER INFORMATION: CDR2

<400> SEQUENCE: 159

His Ile Thr Ile Gly Asp Ala Thr Ser
1               5

<210> SEQ ID NO 160
<211> LENGTH: 9
<212> TYPE: PRT
<213> ORGANISM: Artificial Sequence
<220> FEATURE:
<223> OTHER INFORMATION: CDR2

<400> SEQUENCE: 160

Thr Ile Thr Ile Gly Asp Glu Val Ala
1               5

<210> SEQ ID NO 161
<211> LENGTH: 9
<212> TYPE: PRT
<213> ORGANISM: Artificial Sequence
<220> FEATURE:
<223> OTHER INFORMATION: CDR2

<400> SEQUENCE: 161

His Ile Thr Ile Ala Asp Val Thr Asp
1               5

<210> SEQ ID NO 162
<211> LENGTH: 9
<212> TYPE: PRT
<213> ORGANISM: Artificial Sequence
<220> FEATURE:
<223> OTHER INFORMATION: CDR2

<400> SEQUENCE: 162

His Ile Thr Ile Ala Asp Gln Ala Asp
1               5

<210> SEQ ID NO 163
<211> LENGTH: 9
<212> TYPE: PRT
<213> ORGANISM: Artificial Sequence
<220> FEATURE:
<223> OTHER INFORMATION: CDR2

<400> SEQUENCE: 163

Thr Ile Thr Ile Gly Asp Glu Thr Gln
1               5

```
<210> SEQ ID NO 164
<211> LENGTH: 9
<212> TYPE: PRT
<213> ORGANISM: Artificial Sequence
<220> FEATURE:
<223> OTHER INFORMATION: CDR3

<400> SEQUENCE: 164

Gly Ser Arg Leu Tyr Pro Tyr Asn Tyr
1               5

<210> SEQ ID NO 165
<211> LENGTH: 9
<212> TYPE: PRT
<213> ORGANISM: Artificial Sequence
<220> FEATURE:
<223> OTHER INFORMATION: CDR3

<400> SEQUENCE: 165

Gly Ser Arg Ile Tyr Pro Tyr Asp Tyr
1               5

<210> SEQ ID NO 166
<211> LENGTH: 9
<212> TYPE: PRT
<213> ORGANISM: Artificial Sequence
<220> FEATURE:
<223> OTHER INFORMATION: CDR3

<400> SEQUENCE: 166

Tyr Ser Arg Ile Tyr Pro Tyr Asn Tyr
1               5

<210> SEQ ID NO 167
<211> LENGTH: 9
<212> TYPE: PRT
<213> ORGANISM: Artificial Sequence
<220> FEATURE:
<223> OTHER INFORMATION: CDR3

<400> SEQUENCE: 167

Lys Ser Arg Leu Tyr Pro Tyr Asp Tyr
1               5

<210> SEQ ID NO 168
<211> LENGTH: 9
<212> TYPE: PRT
<213> ORGANISM: Artificial Sequence
<220> FEATURE:
<223> OTHER INFORMATION: CDR3

<400> SEQUENCE: 168

Lys Ser Arg Ile Tyr Pro Tyr Asp Tyr
1               5

<210> SEQ ID NO 169
<211> LENGTH: 9
<212> TYPE: PRT
<213> ORGANISM: Artificial Sequence
<220> FEATURE:
<223> OTHER INFORMATION: CDR3

<400> SEQUENCE: 169

Gly Ser Arg Ile Trp Pro Tyr Asp Tyr
1               5
```

```
<210> SEQ ID NO 170
<211> LENGTH: 9
<212> TYPE: PRT
<213> ORGANISM: Artificial Sequence
<220> FEATURE:
<223> OTHER INFORMATION: CDR3

<400> SEQUENCE: 170

Phe Ser Arg Ile Tyr Pro Tyr Asp Tyr
1               5

<210> SEQ ID NO 171
<211> LENGTH: 9
<212> TYPE: PRT
<213> ORGANISM: Artificial Sequence
<220> FEATURE:
<223> OTHER INFORMATION: CDR3

<400> SEQUENCE: 171

Gly Ser Arg Ile Tyr Pro Tyr Asn Tyr
1               5

<210> SEQ ID NO 172
<211> LENGTH: 9
<212> TYPE: PRT
<213> ORGANISM: Artificial Sequence
<220> FEATURE:
<223> OTHER INFORMATION: CDR3

<400> SEQUENCE: 172

Gly Ser Arg Leu Tyr Pro Tyr Asp Tyr
1               5

<210> SEQ ID NO 173
<211> LENGTH: 9
<212> TYPE: PRT
<213> ORGANISM: Artificial Sequence
<220> FEATURE:
<223> OTHER INFORMATION: CDR3

<400> SEQUENCE: 173

Gly Ser Arg Ile Tyr Pro Tyr Ser Tyr
1               5

<210> SEQ ID NO 174
<211> LENGTH: 9
<212> TYPE: PRT
<213> ORGANISM: Artificial Sequence
<220> FEATURE:
<223> OTHER INFORMATION: CDR3

<400> SEQUENCE: 174

Leu Ser Arg Leu Tyr Pro Tyr Asn Tyr
1               5

<210> SEQ ID NO 175
<211> LENGTH: 25
<212> TYPE: PRT
<213> ORGANISM: Artificial Sequence
<220> FEATURE:
<223> OTHER INFORMATION: FR1

<400> SEQUENCE: 175

Glu Val Gln Leu Val Glu Ser Gly Gly Gly Leu Val Gln Pro Gly Gly
1               5                   10                  15

Ser Leu Arg Leu Ser Cys Ala Ala Ser
```

```
            20                  25

<210> SEQ ID NO 176
<211> LENGTH: 25
<212> TYPE: PRT
<213> ORGANISM: Artificial Sequence
<220> FEATURE:
<223> OTHER INFORMATION: FR1

<400> SEQUENCE: 176

Glu Val Gln Leu Val Glu Ser Gly Gly Gly Leu Val Gln Pro Gly Arg
1               5                   10                  15

Ser Leu Arg Leu Pro Cys Ala Ala Ser
            20                  25

<210> SEQ ID NO 177
<211> LENGTH: 25
<212> TYPE: PRT
<213> ORGANISM: Artificial Sequence
<220> FEATURE:
<223> OTHER INFORMATION: FR1

<400> SEQUENCE: 177

Glu Val Gln Leu Val Glu Ser Gly Gly Gly Leu Val Gln Pro Gly Gly
1               5                   10                  15

Ser Leu Arg Leu Ser Cys Ala Val Ser
            20                  25

<210> SEQ ID NO 178
<211> LENGTH: 25
<212> TYPE: PRT
<213> ORGANISM: Artificial Sequence
<220> FEATURE:
<223> OTHER INFORMATION: FR1

<400> SEQUENCE: 178

Glu Val Gln Leu Val Glu Ser Gly Gly Gly Leu Val Gln Pro Gly Gly
1               5                   10                  15

Ser Leu Lys Leu Ser Cys Ala Ala Ser
            20                  25

<210> SEQ ID NO 179
<211> LENGTH: 25
<212> TYPE: PRT
<213> ORGANISM: Artificial Sequence
<220> FEATURE:
<223> OTHER INFORMATION: FR1

<400> SEQUENCE: 179

Glu Val Gln Leu Val Glu Ser Gly Gly Gly Leu Val Gln Pro Gly Gly
1               5                   10                  15

Ser Leu Arg Leu Ser Cys Arg Ala Ser
            20                  25

<210> SEQ ID NO 180
<211> LENGTH: 25
<212> TYPE: PRT
<213> ORGANISM: Artificial Sequence
<220> FEATURE:
<223> OTHER INFORMATION: FR1

<400> SEQUENCE: 180

Glu Val Gln Leu Val Glu Ser Gly Gly Gly Leu Val Arg Pro Gly Gly
1               5                   10                  15
```

Ser Leu Arg Leu Ser Cys Ala Ala Ser
            20                  25

<210> SEQ ID NO 181
<211> LENGTH: 25
<212> TYPE: PRT
<213> ORGANISM: Artificial Sequence
<220> FEATURE:
<223> OTHER INFORMATION: FR1

<400> SEQUENCE: 181

Glu Val Gln Leu Val Glu Ser Gly Gly Gly Leu Val Gln Pro Gly Gly
1               5                   10                  15

Ser Leu Arg Leu Ser Cys Val Ala Ser
            20                  25

<210> SEQ ID NO 182
<211> LENGTH: 25
<212> TYPE: PRT
<213> ORGANISM: Artificial Sequence
<220> FEATURE:
<223> OTHER INFORMATION: FR1

<400> SEQUENCE: 182

Glu Val Gln Leu Val Glu Ser Gly Gly Gly Ser Val Gln Pro Gly Gly
1               5                   10                  15

Ser Leu Arg Leu Ser Cys Ala Ala Ser
            20                  25

<210> SEQ ID NO 183
<211> LENGTH: 25
<212> TYPE: PRT
<213> ORGANISM: Artificial Sequence
<220> FEATURE:
<223> OTHER INFORMATION: FR1

<400> SEQUENCE: 183

Glu Val Gln Leu Val Glu Ser Gly Gly Gly Leu Val Gln Pro Gly Gly
1               5                   10                  15

Ser Leu Arg Pro Ser Cys Ala Ala Ser
            20                  25

<210> SEQ ID NO 184
<211> LENGTH: 25
<212> TYPE: PRT
<213> ORGANISM: Artificial Sequence
<220> FEATURE:
<223> OTHER INFORMATION: FR1

<400> SEQUENCE: 184

Glu Val Gln Leu Val Glu Ser Gly Gly Gly Leu Val Gln Pro Gly Gly
1               5                   10                  15

Ser Leu Arg Leu Ser Cys Ile Thr Ser
            20                  25

<210> SEQ ID NO 185
<211> LENGTH: 25
<212> TYPE: PRT
<213> ORGANISM: Artificial Sequence
<220> FEATURE:
<223> OTHER INFORMATION: FR1

<400> SEQUENCE: 185

Glu Val Gln Leu Val Glu Ser Gly Gly Gly Leu Val His Pro Gly Gly
1               5                   10                  15

```
Ser Leu Arg Leu Ser Cys Ala Ala Ser
            20                  25

<210> SEQ ID NO 186
<211> LENGTH: 25
<212> TYPE: PRT
<213> ORGANISM: Artificial Sequence
<220> FEATURE:
<223> OTHER INFORMATION: FR1

<400> SEQUENCE: 186

Glu Val Gln Leu Val Glu Ser Gly Gly Gly Leu Val Gln Pro Gly Gly
1               5                   10                  15

Ser Ala Arg Leu Ser Cys Val Ala Ser
            20                  25

<210> SEQ ID NO 187
<211> LENGTH: 25
<212> TYPE: PRT
<213> ORGANISM: Artificial Sequence
<220> FEATURE:
<223> OTHER INFORMATION: FR1

<400> SEQUENCE: 187

Glu Val Gln Leu Val Glu Ser Gly Gly Gly Leu Val Gln Ala Gly Gly
1               5                   10                  15

Ser Leu Thr Leu Ser Cys Ala Ala Ser
            20                  25

<210> SEQ ID NO 188
<211> LENGTH: 25
<212> TYPE: PRT
<213> ORGANISM: Artificial Sequence
<220> FEATURE:
<223> OTHER INFORMATION: FR1

<400> SEQUENCE: 188

Glu Val Gln Leu Val Glu Ser Gly Gly Asp Leu Val Gln Pro Gly Gly
1               5                   10                  15

Ser Leu Arg Leu Ser Cys Ala Ala Ser
            20                  25

<210> SEQ ID NO 189
<211> LENGTH: 25
<212> TYPE: PRT
<213> ORGANISM: Artificial Sequence
<220> FEATURE:
<223> OTHER INFORMATION: FR1

<400> SEQUENCE: 189

Glu Val Gln Leu Val Glu Ser Gly Gly Gly Leu Val Gln Pro Glu Gly
1               5                   10                  15

Ser Leu Arg Leu Ser Cys Ala Ala Ser
            20                  25

<210> SEQ ID NO 190
<211> LENGTH: 25
<212> TYPE: PRT
<213> ORGANISM: Artificial Sequence
<220> FEATURE:
<223> OTHER INFORMATION: FR1

<400> SEQUENCE: 190

Glu Val Gln Leu Val Glu Ser Gly Gly Gly Leu Val Gln Pro Gly Gly
```

```
1               5                   10                  15

Ser Leu Lys Leu Pro Cys Ala Ala Ser
            20                  25
```

<210> SEQ ID NO 191
<211> LENGTH: 25
<212> TYPE: PRT
<213> ORGANISM: Artificial Sequence
<220> FEATURE:
<223> OTHER INFORMATION: FR1

<400> SEQUENCE: 191

```
Glu Val Gln Leu Val Glu Ser Gly Gly Gly Leu Val Gln Pro Gly Gly
1               5                   10                  15

Ser Leu Gly Leu Ser Cys Ala Ala Ser
            20                  25
```

<210> SEQ ID NO 192
<211> LENGTH: 25
<212> TYPE: PRT
<213> ORGANISM: Artificial Sequence
<220> FEATURE:
<223> OTHER INFORMATION: FR1

<400> SEQUENCE: 192

```
Glu Val Gln Leu Val Glu Ser Gly Gly Gly Leu Ala Gln Pro Gly Gly
1               5                   10                  15

Ser Leu Arg Leu Ser Cys Ala Ala Ser
            20                  25
```

<210> SEQ ID NO 193
<211> LENGTH: 25
<212> TYPE: PRT
<213> ORGANISM: Artificial Sequence
<220> FEATURE:
<223> OTHER INFORMATION: FR1

<400> SEQUENCE: 193

```
Glu Val Gln Leu Val Glu Ser Gly Gly Gly Trp Val Gln Pro Gly Gly
1               5                   10                  15

Ser Leu Arg Leu Ser Cys Ala Ala Ser
            20                  25
```

<210> SEQ ID NO 194
<211> LENGTH: 25
<212> TYPE: PRT
<213> ORGANISM: Artificial Sequence
<220> FEATURE:
<223> OTHER INFORMATION: FR1

<400> SEQUENCE: 194

```
Glu Val Gln Leu Val Glu Ser Gly Gly Gly Ser Val Gln Pro Gly Gly
1               5                   10                  15

Ser Leu Arg Pro Ser Cys Ala Ala Ser
            20                  25
```

<210> SEQ ID NO 195
<211> LENGTH: 25
<212> TYPE: PRT
<213> ORGANISM: Artificial Sequence
<220> FEATURE:
<223> OTHER INFORMATION: FR1

<400> SEQUENCE: 195

```
Glu Val Gln Leu Val Glu Ser Gly Gly Gly Leu Val Gln Pro Gly Glu
1               5                   10                  15

Ser Leu Arg Leu Ser Cys Ala Ala Ser
            20                  25
```

<210> SEQ ID NO 196
<211> LENGTH: 26
<212> TYPE: PRT
<213> ORGANISM: Artificial Sequence
<220> FEATURE:
<223> OTHER INFORMATION: FR1

<400> SEQUENCE: 196

```
Glu Val Gln Leu Val Glu Glu Ser Gly Gly Gly Leu Val Gln Pro Gly
1               5                   10                  15

Gly Ser Leu Arg Leu Ser Cys Ile Thr Ser
            20                  25
```

<210> SEQ ID NO 197
<211> LENGTH: 25
<212> TYPE: PRT
<213> ORGANISM: Artificial Sequence
<220> FEATURE:
<223> OTHER INFORMATION: FR1

<400> SEQUENCE: 197

```
Glu Val Gln Leu Val Glu Ser Gly Gly Gly Leu Val Arg Pro Gly Gly
1               5                   10                  15

Ser Leu Arg Leu Ser Cys Val Ala Ser
            20                  25
```

<210> SEQ ID NO 198
<211> LENGTH: 25
<212> TYPE: PRT
<213> ORGANISM: Artificial Sequence
<220> FEATURE:
<223> OTHER INFORMATION: FR1

<400> SEQUENCE: 198

```
Glu Val Gln Leu Val Glu Ser Gly Gly Gly Met Val Gln Pro Gly Gly
1               5                   10                  15

Ser Leu Arg Leu Ser Cys Ala Ala Ser
            20                  25
```

<210> SEQ ID NO 199
<211> LENGTH: 25
<212> TYPE: PRT
<213> ORGANISM: Artificial Sequence
<220> FEATURE:
<223> OTHER INFORMATION: FR1

<400> SEQUENCE: 199

```
Glu Val Gln Leu Val Glu Ser Gly Gly Gly Leu Val Gln Pro Gly Gly
1               5                   10                  15

Ser Leu Arg Leu Ser Cys Leu Thr Ser
            20                  25
```

<210> SEQ ID NO 200
<211> LENGTH: 25
<212> TYPE: PRT
<213> ORGANISM: Artificial Sequence
<220> FEATURE:
<223> OTHER INFORMATION: FR1

<400> SEQUENCE: 200

```
Glu Val Gln Leu Val Glu Ser Gly Gly Gly Leu Val Gln Pro Gly Gly
1               5                   10                  15

Ser Pro Arg Leu Ser Cys Val Ala Ser
            20                  25

<210> SEQ ID NO 201
<211> LENGTH: 25
<212> TYPE: PRT
<213> ORGANISM: Artificial Sequence
<220> FEATURE:
<223> OTHER INFORMATION: FR1

<400> SEQUENCE: 201

Glu Val Gln Leu Val Glu Ser Gly Gly Gly Leu Val Gln Pro Gly Gly
1               5                   10                  15

Ser Leu Arg Pro Ser Cys Val Ala Ser
            20                  25

<210> SEQ ID NO 202
<211> LENGTH: 25
<212> TYPE: PRT
<213> ORGANISM: Artificial Sequence
<220> FEATURE:
<223> OTHER INFORMATION: FR1

<400> SEQUENCE: 202

Glu Val Gln Leu Val Glu Ser Gly Gly Gly Trp Val Gln Ala Gly Gly
1               5                   10                  15

Ser Leu Arg Leu Ser Cys Ala Ala Ser
            20                  25

<210> SEQ ID NO 203
<211> LENGTH: 14
<212> TYPE: PRT
<213> ORGANISM: Artificial Sequence
<220> FEATURE:
<223> OTHER INFORMATION: FR2

<400> SEQUENCE: 203

Trp Tyr Arg Gln Ala Pro Gly Lys Glu Arg Glu Leu Val Ala
1               5                   10

<210> SEQ ID NO 204
<211> LENGTH: 14
<212> TYPE: PRT
<213> ORGANISM: Artificial Sequence
<220> FEATURE:
<223> OTHER INFORMATION: FR2

<400> SEQUENCE: 204

Trp Tyr Arg Gln Ala Pro Gly Lys Glu Arg Gly Leu Val Ala
1               5                   10

<210> SEQ ID NO 205
<211> LENGTH: 14
<212> TYPE: PRT
<213> ORGANISM: Artificial Sequence
<220> FEATURE:
<223> OTHER INFORMATION: FR2

<400> SEQUENCE: 205

Trp Tyr Arg Gln Ala Pro Gly Lys Glu Arg Glu Met Val Ala
1               5                   10
```

-continued

```
<210> SEQ ID NO 206
<211> LENGTH: 14
<212> TYPE: PRT
<213> ORGANISM: Artificial Sequence
<220> FEATURE:
<223> OTHER INFORMATION: FR2

<400> SEQUENCE: 206

Trp Tyr Arg Gln Thr Pro Glu Lys Glu Arg Glu Met Val Ala
1               5                   10

<210> SEQ ID NO 207
<211> LENGTH: 14
<212> TYPE: PRT
<213> ORGANISM: Artificial Sequence
<220> FEATURE:
<223> OTHER INFORMATION: FR2

<400> SEQUENCE: 207

Trp Tyr Arg Gln Ala Pro Ala Lys Glu Arg Glu Met Val Ala
1               5                   10

<210> SEQ ID NO 208
<211> LENGTH: 14
<212> TYPE: PRT
<213> ORGANISM: Artificial Sequence
<220> FEATURE:
<223> OTHER INFORMATION: FR2

<400> SEQUENCE: 208

Trp Tyr Arg Gln Ala Pro Gly Lys Glu Arg Glu Lys Val Ala
1               5                   10

<210> SEQ ID NO 209
<211> LENGTH: 14
<212> TYPE: PRT
<213> ORGANISM: Artificial Sequence
<220> FEATURE:
<223> OTHER INFORMATION: FR2

<400> SEQUENCE: 209

Trp Tyr Arg Gln Cys Pro Gly Lys Glu Arg Glu Met Val Ala
1               5                   10

<210> SEQ ID NO 210
<211> LENGTH: 14
<212> TYPE: PRT
<213> ORGANISM: Artificial Sequence
<220> FEATURE:
<223> OTHER INFORMATION: FR2

<400> SEQUENCE: 210

Trp Tyr Arg Gln Ala Pro Gly Lys Gln Arg Glu Leu Val Ala
1               5                   10

<210> SEQ ID NO 211
<211> LENGTH: 14
<212> TYPE: PRT
<213> ORGANISM: Artificial Sequence
<220> FEATURE:
<223> OTHER INFORMATION: FR2

<400> SEQUENCE: 211

Trp His Arg Gln Pro Pro Gly Lys Glu Arg Glu Lys Val Ala
1               5                   10

<210> SEQ ID NO 212
```

```
<211> LENGTH: 14
<212> TYPE: PRT
<213> ORGANISM: Artificial Sequence
<220> FEATURE:
<223> OTHER INFORMATION: FR2

<400> SEQUENCE: 212

Trp Tyr Arg Gln Ala Pro Gly Lys Arg Arg Glu Leu Val Ala
1               5                   10

<210> SEQ ID NO 213
<211> LENGTH: 14
<212> TYPE: PRT
<213> ORGANISM: Artificial Sequence
<220> FEATURE:
<223> OTHER INFORMATION: FR2

<400> SEQUENCE: 213

Trp His Arg Gln Ala Pro Gly Lys Glu Arg Glu Lys Val Ala
1               5                   10

<210> SEQ ID NO 214
<211> LENGTH: 14
<212> TYPE: PRT
<213> ORGANISM: Artificial Sequence
<220> FEATURE:
<223> OTHER INFORMATION: FR2

<400> SEQUENCE: 214

Trp Tyr Arg Gln Ala Pro Glu Lys Glu Arg Glu Met Val Ala
1               5                   10

<210> SEQ ID NO 215
<211> LENGTH: 14
<212> TYPE: PRT
<213> ORGANISM: Artificial Sequence
<220> FEATURE:
<223> OTHER INFORMATION: FR2

<400> SEQUENCE: 215

Trp Tyr Arg Gln Ala Pro Gly Lys Glu Arg Glu Val Val Ala
1               5                   10

<210> SEQ ID NO 216
<211> LENGTH: 14
<212> TYPE: PRT
<213> ORGANISM: Artificial Sequence
<220> FEATURE:
<223> OTHER INFORMATION: FR2

<400> SEQUENCE: 216

Trp Tyr Arg Gln Ala Pro Gly Lys Glu Arg Gly Val Val Ala
1               5                   10

<210> SEQ ID NO 217
<211> LENGTH: 14
<212> TYPE: PRT
<213> ORGANISM: Artificial Sequence
<220> FEATURE:
<223> OTHER INFORMATION: FR2

<400> SEQUENCE: 217

Trp Tyr Arg Gln Thr Pro Gly Lys Gln Arg Glu Leu Val Ala
1               5                   10

<210> SEQ ID NO 218
<211> LENGTH: 14
```

```
<212> TYPE: PRT
<213> ORGANISM: Artificial Sequence
<220> FEATURE:
<223> OTHER INFORMATION: FR2

<400> SEQUENCE: 218

Trp Tyr Arg Gln Ala Pro Gly Lys Glu Arg Glu Met Val Thr
1               5                   10

<210> SEQ ID NO 219
<211> LENGTH: 14
<212> TYPE: PRT
<213> ORGANISM: Artificial Sequence
<220> FEATURE:
<223> OTHER INFORMATION: FR2

<400> SEQUENCE: 219

Trp Tyr Arg Gln Ala Pro Gly His Glu Arg Glu Leu Val Ala
1               5                   10

<210> SEQ ID NO 220
<211> LENGTH: 14
<212> TYPE: PRT
<213> ORGANISM: Artificial Sequence
<220> FEATURE:
<223> OTHER INFORMATION: FR2

<400> SEQUENCE: 220

Trp Tyr Arg Gln Ala Pro Gly Asn Gln Arg Glu Val Val Ala
1               5                   10

<210> SEQ ID NO 221
<211> LENGTH: 14
<212> TYPE: PRT
<213> ORGANISM: Artificial Sequence
<220> FEATURE:
<223> OTHER INFORMATION: FR2

<400> SEQUENCE: 221

Trp Tyr Arg Gln Ala Pro Gly Asn Gln Arg Gly Val Val Ala
1               5                   10

<210> SEQ ID NO 222
<211> LENGTH: 14
<212> TYPE: PRT
<213> ORGANISM: Artificial Sequence
<220> FEATURE:
<223> OTHER INFORMATION: FR2

<400> SEQUENCE: 222

Trp Tyr Arg Gln Ala Pro Ala Lys Glu Arg Gly Met Val Ala
1               5                   10

<210> SEQ ID NO 223
<211> LENGTH: 14
<212> TYPE: PRT
<213> ORGANISM: Artificial Sequence
<220> FEATURE:
<223> OTHER INFORMATION: FR2

<400> SEQUENCE: 223

Trp Tyr Arg Gln Ala Pro Ala Lys Glu His Glu Met Val Ala
1               5                   10

<210> SEQ ID NO 224
<211> LENGTH: 14
<212> TYPE: PRT
```

```
<213> ORGANISM: Artificial Sequence
<220> FEATURE:
<223> OTHER INFORMATION: FR2

<400> SEQUENCE: 224

Trp Tyr Arg Gln Ala Pro Ala Arg Glu Arg Glu Met Val Ala
1               5                   10

<210> SEQ ID NO 225
<211> LENGTH: 14
<212> TYPE: PRT
<213> ORGANISM: Artificial Sequence
<220> FEATURE:
<223> OTHER INFORMATION: FR2

<400> SEQUENCE: 225

Trp Tyr Arg Gln Gly Pro Gly Lys Gln Arg Glu Leu Val Ala
1               5                   10

<210> SEQ ID NO 226
<211> LENGTH: 14
<212> TYPE: PRT
<213> ORGANISM: Artificial Sequence
<220> FEATURE:
<223> OTHER INFORMATION: FR2

<400> SEQUENCE: 226

Trp Tyr Arg Gln Ala Pro Gly Lys Glu Arg Gly Met Val Ala
1               5                   10

<210> SEQ ID NO 227
<211> LENGTH: 14
<212> TYPE: PRT
<213> ORGANISM: Artificial Sequence
<220> FEATURE:
<223> OTHER INFORMATION: FR2

<400> SEQUENCE: 227

Trp Tyr Arg Gln Ala Pro Ala Lys Glu Arg Glu Met Ile Ala
1               5                   10

<210> SEQ ID NO 228
<211> LENGTH: 14
<212> TYPE: PRT
<213> ORGANISM: Artificial Sequence
<220> FEATURE:
<223> OTHER INFORMATION: FR2

<400> SEQUENCE: 228

Trp Tyr Arg Gln Ala Pro Ala Lys Gly Arg Glu Met Val Ala
1               5                   10

<210> SEQ ID NO 229
<211> LENGTH: 14
<212> TYPE: PRT
<213> ORGANISM: Artificial Sequence
<220> FEATURE:
<223> OTHER INFORMATION: FR2

<400> SEQUENCE: 229

Trp Tyr Arg Gln Val Pro Ala Lys Glu Arg Glu Met Val Ala
1               5                   10

<210> SEQ ID NO 230
<211> LENGTH: 14
<212> TYPE: PRT
<213> ORGANISM: Artificial Sequence
```

```
<220> FEATURE:
<223> OTHER INFORMATION: FR2

<400> SEQUENCE: 230

Trp Tyr Arg Gln Cys Pro Gly Lys Glu Arg Asp Met Val Ala
1               5                   10

<210> SEQ ID NO 231
<211> LENGTH: 14
<212> TYPE: PRT
<213> ORGANISM: Artificial Sequence
<220> FEATURE:
<223> OTHER INFORMATION: FR2

<400> SEQUENCE: 231

Trp Gln Arg Gln Ala Pro Gly Lys Glu Arg Glu Lys Val Ala
1               5                   10

<210> SEQ ID NO 232
<211> LENGTH: 14
<212> TYPE: PRT
<213> ORGANISM: Artificial Sequence
<220> FEATURE:
<223> OTHER INFORMATION: FR2

<400> SEQUENCE: 232

Trp Tyr Cys Gln Ala Pro Gly Lys Glu Arg Glu Met Val Ala
1               5                   10

<210> SEQ ID NO 233
<211> LENGTH: 14
<212> TYPE: PRT
<213> ORGANISM: Artificial Sequence
<220> FEATURE:
<223> OTHER INFORMATION: FR2

<400> SEQUENCE: 233

Trp Tyr Arg Gln Ala Pro Gly Lys Glu Arg Asp Met Val Ala
1               5                   10

<210> SEQ ID NO 234
<211> LENGTH: 14
<212> TYPE: PRT
<213> ORGANISM: Artificial Sequence
<220> FEATURE:
<223> OTHER INFORMATION: FR2

<400> SEQUENCE: 234

Trp His Arg Gln Ala Pro Ala Lys Glu Arg Glu Met Val Ala
1               5                   10

<210> SEQ ID NO 235
<211> LENGTH: 39
<212> TYPE: PRT
<213> ORGANISM: Artificial Sequence
<220> FEATURE:
<223> OTHER INFORMATION: FR3

<400> SEQUENCE: 235

Tyr Ala Asp Ser Ala Lys Gly Arg Phe Thr Ile Ser Arg Asp Glu Ala
1               5                   10                  15

Lys Asn Met Val Tyr Leu Gln Met Asn Ser Leu Lys Pro Glu Asp Thr
            20                  25                  30

Ala Val His Phe Cys Arg Ala
        35
```

```
<210> SEQ ID NO 236
<211> LENGTH: 39
<212> TYPE: PRT
<213> ORGANISM: Artificial Sequence
<220> FEATURE:
<223> OTHER INFORMATION: FR3

<400> SEQUENCE: 236

Tyr Ala Asp Tyr Ala Lys Gly Arg Phe Thr Ile Ser Arg Asp Glu Ala
1               5                   10                  15

Arg Asn Met Val Tyr Leu Gln Met Asn Ser Leu Lys Pro Glu Asp Thr
            20                  25                  30

Ala Val Tyr Phe Cys Arg Ala
        35

<210> SEQ ID NO 237
<211> LENGTH: 39
<212> TYPE: PRT
<213> ORGANISM: Artificial Sequence
<220> FEATURE:
<223> OTHER INFORMATION: FR3

<400> SEQUENCE: 237

Tyr Ala Asp Ser Ala Lys Gly Arg Phe Thr Ile Ser Arg Asp Glu Ala
1               5                   10                  15

Lys Asn Met Val Tyr Leu Gln Met Asn Ser Leu Lys Pro Glu Asp Thr
            20                  25                  30

Ala Val Tyr Phe Cys Arg Ala
        35

<210> SEQ ID NO 238
<211> LENGTH: 39
<212> TYPE: PRT
<213> ORGANISM: Artificial Sequence
<220> FEATURE:
<223> OTHER INFORMATION: FR3

<400> SEQUENCE: 238

Tyr Ser His Phe Ala Lys Gly Arg Phe Thr Ile Ser Arg Asp Glu Ala
1               5                   10                  15

Lys Asn Met Val Tyr Leu Gln Met Asn Ser Leu Arg Pro Glu Asp Thr
            20                  25                  30

Ala Val Tyr Phe Cys Arg Ala
        35

<210> SEQ ID NO 239
<211> LENGTH: 39
<212> TYPE: PRT
<213> ORGANISM: Artificial Sequence
<220> FEATURE:
<223> OTHER INFORMATION: FR3

<400> SEQUENCE: 239

Tyr Ala Asp Ser Ala Lys Gly Arg Phe Thr Ile Ser Arg Asp Glu Ala
1               5                   10                  15

Lys Asn Met Val Tyr Leu Gln Met Thr Ser Leu Lys Pro Glu Asp Thr
            20                  25                  30

Ala Val Tyr Val Cys Arg Ala
        35

<210> SEQ ID NO 240
<211> LENGTH: 39
```

```
<212> TYPE: PRT
<213> ORGANISM: Artificial Sequence
<220> FEATURE:
<223> OTHER INFORMATION: FR3

<400> SEQUENCE: 240

Tyr Ala Glu Ser Ala Lys Gly Arg Phe Thr Ile Ser Arg Asp Glu Ala
1               5                   10                  15
Lys Asn Met Val Tyr Leu Gln Met Asn Ser Leu Lys Pro Glu Asp Thr
            20                  25                  30
Ala Val Tyr Phe Cys Arg Ala
            35

<210> SEQ ID NO 241
<211> LENGTH: 39
<212> TYPE: PRT
<213> ORGANISM: Artificial Sequence
<220> FEATURE:
<223> OTHER INFORMATION: FR3

<400> SEQUENCE: 241

Tyr Ala Asp Ser Ala Lys Gly Arg Phe Thr Ile Ser Arg Asp Glu Ala
1               5                   10                  15
Lys Asn Met Val Tyr Leu Gln Met Asn Ser Leu Ser Pro Glu Asp Thr
            20                  25                  30
Ala Val Tyr Phe Cys Arg Ala
            35

<210> SEQ ID NO 242
<211> LENGTH: 39
<212> TYPE: PRT
<213> ORGANISM: Artificial Sequence
<220> FEATURE:
<223> OTHER INFORMATION: FR3

<400> SEQUENCE: 242

Tyr Ala His Phe Ala Lys Gly Arg Phe Thr Ile Ser Arg Asp Glu Ala
1               5                   10                  15
Lys Asn Met Val Tyr Leu Gln Met Asn Ser Leu Arg Pro Glu Asp Thr
            20                  25                  30
Ala Val Tyr Phe Cys Arg Ala
            35

<210> SEQ ID NO 243
<211> LENGTH: 39
<212> TYPE: PRT
<213> ORGANISM: Artificial Sequence
<220> FEATURE:
<223> OTHER INFORMATION: FR3

<400> SEQUENCE: 243

Tyr Ala Asp Ser Val Lys Gly Arg Phe Thr Ile Ser Glu Asp Ser Ala
1               5                   10                  15
Lys Asn Thr Val Tyr Leu Gln Met Asn Ser Leu Lys Ala Glu Asp Thr
            20                  25                  30
Ala Val Tyr Phe Cys Asn Ala
            35

<210> SEQ ID NO 244
<211> LENGTH: 39
<212> TYPE: PRT
<213> ORGANISM: Artificial Sequence
<220> FEATURE:
```

<223> OTHER INFORMATION: FR3

<400> SEQUENCE: 244

Tyr Ala Asp Ser Ala Lys Gly Arg Phe Thr Ile Ser Arg Asp Glu Ala
1               5                   10                  15

Lys Asn Met Val Tyr Leu Gln Met Thr Ser Leu Thr Pro Glu Asp Thr
            20                  25                  30

Ala Val Tyr Val Cys Arg Ala
        35

<210> SEQ ID NO 245
<211> LENGTH: 39
<212> TYPE: PRT
<213> ORGANISM: Artificial Sequence
<220> FEATURE:
<223> OTHER INFORMATION: FR3

<400> SEQUENCE: 245

Tyr Ala Asp Ser Ala Lys Gly Arg Phe Thr Ile Ser Arg Asp Glu Ala
1               5                   10                  15

Lys Asn Met Val Tyr Leu Gln Met Asn Asn Leu Lys Pro Glu Asp Thr
            20                  25                  30

Ala Val Tyr Phe Cys Arg Ala
        35

<210> SEQ ID NO 246
<211> LENGTH: 39
<212> TYPE: PRT
<213> ORGANISM: Artificial Sequence
<220> FEATURE:
<223> OTHER INFORMATION: FR3

<400> SEQUENCE: 246

Tyr Ala Asp Ser Val Lys Gly Arg Phe Thr Ile Ser Glu Asp Ser Ala
1               5                   10                  15

Lys Asn Thr Val Tyr Leu Gln Met Asn Ser Leu Lys Pro Glu Asp Thr
            20                  25                  30

Ala Val Tyr Phe Cys Asn Ala
        35

<210> SEQ ID NO 247
<211> LENGTH: 39
<212> TYPE: PRT
<213> ORGANISM: Artificial Sequence
<220> FEATURE:
<223> OTHER INFORMATION: FR3

<400> SEQUENCE: 247

Tyr Ala Asp Ser Ala Lys Gly Arg Phe Thr Ile Ser Arg Asp Glu Ala
1               5                   10                  15

Lys Asn Met Val His Leu Gln Met Asn Ser Leu Lys Pro Glu Asp Thr
            20                  25                  30

Ala Val Tyr Phe Cys Arg Ala
        35

<210> SEQ ID NO 248
<211> LENGTH: 39
<212> TYPE: PRT
<213> ORGANISM: Artificial Sequence
<220> FEATURE:
<223> OTHER INFORMATION: FR3

<400> SEQUENCE: 248

Tyr Ala Asp Ser Ala Lys Gly Arg Phe Thr Ile Ser Arg Asp Glu Ala
1               5                   10                  15

Lys Asn Met Val Phe Leu Gln Met Asn Asn Leu Lys Pro Glu Asp Thr
                20                  25                  30

Ala Val Tyr Phe Cys Arg Ala
            35

<210> SEQ ID NO 249
<211> LENGTH: 39
<212> TYPE: PRT
<213> ORGANISM: Artificial Sequence
<220> FEATURE:
<223> OTHER INFORMATION: FR3

<400> SEQUENCE: 249

Tyr Ala Gly Ser Ala Lys Gly Arg Phe Thr Ile Ser Arg Asp Glu Ala
1               5                   10                  15

Lys Asn Met Val Tyr Leu Gln Met Asn Ser Leu Lys Pro Glu Asp Thr
                20                  25                  30

Ala Val Tyr Phe Cys Arg Ala
            35

<210> SEQ ID NO 250
<211> LENGTH: 39
<212> TYPE: PRT
<213> ORGANISM: Artificial Sequence
<220> FEATURE:
<223> OTHER INFORMATION: FR3

<400> SEQUENCE: 250

Tyr Ala Asp Phe Ala Lys Gly Arg Phe Thr Ile Ser Arg Asp Glu Ala
1               5                   10                  15

Lys Asn Met Val Tyr Leu Gln Met Asn Ser Leu Lys Pro Glu Asp Thr
                20                  25                  30

Ala Val Tyr Phe Cys Arg Ala
            35

<210> SEQ ID NO 251
<211> LENGTH: 39
<212> TYPE: PRT
<213> ORGANISM: Artificial Sequence
<220> FEATURE:
<223> OTHER INFORMATION: FR3

<400> SEQUENCE: 251

Tyr Ala Asp Ser Ala Lys Gly Arg Phe Thr Ile Ser Arg Asp Glu Ala
1               5                   10                  15

Lys Asn Met Val Tyr Leu Gln Met Thr Ser Leu Lys Pro Glu Asp Thr
                20                  25                  30

Thr Val Tyr Val Cys Arg Ala
            35

<210> SEQ ID NO 252
<211> LENGTH: 39
<212> TYPE: PRT
<213> ORGANISM: Artificial Sequence
<220> FEATURE:
<223> OTHER INFORMATION: FR3

<400> SEQUENCE: 252

Tyr Ala Glu Ser Ala Lys Gly Arg Phe Thr Ile Ser Arg Asp Glu Ser
1               5                   10                  15

Lys Asn Met Val Tyr Leu Gln Met Asn Ser Leu Lys Pro Glu Asp Thr
            20                  25                  30

Ala Val Tyr Leu Cys Arg Ala
        35

<210> SEQ ID NO 253
<211> LENGTH: 39
<212> TYPE: PRT
<213> ORGANISM: Artificial Sequence
<220> FEATURE:
<223> OTHER INFORMATION: FR3

<400> SEQUENCE: 253

Tyr Ala Asp Ser Ala Lys Gly Arg Phe Ala Ile Ser Arg Asp Glu Ala
1               5                   10                  15

Lys Asn Met Val Tyr Leu Gln Met Asn Ser Leu Lys Pro Glu Asp Thr
            20                  25                  30

Ala Val Tyr Phe Cys Arg Ala
        35

<210> SEQ ID NO 254
<211> LENGTH: 39
<212> TYPE: PRT
<213> ORGANISM: Artificial Sequence
<220> FEATURE:
<223> OTHER INFORMATION: FR3

<400> SEQUENCE: 254

Tyr Ala Asp Phe Ala Gln Gly Arg Phe Thr Ile Ser Arg Asp Glu Ala
1               5                   10                  15

Lys Asn Met Val Tyr Leu Gln Met Asn Ser Leu Lys Pro Glu Asp Thr
            20                  25                  30

Ala Val Tyr Phe Cys Arg Ala
        35

<210> SEQ ID NO 255
<211> LENGTH: 39
<212> TYPE: PRT
<213> ORGANISM: Artificial Sequence
<220> FEATURE:
<223> OTHER INFORMATION: FR3

<400> SEQUENCE: 255

Tyr Ala Glu Phe Ala Lys Gly Arg Phe Thr Ile Ser Arg Asp Glu Pro
1               5                   10                  15

Lys Asn Met Val His Leu Gln Met Asn Ser Leu Lys Pro Glu Asp Thr
            20                  25                  30

Ala Val Tyr Leu Cys Arg Ala
        35

<210> SEQ ID NO 256
<211> LENGTH: 39
<212> TYPE: PRT
<213> ORGANISM: Artificial Sequence
<220> FEATURE:
<223> OTHER INFORMATION: FR3

<400> SEQUENCE: 256

Tyr Ala Asp Phe Ala Lys Gly Arg Leu Thr Ile Ser Arg Asp Glu Ala
1               5                   10                  15

Lys Asn Met Val Tyr Leu Gln Met Asn Ser Leu Lys Pro Glu Asp Thr
            20                  25                  30

```
Ala Val Tyr Phe Cys Arg Ala
        35

<210> SEQ ID NO 257
<211> LENGTH: 39
<212> TYPE: PRT
<213> ORGANISM: Artificial Sequence
<220> FEATURE:
<223> OTHER INFORMATION: FR3

<400> SEQUENCE: 257

Tyr Ala Asp Ser Ala Lys Gly Arg Phe Thr Ile Ser Arg Asp Glu Ser
1               5                   10                  15

Lys Asn Met Val Tyr Leu Gln Met Asn Ser Leu Lys Pro Glu Asp Thr
            20                  25                  30

Ala Val Tyr Phe Cys Arg Ala
        35

<210> SEQ ID NO 258
<211> LENGTH: 39
<212> TYPE: PRT
<213> ORGANISM: Artificial Sequence
<220> FEATURE:
<223> OTHER INFORMATION: FR3

<400> SEQUENCE: 258

Tyr Ala Asp Phe Ala Lys Gly Arg Phe Thr Ile Ser Arg Asp Gly Ala
1               5                   10                  15

Lys Asn Met Val Tyr Leu Gln Met Asn Ser Leu Lys Pro Glu Asp Thr
            20                  25                  30

Ala Val Tyr Phe Cys Arg Ala
        35

<210> SEQ ID NO 259
<211> LENGTH: 39
<212> TYPE: PRT
<213> ORGANISM: Artificial Sequence
<220> FEATURE:
<223> OTHER INFORMATION: FR3

<400> SEQUENCE: 259

Tyr Ala Asp Ser Ala Lys Gly Arg Phe Thr Ile Ser Arg Asp Glu Ala
1               5                   10                  15

Arg Asn Met Val Tyr Leu Gln Met Asn Ser Leu Lys Pro Glu Asp Thr
            20                  25                  30

Ala Leu Tyr Phe Cys His Ala
        35

<210> SEQ ID NO 260
<211> LENGTH: 39
<212> TYPE: PRT
<213> ORGANISM: Artificial Sequence
<220> FEATURE:
<223> OTHER INFORMATION: FR3

<400> SEQUENCE: 260

Tyr Ala Asp Ser Ala Lys Gly Arg Phe Thr Ile Ser Arg Asp Glu Ala
1               5                   10                  15

Lys Asn Met Val Tyr Leu Gln Met Asn Ser Leu Lys Pro Glu Asp Thr
            20                  25                  30

Ala Ala Tyr Phe Cys Arg Ala
        35
```

<210> SEQ ID NO 261
<211> LENGTH: 39
<212> TYPE: PRT
<213> ORGANISM: Artificial Sequence
<220> FEATURE:
<223> OTHER INFORMATION: FR3

<400> SEQUENCE: 261

Tyr Ala Asp Ser Ala Lys Gly Arg Phe Thr Ile Ser Arg Asp Glu Ser
1               5                   10                  15

Arg Asn Met Val Tyr Leu Gln Met Ser Ser Leu Lys Pro Glu Asp Thr
            20                  25                  30

Ala Val Tyr Phe Cys His Ala
        35

<210> SEQ ID NO 262
<211> LENGTH: 39
<212> TYPE: PRT
<213> ORGANISM: Artificial Sequence
<220> FEATURE:
<223> OTHER INFORMATION: FR3

<400> SEQUENCE: 262

Tyr Ala Asp Ser Ala Lys Gly Arg Phe Thr Ile Ser Arg Asp Glu Ser
1               5                   10                  15

Arg Asn Met Val Tyr Leu Gln Met Gly Ser Leu Lys Pro Glu Asp Thr
            20                  25                  30

Ala Val Tyr Phe Cys His Ala
        35

<210> SEQ ID NO 263
<211> LENGTH: 39
<212> TYPE: PRT
<213> ORGANISM: Artificial Sequence
<220> FEATURE:
<223> OTHER INFORMATION: FR3

<400> SEQUENCE: 263

Tyr Ala Asp Ser Ala Lys Gly Arg Phe Thr Ile Ser Arg Asp Glu Ala
1               5                   10                  15

Glu Asn Met Val Tyr Leu Gln Met Asn Ser Leu Lys Pro Glu Asp Thr
            20                  25                  30

Ala Val Tyr Phe Cys Arg Ala
        35

<210> SEQ ID NO 264
<211> LENGTH: 39
<212> TYPE: PRT
<213> ORGANISM: Artificial Sequence
<220> FEATURE:
<223> OTHER INFORMATION: FR3

<400> SEQUENCE: 264

Tyr Ala Asp Ser Ala Lys Gly Arg Phe Thr Ile Ser Arg Asp Glu Ala
1               5                   10                  15

Thr Asn Met Val Tyr Leu Gln Met Thr Ser Leu Lys Pro Glu Asp Thr
            20                  25                  30

Ala Val Tyr Phe Cys Arg Ala
        35

<210> SEQ ID NO 265

```
<211> LENGTH: 39
<212> TYPE: PRT
<213> ORGANISM: Artificial Sequence
<220> FEATURE:
<223> OTHER INFORMATION: FR3

<400> SEQUENCE: 265

Tyr Ala Gly Ser Ala Lys Gly Arg Phe Thr Ile Ser Arg Asp Glu Ala
1               5                   10                  15

Lys Asn Met Val Tyr Leu Gln Leu Asn Asn Leu Lys Pro Glu Asp Thr
            20                  25                  30

Ala Val Tyr Phe Cys Arg Ala
        35

<210> SEQ ID NO 266
<211> LENGTH: 39
<212> TYPE: PRT
<213> ORGANISM: Artificial Sequence
<220> FEATURE:
<223> OTHER INFORMATION: FR3

<400> SEQUENCE: 266

Tyr Ala Asp Ser Ala Lys Gly Arg Phe Thr Ile Ser Arg Asp Glu Ala
1               5                   10                  15

Lys Asn Met Val Tyr Leu Gln Leu Asn Asn Leu Lys Pro Glu Asp Thr
            20                  25                  30

Ala Val Tyr Phe Cys Arg Ala
        35

<210> SEQ ID NO 267
<211> LENGTH: 39
<212> TYPE: PRT
<213> ORGANISM: Artificial Sequence
<220> FEATURE:
<223> OTHER INFORMATION: FR3

<400> SEQUENCE: 267

Tyr Ala Glu Phe Ala Lys Gly Arg Phe Thr Ile Ser Arg Asp Glu Pro
1               5                   10                  15

Lys Asn Met Val Tyr Leu Gln Met Asn Ser Leu Lys Pro Glu Asp Thr
            20                  25                  30

Ala Val Tyr Leu Cys Arg Ala
        35

<210> SEQ ID NO 268
<211> LENGTH: 39
<212> TYPE: PRT
<213> ORGANISM: Artificial Sequence
<220> FEATURE:
<223> OTHER INFORMATION: FR3

<400> SEQUENCE: 268

Tyr Ala His Ser Ala Lys Gly Arg Phe Thr Ile Ser Arg Asp Glu Ala
1               5                   10                  15

Lys Asn Met Val Tyr Leu Gln Met Thr Ser Leu Lys Pro Glu Asp Thr
            20                  25                  30

Ala Val Tyr Val Cys Arg Ala
        35

<210> SEQ ID NO 269
<211> LENGTH: 39
<212> TYPE: PRT
<213> ORGANISM: Artificial Sequence
```

<220> FEATURE:
<223> OTHER INFORMATION: FR3

<400> SEQUENCE: 269

Tyr Ala Asp Phe Ala Lys Gly Arg Phe Thr Ile Ser Arg Asp Glu Val
1               5                   10                  15

Lys Asn Met Val Tyr Leu Gln Met Asn Ser Leu Lys Pro Glu Asp Thr
            20                  25                  30

Ala Val Tyr Phe Cys Arg Ala
        35

<210> SEQ ID NO 270
<211> LENGTH: 39
<212> TYPE: PRT
<213> ORGANISM: Artificial Sequence
<220> FEATURE:
<223> OTHER INFORMATION: FR3

<400> SEQUENCE: 270

Tyr Ala Asp Phe Ala Lys Gly Arg Phe Thr Ile Ser Arg Asp Glu Ala
1               5                   10                  15

Lys Asn Met Val Tyr Leu Gln Met Asn Ser Leu Arg Pro Glu Asp Thr
            20                  25                  30

Ala Val Tyr Phe Cys Arg Ala
        35

<210> SEQ ID NO 271
<211> LENGTH: 39
<212> TYPE: PRT
<213> ORGANISM: Artificial Sequence
<220> FEATURE:
<223> OTHER INFORMATION: FR3

<400> SEQUENCE: 271

Tyr Ser Tyr Phe Ala Lys Gly Arg Phe Thr Ile Ser Arg Asp Glu Ala
1               5                   10                  15

Lys Asn Met Val Tyr Leu Gln Met Asn Ser Leu Arg Pro Glu Asp Thr
            20                  25                  30

Ala Val Tyr Phe Cys Arg Ala
        35

<210> SEQ ID NO 272
<211> LENGTH: 39
<212> TYPE: PRT
<213> ORGANISM: Artificial Sequence
<220> FEATURE:
<223> OTHER INFORMATION: FR3

<400> SEQUENCE: 272

Tyr Ala Asp Ser Ala Lys Gly Arg Phe Thr Ile Ser Arg Asp Glu Ala
1               5                   10                  15

Lys Asn Val Val Tyr Leu Gln Met Asn Ser Leu Lys Pro Glu Asp Thr
            20                  25                  30

Ala Val Tyr Phe Cys Arg Ala
        35

<210> SEQ ID NO 273
<211> LENGTH: 39
<212> TYPE: PRT
<213> ORGANISM: Artificial Sequence
<220> FEATURE:
<223> OTHER INFORMATION: FR3

<400> SEQUENCE: 273

Tyr Glu Asp Ser Ala Lys Gly Arg Phe Thr Ile Ser Arg Asp Glu Ala
1               5                   10                  15

Lys Asn Met Val Tyr Leu Gln Met Thr Gly Leu Lys Pro Glu Asp Thr
            20                  25                  30

Ala Val Tyr Val Cys Arg Ala
        35

<210> SEQ ID NO 274
<211> LENGTH: 39
<212> TYPE: PRT
<213> ORGANISM: Artificial Sequence
<220> FEATURE:
<223> OTHER INFORMATION: FR3

<400> SEQUENCE: 274

Tyr Ala Asp Ser Val Lys Gly Arg Phe Thr Ile Ser Glu Asp Ser Ala
1               5                   10                  15

Lys Asn Thr Val Tyr Leu Gln Met Ser Ser Leu Lys Pro Glu Asp Thr
            20                  25                  30

Ala Val Tyr Phe Cys Asn Ala
        35

<210> SEQ ID NO 275
<211> LENGTH: 39
<212> TYPE: PRT
<213> ORGANISM: Artificial Sequence
<220> FEATURE:
<223> OTHER INFORMATION: FR3

<400> SEQUENCE: 275

Tyr Ser His Phe Ala Lys Gly Arg Phe Thr Ile Ser Arg Asp Glu Ala
1               5                   10                  15

Lys Asn Met Val Tyr Leu Gln Met Asn Gly Leu Arg Pro Glu Asp Thr
            20                  25                  30

Ala Val Tyr Phe Cys Arg Ala
        35

<210> SEQ ID NO 276
<211> LENGTH: 39
<212> TYPE: PRT
<213> ORGANISM: Artificial Sequence
<220> FEATURE:
<223> OTHER INFORMATION: FR3

<400> SEQUENCE: 276

Tyr Ala Asp Ser Ala Lys Gly Arg Phe Thr Ile Ser Arg Asp Glu Ala
1               5                   10                  15

Lys Asn Met Val Tyr Leu Gln Met Asn Ser Leu Lys Pro Glu Asp Thr
            20                  25                  30

Ala Val Tyr Leu Cys Arg Ala
        35

<210> SEQ ID NO 277
<211> LENGTH: 39
<212> TYPE: PRT
<213> ORGANISM: Artificial Sequence
<220> FEATURE:
<223> OTHER INFORMATION: FR3

<400> SEQUENCE: 277

Tyr Ala Glu Phe Ala Lys Gly Arg Phe Thr Ile Ser Arg Asp Glu Pro

```
                 1               5                  10                  15
Lys Asn Met Val Tyr Leu Gln Met Asn Ser Leu Lys Pro Val Asp Thr
                20                  25                  30

Ala Val Tyr Leu Cys Arg Ala
         35

<210> SEQ ID NO 278
<211> LENGTH: 39
<212> TYPE: PRT
<213> ORGANISM: Artificial Sequence
<220> FEATURE:
<223> OTHER INFORMATION: FR3

<400> SEQUENCE: 278

Tyr Ser His Phe Ala Lys Gly Arg Phe Thr Ile Ser Arg Asp Glu Ala
1               5                   10                  15

Lys Asn Met Val Tyr Leu Gln Met Asn Asn Leu Arg Pro Glu Asp Thr
                20                  25                  30

Ala Val Tyr Phe Cys Arg Ala
         35

<210> SEQ ID NO 279
<211> LENGTH: 39
<212> TYPE: PRT
<213> ORGANISM: Artificial Sequence
<220> FEATURE:
<223> OTHER INFORMATION: FR3

<400> SEQUENCE: 279

Tyr Ala Asp Ser Val Lys Gly Arg Phe Thr Ile Ser Glu Asp Ser Ala
1               5                   10                  15

Lys Asp Thr Val Tyr Leu Gln Met Asn Ser Leu Lys Pro Glu Asp Thr
                20                  25                  30

Ala Val Tyr Phe Cys Asn Ala
         35

<210> SEQ ID NO 280
<211> LENGTH: 39
<212> TYPE: PRT
<213> ORGANISM: Artificial Sequence
<220> FEATURE:
<223> OTHER INFORMATION: FR3

<400> SEQUENCE: 280

Tyr Ala Asp Ser Ala Lys Gly Arg Phe Thr Ile Ser Arg Asp Glu Ala
1               5                   10                  15

Lys Asn Met Val Tyr Leu Gln Met Asn Ser Leu Lys Pro Glu Asp Ala
                20                  25                  30

Ala Val Tyr Phe Cys Arg Ala
         35

<210> SEQ ID NO 281
<211> LENGTH: 39
<212> TYPE: PRT
<213> ORGANISM: Artificial Sequence
<220> FEATURE:
<223> OTHER INFORMATION: FR3

<400> SEQUENCE: 281

Tyr Ala Glu Ser Ala Lys Gly Arg Phe Thr Ile Ser Arg Asp Glu Ser
1               5                   10                  15

Lys Asn Met Val Tyr Leu Gln Met Asn Ser Leu Lys Pro Glu Asp Ala
```

```
                    20                  25                  30

Ala Val Tyr Leu Cys Arg Ala
         35

<210> SEQ ID NO 282
<211> LENGTH: 39
<212> TYPE: PRT
<213> ORGANISM: Artificial Sequence
<220> FEATURE:
<223> OTHER INFORMATION: FR3

<400> SEQUENCE: 282

Tyr Ala Asp Ser Ala Lys Gly Arg Phe Thr Ile Ser Arg Asp Glu Ser
1               5                   10                  15

Arg Asn Met Val Tyr Leu Gln Met Ser Ser Leu Lys Pro Glu Asn Thr
            20                  25                  30

Ala Val Tyr Phe Cys His Ala
         35

<210> SEQ ID NO 283
<211> LENGTH: 39
<212> TYPE: PRT
<213> ORGANISM: Artificial Sequence
<220> FEATURE:
<223> OTHER INFORMATION: FR3

<400> SEQUENCE: 283

Tyr Ala Asp Ser Ala Lys Gly Arg Phe Thr Ile Ser Arg Asp Glu Ala
1               5                   10                  15

Lys Asn Met Val Tyr Leu Gln Met Asp Ser Leu Lys Pro Glu Asp Thr
            20                  25                  30

Ala Val Tyr Phe Cys Arg Ala
         35

<210> SEQ ID NO 284
<211> LENGTH: 39
<212> TYPE: PRT
<213> ORGANISM: Artificial Sequence
<220> FEATURE:
<223> OTHER INFORMATION: FR3

<400> SEQUENCE: 284

Tyr Ala Asp Ser Ala Lys Gly Arg Phe Thr Ile Ser Arg Asp Glu Ala
1               5                   10                  15

Lys Asn Met Val Tyr Leu Gln Met Asn Ser Leu Lys Pro Gly Asp Thr
            20                  25                  30

Ala Val Tyr Phe Cys Arg Ala
         35

<210> SEQ ID NO 285
<211> LENGTH: 11
<212> TYPE: PRT
<213> ORGANISM: Artificial Sequence
<220> FEATURE:
<223> OTHER INFORMATION: FR4

<400> SEQUENCE: 285

Trp Gly Gln Gly Thr Gln Val Thr Val Ser Ser
1               5                   10

<210> SEQ ID NO 286
<211> LENGTH: 11
<212> TYPE: PRT
```

```
<213> ORGANISM: Artificial Sequence
<220> FEATURE:
<223> OTHER INFORMATION: FR4

<400> SEQUENCE: 286

Trp Gly Gln Gly Thr Leu Val Thr Val Ser Ser
1               5                   10

<210> SEQ ID NO 287
<211> LENGTH: 11
<212> TYPE: PRT
<213> ORGANISM: Artificial Sequence
<220> FEATURE:
<223> OTHER INFORMATION: FR4

<400> SEQUENCE: 287

Trp Gly Arg Gly Thr Gln Val Thr Val Ser Ser
1               5                   10

<210> SEQ ID NO 288
<211> LENGTH: 11
<212> TYPE: PRT
<213> ORGANISM: Artificial Sequence
<220> FEATURE:
<223> OTHER INFORMATION: FR4

<400> SEQUENCE: 288

Trp Gly His Gly Thr Leu Val Thr Val Ser Ser
1               5                   10

<210> SEQ ID NO 289
<211> LENGTH: 11
<212> TYPE: PRT
<213> ORGANISM: Artificial Sequence
<220> FEATURE:
<223> OTHER INFORMATION: FR4

<400> SEQUENCE: 289

Trp Gly Arg Gly Thr Leu Val Thr Val Ser Ser
1               5                   10

<210> SEQ ID NO 290
<211> LENGTH: 11
<212> TYPE: PRT
<213> ORGANISM: Artificial Sequence
<220> FEATURE:
<223> OTHER INFORMATION: FR4

<400> SEQUENCE: 290

Trp Asp Gln Gly Thr Gln Val Thr Val Ser Ser
1               5                   10

<210> SEQ ID NO 291
<211> LENGTH: 327
<212> TYPE: PRT
<213> ORGANISM: Artificial Sequence
<220> FEATURE:
<223> OTHER INFORMATION: Nanobody sequence

<400> SEQUENCE: 291

Glu Val Gln Leu Val Glu Ser Gly Gly Gly Leu Val Gln Gly Gly
1               5                   10                  15

Ser Leu Ser Leu Ser Cys Ala Ala Ser Gly Arg Thr Phe Ser Ser Tyr
                20                  25                  30

Ala Met Ala Trp Phe Arg Gln Pro Pro Gly Lys Glu Arg Glu Phe Val
            35                  40                  45
```

-continued

```
Ala Ser Ile Ser Trp Ser Gly Glu Asn Thr Asn Tyr Arg Asn Ser Val
         50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Lys Ile Ala Lys Thr Tyr Pro Asp Asn Trp Tyr Trp Thr Lys
                100                 105                 110

Ser Asn Asn Tyr Asn Tyr Trp Gly Gln Gly Thr Leu Val Thr Val Ser
             115                 120                 125

Ser Gly Gly Gly Ser Gly Gly Gly Ser Gly Gly Gly Ser
        130                 135                 140

Gly Gly Gly Gly Ser Gly Gly Gly Ser Gly Gly Gly Ser Gly
145                 150                 155                 160

Gly Gly Gly Ser Glu Val Gln Leu Val Glu Ser Gly Gly Leu Val
                165                 170                 175

Gln Gly Gly Gly Ser Leu Ser Leu Ser Cys Ala Ala Ser Gly Arg Thr
            180                 185                 190

Phe Ser Ser Tyr Ala Met Ala Trp Phe Arg Gln Pro Pro Gly Lys Glu
            195                 200                 205

Arg Glu Phe Val Ala Ser Ile Ser Trp Ser Gly Glu Asn Thr Asn Tyr
210                 215                 220

Arg Asn Ser Val Lys Gly Arg Phe Thr Ile Ser Arg Asp Asn Ala Lys
225                 230                 235                 240

Asn Thr Val Tyr Leu Gln Met Asn Ser Leu Lys Pro Glu Asp Thr Ala
                245                 250                 255

Val Tyr Tyr Cys Ala Ala Lys Ile Ala Lys Thr Tyr Pro Asp Asn Trp
                260                 265                 270

Tyr Trp Thr Lys Ser Asn Asn Tyr Asn Tyr Trp Gly Gln Gly Thr Leu
            275                 280                 285

Val Thr Val Ser Ser Gly Ala Ala Asp Tyr Lys Asp His Asp Gly Asp
            290                 295                 300

Tyr Lys Asp His Asp Ile Asp Tyr Lys Asp Asp Asp Asp Lys Gly Ala
305                 310                 315                 320

Ala His His His His His His
                325

<210> SEQ ID NO 292
<211> LENGTH: 276
<212> TYPE: PRT
<213> ORGANISM: Artificial Sequence
<220> FEATURE:
<223> OTHER INFORMATION: Nanobody sequence

<400> SEQUENCE: 292

Glu Val Gln Leu Val Glu Ser Gly Gly Gly Leu Val Gln Pro Gly Gly
  1               5                  10                  15

Ser Leu Arg Leu Ser Cys Thr Phe Ser Gly Gly Thr Phe Ser Ser Tyr
                 20                  25                  30

Thr Met Gly Trp Phe Arg Gln Ala Pro Gly Lys Glu Arg Glu Phe Val
             35                  40                  45

Ala Glu Val Arg Trp Gly Gly Val Thr Thr Tyr Ser Asn Ser Leu Lys
         50                  55                  60

Asp Arg Phe Ser Ile Ser Glu Asp Ser Val Lys Asn Ala Val Tyr Leu
 65                  70                  75                  80
```

```
Gln Met Asn Ser Leu Lys Pro Glu Asp Thr Ala Val Tyr Tyr Cys Ala
            85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Glu Val Gln
            115                 120                 125

Leu Val Glu Ser Gly Gly Gly Leu Val Gln Pro Gly Gly Ser Leu Arg
        130                 135                 140

Leu Ser Cys Ala Ala Ser Gly Ser Val His Lys Ile Asn Phe Leu Gly
145                 150                 155                 160

Trp Tyr Arg Gln Ala Pro Gly Lys Glu Arg Gly Leu Val Ala Thr Ile
            165                 170                 175

Thr Ile Gly Asp Thr Thr Asp Tyr Ala Asp Tyr Ala Lys Gly Arg Phe
            180                 185                 190

Thr Ile Ser Arg Asp Glu Ala Arg Asn Met Val Tyr Leu Gln Met Asn
            195                 200                 205

Ser Leu Lys Pro Glu Asp Thr Ala Val Tyr Phe Cys Arg Ala Gly Ser
    210                 215                 220

Arg Leu Tyr Pro Tyr Asn Tyr Trp Gly Gln Gly Thr Leu Val Thr Val
225                 230                 235                 240

Ser Ser Gly Ala Ala Asp Tyr Lys Asp His Asp Gly Asp Tyr Lys Asp
            245                 250                 255

His Asp Ile Asp Tyr Lys Asp Asp Asp Lys Gly Ala Ala His His
            260                 265                 270

His His His His
        275

<210> SEQ ID NO 293
<211> LENGTH: 289
<212> TYPE: PRT
<213> ORGANISM: Artificial Sequence
<220> FEATURE:
<223> OTHER INFORMATION: Nanobody sequence

<400> SEQUENCE: 293

Glu Val Gln Leu Gln Ala Ser Gly Gly Gly Ser Val Gln Ala Gly Gly
1               5                   10                  15

Ser Leu Arg Leu Ser Cys Ala Ala Ser Gly Tyr Thr Ile Gly Pro Tyr
            20                  25                  30

Cys Met Gly Trp Phe Arg Gln Ala Pro Gly Lys Glu Arg Glu Gly Val
        35                  40                  45

Ala Ala Ile Asn Met Gly Gly Ile Thr Tyr Tyr Ala Asp Ser Val
50                  55                  60

Lys Gly Arg Phe Thr Ile Ser Gln Asp Asn Ala Lys Asn Thr Val Tyr
65                  70                  75                  80

Leu Leu Met Asn Ser Leu Glu Pro Glu Asp Thr Ala Ile Tyr Tyr Cys
            85                  90                  95

Ala Ala Asp Ser Thr Ile Tyr Ala Ser Tyr Tyr Glu Cys Gly His Gly
            100                 105                 110

Leu Ser Thr Gly Gly Tyr Gly Tyr Asp Ser Trp Gly Gln Gly Thr Gln
            115                 120                 125

Val Thr Val Ser Ser Gly Gly Gly Ser Glu Val Gln Leu Val Glu
        130                 135                 140

Ser Gly Gly Gly Leu Val Gln Pro Gly Gly Ser Leu Arg Leu Ser Cys
145                 150                 155                 160
```

```
Ala Ala Ser Gly Ser Val His Lys Ile Asn Phe Leu Gly Trp Tyr Arg
            165                 170                 175

Gln Ala Pro Gly Lys Glu Arg Gly Leu Val Ala Thr Ile Thr Ile Gly
        180                 185                 190

Asp Thr Thr Asp Tyr Ala Asp Tyr Ala Lys Gly Arg Phe Thr Ile Ser
            195                 200                 205

Arg Asp Glu Ala Arg Asn Met Val Tyr Leu Gln Met Asn Ser Leu Lys
        210                 215                 220

Pro Glu Asp Thr Ala Val Tyr Phe Cys Arg Ala Gly Ser Arg Leu Tyr
225                 230                 235                 240

Pro Tyr Asn Tyr Trp Gly Gln Gly Thr Leu Val Thr Val Ser Ser Gly
            245                 250                 255

Ala Ala Asp Tyr Lys Asp His Asp Gly Asp Tyr Lys Asp His Asp Ile
            260                 265                 270

Asp Tyr Lys Asp Asp Asp Asp Lys Gly Ala Ala His His His His His
        275                 280                 285

His

<210> SEQ ID NO 294
<211> LENGTH: 292
<212> TYPE: PRT
<213> ORGANISM: Artificial Sequence
<220> FEATURE:
<223> OTHER INFORMATION: Nanobody sequence

<400> SEQUENCE: 294

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
            85                  90                  95

Ala Val Arg Gln Met Tyr Met Thr Val Val Pro Asp Tyr Trp Gly Gln
        100                 105                 110

Gly Thr Leu Val Thr Val Ser Ser Gly Gly Gly Ser Asp Val Gln
            115                 120                 125

Leu Gln Ala Ser Gly Gly Ser Val Gln Ala Gly Gly Ser Leu Arg
        130                 135                 140

Leu Ser Cys Ala Ala Ser Gly Tyr Thr Ile Gly Pro Tyr Cys Met Gly
145                 150                 155                 160

Trp Phe Arg Gln Ala Pro Gly Lys Glu Arg Glu Gly Val Ala Ala Ile
            165                 170                 175

Asn Met Gly Gly Gly Ile Thr Tyr Tyr Ala Asp Ser Val Lys Gly Arg
        180                 185                 190

Phe Thr Ile Ser Gln Asp Asn Ala Lys Asn Thr Val Tyr Leu Leu Met
            195                 200                 205

Asn Ser Leu Glu Pro Glu Asp Thr Ala Ile Tyr Tyr Cys Ala Ala Asp
        210                 215                 220
```

```
Ser Thr Ile Tyr Ala Ser Tyr Tyr Glu Cys Gly His Gly Leu Ser Thr
225                 230                 235                 240

Gly Gly Tyr Gly Tyr Asp Ser Trp Gly Gln Gly Thr Gln Val Thr Val
                245                 250                 255

Ser Ser Gly Ala Ala Asp Tyr Lys Asp His Asp Gly Asp Tyr Lys Asp
            260                 265                 270

His Asp Ile Asp Tyr Lys Asp Asp Asp Lys Gly Ala Ala His His
        275                 280                 285

His His His His
        290

<210> SEQ ID NO 295
<211> LENGTH: 276
<212> TYPE: PRT
<213> ORGANISM: Artificial Sequence
<220> FEATURE:
<223> OTHER INFORMATION: Nanobody sequence

<400> SEQUENCE: 295

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Lys Ile Asn
            20                  25                  30

Phe Leu Gly Trp Tyr Arg Gln Ala Pro Gly Lys Glu Arg Gly Leu Val
        35                  40                  45

Ala Thr Ile Thr Ile Gly Asp Thr Thr Asp Tyr Ala Asp Tyr Ala Lys
    50                  55                  60

Gly Arg Phe Thr Ile Ser Arg Asp Glu Ala Arg Asn Met Val Tyr Leu
65                  70                  75                  80

Gln Met Asn Ser Leu Lys Pro Glu Asp Thr Ala Val Tyr Phe Cys Arg
            85                  90                  95

Ala Gly Ser Arg Leu Tyr Pro Tyr Asn Tyr Trp Gly Gln Gly Thr Leu
        100                 105                 110

Val Thr Val Ser Ser Gly Gly Gly Ser Glu Val Gln Leu Val Glu
    115                 120                 125

Ser Gly Gly Gly Leu Val Gln Pro Gly Gly Ser Leu Arg Leu Ser Cys
    130                 135                 140

Thr Phe Ser Gly Gly Thr Phe Ser Ser Tyr Thr Met Gly Trp Phe Arg
145                 150                 155                 160

Gln Ala Pro Gly Lys Glu Arg Glu Phe Val Ala Glu Val Arg Trp Gly
                165                 170                 175

Gly Val Thr Thr Tyr Ser Asn Ser Leu Lys Asp Arg Phe Ser Ile Ser
            180                 185                 190

Glu Asp Ser Val Lys Asn Ala Val Tyr Leu Gln Met Asn Ser Leu Lys
        195                 200                 205

Pro Glu Asp Thr Ala Val Tyr Tyr Cys Ala Ala Val Arg Gln Met Tyr
    210                 215                 220

Met Thr Val Val Pro Asp Tyr Trp Gly Gln Gly Thr Leu Val Thr Val
225                 230                 235                 240

Ser Ser Gly Ala Ala Asp Tyr Lys Asp His Asp Gly Asp Tyr Lys Asp
                245                 250                 255

His Asp Ile Asp Tyr Lys Asp Asp Asp Lys Gly Ala Ala His His
            260                 265                 270

His His His His
        275
```

```
<210> SEQ ID NO 296
<211> LENGTH: 280
<212> TYPE: PRT
<213> ORGANISM: Artificial Sequence
<220> FEATURE:
<223> OTHER INFORMATION: Nanobody sequence

<400> SEQUENCE: 296

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Ser Glu Val Gln Leu Val Glu Ser Gly Gly Gly Leu Val Gln Pro Gly
    130                 135                 140

Gly Ser Leu Arg Leu Ser Cys Ala Ala Ser Gly Ser Val His Lys Ile
145                 150                 155                 160

Asn Phe Leu Gly Trp Tyr Arg Gln Ala Pro Gly Lys Glu Arg Gly Leu
                165                 170                 175

Val Ala Thr Ile Thr Ile Gly Asp Thr Thr Asp Tyr Ala Asp Tyr Ala
            180                 185                 190

Lys Gly Arg Phe Thr Ile Ser Arg Asp Glu Ala Arg Asn Met Val Tyr
        195                 200                 205

Leu Gln Met Asn Ser Leu Lys Pro Glu Asp Thr Ala Val Tyr Phe Cys
    210                 215                 220

Arg Ala Gly Ser Arg Leu Tyr Pro Tyr Asn Tyr Trp Gly Gln Gly Thr
225                 230                 235                 240

Leu Val Thr Val Ser Ser Gly Ala Ala Asp Tyr Lys Asp His Asp Gly
                245                 250                 255

Asp Tyr Lys Asp His Asp Ile Asp Tyr Lys Asp Asp Asp Lys Gly
            260                 265                 270

Ala Ala His His His His His His
        275                 280

<210> SEQ ID NO 297
<211> LENGTH: 293
<212> TYPE: PRT
<213> ORGANISM: Artificial Sequence
<220> FEATURE:
<223> OTHER INFORMATION: Nanobody sequence

<400> SEQUENCE: 297

Glu Val Gln Leu Gln Ala Ser Gly Gly Gly Ser Val Gln Ala Gly Gly
1               5                   10                  15

Ser Leu Arg Leu Ser Cys Ala Ala Ser Gly Tyr Thr Ile Gly Pro Tyr
            20                  25                  30
```

```
Cys Met Gly Trp Phe Arg Gln Ala Pro Gly Lys Glu Arg Glu Gly Val
            35                  40                  45

Ala Ala Ile Asn Met Gly Gly Ile Thr Tyr Tyr Ala Asp Ser Val
 50                  55                  60

Lys Gly Arg Phe Thr Ile Ser Gln Asp Asn Ala Lys Asn Thr Val Tyr
 65                  70                  75                  80

Leu Leu Met Asn Ser Leu Glu Pro Glu Asp Thr Ala Ile Tyr Tyr Cys
                85                  90                  95

Ala Ala Asp Ser Thr Ile Tyr Ala Ser Tyr Tyr Glu Cys Gly His Gly
            100                 105                 110

Leu Ser Thr Gly Gly Tyr Gly Tyr Asp Ser Trp Gly Gln Gly Thr Gln
            115                 120                 125

Val Thr Val Ser Ser Gly Gly Gly Gly Ser Gly Gly Gly Ser Glu Val
130                 135                 140

Gln Leu Val Glu Ser Gly Gly Gly Leu Val Gln Pro Gly Gly Ser Leu
145                 150                 155                 160

Arg Leu Ser Cys Ala Ala Ser Gly Ser Val His Lys Ile Asn Phe Leu
                165                 170                 175

Gly Trp Tyr Arg Gln Ala Pro Gly Lys Glu Arg Gly Leu Val Ala Thr
            180                 185                 190

Ile Thr Ile Gly Asp Thr Thr Asp Tyr Ala Asp Tyr Ala Lys Gly Arg
            195                 200                 205

Phe Thr Ile Ser Arg Asp Glu Ala Arg Asn Met Val Tyr Leu Gln Met
 210                 215                 220

Asn Ser Leu Lys Pro Glu Asp Thr Ala Val Tyr Phe Cys Arg Ala Gly
225                 230                 235                 240

Ser Arg Leu Tyr Pro Tyr Asn Tyr Trp Gly Gln Gly Thr Leu Val Thr
                245                 250                 255

Val Ser Ser Gly Ala Ala Asp Tyr Lys Asp His Asp Gly Asp Tyr Lys
            260                 265                 270

Asp His Asp Ile Asp Tyr Lys Asp Asp Asp Lys Gly Ala Ala His
            275                 280                 285

His His His His His
        290

<210> SEQ ID NO 298
<211> LENGTH: 296
<212> TYPE: PRT
<213> ORGANISM: Artificial Sequence
<220> FEATURE:
<223> OTHER INFORMATION: Nanobody sequence

<400> SEQUENCE: 298

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
            35                  40                  45

Ala Glu Val Arg Trp Gly Gly Val Thr Thr Tyr Ser Asn Ser Leu Lys
 50                  55                  60

Asp Arg Phe Ser Ile Ser Glu Asp Ser Val Lys Asn Ala Val Tyr Leu
 65                  70                  75                  80

Gln Met Asn Ser Leu Lys Pro Glu Asp Thr Ala Val Tyr Tyr Cys Ala
                85                  90                  95
```

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
            115                 120                 125

Ser Asp Val Gln Leu Gln Ala Ser Gly Gly Ser Val Gln Ala Gly
130                 135                 140

Gly Ser Leu Arg Leu Ser Cys Ala Ala Ser Gly Tyr Thr Ile Gly Pro
145                 150                 155                 160

Tyr Cys Met Gly Trp Phe Arg Gln Ala Pro Gly Lys Glu Arg Glu Gly
                165                 170                 175

Val Ala Ala Ile Asn Met Gly Gly Ile Thr Tyr Tyr Ala Asp Ser
            180                 185                 190

Val Lys Gly Arg Phe Thr Ile Ser Gln Asp Asn Ala Lys Asn Thr Val
            195                 200                 205

Tyr Leu Leu Met Asn Ser Leu Glu Pro Glu Asp Thr Ala Ile Tyr Tyr
            210                 215                 220

Cys Ala Ala Asp Ser Thr Ile Tyr Ala Ser Tyr Tyr Glu Cys Gly His
225                 230                 235                 240

Gly Leu Ser Thr Gly Gly Tyr Gly Tyr Asp Ser Trp Gly Gln Gly Thr
                245                 250                 255

Gln Val Thr Val Ser Ser Gly Ala Ala Asp Tyr Lys Asp His Asp Gly
            260                 265                 270

Asp Tyr Lys Asp His Asp Ile Asp Tyr Lys Asp Asp Asp Asp Lys Gly
            275                 280                 285

Ala Ala His His His His His His
            290                 295

<210> SEQ ID NO 299
<211> LENGTH: 280
<212> TYPE: PRT
<213> ORGANISM: Artificial Sequence
<220> FEATURE:
<223> OTHER INFORMATION: Nanobody sequence

<400> SEQUENCE: 299

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Lys Ile Asn
            20                  25                  30

Phe Leu Gly Trp Tyr Arg Gln Ala Pro Gly Lys Glu Arg Gly Leu Val
            35                  40                  45

Ala Thr Ile Thr Ile Gly Asp Thr Thr Asp Tyr Ala Asp Tyr Ala Lys
50                  55                  60

Gly Arg Phe Thr Ile Ser Arg Asp Glu Ala Arg Asn Met Val Tyr Leu
65                  70                  75                  80

Gln Met Asn Ser Leu Lys Pro Glu Asp Thr Ala Val Tyr Phe Cys Arg
                85                  90                  95

Ala Gly Ser Arg Leu Tyr Pro Tyr Asn Tyr Trp Gly Gln Gly Thr Leu
            100                 105                 110

Val Thr Val Ser Ser Gly Gly Gly Gly Ser Gly Gly Gly Ser Glu Val
            115                 120                 125

Gln Leu Val Glu Ser Gly Gly Gly Leu Val Gln Pro Gly Gly Ser Leu
            130                 135                 140

Arg Leu Ser Cys Thr Phe Ser Gly Gly Thr Phe Ser Ser Tyr Thr Met
145                 150                 155                 160

Gly Trp Phe Arg Gln Ala Pro Gly Lys Glu Arg Phe Val Ala Glu
            165                 170                 175

Val Arg Trp Gly Gly Val Thr Thr Tyr Ser Asn Ser Leu Lys Asp Arg
        180                 185                 190

Phe Ser Ile Ser Glu Asp Ser Val Lys Asn Ala Val Tyr Leu Gln Met
        195                 200                 205

Asn Ser Leu Lys Pro Glu Asp Thr Ala Val Tyr Tyr Cys Ala Ala Val
        210                 215                 220

Arg Gln Met Tyr Met Thr Val Val Pro Asp Tyr Trp Gly Gln Gly Thr
225                 230                 235                 240

Leu Val Thr Val Ser Ser Gly Ala Ala Asp Tyr Lys Asp His Asp Gly
            245                 250                 255

Asp Tyr Lys Asp His Asp Ile Asp Tyr Lys Asp Asp Asp Asp Lys Gly
            260                 265                 270

Ala Ala His His His His His His
            275                 280

<210> SEQ ID NO 300
<211> LENGTH: 306
<212> TYPE: PRT
<213> ORGANISM: Artificial Sequence
<220> FEATURE:
<223> OTHER INFORMATION: Nanobody sequence

<400> SEQUENCE: 300

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Ser Val His Lys Ile Asn Phe Leu Gly Trp Tyr
            180                 185                 190

Arg Gln Ala Pro Gly Lys Glu Arg Gly Leu Val Ala Thr Ile Thr Ile
        195                 200                 205

Gly Asp Thr Thr Asp Tyr Ala Asp Tyr Ala Lys Gly Arg Phe Thr Ile
    210                 215                 220

Ser Arg Asp Glu Ala Arg Asn Met Val Tyr Leu Gln Met Asn Ser Leu
225                 230                 235                 240

```
Lys Pro Glu Asp Thr Ala Val Tyr Phe Cys Arg Ala Gly Ser Arg Leu
                245                 250                 255

Tyr Pro Tyr Asn Tyr Trp Gly Gln Gly Thr Leu Val Thr Val Ser Ser
            260                 265                 270

Gly Ala Ala Asp Tyr Lys Asp His Asp Gly Asp Tyr Lys Asp His Asp
        275                 280                 285

Ile Asp Tyr Lys Asp Asp Asp Lys Gly Ala Ala His His His His
290                 295                 300

His His
305

<210> SEQ ID NO 301
<211> LENGTH: 319
<212> TYPE: PRT
<213> ORGANISM: Artificial Sequence
<220> FEATURE:
<223> OTHER INFORMATION: Nanobody sequence

<400> SEQUENCE: 301

Glu Val Gln Leu Gln Ala Ser Gly Gly Gly Val Gln Ala Gly Gly
1               5                   10                  15

Ser Leu Arg Leu Ser Cys Ala Ala Ser Gly Tyr Thr Ile Gly Pro Tyr
                20                  25                  30

Cys Met Gly Trp Phe Arg Gln Ala Pro Gly Lys Glu Arg Glu Gly Val
            35                  40                  45

Ala Ala Ile Asn Met Gly Gly Ile Thr Tyr Tyr Ala Asp Ser Val
        50                  55                  60

Lys Gly Arg Phe Thr Ile Ser Gln Asp Asn Ala Lys Asn Thr Val Tyr
65                  70                  75                  80

Leu Leu Met Asn Ser Leu Glu Pro Glu Asp Thr Ala Ile Tyr Tyr Cys
                85                  90                  95

Ala Ala Asp Ser Thr Ile Tyr Ala Ser Tyr Tyr Glu Cys Gly His Gly
            100                 105                 110

Leu Ser Thr Gly Gly Tyr Gly Tyr Asp Ser Trp Gly Gln Gly Thr Gln
        115                 120                 125

Val Thr Val Ser Ser Gly Gly Gly Gly Ser Gly Gly Gly Gly Ser Gly
    130                 135                 140

Gly Gly Gly Ser Gly Gly Gly Gly Ser Gly Gly Gly Gly Ser Gly Gly
145                 150                 155                 160

Gly Gly Ser Gly Gly Gly Gly Ser Glu Val Gln Leu Val Glu Ser Gly
            165                 170                 175

Gly Gly Leu Val Gln Pro Gly Gly Ser Leu Arg Leu Ser Cys Ala Ala
        180                 185                 190

Ser Gly Ser Val His Lys Ile Asn Phe Leu Gly Trp Tyr Arg Gln Ala
    195                 200                 205

Pro Gly Lys Glu Arg Gly Leu Val Ala Thr Ile Thr Ile Gly Asp Thr
    210                 215                 220

Thr Asp Tyr Ala Asp Tyr Ala Lys Gly Arg Phe Thr Ile Ser Arg Asp
225                 230                 235                 240

Glu Ala Arg Asn Met Val Tyr Leu Gln Met Asn Ser Leu Lys Pro Glu
                245                 250                 255

Asp Thr Ala Val Tyr Phe Cys Arg Ala Gly Ser Arg Leu Tyr Pro Tyr
            260                 265                 270

Asn Tyr Trp Gly Gln Gly Thr Leu Val Thr Val Ser Ser Gly Ala Ala
        275                 280                 285
```

```
Asp Tyr Lys Asp His Asp Gly Asp Tyr Lys Asp Ile Asp Tyr
    290                 295                 300

Lys Asp Asp Asp Lys Gly Ala Ala His His His His His His
305                 310                 315
```

<210> SEQ ID NO 302
<211> LENGTH: 322
<212> TYPE: PRT
<213> ORGANISM: Artificial Sequence
<220> FEATURE:
<223> OTHER INFORMATION: Nanobody sequence

<400> SEQUENCE: 302

```
Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Ser Gly Gly Gly Ser Gly Gly Gly Gly
    130                 135                 140

Ser Gly Gly Gly Ser Gly Gly Gly Ser Asp Val Gln Leu Gln
145                 150                 155                 160

Ala Ser Gly Gly Ser Val Gln Ala Gly Gly Ser Leu Arg Leu Ser
            165                 170                 175

Cys Ala Ala Ser Gly Tyr Thr Ile Gly Pro Tyr Cys Met Gly Trp Phe
            180                 185                 190

Arg Gln Ala Pro Gly Lys Glu Arg Glu Gly Val Ala Ala Ile Asn Met
        195                 200                 205

Gly Gly Gly Ile Thr Tyr Ala Asp Ser Val Lys Gly Arg Phe Thr
    210                 215                 220

Ile Ser Gln Asp Asn Ala Lys Asn Thr Val Tyr Leu Leu Met Asn Ser
225                 230                 235                 240

Leu Glu Pro Glu Asp Thr Ala Ile Tyr Tyr Cys Ala Ala Asp Ser Thr
                245                 250                 255

Ile Tyr Ala Ser Tyr Tyr Glu Cys Gly His Gly Leu Ser Thr Gly Gly
            260                 265                 270

Tyr Gly Tyr Asp Ser Trp Gly Gln Gly Thr Gln Val Thr Val Ser Ser
        275                 280                 285

Gly Ala Ala Asp Tyr Lys Asp His Asp Gly Asp Tyr Lys Asp His Asp
    290                 295                 300

Ile Asp Tyr Lys Asp Asp Asp Lys Gly Ala Ala His His His His
305                 310                 315                 320

His His
```

-continued

```
<210> SEQ ID NO 303
<211> LENGTH: 306
<212> TYPE: PRT
<213> ORGANISM: Artificial Sequence
<220> FEATURE:
<223> OTHER INFORMATION: Nanobody sequence

<400> SEQUENCE: 303

Glu Val Gln Leu Val Glu Ser Gly Gly Leu Val Gln Pro Gly Gly
1               5                   10                  15

Ser Leu Arg Leu Ser Cys Ala Ala Ser Gly Ser Val His Lys Ile Asn
            20                  25                  30

Phe Leu Gly Trp Tyr Arg Gln Ala Pro Gly Lys Glu Arg Gly Leu Val
        35                  40                  45

Ala Thr Ile Thr Ile Gly Asp Thr Thr Asp Tyr Ala Asp Tyr Ala Lys
    50                  55                  60

Gly Arg Phe Thr Ile Ser Arg Asp Glu Ala Arg Asn Met Val Tyr Leu
65                  70                  75                  80

Gln Met Asn Ser Leu Lys Pro Glu Asp Thr Ala Val Tyr Phe Cys Arg
                85                  90                  95

Ala Gly Ser Arg Leu Tyr Pro Tyr Asn Tyr Trp Gly Gln Gly Thr Leu
            100                 105                 110

Val Thr Val Ser Ser Gly Gly Gly Gly Ser Gly Gly Gly Ser Gly
        115                 120                 125

Gly Gly Ser Gly Gly Gly Gly Ser Gly Gly Gly Ser Gly Gly
    130                 135                 140

Gly Gly Ser Gly Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
                165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
        195                 200                 205

Thr Thr Tyr Ser Asn Ser Leu Lys Asp Arg Phe Ser Ile Ser Glu Asp
    210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
                245                 250                 255

Val Val Pro Asp Tyr Trp Gly Gln Gly Thr Leu Val Thr Val Ser Ser
            260                 265                 270

Gly Ala Ala Asp Tyr Lys Asp His Asp Gly Asp Tyr Lys Asp His Asp
        275                 280                 285

Ile Asp Tyr Lys Asp Asp Asp Lys Gly Ala Ala His His His His
    290                 295                 300

His His
305

<210> SEQ ID NO 304
<211> LENGTH: 322
<212> TYPE: PRT
<213> ORGANISM: Artificial Sequence
<220> FEATURE:
<223> OTHER INFORMATION: Nanobody sequence

<400> SEQUENCE: 304
```

Glu Val Gln Leu Gln Ala Ser Gly Gly Gly Ser Val Gln Ala Gly Gly
1               5                   10                  15

Ser Leu Arg Leu Ser Cys Ala Ala Ser Gly Tyr Thr Ile Gly Pro Tyr
                20                  25                  30

Cys Met Gly Trp Phe Arg Gln Ala Pro Gly Lys Glu Arg Glu Gly Val
                35                  40                  45

Ala Ala Ile Asn Met Gly Gly Ile Thr Tyr Tyr Ala Asp Ser Val
        50                  55                  60

Lys Gly Arg Phe Thr Ile Ser Gln Asp Asn Ala Lys Asn Thr Val Tyr
65                  70                  75                  80

Leu Leu Met Asn Ser Leu Glu Pro Glu Asp Thr Ala Ile Tyr Tyr Cys
                85                  90                  95

Ala Ala Asp Ser Thr Ile Tyr Ala Ser Tyr Tyr Glu Cys Gly His Gly
                100                 105                 110

Leu Ser Thr Gly Gly Tyr Gly Tyr Asp Ser Trp Gly Gln Gly Thr Gln
                115                 120                 125

Val Thr Val Ser Ser Gly Gly Gly Gly Ser Gly Gly Gly Gly Ser Gly
                130                 135                 140

Gly Gly Gly Ser Gly Gly Gly Gly Ser Gly Gly Gly Gly Ser Gly Gly
145                 150                 155                 160

Gly Gly Ser Gly Gly Gly Gly Ser Glu Val Gln Leu Val Glu Ser Gly
                165                 170                 175

Gly Gly Leu Val Gln Pro Gly Gly Ser Leu Arg Leu Ser Cys Thr Phe
                180                 185                 190

Ser Gly Gly Thr Phe Ser Ser Tyr Thr Met Gly Trp Phe Arg Gln Ala
                195                 200                 205

Pro Gly Lys Glu Arg Glu Phe Val Ala Glu Val Arg Trp Gly Gly Val
                210                 215                 220

Thr Thr Tyr Ser Asn Ser Leu Lys Asp Arg Phe Ser Ile Ser Glu Asp
225                 230                 235                 240

Ser Val Lys Asn Ala Val Tyr Leu Gln Met Asn Ser Leu Lys Pro Glu
                245                 250                 255

Asp Thr Ala Val Tyr Tyr Cys Ala Ala Val Arg Gln Met Tyr Met Thr
                260                 265                 270

Val Val Pro Asp Tyr Trp Gly Gln Gly Thr Leu Val Thr Val Ser Ser
                275                 280                 285

Gly Ala Ala Asp Tyr Lys Asp His Asp Gly Asp Tyr Lys Asp His Asp
                290                 295                 300

Ile Asp Tyr Lys Asp Asp Asp Lys Gly Ala Ala His His His His His
305                 310                 315                 320

His His

<210> SEQ ID NO 305
<211> LENGTH: 319
<212> TYPE: PRT
<213> ORGANISM: Artificial Sequence
<220> FEATURE:
<223> OTHER INFORMATION: Nanobody sequence

<400> SEQUENCE: 305

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Lys Ile Asn
                20                  25                  30

```
Phe Leu Gly Trp Tyr Arg Gln Ala Pro Gly Lys Glu Arg Gly Leu Val
            35                  40                  45

Ala Thr Ile Thr Ile Gly Asp Thr Thr Asp Tyr Ala Asp Tyr Ala Lys
 50                  55                  60

Gly Arg Phe Thr Ile Ser Arg Asp Glu Ala Arg Asn Met Val Tyr Leu
 65                  70                  75                  80

Gln Met Asn Ser Leu Lys Pro Glu Asp Thr Ala Val Tyr Phe Cys Arg
                85                  90                  95

Ala Gly Ser Arg Leu Tyr Pro Tyr Asn Tyr Trp Gly Gln Gly Thr Leu
            100                 105                 110

Val Thr Val Ser Ser Gly Gly Gly Ser Gly Gly Gly Ser Gly
            115                 120                 125

Gly Gly Gly Ser Gly Gly Gly Ser Gly Gly Gly Ser Gly Gly
130                 135                 140

Gly Gly Ser Gly Gly Gly Ser Asp Val Gln Leu Gln Ala Ser Gly
145                 150                 155                 160

Gly Gly Ser Val Gln Ala Gly Gly Ser Leu Arg Leu Ser Cys Ala Ala
            165                 170                 175

Ser Gly Tyr Thr Ile Gly Pro Tyr Cys Met Gly Trp Phe Arg Gln Ala
            180                 185                 190

Pro Gly Lys Glu Arg Glu Gly Val Ala Ala Ile Asn Met Gly Gly Gly
            195                 200                 205

Ile Thr Tyr Tyr Ala Asp Ser Val Lys Gly Arg Phe Thr Ile Ser Gln
 210                 215                 220

Asp Asn Ala Lys Asn Thr Val Tyr Leu Leu Met Asn Ser Leu Glu Pro
225                 230                 235                 240

Glu Asp Thr Ala Ile Tyr Tyr Cys Ala Ala Asp Ser Thr Ile Tyr Ala
            245                 250                 255

Ser Tyr Tyr Glu Cys Gly His Gly Leu Ser Thr Gly Gly Tyr Gly Tyr
            260                 265                 270

Asp Ser Trp Gly Gln Gly Thr Gln Val Thr Val Ser Ser Gly Ala Ala
            275                 280                 285

Asp Tyr Lys Asp His Asp Gly Asp Tyr Lys Asp His Asp Ile Asp Tyr
            290                 295                 300

Lys Asp Asp Asp Asp Lys Gly Ala Ala His His His His His His
305                 310                 315

<210> SEQ ID NO 306
<211> LENGTH: 306
<212> TYPE: PRT
<213> ORGANISM: Artificial Sequence
<220> FEATURE:
<223> OTHER INFORMATION: Nanobody sequence

<400> SEQUENCE: 306

Glu Val Gln Leu Val Glu Ser Gly Gly Gly Leu Val Gln Pro Gly Gly
 1               5                  10                  15

Ser Leu Arg Leu Ser Cys Ala Ala Ser Gly Asp Val Tyr Lys Ile Asn
            20                  25                  30

Phe Leu Gly Trp His Arg Gln Ala Pro Gly Lys Glu Arg Glu Lys Val
            35                  40                  45

Ala His Ile Thr Ile Gly Asp Ala Thr Asp Tyr Ala Asp Ser Ala Lys
 50                  55                  60

Gly Arg Phe Thr Ile Ser Arg Asp Glu Ala Lys Asn Met Val Tyr Leu
 65                  70                  75                  80
```

Gln Met Asn Ser Leu Lys Pro Glu Asp Thr Ala Val Tyr Phe Cys Arg
                85                  90                  95

Ala Gly Ser Arg Ile Tyr Pro Tyr Asp Tyr Trp Gly Gln Gly Thr Leu
            100                 105                 110

Val Thr Val Ser Ser Gly Gly Gly Ser Gly Gly Gly Gly Ser Gly
        115                 120                 125

Gly Gly Ser Gly Gly Gly Ser Gly Gly Gly Ser Gly Gly
    130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
                165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
        195                 200                 205

Thr Thr Tyr Ser Asn Ser Leu Lys Asp Arg Phe Ser Ile Ser Glu Asp
    210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
                245                 250                 255

Val Val Pro Asp Tyr Trp Gly Gln Gly Thr Leu Val Thr Val Ser Ser
            260                 265                 270

Gly Ala Ala Asp Tyr Lys Asp His Asp Gly Asp Tyr Lys Asp His Asp
        275                 280                 285

Ile Asp Tyr Lys Asp Asp Asp Lys Gly Ala Ala His His His His
    290                 295                 300

His His
305

<210> SEQ ID NO 307
<211> LENGTH: 306
<212> TYPE: PRT
<213> ORGANISM: Artificial Sequence
<220> FEATURE:
<223> OTHER INFORMATION: Nanobody sequence

<400> SEQUENCE: 307

Glu Val Gln Leu Val Glu Ser Gly Gly Gly Leu Val Gln Pro Gly Gly
1               5                   10                  15

Ser Leu Lys Leu Ser Cys Ala Ala Ser Gly Ala Val His Lys Ile Asn
                20                  25                  30

Phe Leu Gly Trp Tyr Arg Gln Thr Pro Glu Lys Glu Arg Glu Met Val
            35                  40                  45

Ala Thr Ile Thr Ile Gly Asp Glu Val Asp Tyr Ala Asp Ser Ala Lys
        50                  55                  60

Gly Arg Phe Thr Ile Ser Arg Asp Glu Ala Lys Asn Met Val Tyr Leu
65                  70                  75                  80

Gln Met Thr Ser Leu Lys Pro Glu Asp Thr Ala Val Tyr Val Cys Arg
                85                  90                  95

Ala Gly Ser Arg Leu Tyr Pro Tyr Asn Tyr Trp Gly Gln Gly Thr Leu
            100                 105                 110

Val Thr Val Ser Ser Gly Gly Gly Gly Ser Gly Gly Gly Gly Ser Gly
        115                 120                 125

```
Gly Gly Gly Ser Gly Gly Gly Gly Ser Gly Gly Gly Ser Gly Gly
    130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
            165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
            195                 200                 205

Thr Thr Tyr Ser Asn Ser Leu Lys Asp Arg Phe Ser Ile Ser Glu Asp
    210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
            245                 250                 255

Val Val Pro Asp Tyr Trp Gly Gln Gly Thr Leu Val Thr Val Ser Ser
            260                 265                 270

Gly Ala Ala Asp Tyr Lys Asp His Asp Gly Asp Tyr Lys Asp His Asp
            275                 280                 285

Ile Asp Tyr Lys Asp Asp Asp Lys Gly Ala Ala His His His His
    290                 295                 300

His His
305

<210> SEQ ID NO 308
<211> LENGTH: 306
<212> TYPE: PRT
<213> ORGANISM: Artificial Sequence
<220> FEATURE:
<223> OTHER INFORMATION: Nanobody sequence

<400> SEQUENCE: 308

Glu Val Gln Leu Val Glu Ser Gly Gly Gly Leu Val Gln Pro Gly Gly
1               5                   10                  15

Ser Leu Arg Leu Ser Cys Ile Thr Ser Gly Thr Phe Lys Ile Asn
            20                  25                  30

Ile Trp Gly Trp Tyr Arg Gln Ala Pro Gly Lys Gln Arg Glu Leu Val
        35                  40                  45

Ala Ser Leu Thr Ile Gly Gly Ala Thr Asn Tyr Ala Asp Ser Val Lys
    50                  55                  60

Gly Arg Phe Thr Ile Ser Glu Asp Ser Ala Lys Asn Thr Val Tyr Leu
65                  70                  75                  80

Gln Met Asn Ser Leu Lys Pro Glu Asp Thr Ala Val Tyr Phe Cys Asn
            85                  90                  95

Ala Lys Ser Arg Leu Tyr Pro Tyr Asp Tyr Trp Gly Gln Gly Thr Leu
            100                 105                 110

Val Thr Val Ser Ser Gly Gly Gly Ser Gly Gly Gly Gly Ser Gly
            115                 120                 125

Gly Gly Ser Gly Gly Gly Gly Ser Gly Gly Gly Ser Gly Gly
    130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
            165                 170                 175
```

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
            195                 200                 205

Thr Thr Tyr Ser Asn Ser Leu Lys Asp Arg Phe Ser Ile Ser Glu Asp
            210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
                    245                 250                 255

Val Val Pro Asp Tyr Trp Gly Gln Gly Thr Leu Val Thr Val Ser Ser
            260                 265                 270

Gly Ala Ala Asp Tyr Lys Asp His Asp Gly Asp Tyr Lys Asp His Asp
            275                 280                 285

Ile Asp Tyr Lys Asp Asp Asp Lys Gly Ala Ala His His His His
290                 295                 300

His His
305

<210> SEQ ID NO 309
<211> LENGTH: 306
<212> TYPE: PRT
<213> ORGANISM: Artificial Sequence
<220> FEATURE:
<223> OTHER INFORMATION: Nanobody sequence

<400> SEQUENCE: 309

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Leu Leu Asn
            20                  25                  30

Phe Leu Gly Trp Tyr Arg Gln Ala Pro Gly Lys Glu Arg Glu Met Val
            35                  40                  45

Ala His Ile Thr Ile Ala Asp Ala Thr Asp Tyr Ala His Phe Ala Lys
        50                  55                  60

Gly Arg Phe Thr Ile Ser Arg Asp Glu Ala Lys Asn Met Val Tyr Leu
65                  70                  75                  80

Gln Met Asn Ser Leu Arg Pro Glu Asp Thr Ala Val Tyr Phe Cys Arg
                85                  90                  95

Ala Gly Ser Arg Ile Tyr Pro Tyr Asp Tyr Trp Gly Gln Gly Thr Leu
            100                 105                 110

Val Thr Val Ser Ser Gly Gly Gly Gly Ser Gly Gly Gly Gly Ser Gly
            115                 120                 125

Gly Gly Ser Gly Gly Gly Ser Gly Gly Gly Ser Gly Gly Gly Ser Gly
            130                 135                 140

Gly Gly Ser Gly Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
            165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
            195                 200                 205

Thr Thr Tyr Ser Asn Ser Leu Lys Asp Arg Phe Ser Ile Ser Glu Asp
            210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
                245                 250                 255

Val Val Pro Asp Tyr Trp Gly Gln Gly Thr Leu Val Thr Val Ser Ser
            260                 265                 270

Gly Ala Ala Asp Tyr Lys Asp His Asp Gly Asp Tyr Lys Asp His Asp
        275                 280                 285

Ile Asp Tyr Lys Asp Asp Asp Lys Gly Ala Ala His His His His
    290                 295                 300

His His
305

<210> SEQ ID NO 310
<211> LENGTH: 306
<212> TYPE: PRT
<213> ORGANISM: Artificial Sequence
<220> FEATURE:
<223> OTHER INFORMATION: Nanobody sequence

<400> SEQUENCE: 310

Glu Val Gln Leu Val Glu Ser Gly Gly Gly Leu Val Gln Pro Gly Gly
1               5                   10                  15

Ser Leu Arg Leu Ser Cys Ile Thr Ser Gly Glu Thr Phe Lys Ile Asn
            20                  25                  30

Ile Trp Gly Trp Tyr Arg Gln Ala Pro Gly Lys Gln Arg Glu Leu Val
        35                  40                  45

Ala Ser Leu Thr Ile Gly Gly Ala Thr Asp Tyr Ala Asp Ser Val Lys
    50                  55                  60

Gly Arg Phe Thr Ile Ser Glu Asp Ser Ala Lys Asn Thr Val Tyr Leu
65                  70                  75                  80

Gln Met Asn Ser Leu Lys Ala Glu Asp Thr Ala Val Tyr Phe Cys Asn
                85                  90                  95

Ala Lys Ser Arg Leu Tyr Pro Tyr Asp Tyr Trp Gly Gln Gly Thr Leu
            100                 105                 110

Val Thr Val Ser Ser Gly Gly Gly Gly Ser Gly Gly Gly Gly Ser Gly
            115                 120                 125

Gly Gly Gly Ser Gly Gly Gly Gly Ser Gly Gly Gly Gly Ser Gly Gly
        130                 135                 140

Gly Gly Ser Gly Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
                165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
        195                 200                 205

Thr Thr Tyr Ser Asn Ser Leu Lys Asp Arg Phe Ser Ile Ser Glu Asp
    210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
                245                 250                 255

Val Val Pro Asp Tyr Trp Gly Gln Gly Thr Leu Val Thr Val Ser Ser
            260                 265                 270

```
Gly Ala Ala Asp Tyr Lys Asp His Asp Gly Asp Tyr Lys Asp His Asp
            275                 280                 285

Ile Asp Tyr Lys Asp Asp Asp Lys Gly Ala Ala His His His His
            290                 295                 300

His His
305

<210> SEQ ID NO 311
<211> LENGTH: 306
<212> TYPE: PRT
<213> ORGANISM: Artificial Sequence
<220> FEATURE:
<223> OTHER INFORMATION: Nanobody sequence

<400> SEQUENCE: 311

Glu Val Gln Leu Val Glu Ser Gly Gly Gly Leu Val Gln Pro Gly Gly
1               5                   10                  15

Ser Leu Arg Leu Ser Cys Ala Ala Ser Gly Glu Val Tyr Lys Ile Asn
            20                  25                  30

Phe Leu Gly Trp Tyr Arg Gln Ala Pro Gly Lys Glu Arg Glu Lys Val
        35                  40                  45

Ala His Ile Thr Ile Ala Asp Ala Asp Tyr Ala Asp Phe Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Arg Pro Glu Asp Thr Ala Val Tyr Phe Cys Arg
                85                  90                  95

Ala Gly Ser Arg Ile Trp Pro Tyr Asp Tyr Trp Gly Gln Gly Thr Leu
            100                 105                 110

Val Thr Val Ser Ser Gly Gly Gly Ser Gly Gly Gly Gly Ser Gly
        115                 120                 125

Gly Gly Ser Gly Gly Gly Ser Gly Gly Gly Ser Gly Gly
            130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
                165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
            195                 200                 205

Thr Thr Tyr Ser Asn Ser Leu Lys Asp Arg Phe Ser Ile Ser Glu Asp
            210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
                245                 250                 255

Val Val Pro Asp Tyr Trp Gly Gln Gly Thr Leu Val Thr Val Ser Ser
            260                 265                 270

Gly Ala Ala Asp Tyr Lys Asp His Asp Gly Asp Tyr Lys Asp His Asp
            275                 280                 285

Ile Asp Tyr Lys Asp Asp Asp Lys Gly Ala Ala His His His His
            290                 295                 300

His His
305
```

<210> SEQ ID NO 312
<211> LENGTH: 306
<212> TYPE: PRT
<213> ORGANISM: Artificial Sequence
<220> FEATURE:
<223> OTHER INFORMATION: Nanobody sequence

<400> SEQUENCE: 312

```
Glu Val Gln Leu Val Glu Ser Gly Gly Leu Val Gln Pro Gly Gly
1               5                   10                  15

Ser Leu Arg Leu Ser Cys Val Ala Ser Gly Asp Val His Lys Ile Asn
            20                  25                  30

Phe Leu Gly Trp Tyr Arg Gln Ala Pro Gly Lys Glu Arg Glu Lys Val
            35                  40                  45

Ala His Ile Ser Ile Gly Asp Gln Thr Asp Tyr Ala Asp Ser Ala Lys
        50                  55                  60

Gly Arg Phe Thr Ile Ser Arg Asp Glu Ser Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Phe Ser Arg Ile Tyr Pro Tyr Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Ser Gly Gly Gly Gly Ser Gly Gly Gly Gly Ser Gly Gly
    130                 135                 140

Gly Gly Ser Gly Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
                165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
        195                 200                 205

Thr Thr Tyr Ser Asn Ser Leu Lys Asp Arg Phe Ser Ile Ser Glu Asp
    210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
                245                 250                 255

Val Val Pro Asp Tyr Trp Gly Gln Gly Thr Leu Val Thr Val Ser Ser
            260                 265                 270

Gly Ala Ala Asp Tyr Lys Asp His Asp Gly Asp Tyr Lys Asp His Asp
        275                 280                 285

Ile Asp Tyr Lys Asp Asp Asp Lys Gly Ala Ala His His His His
    290                 295                 300

His His
305
```

<210> SEQ ID NO 313
<211> LENGTH: 306
<212> TYPE: PRT
<213> ORGANISM: Artificial Sequence
<220> FEATURE:
<223> OTHER INFORMATION: Nanobody sequence

<400> SEQUENCE: 313

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Gly Arg Ile Asn
            20                  25                  30

Phe Tyr Arg Trp Tyr Arg Gln Ala Pro Gly Asn Gln Arg Glu Val Val
            35                  40                  45

Ala Thr Ile Thr Ile Ala Asp Lys Thr Asp Tyr Ala Asp Ser Ala Lys
50                  55                  60

Gly Arg Phe Thr Ile Ser Arg Asp Glu Ser Arg Asn Met Val Tyr Leu
65                  70                  75                  80

Gln Met Ser Ser Leu Lys Pro Glu Asp Thr Ala Val Tyr Phe Cys His
                85                  90                  95

Ala Gly Ser Arg Leu Tyr Pro Tyr Asp Tyr Trp Gly Gln Gly Thr Leu
            100                 105                 110

Val Thr Val Ser Ser Gly Gly Gly Ser Gly Gly Gly Ser Gly
        115                 120                 125

Gly Gly Ser Gly Gly Gly Ser Gly Gly Gly Ser Gly Gly
        130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
            165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
            195                 200                 205

Thr Thr Tyr Ser Asn Ser Leu Lys Asp Arg Phe Ser Ile Ser Glu Asp
            210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
                245                 250                 255

Val Val Pro Asp Tyr Trp Gly Gln Gly Thr Leu Val Thr Val Ser Ser
            260                 265                 270

Gly Ala Ala Asp Tyr Lys Asp His Asp Gly Asp Tyr Lys Asp His Asp
            275                 280                 285

Ile Asp Tyr Lys Asp Asp Asp Lys Gly Ala Ala His His His His
            290                 295                 300

His His
305

<210> SEQ ID NO 314
<211> LENGTH: 306
<212> TYPE: PRT
<213> ORGANISM: Artificial Sequence
<220> FEATURE:
<223> OTHER INFORMATION: Nanobody sequence

<400> SEQUENCE: 314

Glu Val Gln Leu Val Glu Ser Gly Gly Gly Leu Val Gln Pro Gly Gly
1               5                   10                  15

Ser Leu Arg Leu Ser Cys Val Ala Ser Gly Asp Val His Lys Ile Asn
            20                  25                  30

Phe Leu Gly Trp Tyr Arg Gln Ala Pro Gly Lys Glu Arg Glu Lys Val
            35                  40                  45
```

Ala His Ile Thr Ile Gly Asp Gln Ala Asp Tyr Ala Asp Ser Ala Lys
            50                  55                  60

Gly Arg Phe Thr Ile Ser Arg Asp Glu Ala Lys Asn Met Val Tyr Leu
 65                  70                  75                  80

Gln Met Asn Ser Leu Lys Pro Glu Asp Thr Ala Val Tyr Phe Cys Arg
                85                  90                  95

Ala Gly Ser Arg Ile Tyr Pro Tyr Asp Tyr Trp Gly Gln Gly Thr Leu
                100                 105                 110

Val Thr Val Ser Ser Gly Gly Gly Ser Gly Gly Gly Ser Gly
            115                 120                 125

Gly Gly Gly Ser Gly Gly Gly Ser Gly Gly Gly Ser Gly Gly
130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
                165                 170                 175

Ser Gly Gly Thr Phe Ser Ser Tyr Thr Met Gly Trp Phe Arg Gln Ala
                180                 185                 190

Pro Gly Lys Glu Arg Glu Phe Val Ala Glu Val Arg Trp Gly Val
                195                 200                 205

Thr Thr Tyr Ser Asn Ser Leu Lys Asp Arg Phe Ser Ile Ser Glu Asp
210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Arg Gln Met Tyr Met Thr
                245                 250                 255

Val Val Pro Asp Tyr Trp Gly Gln Gly Thr Leu Val Thr Val Ser Ser
                260                 265                 270

Gly Ala Ala Asp Tyr Lys Asp His Asp Gly Asp Tyr Lys Asp His Asp
                275                 280                 285

Ile Asp Tyr Lys Asp Asp Asp Lys Gly Ala Ala His His His His
                290                 295                 300

His His
305

<210> SEQ ID NO 315
<211> LENGTH: 306
<212> TYPE: PRT
<213> ORGANISM: Artificial Sequence
<220> FEATURE:
<223> OTHER INFORMATION: Nanobody sequence

<400> SEQUENCE: 315

Glu Val Gln Leu Val Glu Ser Gly Gly Gly Leu Val Gln Pro Gly Gly
 1               5                   10                  15

Ser Leu Arg Leu Ser Cys Ala Ala Ser Gly Asp Val His Lys Ile Asn
                20                  25                  30

Ile Leu Gly Trp Tyr Arg Gln Ala Pro Ala Lys Glu Arg Glu Met Val
                35                  40                  45

Ala His Ile Thr Ile Gly Asp Ala Thr Asp Tyr Ala Asp Ser Ala Lys
            50                  55                  60

Gly Arg Phe Thr Ile Ser Arg Asp Glu Ala Lys Asn Met Val Tyr Leu
 65                  70                  75                  80

Gln Met Asn Ser Leu Lys Pro Glu Asp Thr Ala Val Tyr Phe Cys Arg
                85                  90                  95

```
Ala Tyr Ser Arg Ile Tyr Pro Tyr Asn Tyr Trp Gly Gln Gly Thr Leu
            100                 105                 110

Val Thr Val Ser Ser Gly Gly Gly Ser Gly Gly Gly Gly Ser Gly
        115                 120                 125

Gly Gly Gly Ser Gly Gly Gly Ser Gly Gly Gly Ser Gly Gly
        130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
                165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
            195                 200                 205

Thr Thr Tyr Ser Asn Ser Leu Lys Asp Arg Phe Ser Ile Ser Glu Asp
210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
                245                 250                 255

Val Val Pro Asp Tyr Trp Gly Gln Gly Thr Leu Val Thr Val Ser Ser
            260                 265                 270

Gly Ala Ala Asp Tyr Lys Asp His Asp Gly Asp Tyr Lys Asp His Asp
                275                 280                 285

Ile Asp Tyr Lys Asp Asp Asp Lys Gly Ala Ala His His His His
            290                 295                 300

His His
305

<210> SEQ ID NO 316
<211> LENGTH: 306
<212> TYPE: PRT
<213> ORGANISM: Artificial Sequence
<220> FEATURE:
<223> OTHER INFORMATION: Nanobody sequence

<400> SEQUENCE: 316

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Lys Ile Asn
            20                  25                  30

Phe Leu Gly Trp Tyr Arg Gln Ala Pro Gly Lys Glu Arg Glu Leu Val
        35                  40                  45

Ala Thr Ile Thr Ile Gly Asp Thr Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Gly Ser Arg Leu Tyr Pro Tyr Asn Tyr Trp Gly Gln Gly Thr Leu
            100                 105                 110

Val Thr Val Ser Ser Gly Gly Gly Ser Gly Gly Gly Gly Ser Gly
        115                 120                 125

Gly Gly Gly Ser Gly Gly Gly Ser Gly Gly Gly Ser Gly Gly
        130                 135                 140
```

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
                165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
        195                 200                 205

Thr Thr Tyr Ser Asn Ser Leu Lys Asp Arg Phe Ser Ile Ser Glu Asp
    210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
                245                 250                 255

Val Val Pro Asp Tyr Trp Gly Gln Gly Thr Leu Val Thr Val Ser Ser
            260                 265                 270

Gly Ala Ala Asp Tyr Lys Asp His Asp Gly Asp Tyr Lys Asp His Asp
        275                 280                 285

Ile Asp Tyr Lys Asp Asp Asp Asp Lys Gly Ala Ala His His His His
    290                 295                 300

His His
305

<210> SEQ ID NO 317
<211> LENGTH: 306
<212> TYPE: PRT
<213> ORGANISM: Artificial Sequence
<220> FEATURE:
<223> OTHER INFORMATION: Nanobody sequence

<400> SEQUENCE: 317

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Lys Ile Asn
            20                  25                  30

Phe Leu Gly Trp Tyr Arg Gln Ala Pro Gly Lys Glu Arg Gly Leu Val
        35                  40                  45

Ala Thr Ile Thr Ile Gly Asp Thr Thr Asp Tyr Ala Asp Tyr Ala Lys
    50                  55                  60

Gly Arg Phe Thr Ile Ser Arg Asp Glu Ala Arg Asn Met Val Tyr Leu
65                  70                  75                  80

Gln Met Asn Ser Leu Lys Pro Glu Asp Thr Ala Val Tyr Phe Cys Arg
            85                  90                  95

Ala Gly Ser Arg Leu Tyr Pro Tyr Asn Tyr Trp Gly Gln Gly Thr Leu
        100                 105                 110

Val Thr Val Ser Ser Gly Gly Gly Gly Ser Gly Gly Gly Gly Ser Gly
    115                 120                 125

Gly Gly Ser Gly Gly Gly Gly Ser Gly Gly Gly Gly Ser Gly Gly
        130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
                165                 170                 175

Ser Gly Gly Thr Phe Ser Ser Tyr Thr Met Gly Trp Phe Arg Gln Ala
            180                 185                 190

```
Pro Gly Lys Glu Arg Glu Phe Val Ala Glu Val Arg Trp Gly Gly Val
        195                 200                 205

Thr Thr Tyr Ser Asn Ser Leu Lys Asp Arg Phe Ser Ile Ser Glu Asp
210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Arg Gln Met Tyr Met Thr
                245                 250                 255

Val Val Pro Asp Tyr Trp Gly Gln Gly Thr Leu Val Thr Val Ser Ser
                260                 265                 270

Gly Ala Ala Asp Tyr Lys Asp His Asp Gly Asp Tyr Lys Asp His Asp
                275                 280                 285

Ile Asp Tyr Lys Asp Asp Asp Lys Gly Ala Ala His His His His
            290                 295                 300

His His
305

<210> SEQ ID NO 318
<211> LENGTH: 306
<212> TYPE: PRT
<213> ORGANISM: Artificial Sequence
<220> FEATURE:
<223> OTHER INFORMATION: Nanobody sequence

<400> SEQUENCE: 318

Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Val His Lys Ile Asn
            20                  25                  30

Ile Leu Gly Trp Tyr Arg Gln Ala Pro Ala Lys Glu Arg Glu Met Val
        35                  40                  45

Ala His Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Leu Cys Arg
                85                  90                  95

Ala Tyr Ser Arg Ile Tyr Pro Tyr Asn Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Ser Gly Gly Gly Gly Ser Gly Gly Gly Ser Gly Gly
    130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
                165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
        195                 200                 205

Thr Thr Tyr Ser Asn Ser Leu Lys Asp Arg Phe Ser Ile Ser Glu Asp
    210                 215                 220

Ser Val Lys Asn Ala Val Tyr Leu Gln Met Asn Ser Leu Lys Pro Glu
225                 230                 235                 240
```

```
Asp Thr Ala Val Tyr Tyr Cys Ala Ala Val Arg Gln Met Tyr Met Thr
                245                 250                 255

Val Val Pro Asp Tyr Trp Gly Gln Gly Thr Leu Val Thr Val Ser Ser
            260                 265                 270

Gly Ala Ala Asp Tyr Lys Asp His Asp Gly Asp Tyr Lys Asp His Asp
        275                 280                 285

Ile Asp Tyr Lys Asp Asp Asp Lys Gly Ala Ala His His His His
    290                 295                 300

His His
305

<210> SEQ ID NO 319
<211> LENGTH: 306
<212> TYPE: PRT
<213> ORGANISM: Artificial Sequence
<220> FEATURE:
<223> OTHER INFORMATION: Nanobody sequence

<400> SEQUENCE: 319

Glu Val Gln Leu Val Glu Ser Gly Gly Gly Leu Val Gln Pro Gly Gly
1               5                   10                  15

Ser Leu Arg Leu Ser Cys Thr Phe Ser Gly Thr Phe Ser Ser Tyr
            20                  25                  30

Thr Met Gly Trp Phe Arg Gln Ala Pro Gly Lys Glu Arg Glu Phe Val
            35                  40                  45

Ala Glu Val Arg Trp Gly Gly Val Thr Thr Tyr Ser Asn Ser Leu Lys
        50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Ser Gly Gly Gly Ser Gly Gly Gly
    130                 135                 140

Ser Gly Gly Gly Ser Gly Gly Gly Ser Glu Val Gln Leu Val
145                 150                 155                 160

Glu Ser Gly Gly Gly Leu Val Gln Pro Gly Gly Ser Leu Arg Leu Ser
            165                 170                 175

Cys Val Ala Ser Gly Asp Val His Lys Ile Asn Phe Leu Gly Trp Tyr
            180                 185                 190

Arg Gln Ala Pro Gly Lys Glu Arg Glu Lys Val Ala His Ile Ser Ile
            195                 200                 205

Gly Asp Gln Thr Asp Tyr Ala Asp Ser Ala Lys Gly Arg Phe Thr Ile
        210                 215                 220

Ser Arg Asp Glu Ser Lys Asn Met Val Tyr Leu Gln Met Asn Ser Leu
225                 230                 235                 240

Lys Pro Glu Asp Thr Ala Val Tyr Phe Cys Arg Ala Phe Ser Arg Ile
            245                 250                 255

Tyr Pro Tyr Asp Tyr Trp Gly Gln Gly Thr Leu Val Thr Val Ser Ser
            260                 265                 270

Gly Ala Ala Asp Tyr Lys Asp His Asp Gly Asp Tyr Lys Asp His Asp
        275                 280                 285
```

```
Ile Asp Tyr Lys Asp Asp Asp Lys Gly Ala Ala His His His His
        290                 295                 300
His His
305

<210> SEQ ID NO 320
<211> LENGTH: 306
<212> TYPE: PRT
<213> ORGANISM: Artificial Sequence
<220> FEATURE:
<223> OTHER INFORMATION: Nanobody sequence

<400> SEQUENCE: 320

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Ser Gly Gly Gly Ser Gly Gly Gly Gly
    130                 135                 140

Ser Gly Gly Gly Ser Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Glu Ile Gly Arg Ile Asn Phe Tyr Arg Trp Tyr
            180                 185                 190

Arg Gln Ala Pro Gly Asn Gln Arg Glu Val Val Ala Thr Ile Thr Ile
        195                 200                 205

Ala Asp Lys Thr Asp Tyr Ala Asp Ser Ala Lys Gly Arg Phe Thr Ile
    210                 215                 220

Ser Arg Asp Glu Ser Arg Asn Met Val Tyr Leu Gln Met Ser Ser Leu
225                 230                 235                 240

Lys Pro Glu Asp Thr Ala Val Tyr Phe Cys His Ala Gly Ser Arg Leu
                245                 250                 255

Tyr Pro Tyr Asp Tyr Trp Gly Gln Gly Thr Leu Val Thr Val Ser Ser
            260                 265                 270

Gly Ala Ala Asp Tyr Lys Asp His Asp Gly Asp Tyr Lys Asp His Asp
        275                 280                 285

Ile Asp Tyr Lys Asp Asp Asp Lys Gly Ala Ala His His His His
    290                 295                 300

His His
305

<210> SEQ ID NO 321
```

<211> LENGTH: 306
<212> TYPE: PRT
<213> ORGANISM: Artificial Sequence
<220> FEATURE:
<223> OTHER INFORMATION: Nanobody sequence

<400> SEQUENCE: 321

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Ser Gly Gly Gly Ser Gly Gly Gly Gly
    130                 135                 140

Ser Gly Gly Gly Ser Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Val Ala Ser Gly Asp Val His Lys Ile Asn Phe Leu Gly Trp Tyr
            180                 185                 190

Arg Gln Ala Pro Gly Lys Glu Arg Glu Lys Val Ala His Ile Thr Ile
        195                 200                 205

Gly Asp Gln Ala Asp Tyr Ala Asp Ser Ala Lys Gly Arg Phe Thr Ile
    210                 215                 220

Ser Arg Asp Glu Ala Lys Asn Met Val Tyr Leu Gln Met Asn Ser Leu
225                 230                 235                 240

Lys Pro Glu Asp Thr Ala Val Tyr Phe Cys Arg Ala Gly Ser Arg Ile
                245                 250                 255

Tyr Pro Tyr Asp Tyr Trp Gly Gln Gly Thr Leu Val Thr Val Ser Ser
            260                 265                 270

Gly Ala Ala Asp Tyr Lys Asp His Asp Gly Asp Tyr Lys Asp His Asp
        275                 280                 285

Ile Asp Tyr Lys Asp Asp Asp Lys Gly Ala Ala His His His His
    290                 295                 300

His His
305

<210> SEQ ID NO 322
<211> LENGTH: 306
<212> TYPE: PRT
<213> ORGANISM: Artificial Sequence
<220> FEATURE:
<223> OTHER INFORMATION: Nanobody sequence

<400> SEQUENCE: 322

Glu Val Gln Leu Val Glu Ser Gly Gly Gly Leu Val Gln Pro Gly Gly

```
  1               5                  10                 15
Ser Leu Arg Leu Ser Cys Thr Phe Ser Gly Gly Thr Phe Ser Ser Tyr
            20                  25                 30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly Gly
        115                 120                 125

Gly Ser Gly Gly Gly Ser Gly Gly Gly Ser Gly Gly Gly Gly
    130                 135                 140

Ser Gly Gly Gly Gly Ser Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Asp Val His Lys Ile Asn Ile Leu Gly Trp Tyr
            180                 185                 190

Arg Gln Ala Pro Ala Lys Glu Arg Glu Met Val Ala His Ile Thr Ile
        195                 200                 205

Gly Asp Ala Thr Asp Tyr Ala Asp Ser Ala Lys Gly Arg Phe Thr Ile
    210                 215                 220

Ser Arg Asp Glu Ala Lys Asn Met Val Tyr Leu Gln Met Asn Ser Leu
225                 230                 235                 240

Lys Pro Glu Asp Thr Ala Val Tyr Phe Cys Arg Ala Tyr Ser Arg Ile
                245                 250                 255

Tyr Pro Tyr Asn Tyr Trp Gly Gln Gly Thr Leu Val Thr Val Ser Ser
            260                 265                 270

Gly Ala Ala Asp Tyr Lys Asp His Asp Gly Asp Tyr Lys Asp His Asp
        275                 280                 285

Ile Asp Tyr Lys Asp Asp Asp Lys Gly Ala Ala His His His His
    290                 295                 300

His His
305

<210> SEQ ID NO 323
<211> LENGTH: 306
<212> TYPE: PRT
<213> ORGANISM: Artificial Sequence
<220> FEATURE:
<223> OTHER INFORMATION: Nanobody sequence

<400> SEQUENCE: 323

Glu Val Gln Leu Val Glu Ser Gly Gly Gly Leu Val Gln Pro Gly Gly
1               5                  10                 15

Ser Leu Arg Leu Ser Cys Thr Phe Ser Gly Gly Thr Phe Ser Ser Tyr
            20                  25                 30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
```

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Ser Gly Gly Gly Ser Gly Gly Gly
    130                 135                 140

Ser Gly Gly Gly Ser Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Ser Val His Lys Ile Asn Phe Leu Gly Trp Tyr
            180                 185                 190

Arg Gln Ala Pro Gly Lys Glu Arg Glu Leu Val Ala Thr Ile Thr Ile
        195                 200                 205

Gly Asp Thr Thr Asp Tyr Ala Asp Ser Ala Lys Gly Arg Phe Thr Ile
210                 215                 220

Ser Arg Asp Glu Ala Lys Asn Met Val Tyr Leu Gln Met Asn Ser Leu
225                 230                 235                 240

Lys Pro Glu Asp Thr Ala Val Tyr Phe Cys Arg Ala Gly Ser Arg Leu
                245                 250                 255

Tyr Pro Tyr Asn Tyr Trp Gly Gln Gly Thr Leu Val Thr Val Ser Ser
            260                 265                 270

Gly Ala Ala Asp Tyr Lys Asp His Asp Gly Asp Tyr Lys Asp His Asp
        275                 280                 285

Ile Asp Tyr Lys Asp Asp Asp Lys Gly Ala Ala His His His His
    290                 295                 300

His His
305

<210> SEQ ID NO 324
<211> LENGTH: 306
<212> TYPE: PRT
<213> ORGANISM: Artificial Sequence
<220> FEATURE:
<223> OTHER INFORMATION: Nanobody sequence

<400> SEQUENCE: 324

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln

```
                100               105               110
Gly Thr Leu Val Thr Val Ser Ser Gly Gly Gly Ser Gly Gly Gly
            115               120               125
Gly Ser Gly Gly Gly Ser Gly Gly Gly Ser Gly Gly Gly
130               135               140
Ser Gly Gly Gly Ser Gly Gly Gly Ser Glu Val Gln Leu Val
145               150               155               160
Glu Ser Gly Gly Leu Val Gln Pro Gly Gly Ser Leu Arg Leu Ser
            165               170               175
Cys Ala Ala Ser Gly Ser Val His Lys Ile Asn Phe Leu Gly Trp Tyr
            180               185               190
Arg Gln Ala Pro Gly Lys Glu Arg Gly Leu Val Ala Thr Ile Thr Ile
            195               200               205
Gly Asp Thr Thr Asp Tyr Ala Asp Tyr Ala Lys Gly Arg Phe Thr Ile
            210               215               220
Ser Arg Asp Glu Ala Arg Asn Met Val Tyr Leu Gln Met Asn Ser Leu
225               230               235               240
Lys Pro Glu Asp Thr Ala Val Tyr Phe Cys Arg Ala Gly Ser Arg Leu
            245               250               255
Tyr Pro Tyr Asn Tyr Trp Gly Gln Gly Thr Leu Val Thr Val Ser Ser
            260               265               270
Gly Ala Ala Asp Tyr Lys Asp His Asp Gly Asp Tyr Lys Asp His Asp
            275               280               285
Ile Asp Tyr Lys Asp Asp Asp Lys Gly Ala Ala His His His His
            290               295               300
His His
305

<210> SEQ ID NO 325
<211> LENGTH: 306
<212> TYPE: PRT
<213> ORGANISM: Artificial Sequence
<220> FEATURE:
<223> OTHER INFORMATION: Nanobody sequence

<400> SEQUENCE: 325

Glu Val Gln Leu Val Glu Ser Gly Gly Gly Leu Val Gln Pro Gly Gly
1               5                   10                  15
Ser Leu Arg Leu Ser Cys Thr Phe Ser Gly Gly Thr Phe Ser Ser Tyr
                20                  25                  30
Thr Met Gly Trp Phe Arg Gln Ala Pro Gly Lys Glu Arg Glu Phe Val
            35                  40                  45
Ala Glu Val Arg Trp Gly Gly Val Thr Thr Tyr Ser Asn Ser Leu Lys
        50                  55                  60
Asp Arg Phe Ser Ile Ser Glu Asp Ser Val Lys Asn Ala Val Tyr Leu
65                  70                  75                  80
Gln Met Asn Ser Leu Lys Pro Glu Asp Thr Ala Val Tyr Tyr Cys Ala
                85                  90                  95
Ala Val Arg Gln Met Tyr Met Thr Val Val Pro Asp Tyr Trp Gly Gln
            100                 105                 110
Gly Thr Leu Val Thr Val Ser Ser Gly Gly Gly Ser Gly Gly Gly
            115                 120                 125
Gly Ser Gly Gly Gly Gly Ser Gly Gly Gly Ser Gly Gly Gly Gly
130                 135                 140
Ser Gly Gly Gly Gly Ser Gly Gly Gly Gly Ser Glu Val Gln Leu Val
```

```
145                 150                 155                 160
Glu Ser Gly Gly Gly Leu Val Gln Pro Gly Gly Ser Leu Arg Leu Ser
                165                 170                 175
Cys Ala Ala Ser Gly Asp Val Tyr Lys Ile Asn Phe Leu Gly Trp His
                180                 185                 190
Arg Gln Ala Pro Gly Lys Glu Arg Glu Lys Val Ala His Ile Thr Ile
                195                 200                 205
Gly Asp Ala Thr Asp Tyr Ala Asp Ser Ala Lys Gly Arg Phe Thr Ile
    210                 215                 220
Ser Arg Asp Glu Ala Lys Asn Met Val Tyr Leu Gln Met Asn Ser Leu
225                 230                 235                 240
Lys Pro Glu Asp Thr Ala Val Tyr Phe Cys Arg Ala Gly Ser Arg Ile
                245                 250                 255
Tyr Pro Tyr Asp Tyr Trp Gly Gln Gly Thr Leu Val Thr Val Ser Ser
                260                 265                 270
Gly Ala Ala Asp Tyr Lys Asp His Asp Gly Asp Tyr Lys Asp His Asp
                275                 280                 285
Ile Asp Tyr Lys Asp Asp Asp Lys Gly Ala Ala His His His His
    290                 295                 300
His His
305

<210> SEQ ID NO 326
<211> LENGTH: 306
<212> TYPE: PRT
<213> ORGANISM: Artificial Sequence
<220> FEATURE:
<223> OTHER INFORMATION: Nanobody sequence

<400> SEQUENCE: 326

Glu Val Gln Leu Val Glu Ser Gly Gly Gly Leu Val Gln Pro Gly Gly
1               5                   10                  15
Ser Leu Arg Leu Ser Cys Thr Phe Ser Gly Gly Thr Phe Ser Ser Tyr
                20                  25                  30
Thr Met Gly Trp Phe Arg Gln Ala Pro Gly Lys Glu Arg Glu Phe Val
                35                  40                  45
Ala Glu Val Arg Trp Gly Gly Val Thr Thr Tyr Ser Asn Ser Leu Lys
    50                  55                  60
Asp Arg Phe Ser Ile Ser Glu Asp Ser Val Lys Asn Ala Val Tyr Leu
65                  70                  75                  80
Gln Met Asn Ser Leu Lys Pro Glu Asp Thr Ala Val Tyr Tyr Cys Ala
                85                  90                  95
Ala Val Arg Gln Met Tyr Met Thr Val Val Pro Asp Tyr Trp Gly Gln
                100                 105                 110
Gly Thr Leu Val Thr Val Ser Ser Gly Gly Gly Gly Ser Gly Gly Gly
                115                 120                 125
Gly Ser Gly Gly Gly Gly Ser Gly Gly Gly Gly Ser Gly Gly Gly Gly
    130                 135                 140
Ser Gly Gly Gly Gly Ser Gly Gly Gly Gly Ser Glu Val Gln Leu Val
145                 150                 155                 160
Glu Ser Gly Gly Gly Leu Val Gln Pro Gly Gly Ser Leu Arg Leu Ser
                165                 170                 175
Cys Ala Ala Ser Gly Glu Val Tyr Lys Ile Asn Phe Leu Gly Trp Tyr
                180                 185                 190
Arg Gln Ala Pro Gly Lys Glu Arg Glu Lys Val Ala His Ile Thr Ile
```

```
            195                 200                 205
Ala Asp Ala Asp Tyr Ala Asp Phe Ala Lys Gly Arg Phe Thr Ile
    210                 215                 220

Ser Arg Asp Glu Ala Lys Asn Met Val Tyr Leu Gln Met Asn Ser Leu
225                 230                 235                 240

Arg Pro Glu Asp Thr Ala Val Tyr Phe Cys Arg Ala Gly Ser Arg Ile
                245                 250                 255

Trp Pro Tyr Asp Tyr Trp Gly Gln Gly Thr Leu Val Thr Val Ser Ser
                260                 265                 270

Gly Ala Ala Asp Tyr Lys Asp His Asp Gly Asp Tyr Lys Asp His Asp
                275                 280                 285

Ile Asp Tyr Lys Asp Asp Asp Lys Gly Ala Ala His His His His
                290                 295                 300

His His
305

<210> SEQ ID NO 327
<211> LENGTH: 306
<212> TYPE: PRT
<213> ORGANISM: Artificial Sequence
<220> FEATURE:
<223> OTHER INFORMATION: Nanobody sequence

<400> SEQUENCE: 327

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
                20                  25                  30

Thr Met Gly Trp Phe Arg Gln Ala Pro Gly Lys Glu Arg Glu Phe Val
                35                  40                  45

Ala Glu Val Arg Trp Gly Gly Val Thr Thr Tyr Ser Asn Ser Leu Lys
            50                  55                  60

Asp Arg Phe Ser Ile Ser Glu Asp Ser Val Lys Asn Ala Val Tyr Leu
65              70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
                100                 105                 110

Gly Thr Leu Val Thr Val Ser Ser Gly Gly Gly Gly Ser Gly Gly Gly
                115                 120                 125

Gly Ser Gly Gly Gly Gly Ser Gly Gly Gly Gly Ser Gly Gly Gly Gly
            130                 135                 140

Ser Gly Gly Gly Gly Ser Gly Gly Gly Gly Ser Glu Val Gln Leu Val
145                 150                 155                 160

Glu Ser Gly Gly Asp Leu Val Gln Pro Gly Gly Ser Leu Arg Leu Ser
                165                 170                 175

Cys Ala Ala Ser Gly Asp Val His Lys Ile Asn Phe Leu Gly Trp Tyr
                180                 185                 190

Arg Gln Ala Pro Gly Lys Glu Arg Glu Met Val Ala His Ile Thr Ile
                195                 200                 205

Ala Asp Ala Thr Asp Tyr Ala Glu Phe Ala Lys Gly Arg Phe Thr Ile
                210                 215                 220

Ser Arg Asp Glu Pro Lys Asn Met Val Tyr Leu Gln Met Asn Ser Leu
225                 230                 235                 240

Lys Pro Glu Asp Thr Ala Val Tyr Leu Cys Arg Ala Gly Ser Arg Ile
```

```
                    245                 250                 255
Tyr Pro Tyr Asn Tyr Trp Gly Gln Gly Thr Leu Val Thr Val Ser Ser
                260                 265                 270
Gly Ala Ala Asp Tyr Lys Asp His Asp Gly Asp Tyr Lys Asp His Asp
            275                 280                 285
Ile Asp Tyr Lys Asp Asp Asp Asp Lys Gly Ala Ala His His His His
        290                 295                 300
His His
305

<210> SEQ ID NO 328
<211> LENGTH: 306
<212> TYPE: PRT
<213> ORGANISM: Artificial Sequence
<220> FEATURE:
<223> OTHER INFORMATION: Nanobody sequence

<400> SEQUENCE: 328

Glu Val Gln Leu Val Glu Ser Gly Gly Gly Leu Val Gln Pro Gly Gly
1               5                   10                  15
Ser Leu Arg Leu Ser Cys Thr Phe Ser Gly Gly Thr Phe Ser Ser Tyr
            20                  25                  30
Thr Met Gly Trp Phe Arg Gln Ala Pro Gly Lys Glu Arg Glu Phe Val
        35                  40                  45
Ala Glu Val Arg Trp Gly Gly Val Thr Thr Tyr Ser Asn Ser Leu Lys
    50                  55                  60
Asp Arg Phe Ser Ile Ser Glu Asp Ser Val Lys Asn Ala Val Tyr Leu
65                  70                  75                  80
Gln Met Asn Ser Leu Lys Pro Glu Asp Thr Ala Val Tyr Tyr Cys Ala
                85                  90                  95
Ala Val Arg Gln Met Tyr Met Thr Val Val Pro Asp Tyr Trp Gly Gln
            100                 105                 110
Gly Thr Leu Val Thr Val Ser Ser Gly Gly Gly Ser Gly Gly Gly Gly
        115                 120                 125
Gly Ser Gly Gly Gly Gly Ser Gly Gly Gly Ser Gly Gly Gly Gly
    130                 135                 140
Ser Gly Gly Gly Gly Ser Gly Gly Gly Ser Glu Val Gln Leu Val
145                 150                 155                 160
Glu Ser Gly Gly Gly Leu Val Gln Pro Gly Gly Ser Leu Arg Leu Ser
                165                 170                 175
Cys Ile Thr Ser Gly Glu Thr Phe Lys Ile Asn Ile Trp Gly Trp Tyr
            180                 185                 190
Arg Gln Ala Pro Gly Lys Gln Arg Glu Leu Val Ala Ser Leu Thr Ile
        195                 200                 205
Gly Gly Ala Thr Asn Tyr Ala Asp Ser Val Lys Gly Arg Phe Thr Ile
    210                 215                 220
Ser Glu Asp Ser Ala Lys Asn Thr Val Tyr Leu Gln Met Asn Ser Leu
225                 230                 235                 240
Lys Pro Glu Asp Thr Ala Val Tyr Phe Cys Asn Ala Lys Ser Arg Leu
                245                 250                 255
Tyr Pro Tyr Asp Tyr Trp Gly Gln Gly Thr Leu Val Thr Val Ser Ser
            260                 265                 270
Gly Ala Ala Asp Tyr Lys Asp His Asp Gly Asp Tyr Lys Asp His Asp
        275                 280                 285
Ile Asp Tyr Lys Asp Asp Asp Asp Lys Gly Ala Ala His His His His
```

```
                290                 295                 300

His His
305

<210> SEQ ID NO 329
<211> LENGTH: 306
<212> TYPE: PRT
<213> ORGANISM: Artificial Sequence
<220> FEATURE:
<223> OTHER INFORMATION: Nanobody sequence

<400> SEQUENCE: 329

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Val Thr Thr Tyr Ser Asn Ser Leu Lys
50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Ser Val His Leu Leu Asn Phe Leu Gly Trp Tyr
            180                 185                 190

Arg Gln Ala Pro Gly Lys Glu Arg Glu Met Val Ala His Ile Thr Ile
        195                 200                 205

Ala Asp Ala Thr Asp Tyr Ala His Phe Ala Lys Gly Arg Phe Thr Ile
    210                 215                 220

Ser Arg Asp Glu Ala Lys Asn Met Val Tyr Leu Gln Met Asn Ser Leu
225                 230                 235                 240

Arg Pro Glu Asp Thr Ala Val Tyr Phe Cys Arg Ala Gly Ser Arg Ile
                245                 250                 255

Tyr Pro Tyr Asp Tyr Trp Gly Gln Gly Thr Leu Val Thr Val Ser Ser
            260                 265                 270

Gly Ala Ala Asp Tyr Lys Asp His Asp Gly Asp Tyr Lys Asp His Asp
        275                 280                 285

Ile Asp Tyr Lys Asp Asp Asp Lys Gly Ala Ala His His His His
    290                 295                 300

His His
305

<210> SEQ ID NO 330
<211> LENGTH: 306
<212> TYPE: PRT
```

<213> ORGANISM: Artificial Sequence
<220> FEATURE:
<223> OTHER INFORMATION: Nanobody sequence

<400> SEQUENCE: 330

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Thr | Phe | Ser | Gly | Thr | Phe | Ser | Ser | Tyr | |
| | | | 20 | | | | | 25 | | | | | 30 | | |
| Thr | Met | Gly | Trp | Phe | Arg | Gln | Ala | Pro | Gly | Lys | Glu | Arg | Glu | Phe | Val |
| | | 35 | | | | | 40 | | | | | 45 | | | |
| Ala | Glu | Val | Arg | Trp | Gly | Gly | Val | Thr | Thr | Tyr | Ser | Asn | Ser | Leu | Lys |
| 50 | | | | | 55 | | | | | 60 | | | | | |
| Asp | Arg | Phe | Ser | Ile | Ser | Glu | Asp | Ser | Val | Lys | Asn | Ala | Val | Tyr | Leu |
| 65 | | | | | 70 | | | | | 75 | | | | | 80 |
| Gln | Met | Asn | Ser | Leu | Lys | Pro | Glu | Asp | Thr | Ala | Val | Tyr | Tyr | Cys | Ala |
| | | | | 85 | | | | | 90 | | | | | 95 | |
| Ala | Val | Arg | Gln | Met | Tyr | Met | Thr | Val | Val | Pro | Asp | Tyr | Trp | Gly | Gln |
| | | | 100 | | | | | 105 | | | | | 110 | | |
| Gly | Thr | Leu | Val | Thr | Val | Ser | Ser | Gly | Gly | Gly | Gly | Ser | Gly | Gly | Gly |
| | | | 115 | | | | | 120 | | | | | 125 | | |
| Gly | Ser | Gly | Gly | Gly | Gly | Ser | Gly | Gly | Gly | Ser | Gly | Gly | Gly | Gly | |
| 130 | | | | | 135 | | | | | 140 | | | | | |
| Ser | Gly | Gly | Gly | Gly | Ser | Gly | Gly | Gly | Ser | Glu | Val | Gln | Leu | Val | |
| 145 | | | | | 150 | | | | | 155 | | | | | 160 |
| Glu | Ser | Gly | Gly | Gly | Leu | Val | Gln | Pro | Gly | Gly | Ser | Leu | Arg | Leu | Ser |
| | | | | 165 | | | | | 170 | | | | | 175 | |
| Cys | Ile | Thr | Ser | Gly | Glu | Thr | Phe | Lys | Ile | Asn | Ile | Trp | Gly | Trp | Tyr |
| | | | 180 | | | | | 185 | | | | | 190 | | |
| Arg | Gln | Ala | Pro | Gly | Lys | Gln | Arg | Glu | Leu | Val | Ala | Ser | Leu | Thr | Ile |
| | | | 195 | | | | | 200 | | | | | 205 | | |
| Gly | Gly | Ala | Thr | Asp | Tyr | Ala | Asp | Ser | Val | Lys | Gly | Arg | Phe | Thr | Ile |
| | | 210 | | | | | 215 | | | | | 220 | | | |
| Ser | Glu | Asp | Ser | Ala | Lys | Asn | Thr | Val | Tyr | Leu | Gln | Met | Asn | Ser | Leu |
| 225 | | | | | 230 | | | | | 235 | | | | | 240 |
| Lys | Ala | Glu | Asp | Thr | Ala | Val | Tyr | Phe | Cys | Asn | Ala | Lys | Ser | Arg | Leu |
| | | | | 245 | | | | | 250 | | | | | 255 | |
| Tyr | Pro | Tyr | Asp | Tyr | Trp | Gly | Gln | Gly | Thr | Leu | Val | Thr | Val | Ser | Ser |
| | | | 260 | | | | | 265 | | | | | 270 | | |
| Gly | Ala | Ala | Asp | Tyr | Lys | Asp | His | Asp | Gly | Asp | Tyr | Lys | Asp | His | Asp |
| | | | 275 | | | | | 280 | | | | | 285 | | |
| Ile | Asp | Tyr | Lys | Asp | Asp | Asp | Asp | Lys | Gly | Ala | Ala | His | His | His | His |
| | | | 290 | | | | | 295 | | | | | 300 | | |
| His | His | | | | | | | | | | | | | | |
| 305 | | | | | | | | | | | | | | | |

<210> SEQ ID NO 331
<211> LENGTH: 306
<212> TYPE: PRT
<213> ORGANISM: Artificial Sequence
<220> FEATURE:
<223> OTHER INFORMATION: Nanobody sequence

<400> SEQUENCE: 331

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |

Ser Leu Arg Leu Ser Cys Ala Ala Ser Gly Asp Val His Lys Ile Asn
            20                  25                  30

Ile Leu Gly Trp Tyr Arg Gln Ala Pro Ala Lys Glu Arg Glu Met Val
                35                  40                  45

Ala His Ile Thr Ile Gly Asp Ala Thr Ser Tyr Ala Asp Ser Ala Lys
 50                  55                  60

Gly Arg Phe Thr Ile Ser Arg Asp Glu Ala Lys Asn Met Val Tyr Leu
 65                  70                  75                  80

Gln Leu Asn Asn Leu Lys Pro Glu Asp Thr Ala Val Tyr Phe Cys Arg
                85                  90                  95

Ala Tyr Ser Arg Ile Tyr Pro Tyr Asn Tyr Trp Gly Gln Gly Thr Leu
            100                 105                 110

Val Thr Val Ser Ser Gly Gly Gly Ser Gly Gly Gly Ser Gly
            115                 120                 125

Gly Gly Gly Ser Gly Gly Gly Ser Gly Gly Gly Ser Gly Gly
        130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
                165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
                195                 200                 205

Thr Thr Tyr Ser Asn Ser Leu Lys Asp Arg Phe Ser Ile Ser Glu Asp
 210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
                245                 250                 255

Val Val Pro Asp Tyr Trp Gly Gln Gly Thr Leu Val Thr Val Ser Ser
            260                 265                 270

Gly Ala Ala Asp Tyr Lys Asp His Asp Gly Asp Tyr Lys Asp His Asp
            275                 280                 285

Ile Asp Tyr Lys Asp Asp Asp Lys Gly Ala Ala His His His His
        290                 295                 300

His His
305

<210> SEQ ID NO 332
<211> LENGTH: 306
<212> TYPE: PRT
<213> ORGANISM: Artificial Sequence
<220> FEATURE:
<223> OTHER INFORMATION: Nanobody sequence

<400> SEQUENCE: 332

Glu Val Gln Leu Val Glu Ser Gly Gly Gly Leu Val Gln Pro Gly Gly
 1               5                   10                  15

Ser Leu Arg Leu Ser Cys Val Ala Ser Gly Asp Val His Lys Ile Asn
            20                  25                  30

Phe Leu Gly Trp Tyr Arg Gln Ala Pro Gly Lys Glu Arg Glu Lys Val
                35                  40                  45

Ala His Ile Ser Ile Gly Asp Gln Thr Asp Tyr Ala Asp Ser Ala Lys
 50                  55                  60

Gly Arg Phe Thr Ile Ser Arg Asp Glu Ser Lys Asn Met Val Tyr Leu
65                  70                  75                  80

Gln Met Asn Ser Leu Lys Pro Glu Asp Thr Ala Val Tyr Phe Cys Arg
            85                  90                  95

Ala Phe Ser Arg Ile Tyr Pro Tyr Asp Tyr Trp Gly Gln Gly Thr Leu
            100                 105                 110

Val Thr Val Ser Ser Gly Gly Gly Ser Gly Gly Gly Ser Gly
        115                 120                 125

Gly Gly Gly Ser Gly Gly Gly Ser Gly Gly Gly Ser Gly Gly
    130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
            165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Val
        195                 200                 205

Thr Thr Tyr Ser Asn Ser Leu Lys Asp Arg Phe Ser Ile Ser Glu Asp
210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
                245                 250                 255

Val Val Pro Asp Tyr Trp Gly Gln Gly Thr Leu Val Thr Val Ser Ser
        260                 265                 270

Gly Ala Ala Asp Tyr Lys Asp His Asp Gly Asp Tyr Lys Asp His Asp
        275                 280                 285

Ile Asp Tyr Lys Asp Asp Asp Lys Gly Ala Ala His His His
    290                 295                 300

His His
305

<210> SEQ ID NO 333
<211> LENGTH: 306
<212> TYPE: PRT
<213> ORGANISM: Artificial Sequence
<220> FEATURE:
<223> OTHER INFORMATION: Nanobody sequence

<400> SEQUENCE: 333

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
            85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser Gly Gly Gly Ser Gly Gly Gly
    130                 135                 140

Ser Gly Gly Gly Ser Gly Gly Gly Ser Glu Val Gln Leu Val
145                 150                 155                 160

Glu Ser Gly Gly Gly Leu Val Gln Pro Gly Ser Leu Arg Leu Ser
                165                 170                 175

Cys Ala Ala Ser Gly Asp Val His Lys Ile Asn Ile Leu Gly Trp Tyr
            180                 185                 190

Arg Gln Ala Pro Ala Lys Glu Arg Glu Met Val Ala His Ile Thr Ile
            195                 200                 205

Gly Asp Ala Thr Ser Tyr Ala Asp Ser Ala Lys Gly Arg Phe Thr Ile
            210                 215                 220

Ser Arg Asp Glu Ala Lys Asn Met Val Tyr Leu Gln Leu Asn Asn Leu
225                 230                 235                 240

Lys Pro Glu Asp Thr Ala Val Tyr Phe Cys Arg Ala Tyr Ser Arg Ile
                245                 250                 255

Tyr Pro Tyr Asn Tyr Trp Gly Gln Gly Thr Leu Val Thr Val Ser Ser
            260                 265                 270

Gly Ala Ala Asp Tyr Lys Asp His Asp Gly Asp Tyr Lys Asp His Asp
            275                 280                 285

Ile Asp Tyr Lys Asp Asp Asp Lys Gly Ala Ala His His His His
            290                 295                 300

His His
305

<210> SEQ ID NO 334
<211> LENGTH: 306
<212> TYPE: PRT
<213> ORGANISM: Artificial Sequence
<220> FEATURE:
<223> OTHER INFORMATION: Nanobody sequence

<400> SEQUENCE: 334

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser Gly Gly Gly Ser Gly Gly Gly
    130                 135                 140

Ser Gly Gly Gly Ser Gly Gly Gly Ser Glu Val Gln Leu Val
145                 150                 155                 160

```
Glu Ser Gly Gly Gly Leu Val Gln Pro Gly Gly Ser Leu Arg Leu Ser
            165                 170                 175

Cys Val Ala Ser Gly Asp Val His Lys Ile Asn Phe Leu Gly Trp Tyr
        180                 185                 190

Arg Gln Ala Pro Gly Lys Glu Arg Glu Lys Val Ala His Ile Ser Ile
            195                 200                 205

Gly Asp Gln Thr Asp Tyr Ala Asp Ser Ala Lys Gly Arg Phe Thr Ile
        210                 215                 220

Ser Arg Asp Glu Ser Lys Asn Met Val Tyr Leu Gln Met Asn Ser Leu
225                 230                 235                 240

Lys Pro Glu Asp Thr Ala Val Tyr Phe Cys Arg Ala Phe Ser Arg Ile
                245                 250                 255

Tyr Pro Tyr Asp Tyr Trp Gly Gln Gly Thr Leu Val Thr Val Ser Ser
            260                 265                 270

Gly Ala Ala Asp Tyr Lys Asp His Asp Gly Asp Tyr Lys Asp His Asp
        275                 280                 285

Ile Asp Tyr Lys Asp Asp Asp Lys Gly Ala Ala His His His His His
    290                 295                 300

His His
305

<210> SEQ ID NO 335
<211> LENGTH: 306
<212> TYPE: PRT
<213> ORGANISM: Artificial Sequence
<220> FEATURE:
<223> OTHER INFORMATION: Nanobody sequence

<400> SEQUENCE: 335

Glu Val Gln Leu Val Glu Ser Gly Gly Asp Leu Val Gln Pro Gly Gly
1               5                   10                  15

Ser Leu Arg Leu Ser Cys Ala Ala Ser Gly Asp Val His Lys Ile Asn
            20                  25                  30

Phe Leu Gly Trp Tyr Arg Gln Ala Pro Gly Lys Glu Arg Glu Met Val
        35                  40                  45

Ala His Ile Thr Ile Ala Asp Thr Asp Tyr Ala Glu Phe Ala Lys
    50                  55                  60

Gly Arg Phe Thr Ile Ser Arg Asp Glu Pro Lys Asn Met Val Tyr Leu
65                  70                  75                  80

Gln Met Asn Ser Leu Lys Pro Glu Asp Thr Ala Val Tyr Leu Cys Arg
            85                  90                  95

Ala Gly Ser Arg Ile Tyr Pro Tyr Asn Tyr Trp Gly Gln Gly Thr Leu
        100                 105                 110

Val Thr Val Ser Ser Gly Gly Gly Gly Ser Gly Gly Gly Ser Gly
    115                 120                 125

Gly Gly Ser Gly Gly Gly Ser Gly Gly Gly Ser Gly Gly
        130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
            165                 170                 175

Ser Gly Gly Thr Phe Ser Ser Tyr Thr Met Gly Trp Phe Arg Gln Ala
        180                 185                 190

Pro Gly Lys Glu Arg Glu Phe Val Ala Glu Val Arg Trp Gly Gly Val
            195                 200                 205
```

-continued

```
Thr Thr Tyr Ser Asn Ser Leu Lys Asp Arg Phe Ser Ile Ser Glu Asp
        210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
                245                 250                 255

Val Val Pro Asp Tyr Trp Gly Gln Gly Thr Leu Val Thr Val Ser Ser
                260                 265                 270

Gly Ala Ala Asp Tyr Lys Asp His Asp Gly Asp Tyr Lys Asp His Asp
                275                 280                 285

Ile Asp Tyr Lys Asp Asp Asp Lys Gly Ala Ala His His His His
        290                 295                 300

His His
305

<210> SEQ ID NO 336
<211> LENGTH: 306
<212> TYPE: PRT
<213> ORGANISM: Artificial Sequence
<220> FEATURE:
<223> OTHER INFORMATION: Nanobody sequence

<400> SEQUENCE: 336

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
            85                  90                  95

Ala Val Arg Gln Met Tyr Met Thr Val Val Pro Asp Tyr Trp Gly Gln
        100                 105                 110

Gly Thr Leu Val Thr Val Ser Ser Gly Gly Gly Gly Ser Gly Gly Gly
        115                 120                 125

Gly Ser Gly Gly Gly Ser Gly Gly Gly Ser Gly Gly Gly
        130                 135                 140

Ser Gly Gly Gly Gly Ser Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Asp Val His Lys Ile Asn Ile Leu Gly Trp Tyr
            180                 185                 190

Arg Gln Ala Pro Ala Lys Glu Arg Glu Met Val Ala His Ile Thr Ile
        195                 200                 205

Gly Asp Ala Thr Asp Tyr Ala Asp Ser Ala Lys Gly Arg Phe Thr Ile
        210                 215                 220

Ser Arg Asp Glu Ala Lys Asn Met Val Tyr Leu Gln Met Asn Ser Leu
225                 230                 235                 240

Lys Pro Glu Asp Thr Ala Val Tyr Leu Cys Arg Ala Tyr Ser Arg Ile
                245                 250                 255
```

```
Tyr Pro Tyr Asn Tyr Trp Gly Gln Gly Thr Leu Val Thr Val Ser Ser
            260                 265                 270

Gly Ala Ala Asp Tyr Lys Asp His Asp Gly Asp Tyr Lys Asp His Asp
        275                 280                 285

Ile Asp Tyr Lys Asp Asp Asp Lys Gly Ala Ala His His His His
        290                 295                 300

His His
305

<210> SEQ ID NO 337
<211> LENGTH: 306
<212> TYPE: PRT
<213> ORGANISM: Artificial Sequence
<220> FEATURE:
<223> OTHER INFORMATION: Nanobody sequence

<400> SEQUENCE: 337

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
            85                  90                  95

Ala Val Arg Gln Met Tyr Met Thr Val Val Pro Asp Tyr Trp Gly Gln
        100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
        130                 135                 140

Ser Gly Gly Gly Gly Ser Gly Gly Gly Gly Ser Glu Val Gln Leu Val
145                 150                 155                 160

Glu Ser Gly Gly Gly Leu Val Gln Pro Gly Gly Ser Leu Lys Leu Ser
                165                 170                 175

Cys Ala Ala Ser Gly Ala Val His Lys Ile Asn Phe Leu Gly Trp Tyr
            180                 185                 190

Arg Gln Thr Pro Glu Lys Glu Arg Glu Met Val Ala Thr Ile Thr Ile
        195                 200                 205

Gly Asp Glu Val Asp Tyr Ala Asp Ser Ala Lys Gly Arg Phe Thr Ile
        210                 215                 220

Ser Arg Asp Glu Ala Lys Asn Met Val Tyr Leu Gln Met Thr Ser Leu
225                 230                 235                 240

Lys Pro Glu Asp Thr Ala Val Tyr Val Cys Arg Ala Gly Ser Arg Leu
                245                 250                 255

Tyr Pro Tyr Asn Tyr Trp Gly Gln Gly Thr Leu Val Thr Val Ser Ser
            260                 265                 270

Gly Ala Ala Asp Tyr Lys Asp His Asp Gly Asp Tyr Lys Asp His Asp
        275                 280                 285

Ile Asp Tyr Lys Asp Asp Asp Lys Gly Ala Ala His His His His
        290                 295                 300
```

His His
305

<210> SEQ ID NO 338
<211> LENGTH: 273
<212> TYPE: PRT
<213> ORGANISM: Artificial Sequence
<220> FEATURE:
<223> OTHER INFORMATION: Nanobody sequence

<400> SEQUENCE: 338

Asp Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Asp Val His Lys Ile Asn Ile Leu Gly Trp Tyr
            180                 185                 190

Arg Gln Ala Pro Ala Lys Glu Arg Glu Met Val Ala His Ile Thr Ile
        195                 200                 205

Gly Asp Ala Thr Asp Tyr Ala Asp Ser Ala Lys Gly Arg Phe Thr Ile
    210                 215                 220

Ser Arg Asp Glu Ala Lys Asn Met Val Tyr Leu Gln Met Asn Ser Leu
225                 230                 235                 240

Lys Pro Glu Asp Thr Ala Val Tyr Phe Cys Arg Ala Tyr Ser Arg Ile
                245                 250                 255

Tyr Pro Tyr Asn Tyr Trp Gly Gln Gly Thr Leu Val Thr Val Ser Ser
            260                 265                 270

Ala

<210> SEQ ID NO 339
<211> LENGTH: 280
<212> TYPE: PRT
<213> ORGANISM: Artificial Sequence
<220> FEATURE:
<223> OTHER INFORMATION: Nanobody sequence

<400> SEQUENCE: 339

Asp Val Gln Leu Val Glu Ser Gly Gly Gly Leu Val Gln Ala Gly Asp
1               5                   10                  15

```
Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Gln Val Thr Val Ser Ser Gly
        115                 120                 125

Gly Gly Gly Ser Gly Gly Gly Ser Gly Gly Gly Gly Ser Gly Gly
    130                 135                 140

Gly Gly Ser Gly Gly Gly Ser Gly Gly Gly Ser Gly Gly
145                 150                 155                 160

Gly Ser Glu Val Gln Leu Val Glu Ser Gly Gly Leu Val Gln Pro
        165                 170                 175

Gly Gly Ser Leu Arg Leu Ser Cys Ala Ala Ser Gly Asp Val His Lys
    180                 185                 190

Ile Asn Ile Leu Gly Trp Tyr Arg Gln Ala Pro Ala Lys Glu Arg Glu
            195                 200                 205

Met Val Ala His Ile Thr Ile Gly Asp Ala Thr Asp Tyr Ala Asp Ser
    210                 215                 220

Ala Lys Gly Arg Phe Thr Ile Ser Arg Asp Glu Ala Lys Asn Met Val
225                 230                 235                 240

Tyr Leu Gln Met Asn Ser Leu Lys Pro Glu Asp Thr Ala Val Tyr Phe
                245                 250                 255

Cys Arg Ala Tyr Ser Arg Ile Tyr Pro Tyr Asn Tyr Trp Gly Gln Gly
            260                 265                 270

Thr Leu Val Thr Val Ser Ser Ala
        275                 280

<210> SEQ ID NO 340
<211> LENGTH: 456
<212> TYPE: PRT
<213> ORGANISM: Artificial Sequence
<220> FEATURE:
<223> OTHER INFORMATION: Nanobody sequence

<400> SEQUENCE: 340

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95
```

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Val Ala Ser Gly Asp Val His Lys Ile Asn Phe Leu Gly Trp Tyr
            180                 185                 190

Arg Gln Ala Pro Gly Lys Glu Arg Glu Lys Val Ala His Ile Ser Ile
        195                 200                 205

Gly Asp Gln Thr Asp Tyr Ala Asp Ser Ala Lys Gly Arg Phe Thr Ile
    210                 215                 220

Ser Arg Asp Glu Ser Lys Asn Met Val Tyr Leu Gln Met Asn Ser Leu
225                 230                 235                 240

Lys Pro Glu Asp Thr Ala Val Tyr Phe Cys Arg Ala Phe Ser Arg Ile
                245                 250                 255

Tyr Pro Tyr Asp Tyr Trp Gly Gln Gly Thr Leu Val Thr Val Ser Ser
            260                 265                 270

Gly Gly Gly Gly Ser Gly Gly Gly Ser Gly Gly Gly Gly Ser Gly
        275                 280                 285

Gly Gly Gly Ser Gly Gly Gly Gly Ser Gly Gly Gly Gly Ser Gly Gly
    290                 295                 300

Gly Gly Ser Glu Val Gln Leu Val Glu Ser Gly Gly Gly Leu Val Gln
305                 310                 315                 320

Pro Gly Asn Ser Leu Arg Leu Ser Cys Ala Ala Ser Gly Phe Thr Phe
                325                 330                 335

Ser Ser Phe Gly Met Ser Trp Val Arg Gln Ala Pro Gly Lys Gly Leu
            340                 345                 350

Glu Trp Val Ser Ser Ile Ser Gly Ser Gly Ser Asp Thr Leu Tyr Ala
        355                 360                 365

Asp Ser Val Lys Gly Arg Phe Thr Ile Ser Arg Asp Asn Ala Lys Thr
    370                 375                 380

Thr Leu Tyr Leu Gln Met Asn Ser Leu Arg Pro Glu Asp Thr Ala Val
385                 390                 395                 400

Tyr Tyr Cys Thr Ile Gly Gly Ser Leu Ser Arg Ser Ser Gln Gly Thr
                405                 410                 415

Leu Val Thr Val Ser Ser Gly Ala Ala Asp Tyr Lys Asp His Asp Gly
            420                 425                 430

Asp Tyr Lys Asp His Asp Ile Asp Tyr Lys Asp Asp Asp Asp Lys Gly
        435                 440                 445

Ala Ala His His His His His His
    450                 455

<210> SEQ ID NO 341
<211> LENGTH: 456
<212> TYPE: PRT
<213> ORGANISM: Artificial Sequence
<220> FEATURE:
<223> OTHER INFORMATION: Nanobody sequence

<400> SEQUENCE: 341

-continued

| | | | | | | | | | | | | | |
|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |

Ser Leu Arg Leu Ser Cys Thr Phe Ser Gly Thr Phe Ser Ser Tyr
           20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
 50                  55                  60

Asp Arg Phe Ser Ile Ser Glu Asp Ser Val Lys Asn Ala Val Tyr Leu
 65                  70                  75                  80

Gln Met Asn Ser Leu Lys Pro Glu Asp Thr Ala Val Tyr Tyr Cys Ala
           85                  90                  95

Ala Val Arg Gln Met Tyr Met Thr Val Val Pro Asp Tyr Trp Gly Gln
             100                 105                 110

Gly Thr Leu Val Thr Val Ser Ser Gly Gly Gly Gly Ser Gly Gly Gly
           115                 120                 125

Gly Ser Gly Gly Gly Gly Ser Gly Gly Gly Gly Ser Gly Gly Gly Gly
     130                 135                 140

Ser Gly Gly Gly Gly Ser Gly Gly Gly Gly Ser Glu Val Gln Leu Val
145                 150                 155                 160

Glu Ser Gly Gly Gly Leu Val Gln Pro Gly Gly Ser Leu Arg Leu Ser
                 165                 170                 175

Cys Ile Thr Ser Gly Glu Thr Phe Lys Ile Asn Ile Trp Gly Trp Tyr
             180                 185                 190

Arg Gln Ala Pro Gly Lys Gln Arg Glu Leu Val Ala Ser Leu Thr Ile
         195                 200                 205

Gly Gly Ala Thr Asn Tyr Ala Asp Ser Val Lys Gly Arg Phe Thr Ile
     210                 215                 220

Ser Glu Asp Ser Ala Lys Asn Thr Val Tyr Leu Gln Met Asn Ser Leu
225                 230                 235                 240

Lys Pro Glu Asp Thr Ala Val Tyr Phe Cys Asn Ala Lys Ser Arg Leu
                 245                 250                 255

Tyr Pro Tyr Asp Tyr Trp Gly Gln Gly Thr Leu Val Thr Val Ser Ser
             260                 265                 270

Gly Gly Gly Gly Ser Gly Gly Gly Ser Gly Gly Gly Gly Ser Gly
         275                 280                 285

Gly Gly Gly Ser Gly Gly Gly Gly Ser Gly Gly Gly Gly Ser Gly Gly
     290                 295                 300

Gly Gly Ser Glu Val Gln Leu Val Glu Ser Gly Gly Gly Leu Val Gln
305                 310                 315                 320

Pro Gly Asn Ser Leu Arg Leu Ser Cys Ala Ala Ser Gly Phe Thr Phe
                 325                 330                 335

Ser Ser Phe Gly Met Ser Trp Val Arg Gln Ala Pro Gly Lys Gly Leu
             340                 345                 350

Glu Trp Val Ser Ser Ile Ser Gly Ser Gly Ser Asp Thr Leu Tyr Ala
             355                 360                 365

Asp Ser Val Lys Gly Arg Phe Thr Ile Ser Arg Asp Asn Ala Lys Thr
     370                 375                 380

Thr Leu Tyr Leu Gln Met Asn Ser Leu Arg Pro Glu Asp Thr Ala Val
385                 390                 395                 400

Tyr Tyr Cys Thr Ile Gly Gly Ser Leu Ser Arg Ser Ser Gln Gly Thr
                 405                 410                 415

Leu Val Thr Val Ser Ser Gly Ala Ala Asp Tyr Lys Asp His Asp Gly

```
                    420                 425                 430
Asp Tyr Lys Asp His Asp Ile Asp Tyr Lys Asp Asp Asp Lys Gly
                435                 440                 445
Ala Ala His His His His His His
    450                 455

<210> SEQ ID NO 342
<211> LENGTH: 304
<212> TYPE: PRT
<213> ORGANISM: Artificial Sequence
<220> FEATURE:
<223> OTHER INFORMATION: Nanobody sequence

<400> SEQUENCE: 342

Glu Val Gln Leu Val Glu Ser Gly Gly Gly Leu Val Gln Ala Gly
1               5                   10                  15

Ser Leu Arg Leu Ser Cys Ala Ala Ser Gly Ile Thr Phe Ser Ile Asn
            20                  25                  30

Thr Met Gly Trp Tyr Arg Gln Ala Pro Gly Lys Gln Arg Glu Leu Val
        35                  40                  45

Ala Leu Ile Ser Ser Ile Gly Asp Thr Tyr Tyr Ala Asp Ser Val Lys
50                  55                  60

Gly Arg Phe Thr Ile Ser Arg Asp Asn Ala Lys Asn Thr Val Tyr Leu
65              70                  75                  80

Gln Met Asn Ser Leu Lys Pro Glu Asp Thr Ala Val Tyr Tyr Cys Lys
                85                  90                  95

Arg Phe Arg Thr Ala Ala Gln Gly Thr Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Gly Gly Gly Ser Gly Gly Gly Ser Gly
    130                 135                 140

Gly Gly Gly Ser Gly Gly Gly Ser Glu Val Gln Leu Val Glu Ser
145                 150                 155                 160

Gly Gly Gly Leu Val Gln Pro Gly Gly Ser Leu Arg Leu Ser Cys Val
                165                 170                 175

Ala Ser Gly Asp Val His Lys Ile Asn Phe Leu Gly Trp Tyr Arg Gln
            180                 185                 190

Ala Pro Gly Lys Glu Arg Glu Lys Val Ala His Ile Ser Ile Gly Asp
        195                 200                 205

Gln Thr Asp Tyr Ala Asp Ser Ala Lys Gly Arg Phe Thr Ile Ser Arg
210                 215                 220

Asp Glu Ser Lys Asn Met Val Tyr Leu Gln Met Asn Ser Leu Lys Pro
225                 230                 235                 240

Glu Asp Thr Ala Val Tyr Phe Cys Arg Ala Phe Ser Arg Ile Tyr Pro
                245                 250                 255

Tyr Asp Tyr Trp Gly Gln Gly Thr Leu Val Thr Val Ser Ser Gly Ala
            260                 265                 270

Ala Asp Tyr Lys Asp His Asp Gly Asp Tyr Lys Asp His Asp Ile Asp
        275                 280                 285

Tyr Lys Asp Asp Asp Lys Gly Ala Ala His His His His His His
290                 295                 300

<210> SEQ ID NO 343
<211> LENGTH: 304
<212> TYPE: PRT
```

```
<213> ORGANISM: Artificial Sequence
<220> FEATURE:
<223> OTHER INFORMATION: Nanobody sequence

<400> SEQUENCE: 343

Glu Val Gln Leu Val Glu Ser Gly Gly Gly Leu Val Gln Pro Gly Gly
1               5                   10                  15

Ser Leu Arg Leu Ser Cys Val Ala Ser Gly Asp Val His Lys Ile Asn
            20                  25                  30

Phe Leu Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
50                  55                  60

Gly Arg Phe Thr Ile Ser Arg Asp Glu Ser Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Phe Ser Arg Ile Tyr Pro Tyr Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
        130                 135                 140

Gly Gly Ser Gly Gly Gly Gly Ser Glu Val Gln Leu Val Glu Ser Gly
145                 150                 155                 160

Gly Gly Leu Val Gln Ala Gly Gly Ser Leu Arg Leu Ser Cys Ala Ala
                165                 170                 175

Ser Gly Ile Thr Phe Ser Ile Asn Thr Met Gly Trp Tyr Arg Gln Ala
            180                 185                 190

Pro Gly Lys Gln Arg Glu Leu Val Ala Leu Ile Ser Ser Ile Gly Asp
        195                 200                 205

Thr Tyr Tyr Ala Asp Ser Val Lys Gly Arg Phe Thr Ile Ser Arg Asp
    210                 215                 220

Asn Ala Lys Asn Thr Val Tyr Leu Gln Met Asn Ser Leu Lys Pro Glu
225                 230                 235                 240

Asp Thr Ala Val Tyr Tyr Cys Lys Arg Phe Arg Thr Ala Ala Gln Gly
                245                 250                 255

Thr Asp Tyr Trp Gly Gln Gly Thr Leu Val Thr Val Ser Ser Gly Ala
            260                 265                 270

Ala Asp Tyr Lys Asp His Asp Gly Asp Tyr Lys Asp His Asp Ile Asp
        275                 280                 285

Tyr Lys Asp Asp Asp Asp Lys Gly Ala Ala His His His His His His
    290                 295                 300

<210> SEQ ID NO 344
<211> LENGTH: 171
<212> TYPE: PRT
<213> ORGANISM: Homo sapiens

<400> SEQUENCE: 344

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45
```

```
Gly Thr Leu Leu Ser Asp Ile Thr Arg Leu Asp Leu Gly Lys Arg Ile
        50                  55                  60

Leu Asp Pro Arg Gly Ile Tyr Arg Cys Asn Gly Thr Asp Ile Tyr Lys
 65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 345
<211> LENGTH: 182
<212> TYPE: PRT
<213> ORGANISM: Homo sapiens

<400> SEQUENCE: 345

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
 65                 70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180

<210> SEQ ID NO 346
<211> LENGTH: 207
<212> TYPE: PRT
<213> ORGANISM: Homo sapiens

<400> SEQUENCE: 346

Met Gln Ser Gly Thr His Trp Arg Val Leu Gly Leu Cys Leu Leu Ser
1               5                   10                  15
```

```
Val Gly Val Trp Gly Gln Asp Gly Asn Glu Met Gly Gly Ile Thr
             20                  25                  30

Gln Thr Pro Tyr Lys Val Ser Ile Ser Gly Thr Thr Val Ile Leu Thr
         35                  40                  45

Cys Pro Gln Tyr Pro Gly Ser Glu Ile Leu Trp Gln His Asn Asp Lys
 50                  55                  60

Asn Ile Gly Gly Asp Glu Asp Lys Asn Ile Gly Ser Asp Glu Asp
 65                  70                  75                  80

His Leu Ser Leu Lys Glu Phe Ser Glu Leu Gln Ser Gly Tyr Tyr
                 85                  90                  95

Val Cys Tyr Pro Arg Gly Ser Lys Pro Glu Asp Ala Asn Phe Tyr Leu
                100                 105                 110

Tyr Leu Arg Ala Arg Val Cys Glu Asn Cys Met Glu Met Asp Val Met
             115                 120                 125

Ser Val Ala Thr Ile Val Ile Val Asp Ile Cys Ile Thr Gly Gly Leu
130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
            195                 200                 205

<210> SEQ ID NO 347
<211> LENGTH: 164
<212> TYPE: PRT
<213> ORGANISM: Homo sapiens

<400> SEQUENCE: 347

Met Lys Trp Lys Ala Leu Phe Thr Ala Ala Ile Leu Gln Ala Gln Leu
 1               5                  10                  15

Pro Ile Thr Glu Ala Gln Ser Phe Gly Leu Leu Asp Pro Lys Leu Cys
             20                  25                  30

Tyr Leu Leu Asp Gly Ile Leu Phe Ile Tyr Gly Val Ile Leu Thr Ala
             35                  40                  45

Leu Phe Leu Arg Val Lys Phe Ser Arg Ser Ala Asp Ala Pro Ala Tyr
 50                  55                  60

Gln Gln Gly Gln Asn Gln Leu Tyr Asn Glu Leu Asn Leu Gly Arg Arg
 65                  70                  75                  80

Glu Glu Tyr Asp Val Leu Asp Lys Arg Arg Gly Arg Asp Pro Glu Met
                 85                  90                  95

Gly Gly Lys Pro Gln Arg Arg Lys Asn Pro Gln Glu Gly Leu Tyr Asn
                100                 105                 110

Glu Leu Gln Lys Asp Lys Met Ala Glu Ala Tyr Ser Glu Ile Gly Met
            115                 120                 125

Lys Gly Glu Arg Arg Arg Gly Lys Gly His Asp Gly Leu Tyr Gln Gly
130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 348
```

<211> LENGTH: 142
<212> TYPE: PRT
<213> ORGANISM: Homo sapiens

<400> SEQUENCE: 348

```
Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Thr Val Leu Asp Met Arg Ser Met Asp Phe Lys Ser Asn Ser Ala Val
50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

Asp Val Lys Leu Val Glu Lys Ser Phe Glu Thr Asp Thr Asn Phe Arg
            100                 105                 110

Ile Leu Leu Leu Lys Val Ala Gly Phe Asn Leu Leu Met Thr Leu Arg
        115                 120                 125

Leu Trp Ser Ser Leu Asn Phe Gln Asn Leu Ser Val Ile Gly
130                 135                 140
```

<210> SEQ ID NO 349
<211> LENGTH: 177
<212> TYPE: PRT
<213> ORGANISM: Homo sapiens

<400> SEQUENCE: 349

```
Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Val Ser
            100                 105                 110

Ala Glu Ala Trp Gly Arg Ala Asp Cys Gly Phe Thr Ser Val Ser Tyr
        115                 120                 125

Gln Gln Gly Val Leu Ser Ala Thr Ile Leu Tyr Glu Ile Leu Leu Gly
130                 135                 140

Lys Ala Thr Leu Tyr Ala Val Leu Val Ser Ala Leu Val Leu Met Ala
145                 150                 155                 160

Met Val Lys Arg Lys Asp Phe Gln Asp Arg Ala Lys Pro Val Thr Gln
                165                 170                 175

Ile
```

<210> SEQ ID NO 350
<211> LENGTH: 118

```
<212> TYPE: PRT
<213> ORGANISM: Artificial Sequence
<220> FEATURE:
<223> OTHER INFORMATION: Nanobody sequence

<400> SEQUENCE: 350
```

Glu Val Gln Leu Val Glu Ser Gly Gly Gly Leu Val Gln Ala Gly Gly
1               5                   10                  15

Ser Leu Arg Leu Ser Cys Ala Ala Ser Gly Ile Thr Phe Ser Ile Asn
            20                  25                  30

Thr Met Gly Trp Tyr Arg Gln Ala Pro Gly Lys Gln Arg Glu Leu Val
        35                  40                  45

Ala Leu Ile Ser Ser Ile Gly Asp Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Lys
                85                  90                  95

Arg Phe Arg Thr Ala Ala Gln Gly Thr Asp Tyr Trp Gly Gln Gly Thr
            100                 105                 110

Leu Val Thr Val Ser Ser
        115

```
<210> SEQ ID NO 351
<211> LENGTH: 119
<212> TYPE: PRT
<213> ORGANISM: Artificial Sequence
<220> FEATURE:
<223> OTHER INFORMATION: Nanobody sequence

<400> SEQUENCE: 351
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Gly Phe Asn
            20                  25                  30

Asp Met Ala Trp Tyr Arg Gln Ala Pro Gly Lys Gln Arg Glu Leu Val
        35                  40                  45

Ala Leu Ile Ser Arg Val Gly Val Thr Ser Ser Ala Asp Ser Val Lys
    50                  55                  60

Gly Arg Phe Thr Ile Ser Arg Val Asn Ala Lys Asp Thr Val Tyr Leu
65                  70                  75                  80

Gln Met Asn Ser Leu Lys Pro Glu Asp Thr Ala Val Tyr Tyr Cys Tyr
                85                  90                  95

Met Asp Gln Arg Leu Asp Gly Ser Thr Leu Ala Tyr Trp Gly Gln Gly
            100                 105                 110

Thr Gln Val Thr Val Ser Ser
        115

```
<210> SEQ ID NO 352
<211> LENGTH: 127
<212> TYPE: PRT
<213> ORGANISM: Artificial Sequence
<220> FEATURE:
<223> OTHER INFORMATION: Nanobody sequence

<400> SEQUENCE: 352
```

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr

```
                    20                  25                  30
Ala Met Gly Trp Phe Arg Gln Ala Pro Gly Lys Glu Arg Glu Phe Val
            35                  40                  45

Val Ala Ile Asn Trp Ser Ser Gly Ser Thr Tyr Tyr Ala Asp Ser Val
        50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Ala Gly Tyr Gln Ile Asn Ser Gly Asn Tyr Asn Phe Lys Asp Tyr
            100                 105                 110

Glu Tyr Asp Tyr Trp Gly Gln Gly Thr Gln Val Thr Val Ser Ser
        115                 120                 125
```

<210> SEQ ID NO 353
<211> LENGTH: 123
<212> TYPE: PRT
<213> ORGANISM: Artificial Sequence
<220> FEATURE:
<223> OTHER INFORMATION: Nanobody sequence

<400> SEQUENCE: 353

```
Glu Val Gln Leu Val Glu Ser Gly Gly Gly Ser Val Gln Ala Gly Gly
1               5                   10                  15

Ser Leu Arg Leu Ser Cys Ala Ala Ser Gly Asp Thr Tyr Gly Ser Tyr
            20                  25                  30

Trp Met Gly Trp Phe Arg Gln Ala Pro Gly Lys Glu Arg Glu Gly Val
            35                  40                  45

Ala Ala Ile Asn Arg Gly Gly Gly Tyr Thr Val Tyr Ala Asp Ser Val
        50                  55                  60

Lys Gly Arg Phe Thr Ile Ser Arg Asp Thr Ala Lys Asn Thr Val Tyr
65                  70                  75                  80

Leu Gln Met Asn Ser Leu Arg Pro Asp Asp Thr Ala Asp Tyr Tyr Cys
                85                  90                  95

Ala Ala Ser Gly Val Leu Gly Gly Leu His Glu Asp Trp Phe Asn Tyr
            100                 105                 110

Trp Gly Gln Gly Thr Leu Val Thr Val Ser Ser
        115                 120
```

<210> SEQ ID NO 354
<211> LENGTH: 123
<212> TYPE: PRT
<213> ORGANISM: Artificial Sequence
<220> FEATURE:
<223> OTHER INFORMATION: Nanobody sequence

<400> SEQUENCE: 354

```
Glu Val Gln Leu Val Glu Ser Gly Gly Gly Ser Val Gln Ala Gly Gly
1               5                   10                  15

Ser Leu Arg Leu Ser Cys Ala Ala Ser Gly Asp Thr Tyr Gly Ser Tyr
            20                  25                  30

Trp Met Gly Trp Phe Arg Gln Ala Pro Gly Gln Glu Arg Glu Ala Val
            35                  40                  45

Ala Ala Ile Asn Arg Gly Gly Gly Tyr Thr Val Tyr Ala Asp Ser Val
        50                  55                  60

Lys Gly Arg Phe Thr Ile Ser Arg Asp Asn Ala Lys Asn Thr Leu Tyr
65                  70                  75                  80
```

```
Leu Gln Met Asn Ser Leu Arg Pro Asp Asp Thr Ala Asp Tyr Tyr Cys
                85                  90                  95

Ala Ala Ser Gly Val Leu Gly Gly Leu His Glu Asp Trp Phe Asn Tyr
            100                 105                 110

Trp Gly Gln Gly Thr Leu Val Thr Val Ser Ser
        115                 120

<210> SEQ ID NO 355
<211> LENGTH: 124
<212> TYPE: PRT
<213> ORGANISM: Artificial Sequence
<220> FEATURE:
<223> OTHER INFORMATION: Nanobody sequence

<400> SEQUENCE: 355

Glu Val Gln Leu Val Glu Ser Gly Gly Ser Val Gln Thr Gly Gly
1               5                   10                  15

Ser Leu Arg Leu Thr Cys Ala Ala Ser Gly Arg Thr Ser Arg Ser Tyr
            20                  25                  30

Gly Met Gly Trp Phe Arg Gln Ala Pro Gly Lys Glu Arg Glu Phe Val
            35                  40                  45

Ser Gly Ile Ser Trp Arg Gly Asp Ser Thr Gly Tyr Ala Asp Ser Val
        50                  55                  60

Lys Gly Arg Phe Thr Ile Ser Arg Asp Asn Ala Lys Asn Thr Val Asp
65                  70                  75                  80

Leu Gln Met Asn Ser Leu Lys Pro Glu Asp Thr Ala Ile Tyr Tyr Cys
                85                  90                  95

Ala Ala Ala Ala Gly Ser Ala Trp Tyr Gly Thr Leu Tyr Glu Tyr Asp
            100                 105                 110

Tyr Trp Gly Gln Gly Thr Leu Val Thr Val Ser Ser
        115                 120

<210> SEQ ID NO 356
<211> LENGTH: 124
<212> TYPE: PRT
<213> ORGANISM: Artificial Sequence
<220> FEATURE:
<223> OTHER INFORMATION: Nanobody sequence

<400> SEQUENCE: 356

Glu Val Gln Leu Val Glu Ser Gly Gly Ser Val Gln Ala Gly Gly
1               5                   10                  15

Ser Leu Arg Leu Thr Cys Ala Ala Ser Gly Ser Thr Ser Arg Ser Tyr
            20                  25                  30

Gly Met Gly Trp Phe Arg Gln Ala Pro Gly Lys Glu Arg Glu Phe Val
            35                  40                  45

Ser Gly Ile Ser Trp Arg Gly Asp Ser Thr Gly Tyr Ala Asp Ser Val
        50                  55                  60

Lys Gly Arg Phe Thr Ile Ser Arg Asp Asn Ala Lys Asn Thr Val Asp
65                  70                  75                  80

Leu Gln Met Asn Ser Leu Lys Pro Glu Asp Thr Ala Ile Tyr Tyr Cys
                85                  90                  95

Ala Ala Ala Ala Gly Ser Thr Trp Tyr Gly Thr Leu Tyr Glu Tyr Asp
            100                 105                 110

Tyr Trp Gly Gln Gly Thr Leu Val Thr Val Ser Ser
        115                 120

<210> SEQ ID NO 357
```

<211> LENGTH: 120
<212> TYPE: PRT
<213> ORGANISM: Artificial Sequence
<220> FEATURE:
<223> OTHER INFORMATION: Nanobody sequence

<400> SEQUENCE: 357

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser
        115                 120

<210> SEQ ID NO 358
<211> LENGTH: 129
<212> TYPE: PRT
<213> ORGANISM: Artificial Sequence
<220> FEATURE:
<223> OTHER INFORMATION: Nanobody sequence

<400> SEQUENCE: 358

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Val Met Gly Trp Phe Arg Gln Ala Thr Gly Lys Glu Arg Glu Phe Val
        35                  40                  45

Ala Thr Ile Ala Trp Asp Ser Gly Ser Thr Tyr Tyr Ala Asp Ser Val
    50                  55                  60

Lys Gly Arg Phe Thr Ile Ser Arg Asp Asn Ala Lys Asn Thr Val His
65                  70                  75                  80

Leu Gln Met Asn Ser Leu Lys Pro Glu Asp Thr Ala Val Tyr Tyr Cys
                85                  90                  95

Ala Ala Ser Tyr Asn Val Tyr Tyr Asn Asn Tyr Tyr Tyr Pro Ile Ser
            100                 105                 110

Arg Asp Glu Tyr Asp Tyr Trp Gly Gln Gly Thr Leu Val Thr Val Ser
        115                 120                 125

Ser

<210> SEQ ID NO 359
<211> LENGTH: 133
<212> TYPE: PRT
<213> ORGANISM: Artificial Sequence
<220> FEATURE:
<223> OTHER INFORMATION: Nanobody sequence

<400> SEQUENCE: 359

Asp Val Gln Leu Gln Ala Ser Gly Gly Gly Ser Val Gln Ala Gly Gly

```
            1               5                  10                 15
Ser Leu Arg Leu Ser Cys Ala Ala Ser Gly Tyr Thr Ile Gly Pro Tyr
                20                  25                 30

Cys Met Gly Trp Phe Arg Gln Ala Pro Gly Lys Glu Arg Glu Gly Val
            35                  40                 45

Ala Ala Ile Asn Met Gly Gly Ile Thr Tyr Tyr Ala Asp Ser Val
        50                  55                 60

Lys Gly Arg Phe Thr Ile Ser Gln Asp Asn Ala Lys Asn Thr Val Tyr
65                  70                  75                 80

Leu Leu Met Asn Ser Leu Glu Pro Glu Asp Thr Ala Ile Tyr Tyr Cys
                85                  90                 95

Ala Ala Asp Ser Thr Ile Tyr Ala Ser Tyr Tyr Glu Cys Gly His Gly
            100                 105                110

Leu Ser Thr Gly Gly Tyr Gly Tyr Asp Ser Trp Gly Gln Gly Thr Gln
            115                 120                125

Val Thr Val Ser Ser
        130
```

<210> SEQ ID NO 360
<211> LENGTH: 127
<212> TYPE: PRT
<213> ORGANISM: Artificial Sequence
<220> FEATURE:
<223> OTHER INFORMATION: Nanobody sequence

<400> SEQUENCE: 360

```
Glu Val Gln Leu Val Glu Ser Gly Gly Gly Leu Val Gln Ala Gly Asp
1               5                  10                 15

Ser Leu Arg Leu Ser Cys Ala Ala Ser Gly Arg Thr Phe Ser Ser Tyr
                20                  25                 30

Ala Met Gly Trp Phe Arg Gln Ala Pro Gly Lys Glu Arg Glu Phe Val
            35                  40                 45

Ala Ala Ile Ser Trp Ser Asp Gly Ser Thr Tyr Tyr Ala Asp Ser Val
        50                  55                 60

Lys Gly Arg Phe Thr Ile Ser Arg Asp Asn Ala Lys Asn Thr Val Tyr
65                  70                  75                 80

Leu Gln Met Asn Ser Leu Lys Pro Glu Asp Thr Ala Val Tyr Tyr Cys
                85                  90                 95

Ala Ala Asp Leu Thr Ser Thr Asn Pro Gly Ser Tyr Ile Tyr Ile Trp
            100                 105                110

Ala Tyr Asp Tyr Trp Gly Gln Gly Thr Gln Val Thr Val Ser Ser
            115                 120                125
```

<210> SEQ ID NO 361
<211> LENGTH: 10
<212> TYPE: PRT
<213> ORGANISM: Artificial Sequence
<220> FEATURE:
<223> OTHER INFORMATION: CDR1

<400> SEQUENCE: 361

```
Gly Asp Thr Tyr Gly Ser Tyr Trp Met Gly
1               5                  10
```

<210> SEQ ID NO 362
<211> LENGTH: 10
<212> TYPE: PRT
<213> ORGANISM: Artificial Sequence
<220> FEATURE:

```
<223> OTHER INFORMATION: CDR1

<400> SEQUENCE: 362

Gly Gly Thr Phe Ser Ser Tyr Thr Met Gly
1               5                   10

<210> SEQ ID NO 363
<211> LENGTH: 10
<212> TYPE: PRT
<213> ORGANISM: Artificial Sequence
<220> FEATURE:
<223> OTHER INFORMATION: CDR2

<400> SEQUENCE: 363

Ala Ile Asn Arg Gly Gly Gly Tyr Thr Val
1               5                   10

<210> SEQ ID NO 364
<211> LENGTH: 9
<212> TYPE: PRT
<213> ORGANISM: Artificial Sequence
<220> FEATURE:
<223> OTHER INFORMATION: CDR2

<400> SEQUENCE: 364

Glu Val Arg Trp Gly Gly Val Thr Thr
1               5

<210> SEQ ID NO 365
<211> LENGTH: 14
<212> TYPE: PRT
<213> ORGANISM: Artificial Sequence
<220> FEATURE:
<223> OTHER INFORMATION: CDR3

<400> SEQUENCE: 365

Ser Gly Val Leu Gly Gly Leu His Glu Asp Trp Phe Asn Tyr
1               5                   10

<210> SEQ ID NO 366
<211> LENGTH: 12
<212> TYPE: PRT
<213> ORGANISM: Artificial Sequence
<220> FEATURE:
<223> OTHER INFORMATION: CDR3

<400> SEQUENCE: 366

Val Arg Gln Met Tyr Met Thr Val Val Pro Asp Tyr
1               5                   10

<210> SEQ ID NO 367
<211> LENGTH: 25
<212> TYPE: PRT
<213> ORGANISM: Artificial Sequence
<220> FEATURE:
<223> OTHER INFORMATION: FR1

<400> SEQUENCE: 367

Glu Val Gln Leu Val Glu Ser Gly Gly Gly Ser Val Gln Ala Gly Gly
1               5                   10                  15

Ser Leu Arg Leu Ser Cys Ala Ala Ser
            20                  25

<210> SEQ ID NO 368
<211> LENGTH: 25
<212> TYPE: PRT
```

```
<213> ORGANISM: Artificial Sequence
<220> FEATURE:
<223> OTHER INFORMATION: FR1

<400> SEQUENCE: 368

Glu Val Gln Leu Val Glu Ser Gly Gly Gly Leu Val Gln Pro Gly Gly
1               5                   10                  15

Ser Leu Arg Leu Ser Cys Thr Phe Ser
            20                  25

<210> SEQ ID NO 369
<211> LENGTH: 14
<212> TYPE: PRT
<213> ORGANISM: Artificial Sequence
<220> FEATURE:
<223> OTHER INFORMATION: FR2

<400> SEQUENCE: 369

Trp Phe Arg Gln Ala Pro Gly Lys Glu Arg Glu Gly Val Ala
1               5                   10

<210> SEQ ID NO 370
<211> LENGTH: 14
<212> TYPE: PRT
<213> ORGANISM: Artificial Sequence
<220> FEATURE:
<223> OTHER INFORMATION: FR2

<400> SEQUENCE: 370

Trp Phe Arg Gln Ala Pro Gly Gln Glu Arg Glu Ala Val Ala
1               5                   10

<210> SEQ ID NO 371
<211> LENGTH: 14
<212> TYPE: PRT
<213> ORGANISM: Artificial Sequence
<220> FEATURE:
<223> OTHER INFORMATION: FR2

<400> SEQUENCE: 371

Trp Phe Arg Gln Ala Pro Gly Lys Glu Arg Glu Phe Val Ala
1               5                   10

<210> SEQ ID NO 372
<211> LENGTH: 39
<212> TYPE: PRT
<213> ORGANISM: Artificial Sequence
<220> FEATURE:
<223> OTHER INFORMATION: FR3

<400> SEQUENCE: 372

Tyr Ala Asp Ser Val Lys Gly Arg Phe Thr Ile Ser Arg Asp Thr Ala
1               5                   10                  15

Lys Asn Thr Val Tyr Leu Gln Met Asn Ser Leu Arg Pro Asp Asp Thr
            20                  25                  30

Ala Asp Tyr Tyr Cys Ala Ala
        35

<210> SEQ ID NO 373
<211> LENGTH: 39
<212> TYPE: PRT
<213> ORGANISM: Artificial Sequence
<220> FEATURE:
<223> OTHER INFORMATION: FR3

<400> SEQUENCE: 373
```

```
Tyr Ala Asp Ser Val Lys Gly Arg Phe Thr Ile Ser Arg Asp Asn Ala
1               5                   10                  15

Lys Asn Thr Leu Tyr Leu Gln Met Asn Ser Leu Arg Pro Asp Asp Thr
            20                  25                  30

Ala Asp Tyr Tyr Cys Ala Ala
        35
```

<210> SEQ ID NO 374
<211> LENGTH: 39
<212> TYPE: PRT
<213> ORGANISM: Artificial Sequence
<220> FEATURE:
<223> OTHER INFORMATION: FR3

<400> SEQUENCE: 374

```
Tyr Ser Asn Ser Leu Lys Asp Arg Phe Ser Ile Ser Glu Asp Ser Val
1               5                   10                  15

Lys Asn Ala Val Tyr Leu Gln Met Asn Ser Leu Lys Pro Glu Asp Thr
            20                  25                  30

Ala Val Tyr Tyr Cys Ala Ala
        35
```

<210> SEQ ID NO 375
<211> LENGTH: 11
<212> TYPE: PRT
<213> ORGANISM: Artificial Sequence
<220> FEATURE:
<223> OTHER INFORMATION: FR4

<400> SEQUENCE: 375

```
Trp Gly Gln Gly Thr Leu Val Thr Val Ser Ser
1               5                   10
```

<210> SEQ ID NO 376
<211> LENGTH: 5
<212> TYPE: PRT
<213> ORGANISM: Artificial Sequence
<220> FEATURE:
<223> OTHER INFORMATION: Linker

<400> SEQUENCE: 376

```
Gly Gly Gly Gly Ser
1               5
```

<210> SEQ ID NO 377
<211> LENGTH: 7
<212> TYPE: PRT
<213> ORGANISM: Artificial Sequence
<220> FEATURE:
<223> OTHER INFORMATION: Linker

<400> SEQUENCE: 377

```
Ser Gly Gly Ser Gly Gly Ser
1               5
```

<210> SEQ ID NO 378
<211> LENGTH: 9
<212> TYPE: PRT
<213> ORGANISM: Artificial Sequence
<220> FEATURE:
<223> OTHER INFORMATION: Linker

<400> SEQUENCE: 378

```
Gly Gly Gly Gly Ser Gly Gly Gly Ser
```

```
1               5
```

<210> SEQ ID NO 379
<211> LENGTH: 10
<212> TYPE: PRT
<213> ORGANISM: Artificial Sequence
<220> FEATURE:
<223> OTHER INFORMATION: Linker

<400> SEQUENCE: 379

```
Gly Gly Gly Gly Ser Gly Gly Gly Gly Ser
1               5                   10
```

<210> SEQ ID NO 380
<211> LENGTH: 15
<212> TYPE: PRT
<213> ORGANISM: Artificial Sequence
<220> FEATURE:
<223> OTHER INFORMATION: Linker

<400> SEQUENCE: 380

```
Gly Gly Gly Gly Ser Gly Gly Gly Gly Ser Gly Gly Gly Gly Ser
1               5                   10                  15
```

<210> SEQ ID NO 381
<211> LENGTH: 18
<212> TYPE: PRT
<213> ORGANISM: Artificial Sequence
<220> FEATURE:
<223> OTHER INFORMATION: Linker

<400> SEQUENCE: 381

```
Gly Gly Gly Gly Ser Gly Gly Gly Gly Ser Gly Gly Gly Gly Gly
1               5                   10                  15

Gly Ser
```

<210> SEQ ID NO 382
<211> LENGTH: 20
<212> TYPE: PRT
<213> ORGANISM: Artificial Sequence
<220> FEATURE:
<223> OTHER INFORMATION: Linker

<400> SEQUENCE: 382

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 383
<211> LENGTH: 25
<212> TYPE: PRT
<213> ORGANISM: Artificial Sequence
<220> FEATURE:
<223> OTHER INFORMATION: Linker

<400> SEQUENCE: 383

```
Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

<210> SEQ ID NO 384
<211> LENGTH: 30
<212> TYPE: PRT

```
<213> ORGANISM: Artificial Sequence
<220> FEATURE:
<223> OTHER INFORMATION: Linker

<400> SEQUENCE: 384

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Ser
                20                  25                  30

<210> SEQ ID NO 385
<211> LENGTH: 35
<212> TYPE: PRT
<213> ORGANISM: Artificial Sequence
<220> FEATURE:
<223> OTHER INFORMATION: Linker

<400> SEQUENCE: 385

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Ser Gly Gly
                20                  25                  30

Gly Gly Ser
        35

<210> SEQ ID NO 386
<211> LENGTH: 3
<212> TYPE: PRT
<213> ORGANISM: Artificial Sequence
<220> FEATURE:
<223> OTHER INFORMATION: Linker

<400> SEQUENCE: 386

Ala Ala Ala
1

<210> SEQ ID NO 387
<211> LENGTH: 423
<212> TYPE: PRT
<213> ORGANISM: Artificial Sequence
<220> FEATURE:
<223> OTHER INFORMATION: Nanobody sequence

<400> SEQUENCE: 387

Asp Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
```

```
                130             135             140
Ser Gly Gly Gly Ser Gly Gly Gly Ser Glu Val Gln Leu Val
145             150             155             160

Glu Ser Gly Gly Gly Leu Val Gln Pro Gly Ser Leu Arg Leu Ser
                165             170             175

Cys Ala Ala Ser Gly Asp Val His Lys Ile Asn Ile Leu Gly Trp Tyr
                180             185             190

Arg Gln Ala Pro Ala Lys Glu Arg Glu Met Val Ala His Ile Thr Ile
                195             200             205

Gly Asp Ala Thr Asp Tyr Ala Asp Ser Ala Lys Gly Arg Phe Thr Ile
            210             215             220

Ser Arg Asp Glu Ala Lys Asn Met Val Tyr Leu Gln Met Asn Ser Leu
225             230             235             240

Lys Pro Glu Asp Thr Ala Val Tyr Phe Cys Arg Ala Tyr Ser Arg Ile
                245             250             255

Tyr Pro Tyr Asn Tyr Trp Gly Gln Gly Thr Leu Val Thr Val Ser Ser
                260             265             270

Gly Gly Gly Gly Ser Gly Gly Gly Ser Gly Gly Gly Gly Ser Gly
            275             280             285

Gly Gly Gly Ser Gly Gly Gly Ser Gly Gly Gly Ser Gly Gly
            290             295             300

Gly Gly Ser Glu Val Gln Leu Val Glu Ser Gly Gly Gly Leu Val Gln
305             310             315             320

Pro Gly Asn Ser Leu Arg Leu Ser Cys Ala Ala Ser Gly Phe Thr Phe
                325             330             335

Ser Ser Phe Gly Met Ser Trp Val Arg Gln Ala Pro Gly Lys Gly Leu
                340             345             350

Glu Trp Val Ser Ser Ile Ser Gly Ser Gly Ser Asp Thr Leu Tyr Ala
                355             360             365

Asp Ser Val Lys Gly Arg Phe Thr Ile Ser Arg Asp Asn Ala Lys Thr
            370             375             380

Thr Leu Tyr Leu Gln Met Asn Ser Leu Arg Pro Glu Asp Thr Ala Val
385             390             395             400

Tyr Tyr Cys Thr Ile Gly Gly Ser Leu Ser Arg Ser Gln Gly Thr
                405             410             415

Leu Val Thr Val Ser Ser Ala
            420

<210> SEQ ID NO 388
<211> LENGTH: 273
<212> TYPE: PRT
<213> ORGANISM: Artificial Sequence
<220> FEATURE:
<223> OTHER INFORMATION: Nanobody sequence

<400> SEQUENCE: 388

Asp Val Gln Leu Val Glu Ser Gly Gly Gly Leu Val Gln Pro Gly Gly
1               5               10              15

Ser Leu Arg Leu Ser Cys Thr Phe Ser Gly Gly Thr Phe Ser Ser Tyr
                20              25              30

Thr Met Gly Trp Phe Arg Gln Ala Pro Gly Lys Glu Arg Glu Phe Val
                35              40              45

Ala Glu Val Arg Trp Gly Gly Val Thr Thr Tyr Ser Asn Ser Leu Lys
            50              55              60

Asp Arg Phe Ser Ile Ser Glu Asp Ser Val Lys Asn Ala Val Tyr Leu
```

```
                65                  70                  75                  80
Gln Met Asn Ser Leu Lys Pro Glu Asp Thr Ala Val Tyr Tyr Cys Ala
                    85                  90                  95

Ala Val Arg Gln Met Tyr Met Thr Val Val Pro Asp Tyr Trp Gly Gln
                100                 105                 110

Gly Thr Leu Val Thr Val Ser Ser Gly Gly Gly Gly Ser Gly Gly Gly
                115                 120                 125

Gly Ser Gly Gly Gly Gly Ser Gly Gly Gly Gly Ser Gly Gly Gly Gly
            130                 135                 140

Ser Gly Gly Gly Ser Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Val Ala Ser Gly Asp Val His Lys Ile Asn Phe Leu Gly Trp Tyr
                180                 185                 190

Arg Gln Ala Pro Gly Lys Glu Arg Glu Lys Val Ala His Ile Ser Ile
                195                 200                 205

Gly Asp Gln Thr Asp Tyr Ala Asp Ser Ala Lys Gly Arg Phe Thr Ile
            210                 215                 220

Ser Arg Asp Glu Ser Lys Asn Met Val Tyr Leu Gln Met Asn Ser Leu
225                 230                 235                 240

Lys Pro Glu Asp Thr Ala Val Tyr Phe Cys Arg Ala Phe Ser Arg Ile
                245                 250                 255

Tyr Pro Tyr Asp Tyr Trp Gly Gln Gly Thr Leu Val Thr Val Ser Ser
                260                 265                 270

Ala

<210> SEQ ID NO 389
<211> LENGTH: 430
<212> TYPE: PRT
<213> ORGANISM: Artificial Sequence
<220> FEATURE:
<223> OTHER INFORMATION: Nanobody sequence

<400> SEQUENCE: 389

Asp Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
                20                  25                  30

Ala Met Gly Trp Phe Arg Gln Ala Pro Gly Lys Glu Arg Glu Phe Val
                35                  40                  45

Ala Ala Ile Ser Trp Ser Asp Gly Ser Thr Tyr Tyr Ala Asp Ser Val
            50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                    85                  90                  95

Ala Ala Asp Leu Thr Ser Thr Asn Pro Gly Ser Tyr Ile Tyr Ile Trp
                100                 105                 110

Ala Tyr Asp Tyr Trp Gly Gln Gly Thr Gln Val Thr Val Ser Ser Gly
                115                 120                 125

Gly Gly Ser Gly Gly Gly Gly Ser Gly Gly Gly Ser Gly Gly
            130                 135                 140

Gly Gly Ser Gly Gly Gly Gly Ser Gly Gly Gly Gly Ser Gly Gly Gly
145                 150                 155                 160
```

```
Gly Ser Glu Val Gln Leu Val Glu Ser Gly Gly Leu Val Gln Pro
                165                 170                 175

Gly Gly Ser Leu Arg Leu Ser Cys Ala Ala Ser Gly Asp Val His Lys
            180                 185                 190

Ile Asn Ile Leu Gly Trp Tyr Arg Gln Ala Pro Ala Lys Glu Arg Glu
        195                 200                 205

Met Val Ala His Ile Thr Ile Gly Asp Ala Thr Asp Tyr Ala Asp Ser
210                 215                 220

Ala Lys Gly Arg Phe Thr Ile Ser Arg Asp Glu Ala Lys Asn Met Val
225                 230                 235                 240

Tyr Leu Gln Met Asn Ser Leu Lys Pro Glu Asp Thr Ala Val Tyr Phe
                245                 250                 255

Cys Arg Ala Tyr Ser Arg Ile Tyr Pro Tyr Asn Tyr Trp Gly Gln Gly
            260                 265                 270

Thr Leu Val Thr Val Ser Ser Gly Gly Gly Gly Ser Gly Gly Gly Gly
        275                 280                 285

Ser Gly Gly Gly Gly Ser Gly Gly Gly Ser Gly Gly Gly Gly Ser
290                 295                 300

Gly Gly Gly Gly Ser Gly Gly Gly Ser Glu Val Gln Leu Val Glu
305                 310                 315                 320

Ser Gly Gly Gly Leu Val Gln Pro Gly Asn Ser Leu Arg Leu Ser Cys
                325                 330                 335

Ala Ala Ser Gly Phe Thr Phe Ser Ser Phe Gly Met Ser Trp Val Arg
            340                 345                 350

Gln Ala Pro Gly Lys Gly Leu Glu Trp Val Ser Ser Ile Ser Gly Ser
        355                 360                 365

Gly Ser Asp Thr Leu Tyr Ala Asp Ser Val Lys Gly Arg Phe Thr Ile
370                 375                 380

Ser Arg Asp Asn Ala Lys Thr Thr Leu Tyr Leu Gln Met Asn Ser Leu
385                 390                 395                 400

Arg Pro Glu Asp Thr Ala Val Tyr Tyr Cys Thr Ile Gly Gly Ser Leu
                405                 410                 415

Ser Arg Ser Ser Gln Gly Thr Leu Val Thr Val Ser Ser Ala
            420                 425                 430

<210> SEQ ID NO 390
<211> LENGTH: 473
<212> TYPE: PRT
<213> ORGANISM: Artificial Sequence
<220> FEATURE:
<223> OTHER INFORMATION: Nanobody sequence

<400> SEQUENCE: 390

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Val Met Gly Trp Phe Arg Gln Ala Thr Gly Lys Glu Arg Glu Phe Val
        35                  40                  45

Ala Thr Ile Ala Trp Asp Ser Gly Ser Thr Tyr Tyr Ala Asp Ser Val
    50                  55                  60

Lys Gly Arg Phe Thr Ile Ser Arg Asp Asn Ala Lys Asn Thr Val His
65                  70                  75                  80

Leu Gln Met Asn Ser Leu Lys Pro Glu Asp Thr Ala Val Tyr Tyr Cys
                85                  90                  95
```

Ala Ala Ser Tyr Asn Val Tyr Asn Asn Tyr Tyr Pro Ile Ser
            100                 105                 110

Arg Asp Glu Tyr Asp Tyr Trp Gly Gln Gly Thr Leu Val Thr Val Ser
            115                 120                 125

Ser Gly Gly Gly Gly Ser Gly Gly Gly Ser Gly Gly Gly Gly Ser
130                 135                 140

Gly Gly Gly Gly Ser Gly Gly Gly Ser Gly Gly Gly Ser Gly
145                 150                 155                 160

Gly Gly Gly Ser Glu Val Gln Leu Val Glu Ser Gly Gly Ser Val
            165                 170                 175

Gln Ala Gly Gly Ser Leu Arg Leu Ser Cys Ala Ala Ser Gly Asp Thr
            180                 185                 190

Tyr Gly Ser Tyr Trp Met Gly Trp Phe Arg Gln Ala Pro Gly Lys Glu
            195                 200                 205

Arg Glu Gly Val Ala Ala Ile Asn Arg Gly Gly Gly Tyr Thr Val Tyr
            210                 215                 220

Ala Asp Ser Val Lys Gly Arg Phe Thr Ile Ser Arg Asp Thr Ala Lys
225                 230                 235                 240

Asn Thr Val Tyr Leu Gln Met Asn Ser Leu Arg Pro Asp Asp Thr Ala
            245                 250                 255

Asp Tyr Tyr Cys Ala Ala Ser Gly Val Leu Gly Gly Leu His Glu Asp
            260                 265                 270

Trp Phe Asn Tyr Trp Gly Gln Gly Thr Leu Val Thr Val Ser Ser Gly
            275                 280                 285

Gly Gly Gly Ser Gly Gly Gly Ser Gly Gly Gly Ser Gly Gly
            290                 295                 300

Gly Gly Ser Gly Gly Gly Ser Gly Gly Gly Ser Gly Gly Gly
305                 310                 315                 320

Gly Ser Glu Val Gln Leu Val Glu Ser Gly Gly Leu Val Gln Pro
            325                 330                 335

Gly Gly Ser Leu Arg Leu Ser Cys Val Ala Ser Gly Asp Val His Lys
            340                 345                 350

Ile Asn Phe Leu Gly Trp Tyr Arg Gln Ala Pro Gly Lys Glu Arg Glu
            355                 360                 365

Lys Val Ala His Ile Ser Ile Gly Asp Gln Thr Asp Tyr Ala Asp Ser
370                 375                 380

Ala Lys Gly Arg Phe Thr Ile Ser Arg Asp Glu Ser Lys Asn Met Val
385                 390                 395                 400

Tyr Leu Gln Met Asn Ser Leu Lys Pro Glu Asp Thr Ala Val Tyr Phe
            405                 410                 415

Cys Arg Ala Phe Ser Arg Ile Tyr Pro Tyr Asp Tyr Trp Gly Gln Gly
            420                 425                 430

Thr Leu Val Thr Val Ser Ser Gly Ala Ala Asp Tyr Lys Asp His Asp
            435                 440                 445

Gly Asp Tyr Lys Asp His Asp Ile Asp Tyr Lys Asp Asp Asp Asp Lys
            450                 455                 460

Gly Ala Ala His His His His His His
465                 470

<210> SEQ ID NO 391
<211> LENGTH: 477
<212> TYPE: PRT
<213> ORGANISM: Artificial Sequence
<220> FEATURE:

<223> OTHER INFORMATION: Nanobody sequence

<400> SEQUENCE: 391

Glu Val Gln Leu Val Glu Ser Gly Gly Gly Ser Val Gln Ala Gly Gly
1               5                   10                  15

Ser Leu Arg Leu Ser Cys Ala Ala Ser Gly Tyr Thr Ile Gly Pro Tyr
            20                  25                  30

Cys Met Gly Trp Phe Arg Gln Ala Pro Gly Lys Glu Arg Glu Gly Val
        35                  40                  45

Ala Ala Ile Asn Met Gly Gly Ile Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Leu Met Asn Ser Leu Glu Pro Glu Asp Thr Ala Ile Tyr Tyr Cys
                85                  90                  95

Ala Ala Asp Ser Thr Ile Tyr Ala Ser Tyr Tyr Glu Cys Gly His Gly
            100                 105                 110

Leu Ser Thr Gly Gly Tyr Gly Tyr Asp Ser Trp Gly Gln Gly Thr Leu
            115                 120                 125

Val Thr Val Ser Ser Gly Gly Gly Gly Ser Gly Gly Gly Gly Ser Gly
130                 135                 140

Gly Gly Ser Gly Gly Gly Gly Ser Gly Gly Gly Gly Ser Gly Gly
145                 150                 155                 160

Gly Gly Ser Gly Gly Gly Gly Ser Glu Val Gln Leu Val Glu Ser Gly
                165                 170                 175

Gly Gly Ser Val Gln Ala Gly Gly Ser Leu Arg Leu Ser Cys Ala Ala
                180                 185                 190

Ser Gly Asp Thr Tyr Gly Ser Tyr Trp Met Gly Trp Phe Arg Gln Ala
            195                 200                 205

Pro Gly Lys Glu Arg Glu Gly Val Ala Ala Ile Asn Arg Gly Gly Gly
        210                 215                 220

Tyr Thr Val Tyr Ala Asp Ser Val Lys Gly Arg Phe Thr Ile Ser Arg
225                 230                 235                 240

Asp Thr Ala Lys Asn Thr Val Tyr Leu Gln Met Asn Ser Leu Arg Pro
                245                 250                 255

Asp Asp Thr Ala Asp Tyr Tyr Cys Ala Ala Ser Gly Val Leu Gly Gly
            260                 265                 270

Leu His Glu Asp Trp Phe Asn Tyr Trp Gly Gln Gly Thr Leu Val Thr
        275                 280                 285

Val Ser Ser Gly Gly Gly Gly Ser Gly Gly Gly Gly Ser Gly Gly Gly
290                 295                 300

Gly Ser Gly Gly Gly Gly Ser Gly Gly Gly Gly Ser Gly Gly Gly Gly
305                 310                 315                 320

Ser Gly Gly Gly Gly Ser Glu Val Gln Leu Val Glu Ser Gly Gly Gly
            325                 330                 335

Leu Val Gln Pro Gly Gly Ser Leu Arg Leu Ser Cys Val Ala Ser Gly
        340                 345                 350

Asp Val His Lys Ile Asn Phe Leu Gly Trp Tyr Arg Gln Ala Pro Gly
            355                 360                 365

Lys Glu Arg Glu Lys Val Ala His Ile Ser Ile Gly Asp Gln Thr Asp
        370                 375                 380

Tyr Ala Asp Ser Ala Lys Gly Arg Phe Thr Ile Ser Arg Asp Glu Ser
385                 390                 395                 400

Lys Asn Met Val Tyr Leu Gln Met Asn Ser Leu Lys Pro Glu Asp Thr
            405                 410                 415

Ala Val Tyr Phe Cys Arg Ala Phe Ser Arg Ile Tyr Pro Tyr Asp Tyr
            420                 425                 430

Trp Gly Gln Gly Thr Leu Val Thr Val Ser Ser Gly Ala Ala Asp Tyr
            435                 440                 445

Lys Asp His Asp Gly Asp Tyr Lys Asp His Asp Ile Asp Tyr Lys Asp
450                 455                 460

Asp Asp Asp Lys Gly Ala Ala His His His His His His
465                 470                 475

<210> SEQ ID NO 392
<211> LENGTH: 483
<212> TYPE: PRT
<213> ORGANISM: Artificial Sequence
<220> FEATURE:
<223> OTHER INFORMATION: Nanobody sequence

<400> SEQUENCE: 392

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Val Met Gly Trp Phe Arg Gln Ala Thr Gly Lys Glu Arg Glu Phe Val
        35                  40                  45

Ala Thr Ile Ala Trp Asp Ser Gly Ser Thr Tyr Tyr Ala Asp Ser Val
    50                  55                  60

Lys Gly Arg Phe Thr Ile Ser Arg Asp Asn Ala Lys Asn Thr Val His
65                  70                  75                  80

Leu Gln Met Asn Ser Leu Lys Pro Glu Asp Thr Ala Val Tyr Tyr Cys
                85                  90                  95

Ala Ala Ser Tyr Asn Val Tyr Tyr Asn Asn Tyr Tyr Tyr Pro Ile Ser
            100                 105                 110

Arg Asp Glu Tyr Asp Tyr Trp Gly Gln Gly Thr Leu Val Thr Val Ser
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Gly Ser Gly
145                 150                 155                 160

Gly Gly Gly Ser Glu Val Gln Leu Val Glu Ser Gly Gly Gly Ser Val
                165                 170                 175

Gln Ala Gly Gly Ser Leu Arg Leu Ser Cys Ala Ala Ser Gly Tyr Thr
            180                 185                 190

Ile Gly Pro Tyr Cys Met Gly Trp Phe Arg Gln Ala Pro Gly Lys Glu
        195                 200                 205

Arg Glu Gly Val Ala Ala Ile Asn Met Gly Gly Ile Thr Tyr Tyr
    210                 215                 220

Ala Asp Ser Val Lys Gly Arg Phe Thr Ile Ser Gln Asp Asn Ala Lys
225                 230                 235                 240

Asn Thr Val Tyr Leu Leu Met Asn Ser Leu Glu Pro Glu Asp Thr Ala
                245                 250                 255

Ile Tyr Tyr Cys Ala Ala Asp Ser Thr Ile Tyr Ala Ser Tyr Tyr Glu
            260                 265                 270

Cys Gly His Gly Leu Ser Thr Gly Gly Tyr Gly Tyr Asp Ser Trp Gly
        275                 280                 285

```
Gln Gly Thr Leu Val Thr Val Ser Ser Gly Gly Gly Ser Gly
            290                 295                 300
Gly Gly Ser Gly Gly Gly Ser Gly Gly Gly Ser Gly Gly Gly
305                 310                 315                 320
Gly Ser Gly Gly Gly Ser Gly Gly Gly Ser Glu Val Gln Leu
                325                 330                 335
Val Glu Ser Gly Gly Gly Leu Val Gln Pro Gly Gly Ser Leu Arg Leu
            340                 345                 350
Ser Cys Val Ala Ser Gly Asp Val His Lys Ile Asn Phe Leu Gly Trp
            355                 360                 365
Tyr Arg Gln Ala Pro Gly Lys Glu Arg Glu Lys Val Ala His Ile Ser
            370                 375                 380
Ile Gly Asp Gln Thr Asp Tyr Ala Asp Ser Ala Lys Gly Arg Phe Thr
385                 390                 395                 400
Ile Ser Arg Asp Glu Ser Lys Asn Met Val Tyr Leu Gln Met Asn Ser
                405                 410                 415
Leu Lys Pro Glu Asp Thr Ala Val Tyr Phe Cys Arg Ala Phe Ser Arg
            420                 425                 430
Ile Tyr Pro Tyr Asp Tyr Trp Gly Gln Gly Thr Leu Val Thr Val Ser
            435                 440                 445
Ser Gly Ala Ala Asp Tyr Lys Asp His Asp Gly Asp Tyr Lys Asp His
450                 455                 460
Asp Ile Asp Tyr Lys Asp Asp Asp Lys Gly Ala Ala His His His His
465                 470                 475                 480
His His His

<210> SEQ ID NO 393
<211> LENGTH: 107
<212> TYPE: PRT
<213> ORGANISM: Homo sapiens

<400> SEQUENCE: 393

Ile Gln Val Glu Gln Ser Pro Pro Asp Leu Ile Leu Gln Glu Gly Ala
1               5                   10                  15
Asn Ser Thr Leu Arg Cys Asn Phe Ser Asp Ser Val Asn Asn Leu Gln
            20                  25                  30
Trp Phe His Gln Asn Pro Trp Gly Gln Leu Ile Asn Leu Phe Tyr Ile
        35                  40                  45
Pro Ser Gly Thr Lys Gln Asn Gly Arg Leu Ser Ala Thr Thr Val Ala
    50                  55                  60
Thr Glu Arg Tyr Ser Leu Leu Tyr Ile Ser Ser Ser Gln Thr Thr Asp
65                  70                  75                  80
Ser Gly Val Tyr Phe Cys Ala Ala Leu Ile Gln Gly Ala Gln Lys Leu
                85                  90                  95
Val Phe Gly Gln Gly Thr Arg Leu Thr Ile Asn
            100                 105

<210> SEQ ID NO 394
<211> LENGTH: 108
<212> TYPE: PRT
<213> ORGANISM: Homo sapiens

<400> SEQUENCE: 394

Gln Leu Leu Glu Gln Ser Pro Gln Phe Leu Ser Ile Gln Glu Gly Glu
1               5                   10                  15
Asn Leu Thr Val Tyr Cys Asn Ser Ser Ser Val Phe Ser Ser Leu Gln
```

```
                20                  25                  30

Trp Tyr Arg Gln Glu Pro Gly Glu Gly Pro Val Leu Leu Val Thr Val
            35                  40                  45

Val Thr Gly Gly Glu Val Lys Lys Leu Lys Arg Leu Thr Phe Gln Phe
 50                  55                  60

Gly Asp Ala Arg Lys Asp Ser Ser Leu His Ile Thr Ala Ala Gln Pro
 65                  70                  75                  80

Gly Asp Thr Gly Leu Tyr Leu Cys Ala Gly Ala Gly Ser Gln Gly Asn
                85                  90                  95

Leu Ile Phe Gly Lys Gly Thr Lys Leu Ser Val Lys
                100                 105
```

```
<210> SEQ ID NO 395
<211> LENGTH: 110
<212> TYPE: PRT
<213> ORGANISM: Homo sapiens

<400> SEQUENCE: 395

Gly Asp Ala Lys Thr Thr Gln Pro Asn Ser Met Glu Ser Asn Glu Glu
 1               5                   10                  15

Glu Pro Val His Leu Pro Cys Asn His Ser Thr Ile Ser Gly Thr Asp
                20                  25                  30

Tyr Ile His Trp Tyr Arg Gln Leu Pro Ser Gln Gly Pro Glu Tyr Val
            35                  40                  45

Ile His Gly Leu Thr Ser Asn Val Asn Asn Arg Met Ala Ser Leu Ala
 50                  55                  60

Ile Ala Glu Asp Arg Lys Ser Ser Thr Leu Ile Leu His Arg Ala Thr
 65                  70                  75                  80

Leu Arg Asp Ala Ala Val Tyr Tyr Cys Thr Val Tyr Gly Gly Ala Thr
                85                  90                  95

Asn Lys Leu Ile Phe Gly Thr Gly Thr Leu Leu Ala Val Gln
                100                 105                 110
```

```
<210> SEQ ID NO 396
<211> LENGTH: 96
<212> TYPE: PRT
<213> ORGANISM: Macaca fascicularis

<400> SEQUENCE: 396

Pro Tyr Ile Gln Asn Pro Asp Pro Ala Val Tyr Gln Leu Arg Gly Ser
 1               5                   10                  15

Lys Ser Asn Asp Thr Ser Val Cys Leu Phe Thr Asp Phe Asp Ser Val
                20                  25                  30

Met Asn Val Ser Gln Ser Lys Asp Ser Asp Val His Ile Thr Asp Lys
            35                  40                  45

Thr Val Leu Asp Met Arg Ser Met Asp Phe Lys Ser Asn Gly Ala Val
 50                  55                  60

Ala Trp Ser Asn Lys Ser Asp Phe Ala Cys Thr Ser Ala Phe Lys Asp
 65                  70                  75                  80

Ser Val Ile Pro Ala Asp Thr Phe Phe Pro Ser Pro Glu Ser Ser Cys
                85                  90                  95
```

```
<210> SEQ ID NO 397
<211> LENGTH: 131
<212> TYPE: PRT
<213> ORGANISM: Macaca mulatta

<400> SEQUENCE: 397
```

Glu Asp Leu Lys Lys Val Phe Pro Pro Lys Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
                35                  40                  45

Gly Lys Glu Val His Ser Gly Val Ser Thr Asp Pro Gln Pro Leu Lys
50                  55                  60

Glu Gln Pro Ala Leu Glu Asp Ser Arg Tyr Ser Leu Ser Ser Arg Leu
65                  70                  75                  80

Arg Val Ser Ala Thr Phe Trp His Asn Pro Arg Asn His Phe Arg Cys
                85                  90                  95

Gln Val Gln Phe Tyr Gly Leu Ser Glu Asp Asp Glu Trp Thr Glu Asp
                100                 105                 110

Arg Asp Lys Pro Ile Thr Gln Lys Ile Ser Ala Glu Ala Trp Gly Arg
            115                 120                 125

Ala Asp Cys
        130

<210> SEQ ID NO 398
<211> LENGTH: 107
<212> TYPE: PRT
<213> ORGANISM: Macaca mulatta

<400> SEQUENCE: 398

Gln Gln Ile Met Gln Ile Pro Gln Tyr Gln His Val Gln Glu Gly Glu
1               5                   10                  15

Asp Phe Thr Thr Tyr Cys Asn Ser Ser Thr Thr Leu Ser Asn Ile Gln
            20                  25                  30

Trp Tyr Lys Gln Arg Pro Gly Gly His Pro Val Phe Leu Ile Met Leu
                35                  40                  45

Val Lys Ser Gly Glu Val Lys Lys Gln Lys Arg Leu Ile Phe Gln Phe
50                  55                  60

Gly Glu Ala Lys Lys Asn Ser Ser Leu His Ile Thr Ala Thr Gln Thr
65                  70                  75                  80

Thr Asp Val Gly Thr Tyr Phe Cys Ala Thr Thr Gly Val Asn Asn Leu
                85                  90                  95

Phe Phe Gly Thr Gly Thr Arg Leu Thr Val Leu
                100                 105

<210> SEQ ID NO 399
<211> LENGTH: 118
<212> TYPE: PRT
<213> ORGANISM: Macaca mulatta

<400> SEQUENCE: 399

Ala Gly Pro Val Asn Ala Gly Val Thr Gln Thr Pro Lys Phe Gln Val
1               5                   10                  15

Leu Lys Thr Gly Gln Ser Met Thr Leu Gln Cys Ala Gln Asp Met Asn
            20                  25                  30

His Asp Tyr Met Tyr Trp Tyr Arg Gln Asp Pro Gly Met Gly Leu Arg
                35                  40                  45

Leu Ile His Tyr Ser Val Gly Glu Gly Ser Thr Glu Lys Gly Glu Val
50                  55                  60

Pro Asp Gly Tyr Asn Val Thr Arg Ser Asn Thr Glu Asp Phe Pro Leu
65                  70                  75                  80

-continued

Arg Leu Glu Ser Ala Ala Pro Ser Gln Thr Ser Val Tyr Phe Cys Ala
                85                  90                  95

Ser Ser Tyr Trp Thr Gly Arg Ser Tyr Glu Gln Tyr Phe Gly Pro Gly
            100                 105                 110

Thr Arg Leu Thr Val Ile
        115

<210> SEQ ID NO 400
<211> LENGTH: 115
<212> TYPE: PRT
<213> ORGANISM: Artificial Sequence
<220> FEATURE:
<223> OTHER INFORMATION: Nanobody sequence

<400> SEQUENCE: 400

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 401
<211> LENGTH: 115
<212> TYPE: PRT
<213> ORGANISM: Artificial Sequence
<220> FEATURE:
<223> OTHER INFORMATION: Nanobody sequence

<400> SEQUENCE: 401

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

```
<210> SEQ ID NO 402
<211> LENGTH: 116
<212> TYPE: PRT
<213> ORGANISM: Artificial Sequence
<220> FEATURE:
<223> OTHER INFORMATION: Nanobody sequence

<400> SEQUENCE: 402

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 403
<211> LENGTH: 116
<212> TYPE: PRT
<213> ORGANISM: Artificial Sequence
<220> FEATURE:
<223> OTHER INFORMATION: Nanobody sequence

<400> SEQUENCE: 403

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 404
<211> LENGTH: 115
<212> TYPE: PRT
<213> ORGANISM: Artificial Sequence
<220> FEATURE:
<223> OTHER INFORMATION: Nanobody sequence

<400> SEQUENCE: 404

Glu Val Gln Leu Val Glu Ser Gly Gly Gly Leu Val Gln Pro Gly Asn
1               5                   10                  15
```

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 405
<211> LENGTH: 116
<212> TYPE: PRT
<213> ORGANISM: Artificial Sequence
<220> FEATURE:
<223> OTHER INFORMATION: Nanobody sequence

<400> SEQUENCE: 405

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Lys
            100                 105                 110

Val Ser Ser Ala
        115

<210> SEQ ID NO 406
<211> LENGTH: 115
<212> TYPE: PRT
<213> ORGANISM: Artificial Sequence
<220> FEATURE:
<223> OTHER INFORMATION: Nanobody sequence

<400> SEQUENCE: 406

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ala Lys Thr Thr Leu Tyr

```
                65                  70                  75                  80
Leu Gln Met Asn Ser Leu Arg Pro Glu Asp Thr Ala Leu Tyr Tyr Cys
                    85                  90                  95

Thr Ile Gly Gly Ser Leu Ser Arg Ser Ser Gln Gly Thr Leu Val Thr
                100                 105                 110

Val Ser Ser
        115

<210> SEQ ID NO 407
<211> LENGTH: 116
<212> TYPE: PRT
<213> ORGANISM: Artificial Sequence
<220> FEATURE:
<223> OTHER INFORMATION: Nanobody sequence

<400> SEQUENCE: 407

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
                35                  40                  45

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                    85                  90                  95

Thr Ile Gly Gly Ser Leu Ser Arg Ser Ser Gln Gly Thr Leu Val Thr
                100                 105                 110

Val Ser Ser Ala
        115

<210> SEQ ID NO 408
<211> LENGTH: 117
<212> TYPE: PRT
<213> ORGANISM: Artificial Sequence
<220> FEATURE:
<223> OTHER INFORMATION: Nanobody sequence

<400> SEQUENCE: 408

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
                35                  40                  45

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                    85                  90                  95

Thr Ile Gly Gly Ser Leu Ser Arg Ser Ser Gln Gly Thr Leu Val Thr
                100                 105                 110

Val Ser Ser Ala Ala
        115
```

<210> SEQ ID NO 409
<211> LENGTH: 118
<212> TYPE: PRT
<213> ORGANISM: Artificial Sequence
<220> FEATURE:
<223> OTHER INFORMATION: Nanobody sequence

<400> SEQUENCE: 409

```
Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala Ala Ala
        115
```

<210> SEQ ID NO 410
<211> LENGTH: 116
<212> TYPE: PRT
<213> ORGANISM: Artificial Sequence
<220> FEATURE:
<223> OTHER INFORMATION: Nanobody sequence

<400> SEQUENCE: 410

```
Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly
        115
```

<210> SEQ ID NO 411
<211> LENGTH: 117
<212> TYPE: PRT
<213> ORGANISM: Artificial Sequence
<220> FEATURE:
<223> OTHER INFORMATION: Nanobody sequence

<400> SEQUENCE: 411

```
Glu Val Gln Leu Val Glu Ser Gly Gly Gly Val Val Gln Pro Gly Asn
```

```
1               5                   10                  15
Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
            85                  90                  95

Thr Ile Gly Gly Ser Leu Ser Arg Ser Ser Gln Gly Thr Leu Val Thr
            100                 105                 110

Val Ser Ser Gly Gly
            115

<210> SEQ ID NO 412
<211> LENGTH: 118
<212> TYPE: PRT
<213> ORGANISM: Artificial Sequence
<220> FEATURE:
<223> OTHER INFORMATION: Nanobody sequence

<400> SEQUENCE: 412

Glu Val Gln Leu Val Glu Ser Gly Gly Gly Val Val Gln Pro Gly Asn
 1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
            85                  90                  95

Thr Ile Gly Gly Ser Leu Ser Arg Ser Ser Gln Gly Thr Leu Val Thr
            100                 105                 110

Val Ser Ser Gly Gly Gly
            115

<210> SEQ ID NO 413
<211> LENGTH: 293
<212> TYPE: PRT
<213> ORGANISM: Artificial Sequence
<220> FEATURE:
<223> OTHER INFORMATION: Nanobody sequence

<400> SEQUENCE: 413

Glu Val Gln Leu Val Glu Ser Gly Gly Gly Leu Val Gln Gly Gly Gly
 1               5                   10                  15

Ser Leu Ser Leu Ser Cys Ala Ala Ser Gly Arg Thr Phe Ser Ser Tyr
            20                  25                  30

Ala Met Ala Trp Phe Arg Gln Pro Pro Gly Lys Glu Arg Glu Phe Val
            35                  40                  45

Ala Ser Ile Ser Trp Ser Gly Glu Asn Thr Asn Tyr Arg Asn Ser Val
            50                  55                  60
```

```
Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Lys Ile Ala Lys Thr Tyr Pro Asp Asn Trp Tyr Trp Thr Lys
            100                 105                 110

Ser Asn Asn Tyr Asn Tyr Trp Gly Gln Gly Thr Leu Val Thr Val Ser
            115                 120                 125

Ser Gly Gly Gly Gly Ser Gly Gly Gly Ser Gly Gly Gly Gly Gly Ser
    130                 135                 140

Gly Gly Gly Gly Ser Gly Gly Gly Ser Gly Gly Gly Ser Gly
145                 150                 155                 160

Gly Gly Gly Ser Glu Val Gln Leu Val Glu Ser Gly Gly Leu Val
            165                 170                 175

Gln Gly Gly Ser Leu Ser Leu Ser Cys Ala Ala Ser Gly Arg Thr
            180                 185                 190

Phe Ser Ser Tyr Ala Met Ala Trp Phe Arg Gln Pro Pro Gly Lys Glu
    195                 200                 205

Arg Glu Phe Val Ala Ser Ile Ser Trp Ser Gly Glu Asn Thr Asn Tyr
    210                 215                 220

Arg Asn Ser Val Lys Gly Arg Phe Thr Ile Ser Arg Asp Asn Ala Lys
225                 230                 235                 240

Asn Thr Val Tyr Leu Gln Met Asn Ser Leu Lys Pro Glu Asp Thr Ala
                245                 250                 255

Val Tyr Tyr Cys Ala Ala Lys Ile Ala Lys Thr Tyr Pro Asp Asn Trp
            260                 265                 270

Tyr Trp Thr Lys Ser Asn Asn Tyr Asn Tyr Trp Gly Gln Gly Thr Leu
            275                 280                 285

Val Thr Val Ser Ser
            290

<210> SEQ ID NO 414
<211> LENGTH: 242
<212> TYPE: PRT
<213> ORGANISM: Artificial Sequence
<220> FEATURE:
<223> OTHER INFORMATION: Nanobody sequence

<400> SEQUENCE: 414

Glu Val Gln Leu Val Glu Ser Gly Gly Gly Leu Val Gln Pro Gly Gly
 1               5                  10                  15

Ser Leu Arg Leu Ser Cys Thr Phe Ser Gly Gly Thr Phe Ser Ser Tyr
                20                  25                  30

Thr Met Gly Trp Phe Arg Gln Ala Pro Gly Lys Glu Arg Glu Phe Val
            35                  40                  45

Ala Glu Val Arg Trp Gly Gly Val Thr Thr Tyr Ser Asn Ser Leu Lys
50                  55                  60

Asp Arg Phe Ser Ile Ser Glu Asp Ser Val Lys Asn Ala Val Tyr Leu
 65                  70                  75                  80

Gln Met Asn Ser Leu Lys Pro Glu Asp Thr Ala Val Tyr Tyr Cys Ala
                 85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Glu Val Gln
            115                 120                 125
```

```
Leu Val Glu Ser Gly Gly Gly Leu Val Gln Pro Gly Gly Ser Leu Arg
130                 135                 140

Leu Ser Cys Ala Ala Ser Gly Ser Val His Lys Ile Asn Phe Leu Gly
145                 150                 155                 160

Trp Tyr Arg Gln Ala Pro Gly Lys Glu Arg Gly Leu Val Ala Thr Ile
                165                 170                 175

Thr Ile Gly Asp Thr Thr Asp Tyr Ala Asp Tyr Ala Lys Gly Arg Phe
                180                 185                 190

Thr Ile Ser Arg Asp Glu Ala Arg Asn Met Val Tyr Leu Gln Met Asn
            195                 200                 205

Ser Leu Lys Pro Glu Asp Thr Ala Val Tyr Phe Cys Arg Ala Gly Ser
210                 215                 220

Arg Leu Tyr Pro Tyr Asn Tyr Trp Gly Gln Gly Thr Leu Val Thr Val
225                 230                 235                 240

Ser Ser
```

<210> SEQ ID NO 415
<211> LENGTH: 255
<212> TYPE: PRT
<213> ORGANISM: Artificial Sequence
<220> FEATURE:
<223> OTHER INFORMATION: Nanobody sequence

<400> SEQUENCE: 415

```
Glu Val Gln Leu Gln Ala Ser Gly Gly Gly Ser Val Gln Ala Gly Gly
1               5                   10                  15

Ser Leu Arg Leu Ser Cys Ala Ala Ser Gly Tyr Thr Ile Gly Pro Tyr
                20                  25                  30

Cys Met Gly Trp Phe Arg Gln Ala Pro Gly Lys Glu Arg Glu Gly Val
            35                  40                  45

Ala Ala Ile Asn Met Gly Gly Gly Ile Thr Tyr Tyr Ala Asp Ser Val
        50                  55                  60

Lys Gly Arg Phe Thr Ile Ser Gln Asp Asn Ala Lys Asn Thr Val Tyr
65                  70                  75                  80

Leu Leu Met Asn Ser Leu Glu Pro Glu Asp Thr Ala Ile Tyr Tyr Cys
                85                  90                  95

Ala Ala Asp Ser Thr Ile Tyr Ala Ser Tyr Tyr Glu Cys Gly His Gly
            100                 105                 110

Leu Ser Thr Gly Gly Tyr Gly Tyr Asp Ser Trp Gly Gln Gly Thr Gln
        115                 120                 125

Val Thr Val Ser Ser Gly Gly Gly Ser Glu Val Gln Leu Val Glu
130                 135                 140

Ser Gly Gly Gly Leu Val Gln Pro Gly Gly Ser Leu Arg Leu Ser Cys
145                 150                 155                 160

Ala Ala Ser Gly Ser Val His Lys Ile Asn Phe Leu Gly Trp Tyr Arg
            165                 170                 175

Gln Ala Pro Gly Lys Glu Arg Gly Leu Val Ala Thr Ile Thr Ile Gly
        180                 185                 190

Asp Thr Thr Asp Tyr Ala Asp Tyr Ala Lys Gly Arg Phe Thr Ile Ser
            195                 200                 205

Arg Asp Glu Ala Arg Asn Met Val Tyr Leu Gln Met Asn Ser Leu Lys
        210                 215                 220

Pro Glu Asp Thr Ala Val Tyr Phe Cys Arg Ala Gly Ser Arg Leu Tyr
225                 230                 235                 240

Pro Tyr Asn Tyr Trp Gly Gln Gly Thr Leu Val Thr Val Ser Ser
```

245          250          255

<210> SEQ ID NO 416
<211> LENGTH: 258
<212> TYPE: PRT
<213> ORGANISM: Artificial Sequence
<220> FEATURE:
<223> OTHER INFORMATION: Nanobody sequence

<400> SEQUENCE: 416

Glu Val Gln Leu Val Glu Ser Gly Gly Gly Leu Val Gln Pro Gly Gly
1               5                   10                  15

Ser Leu Arg Leu Ser Cys Thr Phe Ser Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Asp Val Gln
        115                 120                 125

Leu Gln Ala Ser Gly Gly Ser Val Gln Ala Gly Gly Ser Leu Arg
    130                 135                 140

Leu Ser Cys Ala Ala Ser Gly Tyr Thr Ile Gly Pro Tyr Cys Met Gly
145                 150                 155                 160

Trp Phe Arg Gln Ala Pro Gly Lys Glu Arg Glu Gly Val Ala Ala Ile
                165                 170                 175

Asn Met Gly Gly Gly Ile Thr Tyr Tyr Ala Asp Ser Val Lys Gly Arg
            180                 185                 190

Phe Thr Ile Ser Gln Asp Asn Ala Lys Asn Thr Val Tyr Leu Leu Met
        195                 200                 205

Asn Ser Leu Glu Pro Glu Asp Thr Ala Ile Tyr Tyr Cys Ala Ala Asp
    210                 215                 220

Ser Thr Ile Tyr Ala Ser Tyr Tyr Glu Cys Gly His Gly Leu Ser Thr
225                 230                 235                 240

Gly Gly Tyr Gly Tyr Asp Ser Trp Gly Gln Gly Thr Gln Val Thr Val
                245                 250                 255

Ser Ser

<210> SEQ ID NO 417
<211> LENGTH: 242
<212> TYPE: PRT
<213> ORGANISM: Artificial Sequence
<220> FEATURE:
<223> OTHER INFORMATION: Nanobody sequence

<400> SEQUENCE: 417

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Lys Ile Asn
            20                  25                  30

Phe Leu Gly Trp Tyr Arg Gln Ala Pro Gly Lys Glu Arg Gly Leu Val

```
                35                  40                  45
Ala Thr Ile Thr Ile Gly Asp Thr Thr Asp Tyr Ala Asp Tyr Ala Lys
 50                  55                  60

Gly Arg Phe Thr Ile Ser Arg Asp Glu Ala Arg Asn Met Val Tyr Leu
 65                  70                  75                  80

Gln Met Asn Ser Leu Lys Pro Glu Asp Thr Ala Val Tyr Phe Cys Arg
                 85                  90                  95

Ala Gly Ser Arg Leu Tyr Pro Tyr Asn Tyr Trp Gly Gln Gly Thr Leu
            100                 105                 110

Val Thr Val Ser Ser Gly Gly Gly Ser Glu Val Gln Leu Val Glu
        115                 120                 125

Ser Gly Gly Gly Leu Val Gln Pro Gly Gly Ser Leu Arg Leu Ser Cys
        130                 135                 140

Thr Phe Ser Gly Gly Thr Phe Ser Ser Tyr Thr Met Gly Trp Phe Arg
145                 150                 155                 160

Gln Ala Pro Gly Lys Glu Arg Glu Phe Val Ala Glu Val Arg Trp Gly
                165                 170                 175

Gly Val Thr Thr Tyr Ser Asn Ser Leu Lys Asp Arg Phe Ser Ile Ser
            180                 185                 190

Glu Asp Ser Val Lys Asn Ala Val Tyr Leu Gln Met Asn Ser Leu Lys
        195                 200                 205

Pro Glu Asp Thr Ala Val Tyr Tyr Cys Ala Ala Val Arg Gln Met Tyr
    210                 215                 220

Met Thr Val Val Pro Asp Tyr Trp Gly Gln Gly Thr Leu Val Thr Val
225                 230                 235                 240

Ser Ser
```

<210> SEQ ID NO 418
<211> LENGTH: 246
<212> TYPE: PRT
<213> ORGANISM: Artificial Sequence
<220> FEATURE:
<223> OTHER INFORMATION: Nanobody sequence

<400> SEQUENCE: 418

```
Glu Val Gln Leu Val Glu Ser Gly Gly Gly Leu Val Gln Pro Gly Gly
 1               5                  10                  15

Ser Leu Arg Leu Ser Cys Thr Phe Ser Gly Gly Thr Phe Ser Ser Tyr
             20                  25                  30

Thr Met Gly Trp Phe Arg Gln Ala Pro Gly Lys Glu Arg Glu Phe Val
         35                  40                  45

Ala Glu Val Arg Trp Gly Gly Val Thr Thr Tyr Ser Asn Ser Leu Lys
 50                  55                  60

Asp Arg Phe Ser Ile Ser Glu Asp Ser Val Lys Asn Ala Val Tyr Leu
 65                  70                  75                  80

Gln Met Asn Ser Leu Lys Pro Glu Asp Thr Ala Val Tyr Tyr Cys Ala
                 85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
        115                 120                 125

Ser Glu Val Gln Leu Val Glu Ser Gly Gly Gly Leu Val Gln Pro Gly
        130                 135                 140

Gly Ser Leu Arg Leu Ser Cys Ala Ala Ser Gly Ser Val His Lys Ile
145                 150                 155                 160
```

```
Asn Phe Leu Gly Trp Tyr Arg Gln Ala Pro Gly Lys Glu Arg Gly Leu
                165                 170                 175
Val Ala Thr Ile Thr Ile Gly Asp Thr Thr Asp Tyr Ala Asp Tyr Ala
            180                 185                 190
Lys Gly Arg Phe Thr Ile Ser Arg Asp Glu Ala Arg Asn Met Val Tyr
            195                 200                 205
Leu Gln Met Asn Ser Leu Lys Pro Glu Asp Thr Ala Val Tyr Phe Cys
        210                 215                 220
Arg Ala Gly Ser Arg Leu Tyr Pro Tyr Asn Tyr Trp Gly Gln Gly Thr
225                 230                 235                 240
Leu Val Thr Val Ser Ser
                245

<210> SEQ ID NO 419
<211> LENGTH: 259
<212> TYPE: PRT
<213> ORGANISM: Artificial Sequence
<220> FEATURE:
<223> OTHER INFORMATION: Nanobody sequence

<400> SEQUENCE: 419

Glu Val Gln Leu Gln Ala Ser Gly Gly Gly Ser Val Gln Ala Gly Gly
1               5                   10                  15
Ser Leu Arg Leu Ser Cys Ala Ala Ser Gly Tyr Thr Ile Gly Pro Tyr
            20                  25                  30
Cys Met Gly Trp Phe Arg Gln Ala Pro Gly Lys Glu Arg Glu Gly Val
        35                  40                  45
Ala Ala Ile Asn Met Gly Gly Gly Ile Thr Tyr Tyr Ala Asp Ser Val
    50                  55                  60
Lys Gly Arg Phe Thr Ile Ser Gln Asp Asn Ala Lys Asn Thr Val Tyr
65                  70                  75                  80
Leu Leu Met Asn Ser Leu Glu Pro Glu Asp Thr Ala Ile Tyr Tyr Cys
                85                  90                  95
Ala Ala Asp Ser Thr Ile Tyr Ala Ser Tyr Tyr Glu Cys Gly His Gly
            100                 105                 110
Leu Ser Thr Gly Gly Tyr Gly Tyr Asp Ser Trp Gly Gln Gly Thr Gln
        115                 120                 125
Val Thr Val Ser Ser Gly Gly Gly Gly Ser Gly Gly Ser Glu Val
    130                 135                 140
Gln Leu Val Glu Ser Gly Gly Gly Leu Val Gln Pro Gly Gly Ser Leu
145                 150                 155                 160
Arg Leu Ser Cys Ala Ala Ser Gly Ser Val His Lys Ile Asn Phe Leu
                165                 170                 175
Gly Trp Tyr Arg Gln Ala Pro Gly Lys Glu Arg Gly Leu Val Ala Thr
            180                 185                 190
Ile Thr Ile Gly Asp Thr Thr Asp Tyr Ala Asp Tyr Ala Lys Gly Arg
        195                 200                 205
Phe Thr Ile Ser Arg Asp Glu Ala Arg Asn Met Val Tyr Leu Gln Met
    210                 215                 220
Asn Ser Leu Lys Pro Glu Asp Thr Ala Val Tyr Phe Cys Arg Ala Gly
225                 230                 235                 240
Ser Arg Leu Tyr Pro Tyr Asn Tyr Trp Gly Gln Gly Thr Leu Val Thr
                245                 250                 255
Val Ser Ser
```

```
<210> SEQ ID NO 420
<211> LENGTH: 262
<212> TYPE: PRT
<213> ORGANISM: Artificial Sequence
<220> FEATURE:
<223> OTHER INFORMATION: Nanobody sequence

<400> SEQUENCE: 420

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Ser Asp Val Gln Leu Gln Ala Ser Gly Gly Gly Ser Val Gln Ala Gly
130                 135                 140

Gly Ser Leu Arg Leu Ser Cys Ala Ala Ser Gly Tyr Thr Ile Gly Pro
145                 150                 155                 160

Tyr Cys Met Gly Trp Phe Arg Gln Ala Pro Gly Lys Glu Arg Glu Gly
                165                 170                 175

Val Ala Ala Ile Asn Met Gly Gly Ile Thr Tyr Tyr Ala Asp Ser
            180                 185                 190

Val Lys Gly Arg Phe Thr Ile Ser Gln Asp Asn Ala Lys Asn Thr Val
        195                 200                 205

Tyr Leu Leu Met Asn Ser Leu Glu Pro Glu Asp Thr Ala Ile Tyr Tyr
210                 215                 220

Cys Ala Ala Asp Ser Thr Ile Tyr Ala Ser Tyr Tyr Glu Cys Gly His
225                 230                 235                 240

Gly Leu Ser Thr Gly Gly Tyr Gly Tyr Asp Ser Trp Gly Gln Gly Thr
                245                 250                 255

Gln Val Thr Val Ser Ser
            260

<210> SEQ ID NO 421
<211> LENGTH: 246
<212> TYPE: PRT
<213> ORGANISM: Artificial Sequence
<220> FEATURE:
<223> OTHER INFORMATION: Nanobody sequence

<400> SEQUENCE: 421

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Lys Ile Asn
            20                  25                  30

Phe Leu Gly Trp Tyr Arg Gln Ala Pro Gly Lys Glu Arg Gly Leu Val
        35                  40                  45
```

```
Ala Thr Ile Thr Ile Gly Asp Thr Asp Tyr Ala Asp Tyr Ala Lys
    50                  55                  60

Gly Arg Phe Thr Ile Ser Arg Asp Glu Ala Arg Asn Met Val Tyr Leu
65                  70                  75                  80

Gln Met Asn Ser Leu Lys Pro Glu Asp Thr Ala Val Tyr Phe Cys Arg
                85                  90                  95

Ala Gly Ser Arg Leu Tyr Pro Tyr Asn Tyr Trp Gly Gln Gly Thr Leu
            100                 105                 110

Val Thr Val Ser Ser Gly Gly Gly Ser Gly Gly Ser Glu Val
        115                 120                 125

Gln Leu Val Glu Ser Gly Gly Leu Val Gln Pro Gly Gly Ser Leu
    130                 135                 140

Arg Leu Ser Cys Thr Phe Ser Gly Gly Thr Phe Ser Ser Tyr Thr Met
145                 150                 155                 160

Gly Trp Phe Arg Gln Ala Pro Gly Lys Glu Arg Glu Phe Val Ala Glu
                165                 170                 175

Val Arg Trp Gly Gly Val Thr Thr Tyr Ser Asn Ser Leu Lys Asp Arg
            180                 185                 190

Phe Ser Ile Ser Glu Asp Ser Val Lys Asn Ala Val Tyr Leu Gln Met
        195                 200                 205

Asn Ser Leu Lys Pro Glu Asp Thr Ala Val Tyr Tyr Cys Ala Ala Val
    210                 215                 220

Arg Gln Met Tyr Met Thr Val Val Pro Asp Tyr Trp Gly Gln Gly Thr
225                 230                 235                 240

Leu Val Thr Val Ser Ser
                245

<210> SEQ ID NO 422
<211> LENGTH: 272
<212> TYPE: PRT
<213> ORGANISM: Artificial Sequence
<220> FEATURE:
<223> OTHER INFORMATION: Nanobody sequence

<400> SEQUENCE: 422

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Gly Gly Gly Ser Gly Gly Gly Gly
    130                 135                 140

Ser Gly Gly Gly Gly Ser Gly Gly Gly Gly Ser Glu Val Gln Leu Val
145                 150                 155                 160
```

-continued

Glu Ser Gly Gly Gly Leu Val Gln Pro Gly Ser Leu Arg Leu Ser
             165                 170                 175

Cys Ala Ala Ser Gly Ser Val His Lys Ile Asn Phe Leu Gly Trp Tyr
            180                 185                 190

Arg Gln Ala Pro Gly Lys Glu Arg Gly Leu Val Ala Thr Ile Thr Ile
        195                 200                 205

Gly Asp Thr Thr Asp Tyr Ala Asp Tyr Ala Lys Gly Arg Phe Thr Ile
    210                 215                 220

Ser Arg Asp Glu Ala Arg Asn Met Val Tyr Leu Gln Met Asn Ser Leu
225                 230                 235                 240

Lys Pro Glu Asp Thr Ala Val Tyr Phe Cys Arg Ala Gly Ser Arg Leu
                245                 250                 255

Tyr Pro Tyr Asn Tyr Trp Gly Gln Gly Thr Leu Val Thr Val Ser Ser
            260                 265                 270

<210> SEQ ID NO 423
<211> LENGTH: 285
<212> TYPE: PRT
<213> ORGANISM: Artificial Sequence
<220> FEATURE:
<223> OTHER INFORMATION: Nanobody sequence

<400> SEQUENCE: 423

Glu Val Gln Leu Gln Ala Ser Gly Gly Gly Ser Val Gln Ala Gly Gly
1               5                   10                  15

Ser Leu Arg Leu Ser Cys Ala Ala Ser Gly Tyr Thr Ile Gly Pro Tyr
            20                  25                  30

Cys Met Gly Trp Phe Arg Gln Ala Pro Gly Lys Glu Arg Glu Gly Val
        35                  40                  45

Ala Ala Ile Asn Met Gly Gly Gly Ile Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Leu Met Asn Ser Leu Glu Pro Glu Asp Thr Ala Ile Tyr Tyr Cys
                85                  90                  95

Ala Ala Asp Ser Thr Ile Tyr Ala Ser Tyr Tyr Glu Cys Gly His Gly
            100                 105                 110

Leu Ser Thr Gly Tyr Gly Tyr Asp Ser Trp Gly Gln Gly Thr Gln
        115                 120                 125

Val Thr Val Ser Ser Gly Gly Gly Gly Ser Gly Gly Gly Ser Gly
    130                 135                 140

Gly Gly Gly Ser Gly Gly Gly Gly Ser Gly Gly Gly Gly Ser Gly Gly
145                 150                 155                 160

Gly Gly Ser Gly Gly Gly Gly Ser Glu Val Gln Leu Val Glu Ser Gly
                165                 170                 175

Gly Gly Leu Val Gln Pro Gly Gly Ser Leu Arg Leu Ser Cys Ala Ala
            180                 185                 190

Ser Gly Ser Val His Lys Ile Asn Phe Leu Gly Trp Tyr Arg Gln Ala
        195                 200                 205

Pro Gly Lys Glu Arg Gly Leu Val Ala Thr Ile Thr Ile Gly Asp Thr
    210                 215                 220

Thr Asp Tyr Ala Asp Tyr Ala Lys Gly Arg Phe Thr Ile Ser Arg Asp
225                 230                 235                 240

Glu Ala Arg Asn Met Val Tyr Leu Gln Met Asn Ser Leu Lys Pro Glu
                245                 250                 255

```
Asp Thr Ala Val Tyr Phe Cys Arg Ala Gly Ser Arg Leu Tyr Pro Tyr
            260                 265                 270

Asn Tyr Trp Gly Gln Gly Thr Leu Val Thr Val Ser Ser
    275                 280                 285

<210> SEQ ID NO 424
<211> LENGTH: 288
<212> TYPE: PRT
<213> ORGANISM: Artificial Sequence
<220> FEATURE:
<223> OTHER INFORMATION: Nanobody sequence

<400> SEQUENCE: 424

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Asp Val Gln Leu Gln
145                 150                 155                 160

Ala Ser Gly Gly Gly Ser Val Gln Ala Gly Gly Ser Leu Arg Leu Ser
                165                 170                 175

Cys Ala Ala Ser Gly Tyr Thr Ile Gly Pro Tyr Cys Met Gly Trp Phe
            180                 185                 190

Arg Gln Ala Pro Gly Lys Glu Arg Glu Gly Val Ala Ala Ile Asn Met
        195                 200                 205

Gly Gly Gly Ile Thr Tyr Tyr Ala Asp Ser Val Lys Gly Arg Phe Thr
    210                 215                 220

Ile Ser Gln Asp Asn Ala Lys Asn Thr Val Tyr Leu Leu Met Asn Ser
225                 230                 235                 240

Leu Glu Pro Glu Asp Thr Ala Ile Tyr Tyr Cys Ala Ala Asp Ser Thr
                245                 250                 255

Ile Tyr Ala Ser Tyr Tyr Glu Cys Gly His Gly Leu Ser Thr Gly Gly
            260                 265                 270

Tyr Gly Tyr Asp Ser Trp Gly Gln Gly Thr Gln Val Thr Val Ser Ser
        275                 280                 285

<210> SEQ ID NO 425
<211> LENGTH: 272
<212> TYPE: PRT
<213> ORGANISM: Artificial Sequence
<220> FEATURE:
<223> OTHER INFORMATION: Nanobody sequence
```

<400> SEQUENCE: 425

Glu Val Gln Leu Val Glu Ser Gly Gly Leu Val Gln Pro Gly Gly
1               5                   10                  15

Ser Leu Arg Leu Ser Cys Ala Ala Ser Gly Ser Val His Lys Ile Asn
            20                  25                  30

Phe Leu Gly Trp Tyr Arg Gln Ala Pro Gly Lys Glu Arg Gly Leu Val
        35                  40                  45

Ala Thr Ile Thr Ile Gly Asp Thr Thr Asp Tyr Ala Asp Tyr Ala Lys
    50                  55                  60

Gly Arg Phe Thr Ile Ser Arg Asp Glu Ala Arg Asn Met Val Tyr Leu
65                  70                  75                  80

Gln Met Asn Ser Leu Lys Pro Glu Asp Thr Ala Val Tyr Phe Cys Arg
                85                  90                  95

Ala Gly Ser Arg Leu Tyr Pro Tyr Asn Tyr Trp Gly Gln Gly Thr Leu
            100                 105                 110

Val Thr Val Ser Ser Gly Gly Gly Ser Gly Gly Gly Ser Gly
        115                 120                 125

Gly Gly Ser Gly Gly Gly Ser Gly Gly Gly Ser Gly Gly
    130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
                165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
        195                 200                 205

Thr Thr Tyr Ser Asn Ser Leu Lys Asp Arg Phe Ser Ile Ser Glu Asp
    210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
                245                 250                 255

Val Val Pro Asp Tyr Trp Gly Gln Gly Thr Leu Val Thr Val Ser Ser
            260                 265                 270

<210> SEQ ID NO 426
<211> LENGTH: 288
<212> TYPE: PRT
<213> ORGANISM: Artificial Sequence
<220> FEATURE:
<223> OTHER INFORMATION: Nanobody sequence

<400> SEQUENCE: 426

Glu Val Gln Leu Gln Ala Ser Gly Gly Gly Val Gln Ala Gly Gly
1               5                   10                  15

Ser Leu Arg Leu Ser Cys Ala Ala Ser Gly Tyr Thr Ile Gly Pro Tyr
            20                  25                  30

Cys Met Gly Trp Phe Arg Gln Ala Pro Gly Lys Glu Arg Glu Gly Val
        35                  40                  45

Ala Ala Ile Asn Met Gly Gly Ile Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Leu Met Asn Ser Leu Glu Pro Glu Asp Thr Ala Ile Tyr Tyr Cys

```
                        85                  90                  95
Ala Ala Asp Ser Thr Ile Tyr Ala Ser Tyr Tyr Glu Cys Gly His Gly
                   100                 105                 110

Leu Ser Thr Gly Gly Tyr Gly Tyr Asp Ser Trp Gly Gln Gly Thr Gln
                   115                 120                 125

Val Thr Val Ser Ser Gly Gly Gly Gly Ser Gly Gly Gly Gly Ser Gly
                   130                 135                 140

Gly Gly Gly Ser Gly Gly Gly Ser Gly Gly Gly Ser Gly Gly Ser Gly
145                                 150                 155                 160

Gly Gly Ser Gly Gly Gly Ser Glu Val Gln Leu Val Glu Ser Gly
                   165                 170                 175

Gly Gly Leu Val Gln Pro Gly Gly Ser Leu Arg Leu Ser Cys Thr Phe
                   180                 185                 190

Ser Gly Gly Thr Phe Ser Ser Tyr Thr Met Gly Trp Phe Arg Gln Ala
                   195                 200                 205

Pro Gly Lys Glu Arg Glu Phe Val Ala Glu Val Arg Trp Gly Gly Val
                   210                 215                 220

Thr Thr Tyr Ser Asn Ser Leu Lys Asp Arg Phe Ser Ile Ser Glu Asp
225                                 230                 235                 240

Ser Val Lys Asn Ala Val Tyr Leu Gln Met Asn Ser Leu Lys Pro Glu
                   245                 250                 255

Asp Thr Ala Val Tyr Tyr Cys Ala Ala Val Arg Gln Met Tyr Met Thr
                   260                 265                 270

Val Val Pro Asp Tyr Trp Gly Gln Gly Thr Leu Val Thr Val Ser Ser
                   275                 280                 285

<210> SEQ ID NO 427
<211> LENGTH: 285
<212> TYPE: PRT
<213> ORGANISM: Artificial Sequence
<220> FEATURE:
<223> OTHER INFORMATION: Nanobody sequence

<400> SEQUENCE: 427

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Lys Ile Asn
                20                  25                  30

Phe Leu Gly Trp Tyr Arg Gln Ala Pro Gly Lys Glu Arg Gly Leu Val
                35                  40                  45

Ala Thr Ile Thr Ile Gly Asp Thr Thr Asp Tyr Ala Asp Tyr Ala Lys
        50                  55                  60

Gly Arg Phe Thr Ile Ser Arg Asp Glu Ala Arg Asn Met Val Tyr Leu
65                  70                  75                  80

Gln Met Asn Ser Leu Lys Pro Glu Asp Thr Ala Val Tyr Phe Cys Arg
                85                  90                  95

Ala Gly Ser Arg Leu Tyr Pro Tyr Asn Tyr Trp Gly Gln Gly Thr Leu
                   100                 105                 110

Val Thr Val Ser Ser Gly Gly Gly Gly Ser Gly Gly Gly Gly Ser Gly
                   115                 120                 125

Gly Gly Gly Ser Gly Gly Gly Gly Ser Gly Gly Gly Gly Ser Gly Gly
                   130                 135                 140

Gly Gly Ser Gly Gly Gly Gly Ser Asp Val Gln Leu Gln Ala Ser Gly
145                                 150                 155                 160

Gly Gly Ser Val Gln Ala Gly Gly Ser Leu Arg Leu Ser Cys Ala Ala
```

```
                    165                 170                 175
Ser Gly Tyr Thr Ile Gly Pro Tyr Cys Met Gly Trp Phe Arg Gln Ala
                180                 185                 190

Pro Gly Lys Glu Arg Glu Gly Val Ala Ala Ile Asn Met Gly Gly Gly
            195                 200                 205

Ile Thr Tyr Tyr Ala Asp Ser Val Lys Gly Arg Phe Thr Ile Ser Gln
        210                 215                 220

Asp Asn Ala Lys Asn Thr Val Tyr Leu Leu Met Asn Ser Leu Glu Pro
225                 230                 235                 240

Glu Asp Thr Ala Ile Tyr Tyr Cys Ala Ala Asp Ser Thr Ile Tyr Ala
                245                 250                 255

Ser Tyr Tyr Glu Cys Gly His Gly Leu Ser Thr Gly Gly Tyr Gly Tyr
                260                 265                 270

Asp Ser Trp Gly Gln Gly Thr Gln Val Thr Val Ser Ser
                275                 280                 285

<210> SEQ ID NO 428
<211> LENGTH: 272
<212> TYPE: PRT
<213> ORGANISM: Artificial Sequence
<220> FEATURE:
<223> OTHER INFORMATION: Nanobody sequence

<400> SEQUENCE: 428

Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Val Tyr Lys Ile Asn
            20                  25                  30

Phe Leu Gly Trp His Arg Gln Ala Pro Gly Lys Glu Arg Glu Lys Val
        35                  40                  45

Ala His Ile Thr Ile Gly Asp Ala Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Gly Ser Arg Ile Tyr Pro Tyr Asp Tyr Trp Gly Gln Gly Thr Leu
            100                 105                 110

Val Thr Val Ser Ser Gly Gly Gly Ser Gly Gly Gly Gly Ser Gly
        115                 120                 125

Gly Gly Ser Gly Gly Gly Ser Gly Gly Gly Ser Gly Gly
    130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
                165                 170                 175

Ser Gly Gly Thr Phe Ser Ser Tyr Thr Met Gly Trp Phe Arg Gln Ala
                180                 185                 190

Pro Gly Lys Glu Arg Glu Phe Val Ala Glu Val Arg Trp Gly Gly Val
            195                 200                 205

Thr Thr Tyr Ser Asn Ser Leu Lys Asp Arg Phe Ser Ile Ser Glu Asp
        210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
```

245                 250                 255
Val Val Pro Asp Tyr Trp Gly Gln Gly Thr Leu Val Thr Val Ser Ser
            260                 265                 270

<210> SEQ ID NO 429
<211> LENGTH: 272
<212> TYPE: PRT
<213> ORGANISM: Artificial Sequence
<220> FEATURE:
<223> OTHER INFORMATION: Nanobody sequence

<400> SEQUENCE: 429

Glu Val Gln Leu Val Glu Ser Gly Gly Gly Leu Val Gln Pro Gly Gly
1               5                   10                  15

Ser Leu Lys Leu Ser Cys Ala Ala Ser Gly Ala Val His Lys Ile Asn
            20                  25                  30

Phe Leu Gly Trp Tyr Arg Gln Thr Pro Glu Lys Glu Arg Glu Met Val
        35                  40                  45

Ala Thr Ile Thr Ile Gly Asp Glu Val Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Thr Ser Leu Lys Pro Glu Asp Thr Ala Val Tyr Val Cys Arg
                85                  90                  95

Ala Gly Ser Arg Leu Tyr Pro Tyr Asn Tyr Trp Gly Gln Gly Thr Leu
            100                 105                 110

Val Thr Val Ser Ser Gly Gly Gly Ser Gly Gly Gly Gly Ser Gly
        115                 120                 125

Gly Gly Ser Gly Gly Gly Gly Ser Gly Gly Gly Ser Gly Gly
    130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
                165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
        195                 200                 205

Thr Thr Tyr Ser Asn Ser Leu Lys Asp Arg Phe Ser Ile Ser Glu Asp
    210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
                245                 250                 255

Val Val Pro Asp Tyr Trp Gly Gln Gly Thr Leu Val Thr Val Ser Ser
            260                 265                 270

<210> SEQ ID NO 430
<211> LENGTH: 272
<212> TYPE: PRT
<213> ORGANISM: Artificial Sequence
<220> FEATURE:
<223> OTHER INFORMATION: Nanobody sequence

<400> SEQUENCE: 430

Glu Val Gln Leu Val Glu Ser Gly Gly Gly Leu Val Gln Pro Gly Gly
1               5                   10                  15

Ser Leu Arg Leu Ser Cys Ile Thr Ser Gly Glu Thr Phe Lys Ile Asn
            20                  25                  30

Ile Trp Gly Trp Tyr Arg Gln Ala Pro Gly Lys Gln Arg Glu Leu Val
            35                  40                  45

Ala Ser Leu Thr Ile Gly Gly Ala Thr Asn Tyr Ala Asp Ser Val Lys
50                      55                  60

Gly Arg Phe Thr Ile Ser Glu Asp Ser Ala Lys Asn Thr Val Tyr Leu
65                  70                  75                  80

Gln Met Asn Ser Leu Lys Pro Glu Asp Thr Ala Val Tyr Phe Cys Asn
            85                  90                  95

Ala Lys Ser Arg Leu Tyr Pro Tyr Asp Tyr Trp Gly Gln Gly Thr Leu
            100                 105                 110

Val Thr Val Ser Ser Gly Gly Gly Ser Gly Gly Gly Gly Ser Gly Gly
            115                 120                 125

Gly Gly Ser Gly Gly Gly Gly Ser Gly Gly Gly Gly Ser Gly Gly
            130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
            165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
            195                 200                 205

Thr Thr Tyr Ser Asn Ser Leu Lys Asp Arg Phe Ser Ile Ser Glu Asp
210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
            245                 250                 255

Val Val Pro Asp Tyr Trp Gly Gln Gly Thr Leu Val Thr Val Ser Ser
            260                 265                 270

<210> SEQ ID NO 431
<211> LENGTH: 272
<212> TYPE: PRT
<213> ORGANISM: Artificial Sequence
<220> FEATURE:
<223> OTHER INFORMATION: Nanobody sequence

<400> SEQUENCE: 431

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Leu Leu Asn
            20                  25                  30

Phe Leu Gly Trp Tyr Arg Gln Ala Pro Gly Lys Glu Arg Glu Met Val
            35                  40                  45

Ala His Ile Thr Ile Ala Asp Ala Thr Asp Tyr Ala His Phe Ala Lys
50                  55                  60

Gly Arg Phe Thr Ile Ser Arg Asp Glu Ala Lys Asn Met Val Tyr Leu
65                  70                  75                  80

Gln Met Asn Ser Leu Arg Pro Glu Asp Thr Ala Val Tyr Phe Cys Arg
            85                  90                  95

Ala Gly Ser Arg Ile Tyr Pro Tyr Asp Tyr Trp Gly Gln Gly Thr Leu
            100                 105                 110

Val Thr Val Ser Ser Gly Gly Gly Ser Gly Gly Gly Ser Gly
            115                 120                 125

Gly Gly Gly Ser Gly Gly Gly Ser Gly Gly Gly Ser Gly Gly
        130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
                165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
        195                 200                 205

Thr Thr Tyr Ser Asn Ser Leu Lys Asp Arg Phe Ser Ile Ser Glu Asp
210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
                245                 250                 255

Val Val Pro Asp Tyr Trp Gly Gln Gly Thr Leu Val Thr Val Ser Ser
            260                 265                 270

<210> SEQ ID NO 432
<211> LENGTH: 272
<212> TYPE: PRT
<213> ORGANISM: Artificial Sequence
<220> FEATURE:
<223> OTHER INFORMATION: Nanobody sequence

<400> SEQUENCE: 432

Glu Val Gln Leu Val Glu Ser Gly Gly Gly Leu Val Gln Pro Gly Gly
1               5                   10                  15

Ser Leu Arg Leu Ser Cys Ile Thr Ser Gly Glu Thr Phe Lys Ile Asn
            20                  25                  30

Ile Trp Gly Trp Tyr Arg Gln Ala Pro Gly Lys Gln Arg Glu Leu Val
        35                  40                  45

Ala Ser Leu Thr Ile Gly Gly Ala Thr Asp Tyr Ala Asp Ser Val Lys
    50                  55                  60

Gly Arg Phe Thr Ile Ser Glu Asp Ser Ala Lys Asn Thr Val Tyr Leu
65                  70                  75                  80

Gln Met Asn Ser Leu Lys Ala Glu Asp Thr Ala Val Tyr Phe Cys Asn
                85                  90                  95

Ala Lys Ser Arg Leu Tyr Pro Tyr Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Ser Gly Gly Gly Gly Ser Gly Gly Gly Ser Gly Gly
    130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
                165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
        195                 200                 205

```
Thr Thr Tyr Ser Asn Ser Leu Lys Asp Arg Phe Ser Ile Ser Glu Asp
    210                 215                 220
Ser Val Lys Asn Ala Val Tyr Leu Gln Met Asn Ser Leu Lys Pro Glu
225                 230                 235                 240
Asp Thr Ala Val Tyr Tyr Cys Ala Ala Val Arg Gln Met Tyr Met Thr
                245                 250                 255
Val Val Pro Asp Tyr Trp Gly Gln Gly Thr Leu Val Thr Val Ser Ser
            260                 265                 270

<210> SEQ ID NO 433
<211> LENGTH: 272
<212> TYPE: PRT
<213> ORGANISM: Artificial Sequence
<220> FEATURE:
<223> OTHER INFORMATION: Nanobody sequence

<400> SEQUENCE: 433

Glu Val Gln Leu Val Glu Ser Gly Gly Gly Leu Val Gln Pro Gly Gly
1               5                   10                  15
Ser Leu Arg Leu Ser Cys Ala Ala Ser Gly Glu Val Tyr Lys Ile Asn
            20                  25                  30
Phe Leu Gly Trp Tyr Arg Gln Ala Pro Gly Lys Glu Arg Glu Lys Val
        35                  40                  45
Ala His Ile Thr Ile Ala Asp Ala Ala Asp Tyr Ala Asp Phe Ala Lys
    50                  55                  60
Gly Arg Phe Thr Ile Ser Arg Asp Glu Ala Lys Asn Met Val Tyr Leu
65                  70                  75                  80
Gln Met Asn Ser Leu Arg Pro Glu Asp Thr Ala Val Tyr Phe Cys Arg
                85                  90                  95
Ala Gly Ser Arg Ile Trp Pro Tyr Asp Tyr Trp Gly Gln Gly Thr Leu
            100                 105                 110
Val Thr Val Ser Ser Gly Gly Gly Ser Gly Gly Gly Gly Ser Gly
        115                 120                 125
Gly Gly Ser Gly Gly Gly Gly Ser Gly Gly Gly Ser Gly Gly
    130                 135                 140
Gly Gly Ser Gly Gly Gly Ser Glu Val Gln Leu Val Glu Ser Gly
145                 150                 155                 160
Gly Gly Leu Val Gln Pro Gly Gly Ser Leu Arg Leu Ser Cys Thr Phe
                165                 170                 175
Ser Gly Gly Thr Phe Ser Ser Tyr Thr Met Gly Trp Phe Arg Gln Ala
            180                 185                 190
Pro Gly Lys Glu Arg Glu Phe Val Ala Glu Val Arg Trp Gly Gly Val
        195                 200                 205
Thr Thr Tyr Ser Asn Ser Leu Lys Asp Arg Phe Ser Ile Ser Glu Asp
    210                 215                 220
Ser Val Lys Asn Ala Val Tyr Leu Gln Met Asn Ser Leu Lys Pro Glu
225                 230                 235                 240
Asp Thr Ala Val Tyr Tyr Cys Ala Ala Val Arg Gln Met Tyr Met Thr
                245                 250                 255
Val Val Pro Asp Tyr Trp Gly Gln Gly Thr Leu Val Thr Val Ser Ser
            260                 265                 270

<210> SEQ ID NO 434
<211> LENGTH: 272
<212> TYPE: PRT
<213> ORGANISM: Artificial Sequence
<220> FEATURE:
```

<223> OTHER INFORMATION: Nanobody sequence

<400> SEQUENCE: 434

Glu Val Gln Leu Val Glu Ser Gly Gly Gly Leu Val Gln Pro Gly Gly
1               5                   10                  15

Ser Leu Arg Leu Ser Cys Val Ala Ser Gly Asp Val His Lys Ile Asn
            20                  25                  30

Phe Leu Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
    50                  55                  60

Gly Arg Phe Thr Ile Ser Arg Asp Glu Ser Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Phe Ser Arg Ile Tyr Pro Tyr Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Ser Gly Gly Gly Gly Ser Gly Gly Gly Gly Ser Gly Gly Gly
    130                 135                 140

Gly Gly Ser Gly Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
                165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
        195                 200                 205

Thr Thr Tyr Ser Asn Ser Leu Lys Asp Arg Phe Ser Ile Ser Glu Asp
    210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
                245                 250                 255

Val Val Pro Asp Tyr Trp Gly Gln Gly Thr Leu Val Thr Val Ser Ser
            260                 265                 270

<210> SEQ ID NO 435
<211> LENGTH: 272
<212> TYPE: PRT
<213> ORGANISM: Artificial Sequence
<220> FEATURE:
<223> OTHER INFORMATION: Nanobody sequence

<400> SEQUENCE: 435

Glu Val Gln Leu Val Glu Ser Gly Gly Gly Leu Val Gln Pro Gly Gly
1               5                   10                  15

Ser Leu Arg Leu Ser Cys Ala Ala Ser Gly Glu Ile Gly Arg Ile Asn
            20                  25                  30

Phe Tyr Arg Trp Tyr Arg Gln Ala Pro Gly Asn Gln Arg Glu Val Val
        35                  40                  45

Ala Thr Ile Thr Ile Ala Asp Lys Thr Asp Tyr Ala Asp Ser Ala Lys
    50                  55                  60

Gly Arg Phe Thr Ile Ser Arg Asp Glu Ser Arg Asn Met Val Tyr Leu
65                  70                  75                  80

Gln Met Ser Ser Leu Lys Pro Glu Asp Thr Ala Val Tyr Phe Cys His
                85                  90                  95

Ala Gly Ser Arg Leu Tyr Pro Tyr Asp Tyr Trp Gly Gln Gly Thr Leu
            100                 105                 110

Val Thr Val Ser Ser Gly Gly Gly Ser Gly Gly Gly Ser Gly
        115                 120                 125

Gly Gly Gly Ser Gly Gly Gly Ser Gly Gly Gly Ser Gly Gly
    130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
            165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
            195                 200                 205

Thr Thr Tyr Ser Asn Ser Leu Lys Asp Arg Phe Ser Ile Ser Glu Asp
        210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
            245                 250                 255

Val Val Pro Asp Tyr Trp Gly Gln Gly Thr Leu Val Thr Val Ser Ser
            260                 265                 270

<210> SEQ ID NO 436
<211> LENGTH: 272
<212> TYPE: PRT
<213> ORGANISM: Artificial Sequence
<220> FEATURE:
<223> OTHER INFORMATION: Nanobody sequence

<400> SEQUENCE: 436

Glu Val Gln Leu Val Glu Ser Gly Gly Leu Val Gln Pro Gly Gly
1               5                   10                  15

Ser Leu Arg Leu Ser Cys Val Ala Ser Gly Asp Val His Lys Ile Asn
            20                  25                  30

Phe Leu Gly Trp Tyr Arg Gln Ala Pro Gly Lys Glu Arg Glu Lys Val
        35                  40                  45

Ala His Ile Thr Ile Gly Asp Gln Ala Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Gly Ser Arg Ile Tyr Pro Tyr Asp Tyr Trp Gly Gln Gly Thr Leu
            100                 105                 110

Val Thr Val Ser Ser Gly Gly Gly Ser Gly Gly Gly Ser Gly
        115                 120                 125

Gly Gly Gly Ser Gly Gly Gly Ser Gly Gly Gly Ser Gly Gly
    130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
            165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
            195                 200                 205

Thr Thr Tyr Ser Asn Ser Leu Lys Asp Arg Phe Ser Ile Ser Glu Asp
            210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
            245                 250                 255

Val Val Pro Asp Tyr Trp Gly Gln Gly Thr Leu Val Thr Val Ser Ser
            260                 265                 270

<210> SEQ ID NO 437
<211> LENGTH: 272
<212> TYPE: PRT
<213> ORGANISM: Artificial Sequence
<220> FEATURE:
<223> OTHER INFORMATION: Nanobody sequence

<400> SEQUENCE: 437

Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Val His Lys Ile Asn
            20                  25                  30

Ile Leu Gly Trp Tyr Arg Gln Ala Pro Ala Lys Glu Arg Glu Met Val
            35                  40                  45

Ala His Ile Thr Ile Gly Asp Ala Thr Asp Tyr Ala Asp Ser Ala Lys
        50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
            85                  90                  95

Ala Tyr Ser Arg Ile Tyr Pro Tyr Asn Tyr Trp Gly Gln Gly Thr Leu
            100                 105                 110

Val Thr Val Ser Ser Gly Gly Gly Ser Gly Gly Gly Ser Gly
            115                 120                 125

Gly Gly Gly Ser Gly Gly Gly Ser Gly Gly Gly Ser Gly Gly
            130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
            165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
            195                 200                 205

Thr Thr Tyr Ser Asn Ser Leu Lys Asp Arg Phe Ser Ile Ser Glu Asp
            210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
            245                 250                 255

Val Val Pro Asp Tyr Trp Gly Gln Gly Thr Leu Val Thr Val Ser Ser
            260                 265                 270

<210> SEQ ID NO 438
<211> LENGTH: 272
<212> TYPE: PRT
<213> ORGANISM: Artificial Sequence
<220> FEATURE:
<223> OTHER INFORMATION: Nanobody sequence

<400> SEQUENCE: 438

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Lys Ile Asn
            20                  25                  30

Phe Leu Gly Trp Tyr Arg Gln Ala Pro Gly Lys Glu Arg Glu Leu Val
        35                  40                  45

Ala Thr Ile Thr Ile Gly Asp Thr Thr Asp Tyr Ala Asp Ser Ala Lys
    50                  55                  60

Gly Arg Phe Thr Ile Ser Arg Asp Glu Ala Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Gly Ser Arg Leu Tyr Pro Tyr Asn Tyr Trp Gly Gln Gly Thr Leu
            100                 105                 110

Val Thr Val Ser Ser Gly Gly Gly Ser Gly Gly Gly Gly Ser Gly
        115                 120                 125

Gly Gly Gly Ser Gly Gly Gly Gly Ser Gly Gly Gly Gly Ser Gly Gly
        130                 135                 140

Gly Gly Ser Gly Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
                165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
        195                 200                 205

Thr Thr Tyr Ser Asn Ser Leu Lys Asp Arg Phe Ser Ile Ser Glu Asp
    210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
                245                 250                 255

Val Val Pro Asp Tyr Trp Gly Gln Gly Thr Leu Val Thr Val Ser Ser
            260                 265                 270

<210> SEQ ID NO 439
<211> LENGTH: 272
<212> TYPE: PRT
<213> ORGANISM: Artificial Sequence
<220> FEATURE:
<223> OTHER INFORMATION: Nanobody sequence

<400> SEQUENCE: 439

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val His Lys Ile Asn
            20                  25                  30

Phe Leu Gly Trp Tyr Arg Gln Ala Pro Gly Lys Glu Arg Gly Leu Val

```
            35                  40                  45
Ala Thr Ile Thr Ile Gly Asp Thr Thr Asp Tyr Ala Asp Tyr Ala Lys
 50                  55                  60

Gly Arg Phe Thr Ile Ser Arg Asp Glu Ala Arg Asn Met Val Tyr Leu
 65                  70                  75                  80

Gln Met Asn Ser Leu Lys Pro Glu Asp Thr Ala Val Tyr Phe Cys Arg
                 85                  90                  95

Ala Gly Ser Arg Leu Tyr Pro Tyr Asn Tyr Trp Gly Gln Gly Thr Leu
                100                 105                 110

Val Thr Val Ser Ser Gly Gly Gly Ser Gly Gly Gly Ser Gly
                115                 120                 125

Gly Gly Ser Gly Gly Gly Ser Gly Gly Gly Ser Gly Gly
        130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
                165                 170                 175

Ser Gly Gly Thr Phe Ser Ser Tyr Thr Met Gly Trp Phe Arg Gln Ala
                180                 185                 190

Pro Gly Lys Glu Arg Glu Phe Val Ala Glu Val Arg Trp Gly Gly Val
                195                 200                 205

Thr Thr Tyr Ser Asn Ser Leu Lys Asp Arg Phe Ser Ile Ser Glu Asp
                210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
                245                 250                 255

Val Val Pro Asp Tyr Trp Gly Gln Gly Thr Leu Val Thr Val Ser Ser
                260                 265                 270
```

<210> SEQ ID NO 440
<211> LENGTH: 272
<212> TYPE: PRT
<213> ORGANISM: Artificial Sequence
<220> FEATURE:
<223> OTHER INFORMATION: Nanobody sequence

<400> SEQUENCE: 440

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Asp Val His Lys Ile Asn
                 20                  25                  30

Ile Leu Gly Trp Tyr Arg Gln Ala Pro Ala Lys Glu Arg Glu Met Val
             35                  40                  45

Ala His Ile Thr Ile Gly Asp Ala Thr Asp Tyr Ala Asp Ser Ala Lys
 50                  55                  60

Gly Arg Phe Thr Ile Ser Arg Asp Glu Ala Lys Asn Met Val Tyr Leu
 65                  70                  75                  80

Gln Met Asn Ser Leu Lys Pro Glu Asp Thr Ala Val Tyr Leu Cys Arg
                 85                  90                  95

Ala Tyr Ser Arg Ile Tyr Pro Tyr Asn Tyr Trp Gly Gln Gly Thr Leu
                100                 105                 110

Val Thr Val Ser Ser Gly Gly Gly Gly Ser Gly Gly Gly Gly Ser Gly
                115                 120                 125

Gly Gly Ser Gly Gly Gly Gly Ser Gly Gly Gly Gly Ser Gly Gly
```

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
                165                 170                 175

Ser Gly Gly Thr Phe Ser Ser Tyr Thr Met Gly Trp Phe Arg Gln Ala
                180                 185                 190

Pro Gly Lys Glu Arg Glu Phe Val Ala Glu Val Arg Trp Gly Gly Val
                195                 200                 205

Thr Thr Tyr Ser Asn Ser Leu Lys Asp Arg Phe Ser Ile Ser Glu Asp
        210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
                245                 250                 255

Val Val Pro Asp Tyr Trp Gly Gln Gly Thr Leu Val Thr Val Ser Ser
                260                 265                 270

<210> SEQ ID NO 441
<211> LENGTH: 272
<212> TYPE: PRT
<213> ORGANISM: Artificial Sequence
<220> FEATURE:
<223> OTHER INFORMATION: Nanobody sequence

<400> SEQUENCE: 441

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Val Ala Ser Gly Asp Val His Lys Ile Asn Phe Leu Gly Trp Tyr
            180                 185                 190

Arg Gln Ala Pro Gly Lys Glu Arg Glu Lys Val Ala His Ile Ser Ile
        195                 200                 205

Gly Asp Gln Thr Asp Tyr Ala Asp Ser Ala Lys Gly Arg Phe Thr Ile
    210                 215                 220

Ser Arg Asp Glu Ser Lys Asn Met Val Tyr Leu Gln Met Asn Ser Leu

-continued

```
                225                 230                 235                 240

Lys Pro Glu Asp Thr Ala Val Tyr Phe Cys Arg Ala Phe Ser Arg Ile
                245                 250                 255

Tyr Pro Tyr Asp Tyr Trp Gly Gln Gly Thr Leu Val Thr Val Ser Ser
                260                 265                 270

<210> SEQ ID NO 442
<211> LENGTH: 272
<212> TYPE: PRT
<213> ORGANISM: Artificial Sequence
<220> FEATURE:
<223> OTHER INFORMATION: Nanobody sequence

<400> SEQUENCE: 442

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
                20                  25                  30

Thr Met Gly Trp Phe Arg Gln Ala Pro Gly Lys Glu Arg Glu Phe Val
            35                  40                  45

Ala Glu Val Arg Trp Gly Gly Val Thr Thr Tyr Ser Asn Ser Leu Lys
        50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Glu Ile Gly Arg Ile Asn Phe Tyr Arg Trp Tyr
            180                 185                 190

Arg Gln Ala Pro Gly Asn Gln Arg Glu Val Val Ala Thr Ile Thr Ile
        195                 200                 205

Ala Asp Lys Thr Asp Tyr Ala Asp Ser Ala Lys Gly Arg Phe Thr Ile
    210                 215                 220

Ser Arg Asp Glu Ser Arg Asn Met Val Tyr Leu Gln Met Ser Ser Leu
225                 230                 235                 240

Lys Pro Glu Asp Thr Ala Val Tyr Phe Cys His Ala Gly Ser Arg Leu
                245                 250                 255

Tyr Pro Tyr Asp Tyr Trp Gly Gln Gly Thr Leu Val Thr Val Ser Ser
                260                 265                 270

<210> SEQ ID NO 443
<211> LENGTH: 272
<212> TYPE: PRT
<213> ORGANISM: Artificial Sequence
<220> FEATURE:
<223> OTHER INFORMATION: Nanobody sequence

<400> SEQUENCE: 443
```

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
            35                  40                  45

Ala Glu Val Arg Trp Gly Gly Val Thr Thr Tyr Ser Asn Ser Leu Lys
50                      55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser Gly Gly Gly Gly Ser Gly Gly Gly Gly
            130                 135                 140

Ser Gly Gly Gly Gly Ser Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Val Ala Ser Gly Asp Val His Lys Ile Asn Phe Leu Gly Trp Tyr
            180                 185                 190

Arg Gln Ala Pro Gly Lys Glu Arg Glu Lys Val Ala His Ile Thr Ile
            195                 200                 205

Gly Asp Gln Ala Asp Tyr Ala Asp Ser Ala Lys Gly Arg Phe Thr Ile
            210                 215                 220

Ser Arg Asp Glu Ala Lys Asn Met Val Tyr Leu Gln Met Asn Ser Leu
225                 230                 235                 240

Lys Pro Glu Asp Thr Ala Val Tyr Phe Cys Arg Ala Gly Ser Arg Ile
                245                 250                 255

Tyr Pro Tyr Asp Tyr Trp Gly Gln Gly Thr Leu Val Thr Val Ser Ser
            260                 265                 270

<210> SEQ ID NO 444
<211> LENGTH: 272
<212> TYPE: PRT
<213> ORGANISM: Artificial Sequence
<220> FEATURE:
<223> OTHER INFORMATION: Nanobody sequence

<400> SEQUENCE: 444

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
            35                  40                  45

Ala Glu Val Arg Trp Gly Gly Val Thr Thr Tyr Ser Asn Ser Leu Lys
50                      55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser Gly Gly Gly Gly Ser Gly Gly Gly Gly
            130                 135                 140

Ser Gly Gly Gly Gly Ser Gly Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Asp Val His Lys Ile Asn Ile Leu Gly Trp Tyr
                180                 185                 190

Arg Gln Ala Pro Ala Lys Glu Arg Glu Met Val Ala His Ile Thr Ile
                195                 200                 205

Gly Asp Ala Thr Asp Tyr Ala Asp Ser Ala Lys Gly Arg Phe Thr Ile
                210                 215                 220

Ser Arg Asp Glu Ala Lys Asn Met Val Tyr Leu Gln Met Asn Ser Leu
225                 230                 235                 240

Lys Pro Glu Asp Thr Ala Val Tyr Phe Cys Arg Ala Tyr Ser Arg Ile
                245                 250                 255

Tyr Pro Tyr Asn Tyr Trp Gly Gln Gly Thr Leu Val Thr Val Ser Ser
                260                 265                 270

<210> SEQ ID NO 445
<211> LENGTH: 272
<212> TYPE: PRT
<213> ORGANISM: Artificial Sequence
<220> FEATURE:
<223> OTHER INFORMATION: Nanobody sequence

<400> SEQUENCE: 445

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
                20                  25                  30

Thr Met Gly Trp Phe Arg Gln Ala Pro Gly Lys Glu Arg Glu Phe Val
            35                  40                  45

Ala Glu Val Arg Trp Gly Gly Val Thr Thr Tyr Ser Asn Ser Leu Lys
        50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser Gly Gly Gly Gly Ser Gly Gly Gly Gly
            130                 135                 140

Ser Gly Gly Gly Gly Ser Gly Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Ser Val His Lys Ile Asn Phe Leu Gly Trp Tyr
                180                 185                 190

Arg Gln Ala Pro Gly Lys Glu Arg Glu Leu Val Ala Thr Ile Thr Ile
             195                 200                 205

Gly Asp Thr Thr Asp Tyr Ala Asp Ser Ala Lys Gly Arg Phe Thr Ile
         210                 215                 220

Ser Arg Asp Glu Ala Lys Asn Met Val Tyr Leu Gln Met Asn Ser Leu
225                 230                 235                 240

Lys Pro Glu Asp Thr Ala Val Tyr Phe Cys Arg Ala Gly Ser Arg Leu
             245                 250                 255

Tyr Pro Tyr Asn Tyr Trp Gly Gln Gly Thr Leu Val Thr Val Ser Ser
             260                 265                 270

<210> SEQ ID NO 446
<211> LENGTH: 272
<212> TYPE: PRT
<213> ORGANISM: Artificial Sequence
<220> FEATURE:
<223> OTHER INFORMATION: Nanobody sequence

<400> SEQUENCE: 446

Glu Val Gln Leu Val Glu Ser Gly Gly Gly Leu Val Gln Pro Gly Gly
1               5                   10                  15

Ser Leu Arg Leu Ser Cys Thr Phe Ser Gly Thr Phe Ser Ser Tyr
             20                  25                  30

Thr Met Gly Trp Phe Arg Gln Ala Pro Gly Lys Glu Arg Glu Phe Val
         35                  40                  45

Ala Glu Val Arg Trp Gly Gly Val Thr Thr Tyr Ser Asn Ser Leu Lys
     50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
            115                 120                 125

Gly Ser Gly Gly Gly Ser Gly Gly Gly Ser Gly Gly Gly
        130                 135                 140

Ser Gly Gly Gly Ser Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Ser Val His Lys Ile Asn Phe Leu Gly Trp Tyr
            180                 185                 190

Arg Gln Ala Pro Gly Lys Glu Arg Gly Leu Val Ala Thr Ile Thr Ile
             195                 200                 205

Gly Asp Thr Thr Asp Tyr Ala Asp Tyr Ala Lys Gly Arg Phe Thr Ile
         210                 215                 220

Ser Arg Asp Glu Ala Arg Asn Met Val Tyr Leu Gln Met Asn Ser Leu
225                 230                 235                 240

Lys Pro Glu Asp Thr Ala Val Tyr Phe Cys Arg Ala Gly Ser Arg Leu
             245                 250                 255

Tyr Pro Tyr Asn Tyr Trp Gly Gln Gly Thr Leu Val Thr Val Ser Ser
             260                 265                 270

<210> SEQ ID NO 447
<211> LENGTH: 272

```
<212> TYPE: PRT
<213> ORGANISM: Artificial Sequence
<220> FEATURE:
<223> OTHER INFORMATION: Nanobody sequence

<400> SEQUENCE: 447
```

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 |
| Ser | Leu | Arg | Leu | Ser | Cys | Thr | Phe | Ser | Gly | Gly | Thr | Phe | Ser | Ser | Tyr |
| | | | 20 | | | | | 25 | | | | | 30 | |
| Thr | Met | Gly | Trp | Phe | Arg | Gln | Ala | Pro | Gly | Lys | Glu | Arg | Glu | Phe | Val |
| | | 35 | | | | | 40 | | | | | 45 | | |
| Ala | Glu | Val | Arg | Trp | Gly | Gly | Val | Thr | Thr | Tyr | Ser | Asn | Ser | Leu | Lys |
| 50 | | | | | 55 | | | | | 60 | | | | | |
| Asp | Arg | Phe | Ser | Ile | Ser | Glu | Asp | Ser | Val | Lys | Asn | Ala | Val | Tyr | Leu |
| 65 | | | | | 70 | | | | | 75 | | | | | 80 |
| Gln | Met | Asn | Ser | Leu | Lys | Pro | Glu | Asp | Thr | Ala | Val | Tyr | Tyr | Cys | Ala |
| | | | | 85 | | | | | 90 | | | | | 95 | |
| Ala | Val | Arg | Gln | Met | Tyr | Met | Thr | Val | Val | Pro | Asp | Tyr | Trp | Gly | Gln |
| | | | 100 | | | | | 105 | | | | | 110 | | |
| Gly | Thr | Leu | Val | Thr | Val | Ser | Ser | Gly | Gly | Gly | Ser | Gly | Gly | Gly |
| | | | 115 | | | | | 120 | | | | | 125 | | |
| Gly | Ser | Gly | Gly | Gly | Gly | Ser | Gly | Gly | Gly | Ser | Gly | Gly | Gly |
| | 130 | | | | | 135 | | | | | 140 | | | | |
| Ser | Gly | Gly | Gly | Gly | Ser | Gly | Gly | Gly | Gly | Ser | Glu | Val | Gln | Leu | Val |
| 145 | | | | | 150 | | | | | 155 | | | | | 160 |
| Glu | Ser | Gly | Gly | Gly | Leu | Val | Gln | Pro | Gly | Gly | Ser | Leu | Arg | Leu | Ser |
| | | | | 165 | | | | | 170 | | | | | 175 | |
| Cys | Ala | Ala | Ser | Gly | Asp | Val | Tyr | Lys | Ile | Asn | Phe | Leu | Gly | Trp | His |
| | | | 180 | | | | | 185 | | | | | 190 | | |
| Arg | Gln | Ala | Pro | Gly | Lys | Glu | Arg | Glu | Lys | Val | Ala | His | Ile | Thr | Ile |
| | | | 195 | | | | | 200 | | | | | 205 | | |
| Gly | Asp | Ala | Thr | Asp | Tyr | Ala | Asp | Ser | Ala | Lys | Gly | Arg | Phe | Thr | Ile |
| | | 210 | | | | | 215 | | | | | 220 | | | |
| Ser | Arg | Asp | Glu | Ala | Lys | Asn | Met | Val | Tyr | Leu | Gln | Met | Asn | Ser | Leu |
| 225 | | | | | 230 | | | | | 235 | | | | | 240 |
| Lys | Pro | Glu | Asp | Thr | Ala | Val | Tyr | Phe | Cys | Arg | Ala | Gly | Ser | Arg | Ile |
| | | | | 245 | | | | | 250 | | | | | 255 | |
| Tyr | Pro | Tyr | Asp | Tyr | Trp | Gly | Gln | Gly | Thr | Leu | Val | Thr | Val | Ser | Ser |
| | | | 260 | | | | | 265 | | | | | 270 | | |

```
<210> SEQ ID NO 448
<211> LENGTH: 272
<212> TYPE: PRT
<213> ORGANISM: Artificial Sequence
<220> FEATURE:
<223> OTHER INFORMATION: Nanobody sequence

<400> SEQUENCE: 448
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Thr | Phe | Ser | Gly | Gly | Thr | Phe | Ser | Ser | Tyr |
| | | | 20 | | | | | 25 | | | | | 30 | | |
| Thr | Met | Gly | Trp | Phe | Arg | Gln | Ala | Pro | Gly | Lys | Glu | Arg | Glu | Phe | Val |
| | | 35 | | | | | 40 | | | | | 45 | | | |
| Ala | Glu | Val | Arg | Trp | Gly | Gly | Val | Thr | Thr | Tyr | Ser | Asn | Ser | Leu | Lys |
| 50 | | | | | 55 | | | | | 60 | | | | | |

```
Asp Arg Phe Ser Ile Ser Glu Asp Ser Val Lys Asn Ala Val Tyr Leu
 65                  70                  75                  80

Gln Met Asn Ser Leu Lys Pro Glu Asp Thr Ala Val Tyr Tyr Cys Ala
             85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
            115                 120                 125

Gly Ser Gly Gly Gly Gly Ser Gly Gly Gly Ser Gly Gly Gly Gly
        130                 135                 140

Ser Gly Gly Gly Gly Ser Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Glu Val Tyr Lys Ile Asn Phe Leu Gly Trp Tyr
            180                 185                 190

Arg Gln Ala Pro Gly Lys Glu Arg Glu Lys Val Ala His Ile Thr Ile
            195                 200                 205

Ala Asp Ala Ala Asp Tyr Ala Asp Phe Ala Lys Gly Arg Phe Thr Ile
            210                 215                 220

Ser Arg Asp Glu Ala Lys Asn Met Val Tyr Leu Gln Met Asn Ser Leu
225                 230                 235                 240

Arg Pro Glu Asp Thr Ala Val Tyr Phe Cys Arg Ala Gly Ser Arg Ile
                245                 250                 255

Trp Pro Tyr Asp Tyr Trp Gly Gln Gly Thr Leu Val Thr Val Ser Ser
                260                 265                 270
```

<210> SEQ ID NO 449
<211> LENGTH: 272
<212> TYPE: PRT
<213> ORGANISM: Artificial Sequence
<220> FEATURE:
<223> OTHER INFORMATION: Nanobody sequence

<400> SEQUENCE: 449

```
Glu Val Gln Leu Val Glu Ser Gly Gly Gly Leu Val Gln Pro Gly Gly
  1               5                  10                  15

Ser Leu Arg Leu Ser Cys Thr Phe Ser Gly Gly Thr Phe Ser Ser Tyr
             20                  25                  30

Thr Met Gly Trp Phe Arg Gln Ala Pro Gly Lys Glu Arg Glu Phe Val
             35                  40                  45

Ala Glu Val Arg Trp Gly Gly Val Thr Thr Tyr Ser Asn Ser Leu Lys
 50                  55                  60

Asp Arg Phe Ser Ile Ser Glu Asp Ser Val Lys Asn Ala Val Tyr Leu
 65                  70                  75                  80

Gln Met Asn Ser Leu Lys Pro Glu Asp Thr Ala Val Tyr Tyr Cys Ala
             85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
            115                 120                 125

Gly Ser Gly Gly Gly Gly Ser Gly Gly Gly Ser Gly Gly Gly Gly
        130                 135                 140

Ser Gly Gly Gly Gly Ser Gly Gly Gly Ser Glu Val Gln Leu Val
145                 150                 155                 160
```

```
Glu Ser Gly Gly Asp Leu Val Gln Pro Gly Gly Ser Leu Arg Leu Ser
                165                 170                 175

Cys Ala Ala Ser Gly Asp Val His Lys Ile Asn Phe Leu Gly Trp Tyr
            180                 185                 190

Arg Gln Ala Pro Gly Lys Glu Arg Glu Met Val Ala His Ile Thr Ile
        195                 200                 205

Ala Asp Ala Thr Asp Tyr Ala Glu Phe Ala Lys Gly Arg Phe Thr Ile
210                 215                 220

Ser Arg Asp Glu Pro Lys Asn Met Val Tyr Leu Gln Met Asn Ser Leu
225                 230                 235                 240

Lys Pro Glu Asp Thr Ala Val Tyr Leu Cys Arg Ala Gly Ser Arg Ile
                245                 250                 255

Tyr Pro Tyr Asn Tyr Trp Gly Gln Gly Thr Leu Val Thr Val Ser Ser
                260                 265                 270
```

<210> SEQ ID NO 450
<211> LENGTH: 272
<212> TYPE: PRT
<213> ORGANISM: Artificial Sequence
<220> FEATURE:
<223> OTHER INFORMATION: Nanobody sequence

<400> SEQUENCE: 450

```
Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Ser Gly Gly Gly Ser Gly Gly Gly
            130                 135                 140

Ser Gly Gly Gly Gly Ser Gly Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ile Thr Ser Gly Glu Thr Phe Lys Ile Asn Ile Trp Gly Trp Tyr
            180                 185                 190

Arg Gln Ala Pro Gly Lys Gln Arg Glu Leu Val Ala Ser Leu Thr Ile
        195                 200                 205

Gly Gly Ala Thr Asn Tyr Ala Asp Ser Val Lys Gly Arg Phe Thr Ile
    210                 215                 220

Ser Glu Asp Ser Ala Lys Asn Thr Val Tyr Leu Gln Met Asn Ser Leu
225                 230                 235                 240

Lys Pro Glu Asp Thr Ala Val Tyr Phe Cys Asn Ala Lys Ser Arg Leu
                245                 250                 255
```

```
Tyr Pro Tyr Asp Tyr Trp Gly Gln Gly Thr Leu Val Thr Val Ser Ser
            260                 265                 270

<210> SEQ ID NO 451
<211> LENGTH: 272
<212> TYPE: PRT
<213> ORGANISM: Artificial Sequence
<220> FEATURE:
<223> OTHER INFORMATION: Nanobody sequence

<400> SEQUENCE: 451

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Ser Gly Gly Gly Gly
    130                 135                 140

Ser Gly Gly Gly Gly Ser Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Ser Val His Leu Leu Asn Phe Leu Gly Trp Tyr
            180                 185                 190

Arg Gln Ala Pro Gly Lys Glu Arg Glu Met Val Ala His Ile Thr Ile
        195                 200                 205

Ala Asp Ala Thr Asp Tyr Ala His Phe Ala Lys Gly Arg Phe Thr Ile
    210                 215                 220

Ser Arg Asp Glu Ala Lys Asn Met Val Tyr Leu Gln Met Asn Ser Leu
225                 230                 235                 240

Arg Pro Glu Asp Thr Ala Val Tyr Phe Cys Arg Ala Gly Ser Arg Ile
                245                 250                 255

Tyr Pro Tyr Asp Tyr Trp Gly Gln Gly Thr Leu Val Thr Val Ser Ser
            260                 265                 270

<210> SEQ ID NO 452
<211> LENGTH: 272
<212> TYPE: PRT
<213> ORGANISM: Artificial Sequence
<220> FEATURE:
<223> OTHER INFORMATION: Nanobody sequence

<400> SEQUENCE: 452

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
```

```
                    20                  25                  30
Thr Met Gly Trp Phe Arg Gln Ala Pro Gly Lys Glu Arg Glu Phe Val
                35                  40                  45
Ala Glu Val Arg Trp Gly Gly Val Thr Thr Tyr Ser Asn Ser Leu Lys
        50                  55                  60
Asp Arg Phe Ser Ile Ser Glu Asp Ser Val Lys Asn Ala Val Tyr Leu
65                  70                  75                  80
Gln Met Asn Ser Leu Lys Pro Glu Asp Thr Ala Val Tyr Tyr Cys Ala
                85                  90                  95
Ala Val Arg Gln Met Tyr Met Thr Val Val Pro Asp Tyr Trp Gly Gln
            100                 105                 110
Gly Thr Leu Val Thr Val Ser Ser Gly Gly Gly Ser Gly Gly Gly Gly
            115                 120                 125
Gly Ser Gly Gly Gly Gly Ser Gly Gly Gly Ser Gly Gly Gly Gly
        130                 135                 140
Ser Gly Gly Gly Gly Ser Gly Gly Gly Ser Glu Val Gln Leu Val
145                 150                 155                 160
Glu Ser Gly Gly Gly Leu Val Gln Pro Gly Gly Ser Leu Arg Leu Ser
                165                 170                 175
Cys Ile Thr Ser Gly Glu Thr Phe Lys Ile Asn Ile Trp Gly Trp Tyr
            180                 185                 190
Arg Gln Ala Pro Gly Lys Gln Arg Glu Leu Val Ala Ser Leu Thr Ile
        195                 200                 205
Gly Gly Ala Thr Asp Tyr Ala Asp Ser Val Lys Gly Arg Phe Thr Ile
    210                 215                 220
Ser Glu Asp Ser Ala Lys Asn Thr Val Tyr Leu Gln Met Asn Ser Leu
225                 230                 235                 240
Lys Ala Glu Asp Thr Ala Val Tyr Phe Cys Asn Ala Lys Ser Arg Leu
                245                 250                 255
Tyr Pro Tyr Asp Tyr Trp Gly Gln Gly Thr Leu Val Thr Val Ser Ser
            260                 265                 270

<210> SEQ ID NO 453
<211> LENGTH: 272
<212> TYPE: PRT
<213> ORGANISM: Artificial Sequence
<220> FEATURE:
<223> OTHER INFORMATION: Nanobody sequence

<400> SEQUENCE: 453

Glu Val Gln Leu Val Glu Ser Gly Gly Gly Leu Val Gln Pro Gly Gly
1               5                   10                  15
Ser Leu Arg Leu Ser Cys Ala Ala Ser Gly Asp Val His Lys Ile Asn
                20                  25                  30
Ile Leu Gly Trp Tyr Arg Gln Ala Pro Ala Lys Glu Arg Glu Met Val
                35                  40                  45
Ala His Ile Thr Ile Gly Asp Ala Thr Ser Tyr Ala Asp Ser Ala Lys
        50                  55                  60
Gly Arg Phe Thr Ile Ser Arg Asp Glu Ala Lys Asn Met Val Tyr Leu
65                  70                  75                  80
Gln Leu Asn Asn Leu Lys Pro Glu Asp Thr Ala Val Tyr Phe Cys Arg
                85                  90                  95
Ala Tyr Ser Arg Ile Tyr Pro Tyr Asn Tyr Trp Gly Gln Gly Thr Leu
            100                 105                 110
Val Thr Val Ser Ser Gly Gly Gly Gly Ser Gly Gly Gly Gly Ser Gly
```

```
                     115                 120                 125
Gly Gly Gly Ser Gly Gly Gly Ser Gly Gly Gly Ser Gly Gly
            130                 135                 140
Gly Gly Ser Gly Gly Gly Ser Glu Val Gln Leu Val Glu Ser Gly
145                 150                 155                 160
Gly Gly Leu Val Gln Pro Gly Gly Ser Leu Arg Leu Ser Cys Thr Phe
                165                 170                 175
Ser Gly Gly Thr Phe Ser Ser Tyr Thr Met Gly Trp Phe Arg Gln Ala
            180                 185                 190
Pro Gly Lys Glu Arg Glu Phe Val Ala Glu Val Arg Trp Gly Gly Val
            195                 200                 205
Thr Thr Tyr Ser Asn Ser Leu Lys Asp Arg Phe Ser Ile Ser Glu Asp
    210                 215                 220
Ser Val Lys Asn Ala Val Tyr Leu Gln Met Asn Ser Leu Lys Pro Glu
225                 230                 235                 240
Asp Thr Ala Val Tyr Tyr Cys Ala Ala Val Arg Gln Met Tyr Met Thr
                245                 250                 255
Val Val Pro Asp Tyr Trp Gly Gln Gly Thr Leu Val Thr Val Ser Ser
            260                 265                 270

<210> SEQ ID NO 454
<211> LENGTH: 272
<212> TYPE: PRT
<213> ORGANISM: Artificial Sequence
<220> FEATURE:
<223> OTHER INFORMATION: Nanobody sequence

<400> SEQUENCE: 454

Glu Val Gln Leu Val Glu Ser Gly Gly Gly Leu Val Gln Pro Gly Gly
1               5                   10                  15
Ser Leu Arg Leu Ser Cys Val Ala Ser Gly Asp Val His Lys Ile Asn
            20                  25                  30
Phe Leu Gly Trp Tyr Arg Gln Ala Pro Gly Lys Glu Arg Glu Lys Val
        35                  40                  45
Ala His Ile Ser Ile Gly Asp Gln Thr Asp Tyr Ala Asp Ser Ala Lys
    50                  55                  60
Gly Arg Phe Thr Ile Ser Arg Asp Glu Ser Lys Asn Met Val Tyr Leu
65                  70                  75                  80
Gln Met Asn Ser Leu Lys Pro Glu Asp Thr Ala Val Tyr Phe Cys Arg
                85                  90                  95
Ala Phe Ser Arg Ile Tyr Pro Tyr Asp Tyr Trp Gly Gln Gly Thr Leu
            100                 105                 110
Val Thr Val Ser Ser Gly Gly Gly Gly Ser Gly Gly Gly Gly Ser Gly
        115                 120                 125
Gly Gly Ser Gly Gly Gly Gly Ser Gly Gly Gly Ser Gly Gly
    130                 135                 140
Gly Gly Ser Gly Gly Gly Ser Glu Val Gln Leu Val Glu Ser Gly
145                 150                 155                 160
Gly Gly Leu Val Gln Pro Gly Gly Ser Leu Arg Leu Ser Cys Thr Phe
                165                 170                 175
Ser Gly Gly Thr Phe Ser Ser Tyr Thr Met Gly Trp Phe Arg Gln Ala
            180                 185                 190
Pro Gly Lys Glu Arg Glu Phe Val Ala Glu Val Arg Trp Gly Gly Val
            195                 200                 205
Thr Thr Tyr Ser Asn Ser Leu Lys Asp Arg Phe Ser Ile Ser Glu Asp
```

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
            245                 250                 255

Val Val Pro Asp Tyr Trp Gly Gln Gly Thr Leu Val Thr Val Ser Ser
        260                 265                 270

<210> SEQ ID NO 455
<211> LENGTH: 272
<212> TYPE: PRT
<213> ORGANISM: Artificial Sequence
<220> FEATURE:
<223> OTHER INFORMATION: Nanobody sequence

<400> SEQUENCE: 455

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Ser Gly Gly Gly Ser Gly Gly Gly Gly
    130                 135                 140

Ser Gly Gly Gly Ser Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Asp Val His Lys Ile Asn Ile Leu Gly Trp Tyr
            180                 185                 190

Arg Gln Ala Pro Ala Lys Glu Arg Glu Met Val Ala His Ile Thr Ile
        195                 200                 205

Gly Asp Ala Thr Ser Tyr Ala Asp Ser Ala Lys Gly Arg Phe Thr Ile
    210                 215                 220

Ser Arg Asp Glu Ala Lys Asn Met Val Tyr Leu Gln Leu Asn Asn Leu
225                 230                 235                 240

Lys Pro Glu Asp Thr Ala Val Tyr Phe Cys Arg Ala Tyr Ser Arg Ile
                245                 250                 255

Tyr Pro Tyr Asn Tyr Trp Gly Gln Gly Thr Leu Val Thr Val Ser Ser
            260                 265                 270

<210> SEQ ID NO 456
<211> LENGTH: 272
<212> TYPE: PRT
<213> ORGANISM: Artificial Sequence
<220> FEATURE:
<223> OTHER INFORMATION: Nanobody sequence

```
<400> SEQUENCE: 456

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Val Thr Thr Tyr Ser Asn Ser Leu Lys
50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
                100                 105                 110

Gly Thr Leu Val Thr Val Ser Ser Gly Gly Gly Ser Gly Gly Gly
            115                 120                 125

Gly Ser Gly Gly Gly Gly Ser Gly Gly Gly Gly Ser Gly Gly Gly Gly
130                 135                 140

Ser Gly Gly Gly Gly Ser Gly Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Val Ala Ser Gly Asp Val His Lys Ile Asn Phe Leu Gly Trp Tyr
            180                 185                 190

Arg Gln Ala Pro Gly Lys Glu Arg Glu Lys Val Ala His Ile Ser Ile
        195                 200                 205

Gly Asp Gln Thr Asp Tyr Ala Asp Ser Ala Lys Gly Arg Phe Thr Ile
    210                 215                 220

Ser Arg Asp Glu Ser Lys Asn Met Val Tyr Leu Gln Met Asn Ser Leu
225                 230                 235                 240

Lys Pro Glu Asp Thr Ala Val Tyr Phe Cys Arg Ala Phe Ser Arg Ile
                245                 250                 255

Tyr Pro Tyr Asp Tyr Trp Gly Gln Gly Thr Leu Val Thr Val Ser Ser
            260                 265                 270

<210> SEQ ID NO 457
<211> LENGTH: 272
<212> TYPE: PRT
<213> ORGANISM: Artificial Sequence
<220> FEATURE:
<223> OTHER INFORMATION: Nanobody sequence

<400> SEQUENCE: 457

Glu Val Gln Leu Val Glu Ser Gly Gly Asp Leu Val Gln Pro Gly Gly
1               5                   10                  15

Ser Leu Arg Leu Ser Cys Ala Ala Ser Gly Asp Val His Lys Ile Asn
            20                  25                  30

Phe Leu Gly Trp Tyr Arg Gln Ala Pro Gly Lys Glu Arg Glu Met Val
        35                  40                  45

Ala His Ile Thr Ile Ala Asp Ala Thr Asp Tyr Ala Glu Phe Ala Lys
50                  55                  60

Gly Arg Phe Thr Ile Ser Arg Asp Glu Pro Lys Asn Met Val Tyr Leu
65                  70                  75                  80
```

Gln Met Asn Ser Leu Lys Pro Glu Asp Thr Ala Val Tyr Leu Cys Arg
                85                  90                  95

Ala Gly Ser Arg Ile Tyr Pro Tyr Asn Tyr Trp Gly Gln Gly Thr Leu
            100                 105                 110

Val Thr Val Ser Ser Gly Gly Gly Ser Gly Gly Gly Ser Gly
        115                 120                 125

Gly Gly Gly Ser Gly Gly Gly Ser Gly Gly Gly Ser Gly Gly
        130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Thr Phe
                165                 170                 175

Ser Gly Gly Thr Phe Ser Ser Tyr Thr Met Gly Trp Phe Arg Gln Ala
            180                 185                 190

Pro Gly Lys Glu Arg Glu Phe Val Ala Glu Val Arg Trp Gly Gly Val
            195                 200                 205

Thr Thr Tyr Ser Asn Ser Leu Lys Asp Arg Phe Ser Ile Ser Glu Asp
    210                 215                 220

Ser Val Lys Asn Ala Val Tyr Leu Gln Met Asn Ser Leu Lys Pro Glu
225                 230                 235                 240

Asp Thr Ala Val Tyr Tyr Cys Ala Ala Val Arg Gln Met Tyr Met Thr
                245                 250                 255

Val Val Pro Asp Tyr Trp Gly Gln Gly Thr Leu Val Thr Val Ser Ser
            260                 265                 270

<210> SEQ ID NO 458
<211> LENGTH: 272
<212> TYPE: PRT
<213> ORGANISM: Artificial Sequence
<220> FEATURE:
<223> OTHER INFORMATION: Nanobody sequence

<400> SEQUENCE: 458

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Ser Gly Gly Gly Gly
        130                 135                 140

Ser Gly Gly Gly Gly Ser Gly Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

```
Cys Ala Ala Ser Gly Asp Val His Lys Ile Asn Ile Leu Gly Trp Tyr
            180                 185                 190

Arg Gln Ala Pro Ala Lys Glu Arg Glu Met Val Ala His Ile Thr Ile
        195                 200                 205

Gly Asp Ala Thr Asp Tyr Ala Asp Ser Ala Lys Gly Arg Phe Thr Ile
        210                 215                 220

Ser Arg Asp Glu Ala Lys Asn Met Val Tyr Leu Gln Met Asn Ser Leu
225                 230                 235                 240

Lys Pro Glu Asp Thr Ala Val Tyr Leu Cys Arg Ala Tyr Ser Arg Ile
                245                 250                 255

Tyr Pro Tyr Asn Tyr Trp Gly Gln Gly Thr Leu Val Thr Val Ser Ser
            260                 265                 270
```

<210> SEQ ID NO 459
<211> LENGTH: 272
<212> TYPE: PRT
<213> ORGANISM: Artificial Sequence
<220> FEATURE:
<223> OTHER INFORMATION: Nanobody sequence

<400> SEQUENCE: 459

```
Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Glu Val Gln Leu Val
145                 150                 155                 160

Glu Ser Gly Gly Gly Leu Val Gln Pro Gly Gly Ser Leu Lys Leu Ser
                165                 170                 175

Cys Ala Ala Ser Gly Ala Val His Lys Ile Asn Phe Leu Gly Trp Tyr
            180                 185                 190

Arg Gln Thr Pro Glu Lys Glu Arg Glu Met Val Ala Thr Ile Thr Ile
        195                 200                 205

Gly Asp Glu Val Asp Tyr Ala Asp Ser Ala Lys Gly Arg Phe Thr Ile
        210                 215                 220

Ser Arg Asp Glu Ala Lys Asn Met Val Tyr Leu Gln Met Thr Ser Leu
225                 230                 235                 240

Lys Pro Glu Asp Thr Ala Val Tyr Val Cys Arg Ala Gly Ser Arg Leu
                245                 250                 255

Tyr Pro Tyr Asn Tyr Trp Gly Gln Gly Thr Leu Val Thr Val Ser Ser
            260                 265                 270
```

```
<210> SEQ ID NO 460
<211> LENGTH: 422
<212> TYPE: PRT
<213> ORGANISM: Artificial Sequence
<220> FEATURE:
<223> OTHER INFORMATION: Nanobody sequence

<400> SEQUENCE: 460

Glu Val Gln Leu Val Glu Ser Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Val Ala Ser Gly Asp Val His Lys Ile Asn Phe Leu Gly Trp Tyr
            180                 185                 190

Arg Gln Ala Pro Gly Lys Glu Arg Glu Lys Val Ala His Ile Ser Ile
        195                 200                 205

Gly Asp Gln Thr Asp Tyr Ala Asp Ser Ala Lys Gly Arg Phe Thr Ile
    210                 215                 220

Ser Arg Asp Glu Ser Lys Asn Met Val Tyr Leu Gln Met Asn Ser Leu
225                 230                 235                 240

Lys Pro Glu Asp Thr Ala Val Tyr Phe Cys Arg Ala Phe Ser Arg Ile
                245                 250                 255

Tyr Pro Tyr Asp Tyr Trp Gly Gln Gly Thr Leu Val Thr Val Ser Ser
            260                 265                 270

Gly Gly Gly Gly Ser Gly Gly Gly Ser Gly Gly Gly Gly Ser Gly
        275                 280                 285

Gly Gly Gly Ser Gly Gly Gly Gly Ser Gly Gly Gly Gly Ser Gly Gly
    290                 295                 300

Gly Gly Ser Glu Val Gln Leu Val Glu Ser Gly Gly Gly Leu Val Gln
305                 310                 315                 320

Pro Gly Asn Ser Leu Arg Leu Ser Cys Ala Ala Ser Gly Phe Thr Phe
                325                 330                 335

Ser Ser Phe Gly Met Ser Trp Val Arg Gln Ala Pro Gly Lys Gly Leu
            340                 345                 350

Glu Trp Val Ser Ser Ile Ser Gly Ser Gly Ser Asp Thr Leu Tyr Ala
        355                 360                 365
```

```
Asp Ser Val Lys Gly Arg Phe Thr Ile Ser Arg Asp Asn Ala Lys Thr
370                 375                 380

Thr Leu Tyr Leu Gln Met Asn Ser Leu Arg Pro Glu Asp Thr Ala Val
385                 390                 395                 400

Tyr Tyr Cys Thr Ile Gly Gly Ser Leu Ser Arg Ser Ser Gln Gly Thr
                405                 410                 415

Leu Val Thr Val Ser Ser
                420

<210> SEQ ID NO 461
<211> LENGTH: 422
<212> TYPE: PRT
<213> ORGANISM: Artificial Sequence
<220> FEATURE:
<223> OTHER INFORMATION: Nanobody sequence

<400> SEQUENCE: 461

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Ser Gly Gly Gly Ser Gly Gly Gly Gly
        130                 135                 140

Ser Gly Gly Gly Ser Gly Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ile Thr Ser Gly Glu Thr Phe Lys Ile Asn Ile Trp Gly Trp Tyr
            180                 185                 190

Arg Gln Ala Pro Gly Lys Gln Arg Glu Leu Val Ala Ser Leu Thr Ile
        195                 200                 205

Gly Gly Ala Thr Asn Tyr Ala Asp Ser Val Lys Gly Arg Phe Thr Ile
210                 215                 220

Ser Glu Asp Ser Ala Lys Asn Thr Val Tyr Leu Gln Met Asn Ser Leu
225                 230                 235                 240

Lys Pro Glu Asp Thr Ala Val Tyr Phe Cys Asn Ala Lys Ser Arg Leu
                245                 250                 255

Tyr Pro Tyr Asp Tyr Trp Gly Gln Gly Thr Leu Val Thr Val Ser Ser
            260                 265                 270

Gly Gly Gly Gly Ser Gly Gly Gly Gly Ser Gly Gly Gly Gly Ser Gly
        275                 280                 285

Gly Gly Gly Ser Gly Gly Gly Gly Ser Gly Gly Gly Gly Ser Gly Gly
        290                 295                 300
```

Gly Gly Ser Glu Val Gln Leu Val Glu Ser Gly Gly Leu Val Gln
305                 310                 315                 320

Pro Gly Asn Ser Leu Arg Leu Ser Cys Ala Ala Ser Gly Phe Thr Phe
                325                 330                 335

Ser Ser Phe Gly Met Ser Trp Val Arg Gln Ala Pro Gly Lys Gly Leu
            340                 345                 350

Glu Trp Val Ser Ser Ile Ser Gly Ser Gly Ser Asp Thr Leu Tyr Ala
        355                 360                 365

Asp Ser Val Lys Gly Arg Phe Thr Ile Ser Arg Asp Asn Ala Lys Thr
370                 375                 380

Thr Leu Tyr Leu Gln Met Asn Ser Leu Arg Pro Glu Asp Thr Ala Val
385                 390                 395                 400

Tyr Tyr Cys Thr Ile Gly Gly Ser Leu Ser Arg Ser Ser Gln Gly Thr
                405                 410                 415

Leu Val Thr Val Ser Ser
            420

<210> SEQ ID NO 462
<211> LENGTH: 270
<212> TYPE: PRT
<213> ORGANISM: Artificial Sequence
<220> FEATURE:
<223> OTHER INFORMATION: Nanobody sequence

<400> SEQUENCE: 462

Glu Val Gln Leu Val Glu Ser Gly Gly Gly Leu Val Gln Ala Gly Gly
1               5                   10                  15

Ser Leu Arg Leu Ser Cys Ala Ala Ser Gly Ile Thr Phe Ser Ile Asn
            20                  25                  30

Thr Met Gly Trp Tyr Arg Gln Ala Pro Gly Lys Gln Arg Glu Leu Val
        35                  40                  45

Ala Leu Ile Ser Ser Ile Gly Asp Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Lys
                85                  90                  95

Arg Phe Arg Thr Ala Ala Gln Gly Thr Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Gly Gly Gly Gly Ser Gly Gly Gly Gly Ser Gly
    130                 135                 140

Gly Gly Gly Ser Gly Gly Gly Gly Ser Glu Val Gln Leu Val Glu Ser
145                 150                 155                 160

Gly Gly Gly Leu Val Gln Pro Gly Gly Ser Leu Arg Leu Ser Cys Val
                165                 170                 175

Ala Ser Gly Asp Val His Lys Ile Asn Phe Leu Gly Trp Tyr Arg Gln
            180                 185                 190

Ala Pro Gly Lys Glu Arg Glu Lys Val Ala His Ile Ser Ile Gly Asp
        195                 200                 205

Gln Thr Asp Tyr Ala Asp Ser Ala Lys Gly Arg Phe Thr Ile Ser Arg
    210                 215                 220

Asp Glu Ser Lys Asn Met Val Tyr Leu Gln Met Asn Ser Leu Lys Pro
225                 230                 235                 240

Glu Asp Thr Ala Val Tyr Phe Cys Arg Ala Phe Ser Arg Ile Tyr Pro
            245                 250                 255

Tyr Asp Tyr Trp Gly Gln Gly Thr Leu Val Thr Val Ser Ser
260                 265                 270

<210> SEQ ID NO 463
<211> LENGTH: 270
<212> TYPE: PRT
<213> ORGANISM: Artificial Sequence
<220> FEATURE:
<223> OTHER INFORMATION: Nanobody sequence

<400> SEQUENCE: 463

Glu Val Gln Leu Val Glu Ser Gly Gly Gly Leu Val Gln Pro Gly Gly
1               5                   10                  15

Ser Leu Arg Leu Ser Cys Val Ala Ser Gly Asp Val His Lys Ile Asn
            20                  25                  30

Phe Leu Gly Trp Tyr Arg Gln Ala Pro Gly Lys Glu Arg Glu Lys Val
        35                  40                  45

Ala His Ile Ser Ile Gly Asp Gln Thr Asp Tyr Ala Asp Ser Ala Lys
    50                  55                  60

Gly Arg Phe Thr Ile Ser Arg Asp Glu Ser Lys Asn Met Val Tyr Leu
65                  70                  75                  80

Gln Met Asn Ser Leu Lys Pro Glu Asp Thr Ala Val Tyr Phe Cys Arg
                85                  90                  95

Ala Phe Ser Arg Ile Tyr Pro Tyr Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Gly Gly Gly Gly Ser Glu Val Gln Leu Val Glu Ser Gly
145                 150                 155                 160

Gly Gly Leu Val Gln Ala Gly Gly Ser Leu Arg Leu Ser Cys Ala Ala
                165                 170                 175

Ser Gly Ile Thr Phe Ser Ile Asn Thr Met Gly Trp Tyr Arg Gln Ala
            180                 185                 190

Pro Gly Lys Gln Arg Glu Leu Val Ala Leu Ile Ser Ser Ile Gly Asp
        195                 200                 205

Thr Tyr Tyr Ala Asp Ser Val Lys Gly Arg Phe Thr Ile Ser Arg Asp
    210                 215                 220

Asn Ala Lys Asn Thr Val Tyr Leu Gln Met Asn Ser Leu Lys Pro Glu
225                 230                 235                 240

Asp Thr Ala Val Tyr Tyr Cys Lys Arg Phe Arg Thr Ala Ala Gln Gly
                245                 250                 255

Thr Asp Tyr Trp Gly Gln Gly Thr Leu Val Thr Val Ser Ser
            260                 265                 270

<210> SEQ ID NO 464
<211> LENGTH: 439
<212> TYPE: PRT
<213> ORGANISM: Artificial Sequence
<220> FEATURE:
<223> OTHER INFORMATION: Nanobody sequence

<400> SEQUENCE: 464

Glu Val Gln Leu Val Glu Ser Gly Gly Gly Leu Val Gln Ala Gly Gly
1               5                   10                  15

```
Ser Leu Arg Leu Ser Cys Ala Ala Ser Gly Arg Thr Phe Ser Ser Tyr
         20                  25                  30

Val Met Gly Trp Phe Arg Gln Ala Thr Gly Lys Glu Arg Glu Phe Val
         35                  40                  45

Ala Thr Ile Ala Trp Asp Ser Gly Ser Thr Tyr Tyr Ala Asp Ser Val
 50                  55                  60

Lys Gly Arg Phe Thr Ile Ser Arg Asp Asn Ala Lys Asn Thr Val His
 65                  70                  75                  80

Leu Gln Met Asn Ser Leu Lys Pro Glu Asp Thr Ala Val Tyr Tyr Cys
                 85                  90                  95

Ala Ala Ser Tyr Asn Val Tyr Tyr Asn Asn Tyr Tyr Pro Ile Ser
                100                 105                 110

Arg Asp Glu Tyr Asp Tyr Trp Gly Gln Gly Thr Leu Val Thr Val Ser
            115                 120                 125

Ser Gly Gly Gly Gly Ser Gly Gly Gly Gly Ser Gly Gly Gly Gly Ser
130                 135                 140

Gly Gly Gly Gly Ser Gly Gly Gly Gly Ser Gly Gly Gly Gly Ser Gly
145                 150                 155                 160

Gly Gly Gly Ser Glu Val Gln Leu Val Glu Ser Gly Gly Gly Ser Val
            165                 170                 175

Gln Ala Gly Gly Ser Leu Arg Leu Ser Cys Ala Ala Ser Gly Asp Thr
            180                 185                 190

Tyr Gly Ser Tyr Trp Met Gly Trp Phe Arg Gln Ala Pro Gly Lys Glu
            195                 200                 205

Arg Glu Gly Val Ala Ala Ile Asn Arg Gly Gly Gly Tyr Thr Val Tyr
210                 215                 220

Ala Asp Ser Val Lys Gly Arg Phe Thr Ile Ser Arg Asp Thr Ala Lys
225                 230                 235                 240

Asn Thr Val Tyr Leu Gln Met Asn Ser Leu Arg Pro Asp Asp Thr Ala
            245                 250                 255

Asp Tyr Tyr Cys Ala Ala Ser Gly Val Leu Gly Gly Leu His Glu Asp
            260                 265                 270

Trp Phe Asn Tyr Trp Gly Gln Gly Thr Leu Val Thr Val Ser Ser Gly
            275                 280                 285

Gly Gly Gly Ser Gly Gly Gly Gly Ser Gly Gly Gly Gly Ser Gly Gly
290                 295                 300

Gly Gly Ser Gly Gly Gly Gly Ser Gly Gly Gly Gly Ser Gly Gly Gly
305                 310                 315                 320

Gly Ser Glu Val Gln Leu Val Glu Ser Gly Gly Gly Leu Val Gln Pro
            325                 330                 335

Gly Gly Ser Leu Arg Leu Ser Cys Val Ala Ser Gly Asp Val His Lys
            340                 345                 350

Ile Asn Phe Leu Gly Trp Tyr Arg Gln Ala Pro Gly Lys Glu Arg Glu
            355                 360                 365

Lys Val Ala His Ile Ser Ile Gly Asp Gln Thr Asp Tyr Ala Asp Ser
 370                 375                 380

Ala Lys Gly Arg Phe Thr Ile Ser Arg Asp Glu Ser Lys Asn Met Val
385                 390                 395                 400

Tyr Leu Gln Met Asn Ser Leu Lys Pro Glu Asp Thr Ala Val Tyr Phe
            405                 410                 415

Cys Arg Ala Phe Ser Arg Ile Tyr Pro Tyr Asp Tyr Trp Gly Gln Gly
            420                 425                 430
```

Thr Leu Val Thr Val Ser Ser
        435

<210> SEQ ID NO 465
<211> LENGTH: 443
<212> TYPE: PRT
<213> ORGANISM: Artificial Sequence
<220> FEATURE:
<223> OTHER INFORMATION: Nanobody sequence

<400> SEQUENCE: 465

Glu Val Gln Leu Val Glu Ser Gly Gly Gly Ser Val Gln Ala Gly Gly
1               5                   10                  15

Ser Leu Arg Leu Ser Cys Ala Ala Ser Gly Tyr Thr Ile Gly Pro Tyr
            20                  25                  30

Cys Met Gly Trp Phe Arg Gln Ala Pro Gly Lys Glu Arg Glu Gly Val
        35                  40                  45

Ala Ala Ile Asn Met Gly Gly Ile Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Leu Met Asn Ser Leu Glu Pro Glu Asp Thr Ala Ile Tyr Tyr Cys
                85                  90                  95

Ala Ala Asp Ser Thr Ile Tyr Ala Ser Tyr Tyr Glu Cys Gly His Gly
                100                 105                 110

Leu Ser Thr Gly Gly Tyr Gly Tyr Asp Ser Trp Gly Gln Gly Thr Leu
            115                 120                 125

Val Thr Val Ser Ser Gly Gly Gly Ser Gly Gly Gly Gly Ser Gly
    130                 135                 140

Gly Gly Gly Ser Gly Gly Gly Gly Ser Gly Gly Gly Gly Ser Gly Gly
145                 150                 155                 160

Gly Gly Ser Gly Gly Gly Gly Ser Glu Val Gln Leu Val Glu Ser Gly
                165                 170                 175

Gly Gly Ser Val Gln Ala Gly Gly Ser Leu Arg Leu Ser Cys Ala Ala
                180                 185                 190

Ser Gly Asp Thr Tyr Gly Ser Tyr Trp Met Gly Trp Phe Arg Gln Ala
            195                 200                 205

Pro Gly Lys Glu Arg Glu Gly Val Ala Ala Ile Asn Arg Gly Gly Gly
        210                 215                 220

Tyr Thr Val Tyr Ala Asp Ser Val Lys Gly Arg Phe Thr Ile Ser Arg
225                 230                 235                 240

Asp Thr Ala Lys Asn Thr Val Tyr Leu Gln Met Asn Ser Leu Arg Pro
                245                 250                 255

Asp Asp Thr Ala Asp Tyr Tyr Cys Ala Ala Ser Gly Val Leu Gly Gly
                260                 265                 270

Leu His Glu Asp Trp Phe Asn Tyr Trp Gly Gln Gly Thr Leu Val Thr
            275                 280                 285

Val Ser Ser Gly Gly Gly Gly Ser Gly Gly Gly Ser Gly Gly Gly
        290                 295                 300

Gly Ser Gly Gly Gly Gly Ser Gly Gly Gly Gly Ser Gly Gly Gly Gly
305                 310                 315                 320

Ser Gly Gly Gly Gly Ser Glu Val Gln Leu Val Glu Ser Gly Gly Gly
                325                 330                 335

Leu Val Gln Pro Gly Gly Ser Leu Arg Leu Ser Cys Val Ala Ser Gly
            340                 345                 350

```
Asp Val His Lys Ile Asn Phe Leu Gly Trp Tyr Arg Gln Ala Pro Gly
            355                 360                 365

Lys Glu Arg Glu Lys Val Ala His Ile Ser Ile Gly Asp Gln Thr Asp
        370                 375                 380

Tyr Ala Asp Ser Ala Lys Gly Arg Phe Thr Ile Ser Arg Asp Glu Ser
385                 390                 395                 400

Lys Asn Met Val Tyr Leu Gln Met Asn Ser Leu Lys Pro Glu Asp Thr
            405                 410                 415

Ala Val Tyr Phe Cys Arg Ala Phe Ser Arg Ile Tyr Pro Tyr Asp Tyr
        420                 425                 430

Trp Gly Gln Gly Thr Leu Val Thr Val Ser Ser
            435                 440

<210> SEQ ID NO 466
<211> LENGTH: 449
<212> TYPE: PRT
<213> ORGANISM: Artificial Sequence
<220> FEATURE:
<223> OTHER INFORMATION: Nanobody sequence

<400> SEQUENCE: 466

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Val Met Gly Trp Phe Arg Gln Ala Thr Gly Lys Glu Arg Glu Phe Val
        35                  40                  45

Ala Thr Ile Ala Trp Asp Ser Gly Ser Thr Tyr Tyr Ala Asp Ser Val
    50                  55                  60

Lys Gly Arg Phe Thr Ile Ser Arg Asp Asn Ala Lys Asn Thr Val His
65                  70                  75                  80

Leu Gln Met Asn Ser Leu Lys Pro Glu Asp Thr Ala Val Tyr Tyr Cys
            85                  90                  95

Ala Ala Ser Tyr Asn Val Tyr Tyr Asn Asn Tyr Tyr Pro Ile Ser
                100                 105                 110

Arg Asp Glu Tyr Asp Tyr Trp Gly Gln Gly Thr Leu Val Thr Val Ser
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Ser Gly Gly Gly Gly Ser Gly
145                 150                 155                 160

Gly Gly Gly Ser Glu Val Gln Leu Val Glu Ser Gly Gly Gly Ser Val
                165                 170                 175

Gln Ala Gly Gly Ser Leu Arg Leu Ser Cys Ala Ala Ser Gly Tyr Thr
        180                 185                 190

Ile Gly Pro Tyr Cys Met Gly Trp Phe Arg Gln Ala Pro Gly Lys Glu
    195                 200                 205

Arg Glu Gly Val Ala Ala Ile Asn Met Gly Gly Ile Thr Tyr Tyr
210                 215                 220

Ala Asp Ser Val Lys Gly Arg Phe Thr Ile Ser Gln Asp Asn Ala Lys
225                 230                 235                 240

Asn Thr Val Tyr Leu Leu Met Asn Ser Leu Glu Pro Glu Asp Thr Ala
            245                 250                 255

Ile Tyr Tyr Cys Ala Ala Asp Ser Thr Ile Tyr Ala Ser Tyr Tyr Glu
        260                 265                 270
```

Cys Gly His Gly Leu Ser Thr Gly Tyr Gly Tyr Asp Ser Trp Gly
            275                 280                 285

Gln Gly Thr Leu Val Thr Val Ser Ser Gly Gly Gly Ser Gly Gly
        290                 295                 300

Gly Gly Ser Gly Gly Gly Ser Gly Gly Gly Ser Gly Gly Gly
305                 310                 315                 320

Gly Ser Gly Gly Gly Ser Gly Gly Gly Ser Glu Val Gln Leu
            325                 330                 335

Val Glu Ser Gly Gly Gly Leu Val Gln Pro Gly Gly Ser Leu Arg Leu
                340                 345                 350

Ser Cys Val Ala Ser Gly Asp Val His Lys Ile Asn Phe Leu Gly Trp
            355                 360                 365

Tyr Arg Gln Ala Pro Gly Lys Glu Arg Glu Lys Val Ala His Ile Ser
        370                 375                 380

Ile Gly Asp Gln Thr Asp Tyr Ala Asp Ser Ala Lys Gly Arg Phe Thr
385                 390                 395                 400

Ile Ser Arg Asp Glu Ser Lys Asn Met Val Tyr Leu Gln Met Asn Ser
                405                 410                 415

Leu Lys Pro Glu Asp Thr Ala Val Tyr Phe Cys Arg Ala Phe Ser Arg
            420                 425                 430

Ile Tyr Pro Tyr Asp Tyr Trp Gly Gln Gly Thr Leu Val Thr Val Ser
        435                 440                 445

Ser

<210> SEQ ID NO 467
<211> LENGTH: 422
<212> TYPE: PRT
<213> ORGANISM: Artificial Sequence
<220> FEATURE:
<223> OTHER INFORMATION: Nanobody sequence

<400> SEQUENCE: 467

Asp Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Gly Gly Gly Gly Ser Gly Gly Gly Gly
130                 135                 140

Ser Gly Gly Gly Gly Ser Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Asp Val His Lys Ile Asn Ile Leu Gly Trp Tyr

```
                180             185             190
Arg Gln Ala Pro Ala Lys Glu Arg Glu Met Val Ala His Ile Thr Ile
            195             200             205
Gly Asp Ala Thr Asp Tyr Ala Asp Ser Ala Lys Gly Arg Phe Thr Ile
            210             215             220
Ser Arg Asp Glu Ala Lys Asn Met Val Tyr Leu Gln Met Asn Ser Leu
225             230             235             240
Lys Pro Glu Asp Thr Ala Val Tyr Phe Cys Arg Ala Tyr Ser Arg Ile
            245             250             255
Tyr Pro Tyr Asn Tyr Trp Gly Gln Gly Thr Leu Val Thr Val Ser Ser
            260             265             270
Gly Gly Gly Gly Ser Gly Gly Gly Ser Gly Gly Gly Ser Gly
            275             280             285
Gly Gly Gly Ser Gly Gly Gly Ser Gly Gly Gly Ser Gly Gly
            290             295             300
Gly Gly Ser Glu Val Gln Leu Val Glu Ser Gly Gly Leu Val Gln
305             310             315             320
Pro Gly Asn Ser Leu Arg Leu Ser Cys Ala Ala Ser Gly Phe Thr Phe
            325             330             335
Ser Ser Phe Gly Met Ser Trp Val Arg Gln Ala Pro Gly Lys Gly Leu
            340             345             350
Glu Trp Val Ser Ser Ile Ser Gly Ser Gly Ser Asp Thr Leu Tyr Ala
            355             360             365
Asp Ser Val Lys Gly Arg Phe Thr Ile Ser Arg Asp Asn Ala Lys Thr
            370             375             380
Thr Leu Tyr Leu Gln Met Asn Ser Leu Arg Pro Glu Asp Thr Ala Val
385             390             395             400
Tyr Tyr Cys Thr Ile Gly Gly Ser Leu Ser Arg Ser Gln Gly Thr
            405             410             415
Leu Val Thr Val Ser Ser
            420

<210> SEQ ID NO 468
<211> LENGTH: 272
<212> TYPE: PRT
<213> ORGANISM: Artificial Sequence
<220> FEATURE:
<223> OTHER INFORMATION: Nanobody sequence

<400> SEQUENCE: 468

Asp Val Gln Leu Val Glu Ser Gly Gly Gly Leu Val Gln Pro Gly Gly
1               5               10              15
Ser Leu Arg Leu Ser Cys Thr Phe Ser Gly Gly Thr Phe Ser Ser Tyr
            20              25              30
Thr Met Gly Trp Phe Arg Gln Ala Pro Gly Lys Glu Arg Glu Phe Val
            35              40              45
Ala Glu Val Arg Trp Gly Gly Val Thr Thr Tyr Ser Asn Ser Leu Lys
            50              55              60
Asp Arg Phe Ser Ile Ser Glu Asp Ser Val Lys Asn Ala Val Tyr Leu
65              70              75              80
Gln Met Asn Ser Leu Lys Pro Glu Asp Thr Ala Val Tyr Tyr Cys Ala
            85              90              95
Ala Val Arg Gln Met Tyr Met Thr Val Val Pro Asp Tyr Trp Gly Gln
            100             105             110
Gly Thr Leu Val Thr Val Ser Ser Gly Gly Gly Gly Ser Gly Gly Gly
```

```
            115                 120                 125
Gly Ser Gly Gly Gly Ser Gly Gly Gly Ser Gly Gly Gly
    130                 135                 140

Ser Gly Gly Gly Ser Gly Gly Gly Ser Glu Val Gln Leu Val
145                 150                 155                 160

Glu Ser Gly Gly Gly Leu Val Gln Pro Gly Ser Leu Arg Leu Ser
                165                 170                 175

Cys Val Ala Ser Gly Asp Val His Lys Ile Asn Phe Leu Gly Trp Tyr
            180                 185                 190

Arg Gln Ala Pro Gly Lys Glu Arg Glu Lys Val Ala His Ile Ser Ile
        195                 200                 205

Gly Asp Gln Thr Asp Tyr Ala Asp Ser Ala Lys Gly Arg Phe Thr Ile
    210                 215                 220

Ser Arg Asp Glu Ser Lys Asn Met Val Tyr Leu Gln Met Asn Ser Leu
225                 230                 235                 240

Lys Pro Glu Asp Thr Ala Val Tyr Phe Cys Arg Ala Phe Ser Arg Ile
                245                 250                 255

Tyr Pro Tyr Asp Tyr Trp Gly Gln Gly Thr Leu Val Thr Val Ser Ser
            260                 265                 270

<210> SEQ ID NO 469
<211> LENGTH: 429
<212> TYPE: PRT
<213> ORGANISM: Artificial Sequence
<220> FEATURE:
<223> OTHER INFORMATION: Nanobody sequence

<400> SEQUENCE: 469

Asp Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Gln Val Thr Val Ser Ser Gly
        115                 120                 125

Gly Gly Gly Ser Gly Gly Gly Gly Ser Gly Gly Gly Ser Gly Gly
    130                 135                 140

Gly Gly Ser Gly Gly Gly Gly Ser Gly Gly Gly Ser Gly Gly Gly
145                 150                 155                 160

Gly Ser Glu Val Gln Leu Val Glu Ser Gly Gly Gly Leu Val Gln Pro
                165                 170                 175

Gly Gly Ser Leu Arg Leu Ser Cys Ala Ala Ser Gly Asp Val His Lys
            180                 185                 190

Ile Asn Ile Leu Gly Trp Tyr Arg Gln Ala Pro Ala Lys Glu Arg Glu
        195                 200                 205

Met Val Ala His Ile Thr Ile Gly Asp Ala Thr Asp Tyr Ala Asp Ser
```

```
            210                 215                 220
Ala Lys Gly Arg Phe Thr Ile Ser Arg Asp Glu Ala Lys Asn Met Val
225                 230                 235                 240

Tyr Leu Gln Met Asn Ser Leu Lys Pro Glu Asp Thr Ala Val Tyr Phe
                245                 250                 255

Cys Arg Ala Tyr Ser Arg Ile Tyr Pro Tyr Asn Tyr Trp Gly Gln Gly
                260                 265                 270

Thr Leu Val Thr Val Ser Ser Gly Gly Gly Ser Gly Gly Gly Gly
            275                 280                 285

Ser Gly Gly Gly Gly Ser Gly Gly Gly Gly Ser Gly Gly Gly Gly Ser
            290                 295                 300

Gly Gly Gly Gly Ser Gly Gly Gly Ser Glu Val Gln Leu Val Glu
305                 310                 315                 320

Ser Gly Gly Gly Leu Val Gln Pro Gly Asn Ser Leu Arg Leu Ser Cys
                325                 330                 335

Ala Ala Ser Gly Phe Thr Phe Ser Ser Phe Gly Met Ser Trp Val Arg
                340                 345                 350

Gln Ala Pro Gly Lys Gly Leu Glu Trp Val Ser Ser Ile Ser Gly Ser
                355                 360                 365

Gly Ser Asp Thr Leu Tyr Ala Asp Ser Val Lys Gly Arg Phe Thr Ile
                370                 375                 380

Ser Arg Asp Asn Ala Lys Thr Thr Leu Tyr Leu Gln Met Asn Ser Leu
385                 390                 395                 400

Arg Pro Glu Asp Thr Ala Val Tyr Tyr Cys Thr Ile Gly Gly Ser Leu
                405                 410                 415

Ser Arg Ser Ser Gln Gly Thr Leu Val Thr Val Ser Ser
                420                 425

<210> SEQ ID NO 470
<211> LENGTH: 272
<212> TYPE: PRT
<213> ORGANISM: Artificial Sequence
<220> FEATURE:
<223> OTHER INFORMATION: Nanobody sequence

<400> SEQUENCE: 470

Asp Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
                20                  25                  30

Thr Met Gly Trp Phe Arg Gln Ala Pro Gly Lys Glu Arg Glu Phe Val
            35                  40                  45

Ala Glu Val Arg Trp Gly Gly Val Thr Thr Tyr Ser Asn Ser Leu Lys
50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
                100                 105                 110

Gly Thr Leu Val Thr Val Ser Ser Gly Gly Gly Gly Ser Gly Gly Gly
            115                 120                 125

Gly Ser Gly Gly Gly Gly Ser Gly Gly Gly Gly Ser Gly Gly Gly Gly
            130                 135                 140

Ser Gly Gly Gly Gly Ser Gly Gly Gly Gly Ser Glu Val Gln Leu Val
```

```
145                 150                 155                 160
Glu Ser Gly Gly Gly Leu Val Gln Pro Gly Gly Ser Leu Arg Leu Ser
                165                 170                 175
Cys Ala Ala Ser Gly Asp Val His Lys Ile Asn Ile Leu Gly Trp Tyr
                180                 185                 190
Arg Gln Ala Pro Ala Lys Glu Arg Glu Met Val Ala His Ile Thr Ile
                195                 200                 205
Gly Asp Ala Thr Asp Tyr Ala Asp Ser Ala Lys Gly Arg Phe Thr Ile
        210                 215                 220
Ser Arg Asp Glu Ala Lys Asn Met Val Tyr Leu Gln Met Asn Ser Leu
225                 230                 235                 240
Lys Pro Glu Asp Thr Ala Val Tyr Phe Cys Arg Ala Tyr Ser Arg Ile
                245                 250                 255
Tyr Pro Tyr Asn Tyr Trp Gly Gln Gly Thr Leu Val Thr Val Ser Ser
                260                 265                 270

<210> SEQ ID NO 471
<211> LENGTH: 279
<212> TYPE: PRT
<213> ORGANISM: Artificial Sequence
<220> FEATURE:
<223> OTHER INFORMATION: Nanobody sequence

<400> SEQUENCE: 471

Asp Val Gln Leu Val Glu Ser Gly Gly Gly Leu Val Gln Ala Gly Asp
1               5                   10                  15
Ser Leu Arg Leu Ser Cys Ala Ala Ser Gly Arg Thr Phe Ser Ser Tyr
                20                  25                  30
Ala Met Gly Trp Phe Arg Gln Ala Pro Gly Lys Glu Arg Glu Phe Val
            35                  40                  45
Ala Ala Ile Ser Trp Ser Asp Gly Ser Thr Tyr Tyr Ala Asp Ser Val
        50                  55                  60
Lys Gly Arg Phe Thr Ile Ser Arg Asp Asn Ala Lys Asn Thr Val Tyr
65                  70                  75                  80
Leu Gln Met Asn Ser Leu Lys Pro Glu Asp Thr Ala Val Tyr Tyr Cys
                85                  90                  95
Ala Ala Asp Leu Thr Ser Thr Asn Pro Gly Ser Tyr Ile Tyr Ile Trp
                100                 105                 110
Ala Tyr Asp Tyr Trp Gly Gln Gly Thr Gln Val Thr Val Ser Ser Gly
            115                 120                 125
Gly Gly Gly Ser Gly Gly Gly Gly Ser Gly Gly Gly Gly Ser Gly Gly
        130                 135                 140
Gly Gly Ser Gly Gly Gly Gly Ser Gly Gly Gly Gly Ser Gly Gly Gly
145                 150                 155                 160
Gly Ser Glu Val Gln Leu Val Glu Ser Gly Gly Gly Leu Val Gln Pro
                165                 170                 175
Gly Gly Ser Leu Arg Leu Ser Cys Ala Ala Ser Gly Asp Val His Lys
                180                 185                 190
Ile Asn Ile Leu Gly Trp Tyr Arg Gln Ala Pro Ala Lys Glu Arg Glu
            195                 200                 205
Met Val Ala His Ile Thr Ile Gly Asp Ala Thr Asp Tyr Ala Asp Ser
        210                 215                 220
Ala Lys Gly Arg Phe Thr Ile Ser Arg Asp Glu Ala Lys Asn Met Val
225                 230                 235                 240
Tyr Leu Gln Met Asn Ser Leu Lys Pro Glu Asp Thr Ala Val Tyr Phe
```

```
                    245                 250                 255
Cys Arg Ala Tyr Ser Arg Ile Tyr Pro Tyr Asn Tyr Trp Gly Gln Gly
            260                 265                 270

Thr Leu Val Thr Val Ser Ser
            275

<210> SEQ ID NO 472
<211> LENGTH: 10
<212> TYPE: PRT
<213> ORGANISM: Artificial Sequence
<220> FEATURE:
<223> OTHER INFORMATION: CDR1

<400> SEQUENCE: 472

Gly Phe Thr Phe Ser Ser Phe Gly Met Ser
1               5                   10

<210> SEQ ID NO 473
<211> LENGTH: 10
<212> TYPE: PRT
<213> ORGANISM: Artificial Sequence
<220> FEATURE:
<223> OTHER INFORMATION: CDR1

<400> SEQUENCE: 473

Gly Phe Thr Phe Arg Ser Phe Gly Met Ser
1               5                   10

<210> SEQ ID NO 474
<211> LENGTH: 10
<212> TYPE: PRT
<213> ORGANISM: Artificial Sequence
<220> FEATURE:
<223> OTHER INFORMATION: CDR2

<400> SEQUENCE: 474

Ser Ile Ser Gly Ser Gly Ser Asp Thr Leu
1               5                   10

<210> SEQ ID NO 475
<211> LENGTH: 6
<212> TYPE: PRT
<213> ORGANISM: Artificial Sequence
<220> FEATURE:
<223> OTHER INFORMATION: CDR3

<400> SEQUENCE: 475

Gly Gly Ser Leu Ser Arg
1               5

<210> SEQ ID NO 476
<211> LENGTH: 110
<212> TYPE: PRT
<213> ORGANISM: Homo sapiens

<400> SEQUENCE: 476

Asn Ala Gly Val Thr Gln Thr Pro Lys Phe Arg Ile Leu Lys Ile Gly
1               5                   10                  15

Gln Ser Met Thr Leu Gln Cys Thr Gln Asp Met Asn His Asn Tyr Met
                20                  25                  30

Tyr Trp Tyr Arg Gln Asp Pro Gly Met Gly Leu Lys Leu Ile Tyr Tyr
            35                  40                  45

Ser Val Gly Ala Gly Ile Thr Asp Lys Gly Glu Val Pro Asn Gly Tyr
        50                  55                  60
```

```
Asn Val Ser Arg Ser Thr Thr Glu Asp Phe Pro Leu Arg Leu Glu Leu
 65                  70                  75                  80

Ala Ala Pro Ser Gln Thr Ser Val Tyr Phe Cys Ala Ser Thr Tyr His
                 85                  90                  95

Gly Thr Gly Tyr Phe Gly Glu Gly Ser Trp Leu Thr Val Val
                100                 105                 110

<210> SEQ ID NO 477
<211> LENGTH: 112
<212> TYPE: PRT
<213> ORGANISM: Homo sapiens

<400> SEQUENCE: 477

Asp Gly Gly Ile Thr Gln Ser Pro Lys Tyr Leu Phe Arg Lys Glu Gly
 1               5                  10                  15

Gln Asn Val Thr Leu Ser Cys Glu Gln Asn Leu Asn His Asp Ala Met
                 20                  25                  30

Tyr Trp Tyr Arg Gln Asp Pro Gly Gln Gly Leu Arg Leu Ile Tyr Tyr
                 35                  40                  45

Ser Gln Ile Val Asn Asp Phe Gln Lys Gly Asp Ile Ala Glu Gly Tyr
 50                  55                  60

Ser Val Ser Arg Glu Lys Lys Glu Ser Phe Pro Leu Thr Val Thr Ser
 65                  70                  75                  80

Ala Gln Lys Asn Pro Thr Ala Phe Tyr Leu Cys Ala Ser Ser Ser Arg
                 85                  90                  95

Ser Ser Tyr Glu Gln Tyr Phe Gly Pro Gly Thr Arg Leu Thr Val Thr
                100                 105                 110

<210> SEQ ID NO 478
<211> LENGTH: 114
<212> TYPE: PRT
<213> ORGANISM: Homo sapiens

<400> SEQUENCE: 478

Val Val Ser Gln His Pro Ser Trp Val Ile Ala Lys Ser Gly Thr Ser
 1               5                  10                  15

Val Lys Ile Glu Cys Arg Ser Leu Asp Phe Gln Ala Thr Thr Met Phe
                 20                  25                  30

Trp Tyr Arg Gln Phe Pro Lys Gln Ser Leu Met Leu Met Ala Thr Ser
                 35                  40                  45

Asn Glu Gly Ser Lys Ala Thr Tyr Glu Gln Gly Val Glu Lys Asp Lys
 50                  55                  60

Phe Leu Ile Asn His Ala Ser Leu Thr Leu Ser Thr Leu Thr Val Thr
 65                  70                  75                  80

Ser Ala His Pro Glu Asp Ser Ser Phe Tyr Ile Cys Ser Ala Arg Gly
                 85                  90                  95

Gly Ser Tyr Asn Ser Pro Leu His Phe Gly Asn Gly Thr Arg Leu Thr
                100                 105                 110

Val Thr

<210> SEQ ID NO 479
<211> LENGTH: 96
<212> TYPE: PRT
<213> ORGANISM: Homo sapiens

<400> SEQUENCE: 479

Pro Asn Ile Gln Asn Pro Asp Pro Ala Val Tyr Gln Leu Arg Asp Ser
```

```
                1               5                      10                      15
Lys Ser Ser Asp Lys Ser Val Cys Leu Phe Thr Asp Phe Asp Ser Gln
                    20                      25                      30
Thr Asn Val Ser Gln Ser Lys Asp Ser Asp Val Tyr Ile Thr Asp Lys
                    35                      40                      45
Thr Val Leu Asp Met Arg Ser Met Asp Phe Lys Ser Asn Ser Ala Val
                    50                      55                      60
Ala Trp Ser Asn Lys Ser Asp Phe Ala Cys Asn Ala Phe Asn Asn
 65                     70                      75                      80
Ser Ile Ile Pro Glu Asp Thr Phe Phe Pro Ser Pro Glu Ser Ser Cys
                    85                      90                      95
```

<210> SEQ ID NO 480
<211> LENGTH: 131
<212> TYPE: PRT
<213> ORGANISM: Homo sapiens

<400> SEQUENCE: 480

```
Glu Asp Leu Asn Lys Val Phe Pro Pro Glu Val Ala Val Phe Glu Pro
 1               5                      10                      15
Ser Glu Ala Glu Ile Ser His Thr Gln Lys Ala Thr Leu Val Cys Leu
                    20                      25                      30
Ala Thr Gly Phe Phe Pro Asp His Val Glu Leu Ser Trp Trp Val Asn
                    35                      40                      45
Gly Lys Glu Val His Ser Gly Val Ser Thr Asp Pro Gln Pro Leu Lys
                    50                      55                      60
Glu Gln Pro Ala Leu Asn Asp Ser Arg Tyr Cys Leu Ser Ser Arg Leu
 65                     70                      75                      80
Arg Val Ser Ala Thr Phe Trp Gln Asn Pro Arg Asn His Phe Arg Cys
                    85                      90                      95
Gln Val Gln Phe Tyr Gly Leu Ser Glu Asn Asp Glu Trp Thr Gln Asp
                    100                     105                     110
Arg Ala Lys Pro Val Thr Gln Ile Val Ser Ala Glu Ala Trp Gly Arg
                    115                     120                     125
Ala Asp Cys
    130
```

<210> SEQ ID NO 481
<211> LENGTH: 5
<212> TYPE: PRT
<213> ORGANISM: Artificial Sequence
<220> FEATURE:
<223> OTHER INFORMATION: CDR1

<400> SEQUENCE: 481

```
Ser Phe Gly Met Ser
 1               5
```

<210> SEQ ID NO 482
<211> LENGTH: 17
<212> TYPE: PRT
<213> ORGANISM: Artificial Sequence
<220> FEATURE:
<223> OTHER INFORMATION: CDR2

<400> SEQUENCE: 482

```
Ser Ile Ser Gly Ser Gly Ser Asp Thr Leu Tyr Ala Asp Ser Val Lys
 1               5                      10                      15
Gly
```

```
<210> SEQ ID NO 483
<211> LENGTH: 98
<212> TYPE: PRT
<213> ORGANISM: Artificial Sequence
<220> FEATURE:
<223> OTHER INFORMATION: Nanobody sequence

<400> SEQUENCE: 483

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Ile Gly Trp Phe Arg Gln Ala Pro Gly Lys Glu Arg Glu Gly Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala

<210> SEQ ID NO 484
<211> LENGTH: 142
<212> TYPE: PRT
<213> ORGANISM: Homo sapiens

<400> SEQUENCE: 484

Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Thr Val Leu Asp Met Arg Ser Met Asp Phe Lys Ser Asn Ser Ala Val
    50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

Asp Val Lys Leu Val Glu Lys Ser Phe Glu Thr Asp Thr Asn Leu Asn
            100                 105                 110

Phe Gln Asn Leu Ser Val Ile Gly Phe Arg Ile Leu Leu Leu Lys Val
            115                 120                 125

Ala Gly Phe Asn Leu Leu Met Thr Leu Arg Leu Trp Ser Ser
            130                 135                 140

<210> SEQ ID NO 485
<211> LENGTH: 177
<212> TYPE: PRT
<213> ORGANISM: Homo sapiens

<400> SEQUENCE: 485

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30
```

```
Ala Thr Gly Phe Phe Pro Asp His Val Glu Leu Ser Trp Trp Val Asn
            35                  40                  45

Gly Lys Glu Val His Ser Gly Val Ser Thr Asp Pro Gln Pro Leu Lys
 50                  55                  60

Glu Gln Pro Ala Leu Asn Asp Ser Arg Tyr Cys Leu Ser Ser Arg Leu
 65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
                115                 120                 125

Ala Asp Cys Gly Phe Thr Ser Val Ser Tyr Gln Gln Gly Val Leu Ser
                130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 486
<211> LENGTH: 623
<212> TYPE: PRT
<213> ORGANISM: Artificial Sequence
<220> FEATURE:
<223> OTHER INFORMATION: Nanobody sequence

<400> SEQUENCE: 486

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
                20                  25                  30

Val Met Gly Trp Phe Arg Gln Ala Thr Gly Lys Glu Arg Glu Phe Val
            35                  40                  45

Ala Thr Ile Ala Trp Asp Ser Gly Ser Thr Tyr Tyr Ala Asp Ser Val
 50                  55                  60

Lys Gly Arg Phe Thr Ile Ser Arg Asp Asn Ala Lys Asn Thr Val His
 65                  70                  75                  80

Leu Gln Met Asn Ser Leu Lys Pro Glu Asp Thr Ala Val Tyr Tyr Cys
                85                  90                  95

Ala Ala Ser Tyr Asn Val Tyr Tyr Asn Tyr Tyr Pro Ile Ser
                100                 105                 110

Arg Asp Glu Tyr Asp Tyr Trp Gly Gln Gly Thr Leu Val Thr Val Ser
                115                 120                 125

Ser Gly Gly Gly Ser Gly Gly Gly Ser Gly Gly Gly Ser
                130                 135                 140

Gly Gly Gly Ser Gly Gly Gly Ser Gly Gly Gly Ser Gly
145                 150                 155                 160

Gly Gly Ser Glu Val Gln Leu Val Glu Ser Gly Gly Ser Val
                165                 170                 175

Gln Ala Gly Gly Ser Leu Arg Leu Ser Cys Ala Ala Ser Gly Asp Thr
                180                 185                 190

Tyr Gly Ser Tyr Trp Met Gly Trp Phe Arg Gln Ala Pro Gly Lys Glu
                195                 200                 205
```

```
Arg Glu Gly Val Ala Ala Ile Asn Arg Gly Gly Tyr Thr Val Tyr
    210                 215                 220

Ala Asp Ser Val Lys Gly Arg Phe Thr Ile Ser Arg Asp Thr Ala Lys
225                 230                 235                 240

Asn Thr Val Tyr Leu Gln Met Asn Ser Leu Arg Pro Asp Asp Thr Ala
                245                 250                 255

Asp Tyr Tyr Cys Ala Ala Ser Gly Val Leu Gly Gly Leu His Glu Asp
                260                 265                 270

Trp Phe Asn Tyr Trp Gly Gln Gly Thr Leu Val Thr Val Ser Ser Gly
            275                 280                 285

Gly Gly Gly Ser Gly Gly Gly Ser Gly Gly Gly Gly Ser Gly Gly
290                 295                 300

Gly Gly Ser Gly Gly Gly Ser Gly Gly Gly Ser Gly Gly Gly
305                 310                 315                 320

Gly Ser Glu Val Gln Leu Val Glu Ser Gly Gly Leu Val Gln Pro
                325                 330                 335

Gly Gly Ser Leu Arg Leu Ser Cys Val Ala Ser Gly Asp Val His Lys
            340                 345                 350

Ile Asn Phe Leu Gly Trp Tyr Arg Gln Ala Pro Gly Lys Glu Arg Glu
            355                 360                 365

Lys Val Ala His Ile Ser Ile Gly Asp Gln Thr Asp Tyr Ala Asp Ser
370                 375                 380

Ala Lys Gly Arg Phe Thr Ile Ser Arg Asp Glu Ser Lys Asn Met Val
385                 390                 395                 400

Tyr Leu Gln Met Asn Ser Leu Lys Pro Glu Asp Thr Ala Val Tyr Phe
                405                 410                 415

Cys Arg Ala Phe Ser Arg Ile Tyr Pro Tyr Asp Tyr Trp Gly Gln Gly
            420                 425                 430

Thr Leu Val Thr Val Ser Ser Gly Gly Gly Ser Gly Gly Gly Gly
            435                 440                 445

Ser Gly Gly Gly Gly Ser Gly Gly Gly Ser Gly Gly Gly Gly Ser
450                 455                 460

Gly Gly Gly Gly Ser Gly Gly Gly Ser Glu Val Gln Leu Val Glu
465                 470                 475                 480

Ser Gly Gly Gly Leu Val Gln Pro Gly Asn Ser Leu Arg Leu Ser Cys
                485                 490                 495

Ala Ala Ser Gly Phe Thr Phe Ser Ser Phe Gly Met Ser Trp Val Arg
            500                 505                 510

Gln Ala Pro Gly Lys Gly Leu Glu Trp Val Ser Ser Ile Ser Gly Ser
            515                 520                 525

Gly Ser Asp Thr Leu Tyr Ala Asp Ser Val Lys Gly Arg Phe Thr Ile
            530                 535                 540

Ser Arg Asp Asn Ala Lys Thr Thr Leu Tyr Leu Gln Met Asn Ser Leu
545                 550                 555                 560

Arg Pro Glu Asp Thr Ala Val Tyr Tyr Cys Thr Ile Gly Gly Ser Leu
                565                 570                 575

Ser Arg Ser Ser Gln Gly Thr Leu Val Thr Val Ser Ser Gly Ala Ala
            580                 585                 590

Asp Tyr Lys Asp His Asp Gly Asp Tyr Lys Asp His Asp Ile Asp Tyr
            595                 600                 605

Lys Asp Asp Asp Asp Lys Gly Ala Ala His His His His His His
610                 615                 620
```

<210> SEQ ID NO 487
<211> LENGTH: 589
<212> TYPE: PRT
<213> ORGANISM: Artificial Sequence
<220> FEATURE:
<223> OTHER INFORMATION: Nanobody sequence

<400> SEQUENCE: 487

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Val Met Gly Trp Phe Arg Gln Ala Thr Gly Lys Glu Arg Glu Phe Val
        35                  40                  45

Ala Thr Ile Ala Trp Asp Ser Gly Ser Thr Tyr Tyr Ala Asp Ser Val
    50                  55                  60

Lys Gly Arg Phe Thr Ile Ser Arg Asp Asn Ala Lys Asn Thr Val His
65                  70                  75                  80

Leu Gln Met Asn Ser Leu Lys Pro Glu Asp Thr Ala Val Tyr Tyr Cys
                85                  90                  95

Ala Ala Ser Tyr Asn Val Tyr Tyr Asn Asn Tyr Tyr Pro Ile Ser
            100                 105                 110

Arg Asp Glu Tyr Asp Tyr Trp Gly Gln Gly Thr Leu Val Thr Val Ser
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Gly Ser Gly
145                 150                 155                 160

Gly Gly Gly Ser Glu Val Gln Leu Val Glu Ser Gly Gly Gly Ser Val
                165                 170                 175

Gln Ala Gly Gly Ser Leu Arg Leu Ser Cys Ala Ala Ser Gly Asp Thr
            180                 185                 190

Tyr Gly Ser Tyr Trp Met Gly Trp Phe Arg Gln Ala Pro Gly Lys Glu
        195                 200                 205

Arg Glu Gly Val Ala Ala Ile Asn Arg Gly Gly Gly Tyr Thr Val Tyr
    210                 215                 220

Ala Asp Ser Val Lys Gly Arg Phe Thr Ile Ser Arg Asp Thr Ala Lys
225                 230                 235                 240

Asn Thr Val Tyr Leu Gln Met Asn Ser Leu Arg Pro Asp Asp Thr Ala
                245                 250                 255

Asp Tyr Tyr Cys Ala Ala Ser Gly Val Leu Gly Gly Leu His Glu Asp
            260                 265                 270

Trp Phe Asn Tyr Trp Gly Gln Gly Thr Leu Val Thr Val Ser Ser Gly
        275                 280                 285

Gly Gly Gly Ser Gly Gly Gly Gly Ser Gly Gly Gly Ser Gly Gly
    290                 295                 300

Gly Gly Ser Gly Gly Gly Ser Gly Gly Gly Gly Ser Gly Gly Gly
305                 310                 315                 320

Gly Ser Glu Val Gln Leu Val Glu Ser Gly Gly Gly Leu Val Gln Pro
                325                 330                 335

Gly Gly Ser Leu Arg Leu Ser Cys Val Ala Ser Gly Asp Val His Lys
            340                 345                 350

Ile Asn Phe Leu Gly Trp Tyr Arg Gln Ala Pro Gly Lys Glu Arg Glu
        355                 360                 365

Lys Val Ala His Ile Ser Ile Gly Asp Gln Thr Asp Tyr Ala Asp Ser
```

```
                370                 375                 380
Ala Lys Gly Arg Phe Thr Ile Ser Arg Asp Glu Ser Lys Asn Met Val
385                 390                 395                 400

Tyr Leu Gln Met Asn Ser Leu Lys Pro Glu Asp Thr Ala Val Tyr Phe
                405                 410                 415

Cys Arg Ala Phe Ser Arg Ile Tyr Pro Tyr Asp Tyr Trp Gly Gln Gly
                420                 425                 430

Thr Leu Val Thr Val Ser Ser Gly Gly Gly Gly Ser Gly Gly Gly Gly
                435                 440                 445

Ser Gly Gly Gly Ser Gly Gly Gly Gly Ser Gly Gly Gly Gly Ser
        450                 455                 460

Gly Gly Gly Gly Ser Gly Gly Gly Ser Glu Val Gln Leu Val Glu
465                 470                 475                 480

Ser Gly Gly Gly Leu Val Gln Pro Gly Asn Ser Leu Arg Leu Ser Cys
                485                 490                 495

Ala Ala Ser Gly Phe Thr Phe Ser Ser Phe Gly Met Ser Trp Val Arg
                500                 505                 510

Gln Ala Pro Gly Lys Gly Leu Glu Trp Val Ser Ser Ile Ser Gly Ser
                515                 520                 525

Gly Ser Asp Thr Leu Tyr Ala Asp Ser Val Lys Gly Arg Phe Thr Ile
                530                 535                 540

Ser Arg Asp Asn Ala Lys Thr Thr Leu Tyr Leu Gln Met Asn Ser Leu
545                 550                 555                 560

Arg Pro Glu Asp Thr Ala Val Tyr Tyr Cys Thr Ile Gly Gly Ser Leu
                565                 570                 575

Ser Arg Ser Ser Gln Gly Thr Leu Val Thr Val Ser Ser
                580                 585
```